(12) United States Patent
Andrews et al.

(10) Patent No.: US 8,846,698 B2
(45) Date of Patent: Sep. 30, 2014

(54) PYRROLO[2,3-D]PYRIMIDINE TROPOMYSIN-RELATED KINASE INHIBITORS

(75) Inventors: Mark David Andrews, Sandwich (GB); Sharanjeet Kaur Bagal, Sandwich (GB); Karl Richard Gibson, Sandwich (GB); Kiyoyuki Omoto, Sandwich (GB); Thomas Ryckmans, Sandwich (GB); Sarah Elizabeth Skerratt, Sandwich (GB); Paul Anthony Stupple, Sandwich (GB)

(73) Assignee: Pfizer Limited, New York, NY (US)

( * ) Notice: Subject to any disclaimer, the term of this patent is extended or adjusted under 35 U.S.C. 154(b) by 226 days.

(21) Appl. No.: 13/439,131

(22) Filed: Apr. 4, 2012

(65) Prior Publication Data

US 2012/0258950 A1 Oct. 11, 2012

Related U.S. Application Data

(60) Provisional application No. 61/471,758, filed on Apr. 5, 2011.

(51) Int. Cl.
- *C07D 487/04* (2006.01)
- *A61K 31/519* (2006.01)
- *A61P 25/04* (2006.01)

(52) U.S. Cl.
CPC ............ *C07D 487/04* (2013.01); *A61K 31/519* (2013.01)
USPC ........................................ 514/265.1; 544/280

(58) Field of Classification Search
CPC ............................ C07D 487/04; A61K 31/519
USPC ........................................ 544/280; 514/265.1
See application file for complete search history.

(56) References Cited

U.S. PATENT DOCUMENTS

| 7,417,063 B2 | 8/2008 | Smallheer et al. |
| 2009/0286782 A1 | 11/2009 | Ibrahim et al. |
| 2009/0286783 A1 | 11/2009 | Ibrahim et al. |

FOREIGN PATENT DOCUMENTS

| JP | 2003-321472 | 11/2003 |
| WO | 2005/116035 | 8/2005 |
| WO | 2011/093672 | 8/2011 |

*Primary Examiner* — Susanna Moore
(74) *Attorney, Agent, or Firm* — James T. Wasicak

(57) ABSTRACT

The present invention relates to compounds of Formula (I)

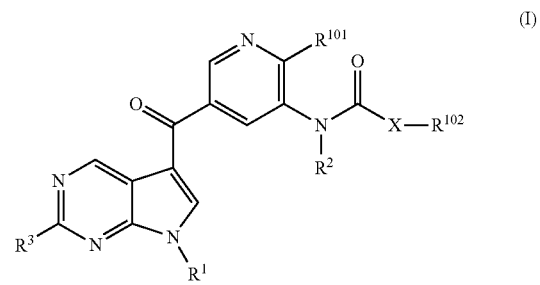

(I)

and their pharmaceutically acceptable salts, wherein the substituents are as described herein, and their use in medicine, in particular as Trk antagonists.

35 Claims, No Drawings

PYRROLO[2,3-D]PYRIMIDINE TROPOMYSIN-RELATED KINASE INHIBITORS

This application claims benefit of U.S. Provisional Application No. 61/471,758, filed Apr. 5, 2011, hereby incorporated by reference in its entirety for any purpose.

FIELD OF THE INVENTION

The invention described herein relates to certain pyrrolo[2,3-d}pyrimidine compounds and the pharmaceutically acceptable salts of such compounds. The invention also relates to the processes for the preparation of the compounds, compositions containing the compounds, and the uses of such compounds and salts in treating diseases or conditions associated with tropomyosin-related kinase (Trk), activity. More specifically the invention relates to the compounds and their salts useful as inhibitors of Trk.

BACKGROUND

Tropomyosin-related kinases (Trks) are a family of receptor tyrosine kinases activated by neurotrophins. Trks play important roles in pain sensation as well as tumour cell growth and survival signaling. Thus, inhibitors of Trk receptor kinases might provide targeted treatments for conditions such as pain and cancer. Recent developments in this field have been reviewed by Wang et al in Expert Opin. Ther. Patents (2009) 19(3): 305-319 and an extract is reproduced below.

"1.1 Trk Receptors

As one of the largest family of proteins encoded by the human genome, protein kinases are the central regulators of signal transduction as well as control of various complex cell processes. Receptor tyrosine kinases (RTKs) are a subfamily of protein kinases (up to 100 members) bound to the cell membrane that specifically act on the tyrosine residues of proteins. One small group within this subfamily is the Trk kinases, with three highly homologous isoforms: TrkA, TrkB, and TrkC. All three isoforms are activated by high affinity growth factors named neurotrophins (NT): i) nerve growth factor (NGF), which activates TrkA; ii) brain-derived neurotrophic factor (BDNF) and NT-4/5, which activate TrkB; and iii) NT-3, which activates TrkC. The binding of neurotrophins to the extracellular domain of Trks causes the Trk kinase to autophosphorylate at several intracellular tyrosine sites and triggers downstream signal transduction pathways. Trks and neurotrophins are well known for their effects on neuronal growth and survival.

1.2 Trks and Cancer

Originally isolated from neuronal tissues, Trks were thought to mainly affect the maintenance and survival of neuronal cells. However, in the past 20 years, increasing evidence has suggested that Trks play key roles in malignant transformation, chemotaxis, metastasis, and survival signaling in human tumors. The association between Trks and cancer focused on prostate cancer in earlier years and the topic has been reviewed. For example, it was reported that malignant prostate epithelial cells secrete a series of neurotrophins and at least one Trks. In pancreatic cancer, it was proposed that paracrine and/or autocrine neurotrophin-Trk interactions may influence the invasive behavior of the cancer. TrkB was also reported to be overexpressed in metastatic human pancreatic cancer cells. Recently, there have been a number of new findings in other cancer settings. For example, a translocation leads to expression of a fusion protein derived from the N-terminus of the ETV6 transcription factor and the C-terminal kinase domain of TrkC. The resulting ETV6-TrkC fusions are oncogenic in vitro and appear causative in secretory breast carcinoma and some acute myelogenous leukemias (AML). Constitutively active TrkA fusions occurred in a subset of papillary thyroid cancers and colon carcinomas. In neuroblastoma, TrkB expression was reported to be a strong predictor of aggressive tumor growth and poor prognosis, and TrkB overexpression was also associated with increased resistance to chemotherapy in neuroblastoma tumor cells in vitro. One report showed that a novel splice variant of TrkA called TrkAIII signaled in the absence of neurotrophins through the inositol phosphate-AKT pathway in a subset of neuroblastoma. Also, mutational analysis of the tyrosine kinome revealed that Trk mutations occurred in colorectal and lung cancers. In summary, Trks have been linked to a variety of human cancers, and discovering a Trk inhibitor and testing it clinically might provide further insight to the biological and medical hypothesis of treating cancer with targeted therapies.

1.3 Trks and Pain

Besides the newly developed association with cancer, Trks are also being recognized as an important mediator of pain sensation. Congenital insensitivity to pain with anhidrosis (CIPA) is a disorder of the peripheral nerves (and normally innervated sweat glands) that prevents the patient from either being able to adequately perceive painful stimuli or to sweat. TrkA defects have been shown to cause CIPA in various ethnic groups.

Currently, non-steroidal anti-inflammatory drugs (NSAIDs) and opiates have low efficacy and/or side effects (e.g., gastrointestinal/renal and psychotropic side effects, respectively) against neuropathic pain and therefore development of novel pain treatments is highly desired. It has been recognized that NGF levels are elevated in response to chronic pain, injury and inflammation and the administration of exogenous NGF increases pain hypersensitivity. In addition, inhibition of NGF function with either anti-NGF antibodies or non-selective small molecule Trk inhibitors has been shown to have effects on pain in animal models. It appears that a selective Trk inhibitor (inhibiting at least NGF's target, the TrkA receptor) might provide clinical benefit for the treatment of pain. Excellent earlier reviews have covered targeting NGF/BDNF for the treatment of pain so this review will only focus on small molecule Trk kinase inhibitors claimed against cancer and pain. However, it is notable that the NGF antibody tanezumab was very recently reported to show good efficacy in a Phase II trial against osteoarthritic knee pain."

International Patent Application publication number WO2009/012283 refers to various fluorophenyl compounds as Trk inhibitors; International Patent Application publication numbers WO2009/152087, WO2008/080015 and WO2008/08001 and WO2009/152083 refer to various fused pyrroles as kinase modulators; International Patent Application publication numbers WO2009/143024 and WO2009/143018 refer to various pyrrolo[2,3-d]pyrimidines substituted as Trk inhibitors; International Patent Application publication numbers WO2004/056830 and WO2005/116035 describe various 4-amino-pyrrolo[2,3-d]pyrimidines as Trk inhibitors. International Patent Application publication number WO2011/133637 describes various pyrrolo[2,3-d]pyrimidines and pyrrolo[2,3-b]pyridines as inhibitors of various kinases.

U.S. provisional application 61/471,758 was filed 5 Apr. 2012 and the whole contents of that application in it's entirety are herewith included by reference thereto.

Thus Trk inhibitors have a wide variety of potential medical uses. There is a need to provide new Trk inhibitors that are good drug candidates. In particular, compounds should preferably bind potently to the Trk receptors in a selective manner compared to other receptors, whilst showing little affinity for other receptors, including other kinase and/or GPC receptors, and show functional activity as Trk receptor antagonists. They should be non-toxic and demonstrate few side-effects. Furthermore, the ideal drug candidate will exist in a physical form that is stable, non-hygroscopic and easily formulated. They should preferably be e.g. well absorbed from the gastrointestinal tract, and/or be injectable directly into the bloodstream, muscle, or subcutaneously, and/or be metabolically stable and possess favourable pharmacokinetic properties.

Among the aims of this invention are to provide orally-active, efficacious, compounds and salts which can be used as active drug substances, particularly Trk antagonists, i.e. that block the intracellular kinase activity of the Trk, e.g. TrkA (NGF) receptor. Other desirable features include good HLM/hepatocyte stability, oral bioavailability, metabolic stability, absorption, selectivity over other types of kinase, dofetilide selectivity. Preferable compounds and salts will show a lack of CYP inhibition/induction, and be CNS-sparing.

SUMMARY

The present invention provides compounds of Formula (I):

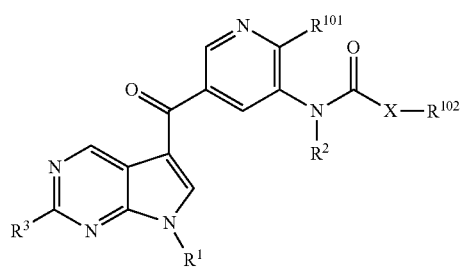

and pharmaceutically acceptable salts thereof wherein the substituents are defined below.

The invention also comprises pharmaceutical compositions comprising a therapeutically effective amount of a compound of formula I as defined herein, or a pharmaceutically acceptable salt thereof, and a pharmaceutically acceptable carrier.

The invention is also directed to a method of treating a disease or condition indicated for treatment with a Trk antagonist, in a subject, by administering to a subject in need thereof a therapeutically effective amount of one or more of the compounds herein, or a pharmaceutically acceptable salt thereof.

Other aspects of the invention will be apparent from the remaining description and claims.

Preferably, the compounds of the present invention are potent antagonists at Trk receptors, and have a suitable PK profile to enable once daily dosing.

The compounds of the present invention are potentially useful in the treatment of a range of disorders where a Trk antagonist is indicated, particularly pain indications. Depending on the disease and condition of the patient, the term "treatment" as used herein may include one or more of curative, palliative and prophylactic treatment.

According to the invention a compound of the present invention may be useful to treat any physiological pain such as inflammatory pain, nociceptive pain, neuropathic pain, acute pain, chronic pain, musculo-skeletal pain, on-going pain, central pain, heart and vascular pain, head pain, orofacial pain. Other pain conditions which may be treated include intense acute pain and chronic pain conditions which may involve the same pain pathways driven by pathophysiological processes and as such cease to provide a protective mechanism and instead contribute to debilitating symptoms associated with a wide range of disease states.

Pain is a feature of many trauma and disease states. When a substantial injury, via disease or trauma, to body tissue occurs the characteristics of nociceptor activation are altered, this leads to hypersensitivity at the site of damage and in nearby normal tissue. In acute pain the sensitivity returns to normal once the injury has healed. However, in many chronic pain states, the hypersensitivity far outlasts the healing process and is normally due to nervous system injury due to maladaptation of the afferent fibres (Woolf & Salter 2000 Science 288: 1765-1768). Clinical pain is present when discomfort and abnormal sensitivity feature among the patient's symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13-44).

Pain can be divided into a number of different areas because of differing pathophysiology, these include nociceptive, inflammatory, neuropathic pain among others. It should be noted that some types of pain have multiple aetiologies and thus can be classified in more than one area, e.g. Back pain, Cancer pain have both nociceptive and neuropathic components.

Nociceptive Pain

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13-44). The activation of nociceptors activates two types of afferent nerve fibres. Myelinated A-delta fibres transmit rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumbar facet joints, sacroiliac joints, paraspinal muscles or the posterior longitudinal ligament.

Neuropathic Pain

According to the invention a compound of the present invention can potentially be used to treat neuropathic pain and the symptoms of neuropathic pain including hyperalgesia, allodynia and ongoing pain. Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959-1964). The symptoms of neuropathic pain are difficult to treat, as they are often heterogeneous even between patients with the same disease (Woolf & Decosterd 1999 Pain Supp. 6: S141-S147; Woolf and Mannion 1999 Lancet 353: 1959-1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

Intense Acute Pain and Chronic Pain

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765-1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) exaggerated pain responses to noxious stimuli (hyperalgesia); 3) pain is produced by normally innocuous stimuli (allodynia) (Meyer et al., 1994 Textbook of Pain 13-44). Although patients with back pain, arthritis pain, CNS trauma, or neuropathic pain may have similar symptoms, the underlying mechanisms are different and, therefore, may require different treatment strategies.

Chronic Pain

Chronic pain comprises one or more of, chronic nociceptive pain, chronic neuropathic pain, chronic inflammatory pain, breakthrough pain, persistent pain hyperalgesia, allodynia, central sensitisation, peripheral sensitisation, disinhibition and augmented facilitation.

Chronic pain includes cancer pain, e.g. cancer pain arising from malignancy, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumour s, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumours, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukaemia, primary or secondary bone cancer, tumours that metastasize to the bone, tumours infiltrating the nerve and hollow viscus, tumours near neural structures. Cancer pain also comprises visceral pain, e.g. visceral pain which arises from pancreatic cancer and/or metastases in the abdomen, somatic pain, e.g. somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

Inflammatory Pain

Inflammatory conditions include acute inflammation, persistent acute inflammation, chronic inflammation, and combined acute and chronic inflammation.

Inflammatory pain includes acute inflammatory pain and/or chronic inflammatory pain wherein the chronic inflammatory pain can be pain involving both peripheral and central sensitisation and/or mixed etiology pain involving both inflammatory pain and neuropathic pain or nociceptive pain components. Inflammatory pain also comprises hyperalgesia, e.g. primary and/or secondary hyperalgesia. Additionally or alternatively the inflammatory pain can include allodynia. Inflammatory pain also comprises pain that persists beyond resolution of an underlying disorder or inflammatory condition or healing of an injury.

Inflammatory pain is pain resulting an inflammatory condition. e.g. in response to acute tissue injury due to trauma, disease e.g. an inflammatory disease, immune reaction, the presence of foreign substances, chemicals or infective particles for example micro-organisms. Inflammatory conditions can be either acute or chronic inflammation or both.

Inflammatory pain can result from an inflammatory condition due to an inflammatory disease such as inflammatory joint diseases, inflammatory connective tissue diseases, inflammatory autoimmune diseases, inflammatory myopathies, inflammatory digestive system diseases, inflammatory air way diseases, cellular immune inflammation diseases, hypersensitivities and allergies, vasular inflammation diseases, non-immune inflammatory disease, synovitis, villonodular synovitis, arthralgias, ankylosing spondylitis, spondyloarthritis, spondyloarthropathy, gout, Pagets disease, periarticular disorders such as bursitis, rheumatoid disease, rheumatoid arthritis and osteoarthritis, rheumatoid arthritis or osteoarthritis. Rheumatoid arthritis in particular, represents ongoing inflammation associated with severe pain. Arthritic pain is a form of inflammatory pain and arises from inflammation in a joint which causes both peripheral sensitization and central sensitization. Under inflammatory conditions the nociceptive system is activated by normally innocuous and nonpainful mechanical stimuli. Additionally when the joint is at rest pain is present and appears as spontaneous pain and hyperalgesia (augmented pain response on noxious stimulation and pain on normally nonpainful stimulation). Inflammatory processes in peripheral tissues lead to central sensitization in the spinal cord, which contributes to hyperalgesia and allodynia typically associated with inflammatory pain.

Other types of inflammatory pain include inflammatory bowel diseases (IBD).

Other Types of Pain

Other types of pain include but are not limited to:

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis;

Central pain or 'thalamic pain' as defined by pain caused by lesion or dysfunction of the nervous system including but not limited to central post-stroke pain, multiple sclerosis, spinal cord injury, Parkinson's disease and epilepsy;

Heart and vascular pain including but not limited to angina, myocardical infarction, mitral stenosis, pericarditis, Raynaud's phenomenon, scleredoma, scleredoma, skeletal muscle ischemia;

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis;

Head pain including but not limited to migraine, migraine with aura, migraine without aura cluster headache, tension-type headache. Orofacial pain including but not limited to dental pain, temporomandibular myofascial pain, tinnitus, hot flushes, restless leg syndrome and blocking development of abuse potential. Further pain conditions may include, back pain (e.g. chronic lower back pain), cancer pain, complex regional syndrome, HIV-related neuropathic pain, post-operative induced neuropathic pain, post-stroke pain, spinal cord injury pain, traumatic nerve injury pain, diabetic peripheral neuropathy, moderate/severe interstitial cystitis pain, irritable bowel syndrome pain, moderate/severe endometriosis pain, moderate/severe pelvic pain, moderate/severe prostatitis pain, moderate/severe osteoarthritis pain, post-herpetic neuralgia, rheumatoid arthritis pain, dysmenorrhea pain, preemptive post-operative pain, trigeminal neuralgia, bursitis, dental pain, fibromyalgia or myofacial pain, menstrual pain, migraine, neuropathic pain (including painful diabetic neuropathy), pain associated with post-herpetic neuralgia, post-operative pain, referred pain, trigeminal neuralgia, visceral pain (including interstitial cystitis and IBS) and pain associated with AIDS, allodynia, burns, cancer, hyperalgesia, hypersensitisation, spinal trauma and/or degeneration and stroke.

DETAILED DESCRIPTION

Embodiment 1 of the invention is a compound of Formula (I):

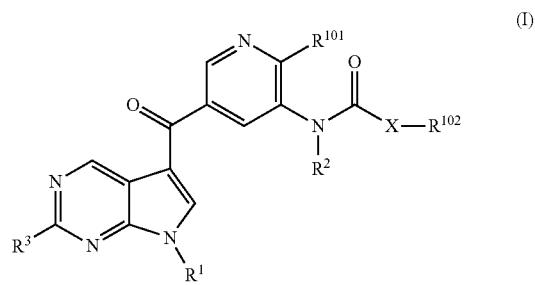

or a pharmaceutically acceptable salt thereof, wherein $R^1$ is

H, or $C_{1-5}$ alkyl optionally substituted by up to 3 substituents independently selected from OH, $CON(R^5R^6)$, $SO_2R^7$, $SR^7$, $OR^7$, $CH_2OH$, $CO_2R^5$, $SONR^7R^7$, $NR^7SO_2R^5$, CN, $NO_2$ and $R^8$, or a ring system selected from $C_{3-5}$ cycloalkyl, propellanyl, or a 4-6 membered saturated heterocyclyl ring, which ring system has up to 3 ring hetero-atoms selected from N, O and S, and which ring system is optionally substituted by up to 3 substituents independently selected from methyl, OH, $CON(R^5R^6)$, $SO_2R^7$, $OR^7$, $CH_2OH$, $CO_2R^5$, $SONR^7R^7$, $NR^7SO_2R^5$, CN, $NO_2$ and $R^8$;

$R^2$ is H or methyl;

$R^3$ is H, $NH_2$ or $NH(C_{1-3}$ alkyl optionally substituted with up to 3 substituents independently selected from OH and $O(C_{1-3}$ alkyl));

$R^{101}$ is H, OH, methyl, cyclopropyl, methoxy, ethyl, ethoxy or CN,

X is a bond, O, $(CH-R^4)_n$, $NR^{104}$, $OCH_2$ or $CH_2O$;

$R^4$ is independently H, $CH_3$, $CH_2OH$, $CH_2OCH_3$, OH, $NH_2$, $NHCH_3$, $N(CH_3)_2$, $CH_2NH_2$, $CH_2NHCH_3$, or $CH_2N(CH_3)_2$;

$R^{104}$ is H, $C_{1-3}$ alkyl or a $C_{4-6}$ saturated carbocycle, each of which is optionally substituted by up to 3 substituents independently selected from $C_{1-3}$ alkyl, $CH_2OH$ and $NH_2$;

n is 1 or 2;

$R^{102}$ is a ring system which is a 3-7 membered monocyclic carbocyclic or heterocyclic system, or an 8-14-membered bicyclic system, which ring system may be saturated or partially or fully unsaturated, wherein the heterocyclic ring system may have up to 5 ring hetero-atoms selected from N, S, and O, wherein the bicyclic ring system can be 2 rings (carbocyclic-carbocyclic, carbocyclic-heterocyclic, heterocyclic-carbocyclic or heterocyclic-heterocyclic) fused or linked by a single bond, which ring system is optionally substituted by up to 3 substituents independently selected from, where possible— halo, CN, $NR^5R^6$, $SO_2R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by up to 3 halogen, OH, $O(C_{1-3}$ alkyl), $O(C_{3-6}$ cycloalkyl optionally substituted by up to 3 OH and/or $C_{1-3}$ alkoxy groups, $O(C_{1-3}$ alkyl substituted by up to 3 halogen), $O(C_{1-3}$ alkyl substituted by up to 3 OH and/or $C_{1-3}$ alkoxy groups), $NR^5SO_2R^7$, =O, $R^8$, $C(O)R^8$, $NO_2$, $NR^5CO_2R^7$, $NR^5COR^7$, $OR^8$, $S(O)R^7$, and $CH_2R^8$;

$R^5$ and $R^6$ are each independently

H, or $C_{1-5}$ alkyl optionally substituted by up to 3 substituents independently selected from OH, $CONR^7R^7$, $SO_2R^7$, $OR^7$, $CH_2OH$, $CO_2R^7$, $SONR^7R^7$, $NR^7SO_2R^7$, CN, $NO_2$ and $R^9$, or a ring system selected from $C_{3-5}$ cycloalkyl, propellanyl, or a 4-6 membered saturated heterocyclyl ring, which ring system is optionally substituted by up to 3 substituents independently selected from OH, $CON(R^7R^7)$, $SO_2R^7$, $CO_2R^7$, $SONR^7R^7$, $NR^7SO_2R^7$, CN, $NO_2$, halo, $NR^7R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by 1 to 3 halogen, $O(C_{3-6}$ cycloalkyl optionally substituted by up to 3 OH and/or $C_{1-3}$ alkoxy groups, $O(C_{1-3}$ alkyl substituted by up to 3 halogen, $O(C_{1-3}$ alkyl substituted by up to 3 OH and/or $C_{1-3}$ alkoxy, $NR^7SO_2R^7$, =O, $NO_2$, $NR^7CO_2R^7$, and $S(O)R^7$ or $R^5$ and $R^6$ together with the N to which they are attached can be a 4-7 membered ring optionally including up to 2 further ring hetero-atoms independently selected from N, O, S, which ring is optionally substituted by $C_{1-3}$ alkoxy and/or $C_{1-3}$ alkyl;

$R^7$ is H, $C_{1-5}$ alkyl or $C_{1-5}$ alkoxy, which $C_{1-5}$ alkyl or $C_{1-5}$ alkoxy is optionally substituted by up to 3 substituents independently selected from halogen;

$R^8$ is a is a ring system which is a 3-7 membered monocyclic carbocyclic or heterocyclic system, or an 8-14-membered bicyclic system, which ring system may be saturated or partially or fully unsaturated, wherein the heterocyclic ring system may have up to 5 ring hetero-atoms selected from N, S, and O, wherein the bicyclic ring system can be 2 rings (carbocyclic-carbocyclic, carbocyclic-heterocyclic, heterocyclic-carbocyclic or heterocyclic-heterocyclic) fused or linked by a single bond, which ring system is optionally substituted by up to 3 substituents independently selected from, where possible— halo, CN, $NR^5R^6$, $SO_2R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by 1 to 3 halogen, OH, $O(C_{1-3}$ alkyl), $O(C_{3-6}$ cycloalkyl optionally substituted by up to 3 OH and/or $C_{1-3}$ alkoxy groups, $O(C_{1-3}$ alkyl substituted by up to 3 halogen, $O(C_{1-3}$ alkyl substituted by up to 3 OH and/or $C_{1-3}$ alkoxy, $NR^5SO_2R^7$, =O, $NO_2$, $NR^7COR^7$, $NR^5CO_2R^7$, and $S(O)R^7$;

$R^9$ is a is a ring system which is a 3-7 membered monocyclic carbocyclic or heterocyclic system, or an 8-14-membered bicyclic system, which ring system may be saturated or partially or fully unsaturated, wherein the heterocyclic ring system may have up to 5 ring hetero-atoms selected from N, S, and O, wherein the bicyclic ring system can be 2 rings (carbocyclic-carbocyclic, carbocyclic-heterocyclic, heterocyclic-carbocyclic or heterocyclic-heterocyclic) fused or linked by a single bond, which ring system is optionally substituted by up to 3 substituents independently selected from, where possible— halo, CN, $NR^7R^7$, $SO_2R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by 1 to 3 halogen, OH, $O(C_{1-3}$ alkyl), $O(C_{3-6}$ cycloalkyl optionally substituted by up to 3 OH and/or $C_{1-3}$ alkoxy groups, $O(C_{1-3}$ alkyl substituted by up to 3 halogen, $O(C_{1-3}$ alkyl substituted by up to 3 OH and/or $C_{1-3}$ alkoxy, $NR^7SO_2R^7$, =O, $NO_2$, $NR^7CO_2R^7$, $NR^7COR^7$, and $S(O)R^7$;

wherein each CH moiety can be replaced by a CF moiety.

Embodiment 2 of the invention is a compound or salt according to embodiment 1 wherein $R^1$ is H, $C_{1-5}$ alkyl optionally substituted by up to 2 OH, or $R^1$ is $C_{1-5}$ alkyl substituted by $CONH_2$, $CONHCH_3$, $CON(CH_3)_2$, $CO_2H$, $CO_2CH_3$, $OCH_3$, $SCH_3$, $SO_2CH_3$, or $R^1$ is a ring system selected from $C_{3-5}$ cycloalkyl, propellanyl, or oxetanyl, which ring system is optionally substituted by methyl, OH or $CH_2OH$.

Embodiment 3 of the invention is a compound or salt according to any one of embodiments 1 or 2 wherein $R^1$ is t-butyl, hydroxy-t-butyl, dihdyroxy-t-butyl, 1-hydroxyprop-2-yl or 1,3-dihydroxyprop-2-yl.

Embodiment 4 of the invention is a compound or salt according to any one of embodiments 1 to 3 wherein $R^2$ is H.

Embodiment 5 of the invention is a compound or salt according to any one of embodiments 1 to 4 wherein $R^3$ is H or $NH_2$.

Embodiment 6 of the invention is a compound or salt according to any one of embodiments 1 to 5 wherein $R^3$ is $NH_2$.

Embodiment 7 of the invention is a compound or salt according to any one of embodiments 1 to 5 wherein $R^3$ is H.

Embodiment 8 of the invention is a compound or salt according to any one of embodiments 1 to 7 wherein $R^{101}$ is H.

Embodiment 9 of the invention is a compound or salt according to any one of embodiments 1 to 7 wherein $R^{101}$ is OH.

Embodiment 10 of the invention is a compound or salt according to any one of embodiments 1 to 9 wherein X is a bond, O, $CH_2$, $C_2H_4$, $CH(CH_3)CH_2$, $CH(CH_3)$, $CH(CH_2OH)$, $CH_2O$, $CH(NH_2)$, $CH(OH)$ or NH.

Embodiment 11 of the invention is a compound or salt according to any one of embodiments 1 to 10 wherein X is $CH_2$.

Embodiment 12 of the invention is a compound or salt according to any one of embodiments 1 to 11 wherein $R^{102}$ is an optionally substituted nitrogen-containing ring system which is linked to the X moiety via a nitrogen ring atom.

Embodiment 13 of the invention is a compound or salt according to any one of embodiments 1 to 11 wherein $R^{102}$ is an optionally substituted ring system where the ring system is selected from— benzimidazolyl, benzisoxazolyl, benzofuranyl, benzoxazolyl, benzotriazolyl, biphenyl, bipyrazolyl, cinnolinyl, cyclobutylimidazolyl, cyclobutylpyrazolyl, cyclobutylthiazolyl, cyclopentyltriazolyl, cyclopropylisoxazolyl, cyclopropyloxazolyl, cyclopropylpyrazolyl, cyclopropyltriazolyl, diazirenylphenyl, dihydronaphthyridinyl, dihydropyrrolopyrazolyl, dioxinopyridinyl, furazanyl, furopyridinyl, furopyrrolyl, imidazolyl, imidazopyrazinyl, imidazopyridazinyl, imidazopyridinyl, imidazopyrimidinyl, imidazothiadiazolyl, imidazothiazolyl, indanyl, indazolyl, indolyl, isoindolyl, isoxazolopyridinyl, isoxazolyl, isoquinolinyl, naphthyridinyl, oxazolyl, phenyl, phenylcyclopropyl, phenylimidazolyl, phenylpyrazolyl, phenylpyrrolyl, phenyltetrazolyl, phthalazinyl, purinyl, pyrazinyl, pyrazolyl, pyrazolopyridinyl, pyrazolopyrimidinyl, pyrazolotriazinyl, pyridinyl, pyridazinyl, pyridinyltriazolyl, pyrimidinyl, pyrroloimidazolyl, pyrrolopyrazinyl, pyrrolopyrimidinyl, pyrrolopyridinyl, pyrrolyl, quinolinyl, quinazolyl, quinoxalinyl, tetrahydrobenzisoxazolyl, tetrahydrocyclopentapyrazolyl, tetrahydrotriazolopyridinyl, tetrazolopyridazinyl, tetrazolopyridinyl, thiazolyl, thiazolopyridinyl, thiazolopyrimidinyl, thienylpyrazolyl, thienopyridinyl, triazolopyridinyl and triazolyl, Embodiment 14 of the invention is a compound or salt according to embodiment 13 where the optional substituents are independently selected from, where possible— halo, methyl, ethyl, propyl, isopropyl, cyclopropyl, $CF_3$, $CHF_2$, $CH_2F$, $CH_2OCH_3$, $CN$, $CH_2OH$, $OCH_3$, =O, $NH_2$, $SCH_3$, $SO_2CH_3$, phenoxy, fluorophenoxy, benzyl, $SCF_3$, $OCF_3$, $SO_2CF_3$, $NHSO_2CH_3$, $NHSO_2CF_3$, $C(O)CF_3$, $C(O)CH_3$, benzoyl, azetidinylmethyl, fluoroazetidinylmethyl and morpholinomethyl.

Embodiment 15 of the invention is a compound or salt according to any one of embodiments 1 to 11, 13 or 14, wherein $R^{102}$ is selected from phenyl, pyrazol-1-yl, 1,2,3-triazol-1-yl, benzotriazol-2-yl, pyridin-2-yl, pyridin-3-yl and pyridin-4-yl, each of which is optionally substituted by halo, methyl, ethyl, propyl, isopropyl, cyclopropyl, $CF_3$, $CHF_2$, $CH_2F$, $CH_2OCH_3$, $CN$, $CH_2OH$, $OCH_3$, =O, $NH_2$, $SCH_3$, $SO_2CH_3$, phenoxy, fluorophenoxy, benzyl, $SCF_3$, $OCF_3$, $SO_2CF_3$, $NHSO_2CH_3$, $NHSO_2CF_3$, $C(O)CF_3$, $C(O)CH_3$, benzoyl, azetidinylmethyl, fluoroazetidinylmethyl and/or morpholinomethyl.

Embodiment 16 of the invention is a compound or salt according to any one of embodiments 1 to 15 with $R^5$ and $R^6$ groups present, wherein $R^5$ and $R^6$ are each independently H, $C_{1-3}$ alkyl optionally substituted by $C_{1-3}$ alkoxy, $C_{3-5}$ cycloalkyl, propellanyl, oxetanyl, tetrahydrofuranyl or pyranyl, or $R^5$ and $R^6$ together with the N to which they are attached can be an azetidine, pyrrolidine, piperidine, piperazine or morpholine ring, which ring is optionally substituted by $C_{1-3}$ alkoxy and/or $C_{1-3}$ alkyl.

Embodiment 17 of the invention is a compound according to embodiment 1 of the Formula (IA):

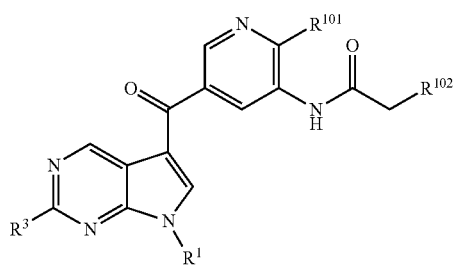

(IA)

or a pharmaceutically acceptable salt thereof, wherein
$R^3$ is H or $NH_2$;
$R^1$ is $C_{2-4}$ alkyl optionally substituted by 1 or 2 OH groups;
$R^{101}$ is H or OH;
and $R^{102}$ is phenyl or an aromatic or partially unsaturated 5- or 6-membered heterocycle, which heterocycle is optionally fused to a further phenyl or 5-7 membered aromatic or partially unsaturated heterocyclic ring, wherein each heterocycle has from 1 to 3 ring heteroatoms selected from N, O and S,
and which ring system is optionally substituted by up to 3 substituents independently selected from
halo, $CF_3$, $C_{1-4}$ alkyl and $C_{3-5}$ cycloalkyl.

Embodiment 18 of the invention is a compound or salt according to embodiment 17 wherein $R^{101}$ is H.

Embodiment 19 of the invention is a compound or salt according to embodiment 18 wherein $R^1$ is t-butyl, hydroxy-t-butyl or 1-hydroxyprop-2-yl;
and $R^{102}$ is 4-trifluoromethylphenyl, 4-chlorophenyl, 2,4-difluorophenyl, 5-chloropyridin-2-yl, 5-fluoropyridin-2-yl, 3-trifluoromethylpyrazolyl-1-yl, 4-trifluoromethylpyrazol-1-yl, 3-trifluoromethyl-5-methylpyrazol-1-yl, 3-cyclopropylpyrazol-1-yl, 4-cyclopropylpyrazol-1-yl, 4-trifluoromethyl (1,2,3-triazol-1-yl), 4-cyclopropyl-(1,2,3-triazol-1-yl), or benzotriazol-2-yl.

Embodiment 20 of the invention is a compound according to embodiment 1, selected from:
N-(5-{[2-amino-7-(2-hydroxy-1,1-dimethylethyl)-7H-pyrrolo[2,3-d]pyrimidin-5-yl]carbonyl}pyridin-3-yl)-2-[4-(trifluoromethyl)phenyl]acetamide;
N-(5-{[2-amino-7-(2-hydroxy-1,1-dimethylethyl)-7H-pyrrolo[2,3-d]pyrimidin-5-yl]carbonyl}pyridin-3-yl)-2-(4-chlorophenyl)acetamide;
N-(5-{[2-amino-7-(2-hydroxy-1,1-dimethylethyl)-7H-pyrrolo[2,3-d]pyrimidin-5-yl]carbonyl}pyridin-3-yl)-2-(5-fluoropyridin-2-yl)acetamide;
N-(5-{[2-amino-7-(2-hydroxy-1,1-dimethylethyl)-7H-pyrrolo[2,3-d]pyrimidin-5-yl]carbonyl}pyridin-3-yl)-2-[3-(trifluoromethyl)-1H-pyrazol-1-yl]acetamide;
N-(5-{[2-amino-7-(2-hydroxy-1,1-dimethylethyl)-7H-pyrrolo[2,3-d]pyrimidin-5-yl]carbonyl}pyridin-3-yl)-2-(3-cyclopropyl-1H-pyrazol-1-yl)acetamide;
N-{5-[(2-amino-7-tert-butyl-7H-pyrrolo[2,3-d]pyrimidin-5-yl)carbonyl]pyridin-3-yl}-2-(4-cyclopropyl-1H-1,2,3-triazol-1-yl)acetamide;
N-{5-[(2-amino-7-tert-butyl-7H-pyrrolo[2,3-d]pyrimidin-5-yl)carbonyl]pyridin-3-yl}-2-[4-(trifluoromethyl)-1H-pyrazol-1-yl]acetamide;
N-{5-[(2-amino-7-tert-butyl-7H-pyrrolo[2,3-d]pyrimidin-5-yl)carbonyl]pyridin-3-yl}-2-[4-(trifluoromethyl)-1H-1,2,3-triazol-1-yl]acetamide;
N-{5-[(2-amino-7-tert-butyl-7H-pyrrolo[2,3-d]pyrimidin-5-yl)carbonyl]pyridin-3-yl}-2-(5-chloropyridin-2-yl)acetamide;
N-(5-{[2-Amino-7-(2-hydroxy-1,1-dimethylethyl)-7H-pyrrolo[2,3-d]pyrimidin-5-yl]carbonyl}pyridin-3-yl)-2-(5-chloropyridin-2-yl)acetamide;
N-{5-[(7-tert-butyl-7H-pyrrolo[2,3-d]pyrimidin-5-yl)carbonyl]pyridin-3-yl}-2-[4-(trifluoromethyl)-1H-1,2,3-triazol-1-yl]acetamide;
2-(4-chlorophenyl)-N-[5-({7-[(1S)-2-hydroxy-1-methylethyl]-7H-pyrrolo[2,3-d]pyrimidin-5-yl}carbonyl)pyridin-3-yl]acetamide
N-{5-[(7-tert-butyl-7H-pyrrolo[2,3-d]pyrimidin-5-yl)carbonyl]pyridin-3-yl}-2-[4-(trifluoromethyl)-1H-pyrazol-1-yl]acetamide;
N-[5-({7-[(1S)-2-Hydroxy-1-methylethyl]-7H-pyrrolo[2,3-d]pyrimidin-5-yl}carbonyl)pyridin-3-yl]-2-[4-(trifluoromethyl)phenyl]acetamide;
N-[5-({7-[(1R)-2-hydroxy-1-methylethyl]-7H-pyrrolo[2,3-d]pyrimidin-5-yl}carbonyl)pyridin-3-yl]-2-[4-(trifluoromethyl)phenyl]acetamide;
2-(4-chlorophenyl)-N-[5-({7-[(1R)-2-hydroxy-1-methylethyl]-7H-pyrrolo[2,3-d]pyrimidin-5-yl}carbonyl)pyridin-3-yl]acetamide;
N-(5-{[7-(2-hydroxy-1,1-dimethylethyl)-7H-pyrrolo[2,3-d]pyrimidin-5-yl]carbonyl}pyridin-3-yl)-2-[5-methyl-3-(trifluoromethyl)-1H-pyrazol-1-yl]acetamide;
2-(5-chloropyridin-2-yl)-N-(5-{[7-(2-hydroxy-1,1-dimethylethyl)-7H-pyrrolo[2,3-d]pyrimidin-5-yl]carbonyl}pyridin-3-yl)acetamide;
N-(5-{[2-Amino-7-(2-hydroxy-1-methylethyl)-7H-pyrrolo[2,3-d]pyrimidin-5-yl]carbonyl}pyridin-3-yl)-2-(4-chlorophenyl)acetamide;

N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)phenyl]acetamide;

N-(5-{[2-amino-7-(2-hydroxy-1-methylethyl)-7H-pyrrolo[2,3-d]pyrimidin-5-yl]carbonyl}pyridin-3-yl)-2-(4-chlorophenyl)acetamide;

N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)phenyl]acetamide;

N-(5-{[2-Amino-7-(2-hydroxy-1,1-dimethylethyl)-7H-pyrrolo[2,3-d]pyrimidin-5-yl]carbonyl}pyridin-3-yl)-2-[5-methyl-3-(trifluoromethyl)-1H-pyrazol-1-yl]acetamide; and N-{5-[(7-tert-butyl-7H-pyrrolo[2,3-d]pyrimidin-5-yl)carbonyl]pyridin-3-yl}-2-(4-cyclopropyl-1H-1,2,3-triazol-1-yl)acetamide;

or a pharmaceutically acceptable salt thereof.

Embodiment 21 of the invention is a pharmaceutical composition comprising a compound of the formula (I) or a pharmaceutically acceptable salt thereof, as defined in any one of the preceding embodiments 1 to 20, and a pharmaceutically acceptable carrier.

Embodiment 22 of the invention is a compound of the formula (I) or a pharmaceutically acceptable salt thereof, as defined in any one of embodiments 1 to 20, for use as a medicament.

Embodiment 23 of the invention is a compound of formula (I) or a pharmaceutically acceptable salt thereof, as defined in any one of embodiments 1 to 20 for use in the treatment of a disease for which an Trk receptor antagonist is indicated Embodiment 24 of the invention is a compound of formula (I) or a pharmaceutically acceptable salt thereof, as defined in any one of embodiments 1 to 20 for use in the treatment of pain.

Embodiment 25 of the invention is the use of a compound of the formula (I) or a pharmaceutically acceptable salt or composition thereof, as defined in any one of embodiments 1 to 20, for the manufacture of a medicament to treat a disease for which a Trk receptor antagonist is indicated Embodiment 26 of the invention is the use of a compound of the formula (I) or a pharmaceutically acceptable salt or composition thereof, as defined in any one of embodiments 1 to 20, for the manufacture of a medicament to treat pain.

Embodiment 27 of the invention is a method of treatment of a mammal, particularly a human, to treat a disease for which an Trk receptor antagonist is indicated, comprising treating said mammal with a therapeutically effective amount of a compound of the formula (I) or a pharmaceutically acceptable salt thereof, as defined in any one of embodiments 1 to 20.

Embodiment 28 of the invention is a method of treatment of pain in a mammal, particularly a human, comprising treating said mammal with a therapeutically effective amount of a compound of the formula (I) or a pharmaceutically acceptable salt thereof, as defined in any one of embodiments 1 to 20.

Embodiment 29 of the invention is compound or salt according to any one of embodiments 1 to 20 for use in a medical treatment in combination with a further drug substance.

Further embodiments of the invention include:

Compounds or salts of formula (I) where $R^1$ has a value as exemplified in the Examples below;

Compounds or salts of formula (I) where X has a value as exemplified in the Examples below;

Compounds or salts of formula (I) where $R^{102}$ has a value as exemplified in the Examples below;

Compounds or salts of formula (I) where $R^1$, $R^2$, $R^3$, $R^{101}$, X and $R^{102}$ have a value as exemplified in the Examples below;

A compound selected from any one of the Examples below or a pharmaceutically acceptable salt thereof; and any novel intermediate compound herein disclosed.

Other embodiments may be envisaged based on the description below.

"Halogen" means a fluoro, chloro, bromo or iodo group.

"Alkyl" groups, containing the requisite number of carbon atoms, can be unbranched or branched. Examples of alkyl include methyl, ethyl, n-propyl, i-propyl, n-butyl, i-butyl, sec-butyl and t-butyl.

"Pharmaceutically acceptable salts" of the compounds of formula I include the acid addition and base addition salts (including disalts, hemisalts, etc.) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base addition salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

The compounds of the invention include compounds of formula I and salts thereof as hereinbefore defined, polymorphs, and isomers thereof (including optical, geometric and tautomeric isomers) as hereinafter defined and isotopically-labelled compounds of formula I.

Unless otherwise specified, compounds of formula (I) containing one or more asymmetric carbon atoms can exist as two or more stereoisomers. Where a compound of formula (I) contains for example, a keto or guanidine group or an aromatic moiety, tautomeric isomerism ('tautomerism') can occur. It follows that a single compound may exhibit more than one type of isomerism.

Included within the scope of the claimed compounds of the present invention are all stereoisomers, geometric isomers and tautomeric forms of the compounds of formula (I), including compounds exhibiting more than one type of isomerism, and mixtures of one or more thereof. Also included are acid addition or base addition salts wherein the counterion is optically active, for example, D-lactate or L-lysine, or racemic, for example, DL-tartrate or DL-arginine.

Examples of types of potential tautomerisms shown by the compounds of the invention include hydroxypyridine ⇔ pyridone; amide ⇔ hydroxyl-imine and keto ⇔ enol tautomersims:

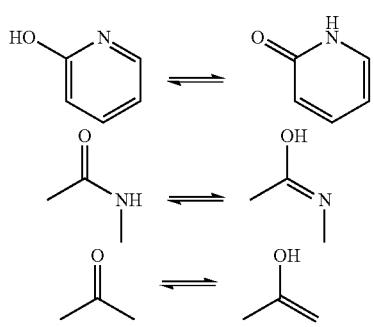

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or other derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagents in place of the non-labelled reagent previously employed.

The routes below, including those mentioned in the Examples and Preparations, illustrate methods of synthesising compounds of formula (I). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

In the general synthetic methods below, unless otherwise specified, the substituents are as defined above with reference to the compounds of formula (I) above. $R^{1011}$ is the same as $R^{101}$ or a suitably protected version thereof.

Scheme 1 illustrates the preparation of the intermediates of general formula (Int 1), where they can be made from amine (Int3) where, in those cases where $R^{1}$ contains an alcohol, a protected form of $R^{1}$ where a suitable hydroxyl protecting group (PG) is used. Any suitable oxygen protecting group may be used (as described in "Protecting Groups in Organic Synthesis" 3$^{rd}$ edition T. W. Greene and P. G. Wuts, Wiley-Interscience, 1999). Common oxygen protecting groups suitable for use herein include tert-butyldimethylsilyl (TBDMS), tetrahydropyranyl (THP) and tertbutylsilyl (TBS).

Compounds of formula (Int 1) can be prepared from compounds of formula (Int 2) as illustrated in Scheme 1.

Scheme 1

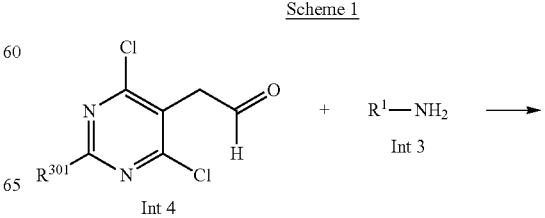

Int 4

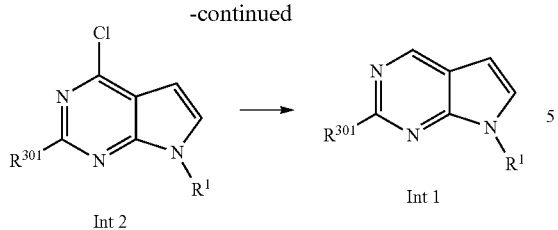

Wherein $R^{301}$ can be H or halogen, typically chlorine.

Compounds of formula (Int 1) may be prepared from amine (Int 3) and (Int4) in a cyclisation step followed by a dechlorination step. Typical conditions employed involve stirring the amine of general formula (Int 3) and the aldehyde (Int 4) together, preferably in ethanol at a temperature from room temperature up to 80° C.

e.g. as exemplified in Preps. 1-5

The intermediate chloride (Int 2) is reduced using standard literature conditions, for example hydrogenation using a suitable catalyst such as palladium on carbon and an additive such as ammonia in a suitable solvent such as ethanol. Alternatively the chloride may be removed by displacing the chloro with methane thiol followed by Raney Nickel removal of the SMe intermediate.

e.g. as exemplified in Preps. 8-13

In those cases where $R^1$ contains one or more alcohols, a protected form of $R^1$ with a suitable hydroxyl protecting group (PG) can be used. Any suitable oxygen protecting group protection/deprotection system may be used (as described in "Protecting Groups in Organic Synthesis" $3^{rd}$ edition T. W. Greene and P. G. Wuts, Wiley-Interscience, 1999). Common oxygen protecting groups suitable for use herein include tert-butyldimethylsilyl (TBDMS) and tetrahydropyranyl (THP).

Intermediates of general formula (Int 3) and (Int 4) are either commercially available or will be well-known to those skilled in the art with reference to literature precedents and/or the preparations herein.

Compounds of formula (Int 1) can be prepared from compounds of formula (Int 7) as illustrated in Scheme 2.

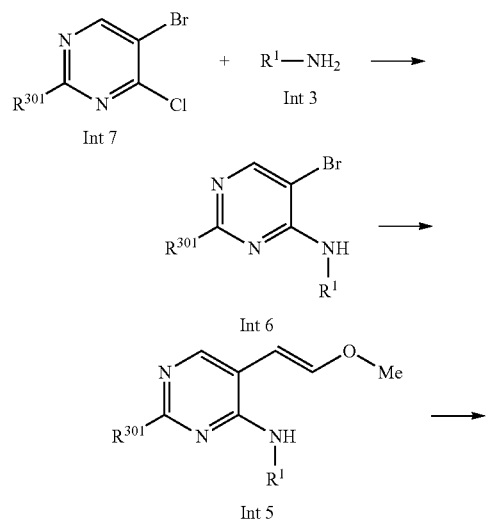

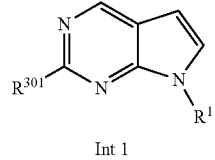

Compounds of formula (Int 1) wherein $R^3$ can be H or halogen, typically chlorine, may also be prepared from compounds of formula (Int 7) through displacement of a halogen, typically chlorine, with amines of formula (Int 3), in a palladium catalysed Suzuki reaction followed by an acidic cyclisation.

Typical conditions comprise stirring the amine of general formula (Int 3) and the intermediate of general formula (Int 7) together with a suitable base, such as triethylamine, in a solvent such as acetonitrile or dichloromethane, to provide compounds of general formula (Int 6).

The vinyl ether can be introduced by reacting intermediate (Int 6) with a suitable boronic ester and a suitable base, such as sodium hydroxide and a suitable catalyst such as tetrakis (triphenylphosphine)palladium (0) in a solvent such as THF at a temperature from room temperature up to 70° C.

Intermediates of formula (Int 1) can be made by treatment of intermediate (Int 5) with an acid such as hydrogen chloride in an organic solvent such as isopropanol at a temperature from room temperature up to 70° C.

e.g. as exemplified in Preps. 60-62

Intermediates of general formula (Int 3) and (Int 7) are either commercially available or will be well-known to those skilled in the art with reference to literature precedents and/or the preparations herein.

Compounds of formula (Int 8) can be prepared from compounds of formula (Int 1) as illustrated in Scheme 3.

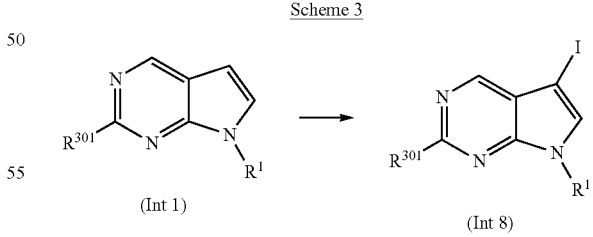

Wherein $R^{301}$ is H or halogen, typically chlorine;

Compounds of formula (Int 8) are typically prepared by iodination of the pyrrolopyrimidine intermediates (Int 1). Typical conditions employed involve stirring the intermediate of general formula (XI) with an iodinating reagent such as N-iodosuccinimide in a suitable solvent, such as DMF or acetonitrile. e.g. as exemplified in Preps. 14-19, 40, 63.

Compounds of formula (Int 8) can also be prepared from compounds of formula (Int 9) as illustrated in Scheme 4.

Scheme 4

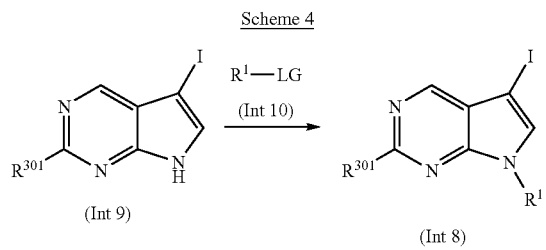

Wherein $R^{301}$ is H or halogen, typically chlorine; LG is halogen or tosylate, triflate or mesylate;

Alternatively intermediates of general formula (Int 8) can be prepared by alkylation of the pyrrolopyrimidine intermediates (Int 9), with compounds of formula (Int 10) using a suitable base such as caesium carbonate or potassium carbonate in an organic solvent. A suitable alternative is to use an additive (such as potassium iodide) as well as a base. Preferred conditions comprise cesium carbonate in DMF at room temperature.

In those cases where $R^1$ contains one or more alcohols, a protected form of $R^1$ can be used as described in Scheme 1.

E.g. as exemplified in Preparation 20.

Compounds of formula (Int 12) can be prepared from compounds of formula (Int 11) as illustrated in Scheme 5.

Wherein $R^{301}$ is H or halogen, typically chlorine;

Intermediates of general formula (Int 9) are reacted in an alkylation reaction to provide an ester intermediate (Int 11) or (Int 13), from which the ester group can be reduced and protected to furnish a compound of general formula (Int 14), where $R^{200}$ is a H or methyl group. As previously mentioned in Scheme 1 the hydroxy group can be protected with a suitable oxygen protecting group (PG), where the preferred protecting groups are TBDMS, TBS and THP.

Typical conditions employed for the alkylation involve stirring the compound of general formula (Int 9) with the appropriate halide together with a suitable base, as described in Scheme 4. Compounds of general formula (Int 11) where $R^{200}$ is H can be converted to intermediates (Int 13) where $R^{200}$ is methyl by a further alkylation, typically involving a suitable alkylating agent such as methyl iodide and a suitable base such as potassium t-butoxide in an organic solvent such as THF.

e.g. as exemplified in Preps. 20, 21, 41, 53

Reduction of the ester intermediates (Int 11) and (Int 13) can be done by using a suitable reducing reagent such as lithium borohydride, lithium aluminium hydride or diisobutylalumnium hydride in a suitable solvent such as ethanol or THF. Alternatively intermediates of general formula (Int 12) can be made in a two step reaction by hydrolysing the ester of formula (Int 11) or (Int 13) to the appropriate acid using a suitable base such as aqueous lithium hydroxide in a suitable organic solvent such as THF then activating the acid using a suitable reagent such as isobutyl chloroformate and using a suitable reducing agent such as sodium borohydride.

e.g. as exemplified in Preps. 22, 42, 43, 54

Compounds of general formula (Int 14) can be made by protection of the hydroxy group of intermediates (Int 12) with Scheme 5

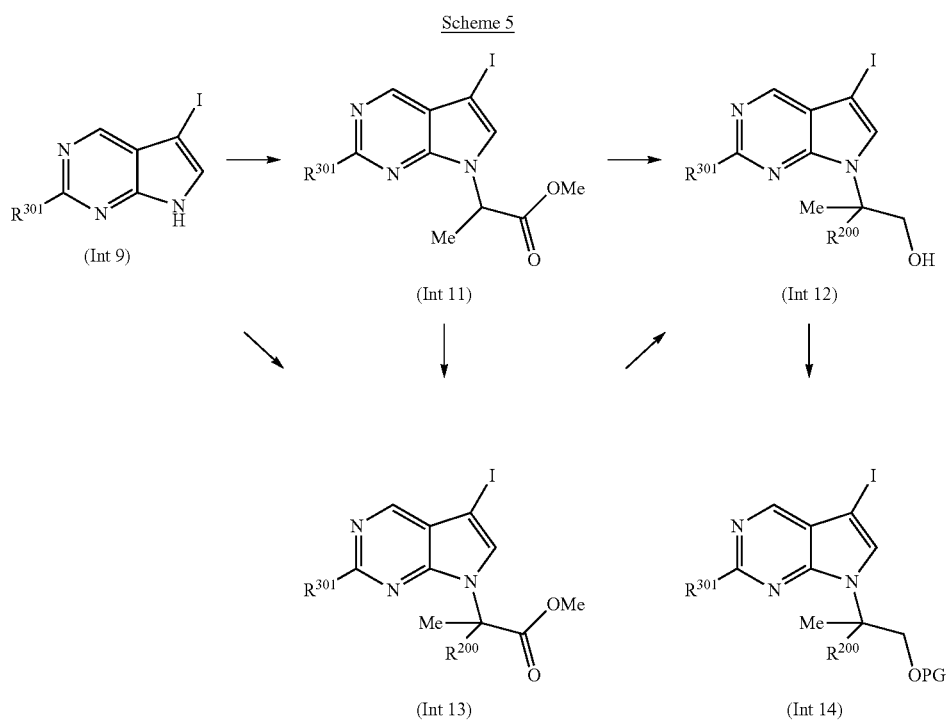

a suitable oxygen protecting group (PG), where the preferred protecting groups are TBDMS and THP, as described in Scheme 1. e.g. as exemplified in Preps. 44, 45, 55.

Compounds of formula (Int 16) can be prepared from compounds of formula (Int 8) as illustrated in Scheme 6.

Corresponding intermediates and compounds of formula (I) where $R^{101}$ is OH are considered as tautomers of pyridones and can be made using an analogous methodology using a benzyl protecting group for the Weinreb amide step, viz $R^{1011}$ is benzyloxy (OBn), e.g. as illustrated below:

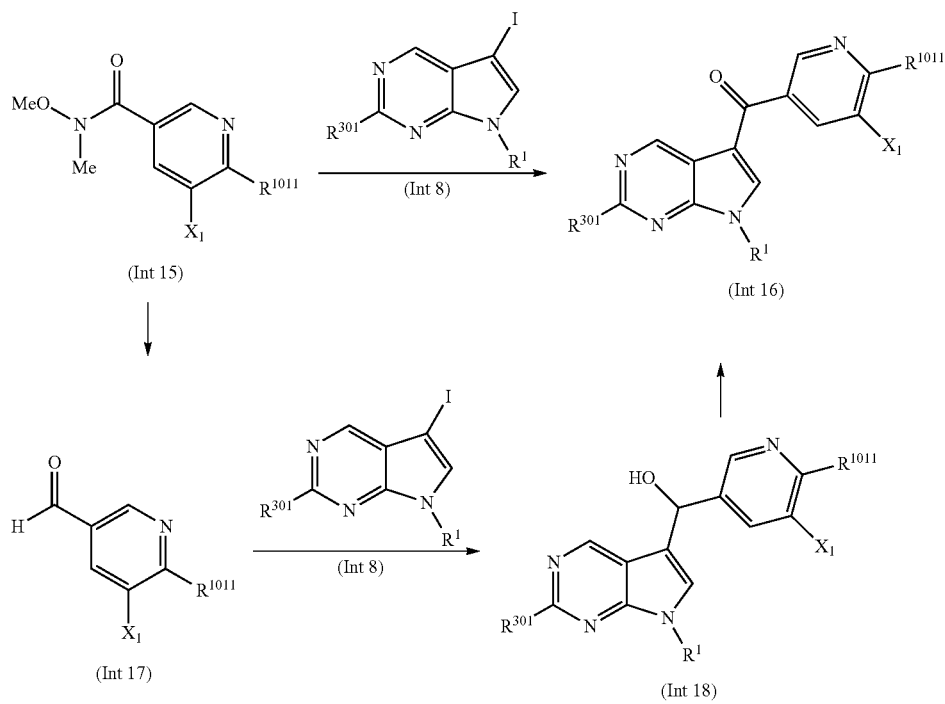

Scheme 6

(Int 15)

(Int 8)

(Int 16)

(Int 17)

(Int 8)

(Int 18)

Wherein $R^{301}$ is H or halogen, typically chlorine; and $X_1$ is a suitable halogen, typically bromine or iodine;

Compounds of formula (Int 16) can be prepared from compounds of formula (Int 8) and (Int 15) through a metallation of intermediate (Int 8) (using a suitable organometallic reagent such as butyllithium or isopropylmagnesium chloride) and reacting with the Weinreb amide intermediate (Int 15) at a temperature from −78° C. up to room temperature.

e.g. as exemplified in Preps. 26, 27, 46, 47, 56, 58, 64

Alternatively compounds of formula (Int 15) may be converted into aldehydes of formula (Int 17) by reduction of the Weinreb amide intermediate using a suitable reducing agent. Preferred conditions comprise diisopropylaluminium hydride in THF at −78° C., exemplified in Preparation 106.

Compounds of formula (Int 17) may then be reacted with compounds of formula (Int 8) according to the same metallation procedure described above. The intermediate alcohol (Int 18) may then be oxidised to the ketone (Int 16). Typical oxidation conditions involve using an oxidising reagent such as the Dess-Martin reagent in DCM or 2-iodoxybenzoic acid in a suitable solvent such as ethyl acetate at a temperature from room temperature to reflux temperature.

e.g. as exemplified in Preps. 29, 30

Intermediates of general formula (Int 15) and (Int 17) are either commercially available or will be well-known to those skilled in the art with reference to literature precedents and/or the preparations herein.

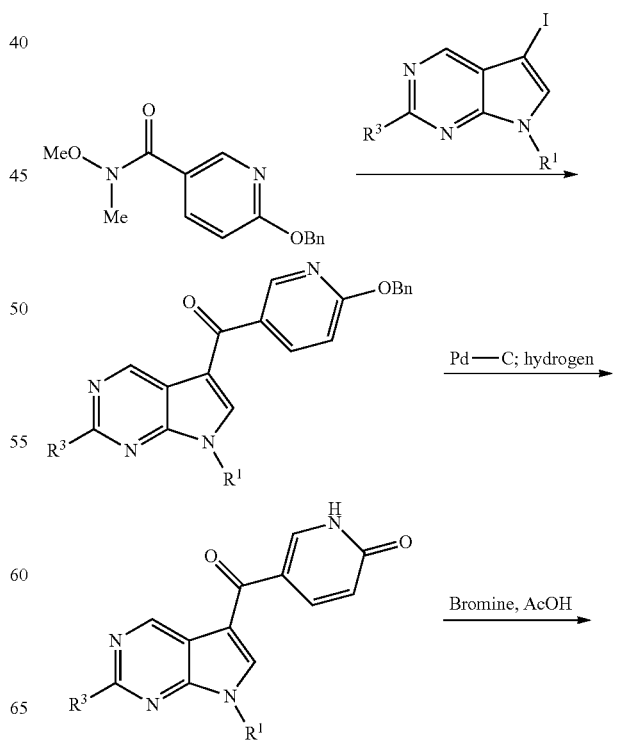

Pd—C; hydrogen

Bromine, AcOH

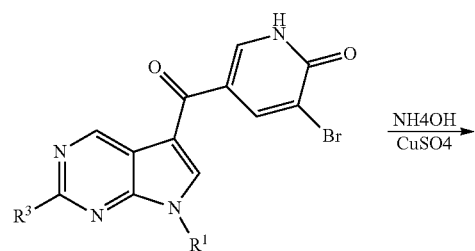

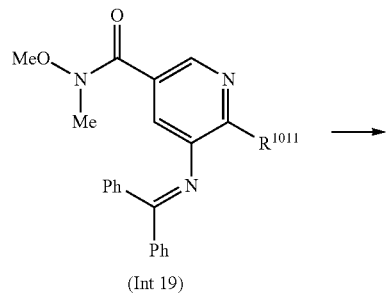

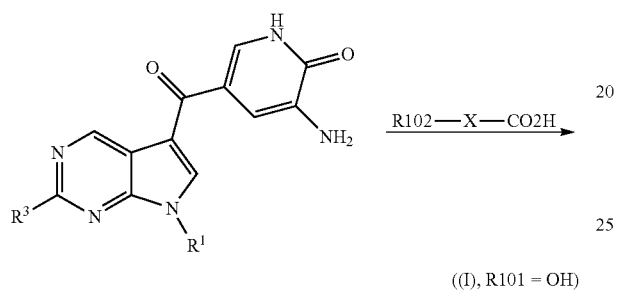

((I), R101 = OH)

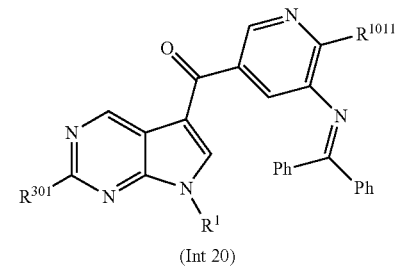

(Int 20)

Wherein $R^{301}$ is H or halogen, typically chlorine;

Compounds of formula (Int 20) may be prepared from compounds of formulae (Int 8) and (Int 19) according to a metallation procedure as described in Scheme 6 above.

Typical conditions employed involve metallation of the intermediate halide (Int 8) (using a suitable organometallic reagent such as butyllithium or isopropylmagnesium chloride) and reacting with the Weinreb amide intermediate (Int 19) at a temperature from −78° C. up to room temperature in a suitable solvent such as THF.

e.g. as exemplified in Preps. 24, 25, 28, 50

Intermediates (Int 19) will be well-known to those skilled in the art with reference to literature precedents and/or the preparations herein.

e.g. as exemplified in Prep. 23

Compounds of formula (Int 21) can be prepared from compounds of formula (Int 16) as illustrated in Scheme 8.

Compounds of formula (Int 20) can be prepared from compounds of formula (Int 8) as illustrated in Scheme 7.

Scheme 7

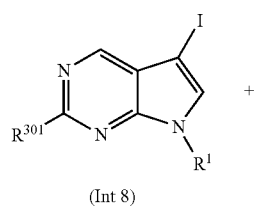

(Int 8)

Scheme 8

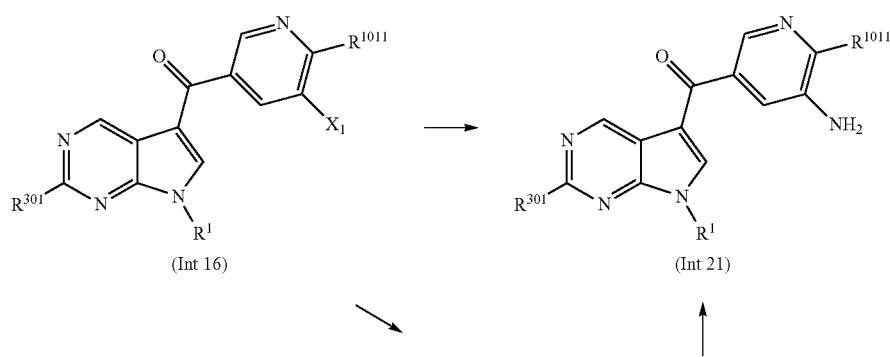

(Int 16)    (Int 21)

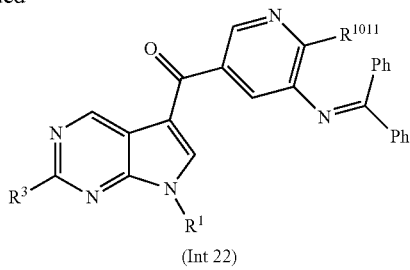

(Int 22)

Wherein $X_1$ is bromine or iodine;

Compounds of formula (Int 21) may be prepared from compounds of formula (Int 16) through direct amination of the halide using standard literature conditions. For example, amine (Int 21) is typically prepared using ammonia with a suitable copper catalyst such as copper (II) sulphate or copper (I) oxide in suitable solvent such as NMP in a sealed vessel at a temperature between room temperature and 140° C. Where $R^{301}$ is Cl this is also displaced by ammonia under the same conditions to provide amines of general formula (Int 21) where $R^3$ is $NH_2$.

e.g. as exemplified in Preps. 31, 32, 36, 48, 49, 57, 59, 65

De-protection of a hydroxyl protecting group on $R^1$ (if present) can also occur under these conditions. In these cases, either the protecting group can be reapplied as previously described in Scheme 5 or the amine of general formula (Int 21) can be used directly.

Alternatively compounds of general formula (Int 21) where $R^3$ is H, can be made by converting intermediates of general formula (Int 16) where $R^{301}$ is H, via compounds (Int 22). Typical conditions employed involve stirring the halide of general formula (Int 16), where $R^{301}$ is H, with benzophenone imine, a suitable base such as potassium phosphate, a suitable ligand such as 2-di-tert-butylphosphino-2',4',6'-tri-isopropylbiphenyl and a suitable catalyst such as tris(dibenzylideneacetone)dipalladium in an organic solvent such as 1,2-dimethoxyethane at a temperature from room temperature up to the boiling point of the solvent.

Intermediate (Int 22) can be deprotected to furnish the amines of general formula (Int 21). Typical conditions employ treatment with an aqueous acid such as hydrogen chloride or citric acid in an organic solvent such as THF.

e.g. as exemplified in Preps. 33, 37-39

Compounds of formula (Int 20) can be prepared from compounds of formula (Int 22 where $R^{301}$ is Cl) as illustrated in Scheme 9.

Scheme 9

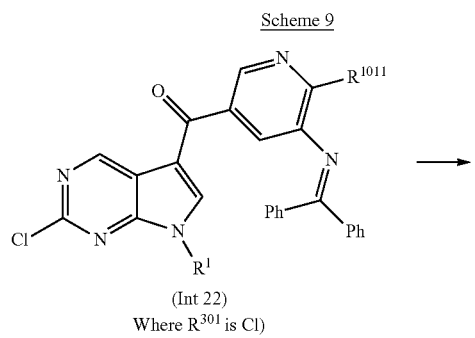

(Int 22)
Where $R^{301}$ is Cl)

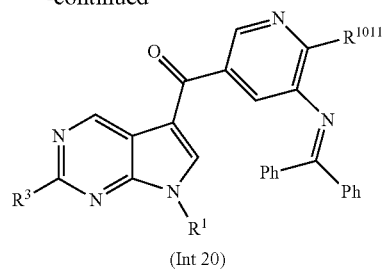

(Int 20)

Compounds of formula (Int 20) may be prepared from compounds of formula (Int 22) where $R^{301}$ is chloro through an amination reaction as described above. Wherein the chlorine is reacted with 2,4-dimethoxybenzylamine and the amine can be deprotected as previously.

Typical conditions employed involve stirring the chloropyrimidine of general formula (Int 22), where $R^{301}$ is Cl, with 2,4-dimethoxybenzylamine and a suitable additive such as 4-dimethylaminopyridine in a suitable solvent such as 1,4 dioxane at a temperature from room temperature up to reflux temperature.

e.g. as exemplified in Prep. 51

Compounds of formula (I) can be prepared from compounds of formula (Int 21) and (Int 23) as illustrated in Scheme 10.

Scheme 10

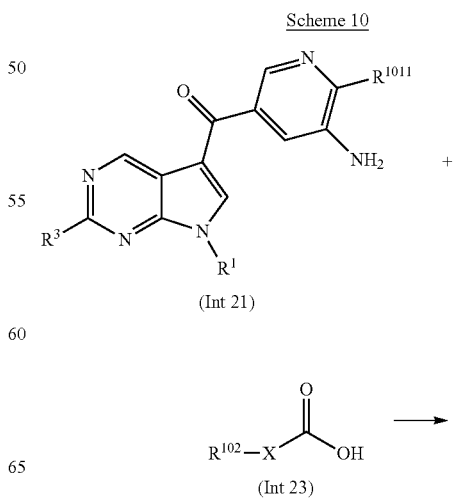

-continued

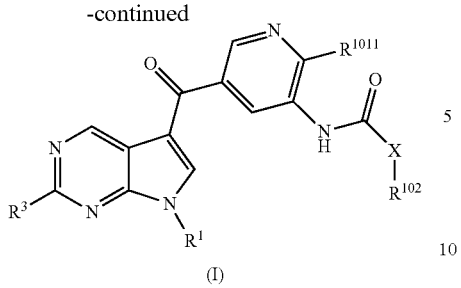

(I)

Compounds of formula (I) may be prepared from compounds of formula (Int 21) and (Int 23) via amide formation, if necessary adding a suitable base (such as DIPEA) and/or additive (such as DMAP), and a suitable solvent (such as pyridine).

Typical conditions employed involve stirring the amine of general formula (Int 21) and the acid of general formula (Int 23) together with a suitable coupling reagent such as HATU or 1-propylphosphonic acid cyclic anhydride, if necessary adding a suitable base such as NMM, DIPEA or TEA in a suitable solvent such as pyridine, THF, DMF or DMA at a temperature from room temperature up to 50° C. A suitable alternative is to use an additive (such as 4-dimethylaminopyridine) as well as a base. Any suitable solvent may be used in place of those mentioned above. At least one equivalent of the acid (Int 23) and at least one equivalent of the coupling reagent should be used and an excess of one or both may be used if desired.

e.g. as exemplified in Examples 1-8, 34-45, 48-53, 57-64, Preps. 34, 35, 52, 66-78

Where $R^1$ contains a suitable hydroxyl protecting group in intermediate (Int 21), removal of the protecting group (PG) can be done in situ or as an additional step, adding a suitable acid and organic solvent to the crude residue after the amide formation has taken place. Common protecting groups to use include TBDMS, which is readily removed by treatment with an acid such as aqueous hydrogen chloride or aqueous citric acid in an organic solvent such as THF or by treatment with a fluoride source such as tetrabutylammonium fluoride in an organic solvent such as THF, and THP, which is also readily removed by treatment with an acid such as aqueous hydrogen chloride in an organic solvent such as THF.

e.g. as exemplified in Examples 9-33, 54-56,

Intermediates of general formula (Int 23) are either commercially available or will be well-known to those skilled in the art with reference to literature precedents and/or the preparations herein.

Compounds of formula (I) where $R^3$ is $NH_2$ can be prepared from compounds of formula (Int 20) as illustrated in Scheme 11.

Scheme 11

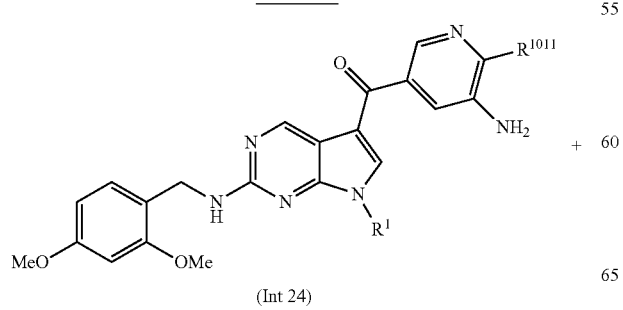

(Int 24)

+

-continued

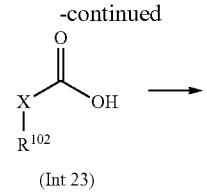

(Int 23)

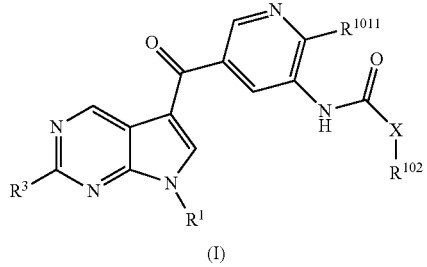

(I)

Compounds of formula (I) can be prepared from compounds of formula (Int 24) via amide bond formation as previously described in Scheme 10 followed by removal of the dimethoxbenzylamine group in situ, by adding a suitable acid and organic solvent to the crude residue after the amide formation has taken place. Suitable acids for this de-protection include hydrogen chloride or trifluoroacetic acid in an organic solvent such as THF.

e.g. as exemplified in Examples 46-47

Compounds of formula (I) where $R^2$ is methyl can be prepared from compounds of formula (I) where $R^2$ is H as illustrated in Scheme 12.

Scheme 12

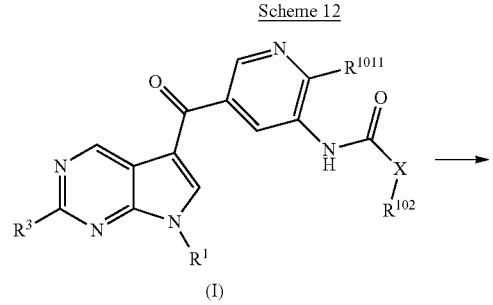

(I)

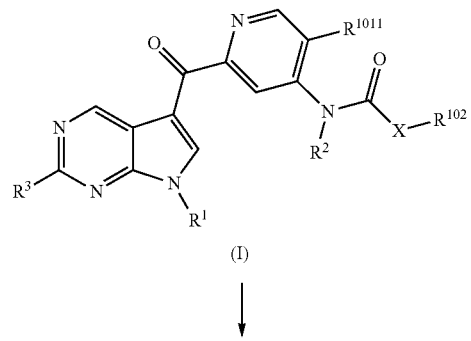

(I)

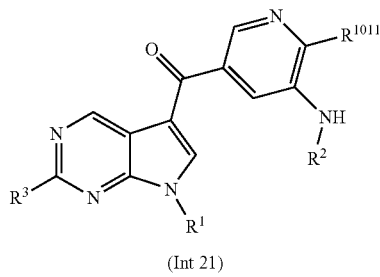

(Int 21)

Compounds of formula (I) where $R^2$ is methyl can be prepared from compounds of formula (I) where $R^2$ is H according to an alkylation reaction with methyl iodide as described in Scheme 4.

When $XR^{102}$ is boc, this can be deprotected using standard protecting group conditions to provide intermediate (Int 21).

Compounds of formula (I) where X is $NR^{104}$ can be prepared from compounds of formula (Int 21) as illustrated in Scheme 13.

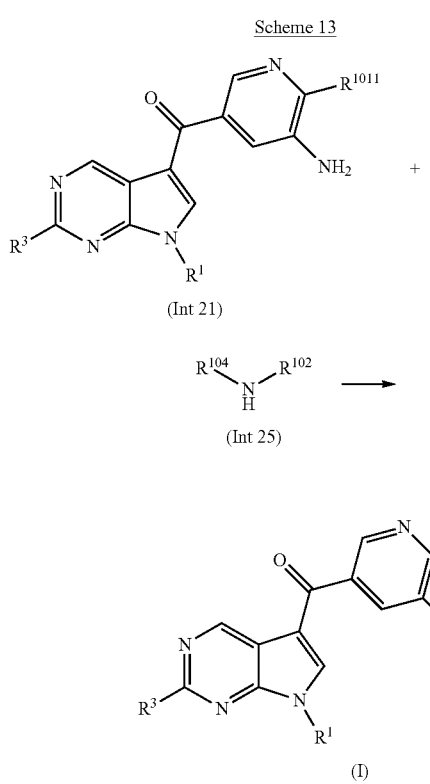

Compounds of formula (I) where X is $NR^{104}$ may be prepared from compounds of formula (Int 21), (Int 25) and phenylchloroformate. Typical conditions comprise phenyl chloroformate and compounds of formula (Int 24) with pyridine in THF from 0 to 100° C., as exemplified in Example 526.

Compounds of formula (I) where a substituent on the ring(s) of $R^{102}$ is an aminomethyl $CH_2NR_2$ group may be prepared from compounds of formula (I) as illustrated in Scheme 14.

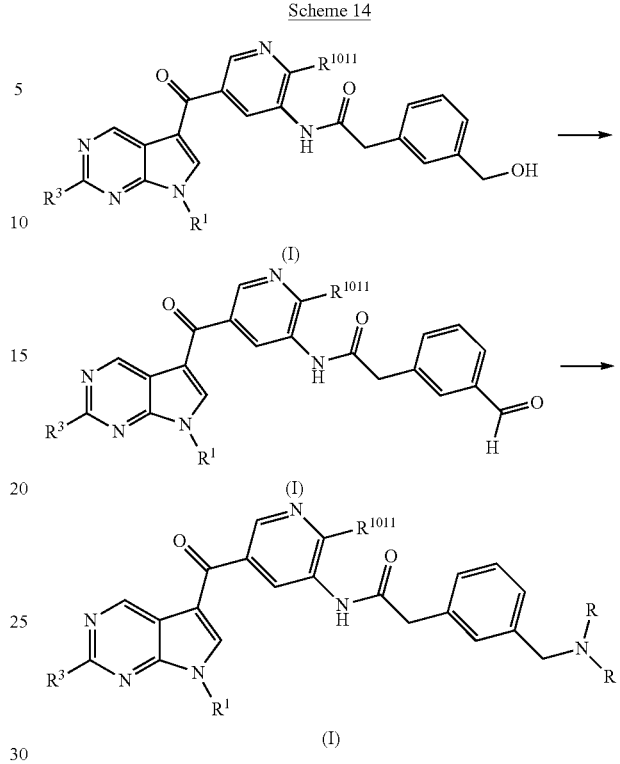

Compounds of formula (I) where a primary alcohol exists may be oxidised to the aldehyde using Dess Martin periodinane in DCM at room temperature followed by a reductive amination with a suitable amine $HNR_2$ using sodium triacetoxyborohydride and acetic acid in DCM.

Compounds of formula (Int 26) can be prepared from compounds of formula (Int 27) as illustrated in Scheme 15.

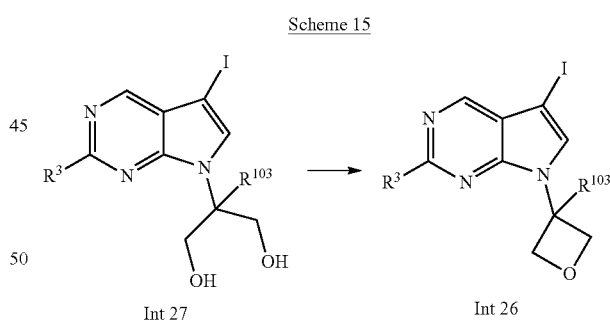

Wherein $R^{103}$ is Me or $CH_2H$;

Compounds of formula (Int 26) can be prepared from compounds of formula (Int 27) through conversion of an alcohol into a suitable leaving group followed by cyclisation under basic conditions. Preferred conditions comprise tosyl chloride with n-butyl lithium in THF.

According to a further embodiment the present invention provides novel intermediate compounds.

Pharmaceutically acceptable salts of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention intended for pharmaceutical use may be administered alone or in combination with one or more other compounds of the invention or in combination with one or more other drug agent (or as any combination thereof). Generally, they will be administered as a formulation in association with one or more pharmaceutically acceptable excipients. The term "excipient" is used herein to describe any biologically inactive ingredient other than the compounds and salts of the invention. The choice of excipient will to a large extent depend on factors such as the particular mode of administration, the effect of the excipient on solubility and stability, and the nature of the dosage form. For example, a compound of the formula I, or a pharmaceutically acceptable salt or solvate thereof, as defined above, may be administered simultaneously (e.g. as a fixed dose combination), sequentially or separately in combination with one or more other drug agent.

Exemplary additional agents could be selected from one or more of:

- a Nav1.7 channel modulator, such as a compound disclosed in WO 2009/012242 or WO2010/079443;
- an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
- an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagoinsist;
- a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene) piperidene-1-carboxamide);
- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g oxybutynin, tolterodine, propiverine, tropsium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
- a vanilloid receptor agonist (e.g. resinferatoxin) or antagonist (e.g. capsazepine);
- a beta-adrenergic such as propranolol;
- a local anaesthetic such as mexiletine;
- a corticosteroid such as dexamethasone;
- a 5-HT receptor agonist or antagonist, particularly a $5-HT_{1B/1D}$ agonist such as eletriptan, sumatriptan, naratriptan, zolmitriptan or rizatriptan;
- a $5-HT_{2A}$ receptor antagonist such as R(+)-alpha-(2,3-dimethoxy-phenyl)-1-[2-(4-fluorophenylethyl)]-4-piperidinemethanol (MDL-100907);
- a $5-HT_3$ antagonist, such as ondansetron
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, $(1\alpha,3\alpha,5\alpha)$(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504).

Pharmaceutical compositions suitable for the delivery of compounds and salts of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Compounds and salts of the invention intended for pharmaceutical use may be prepared and administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. [Make sure these specific ranges are relevant]

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration discussed above may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds and salts of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous.

Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) and salts used in the preparation of parenteral solutions may be increased by the use of appropriate formulation techniques, such as the incorporation of solubility-enhancing agents.

Formulations for parenteral administration may be formulated to be immediate and/or modified release. Thus, compounds and salts of the invention may be formulated as a solid, semi-solid, or thixotropic liquid for administration as an implanted depot providing modified release of the active compound. An example of such formulations include drug-coated stents.

Topical Administration

The compounds and salts of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated [see, for example, Finnin and Morgan, J Pharm Sci, 88 (10), 955-958 (October 1999).] Other means of topical administration include delivery by electroporation, iontophoresis, phonophoresis, sonophoresis and microneedle or needle-free (e.g. Powderject™, Bioject™, etc.) injection.

Inhaled/Intranasal Administration

The compounds and salts of the invention may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

A pressurised container, pump, spray, atomizer, or nebuliser may contain a solution or suspension of the compound(s) or salt(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound or salt of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound or salt of the invention per actuation and the actuation volume may vary from 1 μl to 100 μl. A typical formulation may comprise a compound of formula (I) or salt thereof, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by a prefilled capsule, blister or pocket or by a system that utilises a gravimetrically fed dosing chamber. Units in accordance with the invention are typically arranged to administer a metered dose or "puff" containing from 1 to 5000 μg of the compound or salt. The overall daily dose will typically be in the range 1 μg to 20 mg which may be administered in a single dose or, more usually, as divided doses throughout the day.

Rectal/Intravaginal Administration

The compounds and salts of the invention may be administered rectally or vaginally, for example, in the form of a suppository, pessary, or enema. Cocoa butter is a traditional suppository base, but various well known alternatives may be used as appropriate.

Ocular and Aural Administration

The compounds and salts of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gelan gum, may be incorporated together with a preservative, such as benzalkonium chloride. Such formulations may also be delivered by iontophoresis.

Other Technologies

The compounds and salts of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds and salts of the invention is typically in the range 0.1 mg to 200 mg depending, of course, on the mode of administration, preferred in the range 1 mg to 100 mg and more preferred in the range 1 mg to 50 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the above-mentioned therapeutic uses, the dosage administered will, of course, vary with the compound or salt employed, the mode of administration, the treatment desired and the disorder indicated. The total daily dosage of the compound of formula (I)/salt/solvate (active ingredient) will, generally, be in the range from 1 mg to 1 gram, preferably 1 mg to 250 mg, more preferably 10 mg to 100 mg. The total daily dose may be administered in single or divided doses. The present invention also encompasses sustained release compositions.

The pharmaceutical composition may, for example, be in a form suitable for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

For parenteral dosages, this may conveniently be prepared as a solution or as a dry powder requiring dissolution by a pharmacist, medical practitioner or the patient. It may be provided in a bottle or sterile syringe. For example it may be provided as a powder in a multicompartment syringe which allows the dry powder and solvent to be mixed just prior to administration (to aid long-term stability and storage). Syringes could be used which allow multiple doses to be administered from a single device.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems.

Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J.

R. Robinson, ed., Marcel Dekker, Inc., New York, (1978). Pharmaceutical compositions are preferably manufactured under GMP conditions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The precise dosage administered of each active ingredient will vary depending upon any number of factors, including but not limited to, the type of animal and type of disease state being treated, the age of the animal, and the route(s) of administration.

The following non-limiting Preparations and Examples illustrate the preparation of compounds and salts of the present invention.

GENERAL EXPERIMENTAL

The Preparations and Examples that follow illustrate the invention but do not limit the invention in any way. All starting materials are available commercially or described in the literature. All temperatures are in ° C. Flash column chromatography was carried out using Merck silica gel 60 (9385). Thin layer chromatography (TLC) was carried out on Merck silica gel 60 plates (5729). "$R_f$" represents the distance traveled by a compound divided by the distance traveled by the solvent front on a TLC plate. Melting points were determined using a Gallenkamp MPD350 apparatus and are uncorrected. NMR was carried out using a Varian-Unity Inova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCI mass spectrometer.

Where it is stated that compounds were prepared in the manner described for an earlier Preparation or Example, the skilled person will appreciate that reaction times, number of equivalents of reagents and reaction temperatures may be modified for each specific reaction, and that it may nevertheless be necessary or desirable to employ different work-up or purification conditions.

The invention is illustrated by the following non-limiting examples in which the following abbreviations and definitions are used:

The Preparations and Examples that follow illustrate the invention but do not limit the invention in any way. All starting materials are available commercially or described in the literature. All temperature are in ° C. Flash column chromatography was carried out using Merck silica gel 60 (9385) or Redisep silica. NMR was carried out using a Varian Mercury 400 MHz NMR spectrometer or a Jeol ECX 400 MHz NMR.

The mass spectra were obtained using:
Waters ZQ ESCI
Applied Biosystem's API-2000 5 min LC-MS
Waters Alliance 2795 with ZQ2000 (ESI)
Aglient 110 HPLC 5 min (System 5)
Waters ZQ ESCI 8 min LC-MS
Waters Alliance 2695 with ZQ2000 (ESI) 25 min
HP 1100 HPLC with Waters Micromass ZQ mass detector 12.5 min LC-MS
HPLC mass spectra were obtained using a Waters Acquity ZQD (ESI) 1.5 min LC-MS
WATERS ACQUITY HPLC/WATERS 3100 MSD/PL-ELS 2100 ICE ELSD Where singleton compounds have been analysed by LCMS, there are six methods used. These are illustrated below.

System 1
6 minute LC-MS gradient and instrument conditions
A: 0.1% formic acid in water
B: 0.1% formic acid in acetonitrile
Column: C18 phase Waters Sunfire 50×4.6 mm with 5 micron particle size
Gradient: 95-5% A over 3 min, 1 min hold, 2 min re-equilibration, 1.5 mL/min flow rate
UV: 210 nm-450 nm DAD
Temperature: 50° C.

System 2
2 minute LC-MS gradient and instrument conditions
A: 0.1% formic acid in water
B: 0.1% formic acid in acetonitrile
Column: C18 phase Phenomenex 20×4.0 mm with 3 micron particle size
Gradient: 70-2% A over 1.5 min, 0.3 min hold, 0.2 re-equilbration, 1.8 mL/min flow rate
UV: 210 nm-450 nm DAD
Temperature: 75° C.

System 3
5 minute LC-MS gradient and instrument conditions
A: 0.1% formic acid in water
B: 0.1% formic acid in acetonitrile
Column: C18 phase Waters Sunfire 50×4.6 mm with 5 micron particle size
Gradient: 95-5% A over 3 min, 1 min hold, 1 min re-equilibration, 1.5 mL/min flow rate
UV: 225 nm-ELSD-MS
Temperature: ambient System 4
5 minute LC-MS gradient and instrument conditions
A: 0.1% ammonium hydroxide in water
B: 0.1% ammonium hydroxide in acetonitrile
Column: C18 phase XTerra 50×4.6 mm with 5 micron particle size
Gradient: 95-5% A over 3 min, 1 min hold, 1 min re-equilibration, 1.5 mL/min flow rate
UV: 225 nm-ELSD-MS
Temperature: ambient System 5
5 minute LC-MS gradient and instrument conditions
A: 0.0375% TFA in water
B: 0.01875% TFA in acetonitrile
Column: C18 phase Welch XB 50×2.1 mm with 5 micron particle size
Gradient: 99-0% A over 4 min, 0.70 min re-equilibration, 0.8 mL/min flow rate
UV: 225 nm-ELSD-MS
Temperature: 50° C.

System 6
5 minute LC-MS gradient and instrument conditions

A: 0.0375% TFA in water
B: 0.01875% TFA in acetonitrile
Column: C18 phase Welch XB 50×2.1 mm with 5 micron particle size
Gradient: 90-0% A over 4 min, 0.70 min re-equilibration, 0.8 mL/min flow rate
UV: 225 nm-ELSD-MS
Temperature: 50° C.
System 7
25 minute LC-MS gradient and instrument conditions
A: 10 mmol ammonium bicarbonate in water
B: acetonitrile
Column: C18 phase XBridge 150×3.0 mm with 5 micron particle size
Gradient: 95-5% A over 15 min, 10 min hold, 2 min re-equilibration, 0.5 mL/min flow rate
UV: 200 nm-350 nm DAD
Temperature: 30° C.
System 8
3 minute LC-MS gradient and instrument conditions
A: 0.05% formic acid in water
B: acetonitrile
Column: C18 phase Restek 30×2.1 mm with 3 micron particle size
Gradient: 98-2% A over 2 min, 0.25 min hold, 0.75 min re-equilibration, 1.5 mL/min flow rate
UV: 200 nm-350 nm DAD
Temperature: 50° C.
System 9
5 minute LC-MS gradient and instrument conditions
A: 0.05% formic acid in water
B: acetonitrile
Column: C18 phase XBridge 50×4.6 mm with 5 micron particle size
Gradient: 90-10% A over 3 min, 1 min hold, 1 min re-equilibration, 1.2 mL/min flow rate
UV: 200 nm-260 nm DAD
Temperature: 25° C.
System 10
5 minute LC-MS gradient and instrument conditions
A: 10 mM ammonium acetate in water
B: acetonitrile
Column: C18 phase Gemini NX 50×4.6 mm with 5 micron particle size
Gradient: 90-10% A over 3 min, 1 min hold, 1 min re-equilibration, 1.2 mL/min flow rate
UV: 200 nm-260 nm DAD
Temperature: 25° C.
Where singleton compounds have been purified by High Performance Liquid Chromatography, unless otherwise stated, one of four methods were used, and these are shown below.
Waters Purification Systems with mass spec or UV detection
Prep System 1
10 minute prep LC-MS gradient and instrument conditions
A: 0.1% formic acid in water
B: 0.1% formic acid in acetonitrile
Column: C18 phase Sunfire 100×19.0 mm
Gradient: 95-2% A over 7 min, 2 min hold, 1 min re-equilibration, 18 mL/min flow rate
Temperature: ambient
Prep System 2
10 minute prep LC-MS gradient and instrument conditions
A: 0.1% DEA in water
B: 0.1% DEA in acetonitrile
Column: C18 phase Xterra 100×19.0 mm
Gradient: 95-2% A over 7 min, 2 min hold, 1 min re-equilibration, 18 mL/min flow rate
Temperature: ambient
Prep System 3
7 minute prep LC-MS gradient and instrument conditions
A: 0.05% ammonia in water
B: acetonitrile
Column: C18 phase Xbridge 50×19.0 mm
Gradient: 90-20% A over 7 min, 20 mL/min flow rate
Temperature: ambient
Prep System 4
8 minute prep LC-MS gradient and instrument conditions
A: 0.1% TFA in water
B: acetonitrile
Column: C18 phase Sepax BR 100×21.2 mm
Gradient: 96-33% A over 8 min, 30 mL/min flow rate
Temperature: ambient Where it is stated that compounds were prepared in the manner described for an earlier Preparation or Example, the skilled person will appreciate that reaction times, number of equivalents of reagents and reaction temperatures may have been modified for each specific reaction, and that it may nevertheless be necessary, or desirable, to employ different work-up or purification conditions. The invention is illustrated by the following non-limiting Examples in which the following abbreviations and definitions are used: AcOH—acetic acid; APCI—atmospheric pressure chemical ionization; Arbocel is a filter agent; br s—broad singlet; BINAP—2,2'-bis(diphenylphosphino)-1,1'-binapthyl; nBuLi—n-Butyllithium; $CDCl_3$—deuterated chloroform; $Cs_2CO_3$ is caesium carbonate; CuI is copper (I) iodide; $Cu(OAc)_2$ is copper (II) acetate; δ—chemical shift; d—doublet; DAD—diode array detector; DCE—1,2-dichloroethane DCM—dichloromethane; DEA—diethylamine; DIBAL—Diisobutylaluminium hydride; DIPEA—diisopropylethylamine; DMAP—4-dimethylaminopyridine; DME—dimethoxyethane; DMF—N,N-dimethylformamide; DMF-DMA—N,N-dimethylformamide-dimethylacetal; DMSO—dimethylsulphoxide DPPF—1,1'-bis(diphenylphosphino)ferrocene; ELSD—evaporative light scattering detector; ESI—electrospray ionization; $Et_2O$—diethylether; EtOAc/EA—ethyl acetate; EtOH—ethanol; g—gram; HATU—2-(7-azabenzotriazol-1-yl)-1,1,3,3-tetramethyluronium hexafluorophosphate; HBTU is O-benzotriazol-1-yl-N,N,N',N'-tetramethyluronium hexafluorophosphate; HCl is hydrochloric acid; HOBT is N-hydroxybenzotriazole hydrate; HPLC—high pressure liquid chromatography; IPA—isopropyl alcohol; $K_2CO_3$ is potassium carbonate; $KHSO_4$ is potassium hydrogen sulphate; KOAc is potassium acetate; KOH is potassium hydroxide; $K_3PO_4$ is potassium phosphate tribasic; KF—potassium fluoride; L is liter; LCMS—liquid chromatography mass spectrometry; LiHMDS—Lithium hexamethyldisilazide; m—multiplet; mg—milligram; mL—milliliter; M/Z—Mass Spectrum Peak; MeCN—acetonitrile; MeOH—methanol; 2-MeTHF—2-methyltetrahydrofuran; $MgSO_4$ is magnesium sulphate; $MnO_2$—manganese dioxide; $NaClO_2$—sodium chlorite; NaH—sodium hydride; $NaHCO_3$—sodium hydrogencarbonate; $Na_2CO_3$—sodium carbonate; $NaH_2PO_4$—sodium phosphate; $NaHSO_3$—sodium bisulphite; $NaHSO_4$—sodium hydrogensulphate; NaOH—sodium hydroxide; $Na_2SO_4$—sodium sulphate; $NH_3$—ammonia; $NH_4Cl$—ammonium chloride; NMM—N-MethylMorpholine; NMR—nuclear magnetic resonance; Pd/C—palladium on carbon; $PdCl_2$—palladium dichloride; $Pd_2(dba)_3$ is tris(dibenzylideneacetone)dipalladium(0); $Pd(PPh_3)_4$—palladium tetrakis(triphenylphosphine); $Pd(OAc)_2$—palladium acetate; PTSA—para-toluenesulfonic acid; Prep—preparation; Rt—retention time; q—quartet; s—singlet; TBDMS—tertbutyldimethylsilyl; TBME—tert-butyldimethylether; TCP—1-propylphosphonic acid cyclic anhydride; TEA—triethylamine; TFA—trifluoroacetic acid; THF—tetrahydrofuran; TLC—thin layer chromatography; (R,S)—racemic mixture; WSCDI—1-(3-dimethylaminopropyl)-3-ethylcarbodiimide hydrochloride.

For the avoidance of doubt, named compounds used herein have been named using IUAPC, Chemdraw and/or Name Pro ACD Labs Name Software v7.11™ or using other standard nomenclature. NMR spectra were measured in deuterated solvents and were consistent with the names/structures given below.

vacuo and the residue was triturated with pentane:diethyl ether (3:1, 1 mL) to afford the title compound as an off white solid in 65% yield, 38 mg.

$^1$H NMR (400 MHz, DMSO) δ: 1.79 (s, 9H), 3.95 (s, 2H), 7.50 (m, 1H), 7.72 (m, 1H), 8.21 (s, 1H), 8.50 (d, 1H), 8.76 (d, 1H), 8.95 (d, 1H), 9.00 (s, 1H), 9.48 (s, 1H), 10.72 (s, 1H); LCMS (System 4): $R_t$=2.86 min; m/z 433 [M+H]$^+$.

Examples 2 to 8 were prepared according to the method described above for Example 1, starting from (5-aminopyridin-3-yl)(7-tert-butyl-7H-pyrrolo[2,3-d]pyrimidin-5-yl)methanone (see Preparation 31) and the appropriate acids.

| Example | Name | Data |
|---|---|---|
| 2 | N-{5-[(7-tert-butyl-7H-pyrrolo[2,3-d]pyrimidin-5-yl)carbonyl]pyridin-3-yl}-2-[4-(trifluoromethyl)-1H-1,2,3-triazol-1-yl]acetamide | LCMS (system 4): $R_t$ = 3.26 min; m/z 473 [M + H]$^+$ |
| 3 | N-{5-[(7-tert-butyl-7H-pyrrolo[2,3-d]pyrimidin-5-yl)carbonyl]pyridin-3-yl}-2-(3-cyclopropyl-1H-pyrazol-1-yl)acetamide | LCMS (system 4): $R_t$ = 3.04 min; m/z 444 [M + H]$^+$ |
| 4 | N-{5-[(7-tert-butyl-7H-pyrrolo[2,3-d]pyrimidin-5-yl)carbonyl]pyridin-3-yl}-2-(4-cyclopropyl-1H-1,2,3-triazol-1-yl)acetamide | LCMS (system 4): $R_t$ = 2.75 min; m/z 445 [M + H]$^+$ |
| 5 | N-{5-[(7-tert-butyl-7H-pyrrolo[2,3-d]pyrimidin-5-yl)carbonyl]pyridin-3-yl}-2-[3-(trifluoromethyl)-1H-pyrazol-1-yl]acetamide | LCMS (system 4): $R_t$ = 3.04 min; m/z 472 [M + H]$^+$ |
| 6 | N-{5-[(7-tert-butyl-7H-pyrrolo[2,3-d]pyrimidin-5-yl)carbonyl]pyridin-3-yl}-2-(5-chloropyridin-2-yl)acetamide | LCMS (system 4): $R_t$ = 2.92 min; m/z 449 [M + H]$^+$ |
| 7 | N-{5-[(7-tert-butyl-7H-pyrrolo[2,3-d]pyrimidin-5-yl)carbonyl]pyridin-3-yl}-2-(4-cyclopropyl-1H-pyrazol-1-yl)acetamide | LCMS (system 4): $R_t$ = 2.96 min; m/z 443 [M + H]$^+$ |
| 8 | N-{5-[(7-tert-butyl-7H-pyrrolo[2,3-d]pyrimidin-5-yl)carbonyl]pyridin-3-yl}-2-[4-(trifluoromethyl)-1H-pyrazol-1-yl]acetamide | LCMS(system 4): $R_t$ = 3.00 min; m/z 472 [M + H]$^+$ |

Example 1

N-{5-[(7-tert-Butyl-7H-pyrrolo[2,3-d]pyrimidin-5-yl)carbonyl]pyridin-3-yl}-2-(5-fluoropyridin-2-yl)acetamide

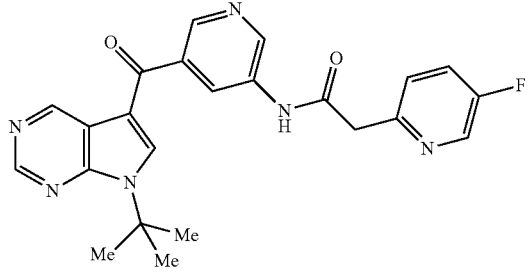 [SMILES: CC(C)(C)n1cc(C(=O)c2cncc(NC(=O)Cc3ccc(F)cn3)c2)c2cncnc21]

2-(5-Fluoropyridin-2-yl)acetic acid (23.1 mg, 0.149 mmol) (see Preparation 92) was added to (5-aminopyridin-3-yl)(7-tert-butyl-7H-pyrrolo[2,3-d]pyrimidin-5-yl)methanone (40 mg, 0.135 mmol) (see Preparation 31), 1-propylphosphonic acid cyclic anhydride (0.2 mL, 0.338 mmol, 50% in EtOAc) and triethylamine (0.65 mL, 0.474 mmol) in THF (3 mL). The mixture was stirred at 25° C. for 18 hours, evaporated in vacuo and partitioned between saturated aqueous sodium bicarbonate (5 mL) and ethyl acetate (5 mL). The organic phase was dried over sodium sulfate, evaporated in

Example 9

N-[5-({7-[(1S)-2-Hydroxy-1-methylethyl]-7H-pyrrolo[2,3-d]pyrimidin-5-yl}carbonyl)pyridin-3-yl]-2-[4-(trifluoromethyl)phenyl]acetamide

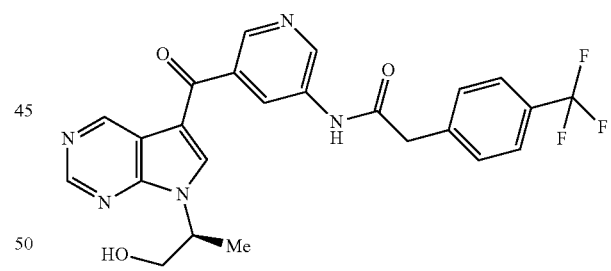

4-(Trifluoromethyl)phenylacetic acid (33.6 g, 165 mmol) was added to (5-aminopyridin-3-yl){7-[(1S)-2-{[tert-butyl (dimethyl)silyl]oxy}-1-methylethyl]-7H-pyrrolo[2,3-d]pyrimidin-5-yl}methanone (45.2 g, 110 mmol) (see Preparation 37), 1-propylphosphonic acid cyclic anhydride (194 mL, 329 mmol, 50% solution in EtOAc) and triethylamine (53.6 mL, 384 mmol) in THF (400 mL). The mixture was stirred at 25° C. for 2 hours then saturated aqueous sodium bicarbonate (250 mL) was added and the organic layer was separated. The aqueous phase was extracted with EtOAc (2×200 mL) and all organic phases were combined and dried over sodium sulfate then evaporated in vacuo.

The residue brown solid was dissolved in THF (400 mL) and aqueous HCl (200 mL, 2M) was added. The mixture was stirred at room temperature for 2 hours then cooled to 0° C.

and sodium hydroxide (28 g) was added. The mixture was stirred for 3 hours then water (100 mL) was added. The organic layer was separated and the aqueous phase was extracted with EtOAc (2×300 mL) and all organic phases were combined and dried over sodium sulfate then evaporated in vacuo. The crude solid was recrystallised using ethyl acetate (150 mL) to afford the title compound as a white solid in 63% yield, 33.4 g.

$^1$H NMR (400 MHz, DMSO) δ: 1.51 (d, 3H), 3.68-3.79 (m, 1H), 3.81-3.93 (m, 3H), 4.93-5.06 (m, 2H), 7.55-7.63 (m, 2H), 7.67-7.75 (m, 2H), 8.41-8.49 (m, 2H), 8.73 (d, 1H), 8.98 (s, 1H), 9.00 (d, 1H), 9.44 (s, 1H), 10.72 (s, 1H); LCMS (System 1): Rt=4.53 min; m/z 484 [M+H]$^+$.

Example 10

N-[5-({7-[(1S)-2-Hydroxy-1-methylethyl]-7H-pyrrolo[2,3-d]pyrimidin-5-yl}carbonyl)pyridin-3-yl]-2-[5-methyl-3-(trifluoromethyl)-1H-pyrazol-1-yl]acetamide

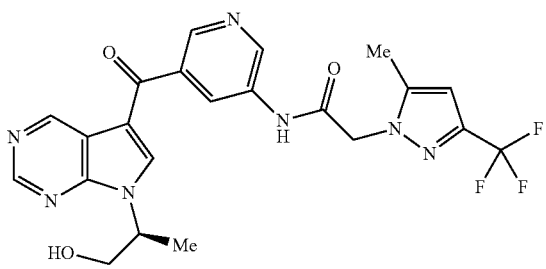 [SMILES: Cc1cc(C(F)(F)F)nn1CC(=O)Nc1cncc(C(=O)c2cn([C@@H](C)CO)c3ncncc23)c1]

10% Hydrochloric acid in 1,4-dioxane (0.2 mL) was added to Preparation 66 (59 mg, 0.098 mmol) in THF (2 mL) and the mixture was stirred at room temperature for 18 hours. The mixture was evaporated in vacuo and triturated with pentane:diethyl ether (3:1, 1 mL) to afford the title compound as an off white solid in 86% yield, 41 mg.

LCMS (system 4): Rt=2.85 min; m/z 488.2 [M+H]$^+$.

Examples 11 to 16 were prepared according to the method described above for Example 10, starting from the appropriate protected alcohol.

Example 17

N-[5-({7-[(1R)-2-Hydroxy-1-methylethyl]-7H-pyrrolo[2,3-d]pyrimidin-5-yl}carbonyl)pyridin-3-yl]-2-[5-methyl-3-(trifluoromethyl)-1H-pyrazol-1-yl]acetamide

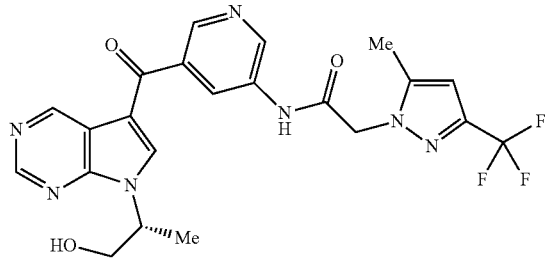 [SMILES: Cc1cc(C(F)(F)F)nn1CC(=O)Nc1cncc(C(=O)c2cn([C@H](C)CO)c3ncncc23)c1]

(5-Methyl-3-trifluoromethyl-pyrazol-1-yl)acetic acid (46.8 mg, 0.225 mmol) was added to (R,S) (5-aminopyridin-3-yl){7-[(1R)-1-methyl-2-(tetrahydro-2H-pyran-2-yloxy)ethyl]-7H-pyrrolo[2,3-d]pyrimidin-5-yl}methanone (66 mg, 0.173 mmol) (see Preparation 36), 1-propylphosphonic acid cyclic anhydride (0.31 mL, 0.519 mmol) and DIPEA (0.09 mL, 0.606 mmol) in THF (5 mL). The mixture was heated at reflux for 48 hours, evaporated in vacuo and partitioned between saturated aqueous sodium bicarbonate (5 mL) and ethyl acetate (5 mL). The organic phase was dried over sodium sulfate, evaporated in vacuo and the residue was purified by column chromatography on silica gel (gradient of EtOAc:Hexane 85:15) to afford the intermediate as an off white solid in 53% yield, 52 mg.

10% Hydrochloric acid in 1,4-dioxane (0.4 mL) was added to the intermediate (52 mg, 0.091 mmol) in THF (2 mL) and the mixture was stirred at room temperature for 1.5 hours. The mixture was evaporated in vacuo and triturated with pentane:diethyl ether (3:1, 1 mL) to afford the title compound as an off white solid in 94% yield, 42 mg.

$^1$H NMR (400 MHz, DMSO) δ: 1.49 (d, 3H), 2.32 (d, 3H), 3.56 (m, 1H), 5.00 (m, 1H), 5.20 (s, 2H), 6.56 (s, 1H), 8.45 (s, 1H), 8.54 (s, 1H), 8.79 (s, 1H), 9.02 (s, 2H), 9.48 (s, 1H), 11.05 (s, 1H);

LCMS (system 4): R$_t$=2.86 min; m/z 488 [M+H]$^+$.

Examples 18 to 24 were prepared according to the method described above for Example 17, starting from (5-aminopyridin-3-yl){7-[(1R)-1-methyl-2-(tetrahydro-2H-pyran-2-yloxy)ethyl]-7H-pyrrolo[2,3-d]pyrimidin-5-yl}methanone (see Preparation 36).

| Example | Name | Data |
|---|---|---|
| 11 | 2-(4-chlorophenyl)-N-[5-({7-[(1S)-2-hydroxy-1-methylethyl]-7H-pyrrolo[2,3-d]pyrimidin-5-yl}carbonyl)pyridin-3-yl]acetamide | LCMS (system 4): Rt = 2.89 min; m/z 450 [M + H]$^+$ |
| 12 | N-[5-({7-[(1S)-2-hydroxy-1-methylethyl]-7H-pyrrolo[2,3-d]pyrimidin-5-yl}carbonyl)pyridin-3-yl]-2-[3-(trifluoromethyl)-1H-pyrazol-1-yl]acetamide | LCMS (system 4): Rt = 2.88 min; m/z 474 [M + H]$^+$ |
| 13 | N-[5-({7-[(1S)-2-hydroxy-1-methylethyl]-7H-pyrrolo[2,3-d]pyrimidin-5-yl}carbonyl)pyridin-3-yl]-2-[4-(trifluoromethyl)-1H-1,2,3-triazol-1-yl]acetamide | LCMS (system 4): Rt = 2.68 min; m/z 475 [M + H]$^+$ |
| 14 | 2-(5-chloropyridin-2-yl)-N-[5-({7-[(1S)-2-hydroxy-1-methylethyl]-7H-pyrrolo[2,3-d]pyrimidin-5-yl}carbonyl)pyridin-3-yl]acetamide | LCMS (system 4): Rt = 2.72 min; m/z 451 [M + H]$^+$ |
| 15 | 2-(2H-benzotriazol-2-yl)-N-[5-({7-[(1S)-2-hydroxy-1-methylethyl]-7H-pyrrolo[2,3-d]pyrimidin-5-yl}carbonyl)pyridin-3-yl]acetamide | LCMS (system 4): Rt = 2.64 min; m/z 457 [M + H]$^+$ |
| 16 | 2-(2,4-difluorophenyl)-N-[5-({7-[(1S)-2-hydroxy-1-methylethyl]-7H-pyrrolo[2,3-d]pyrimidin-5-yl}carbonyl)pyridin-3-yl]acetamide | LCMS (system 4) Rt = 2.74 min; m/z 452 [M + H]$^+$ |

| Example | Name | Data |
|---|---|---|
| 18 | 2-(4-cyclopropyl-1H-1,2,3-triazol-1-yl)-N-[5-({7-[(1R)-2-hydroxy-1-methylethyl]-7H-pyrrolo[2,3-d]pyrimidin-5-yl}carbonyl)pyridin-3-yl]acetamide | LCMS (system 4): Rt = 2.21 min; m/z 474 [M + H]+ |
| 19 | 2-(5-fluoropyridin-2-yl)-N-[5-({7-[(1R)-2-hydroxy-1-methylethyl]-7H-pyrrolo[2,3-d]pyrimidin-5-yl}carbonyl)pyridin-3-yl]acetamide | LCMS (system 4): Rt = 2.24 min; m/z 435 [M + H]+ |
| 20 | N-[5-({7-[(1R)-2-hydroxy-1-methylethyl]-7H-pyrrolo[2,3-d]pyrimidin-5-yl}carbonyl)pyridin-3-yl]-2-[4-(trifluoromethyl)phenyl]acetamide | LCMS (system 4): Rt = 2.98 min; m/z 484 [M + H]+ |
| 21 | N-[5-({7-[(1R)-2-hydroxy-1-methylethyl]-7H-pyrrolo[2,3-d]pyrimidin-5-yl}carbonyl)pyridin-3-yl]-2-[4-(trifluoromethyl)-1H-1,2,3-triazol-1-yl]acetamide | LCMS (system 4): Rt = 2.70 min; m/z 475 [M + H]+ |
| 22 | N-[5-({7-[(1R)-2-hydroxy-1-methylethyl]-7H-pyrrolo[2,3-d]pyrimidin-5-yl}carbonyl)pyridin-3-yl]-2-[3-(trifluoromethyl)-1H-pyrazol-1-yl]acetamide | LCMS (system 4): Rt = 2.80 min; m/z 474 [M + H]+ |
| 23 | 2-(5-chloropyridin-2-yl)-N-[5-({7-[(1R)-2-hydroxy-1-methylethyl]-7H-pyrrolo[2,3-d]pyrimidin-5-yl}carbonyl)pyridin-3-yl]acetamide | LCMS (system 4): $R_t$ = 2.49 min; m/z 451 [M + H]+ |
| 24 | 2-(4-chlorophenyl)-N-[5-({7-[(1R)-2-hydroxy-1-methylethyl]-7H-pyrrolo[2,3-d]pyrimidin-5-yl}carbonyl)pyridin-3-yl]acetamide | LCMS (System 2): $R_t$ = 1.01 min; m/z 450 [M + H]+ |

Example 25

(R,S) 2-(4-Cyclopropyl-1H-pyrazol-1-yl)-N-(5-{[7-(2-hydroxy-1-methylethyl)-7H-pyrrolo[2,3-d]pyrimidin-5-yl]carbonyl}pyridin-3-yl)acetamide

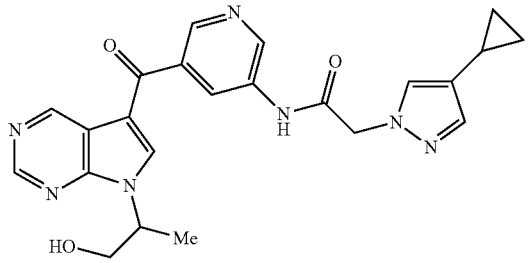 [SMILES: CC(CO)n1cc(C(=O)c2cncc(NC(=O)Cn3cc(C4CC4)cn3)c2)c2cncnc21]

The title compound was prepared according to the method described for Example 9 using (R,S) (5-aminopyridin-3-yl){7-[2-{[tert-butyl(dimethyl)silyl]oxy}-1-methylethyl]-7H-pyrrolo[2,3-d]pyrimidin-5-yl}methanone (see Preparation 39) and (4-cyclopropyl-1H-pyrazol-1-yl)acetic acid (see Preparation 88) to afford the title compound as a white solid in 14% yield, 20 mg.

$^1$H NMR (400 MHz, DMSO) δ: 0.46 (d, 2H), 0.79 (d, 2H), 1.49 (d, 3H), 1.70 (m, 1H), 3.73 (m, 1H), 3.87 (m, 1H), 5.00 (s, 4H), 7.26 (s, 1H), 7.54 (s, 1H), 8.40 (s, 1H), 8.47 (s, 1H), 8.75 (d, 1H), 8.98 (s, 1H), 9.00 (d, 1H), 9.44 (s, 1H), 10.75 (s, 1H); LCMS (system 4): $R_t$=2.53 min; m/z 445 [M+H]+.

Examples 26 to 33 were prepared according to the method described above for Example 10, starting from the appropriate protected alcohol TBDMS ether.

| Example | Name | Data |
|---|---|---|
| 26 | N-(5-{[7-(2-hydroxy-1,1-dimethylethyl)-7H-pyrrolo[2,3-d]pyrimidin-5-yl]carbonyl}pyridin-3-yl)-2-[5-methyl-3-(trifluoromethyl)-1H-pyrazol-1-yl]acetamide | LCMS (system 4): $R_t$ = 2.89 min; m/z 502 [M + H]+ |
| 27 | N-(5-{[7-(2-hydroxy-1,1-dimethylethyl)-7H-pyrrolo[2,3-d]pyrimidin-5-yl]carbonyl}pyridin-3-yl)-2-[4-(trifluoromethyl)phenyl]acetamide | LCMS (system 4): $R_t$ = 3.03 min; m/z 498 [M + H]+ |
| 28 | 2-(4-chlorophenyl)-N-(5-{[7-(2-hydroxy-1,1-dimethylethyl)-7H-pyrrolo[2,3-d]pyrimidin-5-yl]carbonyl}pyridin-3-yl)acetamide | $^1$H NMR (400 MHz, DMSO) δ: 1.73 (s, 6H), 3.75 (s, 2H), 3.96 (s, 2H), 7.39 (s, 4H), 8.22 (s, 1H), 8.51 (s, LCMS (system 4): $R_t$ = 3.02 min; m/z 464.1 [M + H]+ |
| 29 | 2-(5-chloropyridin-2-yl)-N-(5-{[7-(2-hydroxy-1,1-dimethylethyl)-7H-pyrrolo[2,3-d]pyrimidin-5-yl]carbonyl}pyridin-3-yl)acetamide | LCMS (system 4): $R_t$ = 2.72 min; m/z 465 [M + H]+ |
| 30 | N-(5-{[7-(2-hydroxy-1,1-dimethylethyl)-7H-pyrrolo[2,3-d]pyrimidin-5-yl]carbonyl}pyridin-3-yl)-2-[3-(trifluoromethyl)-1H-pyrazol-1-yl]acetamide | LCMS (system 4): $R_t$ = 2.80 min; m/z 488 [M + H]+ |

-continued

| Example | Name | Data |
|---|---|---|
| 31 | 2-(4-cyclopropyl-1H-1,2,3-triazol-1-yl)-N-(5-{[7-(2-hydroxy-1,1-dimethylethyl)-7H-pyrrolo[2,3-d]pyrimidin-5-yl]carbonyl}pyridin-3-yl)acetamide | LCMS (system 4): $R_t$ = 2.47 min; m/z 461 [M + H]$^+$ |
| 32 | N-(5-{[7-(2-hydroxy-1,1-dimethylethyl)-7H-pyrrolo[2,3-d]pyrimidin-5-yl]carbonyl}pyridin-3-yl)-2-[4-(trifluoromethyl)-1H-1,2,3-triazol-1-yl]acetamide | LCMS (system 4): $R_t$ = 2.78 min; m/z 489 [M + H]$^+$ |
| 33 | 2-(4-cyclopropyl-1H-pyrazol-1-yl)-N-(5-{[7-(2-hydroxy-1,1-dimethylethyl)-7H-pyrrolo[2,3-d]pyrimidin-5-yl]carbonyl}pyridin-3-yl)acetamide | LCMS(system 4): $R_t$ = 2.68 min; m/z 460 [M + H]$^+$ |

Example 34

N-(5-{[2-Amino-7-(2-hydroxy-1-methylethyl)-7H-pyrrolo[2,3-d]pyrimidin-5-yl]carbonyl}pyridin-3-yl)-2-(4-chlorophenyl)acetamide (enantiomer 1)

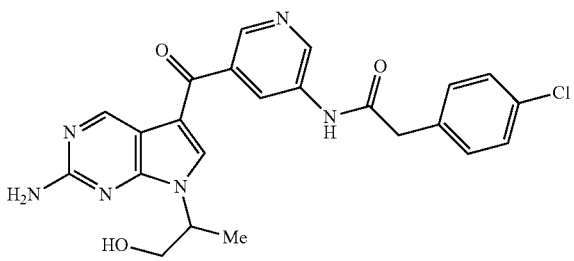 [SMILES: CC(CO)n1cc(C(=O)c2cncc(NC(=O)Cc3ccc(Cl)cc3)c2)c2cnc(N)nc21]

4-Chlorophenylacetic acid (25 mg, 0.14 mmol) was added to [2-amino-7-(2-hydroxy-1-methylethyl)-7H-pyrrolo[2,3-d]pyrimidin-5-yl](5-aminopyridin-3-yl)methanone (50 mg, 0.16 mmol) (see Preparation 57) and HATU (91 mg, 0.24 mmol) in pyridine (2 mL). The mixture was stirred at room temperature for 16 hours. Saturated aqueous sodium bicarbonate (5 mL) was added then extracted with ethyl acetate (3×5 mL). The combined organic phases were washed with brine (5 mL) then dried over sodium sulfate and evaporated in vacuo. The residue was purified by preparative TLC (95:5 DCM:MeOH) to afford the title compound as a yellow solid in 48% yield, 32 mg.

LCMS (system 5): Rt=2.90 min; m/z 465 [M+H]$^+$.

Examples 35 to 45 were prepared according to the method described above for Example 34, starting from [2-amino-7-(2-hydroxy-1-methylethyl)-7H-pyrrolo[2,3-d]pyrimidin-5-yl](5-aminopyridin-3-yl)methanone (see Preparation 57, enantiomer 1 or Preparation 59, enantiomer 2) and the appropriate acids.

| Example | Name | Data |
|---|---|---|
| 35 | N-(5-{[2-amino-7-(2-hydroxy-1-methylethyl)-7H-pyrrolo[2,3-d]pyrimidin-5-yl]carbonyl}pyridin-3-yl)-2-(5-chloropyridin-2-yl)acetamide | Enantiomer 1 LCMS (system 5): Rt = 2.63 min; m/z 466 [M + H]$^+$ |
| 36 | N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)phenyl]acetamide | Enantiomer 1 LCMS (system 5): Rt = 2.88 min; m/z 499 [M + H]$^+$ |
| 37 | N-(5-{[2-amino-7-(2-hydroxy-1-methylethyl)-7H-pyrrolo[2,3-d]pyrimidin-5-yl]carbonyl}pyridin-3-yl)-2-(5-fluoropyridin-2-yl)acetamide | Enantiomer 1 LCMS (system 5): Rt = 2.25 min; m/z 450 [M + H]$^+$ |
| 38 | N-(5-{[2-amino-7-(2-hydroxy-1-methylethyl)-7H-pyrrolo[2,3-d]pyrimidin-5-yl]carbonyl}pyridin-3-yl)-2-[3-(trifluoromethyl)-1H-pyrazol-1-yl]acetamide | Enantiomer 1 LCMS (system 4): Rt = 2.39 min; m/z 489 [M + H]$^+$ |
| 39 | N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)-1H-1,2,3-triazol-1-yl]acetamide | Enantiomer 1 LCMS (system 5): Rt = 2.61 min; m/z 490 [M + H]$^+$ |
| 40 | N-(5-{[2-amino-7-(2-hydroxy-1-methylethyl)-7H-pyrrolo[2,3-d]pyrimidin-5-yl]carbonyl}pyridin-3-yl)-2-(5-fluoropyridin-2-yl)acetamide | Enantiomer 2 LCMS (system 4): Rt = 1.89 min; m/z 450 [M + H]$^+$ |
| 41 | N-(5-{[2-amino-7-(2-hydroxy-1-methylethyl)-7H-pyrrolo[2,3-d]pyrimidin-5-yl]carbonyl}pyridin-3-yl)-2-(5-chloropyridin-2-yl)acetamide | Enantiomer 2 LCMS (system 4): Rt = 2.16 min; m/z 466 [M + H]$^+$ |
| 42 | N-(5-{[2-amino-7-(2-hydroxy-1-methylethyl)-7H-pyrrolo[2,3-d]pyrimidin-5-yl]carbonyl}pyridin-3-yl)-2-(4-chlorophenyl)acetamide | Enantiomer 2 LCMS (system 4): Rt = 2.63 min; m/z 465 [M + H]$^+$ |
| 43 | N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)phenyl]acetamide | Enantiomer 2 LCMS (system 4): Rt = 2.73 min; m/z 499 [M + H]$^+$ |
| 44 | N-(5-{[2-amino-7-(2-hydroxy-1-methylethyl)-7H-pyrrolo[2,3-d]pyrimidin-5-yl]carbonyl}pyridin-3-yl)-2-[3-(trifluoromethyl)-1H-pyrazol-1-yl]acetamide | Enantiomer 2 LCMS (system 4): Rt = 2.38 min; m/z 489 [M + H]$^+$ |

-continued

| Example | Name | Data |
|---|---|---|
| 45 | N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)-1H-1,2,3-triazol-1-yl]acetamide | Enantiomer 2 LCMS (system 5): Rt = 2.60 min; m/z 490 [M + H]$^+$ |

Example 46

N-(5-{[2-Amino-7-(2-hydroxy-1,1-dimethylethyl)-7H-pyrrolo[2,3-d]pyrimidin-5-yl]carbonyl}pyridin-3-yl)-2-(5-chloropyridin-2-yl)acetamide

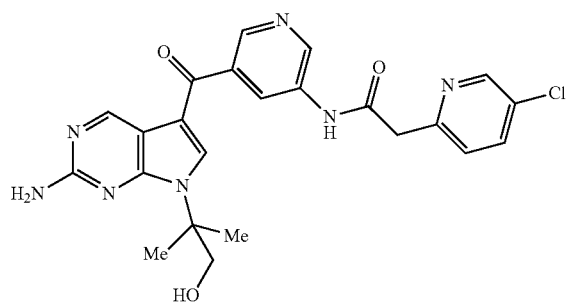 [SMILES: CC(C)(CO)n1cc(C(=O)c2cncc(NC(=O)Cc3ccc(Cl)cn3)c2)c2cnc(N)nc21]

(5-Chloropyridin-2-yl)acetic acid (26.1 g, 152 mmol) (see Preparation 90) was added to (5-aminopyridin-3-yl){7-(2-{[tert-butyl(dimethyl)silyl]oxy}-1,1-dimethylethyl)-2-[(2,4-dimethoxybenzyl)amino]-7H-pyrrolo[2,3-d]pyrimidin-5-yl}methanone (75.0 g, 130 mmol) (see Preparation 51), 1-propylphosphonic acid cyclic anhydride (187 mL, 317 mmol, 50% solution in EtOAc) and triethylamine (61.9 mL, 444 mmol) in THF (423 mL). The mixture was stirred at 25° C. for 2 hours then saturated aqueous sodium bicarbonate (400 mL) was added and the organic layer was separated. The aqueous phase was extracted with EtOAc (400 mL) and all organic phases were combined and dried over sodium sulfate then evaporated in vacuo.

The residue brown solid was dissolved in trifluoroacetic acid (300 mL) and the solution was stirred at 50° C. for 3 hours then evaporated in vacuo. Methanol (1800 mL) was added to the residue and the mixture was filtered. The filtrate was evaporated in vacuo and azeotroped with ethanol (3×200 mL).

Potassium carbonate (87.7 g, mmol) was added to the crude trifluoroacetamide in methanol (300 mL) and the mixture was stirred at room temperature for 16 hours. The mixture was poured into water (2000 mL) and filtered. The solid was washed with water (200 mL) then triturated with ethanol (2×200 mL at room temperature then 380 mL at 50° C.) to afford the title compound as a yellow solid in 48% yield, 29.9 g.

$^1$H NMR (400 MHz, DMSO-d6) δ: 1.64 (s, 6H), 3.90 (d, 2H), 3.95 (s, 2H), 5.05 (t, 1H), 6.54 (br s, 2H), 7.49 (d, 1H), 7.69 (s, 1H), 7.92 (dd, 1H), 8.40 (m, 1H), 8.56 (m, 1H), 8.64 (d, 1H), 8.94 (d, 1H), 8.96 (s, 1H), 10.71 (s, 1H); LCMS (System 3): R$_t$=9.92 min; m/z 480 [M+H]$^+$.

Example 47

N-(5-{[2-Amino-7-(2-hydroxy-1,1-dimethylethyl)-7H-pyrrolo[2,3-d]pyrimidin-5-yl]carbonyl}pyridin-3-yl)-2-[5-methyl-3-(trifluoromethyl)-1H-pyrazol-1-yl]acetamide

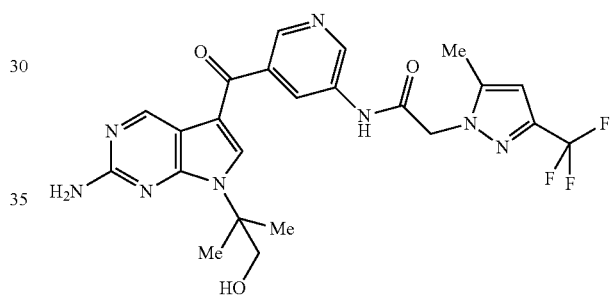

The title compound was prepared according to the method described for Example 46 using (5-aminopyridin-3-yl){7-(2-{[tert-butyl(dimethyl)silyl]oxy}-1,1-dimethylethyl)-2-[(2,4-dimethoxybenzyl)amino]-7H-pyrrolo[2,3-d]pyrimidin-5-yl}methanone (see Preparation 51) and (5-methyl-3-trifluoromethyl-pyrazol-1-yl)acetic acid (46.8 mg, 0.225 mmol) to afford the title compound as a brown solid in 79% yield, 82 mg.

LCMS (System 1): R$_t$=2.83 min; m/z 517 [M+H]$^+$.

Examples 48 to 53 were prepared according to the method described above for Example 34, starting from [2-amino-7-(2-hydroxy-1,1-dimethylethyl)-7H-pyrrolo[2,3-d]pyrimidin-5-yl](5-aminopyridin-3-yl)methanone (see Preparation 48) and the appropriate acids.

| Example | Name | Data |
|---|---|---|
| 48 | N-(5-{[2-amino-7-(2-hydroxy-1,1-dimethylethyl)-7H-pyrrolo[2,3-d]pyrimidin-5-yl]carbonyl}pyridin-3-yl)-2-[4-(trifluoromethyl)phenyl]acetamide | LCMS (system5): R$_t$ = 3.12 min; m/z 513 [M + H]$^+$ |
| 49 | N-(5-{[2-amino-7-(2-hydroxy-1,1-dimethylethyl)-7H-pyrrolo[2,3-d]pyrimidin-5-yl]carbonyl}pyridin-3-yl)-2-(4-chlorophenyl)acetamide | LCMS (system 5): R$_t$ = 2.89 min; m/z 479 [M + H]$^+$ |

-continued

| Example | Name | Data |
|---|---|---|
| 50 | N-(5-{[2-amino-7-(2-hydroxy-1,1-dimethylethyl)-7H-pyrrolo[2,3-d]pyrimidin-5-yl]carbonyl}pyridin-3-yl)-2-(2,4-difluorophenyl)acetamide | MS (ESCI): m/z 481 [M + H]$^+$ |
| 51 | N-(5-{[2-amino-7-(2-hydroxy-1,1-dimethylethyl)-7H-pyrrolo[2,3-d]pyrimidin-5-yl]carbonyl}pyridin-3-yl)-2-(5-fluoropyridin-2-yl)acetamide | LCMS (system 5): $R_t$ = 2.42 min; m/z 464 [M + H]$^+$ |
| 52 | N-(5-{[2-amino-7-(2-hydroxy-1,1-dimethylethyl)-7H-pyrrolo[2,3-d]pyrimidin-5-yl]carbonyl}pyridin-3-yl)-2-[3-(trifluoromethyl)-1H-pyrazol-1-yl]acetamide | LCMS (system 4): $R_t$ = 2.54 min; m/z 503 [M + H]$^+$ |
| 53 | N-(5-{[2-amino-7-(2-hydroxy-1,1-dimethylethyl)-7H-pyrrolo[2,3-d]pyrimidin-5-yl]carbonyl}pyridin-3-yl)-2-(3-cyclopropyl-1H-pyrazol-1-yl)acetamide | LCMS (system 4) $R_t$ = 2.23 min; m/z 475 [M + H]$^+$ |

Example 54

N-(5-{[2-Amino-7-(2-hydroxy-1,1-dimethylethyl)-7H-pyrrolo[2,3-d]pyrimidin-5-yl]carbonyl}pyridin-3-yl)-2-[4-(trifluoromethyl)-1H-1,2,3-triazol-1-yl]acetamide

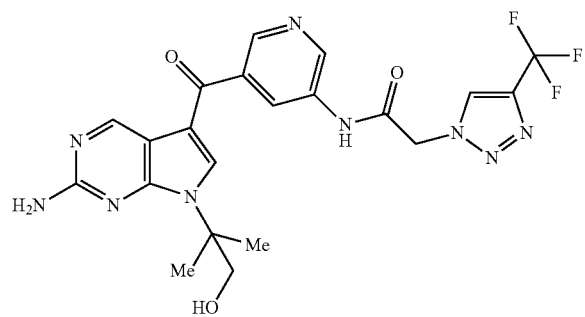 [SMILES: CC(C)(CO)n1cc(C(=O)c2cncc(NC(=O)Cn3cc(C(F)(F)F)nn3)c2)c2cnc(N)nc21]

The title compound was prepared according to the method described for Example 9 using [7-(2-{[tert-butyl(dimethyl)silyl]oxy}-1,1-dimethylethyl)-2-amino-7H-pyrrolo[2,3-d]pyrimidin-5-yl]{5-aminopyridin-3-yl}methanone (see Preparation 48a) and [4-(trifluoromethyl)-1H-1,2,3-triazol-1-yl]acetic acid (see Preparation 81) to afford the title compound as a brown solid in 85% yield, 62 mg.

$^1$H NMR (400 MHz, DMSO-d6) δ: 1.63 (s, 6H), 3.89 (d, 2H), 5.01 (br, 1H), 5.56 (s, 2H), 6.67 (br s, 2H), 7.72 (s, 1H), 8.36 (s, 1H), 8.70 (s, 1H), 8.94-8.96 (m, 3H), 11.05 (s, 1H); LCMS (system 5): $R_t$=2.71 min; m/z 502 [M−H]$^+$.

Example 55

N-(5-{[2-Amino-7-(2-hydroxy-1,1-dimethylethyl)-7H-pyrrolo[2,3-d]pyrimidin-5-yl]carbonyl}pyridin-3-yl)-2-(2H-benzotriazol-2-yl)acetamide

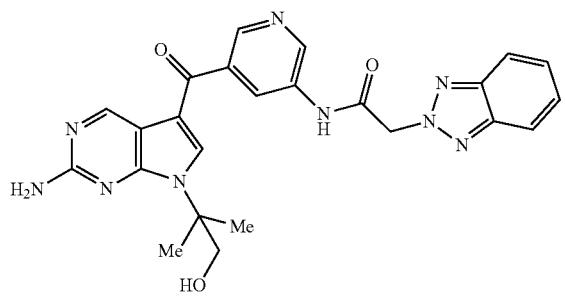 [SMILES: CC(C)(CO)n1cc(C(=O)c2cncc(NC(=O)Cn3nc4ccccc4n3)c2)c2cnc(N)nc21]

The title compound was prepared according to the method described for Example 9 using {2-amino-7-[1,1-dimethyl-2-(tetrahydro-2H-pyran-2-yloxy)ethyl]-7H-pyrrolo[2,3-d]pyrimidin-5-yl}(5-aminopyridin-3-yl)methanone (see Preparation 49) to afford the title compound as a brown solid in 46% yield, 20 mg.

$^1$H NMR (400 MHz, DMSO-d6) δ: 1.63 (s, 6H), 3.88 (d, 2H), 5.04 (t, 1H), 5.80 (s, 2H), 6.54 (s, 2H), 7.46-7.49 (m, 2H), 7.69 (s, 1H), 7.95-7.97 (m, 2H), 8.35 (s, 1H), 8.69 (s, 1H), 8.96 (s, 1H), 8.98 (s, 1H), 11.06 (s, 1H); MS (ESCI): m/z 486 [M+H]$^+$.

Example 56

N-(5-{[2-Amino-7-(2-hydroxy-1,1-dimethylethyl)-7H-pyrrolo[2,3-d]pyrimidin-5-yl]carbonyl}pyridin-3-yl)-2-(4-cyclopropyl-1H-1,2,3-triazol-1-yl)acetamide

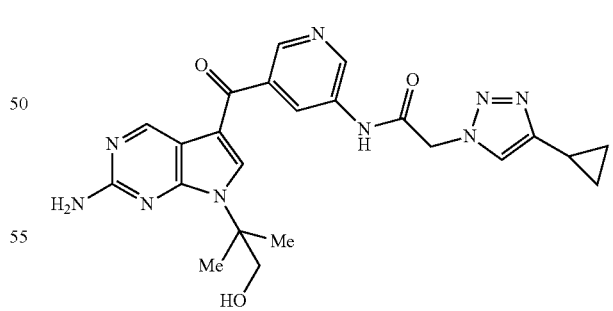

The title compound was prepared according to the method described for Example 10 using N-[5-({2-amino-7-[1,1-dimethyl-2-(tetrahydro-2H-pyran-2-yloxy)ethyl]-7H-pyrrolo[2,3-d]pyrimidin-5-yl}carbonyl)pyridin-3-yl]-2-(4-cyclopropyl-1H-1,2,3-triazol-1-yl)acetamide (see Preparation 52) to afford the title compound as a yellow solid in 24% yield, 14 mg.

$^1$H NMR (400 MHz, DMSO-D$_6$) δ: 0.71-0.72 (m, 2H), 0.89-0.91 (m, 2H), 1.64 (s, 6H), 1.94-1.99 (m, 1H), 3.89 (d, 2H), 5.07 (t, 1H), 5.31 (s, 2H), 6.53 (s, 2H), 7.69 (s, 1H), 7.86 (s, 1H), 8.35 (s, 1H), 8.65 (s, 1H), 8.95 (m, 2H), 11.04 (s, 1H); LCMS (system 5): R$_t$=2.42 min; m/z 476 [M+H]$^+$.

Examples 57 to 64 were prepared according to the method described above for Example 1, starting from (2-amino-7-tert-butyl-7H-pyrrolo[2,3-d]pyrimidin-5-yl)(5-aminopyridin-3-yl)methanone (see Preparation 65) and the appropriate acids.

| Example | Name | Data |
|---|---|---|
| 57 | N-{5-[(2-amino-7-tert-butyl-7H-pyrrolo[2,3-d]pyrimidin-5-yl)carbonyl]pyridin-3-yl}-2-(3-cyclopropyl-1H-pyrazol-1-yl)acetamide | LCMS (system 5): R$_t$ = 2.90 min; m/z 459 [M + H]$^+$ |
| 58 | N-{5-[(2-amino-7-tert-butyl-7H-pyrrolo[2,3-d]pyrimidin-5-yl)carbonyl]pyridin-3-yl}-2-(4-cyclopropyl-1H-1,2,3-triazol-1-yl)acetamide | LCMS (system 5, 12 min run): R$_t$ = 6.13 min; m/z 460 [M + H]$^+$ |
| 59 | N-{5-[(2-amino-7-tert-butyl-7H-pyrrolo[2,3-d]pyrimidin-5-yl)carbonyl]pyridin-3-yl}-2-(5-fluoropyridin-2-yl)acetamide | LCMS (system 4): R$_t$ = 2.60 min; m/z 448 [M + H]$^+$ |
| 60 | N-{5-[(2-amino-7-tert-butyl-7H-pyrrolo[2,3-d]pyrimidin-5-yl)carbonyl]pyridin-3-yl}-2-[4-(trifluoromethyl)-1H-pyrazol-1-yl]acetamide | LCMS (system 5): R$_t$ = 2.99 min; m/z 487 [M + H]$^+$ |
| 61 | N-{5-[(2-amino-7-tert-butyl-7H-pyrrolo[2,3-d]pyrimidin-5-yl)carbonyl]pyridin-3-yl}-2-[4-(trifluoromethyl)-1H-1,2,3-triazol-1-yl]acetamide | LCMS (system 5): R$_t$ = 3.04 min; m/z 488 [M + H]$^+$ |
| 62 | N-{5-[(2-amino-7-tert-butyl-7H-pyrrolo[2,3-d]pyrimidin-5-yl)carbonyl]pyridin-3-yl}-2-[3-(trifluoromethyl)-1H-pyrazol-1-yl]acetamide | LCMS (system 5): R$_t$ = 3.09 min; m/z 487 [M + H]$^+$ |
| 63 | N-{5-[(2-amino-7-tert-butyl-7H-pyrrolo[2,3-d]pyrimidin-5-yl)carbonyl]pyridin-3-yl}-2-(5-chloropyridin-2-yl)acetamide | LCMS (system 5): R$_t$ = 2.95 min; m/z 464 [M + H]$^+$ |
| 64 | N-{5-[(2-amino-7-tert-butyl-7H-pyrrolo[2,3-d]pyrimidin-5-yl)carbonyl]pyridin-3-yl}-2-[5-methyl-3-(trifluoromethyl)-1H-pyrazol-1-yl]acetamide | LCMS (system 5): R$_t$ = 3.09 min; m/z 501 [M + H]$^+$ |

The following Examples were prepared according to Method a (Example 34 at 50° C.) or Method b (Example 1 using DIPEA) as described above starting from (5-Aminopyridin-3-yl)(7-isopropyl-7H-pyrrolo[2,3-d]pyrimidin-5-yl)methanone (Preparation 95) and the appropriate acid.

| Example | Name | Data |
|---|---|---|
| 65 | 2-(4-fluorophenyl)-N-{5-[(7-isopropyl-7H-pyrrolo[2,3-d]pyrimidin-5-yl)carbonyl]pyridin-3-yl}acetamide | LCMS (system 1): R$_t$ = 2.73 min; m/z 418 [M + H]$^+$. |
| 66 | N-{5-[(7-isopropyl-7H-pyrrolo[2,3-d]pyrimidin-5-yl)carbonyl]pyridin-3-yl}-2-[3-(trifluoromethyl)phenyl]acetamide | LCMS (system 9): R$_t$ = 3.22 min; m/z 468 [M + H]$^+$. |
| 67 | N-{5-[(7-isopropyl-7H-pyrrolo[2,3-d]pyrimidin-5-yl)carbonyl]pyridin-3-yl}-2-[4-(trifluoromethyl)phenyl]acetamide | LCMS (system 9): R$_t$ = 3.22 min; m/z 468 [M + H]$^+$. |
| 68 | 2-(3,4-dichlorophenyl)-N-{5-[(7-isopropyl-7H-pyrrolo[2,3-d]pyrimidin-5-yl)carbonyl]pyridin-3-yl}acetamide | LCMS (system 7): R$_t$ = 11.34 min; m/z 468 [M + H]$^+$ |
| 69 | 2-(4-chlorophenyl)-N-{5-[(7-isopropyl-7H-pyrrolo[2,3-d]pyrimidin-5-yl)carbonyl]pyridin-3-yl}acetamide | m/z 434 [M + H]$^+$ |
| 70 | 2-[2-(cyclopropyloxy)phenyl]-N-{5-[(7-isopropyl-7H-pyrrolo[2,3-d]pyrimidin-5-yl)carbonyl]pyridin-3-yl}acetamide | LCMS (system 4): R$_t$ = 3.13 min; m/z 456 [M + H]$^+$ Prep HPLC (method 2) Using [2-(cyclopropyloxy)phenyl]acetic acid (Preparation 160). |
| 71 | 2-(4-cyanophenyl)-N-{5-[(7-isopropyl-7H-pyrrolo[2,3-d]pyrimidin-5-yl)carbonyl]pyridin-3-yl}acetamide | LCMS (system 2): R$_t$ = 1.16 min; m/z 425 [M + H]$^+$ |
| 72 | 2-[4-cyano-3-(trifluoromethyl)phenyl]-N-{5-[(7-isopropyl-7H-pyrrolo[2,3-d]pyrimidin-5-yl)carbonyl]pyridin-3-yl}acetamide | LCMS (system 1): R$_t$ = 2.82 min; m/z 493 [M + H]$^+$ Using [4-cyano-3-(trifluoromethyl)phenyl]acetic acid (Preparation 164). |
| 73 | 2-[4-(cyclopropyloxy)phenyl]-N-{5-[(7-isopropyl-7H-pyrrolo[2,3-d]pyrimidin-5-yl)carbonyl]pyridin-3-yl}acetamide | LCMS (System 3) R$_t$ = 3.05 min; m/z 456 [M + H]$^+$ Using [4-(cyclopropyloxy)phenyl]acetic acid (Preparation 161). Prep method 2 |

-continued

| Example | Name | Data |
|---|---|---|
| 74 | 2-[3-(cyclopyloxy)phenyl]-N-{5-[(7-isopropyl-7H-pyrrolo[2,3-d]pyrimidin-5-yl)carbonyl]pyridin-3-yl}acetamide | LCMS (system 1) $R_t$ = 2.52 min; m/z 456 [M + H]$^+$ Using [3-(cyclopropyloxy)phenyl]acetic acid (Preparation 162). |
| 75 | 2-[3-(hydroxymethyl)phenyl]-N-{5-[(7-isopropyl-7H-pyrrolo[2,3-d]pyrimidin-5-yl)carbonyl]pyridin-3-yl}acetamide | LCMS (System 2): $R_t$ = 1.3 min; m/z 430 [M + H]$^+$ |
| 76 | 2-(4-cyano-3-fluorophenyl)-N-{5-[(7-isopropyl-7H-pyrrolo[2,3-d]pyrimidin-5-yl)carbonyl]pyridin-3-yl}acetamide | LCMS (System 2): $R_t$ = 1.5 min; m/z 443 [M + H]$^+$ |
| 77 | 2-(4-cyano-3-methoxyphenyl)-N-{5-[(7-isopropyl-7H-pyrrolo[2,3-d]pyrimidin-5-yl)carbonyl]pyridin-3-yl}acetamide | LCMS (System 2): $R_t$ = 1.3 min; m/z 455 [M + H]$^+$ |
| 78 | 2-(6-fluoro-1-oxo-1,3-dihydro-2H-isoindol-2-yl)-N-{5-[(7-isopropyl-7H-pyrrolo[2,3-d]pyrimidin-5-yl)carbonyl]pyridin-3-yl}acetamide | LCMS (System 2): $R_t$ = 1.5 min; m/z 473 [M + H]$^+$ |
| 79 | N-{5-[(7-isopropyl-7H-pyrrolo[2,3-d]pyrimidin-5-yl)carbonyl]pyridin-3-yl}-2-(3-pyridin-2-yl-1H-pyrazol-1-yl)acetamide | LCMS (System 2): $R_t$ = 1.2 min; m/z 467 [M + H]+. |
| 80 | 2-(1H-benzimidazol-5-yl)-N-{5-[(7-isopropyl-7H-pyrrolo[2,3-d]pyrimidin-5-yl)carbonyl]pyridin-3-yl}acetamide | LCMS (System 2): $R_t$ = 1.0 min; m/z 440 [M + H]$^+$ |
| 81 | N-{5-[(7-isopropyl-7H-pyrrolo[2,3-d]pyrimidin-5-yl)carbonyl]pyridin-3-yl}-2-quinoxalin-6-ylacetamide | LCMS (System 2): $R_t$ = 1.1 min; m/z 452 [M + H]$^+$ |
| 82 | N-{5-[(7-isopropyl-7H-pyrrolo[2,3-d]pyrimidin-5-yl)carbonyl]pyridin-3-yl}-2-(1,5-naphthyridin-3-yl)acetamide | LCMS (System 9): $R_t$ = 2.63 min; m/z 452 [M + H]$^+$ Using 1,5-naphthyridin-3-ylacetic acid (Preparation 188). |
| 83 | 2-(3-amino-1,2-benzisoxazol-5-yl)-N-{5-[(7-isopropyl-7H-pyrrolo[2,3-d]pyrimidin-5-yl)carbonyl]pyridin-3-yl}acetamide | LCMS (System 9): $R_t$ = 2.76 min; m/z 456 [M + H]$^+$ using (3-amino-benzo[d]isoxazol-5-yl)-acetic acid ethyl ester (Preparation 129) |
| 84 | N-{5-[(7-isopropyl-7H-pyrrolo[2,3-d]pyrimidin-5-yl)carbonyl]pyridin-3-yl}-2-[2-(trifluoromethyl)-1H-benzimidazol-5-yl]acetamide | LCMS (System 9): $R_t$ = 2.90 min; m/z 508 [M + H]$^+$ |
| 85 | 2-imidazo[1,2-a]pyridin-7-yl-N-{5-[(7-isopropyl-7H-pyrrolo[2,3-d]pyrimidin-5-yl)carbonyl]pyridin-3-yl}acetamide | LCMS (System 10): $R_t$ = 2.57 min; m/z 440 [M + H]$^+$ using imidazo[1,2-a]pyridin-7-yl-acetic acid (Preparation 132) |
| 86 | N-{5-[(7-isopropyl-7H-pyrrolo[2,3-d]pyrimidin-5-yl)carbonyl]pyridin-3-yl}-2-(1H-pyrazolo[4,3-b]pyridin-1-yl)acetamide | LCMS (System 9): $R_t$ = 2.54 min; m/z 441 [M + H]$^+$ Using 1H-pyrazolo[4,3-b]pyridin-1-yl)acetic acid (Preparation 190). |
| 87 | N-{5-[(7-isopropyl-7H-pyrrolo[2,3-d]pyrimidin-5-yl)carbonyl]pyridin-3-yl}-2-[3-(methylsulfonyl)phenyl]acetamide | LCMS (System 9): $R_t$ = 2.74 min; m/z 478 [M + H]$^+$ |
| 88 | 2-(4-cyclopropyl-1H-1,2,3-triazol-1-yl)-N-{5-[(7-isopropyl-7H-pyrrolo[2,3-d]pyrimidin-5-yl)carbonyl]pyridin-3-yl}acetamide | LCMS (System 9): $R_t$ = 2.68 min; m/z 431 [M + H]$^+$. Using 4-cyclopropyl-1H-1,2,3-triazol-1-ylacetic acid (Preparation 83). |
| 89 | 2-(1,3-benzoxazol-5-yl)-N-{5-[(7-isopropyl-7H-pyrrolo[2,3-d]pyrimidin-5-yl)carbonyl]pyridin-3-yl}acetamide | LCMS (System 9): $R_t$ = 2.79 min; m/z 441.1 [M + H]$^+$ |
| 90 | 2-(3-cyclopropyl-1H-pyrazol-1-yl)-N-{5-[(7-isopropyl-7H-pyrrolo[2,3-d]pyrimidin-5-yl)carbonyl]pyridin-3-yl}acetamide | LCMS (System 9): $R_t$ = 2.75 min; m/z 430 [M + H]$^+$ (3-cyclopropyl-1H-pyrazol-1-yl)acetic acid (Preparation 80). |
| 91 | 2-[5-(cyclopropyloxy)pyridin-3-yl]-N-{5-[(7-isopropyl-7H-pyrrolo[2,3-d]pyrimidin-5-yl)carbonyl]pyridin-3-yl}acetamide | LCMS (system 3) $R_t$ = 2.36 min; m/z 457 [M + H]$^+$ Prep method 2 Using [5-(cyclopropyloxy)pyridin-3-yl]acetic acid (Preparation 163). |
| 92 | 2-(2,3-dihydro-1-benzofuran-5-yl)-N-{5-[(7-isopropyl-7H-pyrrolo[2,3-d]pyrimidin-5-yl)carbonyl]pyridin-3-yl}acetamide | LCMS (system 3): $R_t$ = 2.91 min; m/z 442 [M + H]$^+$ Prep HPLC (method 1) |

| Example | Name | Data |
|---|---|---|
| 93 | 2-(2H-indazol-2-yl)-N-{5-[(7-isopropyl-7H-pyrrolo[2,3-d]pyrimidin-5-yl)carbonyl]pyridin-3-yl}acetamide | LCMS (system 3): $R_t$ = 2.74 min; m/z 440 [M + H]$^+$ Prep HPLC (method 1) |
| 94 | 2-(5-fluoro-2H-indazol-2-yl)-N-{5-[(7-isopropyl-7H-pyrrolo[2,3-d]pyrimidin-5-yl)carbonyl]pyridin-3-yl}acetamide | LCMS (system 9): $R_t$ = 2.96 min; m/z 458 [M + H]$^+$ Using -(5-fluoro-2H-indazol-2-yl)acetic acid (Preparation 174). |
| 95 | 2-(5-fluoro-1H-indazol-1-yl)-N-{5-[(7-isopropyl-7H-pyrrolo[2,3-d]pyrimidin-5-yl)carbonyl]pyridin-3-yl}acetamide | LCMS (system 9): $R_t$ = 2.97 min; m/z 458 [M + H]$^+$ Using (5-fluoro-1H-indazol-1-yl)acetic acid (Preparation 172). |
| 96 | N-{5-[(7-isopropyl-7H-pyrrolo[2,3-d]pyrimidin-5-yl)carbonyl]pyridin-3-yl}-2-[5-methyl-3-(trifluoromethyl)-1H-pyrazol-1-yl]acetamide | LCMS (system 8): $R_t$ = 1.62 min; m/z 472 [M + H]$^+$ |
| 97 | N-{5-[(7-isopropyl-7H-pyrrolo[2,3-d]pyrimidin-5-yl)carbonyl]pyridin-3-yl}-2-[3-(trifluoromethyl)-1H-pyrazol-1-yl]acetamide | LCMS (system 3): $R_t$ = 2.97 min; m/z 458 [M + H]$^+$ Prep HPLC (method 1) |
| 98 | 2-(5-chloropyridin-2-yl)-N-{5-[(7-isopropyl-7H-pyrrolo[2,3-d]pyrimidin-5-yl)carbonyl]pyridin-3-yl}acetamide | LCMS (system 9): $R_t$ = 2.86 min; m/z 435 [M + H]$^+$ Using (5-chloropyridin-2-yl)acetic acid (Preparation 90). |
| 99 | 2-(1H-indazol-6-yl)-N-{5-[(7-isopropyl-7H-pyrrolo[2,3-d]pyrimidin-5-yl)carbonyl]pyridin-3-yl}acetamide | m/z 440 [M + H]$^+$ Using 1H-indazol-6-ylacetic acid (Preparation 182). |
| 100 | N-{5-[(7-isopropyl-7H-pyrrolo[2,3-d]pyrimidin-5-yl)carbonyl]pyridin-3-yl}-2-quinolin-7-ylacetamide | LCMS (system 7): $R_t$ = 8.73 min; m/z 451 [M + H]$^+$ |
| 101 | 2-(7-fluoro-2H-indazol-2-yl)-N-{5-[(7-isopropyl-7H-pyrrolo[2,3-d]pyrimidin-5-yl)carbonyl]pyridin-3-yl}acetamide | LCMS (system 9): $R_t$ = 2.95 min; m/z 458 [M + H]$^+$ Using (7-fluoro-2H-indazol-2-yl)acetic acid (Preparation 178). |
| 102 | N-{5-[(7-isopropyl-7H-pyrrolo[2,3-d]pyrimidin-5-yl)carbonyl]pyridin-3-yl}-2-(1H-pyrazolo[3,4-b]pyridin-1-yl)acetamide | LCMS (system 9): $R_t$ = 2.72 min; m/z 441 [M + H]$^+$ Using 1H-pyrazolo[3,4-b]pyridin-1-yl)acetic acid (Preparation 180). |
| 103 | 2-(1H-indazol-1-yl)-N-{5-[(7-isopropyl-7H-pyrrolo[2,3-d]pyrimidin-5-yl)carbonyl]pyridin-3-yl}acetamide | LCMS (system 3): $R_t$ = 2.82 min; m/z 440 [M + H]$^+$ Prep HPLC (method 1) |
| 104 | 2-(3-isopropyl-5-methyl-1H-pyrazol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.65 min; m/z 446 [M + H]$^+$ Using (3-isopropyl-5-methyl-1H-pyrazol-1-yl)acetic acid (Preparation 167). |
| 105 | N-{5-[(7-isopropyl-7H-pyrrolo[2,3-d]pyrimidin-5-yl)carbonyl]pyridin-3-yl}-2-(4-isopropyl-1H-1,2,3-triazol-1-yl)acetamide | LCMS (system 8): $R_t$ = 1.52 min; m/z 433 [M + H]$^+$ |
| 106 | N-{5-[(7-isopropyl-7H-pyrrolo[2,3-d]pyrimidin-5-yl)carbonyl]pyridin-3-yl}-2-[4-(trifluoromethyl)-1H-1,2,3-triazol-1-yl]acetamide | LCMS (system 9): $R_t$ = 2.98 min; m/z 459 [M + H]$^+$ Using [4-(trifluoromethyl)-1H-1,2,3-triazol-1-yl]acetic acid (Preparation 81). |
| 107 | 2-(7-fluoro-1H-indazol-1-yl)-N-{5-[(7-isopropyl-7H-pyrrolo[2,3-d]pyrimidin-5-yl)carbonyl]pyridin-3-yl}acetamide | LCMS (system 9): $R_t$ = 2.96 min; m/z 458 [M + H]$^+$ Using (7-fluoro-1H-indazol-1-yl)acetic acid (Preparation 176). |
| 108 | 2-(2H-benzotriazol-2-yl)-N-{5-[(7-isopropyl-7H-pyrrolo[2,3-d]pyrimidin-5-yl)carbonyl]pyridin-3-yl}acetamide | LCMS (system 8): $R_t$ = 1.57 min; m/z 441 [M + H]$^+$ |
| 109 | 2-(7-fluoro-2-methyl-1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.64 min; m/z 471 [M + H]$^+$ |
| 110 | 2-(5-chloro-2-methyl-1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.69 min; m/z 487 [M + H]$^+$ |
| 111 | 2-(1H-indol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.66 min; m/z 439 [M + H]$^+$ |

| Example | Name | Data |
|---|---|---|
| 112 | N-{5-[(7-isopropyl-7H-pyrrolo[2,3-d]pyrimidin-5-yl)carbonyl]pyridin-3-yl}-2-[1-isopropyl-5-(trifluoromethyl)-1H-pyrazol-4-yl]acetamide | LCMS (system 9): $R_t$ = 3.13 min; m/z 500 [M + H]$^+$ Using 1-isopropyl-5-(trifluoromethyl)-1H-pyrazol-4-yl]acetic acid (Preparation 185). |
| 113 | N-{5-[(7-isopropyl-7H-pyrrolo[2,3-d]pyrimidin-5-yl)carbonyl]pyridin-3-yl}-2-(3-methyl-1H-pyrazol-1-yl)acetamide | LCMS (system 8): $R_t$ = 1.50 min; m/z 404 [M + H]$^+$ |
| 114 | N-{5-[(7-isopropyl-7H-pyrrolo[2,3-d]pyrimidin-5-yl)carbonyl]pyridin-3-yl}-2-(1H-pyrazol-1-yl)acetamide | LCMS (system 8): $R_t$ = 1.45 min; m/z 390 [M + H]$^+$ |
| 115 | 2-(3,5-dimethyl-1H-pyrazol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.55 min; m/z 418 [M + H]$^+$ |
| 116 | N-{5-[(7-isopropyl-7H-pyrrolo[2,3-d]pyrimidin-5-yl)carbonyl]pyridin-3-yl}-2-(2-methyl-1H-indol-3-yl)acetamide | LCMS (system 8): $R_t$ = 1.62 min; m/z 453 [M + H]$^+$ |
| 117 | N-{5-[(7-isopropyl-7H-pyrrolo[2,3-d]pyrimidin-5-yl)carbonyl]pyridin-3-yl}-2-(5-methoxy-1H-indol-3-yl)acetamide | LCMS (system 8): $R_t$ = 1.57 min; m/z 469 [M + H]$^+$ |
| 118 | N-{5-[(7-isopropyl-7H-pyrrolo[2,3-d]pyrimidin-5-yl)carbonyl]pyridin-3-yl}-2-pyridin-3-ylacetamide | LCMS (system 8): $R_t$ = 1.35 min; m/z 401 [M + H]$^+$ |
| 119 | 2-(5-chloro-1H-benzotriazol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.61 min; m/z 475 [M + H]$^+$ |
| 120 | N-{5-[(7-isopropyl-7H-pyrrolo[2,3-d]pyrimidin-5-yl)carbonyl]pyridin-3-yl}-2-[3-(2-thienyl)-1H-pyrazol-1-yl]acetamide | LCMS (system 8): $R_t$ = 1.61 min; m/z 472 [M + H]$^+$ |
| 121 | N-{5-[(7-isopropyl-7H-pyrrolo[2,3-d]pyrimidin-5-yl)carbonyl]pyridin-3-yl}-2-(7-methylimidazo[1,2-a]pyrimidin-2-yl)acetamide | LCMS (system 8): $R_t$ = 1.37 min; m/z 455 [M + H]$^+$ |
| 122 | 2-(2,6-dimethyl-9H-purin-9-yl)-N-{5-[(7-isopropyl-7H-pyrrolo[2,3-d]pyrimidin-5-yl)carbonyl]pyridin-3-yl}acetamide | LCMS (system 8): $R_t$ = 1.43 min; m/z 470 [M + H]$^+$ |
| 123 | N-{5-[(7-isopropyl-7H-pyrrolo[2,3-d]pyrimidin-5-yl)carbonyl]pyridin-3-yl}-2-(6-nitro-1H-indazol-1-yl)acetamide | LCMS (system 8): $R_t$ = 1.60 min; m/z 485 [M + H]$^+$ |
| 124 | 2-(5-chloro-1-methyl-1H-indazol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.73 min; m/z 488 [M + H]$^+$ J. Med Chem. 1992, 35, 2155-2165 |
| 125 | 2-(5-fluoro-2-methyl-1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.63 min; m/z 471 [M + H]$^+$ |
| 126 | 2-(6-chloroimidazo[1,2-a]pyridin-2-yl)-N-{5-[(7-isopropyl-7H-pyrrolo[2,3-d]pyrimidin-5-yl)carbonyl]pyridin-3-yl}acetamide | LCMS (system 8): $R_t$ = 1.45 min; m/z 474 [M + H]$^+$ |
| 127 | N-{5-[(7-isopropyl-7H-pyrrolo[2,3-d]pyrimidin-5-yl)carbonyl]pyridin-3-yl}-2-(2-methyl-1H-benzimidazol-1-yl)acetamide | LCMS (system 8): $R_t$ = 1.36 min; m/z 454 [M + H]$^+$ |
| 128 | 2-imidazo[1,2-a]pyridin-2-yl-N-{5-[(7-isopropyl-7H-pyrrolo[2,3-d]pyrimidin-5-yl)carbonyl]pyridin-3-yl}acetamide | LCMS (system 8): $R_t$ = 1.31 min; m/z 440 [M + H]$^+$ |
| 129 | N-{5-[(7-isopropyl-7H-pyrrolo[2,3-d]pyrimidin-5-yl)carbonyl]pyridin-3-yl}-2-(5-methoxy-1H-pyrrolo[3,2-b]pyridin-1-yl)acetamide | LCMS (system 8): $R_t$ = 1.49 min; m/z 470 [M + H]$^+$ |
| 130 | N-{5-[(7-isopropyl-7H-pyrrolo[2,3-d]pyrimidin-5-yl)carbonyl]pyridin-3-yl}-2-(5-methyl-1H-pyrazol-1-yl)acetamide | LCMS (system 8): $R_t$ = 1.49 min; m/z 404 [M + H]$^+$ |
| 131 | N-{5-[(7-isopropyl-7H-pyrrolo[2,3-d]pyrimidin-5-yl)carbonyl]pyridin-3-yl}-2-(7-methyl-1H-benzimidazol-1-yl)acetamide | LCMS (system 8): $R_t$ = 1.43 min; m/z 454 [M + H]$^+$ |
| 132 | 2-(1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.59 min; m/z 439 [M + H]$^+$ |

-continued

| Example | Name | Data |
|---------|------|------|
| 133 | 2-(1H-benzimidazol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.40 min; m/z 440 [M + H]$^+$ |
| 134 | N-{5-[(7-isopropyl-7H-pyrrolo[2,3-d]pyrimidin-5-yl)carbonyl]pyridin-3-yl}-2-(3-methyl-1H-pyrazol-5-yl)acetamide | LCMS (system 8): $R_t$ = 1.45 min; m/z 404 [M + H]$^+$ |
| 135 | 2-(1H-benzotriazol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.52 min; m/z 441 [M + H]$^+$ |
| 136 | N-{5-[(7-isopropyl-7H-pyrrolo[2,3-d]pyrimidin-5-yl)carbonyl]pyridin-3-yl}-2-(1-methyl-1H-indol-3-yl)acetamide | LCMS (system 8): $R_t$ = 1.68 min; m/z 453 [M + H]$^+$ |
| 137 | N-{5-[(7-isopropyl-7H-pyrrolo[2,3-d]pyrimidin-5-yl)carbonyl]pyridin-3-yl}-2-(4-phenyl-1H-pyrrol-2-yl)acetamide | LCMS (system 8): $R_t$ = 1.66 min; m/z 465 [M + H]$^+$ |
| 138 | 2-(2-ethyl-3H-imidazo[4,5-b]pyridin-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.49 min; m/z 469 [M + H]$^+$ |
| 139 | 2-(5-chloro-1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.67 min; m/z 473 [M + H]$^+$ |
| 140 | N-{5-[(7-isopropyl-7H-pyrrolo[2,3-d]pyrimidin-5-yl)carbonyl]pyridin-3-yl}-2-(1-phenyl-1H-pyrrol-3-yl)acetamide | LCMS (system 8): $R_t$ = 1.71 min; m/z 465 [M + H]$^+$ Can be prepared by a similar method to Harrak, Y. et al. Bioorganic & Medicinal Chemistry (2007), 15(14), 4876-4890. |
| 141 | N-{5-[(7-isopropyl-7H-pyrrolo[2,3-d]pyrimidin-5-yl)carbonyl]pyridin-3-yl}-2-(5-methyl-1H-indol-3-yl)acetamide | LCMS (system 8): $R_t$ = 1.63 min; m/z 453 [M + H]$^+$ |
| 142 | 2-(2-ethyl-1H-benzimidazol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.37 min; m/z 468 [M + H]$^+$ |
|  | 2-imidazo[1,2-a]pyrimidin-2-yl-N-{5-[(7-isopropyl-7H-pyrrolo[2,3-d]pyrimidin-5-yl)carbonyl]pyridin-3-yl}acetamide | LCMS (system 8): $R_t$ = 1.38 min; m/z 441 [M + H]$^+$ |
| 144 | 2-(1H-indazol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.55 min; m/z 440 [M + H]$^+$ |
| 145 | 2-(5-fluoro-7-methoxy-1H-indol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.67 min; m/z 487 [M + H]$^+$ |
| 146 | 2-(1-benzyl-1H-1,2,3-triazol-4-yl)-N-{5-[(7-isopropyl-7H-pyrrolo[2,3-d]pyrimidin-5-yl)carbonyl]pyridin-3-yl}acetamide | LCMS (system 8): $R_t$ = 1.57 min; m/z 481 [M + H]$^+$ |
| 147 | 2-(6-chloro-1-methyl-1H-indazol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.72 min; m/z 488 [M + H]$^+$ Using -(6-chloro-1-methyl-1H-indazol-3-yl)acetic acid (Preparation 170). |
| 148 | 2-(7-chloro-1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.67 min; m/z 473 [M + H]$^+$ |
| 149 | N-{5-[(7-isopropyl-7H-pyrrolo[2,3-d]pyrimidin-5-yl)carbonyl]pyridin-3-yl}-2-(5-methyl-4-phenyl-1H-pyrazol-1-yl)acetamide | LCMS (system 8): $R_t$ = 1.68 min; m/z 480 [M + H]$^+$ |
| 150 | 2-(5-bromopyridin-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.60 min; m/z 479 [M + H]$^+$ |
| 151 | N-{5-[(7-isopropyl-7H-pyrrolo[2,3-d]pyrimidin-5-yl)carbonyl]pyridin-3-yl}-2-pyridin-2-ylacetamide | LCMS (system 8): $R_t$ = 1.41 min; m/z 401 [M + H]$^+$ |
| 152 | N-{5-[(7-isopropyl-7H-pyrrolo[2,3-d]pyrimidin-5-yl)carbonyl]pyridin-3-yl}-2-(6-methoxypyridin-3-yl)acetamide | LCMS (system 8): $R_t$ = 1.55 min; m/z 431 [M + H]$^+$ |
| 153 | 2-(2,5-dimethyl-1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.67 min; m/z 467 [M + H]$^+$ |

| Example | Name | Data |
|---|---|---|
| 154 | N-{5-[(7-isopropyl-7H-pyrrolo[2,3-d]pyrimidin-5-yl)carbonyl]pyridin-3-yl}-2-(6-methylpyridin-3-yl)acetamide | LCMS (system 8): $R_t$ = 1.33 min; m/z 415 [M + H]$^+$ |
| 155 | N-{5-[(7-isopropyl-7H-pyrrolo[2,3-d]pyrimidin-5-yl)carbonyl]pyridin-3-yl}-2-(2-methylquinolin-7-yl)acetamide | LCMS (system 8): $R_t$ = 1.40 min; m/z 465 [M + H]$^+$ Using (2-methylquinolin-7-yl)acetic acid (Preparation 165). |
| 156 | N-{5-[(7-isopropyl-7H-pyrrolo[2,3-d]pyrimidin-5-yl)carbonyl]pyridin-3-yl}-2-(5-methoxy-2-methyl-1H-indol-3-yl)acetamide | LCMS (system 8): $R_t$ = 1.60 min; m/z 483 [M + H]$^+$ |
| 157 | N-{5-[(7-isopropyl-7H-pyrrolo[2,3-d]pyrimidin-5-yl)carbonyl]pyridin-3-yl}-2-tetrazolo[1,5-b]pyridazin-6-ylacetamide | LCMS (system 8): $R_t$ = 1.46 min; m/z 443 [M + H]$^+$. (can be prepared via a similar method to WO2010/129379, 11 Nov. 2010) |
| 158 | 2-(5-hydroxy-1H-indol-3-yl)-N-{5-[(7-isopropyl-7H-pyrrolo[2,3-d]pyrimidin-5-yl)carbonyl]pyridin-3-yl}acetamide | LCMS (system 8): $R_t$ = 1.45 min; m/z 455 [M + H]$^+$ |
| 159 | N-{5-[(7-isopropyl-7H-pyrrolo[2,3-d]pyrimidin-5-yl)carbonyl]pyridin-3-yl}-2-(5H-pyrrolo[2,3-b]pyrazin-7-yl)acetamide | LCMS (system 8): $R_t$ = 1.47 min; m/z 441 [M + H]$^+$ |
| 160 | 2-(5,6-dimethyl-1H-benzimidazol-1-yl)-N-{5-[(7-isopropyl-7H-pyrrolo[2,3-d]pyrimidin-5-yl)carbonyl]pyridin-3-yl}acetamide | LCMS (system 8): $R_t$ = 1.43 min; m/z 468 [M + H]$^+$ |
| 161 | N-{5-[(7-isopropyl-7H-pyrrolo[2,3-d]pyrimidin-5-yl)carbonyl]pyridin-3-yl}-2-(4-pyridin-2-yl-1H-1,2,3-triazol-1-yl)acetamide | LCMS (system 8): $R_t$ = 1.48 min; m/z 468 [M + H]$^+$ |
| 162 | N-{5-[(7-isopropyl-7H-pyrrolo[2,3-d]pyrimidin-5-yl)carbonyl]pyridin-3-yl}-2-(4-methyl-1H-1,2,3-triazol-1-yl)acetamide | LCMS (system 8): $R_t$ = 1.43 min; m/z 405 [M + H]$^+$ |
| 163 | N-{5-[(7-isopropyl-7H-pyrrolo[2,3-d]pyrimidin-5-yl)carbonyl]pyridin-3-yl}-2-(5-methyl-3-phenyl-1H-pyrazol-4-yl)acetamide | LCMS (system 8): $R_t$ = 1.55 min; m/z 480 [M + H]$^+$ |
| 164 | N-{5-[(7-isopropyl-7H-pyrrolo[2,3-d]pyrimidin-5-yl)carbonyl]pyridin-3-yl}-2-[2-(methylthio)pyrimidin-5-yl]acetamide | LCMS (system 8): $R_t$ = 1.55 min; m/z 448 [M + H]$^+$ can be prepared via a similar method to Smrz, R. et al. Collection of Czechoslovak Chemical Communications (1976), 41(9), 2771-87 |
| 165 | N-{5-[(7-isopropyl-7H-pyrrolo[2,3-d]pyrimidin-5-yl)carbonyl]pyridin-3-yl}-2-pyrimidin-2-ylacetamide | LCMS (system 8): $R_t$ = 1.44 min; m/z 402 [M + H]$^+$ |

Example 166

2-(5-Cyanopyridin-2-yl)-N-{5-[(7-isopropyl-7H-pyrrolo[2,3-d]pyrimidin-5-yl)carbonyl]pyridin-3-yl}acetamide

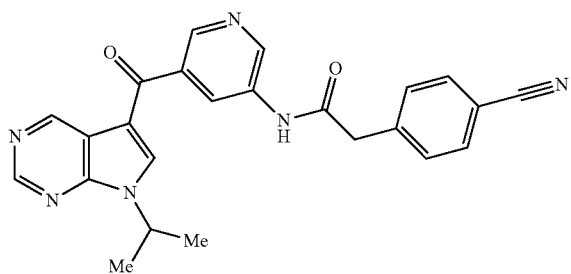 [SMILES: CC(C)n1cc(C(=O)c2cncc(NC(=O)Cc3ccc(C#N)cc3)c2)c2cncnc21]

Zinc cyanide (28 mg, 0.23 mmol) was added to 2-(5-Bromo-pyridin-2-yl)-N-[5-(7-(propan-2-yl)-7H-pyrrolo[2,3-d]pyrimidine-5-carbonyl)-pyridin-3-yl]-acetamide (Example 317, 75 mg, 0.16 mmol) in DMF (2 mL) and the mixture was degassed with argon for 10 minutes. Then tris(dibenzylideneacetone)dipalladium (3 mg, 0.003 mmol) and 1,1'-bis(diphenylphosphino)ferrocene (7 mg, 0.012 mmol) were added and the mixture was heated at 100° C. for 40 mins under microwave irradiation. The mixture was diluted with EtOAc (5 mL) and washed with water (2 mL), brine (2 mL) and dried over sodium sulphate. The filtrate was evaporated in vacuo and purified by preparative TLC (3% MeOH in DCM) to afford the title compound as a light brown solid in 18% yield, 12 mg.

$^1$H NMR (400 MHz, DMSO) δ: 1.55 (d, 6H), 4.07 (s, 2H), 5.09 (m, 1H), 7.67 (d, 1H), 8.30 (m, 1H), 8.44 (s, 1H), 8.52 (s, 1H), 8.74 (d, 1H), 8.98-8.99 (m, 3H), 9.44 (s, 1H), 10.79 (s, 1H);

LCMS (System 9): $R_t$=2.75 min; m/z 426 [M+H]$^+$.

Example 167

2-[5-Fluoro-2-(trifluoromethyl)phenyl]-N-{5-[(7-methyl-7H-pyrrolo[2,3-d]pyrimidin-5-yl)carbonyl]pyridin-3-yl}acetamide

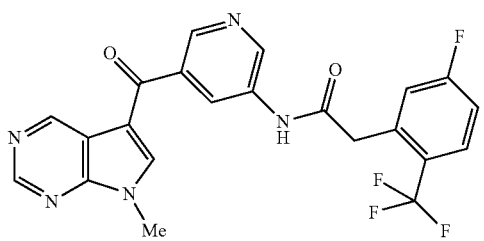 [SMILES: Cn1cc(C(=O)c2cncc(NC(=O)Cc3cc(F)ccc3C(F)(F)F)c2)c2cncnc21]

1-(3-Dimethylaminopropyl)-3-ethylcarbodiimide HCl (150 μL, 0.5M in DMF) was added to 5-fluoro-2-(trifluoromethyl)phenylacetic acid (90 μmol), N-methylmorpholine (25 μL, 150 μmol), 1-hydroxybenzotriazole (15 μmol, 0.05M in DMF) and (5-aminopyridin-3-yl)(7-methyl-7H-pyrrolo[2,3-d]pyrimidin-5-yl)methanone (Preparation 110, 75 μmol, 0.25 M in DMF). The mixture was stirred at 50° C. for 2 hours and then evaporated in vacuo and purified by prep-HPLC (method 4) to afford the title compound.

LCMS (system 5): $R_t$=2.66 min; m/z 458 [M+H]$^+$

The following Examples were prepared according to the method described above for Example 167 starting from (5-aminopyridin-3-yl)(7-methyl-7H-pyrrolo[2,3-d]pyrimidin-5-yl)methanone (Preparation 110) and the appropriate acid.

| Example | Name | Data |
|---|---|---|
| 168 | 2-(3-methylphenyl)-N-{5-[(7-methyl-7H-pyrrolo[2,3-d]pyrimidin-5-yl)carbonyl]pyridin-3-yl}acetamide | LCMS (system 5): $R_t$ = 2.53 min; m/z 386 [M + H]$^+$ |
| 169 | N-{5-[(7-methyl-7H-pyrrolo[2,3-d]pyrimidin-5-yl)carbonyl]pyridin-3-yl}-2-[2-(trifluoromethyl)phenyl]acetamide | LCMS (system 5): $R_t$ = 2.61 min; m/z 440 [M + H]$^+$ |
| 170 | 2-(3,5-difluorophenyl)-N-{5-[(7-methyl-7H-pyrrolo[2,3-d]pyrimidin-5-yl)carbonyl]pyridin-3-yl}acetamide | LCMS (system 5): $R_t$ = 2.52 min; m/z 408 [M + H]$^+$ |
| 171 | N-{5-[(7-methyl-7H-pyrrolo[2,3-d]pyrimidin-5-yl)carbonyl]pyridin-3-yl}-2-(2,4,6-trifluorophenyl)acetamide | LCMS (system 5): $R_t$ = 2.50 min; m/z 426 [M + H]$^+$ |
| 172 | N-{5-[(7-methyl-7H-pyrrolo[2,3-d]pyrimidin-5-yl)carbonyl]pyridin-3-yl}-2-(2,3,6-trifluorophenyl)acetamide | LCMS (system 5): $R_t$ = 2.49 min; m/z 426 [M + H]$^+$ |
| 173 | N-{5-[(7-methyl-7H-pyrrolo[2,3-d]pyrimidin-5-yl)carbonyl]pyridin-3-yl}-2-[4-(methylsulfonyl)phenyl]acetamide | LCMS (system 5): $R_t$ = 2.13 min; m/z 450 [M + H]$^+$ |
| 174 | 2-[3-fluoro-4-(trifluoromethyl)phenyl]-N-{5-[(7-methyl-7H-pyrrolo[2,3-d]pyrimidin-5-yl)carbonyl]pyridin-3-yl}acetamide | LCMS (system 5): $R_t$ = 2.77 min; m/z 458 [M + H]$^+$ |
| 175 | 2-(3-methoxyphenyl)-N-{5-[(7-methyl-7H-pyrrolo[2,3-d]pyrimidin-5-yl)carbonyl]pyridin-3-yl}acetamide | LCMS: $R_t$ = 2.34 min; m/z 402 [M + H]$^+$ |
| 176 | N-{5-[(7-methyl-7H-pyrrolo[2,3-d]pyrimidin-5-yl)carbonyl]pyridin-3-yl}-2-[3-(trifluoromethoxy)phenyl]acetamide | LCMS (system 5): $R_t$ = 2.76 min; m/z 456 [M + H]$^+$ |
| 177 | N-{5-[(7-methyl-7H-pyrrolo[2,3-d]pyrimidin-5-yl)carbonyl]pyridin-3-yl}-2-(2,3,5-trifluorophenyl)acetamide | LCMS (system 5): $R_t$ = 2.54 min; m/z 426 [M + H]$^+$ |
| 178 | N-{5-[(7-methyl-7H-pyrrolo[2,3-d]pyrimidin-5-yl)carbonyl]pyridin-3-yl}-2-(2-methylquinolin-7-yl)acetamide | LCMS (system 5): $R_t$ = 1.95 min; m/z 437 [M + H]$^+$ Using (2-methylquinolin-7-yl)acetic acid (Preparation 165). |
| 179 | N-{5-[(7-methyl-7H-pyrrolo[2,3-d]pyrimidin-5-yl)carbonyl]pyridin-3-yl}-2-phenylacetamide | LCMS (system 5): $R_t$ = 2.37 min; m/z 372 [M + H]$^+$ |
| 180 | 2-(2-chloro-6-fluorophenyl)-N-{5-[(7-methyl-7H-pyrrolo[2,3-d]pyrimidin-5-yl)carbonyl]pyridin-3-yl}acetamide | LCMS (system 5): $R_t$ = 2.51 min; m/z 424 [M + H]$^+$ |
| 181 | 2-(4-methoxyphenyl)-N-{5-[(7-methyl-7H-pyrrolo[2,3-d]pyrimidin-5-yl)carbonyl]pyridin-3-yl}acetamide | LCMS: $R_t$ = 2.22 min; m/z 402 [M + H]$^+$ |
| 182 | N-{5-[(7-methyl-7H-pyrrolo[2,3-d]pyrimidin-5-yl)carbonyl]pyridin-3-yl}-2-{4-[(trifluoromethyl)thio]phenyl}acetamide | LCMS (system 5): $R_t$ = 2.90 min; m/z 472 [M + H]$^+$ |
| 183 | 2-biphenyl-4-yl-N-{5-[(7-methyl-7H-pyrrolo[2,3-d]pyrimidin-5-yl)carbonyl]pyridin-3-yl}acetamide | LCMS (system 6): $R_t$ = 2.67 min; m/z 448 [M + H]$^+$ |
| 184 | N-{5-[(7-methyl-7H-pyrrolo[2,3-d]pyrimidin-5-yl)carbonyl]pyridin-3-yl}-2-(2,4,5-trifluorophenyl)acetamide | LCMS (system 5): $R_t$ = 2.54 min; m/z 426 [M + H]$^+$ |

-continued

| Example | Name | Data |
|---|---|---|
| 185 | N-{5-[(7-methyl-7H-pyrrolo[2,3-d]pyrimidin-5-yl)carbonyl]pyridin-3-yl}-2-{3-[(trifluoromethyl)thio]phenyl}acetamide | LCMS (system 5): $R_t$ = 2.86 min; m/z 472 [M + H]$^+$ |
| 186 | 2-(4-methylphenyl)-N-{5-[(7-methyl-7H-pyrrolo[2,3-d]pyrimidin-5-yl)carbonyl]pyridin-3-yl}acetamide | LCMS (system 5): $R_t$ = 2.53 min; m/z 386 [M + H]$^+$ |
| 187 | N-{5-[(7-methyl-7H-pyrrolo[2,3-d]pyrimidin-5-yl)carbonyl]pyridin-3-yl}-2-(3,4,5-trifluorophenyl)acetamide | LCMS (system 5): $R_t$ = 2.62 min; m/z 426 [M + H]$^+$ |
| 188 | 2-(2,4-dimethylphenyl)-N-{5-[(7-methyl-7H-pyrrolo[2,3-d]pyrimidin-5-yl)carbonyl]pyridin-3-yl}acetamide | LCMS (system 5): $R_t$ = 2.64 min; m/z 400 [M + H]$^+$ |
| 189 | 2-(2,3-dihydro-1-benzofuran-5-yl)-N-{5-[(7-methyl-7H-pyrrolo[2,3-d]pyrimidin-5-yl)carbonyl]pyridin-3-yl}acetamide | LCMS (system 5): $R_t$ = 2.37 min; m/z 414 [M + H]$^+$ |
| 190 | 2-(2,5-difluorophenyl)-N-{5-[(7-methyl-7H-pyrrolo[2,3-d]pyrimidin-5-yl)carbonyl]pyridin-3-yl}acetamide | LCMS (system 5): $R_t$ = 2.44 min; m/z 408 [M + H]$^+$ |
| 191 | 2-(2,4-difluorophenyl)-N-{5-[(7-methyl-7H-pyrrolo[2,3-d]pyrimidin-5-yl)carbonyl]pyridin-3-yl}acetamide | LCMS (system 5): $R_t$ = 2.46 min; m/z 408 [M + H]$^+$ |
| 192 | 2-[2-fluoro-3-(trifluoromethyl)phenyl]-N-{5-[(7-methyl-7H-pyrrolo[2,3-d]pyrimidin-5-yl)carbonyl]pyridin-3-yl}acetamide | LCMS (system 5): $R_t$ = 2.72 min; m/z 458 [M + H]$^+$ |
| 193 | 2-(2,6-difluorophenyl)-N-{5-[(7-methyl-7H-pyrrolo[2,3-d]pyrimidin-5-yl)carbonyl]pyridin-3-yl}acetamide | LCMS (system 5): $R_t$ = 2.41 min; m/z 408 [M + H]$^+$ |
| 194 | N-{5-[(7-methyl-7H-pyrrolo[2,3-d]pyrimidin-5-yl)carbonyl]pyridin-3-yl}-2-[3-(trifluoromethyl)phenyl]acetamide | LCMS (System 2): Rt = 1.6 min; m/z 440 [M + H]$^+$ |
| 195 | 2-(3,4-difluorophenyl)-N-{5-[(7-methyl-7H-pyrrolo[2,3-d]pyrimidin-5-yl)carbonyl]yridine-3-yl}acetamide | LCMS (System 2): Rt = 1.5 min; m/z 408 [M + H]$^+$ |
| 196 | N-{5-[(7-methyl-7H-pyrrolo[2,3-d]pyrimidin-5-yl)carbonyl]yridine-3-yl}-2-[4-(trifluoromethoxy)phenyl]acetamide | LCMS (System 2): Rt = 1.6 min; m/z 456 [M + H]$^+$ |
| 197 | 2-(3-chlorophenyl)-N-{5-[(7-methyl-7H-pyrrolo[2,3-d]pyrimidin-5-yl)carbonyl]yridine-3-yl}acetamide | LCMS (System 2): $R_t$ = 1.5 min; m/z 406 [M + H]$^+$ |

Example 198

3-(2-chlorophenyl)-N-{5-[(7-methyl-7H-pyrrolo[2,3-d]pyrimidin-5-yl)carbonyl]pyridin-3-yl}propanamide

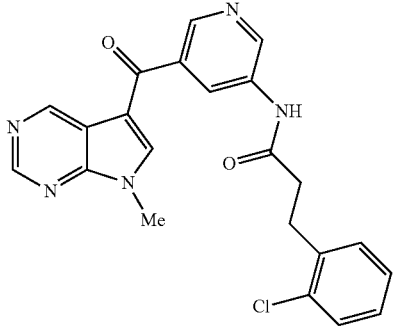 [SMILES: Cn1cc(C(=O)c2cncc(NC(=O)CCc3ccccc3Cl)c2)c2cncnc21]

The title compound was prepared according to the method described above for Example 167 starting from (5-aminopyridin-3-yl)(7-methyl-7H-pyrrolo[2,3-d]pyrimidin-5-yl)methanone (Preparation 110) and 3-(2-chlorophenyl)propanoic acid.

LCMS (system 5): $R_t$=2.66 min; m/z 420 [M+H]$^+$

The following Examples were prepared according to Method b (Example 1 using DIPEA) as described above starting from (5-aminopyridin-3-yl)(7-tert-butyl-7H-pyrrolo[2,3-d]pyrimidin-5-yl)methanone (Preparation 31) and the appropriate acids.

| Example | Name | Data |
|---|---|---|
| 199 | N-{5-[(7-tert-butyl-7H-pyrrolo[2,3-d]pyrimidin-5-yl)carbonyl]pyridin-3-yl}-2-(2-cyclopropyl-1,3-oxazol-4-yl)acetamide | LCMS (system 9): $R_t$ = 3.16 min; m/z 445 [M + H]$^+$ using (2-cyclopropyl-1,3-oxazol-4-yl)acetic acid (Preparation 155). |

-continued

| Example | Name | Data |
|---|---|---|
| 200 | N-{5-[(7-tert-butyl-7H-pyrrolo[2,3-d]pyrimidin-5-yl)carbonyl]pyridin-3-yl}-2-[3-(methylsulfonyl)phenyl]acetamide | LCMS (system 9): $R_t$ = 2.87 min; m/z 492 [M + H]$^+$ |
| 201 | N-{5-[(7-tert-butyl-7H-pyrrolo[2,3-d]pyrimidin-5-yl)carbonyl]pyridin-3-yl}-2-(1,3-dimethyl-1H-pyrazol-4-yl)acetamide | LCMS (system 9): $R_t$ = 2.76 min; m/z 432[M + H]$^+$ |
| 202 | N-{5-[(7-tert-butyl-7H-pyrrolo[2,3-d]pyrimidin-5-yl)carbonyl]pyridin-3-yl}-2-(1-methyl-1H-pyrazol-4-yl)acetamide | LCMS (system 9): $R_t$ = 2.73 min; m/z 418[M + H]$^+$ |
| 203 | N-{5-[(7-tert-butyl-7H-pyrrolo[2,3-d]pyrimidin-5-yl)carbonyl]pyridin-3-yl}-2-(3-cyclopropyl-1-methyl-1H-pyrazol-4-yl)acetamide | LCMS (system 9): $R_t$ = 2.80 min; m/z 458 [M + H]$^+$ using (3-Cyclopropyl-1-methyl-1H-pyrazol-4-yl)-acetic acid (Preparation 125) |

Example 204

N-[5-({7-[(1S)-2-hydroxy-1-methylethyl]-7H-pyrrolo[2,3-d]pyrimidin-5-yl}carbonyl)pyridin-3-yl]-2-[3-(trifluoromethyl)phenyl]acetamide

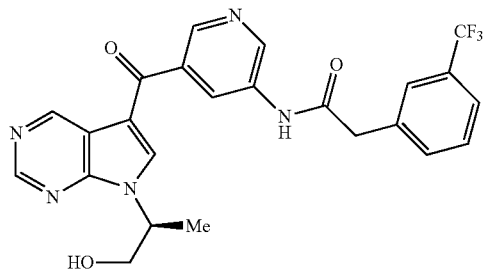 [SMILES: C[C@@H](CO)n1cc(C(=O)c2cncc(NC(=O)Cc3cccc(C(F)(F)F)c3)c2)c2cncnc21]

10% Hydrochloric acid in 1,4-dioxane (0.2 mL) was added to N-(5-{7-[(S)-2-(tert-Butyl-dimethyl-silanyloxy)-1-methyl-ethyl]-7H-pyrrolo[2,3-d]pyrimidine-5-carbonyl}-pyridin-3-yl)-2-(3-trifluoromethyl-phenyl)-acetamide (Preparation 105, 59 mg, 0.098 mmol) in THF (2 mL) and the mixture was stirred at room temperature for 18 hours. The mixture was evaporated in vacuo and triturated with ether-pentane to afford the title compound as an off white solid in 86% yield, 41 mg.

LCMS (system 9): Rt=2.97 min; m/z 484 [M+H]$^+$.

The following Examples were prepared according to the method described above for Example 204 using the appropriate preparations as described.

| Example | Name | Data |
|---|---|---|
| 205 | N-[5-({7-[(1R)-2-hydroxy-1-methylethyl]-7H-pyrrolo[2,3-d]pyrimidin-5-yl}carbonyl)pyridin-3-yl]-2-[3-(trifluoromethyl)phenyl]acetamide | LCMS (system 9): Rt = 2.89 min; m/z 484 [M + H]$^+$ Using (Preparation 142). |
| 206 | N-[5-({7-[(1R)-2-hydroxy-1-methylethyl]-7H-pyrrolo[2,3-d]pyrimidin-5-yl}carbonyl)pyridin-3-yl]-2-(4-isopropyl-1H-1,2,3-triazol-1-yl)acetamide | LCMS (system 9): Rt = 2.52 min; m/z 449 [M + H]$^+$ Using (Preparation 144). |
| 207 | N-[5-({7-[(1R)-2-hydroxy-1-methylethyl]-7H-pyrrolo[2,3-d]pyrimidin-5-yl}carbonyl)pyridin-3-yl]-2-[1-isopropyl-5-(trifluoromethyl)-1H-pyrazol-4-yl]acetamide | LCMS (system 9): Rt = 2.87 min; m/z 516 [M + H]$^+$ Using (Preparation 150). |
| 208 | 2-(4-cyanophenyl)-N-[5-({7-[(1R)-2-hydroxy-1-methylethyl]-7H-pyrrolo[2,3-d]pyrimidin-5-yl}carbonyl)pyridin-3-yl]acetamide | LCMS (system 9): Rt = 2.68 min; m/z 441 [M + H]$^+$ Using (Preparation 151). |
| 209 | N-[5-({7-[(1R)-2-hydroxy-1-methylethyl]-7H-pyrrolo[2,3-d]pyrimidin-5-yl}carbonyl)pyridin-3-yl]-2-[3-(methylsulfonyl)phenyl]acetamide | LCMS (system 9): Rt = 2.57 min; m/z 494 [M + H]$^+$ Using (Preparation 152). |
| 210 | N-[5-({7-[(1R)-2-hydroxy-1-methylethyl]-7H-pyrrolo[2,3-d]pyrimidin-5-yl}carbonyl)pyridin-3-yl]-2-quinolin-7-ylacetamide | LCMS (system 9): Rt = 1.96 min; m/z 467 [M + H]$^+$ Using (Preparation 153). |

The following Examples were prepared according to the method described above for Example 34 at 50° C., starting from [2-amino-7-(2-hydroxy-1-methylethyl)-7H-pyrrolo[2,3-d]pyrimidin-5-yl](5-aminopyridin-3-yl)methanone (enantiomer 1, Preparation 57) and the appropriate acids.

| Example | Name | Data |
|---|---|---|
| 211 | N-(5-{[2-amino-7-(2-hydroxy-1-methylethyl)-7H-pyrrolo[2,3-d]pyrimidin-5-yl]carbonyl}pyridin-3-yl)-2-quinolin-7-ylacetamide | LCMS (system 10): Rt = 2.48 min; m/z 482 [M + H]+ |
| 212 | N-(5-{[2-amino-7-(2-hydroxy-1-methylethyl)-7H-pyrrolo[2,3-d]pyrimidin-5-yl]carbonyl}pyridin-3-yl)-2-(4-cyanophenyl)acetamide | LCMS (system 10): Rt = 2.57 min; m/z 456 [M + H]+ |
| 213 | N-(5-{[2-amino-7-(2-hydroxy-1-methylethyl)-7H-pyrrolo[2,3-d]pyrimidin-5-yl]carbonyl}pyridin-3-yl)-2-[3-(trifluoromethyl)phenyl]acetamide | LCMS (system 10): Rt = 2.87 min; m/z 499 [M + H]+ |

The following Examples were prepared according to the method described above for Example 34 at 50° C., starting from [2-amino-7-(2-hydroxy-1-methylethyl)-7H-pyrrolo[2,3-d]pyrimidin-5-yl](5-aminopyridin-3-yl)methanone (enantiomer 2, Preparation 59) and the appropriate acids.

| Example | Name | Data |
|---|---|---|
| 214 | N-(5-{[2-amino-7-(2-hydroxy-1-methylethyl)-7H-pyrrolo[2,3-d]pyrimidin-5-yl]carbonyl}pyridin-3-yl)-2-(4-cyanophenyl)acetamide | LCMS (system 9): Rt = 2.26 min; m/z 456 [M + H]+ |
| 215 | N-(5-{[2-amino-7-(2-hydroxy-1-methylethyl)-7H-pyrrolo[2,3-d]pyrimidin-5-yl]carbonyl}pyridin-3-yl)-2-[3-(trifluoromethyl)phenyl]acetamide | LCMS (system 9): Rt = 2.72 min; m/z 499 [M + H]+ |
| 216 | N-(5-{[2-amino-7-(2-hydroxy-1-methylethyl)-7H-pyrrolo[2,3-d]pyrimidin-5-yl]carbonyl}pyridin-3-yl)-2-quinolin-7-ylacetamide | LCMS (system 9): Rt = 1.62 min; m/z 482 [M + H]+ |

The following Examples were prepared according to the method described above for Example 34 at 50° C. starting from (5-aminopyridin-3-yl)(7-oxetan-3-yl-7H-pyrrolo[2,3-d]pyrimidin-5-yl)methanone (Preparation 100) and the appropriate acid.

| Example | Name | Data |
|---|---|---|
| 217 | 2-(3,4-dichlorophenyl)-N-{5-[(7-oxetan-3-yl-7H-pyrrolo[2,3-d]pyrimidin-5-yl)carbonyl]pyridin-3-yl}acetamide | LCMS (system 3): R$_t$ = 3.04 min; m/z 482 [M + H]+ |
| 218 | 2-(4-cyanophenyl)-N-{5-[(7-oxetan-3-yl-7H-pyrrolo[2,3-d]pyrimidin-5-yl)carbonyl]pyridin-3-yl}acetamide | LCMS (System 2): Rt = 1.3 min; m/z 439 [M + H]+ |
| 219 | 2-(4-chlorophenyl)-N-{5-[(7-oxetan-3-yl-7H-pyrrolo[2,3-d]pyrimidin-5-yl)carbonyl]pyridin-3-yl}acetamide | LCMS (System 2): Rt = 1.5 min; m/z 448 [M + H]+ |
| 220 | 2-(3-chlorophenyl)-N-{5-[(7-oxetan-3-yl-7H-pyrrolo[2,3-d]pyrimidin-5-yl)carbonyl]pyridin-3-yl}acetamide | LCMS (System 2): Rt = 1.5 min; m/z 448 [M + H]+ |
| 221 | 2-(3-cyanophenyl)-N-{5-[(7-oxetan-3-yl-7H-pyrrolo[2,3-d]pyrimidin-5-yl)carbonyl]pyridin-3-yl}acetamide | LCMS (System 2): Rt = 1.3 min; m/z 439 [M + H]+ |
| 222 | N-{5-[(7-oxetan-3-yl-7H-pyrrolo[2,3-d]pyrimidin-5-yl)carbonyl]pyridin-3-yl}-2-quinolin-7-ylacetamide | LCMS (System 2): Rt = 1.0 min; m/z 465 [M + H]+ |
| 223 | 2-(6-chloroimidazo[1,2-a]pyridin-2-yl)-N-{5-[(7-oxetan-3-yl-7H-pyrrolo[2,3-d]pyrimidin-5-yl)carbonyl]pyridin-3-yl}acetamide | LCMS (System 2): Rt = 1.0 min; m/z 488 [M + H]+ |
| 224 | N-{5-[(7-oxetan-3-yl-7H-pyrrolo[2,3-d]pyrimidin-5-yl)carbonyl]pyridin-3-yl}-2-(1-oxo-1,3-dihydro-2H-isoindol-2-yl)acetamide | LCMS (System 2): Rt = 1.3 min; m/z 469 [M + H]+ |

The following Examples were prepared according to the method described above for Example 204, using the preparations as described.

| Example | Name | data |
|---|---|---|
| 225 | 2-(4-cyanophenyl)-N-(5-{[7-(2-hydroxy-1,1-dimethylethyl)-7H-pyrrolo[2,3-d]pyrimidin-5-yl]carbonyl}pyridin-3-yl)acetamide | LCMS (System 9): $R_t$ = 2.74 min; m/z 455.4 [M + H]$^+$ Using Preparation 131 |
| 226 | N-(5-{[7-(2-hydroxy-1,1-dimethylethyl)-7H-pyrrolo[2,3-d]pyrimidin-5-yl]carbonyl}pyridin-3-yl)-2-[3-(trifluoromethyl)phenyl]acetamide | LCMS (System 9): $R_t$ = 2.99 min; m/z 498 [M + H]$^+$ Using Preparation 136 |
| 227 | N-(5-{[7-(2-hydroxy-1,1-dimethylethyl)-7H-pyrrolo[2,3-d]pyrimidin-5-yl]carbonyl}pyridin-3-yl)-2-(4-isopropyl-1H-1,2,3-triazol-1-yl)acetamide | $^1$H NMR (400 MHz, DMSO) δ: 1.22 (d, 6H), 1.71 (s, 6H), 2.96 (m, 2H), 3.94 (s, 2H), 5.35 (s, 2H), 7.87 (s, 1H), 8.20 (s, 1H), 8.44 (s, 1H), 8.75 (s, 1H), 8.98 (m, 2H), 9.46 (s, 1H), 11 (s, 1H) Using Preparation 144 |
| 228 | N-(5-{[7-(2-hydroxy-1,1-dimethylethyl)-7H-pyrrolo[2,3-d]pyrimidin-5-yl]carbonyl}pyridin-3-yl)-2-quinolin-7-ylacetamide | LCMS (System 9): $R_t$ = 2.61 min; m/z 481 [M + H]$^+$ Using Preparation 140 |

Example 229 racemic 2-{5-[(5-{[(4-Chlorophenyl)acetyl]amino}pyridin-3-yl)carbonyl]-7H-pyrrolo[2,3-d]pyrimidin-7-yl}propanamide

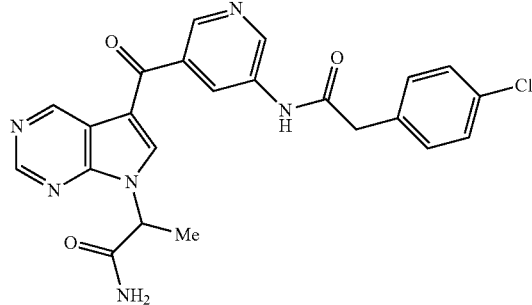 [SMILES: CC(C(N)=O)n1cc(C(=O)c2cncc(NC(=O)Cc3ccc(Cl)cc3)c2)c2cncnc21]

2-bromopropionamide (46.5 mg, 0.31 mmol) was added to a mixture of 2-(4-chlorophenyl)-N-[5-(7H-pyrrolo[2,3-d]pyrimidin-5-ylcarbonyl)pyridin-3-yl]acetamide (Example 308, 100 mg, 0.26 mmol) and cesium carbonate (150 mg, 0.46 mmol) in DMF (1.3 mL). The mixture was stirred at 60° C. for 3 hours. The reaction mixture was cooled and water (10 mL) was added. The mixture was extracted with EtOAc (3×10 mL) and the combined organic phases were passed through a phase separator and evaporated in vacuo. Purification by preparative HPLC gave the title compound as a white solid in 34% yield, 15 mg.

LCMS (System 3): $R_t$=2.13 min; m/z 463 [M+H]$^+$.

Example 230 racemic 2-{5-[(5-{[(4-Chlorophenyl)acetyl]amino}pyridin-3-yl)carbonyl]-7H-pyrrolo[2,3-d]pyrimidin-7-yl}-N,N-dimethylpropanamide The title compound was prepared according to the method described for Example 34 at 50° C. using racemic 2-{5-[(5-{[(4-chlorophenyl)acetyl]amino}pyridin-3-yl)carbonyl]-7H-pyrrolo[2,3-d]pyrimidin-7-yl}propanoic acid (Example 354) and dimethylamine.

Purification was accomplished by preparative HPLC (method 1) to afford the title compound.

LCMS (system 3): $R_t$=2.39 min; m/z 491 [M+H]$^+$.

Example 231 racemic 2-{5-[(5-{[(4-Chlorophenyl)acetyl]amino}pyridin-3-yl)carbonyl]-7H-pyrrolo[2,3-d]pyrimidin-7-yl}-N-methylpropanamide The title compound was prepared according to the method described for Example 34 at 50° C. using 2-{5-[(5-{[(4-chlorophenyl)acetyl]amino}pyridin-3-yl)carbonyl]-7H-pyrrolo[2,3-d]pyrimidin-7-yl}propanoic acid (Example 354) and methylamine. Purification was accomplished by preparative HPLC (method 1) to afford the title compound.

LCMS (system 3): $R_t$=2.31 min; m/z 477 [M+H]$^+$.

Example 232

2-(4-Cyanophenyl)-N-[5-({7-[2-hydroxy-1-(hydroxymethyl)-1-methylethyl]-7H-pyrrolo[2,3-d]pyrimidin-5-yl}carbonyl)pyridin-3-yl]acetamide

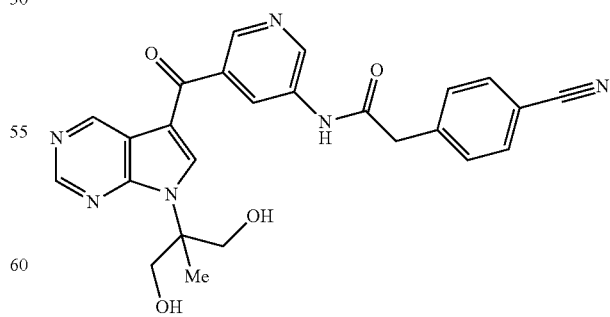

4-Cyanophenylacetic acid (19 mg, 0.10 mmol) was added to (5-aminopyridin-3-yl){7-[2-{[tert-butyl(dimethyl)silyl]oxy}-1-({[tert-butyl(dimethyl)silyl]oxy}methyl)-1-methylethyl]-7H-pyrrolo[2,3-d]pyrimidin-5-yl}methanone (Preparation 116, 54 mg, 0.97 mmol), 1-propylphosphonic acid cyclic anhydride (0.17 mL, 0.291 mmol) and triethylamine (0.047 mL, 0.291 mmol) in tetrahydrofuran (3 mL). The mixture was stirred at 50° C. for 16 hours. Saturated aqueous sodium bicarbonate (5 mL) was added then extracted with dichloromethane (3×7 mL). The combined organic phases were dried over magnesium sulphate and evaporated in vacuo.

The residue was dissolved in tetrahydrofuran (3 mL) and a tetrabutylammonium fluoride solution in THF (1 mL of a 1M solution, 1 mmol) was added and the solution was stirred for 1 hour. Saturated aqueous sodium bicarbonate (5 mL) was added then extracted with dichloromethane (3×5 mL). The combined organic phases were dried over magnesium sulphate, evaporated in vacuo and purified by preparative HPLC (method 2).

LCMS (system 4): $R_t$=2.52 min; m/z 471 [M+H]$^+$

The following Examples were prepared according to the method described above for Example 232 starting from (5-aminopyridin-3-yl){7-[2-{[tert-butyl(dimethyl)silyl]oxy}-1-({[tert-butyl(dimethyl)silyl]oxy}methyl)-1-methylethyl]-7H-pyrrolo[2,3-d]pyrimidin-5-yl}methanone (Preparation 116) and the appropriate acids.

| Example | Name | Data |
|---|---|---|
| 233 | N-[5-({7-[2-hydroxy-1-(hydroxymethyl)-1-methylethyl]-7H-pyrrolo[2,3-d]pyrimidin-5-yl}carbonyl)pyridin-3-yl]-2-quinolin-7-ylacetamide | LCMS (system 4) Rt = 2.52 min; m/z 497 [M + H]$^+$ Prep method 1 |
| 234 | N-[5-({7-[2-hydroxy-1-(hydroxymethyl)-1-methylethyl]-7H-pyrrolo[2,3-d]pyrimidin-5-yl}carbonyl)pyridin-3-yl]-2-[5-methyl-3-(trifluoromethyl)-1H-pyrazol-1-yl]acetamide | LCMS (system 4) Rt = 2.69 min; m/z 518 [M + H]$^+$ Prep method 1 |
| 235 | 2-(4-chlorophenyl)-N-[5-({7-[2-hydroxy-1-(hydroxymethyl)-1-methylethyl]-7H-pyrrolo[2,3-d]pyrimidin-5-yl}carbonyl)pyridin-3-yl]acetamide | LCMS (system 4) Rt = 2.83 min; m/z 480 [M + H]$^+$ Prep method 1 |
| 236 | N-[5-({7-[2-hydroxy-1-(hydroxymethyl)-1-methylethyl]-7H-pyrrolo[2,3-d]pyrimidin-5-yl}carbonyl)pyridin-3-yl]-2-[4-(trifluoromethyl)phenyl]acetamide | LCMS (system 4) Rt = 2.81 min; m/z 514 [M + H]$^+$ Prep method 1 |
| 237 | 2-(5-chloropyridin-2-yl)-N-[5-({7-[2-hydroxy-1-(hydroxymethyl)-1-methylethyl]-7H-pyrrolo[2,3-d]pyrimidin-5-yl}carbonyl)pyridin-3-yl]acetamide | LCMS (system 3) Rt = 2.37 min; m/z 481 [M + H]$^+$ Prep method 1 Using (5-chloropyridin-2-yl)acetic acid (Preparation 90). |
| 238 | N-[5-({7-[2-hydroxy-1-(hydroxymethyl)-1-methylethyl]-7H-pyrrolo[2,3-d]pyrimidin-5-yl}carbonyl)pyridin-3-yl]-2-[3-(trifluoromethyl)phenyl]acetamide | LCMS (system 4) Rt = 2.84 min; m/z 514 [M + H]$^+$ Prep method 1 |
| 239 | N-[5-({7-[2-hydroxy-1-(hydroxymethyl)-1-methylethyl]-7H-pyrrolo[2,3-d]pyrimidin-5-yl}carbonyl)pyridin-3-yl]-2-[3-(trifluoromethyl)-1H-pyrazol-1-yl]acetamide | LCMS (system 3) Rt = 2.59 min; m/z 504 [M + H]$^+$ Prep method 2 |

The following Examples were prepared according to the method described above for Example 1 using DIPEA and purification by preparative HPLC, starting from (2-amino-7-isopropyl-7H-pyrrolo[2,3-d]pyrimidin-5-yl)(5-aminopyridin-3-yl)methanone (Preparation 122) and the appropriate acids.

| Example | Name | Data |
|---|---|---|
| 240 | N-{5-[(2-amino-7-isopropyl-7H-pyrrolo[2,3-d]pyrimidin-5-yl)carbonyl]pyridin-3-yl}-2-[4-(trifluoromethyl)-1H-1,2,3-triazol-1-yl]acetamide | LCMS (System 9): $R_t$ = 2.57 min; m/z 474 [M + H]$^+$ Using 4-(trifluoromethyl)-1H-1,2,3-triazol-1-yl]acetic acid (Preparation 81). |
| 241 | N-{5-[(2-amino-7-isopropyl-7H-pyrrolo[2,3-d]pyrimidin-5-yl)carbonyl]pyridin-3-yl}-2-(4-cyanophenyl)acetamide | LCMS (System 9): $R_t$ = 2.56 min; m/z 440 [M + H]$^+$ |
| 242 | N-{5-[(2-amino-7-isopropyl-7H-pyrrolo[2,3-d]pyrimidin-5-yl)carbonyl]pyridin-3-yl}-2-(5-chloropyridin-2-yl)acetamide | LCMS (System 9): $R_t$ = 2.46 min; m/z 450 [M + H]$^+$ Using-(5-chloropyridin-2-yl)acetic acid (Preparation 90). |
| 243 | N-{5-[(2-amino-7-isopropyl-7H-pyrrolo[2,3-d]pyrimidin-5-yl)carbonyl]pyridin-3-yl}-2-(5-fluoropyridin-2-yl)acetamide | LCMS (System 9): $R_t$ = 2.20 min; m/z 434 [M + H]$^+$ Using (5-fluoropyridin-2-yl)acetic acid (Preparation 92). |
| 244 | N-{5-[(2-amino-7-isopropyl-7H-pyrrolo[2,3-d]pyrimidin-5- | LCMS (System 10): $R_t$ = 3.22 min; m/z 483 [M + H]$^+$ |

-continued

| Example | Name | Data |
|---|---|---|
|  | yl)carbonyl]pyridin-3-yl}-2-[4-(trifluoromethyl)phenyl]acetamide | |
| 245 | N-{5-[(2-amino-7-isopropyl-7H-pyrrolo[2,3-d]pyrimidin-5-yl)carbonyl]pyridin-3-yl}-2-[3-(trifluoromethyl)phenyl]acetamide | LCMS (System 10): $R_t$ = 3.22 min; m/z 483 [M + H]$^+$ |
| 246 | N-{5-[(2-amino-7-isopropyl-7H-pyrrolo[2,3-d]pyrimidin-5-yl)carbonyl]pyridin-3-yl}-2-(1,3-benzoxazol-5-yl)acetamide | LCMS (System 9): $R_t$ = 2.22 min; m/z 456 [M + H]$^+$ |
| 247 | N-{5-[(2-amino-7-isopropyl-7H-pyrrolo[2,3-d]pyrimidin-5-yl)carbonyl]pyridin-3-yl}-2-[3-(methylsulfonyl)phenyl]acetamide | LCMS (System 9): $R_t$ = 2.15 min; m/z 493 [M + H]$^+$ |
| 248 | N-{5-[(2-amino-7-isopropyl-7H-pyrrolo[2,3-d]pyrimidin-5-yl)carbonyl]pyridin-3-yl}-2-(4-isopropyl-1H-1,2,3-triazol-1-yl)acetamide | LCMS (System 9): $R_t$ = 2.16 min; m/z 448 [M + H]$^+$ |
| 249 | N-{5-[(2-amino-7-isopropyl-7H-pyrrolo[2,3-d]pyrimidin-5-yl)carbonyl]pyridin-3-yl}-2-(4-cyclopropyl-1H-1,2,3-triazol-1-yl)acetamide | LCMS (System 9): $R_t$ = 2.01 min; m/z 446 [M + H]$^+$ Using Preparation 83 |
| 250 | N-{5-[(2-amino-7-isopropyl-7H-pyrrolo[2,3-d]pyrimidin-5-yl)carbonyl]pyridin-3-yl}-2-(4-chlorophenyl)acetamide | LCMS (System 10): $R_t$ = 3.03 min; m/z 449 [M + H]$^+$ |
| 251 | N-{5-[(2-amino-7-isopropyl-7H-pyrrolo[2,3-d]pyrimidin-5-yl)carbonyl]pyridin-3-yl}-2-[1-isopropyl-5-(trifluoromethyl)-1H-pyrazol-4-yl]acetamide | LCMS (System 10): $R_t$ = 3.03 min; m/z 515 [M + H]$^+$ Using Prep 185 |
| 252 | N-{5-[(2-amino-7-isopropyl-7H-pyrrolo[2,3-d]pyrimidin-5-yl)carbonyl]pyridin-3-yl}-2-[3-(trifluoromethyl)-1H-pyrazol-1-yl]acetamide | LCMS (System 10): $R_t$ = 2.92 min; m/z 473 [M + H]$^+$ |
| 253 | N-{5-[(2-amino-7-isopropyl-7H-pyrrolo[2,3-d]pyrimidin-5-yl)carbonyl]pyridin-3-yl}-2-(3-cyclopropyl-1H-pyrazol-1-yl)acetamide | LCMS (System 9) $R_t$ 2.46 min; m/z 445 [M + H]$^+$ |
| 254 | N-{5-[(2-amino-7-isopropyl-7H-pyrrolo[2,3-d]pyrimidin-5-yl)carbonyl]pyridin-3-yl}-2-[1-isopropyl-3-(trifluoromethyl)-1H-pyrazol-4-yl]acetamide | LCMS (System 9): $R_t$ = 2.77 min; m/z 515 [M + H]$^+$ |

Example 255

N-{5-[(2-amino-7-isopropyl-7H-pyrrolo[2,3-d]pyrimidin-5-yl)carbonyl]pyridin-3-yl}-2-(5-cyanopyridin-2-yl)acetamide

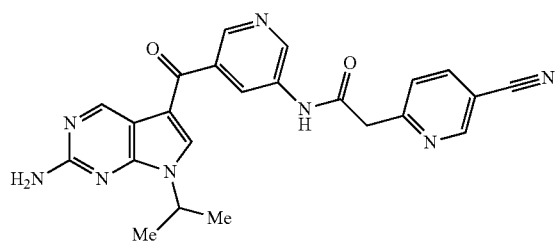 [SMILES: CC(C)n1cc(C(=O)c2cncc(NC(=O)Cc3ccc(C#N)cn3)c2)c2cnc(N)nc21]

The title compound was prepared according to the method described for Example 166 using N-{5-[(2-amino-7-isopropyl-7H-pyrrolo[2,3-d]pyrimidin-5-yl)carbonyl]pyridin-3-yl}-2-(5-bromopyridin-2-yl)acetamide (Example 318) to afford the title compound in 45% yield, 30 mg. $^1$H NMR (400 MHz, DMSO-d6) δ: 1.45 (d, 6H), 4.06 (s, 2H), 4.84 (m, 1H), 6.62 (s, 2H), 7.66 (d, 1H), 7.97 (s, 1H), 8.29 (dd, 1H), 8.37 (t, 1H), 8.66 (d, 1H), 8.92 (s, 1H), 8.95-8.98 (m, 2H), 10.75 (s, 1H); LCMS (System 10): $R_t$=2.49 min; m/z 441 [M+H]$^+$.

The following Examples were prepared according to the method described above for Example 34 at 50° C. starting from [2-amino-7-(2-hydroxy-1,1-dimethylethyl)-7H-pyrrolo[2,3-d]pyrimidin-5-yl](5-aminopyridin-3-yl)methanone (Preparation 48) and the appropriate acids.

| Example | Name | Data |
|---|---|---|
| 256 | N-(5-{[2-amino-7-(2-hydroxy-1,1-dimethylethyl)-7H-pyrrolo[2,3-d]pyrimidin-5-yl]carbonyl}pyridin-3-yl)-2-[3-(trifluoromethyl)phenyl]acetamide | LCMS (System 10): $R_t$ = 2.91 min; m/z 513 [M + H]$^+$ |

| Example | Name | Data |
|---|---|---|
| 257 | N-(5-{[2-amino-7-(2-hydroxy-1,1-dimethylethyl)-7H-pyrrolo[2,3-d]pyrimidin-5-yl]carbonyl}pyridin-3-yl)-2-(1,3-benzoxazol-5-yl)acetamide | LCMS (System 10): $R_t$ = 2.48 min; m/z 486 [M + H]$^+$ |
| 258 | N-(5-{[2-amino-7-(2-hydroxy-1,1-dimethylethyl)-7H-pyrrolo[2,3-d]pyrimidin-5-yl]carbonyl}pyridin-3-yl)-2-[3-(methylsulfonyl)phenyl]acetamide | LCMS (System 10): $R_t$ = 2.50 min; m/z 523 [M + H]$^+$ |
| 259 | N-(5-{[2-amino-7-(2-hydroxy-1,1-dimethylethyl)-7H-pyrrolo[2,3-d]pyrimidin-5-yl]carbonyl}pyridin-3-yl)-2-(4-cyanophenyl)acetamide | LCMS (System 10): $R_t$ = 2.62 min; m/z 470 [M + H]$^+$ |
| 260 | N-(5-{[2-amino-7-(2-hydroxy-1,1-dimethylethyl)-7H-pyrrolo[2,3-d]pyrimidin-5-yl]carbonyl}pyridin-3-yl)-2-[1-isopropyl-5-(trifluoromethyl)-1H-pyrazol-4-yl]acetamide | LCMS (System 10): $R_t$ = 2.89 min; m/z 545 [M + H]$^+$ Using Prep 185 |

Example 261

4-cyano-3-(trifluoromethyl)phenyl)-N-(5-(7-(1,3-dihydroxy-2-methylpropan-2-yl)-7H-pyrrolo[2,3-d]pyrimidine-5-carbonyl)pyridin-3-yl)acetamide

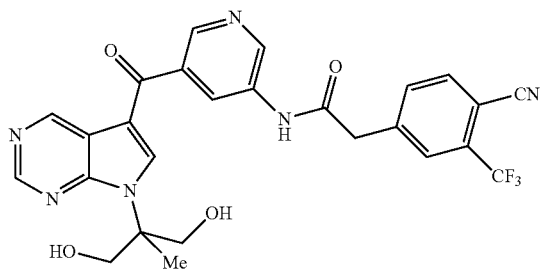 [SMILES: CC(CO)(CO)n1cc(C(=O)c2cncc(NC(=O)Cc3ccc(C#N)c(C(F)(F)F)c3)c2)c2cncnc21]

2-(4-cyano-3-(trifluoromethyl)phenyl)acetic acid (Preparation 164, 29.8 mg, 0.13 mmol) was added to a stirred solution of (5-aminopyridin-3-yl){7-[2-{[tert-butyl(dimethyl)silyl]oxy}-1-({[tert-butyl(dimethyl)silyl]oxy}methyl)-1-methylethyl]-7H-pyrrolo[2,3-d]pyrimidine-5-yl)methanone (Preparation 116, 55.6 mg, 0.10 mmol) and 2-(7-aza-1H-benzotriazol-1-yl)-1,1,3,3-tetramethyluronium hexafluorophosphate (57 mg, 0.15 mmol) in pyridine (0.5 mL). The mixture was stirred at 50° C. for 16 hours, then cooled to room temperature and partitioned between saturated aqueous sodium bicarbonate (5 mL) and DCM (5 mL). The organic phase was separated and concentrated in vacuo to provide a residue that was dissolved in 3 mL of THF and then treated with 3 mL of a 1N aqueous solution of HCl. The mixture was stirred rapidly for 4 hours at room temperature and then basified by the addition of 4 mL of a 1N aqueous NaOH solution. The mixture was extracted with three separate 5 mL portions of a 95/5 DCM/MeOH mixture. The combined organic extracts were dried by passage through a phase separator and then concentrated in vacuo to obtain a crude residue. This residue was dissolved in 1 mL DMSO and purified by preparative HPLC to afford the title compound as an off white solid in 56% yield, 30 mg. $^1$H NMR (400 MHz, DMSO) δ: 1.68 (s, 3H), 3.83 (m, 2H), 4.01 (s, 2H), 4.19 (m, 2H), 5.00 (m, 2H), 7.82 (m, 1H), 8.01 (d, 1H), 8.18 (m, 1H), 8.21 (s, 1H), 8.66 (s, 1H), 8.97 (m, 2H), 9.40 (s, 1H), 10.78 (s, 1H).

LCMS (System 2): $R_t$=0.90 min; m/z 539 [M+H]$^+$.

The following Examples were prepared according to the method described above for Example 261, starting from ((5-aminopyridin-3-yl){7-[2-{[tert-butyl(dimethyl)silyl]oxy}-1-({[tert-butyl(dimethyl)silyl]oxy}methyl)-1-methylethyl]-7H-pyrrolo[2,3-d]pyrimidine-5-yl)methanone (Preparation 116) and the appropriate acids followed by silyl group deprotection.

| Example | Name | Data |
|---|---|---|
| 262 | N-(5-(7-(1,3-dihydroxy-2-methylpropan-2-yl)-7H-pyrrolo[2,3-d]pyrimidine-5-carbonyl)pyridin-3-yl)-2-(3-trifluoromethoxy)phenyl)acetamide | LCMS (system 2): $R_t$ = 0.96 min; m/z 516 [M + H]$^+$ |
| 263 | N-(5-(7-(1,3-dihydroxy-2-methylpropan-2-yl)-7H-pyrrolo[2,3-d]pyrimidine-5-carbonyl)pyridin-3-yl)-2-(4-fluoro-3-(trifluoromethyl)phenyl)acetamide | LCMS (system 2): $R_t$ = 1.05 min; m/z 532 [M + H]$^+$ |
| 264 | N-(5-(7-(1,3-dihydroxy-2-methylpropan-2-yl)-7H-pyrrolo[2,3-d]pyrimidine-5-carbonyl)pyridin-3-yl)-3-(trifluoromethyl)benzamide | LCMS (system 2): $R_t$ = 1.04 min; m/z 500 [M + H]$^+$ |
| 265 | N-(5-(7-(1,3-dihydroxy-2-methylpropan-2-yl)-7H-pyrrolo[2,3-d]pyrimidine-5-carbonyl)pyridin-3-yl)-3-fluoro-4-(trifluoromethyl)benzamide | LCMS (system 2): $R_t$ = 1.09 min; m/z 532 [M + H]$^+$ |

Example 266

2-[3-(azetidin-1-ylmethyl)phenyl]-N-{5-[(7-isopropyl-7H-pyrrolo[2,3-d]pyrimidin-5-yl)carbonyl]pyridin-3-yl}acetamide formate salt

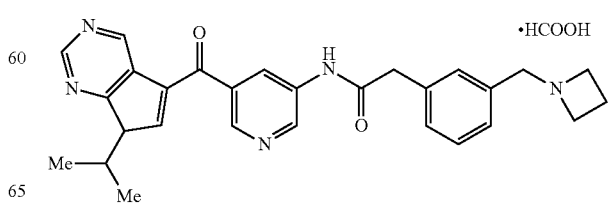

Azetidine hydrochloride (10 mg, 0.11 mmol) was added to a stirred solution of 2-(3-formylphenyl)-N-{5-[(7-isopropyl-7H-pyrrolo[2,3-d]pyrimidin-5-yl)carbonyl]pyridin-3-yl}acetamide (Preparation 192, 23 mg, 0.05 mmol) in DCM (1 mL) and acetic acid (0.04 mL, 0.60 mmol). The reaction mixture was stirred for 30 min at room temperature before addition of sodium triacetoxyborohydride (29 mg, 0.14 mmol) and stirring continued for 3 hours. Water (1 mL) was added and the mixture concentrated in vacuo (with toluene azeotroping). The residue was purified by preparative HPLC to afford the title compound as a formate salt in 12% yield, 3.4 mg.

LCMS: $R_t$=2.95 min; m/z 469 [M+H]$^+$.

Example 267

2-{3-[(3-fluoroazetidin-1-yl)methyl]phenyl}-N-{5-[(7-isopropyl-7H-pyrrolo[2,3-d]pyrimidin-5-yl)carbonyl]pyridin-3-yl}acetamide The title compound was prepared according to the method described for Example 266 using 2-(3-formylphenyl)-N-{5-[(7-isopropyl-7H-pyrrolo[2,3-d]pyrimidin-5-yl)carbonyl]pyridin-3-yl}acetamide (Preparation 192, 60 mg, 0.14 mmol) and 3-fluoroazetidine to afford the title compound in 16% yield, 11 mg.

LCMS: $R_t$=2.75 min; m/z 487 [M+H]$^+$.

Example 268

N-{5-[(7-isopropyl-7H-pyrrolo[2,3-d]pyrimidin-5-yl)carbonyl]pyridin-3-yl}-2-[3-(morpholin-4-ylmethyl)phenyl]acetamide formate salt The title compound was prepared according to the method described for Example 266 using 2-(3-formylphenyl)-N-{5-[(7-isopropyl-7H-pyrrolo[2,3-d]pyrimidin-5-yl)carbonyl]pyridin-3-yl}acetamide (Preparation 192, 60 mg, 0.14 mmol) and morpholine to afford the title compound as a formate salt in 30% yield, 21 mg.

LCMS: $R_t$=2.70 min; m/z 499 [M+H]$^+$

Examples 269-283

General Method

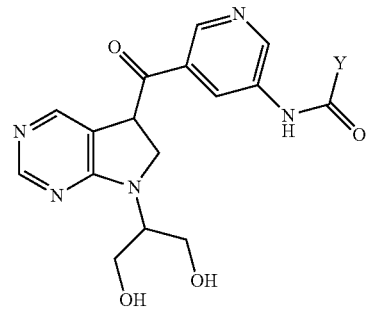

The mixture of (5-aminopyridin-3-yl)(7-(2,2,3,3,9,9,10,10-octamethyl-4,8-dioxa-3,9-disilaundecan-6-yl)-7H-pyrrolo[2,3-d]pyrimidin-5-yl)methanone (Preparation 196, 54.2 mg, 0.10 mmol), HATU (57 mg, 0.15 mmol) and the requisite carboxylic acid (0.13 mmol) in pyridine (0.5 mL) were stirred at 50° C. for 16 hours. After cooling to room temperature, saturated sodium bicarbonate solution (5 mL) was added and the mixture was extracted with DCM (5 mL). The organic layer was passed through a phase separator and concentrated in vacuo. The resulting residue was dissolved in THF (2 mL) and 1 N aqueous HCl (2 mL) added to the solution. The reaction mixture was stirred for 2 hours at room temperature and quenched with 1 N aqueous NaOH (3 mL). The mixture was then treated according to one of the following methods:

Method A

The mixture was extracted with a mixture of DCM/MeOH (95/5, 5 mL×3), the combined organic layers passed through a phase separator and concentrated in vacuo to obtain a crude residue. This residue was dissolved in DMSO (1 mL) and purified via HPLC to yield the desired compound.

Method B

The mixture was suspended in DCM/MeOH (95/5, 5 mL), the solid filtered and washed with water (5 mL) and DCM (5 mL) and dried in vacuo to yield the desired compound.

Method C

The mixture was extracted with a mixture of EtOAc/MeOH (95:5, 5 mL×3), the combined organic layers passed through a phase separator and concentrated in vacuo to obtain a crude residue. This residue was dissolved in DMSO (1 mL) and purified via preparative HPLC to yield the desired compound.

| Example | Name | Data |
| --- | --- | --- |
| 269 | N-(5-(7-(1,3-dihydroxypropan-2-yl)-7H-pyrrolo[2,3-d]pyrimidine-5-carbonyl)pyridin-3-yl)-3-(trifluoromethyl)benzamide | LCMS: $R_t$ = 2.69 min; m/z 486 [M + H]$^+$ |
| 270 | 2-(4-chlorophenyl)-N-(5-(7-(1,3-dihydroxypropan-2-yl)-7H-pyrrolo[2,3-d]pyrimidine-5-carbonyl)pyridin-3-yl)acetamide | LCMS: $R_t$ = 2.63 min; m/z 466 [M + H]$^+$ |
| 271 | N-(5-(7-(1,3-dihydroxypropan-2-yl)-7H-pyrrolo[2,3-d]pyrimidine-5-carbonyl)pyridin-3-yl)-3-(trifluoromethoxy)benzamide | LCMS: $R_t$ = 2.68 min; m/z 502 [M + H]$^+$ |
| 272 | N-(5-(7-(1,3-dihydroxypropan-2-yl)-7H-pyrrolo[2,3-d]pyrimidine-5-carbonyl)pyridin-3-yl)-2-(quinolin-7-yl)acetamide | LCMS: $R_t$ = 1.27 min; m/z 483 [M + H]$^+$ |
| 273 | N-(5-(7-(1,3-dihydroxypropan-2-yl)-7H-pyrrolo[2,3-d]pyrimidine-5-carbonyl)pyridin-3-yl)-2-(4-(trifluoromethyl)phenyl)acetamide | LCMS: $R_t$ = 2.69 min; m/z 500 [M + H]$^+$ |
| 274 | N-(5-(7-(1,3-dihydroxypropan-2-yl)-7H-pyrrolo[2,3-d]pyrimidine-5-carbonyl)pyridin-3-yl)-2-(3-(trifluoromethyl)phenyl)acetamide | m/z 500 [M + H]$^+$ |

-continued

| Example | Name | Data |
|---|---|---|
| 275 | N-[5-({7-[2-hydroxy-1-(hydroxymethyl)ethyl]-7H-pyrrolo[2,3-d]pyrimidin-5-yl}carbonyl)pyridin-3-yl]-2-(2-methylquinolin-7-yl)acetamide | m/z 497 [M + H]$^+$ Preparation 165 |
| 276 | 2-(3,4-dichlorophenyl)-N-[5-({7-[2-hydroxy-1-(hydroxymethyl)ethyl]-7H-pyrrolo[2,3-d]pyrimidin-5-yl}carbonyl)pyridin-3-yl]acetamide | m/z 500 [M + H]$^+$ |
| 277 | 2-[3-fluoro-4-(trifluoromethyl)phenyl]-N-[5-({7-[2-hydroxy-1-(hydroxymethyl)ethyl]-7H-pyrrolo[2,3-d]pyrimidin-5-yl}carbonyl)pyridin-3-yl]acetamide | m/z 518 [M + H]$^+$ |
| 278 | 2-(2,4-dichlorophenyl)-N-[5-({7-[2-hydroxy-1-(hydroxymethyl)ethyl]-7H-pyrrolo[2,3-d]pyrimidin-5-yl}carbonyl)pyridin-3-yl]acetamide | m/z 500 [M + H]$^+$ |
| 279 | N-[5-({7-[2-hydroxy-1-(hydroxymethyl)ethyl]-7H-pyrrolo[2,3-d]pyrimidin-5-yl}carbonyl)pyridin-3-yl]-2-[3-(trifluoromethoxy)phenyl]acetamide | m/z 516 [M + H]$^+$ |
| 280 | N-[5-({7-[2-hydroxy-1-(hydroxymethyl)ethyl]-7H-pyrrolo[2,3-d]pyrimidin-5-yl}carbonyl)pyridin-3-yl]-2-[4-(trifluoromethoxy)phenyl]acetamide | m/z 516 [M + H]$^+$ |
| 281 | 3-fluoro-N-[5-({7-[2-hydroxy-1-(hydroxymethyl)ethyl]-7H-pyrrolo[2,3-d]pyrimidin-5-yl}carbonyl)pyridin-3-yl]-5-(trifluoromethyl)benzamide | m/z 504 [M + H]$^+$ |
| 282 | 2-(5-chloropyridin-2-yl)-N-[5-({7-[2-hydroxy-1-(hydroxymethyl)ethyl]-7H-pyrrolo[2,3-d]pyrimidin-5-yl}carbonyl)pyridin-3-yl]acetamide | LCMS: $R_t$ = 0.90 min, m/z 467 [M + H]$^+$ |
| 283 | N-[5-({7-[2-hydroxy-1-(hydroxymethyl)ethyl]-7H-pyrrolo[2,3-d]pyrimidin-5-yl}carbonyl)pyridin-3-yl]-2-[3-(trifluoromethyl)-1H-pyrazol-1-yl]acetamide | LCMS: Rt = 1.81 min, m/z 490 [M + H]$^+$ |

Example 284

4-benzoyl-N-alpha-(tert-butoxycarbonyl)-N-{5-[(7-isopropyl-7H-pyrrolo[2,3-d]pyrimidin-5-yl)carbonyl]pyridin-3-yl}-L-phenylalaninamide

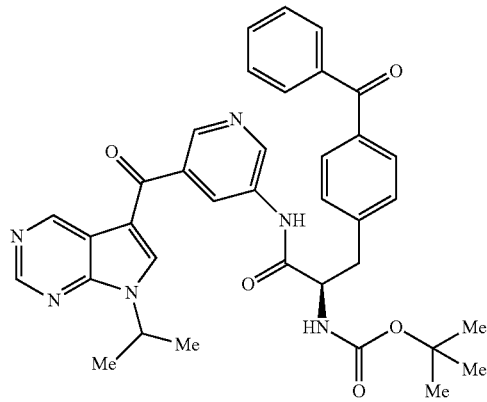 [SMILES: CC(C)n1cc(C(=O)c2cncc(NC(=O)[C@@H](Cc3ccc(C(=O)c4ccccc4)cc3)NC(=O)OC(C)(C)C)c2)c2cncnc21]

(5-aminopyridin-3-yl)(7-isopropyl-7H-pyrrolo[2,3-d]pyrimidin-5-yl)methanone (20 mg, 0.07 mmol) (see Preparation 95) was dissolved in pyridine (1 mL) and 4-benzoyl-N-(tert-butoxycarbonyl)-D-phenylalanine was added (26 mg, 0.07 mmol) followed by HATU (27 mg, 0.07 mmol). The mixture was stirred at 50° C. for 5 hours and then cooled, evaporated in vacuo and the crude material was purified by column chromatography on silica gel (gradient of DCM: Methanol 100:0 to 95:5) to afford the title compound as a yellow solid in 52% yield, 23 mg.

Example 285

4-benzoyl-N-{5-[(7-isopropyl-7H-pyrrolo[2,3-d]pyrimidin-5-yl)carbonyl]pyridin-3-yl}-D-phenylalaninamide

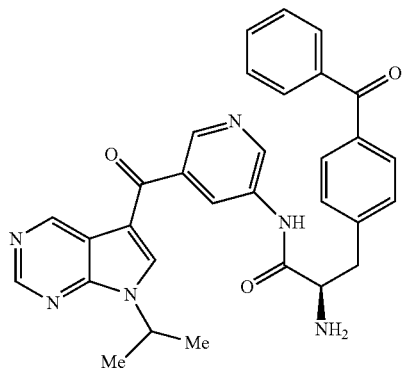 [SMILES: CC(C)n1cc(C(=O)c2cncc(NC(=O)[C@H](N)Cc3ccc(C(=O)c4ccccc4)cc3)c2)c2cncnc21]

4-benzoyl-Nalpha-(tert-butoxycarbonyl)-N-{5-[(7-isopropyl-7H-pyrrolo[2,3-d]pyrimidin-5-yl)carbonyl]pyridin-3-yl}-D-phenylalaninamide (Example 284, 20 mg, 0.03 mmol) was stirred with 10% hydrochloric acid in 1,4-dioxane (5 mL) at room temperature for 1 hour. The mixture was evaporated in vacuo and purified by preparative HPLC to afford the title compound as a gum in 56% yield, 9 mg.

LCMS (system 5): $R_t$=2.89 min; m/z 533 [M+H]$^+$.

Example 286

4-benzoyl-N-alpha-(tert-butoxycarbonyl)-N-{5-[(7-isopropyl-7H-pyrrolo[2,3-d]pyrimidin-5-yl)carbonyl]pyridin-3-yl}-L-phenylalaninamide

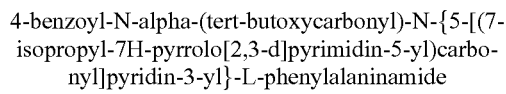

The title compound was prepared according to Example 284 using (5-aminopyridin-3-yl)(7-isopropyl-7H-pyrrolo[2,3-d]pyrimidin-5-yl)methanone (Preparation 95) and 4-benzoyl-N-(tert-butoxycarbonyl)-L-phenylalanine

Example 287

4-benzoyl-N-{5-[(7-isopropyl-7H-pyrrolo[2,3-d]pyrimidin-5-yl)carbonyl]pyridin-3-yl}-L-phenylalaninamide

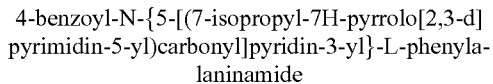

The title compound was prepared according to the method described for Example 285 using 4-benzoyl-Nalpha-(tert-butoxycarbonyl)-N-{5-[(7-isopropyl-7H-pyrrolo[2,3-d]pyrimidin-5-yl)carbonyl]pyridin-3-yl}-L-phenylalaninamide (Example 286) to afford the title compound in 36% yield, 5 mg.

LCMS (system 4): $R_t$=2.30 min; m/z 533 [M+H]$^+$.

Example 288

2-(3-benzoylphenyl)-N-(5-(7-isopropyl-7H-pyrrolo[2,3-d]pyrimidine-5-carbonyl)pyridin-3-yl)acetamide

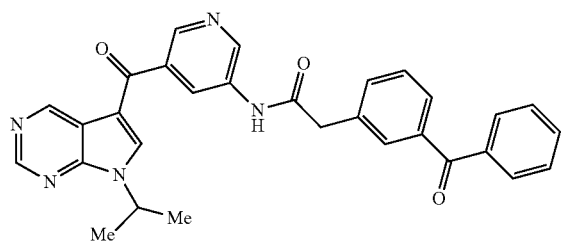 [SMILES: CC(C)n1cc(C(=O)c2cncc(NC(=O)Cc3cccc(C(=O)c4ccccc4)c3)c2)c2cncnc21]

The title compound was prepared according to the method described for Example 34 starting from (5-aminopyridin-3-yl)(7-isopropyl-7H-pyrrolo[2,3-d]pyrimidin-5-yl)methanone (Preparation 95) and 2-(3-benzoylphenyl)acetic acid to afford the title compound in 86% yield, 31 mg.

LCMS (system 3): $R_t$=3.05 min; m/z 504 [M+H]$^+$.

Example 289

2-(4-benzoylphenyl)-N-(5-(7-isopropyl-7H-pyrrolo[2,3-d]pyrimidine-5-carbonyl)pyridin-3-yl)acetamide

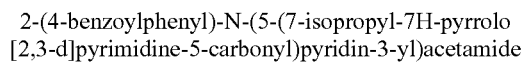

The title compound was prepared according to the method described for Example 34 starting from (5-aminopyridin-3-yl)(7-isopropyl-7H-pyrrolo[2,3-d]pyrimidin-5-yl)methanone (Preparation 95) and 2-(4-benzoylphenyl)acetic acid (JOC, 1961, 1635) to afford the title compound in 94% yield, 34 mg. LCMS (system 3): $R_t$=3.12 min; m/z 504 [M+H]$^+$.

Example 290

N-{5-[(7-isopropyl-7H-pyrrolo[2,3-d]pyrimidin-5-yl)carbonyl]pyridin-3-yl}-3-[3-(trifluoromethyl)-3H-diaziren-3-yl]benzamide

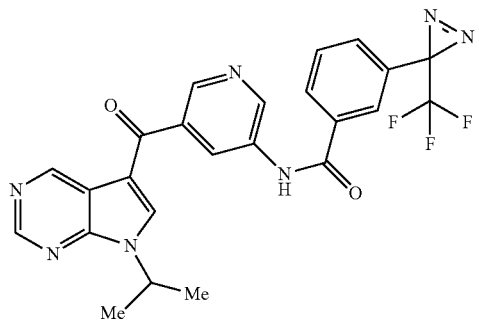 [SMILES: CC(C)n1cc(C(=O)c2cncc(NC(=O)c3cccc(C4(C(F)(F)F)N=N4)c3)c2)c2cncnc21]

The title compound was prepared according to the method described for Example 34 starting from (5-aminopyridin-3-yl)(7-isopropyl-7H-pyrrolo[2,3-d]pyrimidin-5-yl)methanone (Preparation 95) and 3-[3-(trifluoromethyl)-3H-diaziren-3-yl]benzoic acid (Preparation 197) to afford the title compound as a white solid in 36% yield, 23 mg.

$^1$H NMR (400 MHz, d4-MeOH) δ:1.65 (s, 6H), 5.20 (m, 1H), 7.52-7.61 (m, 4H), 7.79 (s, 1H), 8.07 (m, 1H), 8.29 (s, 1H), 8.94 (s, 1H), 8.81 (m, 1H), 9.55 (s, 1H).

Example 291

N-{5-[(7-isopropyl-7H-pyrrolo[2,3-d]pyrimidin-5-yl)carbonyl]pyridin-3-yl}-4-[3-(trifluoromethyl)-3H-diaziren-3-yl]benzamide The title compound was prepared according to the method described for Example 34 starting from (5-aminopyridin-3-yl)(7-isopropyl-7H-pyrrolo[2,3-d]pyrimidin-5-yl)methanone (Preparation 95) and 4-[3-(trifluoromethyl)-3H-diaziren-3-yl]benzoic acid to afford the title compound as a white solid in 4% yield, 2 mg. LCMS (system 3): $R_t$=3.64 min; m/z 494 [M+H]$^+$.

Example 292

N-{5-[(7-isopropyl-7H-pyrrolo[2,3-d]pyrimidin-5-yl)carbonyl]pyridin-3-yl}-3-(trifluoroacetyl)benzamide

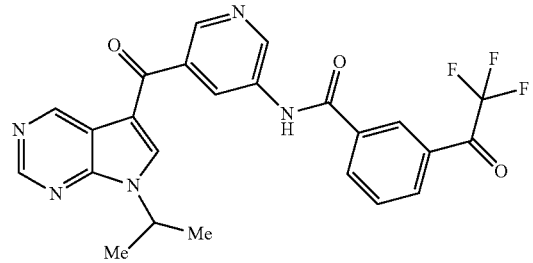 [SMILES: CC(C)n1cc(C(=O)c2cncc(NC(=O)c3cccc(C(=O)C(F)(F)F)c3)c2)c2cncnc21]

The title compound was prepared according to the method described for Example 34 starting from (5-aminopyridin-3-yl)(7-isopropyl-7H-pyrrolo[2,3-d]pyrimidin-5-yl)methanone (Preparation 95) and 3-(trifluoroacetyl)benzoic acid (Preparation 200) to afford the title compound as a white solid in 80% yield, 41 mg. LCMS (system 3): $R_t$=2.52 min; m/z 482 [M+H]$^+$.

Example 293

1-(4-chlorophenyl)-3-{5-[(7-methyl-7H-pyrrolo[2,3-d]pyrimidin-5-yl)carbonyl]pyridin-3-yl}urea

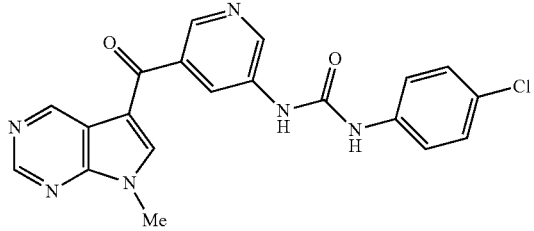 [SMILES: Cn1cc(C(=O)c2cncc(NC(=O)Nc3ccc(Cl)cc3)c2)c2cncnc21]

1-chloro-4-isocyanatobenzene (24 mg, 0.15 mmol) was added to (5-aminopyridin-3-yl)(7-methyl-7H-pyrrolo[2,3-d]pyrimidin-5-yl)methanone (30 mg, 0.12 mmol) (Preparation 232) in pyridine (1.0 mL). The mixture was stirred at room temperature overnight then evaporated in vacuo to yield the product as a crude residue. The crude residue was purified by preparative HPLC to afford the title compound in 49% yield, 24 mg.

LCMS: $R_t$=1.58 min; m/z 407 [M+H]$^+$

The following Examples were prepared according to the method described above for Example 293, starting from (5-aminopyridin-3-yl)(7-methyl-7H-pyrrolo[2,3-d]pyrimidin-5-yl)methanone (Preparation 232) and the appropriate isocyanates.

| Example | Name | Data |
|---|---|---|
| 294 | 1-{5-[(7-methyl-7H-pyrrolo[2,3-d]pyrimidin-5-yl)carbonyl]pyridin-3-yl}-3-[4-(trifluoromethyl)phenyl]urea | LCMS: $R_t$ = 1.64 min; m/z 441 [M + H]$^+$ |
| 295 | 1-{5-[(7-methyl-7H-pyrrolo[2,3-d]pyrimidin-5-yl)carbonyl]pyridin-3-yl}-3-[3-(trifluoromethyl)phenyl]urea | LCMS: Rt = 1.64 min; m/z 441 [M + H]$^+$ |
| 296 | 1-{5-[(7-methyl-7H-pyrrolo[2,3-d]pyrimidin-5-yl)carbonyl]pyridin-3-yl}-3-[4-(trifluoromethoxy)phenyl]urea | LCMS: Rt = 1.67 min; m/z 457 [M + H]$^+$ |

Example 297

2-(4-chlorophenyl)-N-{5-[(7-isopropyl-7H-pyrrolo[2,3-d]pyrimidin-5-yl)carbonyl]pyridin-3-yl}-N-methylacetamide

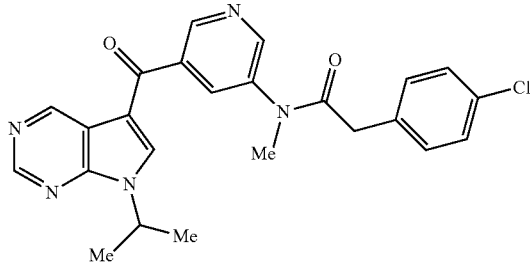 [SMILES: CC(C)n1cc(C(=O)c2cncc(N(C)C(=O)Cc3ccc(Cl)cc3)c2)c2cncnc21]

(4-chlorophenyl)acetic acid (22 mg, 0.13 mmol) was added to a stirring mixture of (7-isopropyl-7H-pyrrolo[2,3-d]pyrimidin-5-yl)[5-(methylamino)pyridin-3-yl]methanone (30 mg, 0.10 mmol) (Preparation 149) and N-[(dimethylamino)(3H-[1,2,3]triazolo[4,5-b]pyridin-3-yloxy)methylene]-N-methylmethanaminium hexafluorophosphate (57 mg, 0.15 mmol) in pyridine (1.0 mL). The mixture was heated to 50° C. for 16 hours, evaporated in vacuo and partitioned between saturated aqueous sodium bicarbonate (10 mL) and EtOAc (10 mL). The aqueous layer was washed with further EtOAc (2×10 mL). The combined organics were dried over Na$_2$SO$_4$, filtered and concentrated in vacuo and purified by preparative HPLC to afford the title compound 43% yield, 19 mg, $^1$H NMR (400 MHz, DMSO) δ: 1.52 (d, 6H), 3.40 (br. s, 3H), 3.59 (s, 2H), 5.00-5.18 (m, 1H), 7.00-7.42 (m, 4H), 8.21 (s, 1H), 8.50 (s, 1H), 8.86 (s, 1H), 8.90-9.12 (m, 2H), 9.48 (s, 1H);

LCMS: $R_t$=2.99 min; m/z 448 [M+H]$^+$

The following Example was prepared according to the method described above for Example 297, starting from (7-isopropyl-7H-pyrrolo[2,3-d]pyrimidin-5-yl)[5-(methylamino)pyridin-3-yl]methanone (Preparation 149) and the appropriate acid.

| Example | Name | Data |
|---|---|---|
| 298 | 2-(4-cyanophenyl)-N-{5-[(7-isopropyl-7H-pyrrolo[2,3-d]pyrimidin-5-yl)carbonyl]pyridin-3-yl}-N-methylacetamide | LCMS: $R_t$ = 2.86 min; m/z 439 [M + H]$^+$ |

Example 299

2-(4-Chloro-phenyl)-N-{5-[7-(3-hydroxymethyl-oxetan-3-yl)-7H-pyrrolo[2,3-d]pyrimidine-5-carbonyl]-pyridin-3-yl}-acetamide

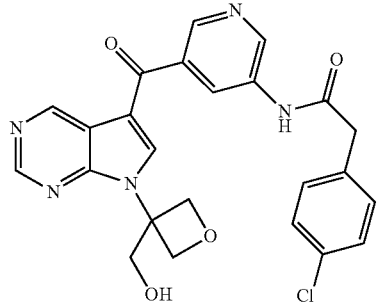 [SMILES: O=C(Cc1ccc(Cl)cc1)Nc1cncc(C(=O)c2cn(C3(CO)COC3)c3ncncc23)c1]

N-(5-{7-[3-(tert-Butyl-dimethyl-silanyloxymethyl)-oxetan-3-yl]-7H-pyrrolo[2,3-d]pyrimidine-5-carbonyl}-pyridin-3-yl)-2-(4-chloro-phenyl)-acetamide (Preparation 203 mg, 0.059 mmol) was dissolved in dry THF (0.5 mL) and tetrabutylammonium fluoride (0.065 mL of a 1M solution in THF, 0.065 mmol.) was added. The reaction was stirred for 30 min at room temperature. The mixture was partitioned between water and EtOAc. The layers were separated and the aqueous layer was extracted twice with EtOAc. The combined organic layers were concentrated and purified by preparative HPLC to give the title compound in quantitative yield 28 mg.

LCMS (System 4): $R_t$=3.03 min; m/z 478 [M+H]$^+$

Example 300

N-{5-[7-(3-Hydroxymethyl-oxetan-3-yl)-7H-pyrrolo
[2,3-d]pyrimidine-5-carbonyl]-pyridin-3-yl}-2-(4-
trifluoromethyl-phenyl)-acetamide The title compound was prepared according to the method described for Example 299 starting from N-(5-{7-[3-(tert-butyl-dimethyl-silanyloxymethyl)-oxetan-3-yl]-7H-pyrrolo[2,3-d]pyrimidine-5-carbonyl}-pyridin-3-yl)-2-(4-trifluoromethyl-phenyl)-acetamide (Preparation 204) to afford the title compound as a white solid in quantitative yield, 30 mg. LCMS: $R_t$=2.74 min; m/z 512 [M+H]$^+$.

Example 301

2-(5-chloropyridin-2-yl)-N-[5-({7-[3-(hydroxymethyl)oxetan-3-yl]-7H-pyrrolo[2,3-d]pyrimidin-5-yl}carbonyl)pyridin-3-yl]acetamide The title compound was prepared according to the method described for Example 299 starting from N-[5-({7-[3-({[tert-butyl(dimethyl)silyl]oxy}methyl)oxetan-3-yl]-7H-pyrrolo[2,3-d]pyrimidin-5-yl}carbonyl)pyridin-3-yl]-2-(5-chloropyridin-2-yl)acetamide (Preparation 223) to afford the title compound as a pale yellow liquid in 87% yield, 23 mg. LCMS (System 4): $R_t$=1.57 min; m/z 479 [M+H]$^+$.

Example 302

N-[5-({7-[3-(hydroxymethyl)oxetan-3-yl]-7H-pyrrolo[2,3-d]pyrimidin-5-yl}carbonyl)pyridin-3-yl]-2-[3-(trifluoromethyl)-1H-pyrazol-1-yl]acetamide

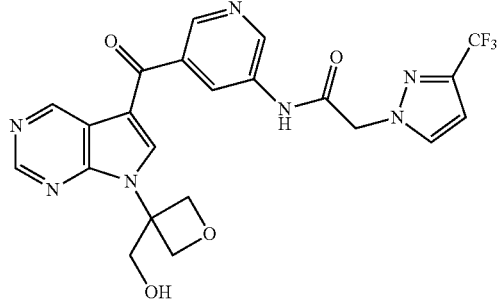 [SMILES: O=C(Cn1ccc(C(F)(F)F)n1)Nc1cncc(C(=O)c2cn(C3(CO)COC3)c3ncncc23)c1]

The title compound was prepared according to the method described for Example 299 starting from N-[5-({7-[3-({[tert-butyl(dimethyl)silyl]oxy}methyl)oxetan-3-yl]-7H-pyrrolo[2,3-d]pyrimidin-5-yl}carbonyl)pyridin-3-yl]-2-[3-(trifluoromethyl)-1H-pyrazol-1-yl]acetamide (34 mg, 0.055 mmol) (Preparation 224) to give the title compound in 63% yield, 17.7 mg.

LCMS (System 5) $R_t$=1.57 min; m/z 502 [M+H]$^+$.

Example 303

N-(5-{[7-(2-amino-2-oxoethyl)-7H-pyrrolo[2,3-d]pyrimidin-5-yl]carbonyl}pyridin-3-yl)-2-(4-chlorophenyl)acetamide

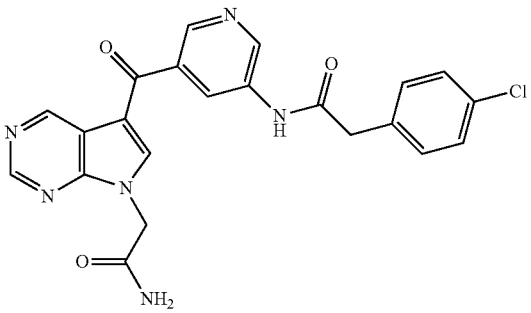 [SMILES: NC(=O)Cn1cc(C(=O)c2cncc(NC(=O)Cc3ccc(Cl)cc3)c2)c2cncnc21]

To a stirred solution of 2-(4-chlorophenyl)-N-[5-(7H-pyrrolo[2,3-d]pyrimidin-5-ylcarbonyl)pyridin-3-yl]acetamide (Example 308, 50 mg, 0.13 mmol) in DMF (1 ml) was added $Cs_2CO_3$ (75 mg, 0.23 mmol) followed by 2-bromoacetamide (21.3 mg, 0.154 mmol). The reaction was then stirred at room temperature overnight. The reaction was quenched with water (5 mL) and extracted with EtOAc (3×5 mL). The organics were combined, washed with water (5 mL) then brine (5 mL), dried over anhydrous magnesium sulfate and concentrated in vacuo. Purification by preparative HPLC gave the title compound in 59% yield, 34 mg.

LCMS (System 4): $R_t$=1.56 min; m/z 449 [M+H]$^+$.

Example 304

2-{5-[(5-{[(4-chlorophenyl)acetyl]amino}pyridin-3-yl)carbonyl]-7H-pyrrolo[2,3-d]pyrimidin-7-yl}-N,N-dimethylacetamide {5-[(5-{[(4-chlorophenyl)acetyl]amino}pyridin-3-yl)carbonyl]-7H-pyrrolo[2,3-d]pyrimidin-7-yl}acetic acid potassium salt (Example 307, 50 mg, 0.102 mmol) was added to a stirred solution of dimethyl amine HCl (12.5 mg, 0.153 mmol) and HATU (58.2 mg, 0.153 mmol) in pyridine (2 mL) and the resultant solution was stirred at 50° C. (reactivial) for 14 hours. The reaction was cooled to 25° C., diluted with DCM (5 mL) then quenched with saturated $NaHCO_3$ (aq) (5 mL) and extracted with further DCM (3×5 mL). The organics were combined, washed with saturated brine (5 mL), dried over anhydrous magnesium sulfate and concentrated in vacuo. Purification by preparative HPLC gave the title compound in 55% yield, 26.6 mg.

LCMS: $R_t$=1.86 min; m/z 477 [M+H]$^+$.

Example 305

2-(4-chlorophenyl)-N-[5-({7-[2-(methylamino)-2-oxoethyl]-7H-pyrrolo[2,3-d]pyrimidin-5-yl}carbonyl)pyridin-3-yl]acetamide {5-[(5-{[(4-chlorophenyl)acetyl]amino}pyridin-3-yl)carbonyl]-7H-pyrrolo[2,3-d]pyrimidin-7-yl}acetic acid potassium salt (Example 307, 50 mg, 0.102 mmol) was added to a stirred solution of methyl amine hydrochloride (10.3 mg, 0.153 mmol) and HATU (58.2 mg, 0.153 mmol) in pyridine (2 mL). The resultant solution was stirred at 50° C. (reactivial) for 14 hours. The reaction was cooled to 25° C., diluted with DCM (5 mL) then quenched with saturated NaHCO$_3$ (aq) (5 mL) and extracted with further DCM (3×5 mL).

The organics were combined, washed with saturated brine (5 mL), dried over anhydrous magnesium sulfate and concentrated in vacuo. Purification by preparative HPLC gave the title compound in 65% yield, 30.5 mg.

LCMS: R$_t$=2.63 min; m/z 463 [M+H]$^+$.

Example 306

Methyl {5-[(5-{[(4-chlorophenyl)acetyl]amino}pyridin-3-yl)carbonyl]-7H-pyrrolo[2,3-d]pyrimidin-7-yl}acetate

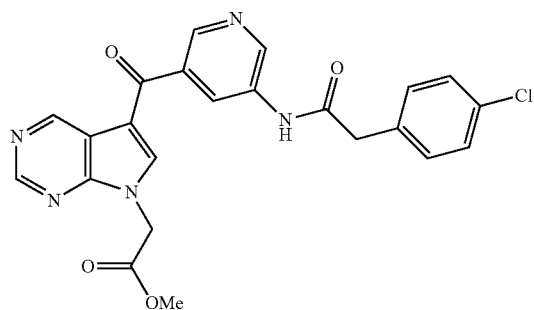 [SMILES: COC(=O)Cn1cc(C(=O)c2cncc(NC(=O)Cc3ccc(Cl)cc3)c2)c2cncnc21]

To a stirred solution of 2-(4-chlorophenyl)-N-[5-(7H-pyrrolo[2,3-d]pyrimidin-5-ylcarbonyl)pyridin-3-yl]acetamide (Example 308, 250 mg, 0.638 mmol) in DMF (4 mL) was added Cs$_2$CO$_3$ (374 mg, 1.15 mmol) followed by methyl bromoacetate (73 uL, 0.766 mmol). The reaction was stirred at 25° C. for 3 hours and then quenched with water (10 mL) and extracted with EtOAc (3×10 mL). The organics were combined, washed with water (10 mL) and saturated brine (10 mL), dried over anhydrous magnesium sulfate and concentrated in vacuo to give a pale yellow oil (356 mg) which solidified on standing. Purification by column chromatography on silica gel (gradient of 0-100% 90:10:1 DCM/MeOH/NH3 in DCM) gave the title compound as a pale yellow solid in 70% yield, 208 mg. $^1$HNMR (400 MHz, CDCl$_3$) δ 3.78 (s, 2H), 3.81 (s, 3H), 5.15 (s, 2H), 7.29-7.41 (m, 4H), 7.51 (s, 1H), 7.88 (s, 1H), 8.46 (m, 1H), 8.78-8.82 (m, 2H), 9.04 (s, 1H), 9.65 (s, 1H). LCMS (System 4): R$_t$=2.07 min; m/z 464 [M+H]$^+$.

Example 307

{5-[(5-{[(4-chlorophenyl)acetyl]amino}pyridin-3-yl)carbonyl]-7H-pyrrolo[2,3-d]pyrimidin-7-yl}acetic acid potassium salt To a suspension of methyl {5-[(5-{[(4-chlorophenyl)acetyl]amino}pyridin-3-yl)carbonyl]-7H-pyrrolo[2,3-d]pyrimidin-7-yl}acetate (Example 306, 197 mg, 0.425 mmol) in MeOH (4 mL) was added an aqueous solution of KOH (0.425 mL of a 1M solution, 0.425 mmol) and then further MeOH (4 mL) was added. The reaction was stirred for 2 hours at room temperature. The reaction was concentrated in vacuo to give the title compound as a light brown solid in 99% yield, 205 mg.

LCMS (System 4): R$_t$=1.76 min; m/z 450 [M+H]$^+$.

Example 308

2-(4-Chlorophenyl)-N-[5-(7H-pyrrolo[2,3-d]pyrimidin-5-ylcarbonyl)pyridin-3-yl]acetamide The title compound was prepared according to the method described for Example 46 to afford the title compound as a white solid in 87% yield, 930 mg.

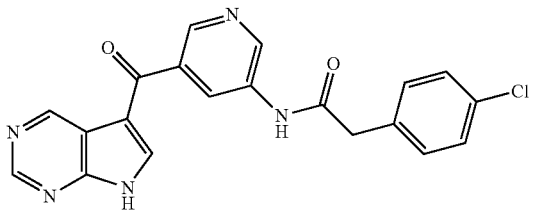 [SMILES: O=C(Cc1ccc(Cl)cc1)Nc1cncc(C(=O)c2c[nH]c3ncncc23)c1]

$^1$H NMR (400 MHz, DMSO) ä: 3.74 (s, 2H), 7.38 (m, 4H), 8.34 (s, 1H), 8.46 (s, 1H), 8.71 (s, 1H), 8.94 (s, 1H), 8.97 (s, 1H), 9.45 (s, 1H), 10.66 (s, 1H), 13.14 (s, 1H); LCMS (system 9): R$_t$=2.87 min; m/z 392 [M+H]$^+$.

Example 309

2-(4-chlorophenyl)-N-(5-{[7-(3-methyloxetan-3-yl)-7H-pyrrolo[2,3-d]pyrimidin-5-yl]carbonyl}pyridin-3-yl)acetamide

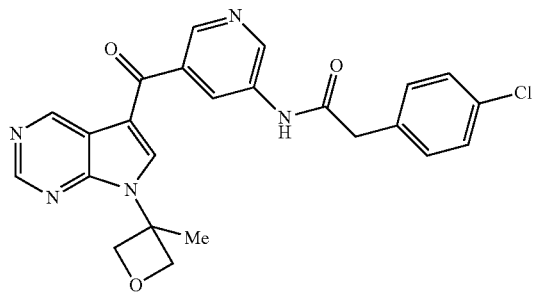 [SMILES: CC1(n2cc(C(=O)c3cncc(NC(=O)Cc4ccc(Cl)cc4)c3)c3cncnc32)COC1]

(5-aminopyridin-3-yl)[7-(3-methyloxetan-3-yl)-7H-pyrrolo[2,3-d]pyrimidin-5-yl]methanone (Preparation 222, 15.5 mg, 0.05 mmol) was added to a stirring mixture of 4-chlorophenylacetic acid (11.1 mg, 0.065 mmol) and HATU (28.5 mg, 0.075 mmol) in pyridine (0.25 mL). The mixture was heated to 50° C. and stirred for 16 hours. The mixture was allowed to cool to room temperature and saturated sodium bicarbonate solution (5 mL) was added. The mixture was extracted with ethyl acetate (3×5 mL) and the combined organic fractions were washed with brine, dried (MgSO$_4$) and the solvent was removed under reduced pressure to obtain the crude product which was autopurified.

LCMS (system 4): R$_t$=3.08 min; m/z 462[M+H]$^+$.

The following Examples were prepared according to the method described above for Example 309 starting from 5-aminopyridin-3-yl)[7-(3-methyloxetan-3-yl)-7H-pyrrolo[2,3-d]pyrimidin-5-yl]methanone (Preparation 222) and the appropriate acids.

| Example | Name | Data |
|---|---|---|
| 310 | 2-(5-chloropyridin-2-yl)-N-(5-{[7-(3-methyloxetan-3-yl)-7H-pyrrolo[2,3-d]pyrimidin-5-yl]carbonyl}pyridin-3-yl)acetamide | LCMS (System 2): $R_t$ = 0.88 min; m/z 463 [M + H]$^+$ Using Preparation 90 |
| 311 | N-(5-{[7-(3-methyloxetan-3-yl)-7H-pyrrolo[2,3-d]pyrimidin-5-yl]carbonyl}pyridin-3-yl)-2-[3-(trifluoromethyl)-1H-pyrazol-1-yl]acetamide | LCMS (System 2): $R_t$ = 0.97 min; m/z 486 [M + H]$^+$ |
| 312 | N-(5-{[7-(3-methyloxetan-3-yl)-7H-pyrrolo[2,3-d]pyrimidin-5-yl]carbonyl}pyridin-3-yl)-2-[4-(trifluoromethyl)-1H-1,2,3-triazol-1-yl]acetamide | LCMS (System 2): $R_t$ = 0.92 min; m/z 487 [M + H]$^+$ Using Preparation 85 |

Example 313

2-(4-chlorophenyl)-N-[5-({7-[(methylthio)methyl]-7H-pyrrolo[2,3-d]pyrimidin-5-yl}carbonyl)pyridin-3-yl]acetamide

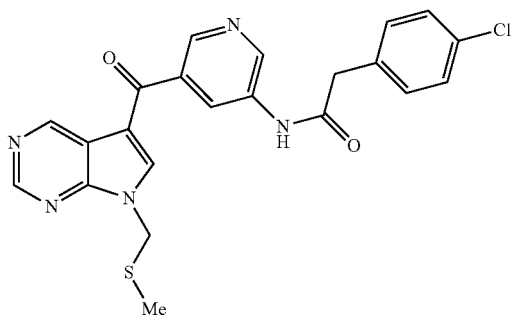 [SMILES: CSCn1cc(C(=O)c2cncc(NC(=O)Cc3ccc(Cl)cc3)c2)c2cncnc21]

Potassium carbonate (38 mg, 0.275 mmol) was added to a stirring solution of 2-(4-chlorophenyl)-N-[5-(7H-pyrrolo[2,3-d]pyrimidin-5-ylcarbonyl)pyridin-3-yl]acetamide (Example 308, 60.0 mg, 0.153 mmol) in DMF (1.0 mL) at room temperature. After 10 min, chloromethyl methyl sulfide (19 µL, 0.23 mmol) was added to the mixture and the reaction was stirred for 24 hours at room temperature. Water (3 mL) was added to the mixture and it was extracted with EtOAc (3×5 mL). The combined organic fractions were washed with water (5 mL), brine (5 mL), dried over magnesium sulfate and concentrated under reduced pressure to give a pale yellow oil. The crude material was purified by column chromatography on silica gel (gradient of 100% DCM to 90:10:1 DCM/MeOH/NH$_3$) to give the title compound as a pale yellow solid in 36% yield, 25 mg.
$^1$H NMR (400 MHz, CDCl$_3$) δ: 2.13 (s, 3H), 3.79 (s, 2H), 5.39 (s, 2H), 7.30-7.34 (m, 3H), 7.40-7.43 (m, 2H), 8.02 (s, 1H), 8.52 (m, 1H), 8.74-8.75 (d, 1H), 8.82-8.83 (d, 1H), 9.05 (s, 1H), 9.65 (s, 1H); LCMS (system 4): $R_t$=1.97 min; m/z 452; 454 [M+H]$^+$.

Example 314

2-(4-chlorophenyl)-N-[5-({7-[(methylsulfonyl)methyl]-7H-pyrrolo[2,3-d]pyrimidin-5-yl}carbonyl)pyridin-3-yl]acetamide Potassium peroxomonosulfate (Oxone, 67.2 mg, 0.110 mmol) was added to a stirring solution of 2-(4-chlorophenyl)-N-[5-({7-[(methylthio)methyl]-7H-pyrrolo[2,3-d]pyrimidin-5-yl}carbonyl)pyridin-3-yl]acetamide (Example 313, 25.0 mg, 0.055 mmol) in methanol (1.0 mL) and water (0.25 mL) at 0° C. After 1 hour, the reaction was allowed to warm to room temperature and stirred for 24 hours. The reaction mixture was cooled to 0° C. and sodium metabisulfite (0.5M, 1 ml) was added. The reaction mixture was evaporated under reduced pressure to remove the methanol. Water (3 mL) was added to the mixture and it was extracted with EtOAc (3×5 mL). The combined organic fractions were washed with water (5 mL), brine (5 mL), dried over magnesium sulfate the solvent was removed under reduced pressure to give the crude product as an off-white solid.
The crude material was purified by column chromatography on silica gel (gradient of 100% DCM to 90:10:1 DCM/MeOH/NH$_3$) to give the title compound as a pale yellow solid in 17% yield, 27 mg. LCMS (system 4): $R_t$=1.91 min; m/z 484; 486 [M+H]$^+$.

Example 315

2-(1-Cyclopropyl-5-trifluoromethyl-1H-pyrazol-4-yl)-N-[5-(7-isopropyl-7H-pyrrolo[2,3-d]pyrimidine-5-carbonyl)-pyridin-3-yl]-acetamide

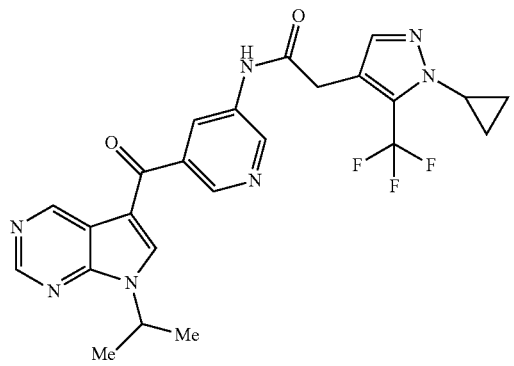 [SMILES: CC(C)n1cc(C(=O)c2cncc(NC(=O)Cc3cnn(C4CC4)c3C(F)(F)F)c2)c2cncnc21]

To a solution of (5-Amino-pyridin-3-yl)-(7-isopropyl-7H-pyrrolo[2,3-d]pyrimidin-5-yl)-methanone (Preparation 95, 50 mg, 0.17 mmol), (1-Cyclopropyl-5-trifluoromethyl-1H-pyrazol-4-yl)-acetic acid (Preparation 141, 47.1 mg, 0.21 mmol) and TEA (0.08 mL, 0.62 mmol) in THF (1 mL), 1-propylphosphonic acid cyclic anhydride (50% solution in EtOAc, 0.26 mL, 0.44 mmol) was added and the mixture was stirred at room temperature for 14 hours. The reaction mixture was evaporated under reduced pressure and the residue partitioned between water and ethyl acetate. The organic layer was washed with saturated sodium bicarbonate solution and dried (Na$_2$SO$_4$) and evaporated in vacuo. Purification by column chromatography on silica gel (gradient of EtOAc: Hexane 0:100 to 80:20) gave the title compound as a white solid in 76% yield, 67 mg. $^1$H NMR (400 MHz, DMSO-D6) δ: 1.05-1.07 (m, 2H), 1.08-1.15 (m, 2H), 1.54 (d, 6H), 3.73-3.76 (m, 3H), 5.06-5.13 (m, 1H), 7.55 (s, 1H), 8.44 (s, 1H), 8.51 (s, 1H), 8.73 (s, 1H), 8.94 (d, 1H), 8.99 (s, 1H), 9.44 (s, 1H), 10.61 (s, 1H). LCMS (System 10): $R_t$=3.03 min m/z 498 [M+H]$^+$ Example 316

N-(5-{[2-amino-7-(1-hydroxy-2-methylpropan-2-yl)-7H-pyrrolo[2,3-d]pyrimidin-5-yl]carbonyl}pyridin-3-yl)-2-(5-bromopyridin-2-yl)acetamide The title compound was prepared according to the method described for Example 34 at 50° C. using [2-amino-7-(2-hydroxy-1,1-dimethylethyl)-7H-pyrrolo[2,3-d]pyrimidin-5-yl](5-aminopyridin-3-yl)methanone (Preparation 48) and (5-bromopyridin-2-yl)acetic acid to afford the title compound as a yellow solid in 60% yield, 75 mg. LCMS (System 10): $R_t$=2.69 min; m/z 524 [M+H]$^+$ Example 317

2-(5-bromopyridin-2-yl)-N-(5-{[7-(propan-2-yl)-7H-pyrrolo[2,3-d]pyrimidin-5-yl]carbonyl}pyridin-3-yl)acetamide The title compound was prepared according to the method described for Example 1 with DIPEA using (5-aminopyridin-3-yl)(7-isopropyl-7H-pyrrolo[2,3-d]pyrimidin-5-yl)methanone (Preparation 95) and (5-bromopyridin-2-yl)acetic acid to afford the title compound as a yellow solid in 45% yield, 75 mg. LCMS (System 9): $R_t$=2.97 min; m/z 479 [M+H]$^+$.

Example 318

N-{5-[(2-Amino-7-isopropyl-7H-pyrrolo[2,3-d]pyrimidin-5-yl)carbonyl]pyridin-3-yl}-2-(5-bromopyridin-2-yl)acetamide The title compound was prepared according to the method described for Example 1 with DIPEA using (2-amino-7-isopropyl-7H-pyrrolo[2,3-d]pyrimidin-5-yl)(5-aminopyridin-3-yl)methanone (Preparation 122) and (5-bromopyridin-2-yl)acetic acid to afford the title compound as a colourless oil in 57% yield, 75 mg.

LCMS (System 10): $R_t$=2.81 min; m/z 494 [M+H]$^+$.

Library Protocol 1

The compounds below were prepared in parallel in the following manner.

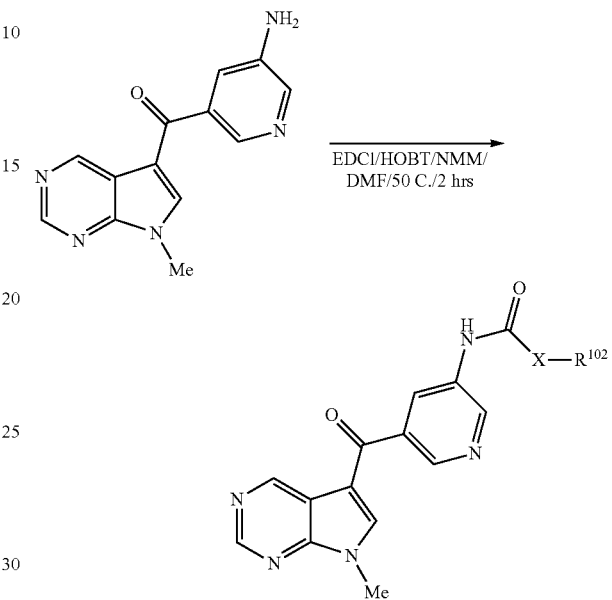

A 0.25 M stock solution of (5-amino-pyridin-3-yl)-(7-methyl-7H-pyrrolo[2,3-d]pyrimidin-5-yl)-methanone (Preparation 110) in anhydrous DMF was prepared. Stock solutions (0.30 M) of each acid monomer was prepared in anhydrous DMF. A stock solution of EDCI (0.5 M) and HOBT (0.05 M) in anhydrous DMF were prepared. 300 μl (90 μmol) of each acid monomer solution was dispensed to 8 mL vials, followed by 300 μl (75 umol) of (5-amino-pyridin-3-yl)-(7-methyl-7H-pyrrolo[2,3-d]pyrimidin-5-yl)-methanone solution. N-methyl morpholine (150 μmol, 2.0 eq), 300 μl EDCI solution (150 μmol) and HOBT (15 μmol) were added to each vial. The vials were capped and shaken at 50° C. for 2 hours. The solvent was removed using a Speedvac, and the final product purified by HPLC under the conditions listed to provide the final compounds.

| Example | Name | Data |
| --- | --- | --- |
| 319 | 2-(4-chlorophenyl)-N-{5-[(7-methyl-7H-pyrrolo[2,3-d]pyrimidin-5-yl)carbonyl]pyridin-3-yl}acetamide | LCMS: $R_t$ = 2.59 min; m/z 406 [M + H]$^+$ |
| 320 | 3-(4-chlorophenyl)-N-{5-[(7-methyl-7H-pyrrolo[2,3-d]pyrimidin-5-yl)carbonyl]pyridin-3-yl}propanamide | LCMS: $R_t$ = 2.70 min; m/z 420 [M + H]$^+$ |
| 321 | 3-(3-methylphenyl)-N-{5-[(7-methyl-7H-pyrrolo[2,3-d]pyrimidin-5-yl)carbonyl]pyridin-3-yl}propanamide | LCMS: $R_t$ = 2.69 min; m/z 400 [M + H]$^+$ |
| 322 | N-{5-[(7-methyl-7H-pyrrolo[2,3-d]pyrimidin-5-yl)carbonyl]pyridin-3-yl}-3-(pyridin-3-yl)propanamide | LCMS: $R_t$ = 1.80 min; m/z 387 [M + H]$^+$ |
| 323 | 3-(3-chlorophenyl)-N-{5-[(7-methyl-7H-pyrrolo[2,3-d]pyrimidin-5-yl)carbonyl]pyridin-3-yl}propanamide | LCMS: $R_t$ = 2.69 min; m/z 420 [M + H]$^+$ |
| 324 | 3-(3-fluorophenyl)-N-{5-[(7-methyl-7H-pyrrolo[2,3-d]pyrimidin-5-yl)carbonyl]pyridin-3-yl}propanamide | LCMS: $R_t$ = 2.56 min; m/z 404 [M + H]$^+$ |

-continued

| Example | Name | Data |
|---|---|---|
| 325 | N-{5-[(7-methyl-7H-pyrrolo[2,3-d]pyrimidin-5-yl)carbonyl]pyridin-3-yl}-2-[2-(trifluoromethoxy)phenoxy]acetamide | LCMS: $R_t$ = 2.80 min; m/z 472 [M + H]$^+$ |
| 326 | 3-(2-methylphenyl)-N-{5-[(7-methyl-7H-pyrrolo[2,3-d]pyrimidin-5-yl)carbonyl]pyridin-3-yl}propanamide | LCMS: $R_t$ = 2.63 min; m/z 400 [M + H]$^+$ |
| 327 | 3-(2-fluorophenyl)-N-{5-[(7-methyl-7H-pyrrolo[2,3-d]pyrimidin-5-yl)carbonyl]pyridin-3-yl}propanamide | LCMS: $R_t$ = 2.53 min; m/z 404 [M + H]$^+$ |
| 328 | 3-(4-fluorophenyl)-N-{5-[(7-methyl-7H-pyrrolo[2,3-d]pyrimidin-5-yl)carbonyl]pyridin-3-yl}propanamide | LCMS: $R_t$ = 2.55 min; m/z 404 [M + H]$^+$ |
| 329 | N-{5-[(7-methyl-7H-pyrrolo[2,3-d]pyrimidin-5-yl)carbonyl]pyridin-3-yl}-3-phenylpropanamide | LCMS: $R_t$ = 2.50 min; m/z 386 [M + H]$^+$ |
| 330 | 3-(4-methylphenyl)-N-{5-[(7-methyl-7H-pyrrolo[2,3-d]pyrimidin-5-yl)carbonyl]pyridin-3-yl}propanamide | LCMS: $R_t$ = 2.65 min; m/z 400 [M + H]$^+$ |
| 331 | N-{5-[(7-methyl-7H-pyrrolo[2,3-d]pyrimidin-5-yl)carbonyl]pyridin-3-yl}-2-(4-{[(trifluoromethyl)sulfonyl]amino}phenyl)acetamide | LCMS: $R_t$ = 2.60 min; m/z 519 [M + H]$^+$ |
| 332 | N-{5-[(7-methyl-7H-pyrrolo[2,3-d]pyrimidin-5-yl)carbonyl]pyridin-3-yl}-2-phenoxyacetamide | LCMS: $R_t$ = 2.53 min; m/z 388 [M + H]$^+$ |
| 333 | 2-[4-(methoxymethyl)phenyl]-N-{5-[(7-methyl-7H-pyrrolo[2,3-d]pyrimidin-5-yl)carbonyl]pyridin-3-yl}acetamide | LCMS: $R_t$ = 2.31 min; m/z 416 [M + H]$^+$ |
| 334 | 2-(4-fluorophenoxy)-N-{5-[(7-methyl-7H-pyrrolo[2,3-d]pyrimidin-5-yl)carbonyl]pyridin-3-yl}acetamide | LCMS: $R_t$ = 2.44 min; m/z 406 [M + H]$^+$ |

Example 336

N-{5-[(7-methyl-7H-pyrrolo[2,3-d]pyrimidin-5-yl)carbonyl]pyridin-3-yl}-1-phenylcyclopropanecarboxamide

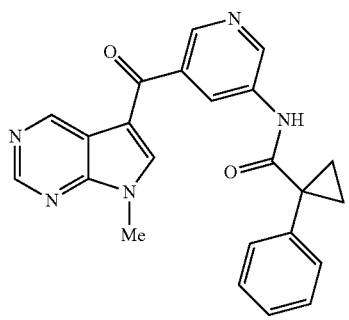 [SMILES: Cn1cc(C(=O)c2cncc(NC(=O)C3(c4ccccc4)CC3)c2)c2cncnc21]

The title compound was prepared according to the method described for Library protocol 1 starting from (5-amino-pyridin-3-yl)-(7-methyl-7H-pyrrolo[2,3-d]pyrimidin-5-yl)-methanone (Preparation 110) and 1-phenylcyclopropanecarboxylic acid to afford the title compound. LCMS: $R_t$=2.61 min; m/z 398 [M+H]$^+$.

Example 337

N-{5-[(7-methyl-7H-pyrrolo[2,3-d]pyrimidin-5-yl)carbonyl]pyridin-3-yl}indane-2-carboxamide The title compound was prepared according to the method described for Library protocol 1 starting from (5-amino-pyridin-3-yl)-(7-methyl-7H-pyrrolo[2,3-d]pyrimidin-5-yl)-methanone (Preparation 110) and indane-2-carboxylic acid to afford the title compound. LCMS: $R_t$=2.58 min; m/z 398 [M+H].

Example 338

(2R)—N-{5-[(7-methyl-7H-pyrrolo[2,3-d]pyrimidin-5-yl)carbonyl]pyridin-3-yl}-2-phenylpropanamide The title compound was prepared according to the method described for Library protocol 1 starting from (5-amino-pyridin-3-yl)-(7-methyl-7H-pyrrolo[2,3-d]pyrimidin-5-yl)-methanone (Preparation 110) and (2R)-2-phenylpropanoic acid to afford the title compound. LCMS: $R_t$=2.52 min; m/z 386 [M+H]$^+$.

Example 339

3-hydroxy-2-phenyl-N-(5-{[7-(propan-2-yl)-7H-pyrrolo[2,3-d]pyrimidin-5-yl]carbonyl}pyridin-3-yl)propanamide

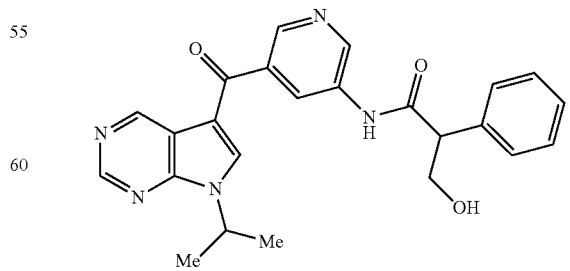

The title compound was prepared according to the method described for Example 167 using (5-aminopyridin-3-yl)(7- isopropyl-7H-pyrrolo[2,3-d]pyrimidin-5-yl)methanone (Preparation 95) and tropic acid to afford the title compound as a yellow solid in 7% yield, 15 mg.

$^1$H NMR (400 MHz, DMSO-d6) δ: 1.57 (d, 6H), 3.16-3.22 (m, 1H), 3.37-3.41 (m, 1H), 3.60-3.64 (m, 1H), 5.10 (m, 1H), 6.30 (t, 1H), 7.10 (t, 1H), 7.20 (t, 2H), 7.30-7.32 (m, 3H), 8.12 (s, 1H), 8.15 (d, 1H), 8.61 (s, 1H), 8.96 (s, 1H), 9.44 (s, 1H).

LCMS (system 10): $R_t$=2.36 min; m/z 430 [M+H]$^+$.

The following Example was prepared according to Examples 1 and 34 for Methods a and b as described above.

| Example | Name | Data |
|---|---|---|
| 340 | N-{5-[(7-isopropyl-7H-pyrrolo[2,3-d]pyrimidin-5-yl)carbonyl]-pyridin-3-yl}-2-(5-methoxy-1H-indol-1-yl)acetamide | LCMS (system 8): $R_t$ = 1.63 min; m/z 469 [M + H]$^+$ |

The following examples were prepared according to Example 356 using (5-amino-pyridin-3-yl)-(7-isopropyl-7H-pyrrolo[2,3-d]pyrimidin-5-yl)-methanone (Preparation 95) and the appropriate acid.

| Example | Name | Data |
|---|---|---|
| 343 | 3-chloro-N-(5-{[7-(propan-2-yl)-7H-pyrrolo[2,3-d]pyrimidin-5-yl]carbonyl}pyridin-3-yl)benzamide | LCMS $R_t$ = 2.95 min; m/z 420 [M + H]$^+$. |
| 344 | 4-chloro-N-(5-{[7-(propan-2-yl)-7H-pyrrolo[2,3-d]pyrimidin-5-yl]carbonyl}pyridin-3-yl)benzamide | LCMS $R_t$ = 2.93 min; m/z 420 [M + H]$^+$. |
| 345 | N-(5-{[7-(propan-2-yl)-7H-pyrrolo[2,3-d]pyrimidin-5-yl]carbonyl}pyridin-3-yl)-4-(trifluoromethyl)benzamide | LCMS $R_t$ = 2.99 min; m/z 454 [M + H]$^+$. |
| 346 | N-(5-{[7-(propan-2-yl)-7H-pyrrolo[2,3-d]pyrimidin-5-yl]carbonyl}pyridin-3-yl)-4-(trifluoromethoxy)benzamide | LCMS $R_t$ = 3.05 min; m/z 470 [M + H]$^+$. |
| 347 | 2-(2-cyanophenoxy)-N-(5-{[7-(propan-2-yl)-7H-pyrrolo[2,3-d]pyrimidin-5-yl]carbonyl}pyridin-3-yl)acetamide | LCMS $R_t$ = 0.67 min; m/z 441 [M + H]$^+$. |
| 348 | N-(5-{[7-(propan-2-yl)-7H-pyrrolo[2,3-d]pyrimidin-5-yl]carbonyl}pyridin-3-yl)-2-[4-(trifluoromethoxy)phenoxy]acetamide | LCMS $R_t$ = 3.01 min; m/z 500 [M + H]$^+$. |

Example 350

2-amino-2-(4-chlorophenyl)-N-(5-(7-isopropyl-7H-pyrrolo[2,3-d]pyrimidine-5-carbonyl)pyridin-3-yl)acetamide

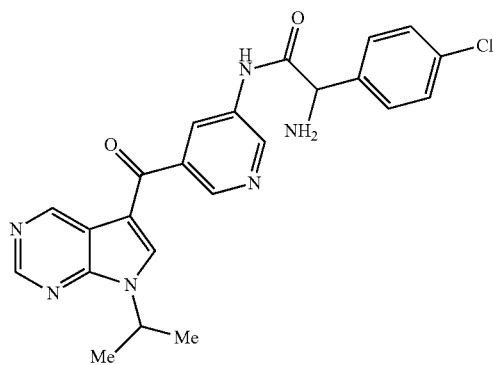 [SMILES: CC(C)n1cc(C(=O)c2cncc(NC(=O)C(N)c3ccc(Cl)cc3)c2)c2cncnc21]

To tert-butyl (1-(4-chlorophenyl)-2-((5-(7-isopropyl-7H-pyrrolo[2,3-d]pyrimidine-5-carbonyl)pyridin-3-yl)amino)-2-oxoethyl)carbamate (Preparation 299, 64 mg, 0.11 mmol) was added 4M HCl/dioxane (5 mL) and the reaction stirred at room temperature for 18 hours. The mixture was evaporated in vacuo and purified by preparative reverse phase HPLC to give the title compound as a beige solid in 8% yield, 4 mg.

$^1$H NMR (400 MHz, MeOD) δ: 1.59 (d, 6H), 4.63 (s, 1H), 5.16 (m, 1H), 7.35 (d, 2H), 7.47 (d, 2H), 8.33 (s, 1H), 8.62 (s, 1H), 8.69 (s, 1H), 8.88 (s, 1H), 8.92 (s, 1H), 9.47 (s, 1H).

LCMS $R_t$=2.81 min; MS m/z 449 [M+H]$^+$

Example 351

N-{5-[2-Amino-7-(2-hydroxy-1,1-dimethyl-ethyl)-7H-pyrrolo[2,3-d]pyrimidine-5-carbonyl]-pyridin-3-yl}-2-(5-cyano-pyridin-2-yl)-acetamide

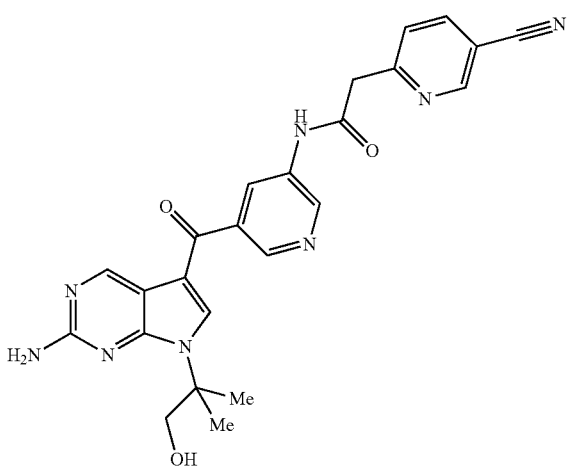 [SMILES: CC(C)(CO)n1cc(C(=O)c2cncc(NC(=O)Cc3ccc(C#N)cn3)c2)c2cnc(N)nc21]

To a solution of N-{5-[2-Amino-7-(2-hydroxy-1,1-dimethyl-ethyl)-7H-pyrrolo[2,3-d]pyrimidine-5-carbonyl]-pyridin-3-yl}-2-(5-bromo-pyridin-2-yl)-acetamide (Example 316, 75 mg, 0.143 mmol) in DMF (2 mL) was added Zn(CN)$_2$ (25 mg, 0.215 mmol) and the reaction mixture was degassed with argon for 10 minutes. Pd$_2$(dba)$_3$ (3 mg, 0.002 mmol) and 1,1'-bis(diphenylphosphino)ferrocene 6 mg, 0.011 mmol) were then added and the resultant reaction mixture was heated at 100° C. for 40 minutes under microwave irradiation. The reaction mixture was diluted with EtOAc (20 mL) and washed with water (2×10 mL) and brine (10 mL). The organic layer was dried (Na$_2$SO$_4$) and evaporated in vacuo. The crude material was purified by preparative TLC (7% MeOH in DCM) to afford the title compound as yellow solid in 31% yield, 21 mg.

$^1$H NMR (400 MHz, DMSO-D6) δ: 1.63 (s, 6H), 3.89 (d, 2H), 4.06 (s, 2H), 5.04 (t, 1H), 6.53 (s, 2H), 7.65-7.68 (m, 2H), 8.29 (dd, 1H), 8.40 (s, 1H), 8.64 (d, 1H), 8.93-8.97 (m, 3H), 10.75 (s, 1H).

LCMS (system 10): $R_t$=2.50 min MS m/z 471[M+H]$^+$

Example 352

2-(1-Cyclopropyl-3-trifluoromethyl-1H-pyrazol-4-yl)-N-[5-(7-isopropyl-7H-pyrrolo[2,3-d]pyrimidine-5-carbonyl)-pyridin-3-yl]-acetamide

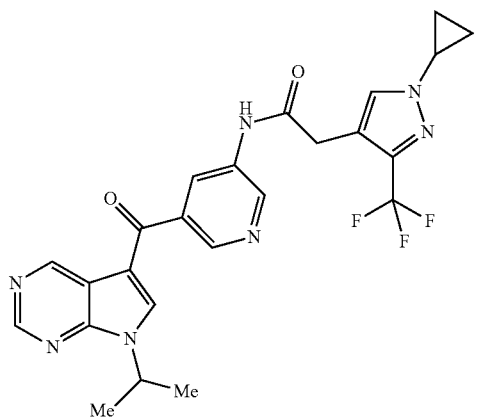 [SMILES: CC(C)n1cc(C(=O)c2cncc(NC(=O)Cc3cn(C4CC4)nc3C(F)(F)F)c2)c2cncnc21]

To a solution of (5-Amino-pyridin-3-yl)-(7-isopropyl-7H-pyrrolo[2,3-d]pyrimidin-5-yl)-methanone (Preparation 95, 50 mg, 0.17 mmol), (1-Cyclopropyl-3-trifluoromethyl-1H-pyrazol-4-yl)-acetic acid (Preparation 148, 47.1 mg, 0.21 mmol) and TEA (0.08 mL, 0.62 mmol) in THF (1 mL), 1-propylphosphonic acid cyclic anhydride (50% solution in EtOAc, 0.26 mL, 0.44 mmol) was added and the mixture was stirred at room temperature for 18 hours. The reaction mixture was evaporated under reduced pressure and the residue partitioned between water and EtOAc. The organic layer was washed with saturated sodium bicarbonate solution, dried (Na$_2$SO$_4$) and evaporated in vacuo. Purification by column chromatography on silica gel (EtOAc) gave the title compound as a white solid in 77% yield, 68 mg.

$^1$H NMR (400 MHz, DMSO-D6) δ: 1.00-1.01 (m, 2H), 1.06-1.14 (m, 2H), 1.54 (d, 6H), 3.70 (s, 2H), 3.84 (m, 1H), 5.08-5.12 (m, 1H), 7.98 (s, 1H), 8.45 (s, 1H), 8.51 (s, 1H), 8.74 (s, 1H), 8.96 (d, 1H), 8.99 (s, 1H), 9.44 (s, 1H), 10.60 (s, 1H).

LCMS (system 10): R$_t$=3.02 min MS m/z 498 [M+H]$^+$.

Example 353 racemic Methyl 2-{5-[(5-{[(4-chlorophenyl)acetyl]amino}pyridin-3-yl)carbonyl]-7H-pyrrolo[2,3-d]pyrimidin-7-yl}propanoate The title compound was prepared according to the method described for Example 229 using 2-(4-chlorophenyl)-N-[5-(7H-pyrrolo[2,3-d]pyrimidin-5-ylcarbonyl)pyridin-3-yl]acetamide (Example 308), methyl 2-bromopropionate and cesium carbonate. Purified using preparative HPLC (method 1) to afford the title compound.

LCMS (system 2): R$_t$=1.42 min MS m/z 478 [M+H]$^+$

Example 354 racemic 2-{5-[(5-{[(4-Chlorophenyl)acetyl]amino}pyridin-3-yl)carbonyl]-7H-pyrrolo[2,3-d]pyrimidin-7-yl}propanoic acid The title compound was prepared according to the method described for Preparation 155 using methyl 2-{5-[(5-{[(4-chlorophenyl)acetyl]amino}pyridin-3-yl)carbonyl]-7H-pyrrolo[2,3-d]pyrimidin-7-yl}propanoate (Example 353) to afford the title compound as a white solid in 100% yield, 97 mg.

LCMS (system 2): R$_t$=1.40 min; m/z 464 [M+H]$^+$.

Example 355

2-(4,5-Dichloro-imidazol-1-yl)-N-[5-(7-isopropyl-7H-pyrrolo[2,3-d]pyrimidine-5-carbonyl)-pyridin-3-yl]-acetamide (method d)

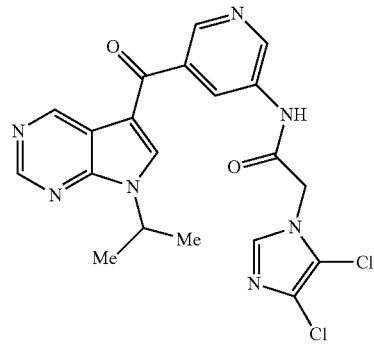 [SMILES: CC(C)n1cc(C(=O)c2cncc(NC(=O)Cn3cnc(Cl)c3Cl)c2)c2cncnc21]

(4,5-Dichloro-imidazol-1-yl)-acetic acid (25.2 mg, 0.130 mmol) was added to (5-amino-pyridin-3-yl)-(7-isopropyl-7H-pyrrolo[2,3-d]pyrimidin-5-yl)-methanone (28.1 mg, 0.1 mmol), HATU (49.4 mg, 0.130 mmol) and DIPEA (51.7 uL, 0.300 mmol) in anhydrous DMF (1 mL). The mixture was stirred at 50° C. for 16 hours and then evaporated in vacuo and purified by prep-HPLC (method 5) to afford the title compound in 46% yield, 21.2 mg.

LCMS (system 8): R$_t$=1.55 min; m/z 458 [M+H]

Example 356

7-Difluoromethyl-5-methyl-[1,2,4]triazolo[1,5-a]pyrimidine-2-carboxylic acid [5-(7-isopropyl-7H-pyrrolo[2,3-d]pyrimidine-5-carbonyl)-pyridin-3-yl]-amide (method e)

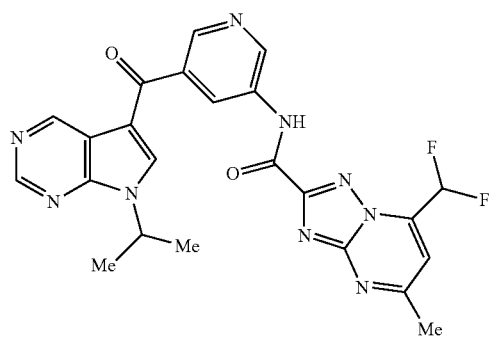 [SMILES: Cc1cc(C(F)F)n2nc(C(=O)Nc3cncc(C(=O)c4cn(C(C)C)c5ncncc45)c3)nc2n1]

7-Difluoromethyl-5-methyl-[1,2,4]triazolo[1,5-a]pyrimidine-2-carboxylic acid (29.64 mg, 0.130 mmol) was added to (5-amino-pyridin-3-yl)-(7-isopropyl-7H-pyrrolo[2,3-d]pyrimidin-5-yl)-methanone (28.1 mg, 0.1 mmol), HATU (49.42 mg, 0.130 mmol) and DIPEA (22.4 uL, 0.13 mmol) in anhydrous DMF (1 mL). The mixture was stirred at 50° C. for 16 hours and then evaporated in vacuo and purified by prep-HPLC (method 5) to afford the title compound in 12% yield, 6.1 mg.

LCMS (system 8): $R_t$=1.56 min; m/z 492 [M+H]$^+$

The following Examples were prepared according to one of the methods for Examples 355 (Method d) and 356 (Method e) using (5-aminopyridin-3-yl)(7-isopropyl-7H-pyrrolo[2,3-d]pyrimidin-5-yl)methanone (Preparation 95).

| Example | Name | Data |
|---|---|---|
| 357 | 2-(4,5-Dichloro-imidazol-1-yl)-N-[5-(7-isopropyl-7H-pyrrolo[2,3-d]pyrimidine-5-carbonyl)-pyridin-3-yl]-acetamide | LCMS (system 8): $R_t$ = 1.55 min; m/z 458 [M + H]$^+$. Prep HPLC (method 5) |
| 358 | 2-(3,5-Dimethyl-1,2,4-triazol-1-yl)-N-[5-(7-isopropyl-7H-pyrrolo[2,3-d]pyrimidine-5-carbonyl)-pyridin-3-yl]-acetamide | LCMS (system 8): $R_t$ = 1.43 min; m/z 419 [M + H]$^+$. Prep HPLC (method 5) |
| 359 | N-[5-(7-Isopropyl-7H-pyrrolo[2,3-d]pyrimidine-5-carbonyl)-pyridin-3-yl]-2-(2-methyl-imidazol-1-yl)-acetamide | LCMS (system 8): $R_t$ = 1.27 min; m/z 404 [M + H]$^+$. Prep HPLC (method 5) |
| 360 | 2-Imidazo[2,1-b]thiazol-6-yl-N-[5-(7-isopropyl-7H-pyrrolo[2,3-d]pyrimidine-5-carbonyl)-pyridin-3-yl]-acetamide | LCMS (system 8): $R_t$ = 1.42 min; m/z 446 [M + H]$^+$. Prep HPLC (method 5) |
| 361 | 2-(4-Hydroxy-phthalazin-1-yl)-N-[5-(7-isopropyl-7H-pyrrolo[2,3-d]pyrimidine-5-carbonyl)-pyridin-3-yl]-acetamide | LCMS (system 8): $R_t$ = 1.46 min; m/z 468 [M + H]$^+$. Prep HPLC (method 5) |
| 362 | 2-(2,3-Dimethyl-imidazo[2,1-b]thiazol-6-yl)-N-[5-(7-isopropyl-7H-pyrrolo[2,3-d]pyrimidine-5-carbonyl)-pyridin-3-yl]-acetamide | LCMS (system 8): $R_t$ = 1.48 min; m/z 474 [M + H]$^+$. Prep HPLC (method 5) |
| 363 | 2-[4-(1-Hydroxy-cyclopentyl)-1,2,3-triazol-1-yl]-N-[5-(7-isopropyl-7H-pyrrolo[2,3-d]pyrimidine-5-carbonyl)-pyridin-3-yl]-acetamide | LCMS (system 8): $R_t$ = 1.44 min; m/z 475 [M + H]$^+$. Prep HPLC (method 5) (From Prep 294) |
| 364 | N-[5-(7-Isopropyl-7H-pyrrolo[2,3-d]pyrimidine-5-carbonyl)-pyridin-3-yl]-2-(5-m-tolyl-tetrazol-1-yl)-acetamide | LCMS (system 8): $R_t$ = 1.57 min; m/z 482 [M + H]$^+$. Prep HPLC (method 5) |
| 365 | 2-[4-(4-Fluoro-phenyl)-imidazol-1-yl]-N-[5-(7-isopropyl-7H-pyrrolo[2,3-d]pyrimidine-5-carbonyl)-pyridin-3-yl]-acetamide | LCMS (system 8): $R_t$ = 1.45 min; m/z 484 [M + H]$^+$. Prep HPLC (method 5) |
| 366 | 2-(5-Isopropyl-pyrazol-1-yl)-N-[5-(7-isopropyl-7H-pyrrolo[2,3-d]pyrimidine-5-carbonyl)-pyridin-3-yl]-acetamide | LCMS (system 8): $R_t$ = 1.60 min; m/z 432 [M + H]$^+$. Prep HPLC (method 5) (Acid can be prepared in an analogus to method given in WO03/072572) |
| 367 | 2-(2-Ethyl-imidazo[2,1-b]-1,3,4-thiadiazol-6-yl)-N-[5-(7-isopropyl-7H-pyrrolo[2,3-d]pyrimidine-5-carbonyl)-pyridin-3-yl]-acetamide | LCMS (system 8): $R_t$ = 1.60 min; m/z 475 [M + H]$^+$. Prep HPLC (method 5) |
| 368 | N-[5-(7-Isopropyl-7H-pyrrolo[2,3-d]pyrimidine-5-carbonyl)-pyridin-3-yl]-2-(2-methyl-imidazo[2,1-b]thiazol-6-yl)-acetamide | LCMS (system 8): $R_t$ = 1.45 min; m/z 460 [M + H]$^+$. Prep HPLC (method 5) (from Prep 289) |
| 369 | 2-(3-Chloro-5-methyl-1,2,4-triazol-1-yl)-N-[5-(7-isopropyl-7H-pyrrolo[2,3-d]pyrimidine-5-carbonyl)-pyridin-3-yl]-acetamide | LCMS (system 8): $R_t$ = 1.48 min; m/z 439 [M + H]$^+$. Prep HPLC (method 5) |
| 370 | N-[5-(7-Isopropyl-7H-pyrrolo[2,3-d]pyrimidine-5-carbonyl)-pyridin-3-yl]-2-(2-phenyl-imidazol-1-yl)-acetamide | LCMS (system 8): $R_t$ = 1.34 min; m/z 466 [M + H]$^+$. Prep HPLC (method 5) |
| 371 | 2-(2-Chloro-imidazo[2,1-b]thiazol-6-yl)-N-[5-(7-isopropyl-7H-pyrrolo[2,3-d]pyrimidine-5-carbonyl)-pyridin-3-yl]-acetamide | LCMS (system 8): $R_t$ = 1.59 min; m/z 480 [M + H]$^+$. Prep HPLC (method 5) |
| 372 | 2-Imidazol-1-yl-N-[5-(7-isopropyl-7H-pyrrolo[2,3-d]pyrimidine-5-carbonyl)-pyridin-3-yl]-acetamide | LCMS (system 8): $R_t$ = 1.26 min; m/z 390 [M + H]$^+$. Prep HPLC (method 5) |
| 373 | N-[5-(7-Isopropyl-7H-pyrrolo[2,3-d]pyrimidine-5-carbonyl)-pyridin-3-yl]-2-(3-methyl-imidazo[2,1-b]thiazol-6-yl)-acetamide | LCMS (system 8): $R_t$ = 1.46 min; m/z 460 [M + H]$^+$. Prep HPLC (method 5) |

-continued

| Example | Name | Data |
|---|---|---|
| 374 | 2-[1-(4-Hydroxy-phenyl)-1H-pyrrol-3-yl]-N-[5-(7-isopropyl-7H-pyrrolo[2,3-d]pyrimidine-5-carbonyl)-pyridin-3-yl]-acetamide | LCMS (system 8): $R_t$ = 1.57 min; m/z 481 [M + H]$^+$. Prep HPLC (method 5) |
| 375 | N-[5-(7-Isopropyl-7H-pyrrolo[2,3-d]pyrimidine-5-carbonyl)-pyridin-3-yl]-2-[1,2,4]triazolo[1,5-a]pyrimidin-6-yl-acetamide | LCMS (system 8): $R_t$ = 1.41 min; m/z 442 [M + H]$^+$. Prep HPLC (method 5) |
| 376 | N-[5-(7-Isopropyl-7H-pyrrolo[2,3-d]pyrimidine-5-carbonyl)-pyridin-3-yl]-2-pyrazin-2-yl-acetamide | LCMS (system 8): $R_t$ = 1.44 min; m/z 402 [M + H]$^+$. Prep HPLC (method 5) |
| 377 | 2-[4-(3-Hydroxy-phenyl)-1,2,3-triazol-1-yl]-N-[5-(7-isopropyl-7H-pyrrolo[2,3-d]pyrimidine-5-carbonyl)-pyridin-3-yl]-acetamide | LCMS (system 8): $R_t$ = 1.48 min; m/z 483 [M + H]$^+$. Prep HPLC (method 5) (from Prep 292) |
| 378 | N-[5-(7-Isopropyl-7H-pyrrolo[2,3-d]pyrimidine-5-carbonyl)-pyridin-3-yl]-2-(5-phenyl-tetrazol-1-yl)-acetamide | LCMS (system 8): $R_t$ = 1.63 min; m/z 468 [M + H]$^+$. Prep HPLC (method 5) |
| 379 | 7-Difluoromethyl-5-methyl-[1,2,4]triazolo[1,5-a]pyrimidine-2-carboxylic acid [5-(7-isopropyl-7H-pyrrolo[2,3-d]pyrimidine-5-carbonyl)-pyridin-3-yl]-amide | LCMS (system 8): $R_t$ = 1.56 min; m/z 492 [M + H]$^+$. Prep HPLC (method 5) |
| 380 | Furo[3,2-c]pyridine-4-carboxylic acid [5-(7-isopropyl-7H-pyrrolo[2,3-d]pyrimidine-5-carbonyl)-pyridin-3-yl]-amide | LCMS (system 8): $R_t$ = 1.73 min; m/z 427 [M + H]$^+$. Prep HPLC (method 5) |
| 381 | 4-Methyl-furazan-3-carboxylic acid [5-(7-isopropyl-7H-pyrrolo[2,3-d]pyrimidine-5-carbonyl)-pyridin-3-yl]-amide | LCMS (system 8): $R_t$ = 1.61 min; m/z 392 [M + H]$^+$. Prep HPLC (method 5) |
| 382 | 1-Methyl-1H-indazole-3-carboxylic acid [5-(7-isopropyl-7H-pyrrolo[2,3-d]pyrimidine-5-carbonyl)-pyridin-3-yl]-amide | LCMS (system 8): $R_t$ = 1.75 min; m/z 440 [M + H]$^+$. Prep HPLC (method 5) |
| 383 | 1H-Indole-2-carboxylic acid [5-(7-isopropyl-7H-pyrrolo[2,3-d]pyrimidine-5-carbonyl)-pyridin-3-yl]-amide | LCMS (system 8): $R_t$ = 1.67 min; m/z 425 [M + H]$^+$. Prep HPLC (method 5) |
| 384 | 2-Methyl-4-trifluoromethyl-thiazole-5-carboxylic acid [5-(7-isopropyl-7H-pyrrolo[2,3-d]pyrimidine-5-carbonyl)-pyridin-3-yl]-amide | LCMS (system 8): $R_t$ = 1.62 min; m/z 475 [M + H]$^+$. Prep HPLC (method 5) |
| 385 | 5-Cyclopropyl-oxazole-4-carboxylic acid [5-(7-isopropyl-7H-pyrrolo[2,3-d]pyrimidine-5-carbonyl)-pyridin-3-yl]-amide | LCMS (system 8): $R_t$ = 1.67 min; m/z 417 [M + H]$^+$. Prep HPLC (method 5) |
| 386 | Pyridazine-3-carboxylic acid [5-(7-isopropyl-7H-pyrrolo[2,3-d]pyrimidine-5-carbonyl)-pyridin-3-yl]-amide | LCMS (system 8): $R_t$ = 1.52 min; m/z 388 [M + H]$^+$. Prep HPLC (method 5) |
| 387 | 3-Methyl-5-trifluoromethyl-1H-pyrazole-4-carboxylic acid [5-(7-isopropyl-7H-pyrrolo[2,3-d]pyrimidine-5-carbonyl)-pyridin-3-yl]-amide | LCMS (system 8): $R_t$ = 1.53 min; m/z 458 [M + H]$^+$. Prep HPLC (method 5) (Acid from prep 290) |
| 388 | 4-Methyl-pyridine-2-carboxylic acid [5-(7-isopropyl-7H-pyrrolo[2,3-d]pyrimidine-5-carbonyl)-pyridin-3-yl]-amide | LCMS (system 8): Rt = 1.70 min; m/z 401 [M + H]+. Prep HPLC (method 5) |
| 389 | 3-Cyclobutyl-1H-pyrazole-4-carboxylic acid [5-(7-isopropyl-7H-pyrrolo[2,3-d]pyrimidine-5-carbonyl)-pyridin-3-yl]-amide | LCMS (system 8): Rt = 1.59 min; m/z 430 [M + H]+. Prep HPLC (method 5) |
| 390 | Oxazole-5-carboxylic acid [5-(7-isopropyl-7H-pyrrolo[2,3-d]pyrimidine-5-carbonyl)-pyridin-3-yl]-amide | LCMS (system 8): Rt = 1.46 min; m/z 377 [M + H]+. Prep HPLC (method 5) |
| 391 | 4-Methyl-1H-imidazole-2-carboxylic acid [5-(7-isopropyl-7H-pyrrolo[2,3-d]pyrimidine-5-carbonyl)-pyridin-3-yl]-amide | LCMS (system 8): Rt = 1.52 min; m/z 390 [M + H]+. Prep HPLC (method 5) |
| 392 | 1H-Pyrrolo[2,3-c]pyridine-5-carboxylic acid [5-(7-isopropyl-7H- | LCMS (system 8): Rt = 1.56 min; m/z 426 [M + H]+. |

-continued

| Example | Name | Data |
|---|---|---|
| | pyrrolo[2,3-d]pyrimidine-5-carbonyl)-pyridin-3-yl]-amide | Prep HPLC (method 5)<br>(Acid: Synthesis, 1993, 295-297) |
| 393 | 5-Methyl-pyrazine-2-carboxylic acid[5-(7-isopropyl-7H-pyrrolo[2,3-d]pyrimidine-5-carbonyl)-pyridin-3-yl]-amide | LCMS (system 8): Rt = 1.58 min; m/z 402 [M + H]+.<br>Prep HPLC (method 5) |
| 394 | 1,3-Dimethyl-1H-pyrazole-4-carboxylic acid [5-(7-isopropyl-7H-pyrrolo[2,3-d]pyrimidine-5-carbonyl)-pyridin-3-yl]-amide | LCMS (system 8): Rt = 1.53 min; m/z 404 [M + H]+.<br>Prep HPLC (method 6) |
| 395 | 1H-Pyrazolo[4,3-b]pyridine-6-carboxylic acid [5-(7-isopropyl-7H-pyrrolo[2,3-d]pyrimidine-5-carbonyl)-pyridin-3-yl]-amide | LCMS (system 8): Rt = 1.46 min; m/z 427 [M + H]+.<br>Prep HPLC (method 5)<br>(Acid: see US 20110111046) |
| 396 | 5-Ethyl-isoxazole-3-carboxylic acid[5-(7-isopropyl-7H-pyrrolo[2,3-d]pyrimidine-5-carbonyl)-pyridin-3-yl]-amide | LCMS (system 8): Rt = 1.63 min; m/z 405 [M + H]+.<br>Prep HPLC (method 5) |
| 397 | 2-Methyl-2H-pyrazole-3-carboxylic acid [5-(7-isopropyl-7H-pyrrolo[2,3-d]pyrimidine-5-carbonyl)-pyridin-3-yl]-amide | LCMS (system 8): Rt = 1.54 min; m/z 390 [M + H]+.<br>Prep HPLC (method 5) |
| 398 | Quinoline-3-carboxylic acid [5-(7-isopropyl-7H-pyrrolo[2,3-d]pyrimidine-5-carbonyl)-pyridin-3-yl]-amide | LCMS (system 8): Rt = 1.66 min; m/z 437 [M + H]+.<br>Prep HPLC (method 5) |
| 399 | 5-Fluoro-1H-pyrrolo[2,3-b]pyridine-2-carboxylic acid [5-(7-isopropyl-7H-pyrrolo[2,3-d]pyrimidine-5-carbonyl)-pyridin-3-yl]-amide | LCMS (system 8): Rt = 1.61 min; m/z 444 [M + H]+.<br>Prep HPLC (method 5)<br>(Acid: WO2008/107543) |
| 400 | 1,5-Dimethyl-1H-pyrazole-3-carboxylic acid [5-(7-isopropyl-7H-pyrrolo[2,3-d]pyrimidine-5-carbonyl)-pyridin-3-yl]-amide | LCMS (system 8): Rt = 1.57 min; m/z 404 [M + H]+.<br>Prep HPLC (method 5) |
| 401 | 2-Cyclopropyl-oxazole-4-carboxylic acid [5-(7-isopropyl-7H-pyrrolo[2,3-d]pyrimidine-5-carbonyl)-pyridin-3-yl]-amide | LCMS (system 8): Rt = 1.64 min; m/z 417 [M + H]+.<br>Prep HPLC (method 5) |
| 402 | 4-Trifluoromethyl-thiazole-5-carboxylic acid [5-(7-isopropyl-7H-pyrrolo[2,3-d]pyrimidine-5-carbonyl)-pyridin-3-yl]-amide | LCMS (system 8): Rt = 1.58 min; m/z 461 [M + H]+.<br>Prep HPLC (method 5) |
| 403 | 6,7-Dihydro-5H-pyrrolo[1,2-c]imidazole-1-carboxylic acid [5-(7-isopropyl-7H-pyrrolo[2,3-d]pyrimidine-5-carbonyl)-pyridin-3-yl]-amide | LCMS (system 8): Rt = 1.51 min; m/z 416 [M + H]+.<br>Prep HPLC (method 5)<br>(Acid can be preparaed by oxidation of aldehyde described in Tetrahedron, 1999, 8111) |
| 404 | Thieno[3,2-c]pyridine-6-carboxylic acid [5-(7-isopropyl-7H-pyrrolo[2,3-d]pyrimidine-5-carbonyl)-pyridin-3-yl]-amide | LCMS (system 8): Rt = 1.77 min; m/z 443 [M + H]+.<br>Prep HPLC (method 5) |
| 405 | 1-Methyl-3-trifluoromethyl-1H-pyrazole-4-carboxylic acid [5-(7-isopropyl-7H-pyrrolo[2,3-d]pyrimidine-5-carbonyl)-pyridin-3-yl]-amide | LCMS (system 8): Rt = 1.60 min; m/z 458 [M + H]+.<br>Prep HPLC (method 5) |
| 406 | Imidazo[1,5-a]pyridine-7-carboxylicacid [5-(7-isopropyl-7H-pyrrolo[2,3-d]pyrimidine-5-carbonyl)-pyridin-3-yl]-amide | LCMS (system 8): Rt = 1.47 min; m/z 426 [M + H]+.<br>Prep HPLC (method 5) |
| 407 | 1H-Pyrrolo[2,3-b]pyridine-4-carboxylic acid [5-(7-isopropyl-7H-pyrrolo[2,3-d]pyrimidine-5-carbonyl)-pyridin-3-yl]-amide | LCMS (system 8): Rt = 1.54 min; m/z 426 [M + H]+.<br>Prep HPLC (method 5) |
| 408 | 3-Ethyl-isoxazole-5-carboxylic acid[5-(7-isopropyl-7H-pyrrolo[2,3-d]pyrimidine-5-carbonyl)-pyridin-3-yl]-amide | LCMS (system 8): Rt = 1.60 min; m/z 405 [M + H]+.<br>Prep HPLC (method 5) |
| 409 | 4-Methoxy-pyridine-2-carboxylic acid [5-(7-isopropyl-7H-pyrrolo[2,3-d]pyrimidine-5-carbonyl)-pyridin-3-yl]-amide | LCMS (system 8): Rt = 1.67 min; m/z 417 [M + H]+.<br>Prep HPLC (method 5) |

| Example | Name | Data |
|---|---|---|
| 410 | Pyrimidine-5-carboxylic acid [5-(7-isopropyl-7H-pyrrolo[2,3-d]pyrimidine-5-carbonyl)-pyridin-3-yl]-amide | LCMS (system 8): Rt = 1.46 min; m/z 388 [M + H]+. Prep HPLC (method 5) |
| 411 | 3-Methyl-1H-pyrazole-4-carboxylic acid [5-(7-isopropyl-7H-pyrrolo[2,3-d]pyrimidine-5-carbonyl)-pyridin-3-yl]-amide | LCMS (system 8): Rt = 1.46 min; m/z 390 [M + H]+. Prep HPLC (method 5) |
| 412 | 5-Methyl-1H-pyrrolo[2,3-b]pyridine-3-carboxylic acid [5-(7-isopropyl-7H-pyrrolo[2,3-d]pyrimidine-5-carbonyl)-pyridin-3-yl]-amide | LCMS (system 8): Rt = 1.54 min; m/z 440 [M + H]+. Prep HPLC (method 5) |
| 413 | 5-Methyl-pyrimidine-4-carboxylic acid [5-(7-isopropyl-7H-pyrrolo[2,3-d]pyrimidine-5-carbonyl)-pyridin-3-yl]-amide | LCMS (system 8): Rt = 1.60 min; m/z 402 [M + H]+. Prep HPLC (method 5) |
| 414 | Thieno[3,2-b]pyridine-6-carboxylic acid [5-(7-isopropyl-7H-pyrrolo[2,3-d]pyrimidine-5-carbonyl)-pyridin-3-yl]-amide | LCMS (system 8): Rt = 1.64 min; m/z 443 [M + H]+. Prep HPLC (method 5) |
| 415 | Pyrazolo[1,5-a]pyrimidine-6-carboxylic acid [5-(7-isopropyl-7H-pyrrolo[2,3-d]pyrimidine-5-carbonyl)-pyridin-3-yl]-amide | LCMS (system 8): Rt = 1.54 min; m/z 427 [M + H]+. Prep HPLC (method 5) |
| 416 | 4,5,6,7-Tetrahydro-1,2-benzisoxazole-3-carboxylic acid [5-(7-isopropyl-7H-pyrrolo[2,3-d]pyrimidine-5-carbonyl)-pyridin-3-yl]-amide | LCMS (system 8): Rt = 1.75 min; m/z 431 [M + H]+. Prep HPLC (method 5) |
| 417 | Imidazo[1,5-a]pyridine-3-carboxylicacid [5-(7-isopropyl-7H-pyrrolo[2,3-d]pyrimidine-5-carbonyl)-pyridin-3-yl]-amide | LCMS (system 8): Rt = 1.75 min; m/z 426 [M + H]+. Prep HPLC (method 5) |
| 418 | 1H-Pyrrolo[2,3-b]pyridine-6-carboxylic acid [5-(7-isopropyl-7H-pyrrolo[2,3-d]pyrimidine-5-carbonyl)-pyridin-3-yl]-amide | LCMS (system 8): Rt = 1.65 min; m/z 426 [M + H]+. Prep HPLC (method 5) |
| 419 | 1,4,5,6-Tetrahydro-cyclopentapyrazole-3-carboxylic acid [5-(7-isopropyl-7H-pyrrolo[2,3-d]pyrimidine-5-carbonyl)-pyridin-3-yl]-amide | LCMS (system 8): Rt = 1.59 min; m/z 416 [M + H]+. Prep HPLC (method 5) |
| 420 | 4-Amino-pyrimidine-5-carboxylic acid [5-(7-isopropyl-7H-pyrrolo[2,3-d]pyrimidine-5-carbonyl)-pyridin-3-yl]-amide | LCMS (system 8): Rt = 1.41 min; m/z 403 [M + H]+. Prep HPLC (method 5) |
| 421 | 1H-Pyrrolo[2,3-c]pyridine-3-carboxylic acid [5-(7-isopropyl-7H-pyrrolo[2,3-d]pyrimidine-5-carbonyl)-pyridin-3-yl]amide | LCMS (system 8): Rt = 1.32 min; m/z 426 [M + H]+. Prep HPLC (method 5) |
| 422 | N-[5-(7-Isopropyl-7H-pyrrolo[2,3-d]pyrimidine-5-carbonyl)-pyridin-3-yl]-2-methyl-isonicotinamide | LCMS (system 8): Rt = 1.51 min; m/z 401 [M + H]+. Prep HPLC (method 5) |
| 423 | Imidazo[1,2-a]pyridine-6-carboxylicacid [5-(7-isopropyl-7H-pyrrolo[2,3-d]pyrimidine-5-carbonyl)-pyridin-3-yl]amide | LCMS (system 8): Rt = 1.33 min; m/z 426 [M + H]+. Prep HPLC (method 5) |
| 424 | 1H-1,2,4-Triazole-3-carboxylic acid[5-(7-isopropyl-7H-pyrrolo[2,3-d]pyrimidine-5-carbonyl)-pyridin-3-yl]-amide | LCMS (system 8): Rt = 1.38 min; m/z 377 [M + H]+. Prep HPLC (method 7) |
| 425 | 5-Methoxy-pyridine-2-carboxylic acid [5-(7-isopropyl-7H-pyrrolo[2,3-d]pyrimidine-5-carbonyl)-pyridin-3-yl]-amide | LCMS (system 8): Rt = 1.66 min; m/z 417 [M + H]+. Prep HPLC (method 5) |
| 426 | Cinnoline-4-carboxylic acid [5-(7-isopropyl-7H-pyrrolo[2,3-d]pyrimidine-5-carbonyl)-pyridin-3-yl]-amide | LCMS (system 8): Rt = 1.57 min; m/z 438 [M + H]+. Prep HPLC (method 5) |
| 427 | [1,2,4]Triazolo[1,5-a]pyridine-7-carboxylic acid [5-(7-isopropyl-7H-pyrrolo[2,3-d]pyrimidine-5-carbonyl)-pyridin-3-yl]amide | LCMS (system 8): Rt = 1.51 min; m/z 427 [M + H]+. Prep HPLC (method 5) |
| 428 | Pyrazolo[1,5-a]pyrimidine-2-carboxylic acid [5-(7-isopropyl-7H-pyrrolo[2,3-d]pyrimidine-5-carbonyl)-pyridin-3-yl]amide | LCMS (system 8): Rt = 1.54 min; m/z 427 [M + H]+. Prep HPLC (method 5) |

-continued

| Example | Name | Data |
|---|---|---|
| 429 | Pyridine-2-carboxylic acid [5-(7-isopropyl-7H-pyrrolo[2,3-d]pyrimidine-5-carbonyl)-pyridin-3-yl]-amide | LCMS (system 8): Rt = 1.62 min; m/z 387 [M + H]+. Prep HPLC (method 5) |
| 430 | 5-Chloro-N-[5-(7-isopropyl-7H-pyrrolo[2,3-d]pyrimidine-5-carbonyl)-pyridin-3-yl]-nicotinamide | LCMS (system 8): Rt = 1.62 min; m/z 421 [M + H]+. Prep HPLC (method 5) |
| 431 | 4H-Furo[3,2-b]pyrrole-5-carboxylic acid [5-(7-isopropyl-7H-pyrrolo1[2,3-d]pyrimidine-5-carbonyl)-pyridin-3-yl]-amide | LCMS (system 8): $R_t$ = 1.59 min; m/z 415 [M + H]$^+$. Prep HPLC (method 5) |
| 432 | Imidazo[1,2-a]pyridine-7-carboxylicacid [5-(7-isopropyl-7H-pyrrolo[2,3-d]pyrimidine-5-carbonyl)-pyridin-3-yl]amide | LCMS (system 8): $R_t$ = 1.34 min; m/z 426 [M + H]$^+$. Prep HPLC (method 5) |
| 433 | 1-Ethyl-1H-pyrazole-4-carboxylic acid [5-(7-isopropyl-7H-pyrrolo[2,3-d]pyrimidine-5-carbonyl)-pyridin-3-yl]-amide | LCMS (system 8): $R_t$ = 1.52 min; m/z 404 [M + H]$^+$. Prep HPLC (method 5) |
| 434 | 1-Isopropyl-1H-imidazole-4-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 418 [M + H]$^+$. Prep HPLC (method 5) (Acid: WO2010/009062 |
| 435 | 8-Methoxy-imidazo[1,2-a]pyrazine-6-carboxylic acid [5-(7-isopropyl-7H-pyrrolo[2,3-d]pyrimidine-5-carbonyl)-pyridin-3-yl]amide | LCMS (system 8): $R_t$ = 1.62 min; m/z 457 [M + H]$^+$. Prep HPLC (method 5) (Acid can be prepared by carbonylation of the bromide e.g. WO2010/078408) |
| 436 | 1H-Pyrrolo[2,3-b]pyridine-5-carboxylic acid [5-(7-isopropyl-7H-pyrrolo[2,3-d]pyrimidine-5-carbonyl)-pyridin-3-yl]amide | LCMS (system 8): $R_t$ = 1.55 min; m/z 426 [M + H]$^+$. Prep HPLC (method 5) |
| 437 | 2-Methyl-5-propyl-2H-pyrazole-3-carboxylic acid [5-(7-isopropyl-7H-pyrrolo[2,3-d]pyrimidine-5-carbonyl)-pyridin-3-yl]amide | LCMS (system 8): $R_t$ = 1.69 min; m/z 432 [M + H]$^+$. Prep HPLC (method 5) |
| 438 | 4-Isopropyl-thiazole-2-carboxylic acid [5-(7-isopropyl-7H-pyrrolo[2,3-d]pyrimidine-5-carbonyl)-pyridin-3-yl]-amide | LCMS (system 8): $R_t$ = 1.79 min; m/z 435 [M + H]$^+$. Prep HPLC (method 5) (Acid: WO2007/017144 |
| 439 | 3-Methyl-furo[2,3-c]pyridine-5-carboxylic acid [5-(7-isopropyl-7H-pyrrolo[2,3-d]pyrimidine-5-carbonyl)-pyridin-3-yl]-amide | LCMS (system 8): $R_t$ = 1.77 min; m/z 441 [M + H]$^+$. Prep HPLC (method 5) (Acid: WO04052348) |
| 440 | 6-Methyl-pyridine-2-carboxylic acid[5-(7-isopropyl-7H-pyrrolo[2,3-d]pyrimidine-5-carbonyl)-pyridin-3-yl]-amide | LCMS (system 8): $R_t$ = 1.69 min; m/z 401 [M + H]$^+$. Prep HPLC (method 5) |
| 441 | 5-Chloro-1-methyl-3-trifluoromethyl-1H-pyrazole-4-carboxylic acid [5-(7-isopropyl-7H-pyrrolo[2,3-d]pyrimidine-5-carbonyl)-pyridin-3-yl]-amide | LCMS (system 8): $R_t$ = 1.63 min; m/z 492 [M + H]$^+$. Prep HPLC (method 5) |
| 442 | 5-Methoxy-1H-benzimidazole-2-carboxylic acid [5-(7-isopropyl-7H-pyrrolo[2,3-d]pyrimidine-5-carbonyl)-pyridin-3-yl]amide | LCMS (system 8): $R_t$ = 1.63 min; m/z 456 [M + H]$^+$. Prep HPLC (method 5) (Acid: US2007/017144) |
| 443 | 4-Chloro-1,5-dimethyl-1H-pyrazole-3-carboxylic acid [5-(7-isopropyl-7H-pyrrolo[2,3-d]pyrimidine-5-carbonyl)-pyridin-3-yl]amide | LCMS (system 8): $R_t$ = 1.65 min; m/z 438 [M + H]$^+$. Prep HPLC (method 5) |
| 444 | 1H-Pyrrolo[3,2-c]pyridine-4-carboxylic acid [5-(7-isopropyl-7H-pyrrolo[2,3-d]pyrimidine-5-carbonyl)-pyridin-3-yl]amide | LCMS (system 8): $R_t$ = 1.58 min; m/z 426 [M + H]$^+$. Prep HPLC (method 5) |
| 445 | 4-Ethyl-pyridine-2-carboxylic acid [5-(7-isopropyl-7H-pyrrolo[2,3-d]pyrimidine-5-carbonyl)-pyridin-3-yl]-amide | LCMS (system 8): $R_t$ = 1.76 min; m/z 415 [M + H]$^+$. Prep HPLC (method 5) (Acid: JOC, 1990, 55, 738-741) |
| 446 | 2,3-Dihydro-1,4-dioxino[2,3-b]pyridine-7-carboxylic acid [5-(7-isopropyl-7H-pyrrolo[2,3-d]pyrimidine-5-carbonyl)-pyridin-3-yl]-amide | LCMS (system 8): $R_t$ = 1.54 min; m/z 445 [M + H]$^+$. Prep HPLC (method 5) |

| Example | Name | Data |
|---|---|---|
| 447 | 1H-Pyrrolo[3,2-b]pyridine-5-carboxylic acid [5-(7-isopropyl-7H-pyrrolo[2,3-d]pyrimidine-5-carbonyl)-pyridin-3-yl]amide | LCMS (system 8): $R_t$ = 1.58 min; m/z 426 [M + H]$^+$.<br>Prep HPLC (method 5) |
| 448 | Pyrazolo[1,5-a]pyridine-5-carboxylic acid [5-(7-isopropyl-7H-pyrrolo[2,3-d]pyrimidine-5-carbonyl)-pyridin-3-yl]-amide | LCMS (system 8): $R_t$ = 1.59 min; m/z 426 [M + H]$^+$.<br>Prep HPLC (method 5)<br>(Acid: J. Med. Chem. (2007), 45(21), 4594-4597) |
| 449 | 6-Methoxy-quinoline-3-carboxylic acid [5-(7-isopropyl-7H-pyrrolo[2,3-d]pyrimidine-5-carbonyl)-pyridin-3-yl]-amide | LCMS (system 8): $R_t$ = 1.68 min; m/z 467 [M + H]$^+$.<br>Prep HPLC (method 5) |
| 450 | 5-Methyl-2-(2,2,2-trifluoro-ethyl)-2H-pyrazole-3-carboxylic acid [5-(7-isopropyl-7H-pyrrolo[2,3-d]pyrimidine-5-carbonyl)-pyridin-3-yl]-amide | LCMS (system 8): $R_t$ = 1.66 min; m/z 472 [M + H]$^+$.<br>Prep HPLC (method 5)<br>(Acid: WO 2008/016192) |
| 451 | N-[5-(7-Isopropyl-7H-pyrrolo[2,3-d]pyrimidine-5-carbonyl)-pyridin-3-yl]-4-trifluoromethyl-nicotinamide | LCMS (system 8): $R_t$ = 1.58 min; m/z 455 [M + H]$^+$.<br>Prep HPLC (method 5) |
| 452 | 1-(2-Cyano-ethyl)-1H-pyrazole-4-carboxylic acid [5-(7-isopropyl-7H-pyrrolo[2,3-d]pyrimidine-5-carbonyl)-pyridin-3-yl]amide | LCMS (system 8): $R_t$ = 1.46 min; m/z 429 [M + H]$^+$.<br>Prep HPLC (method 5) |
| 453 | Furo[3,2-c]pyridine-2-carboxylic acid [5-(7-isopropyl-7H-pyrrolo[2,3-d]pyrimidine-5-carbonyl)-pyridin-3-yl]-amide | LCMS (system 8): $R_t$ = 1.45 min; m/z 427 [M + H]$^+$.<br>Prep HPLC (method 5)<br>(Acid: J. Het. Chem. (1987), 24(2), 373-6) |
| 454 | 1H-Pyrrolo[3,2-c]pyridine-2-carboxylic acid [5-(7-isopropyl-7H-pyrrolo[2,3-d]pyrimidine-5-carbonyl)-pyridin-3-yl]-amide | LCMS (system 8): $R_t$ = 1.32 min; m/z 426 [M + H]$^+$.<br>Prep HPLC (method 5) |
| 455 | Furo[3,2-c]pyridine-6-carboxylic acid [5-(7-isopropyl-7H-pyrrolo[2,3-d]pyrimidine-5-carbonyl)-pyridin-3-yl]-amide | LCMS (system 8): $R_t$ = 1.70 min; m/z 427 [M + H]$^+$.<br>Prep HPLC (method 5) |
| 456 | 2,4-Dimethyl-oxazole-5-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 405 [M + H]$^+$.<br>Prep HPLC (method 5) |
| 457 | 1-Methyl-1H-pyrrolo[2,3-c]pyridine-3-carboxylic acid [5-(7-isopropyl-7H-pyrrolo[2,3-d]pyrimidine-5-carbonyl)-pyridin-3-yl]-amide | LCMS (system 8): $R_t$ = 1.32 min; m/z 440 [M + H]$^+$.<br>Prep HPLC (method 5)<br>(Acid: WO07017144) |
| 458 | 5,6-Dihydro-4H-pyrrolo[1,2-b]pyrazole-2-carboxylic acid [5-(7-isopropyl-7H-pyrrolo[2,3-d]pyrimidine-5-carbonyl)-pyridin-3-yl]-amide | LCMS (system 8): $R_t$ = 1.59 min; m/z 416 [M + H]$^+$.<br>Prep HPLC (method 5) |
| 459 | 2-Cyclobutyl-thiazole-4-carboxylic acid [5-(7-isopropyl-7H-pyrrolo[2,3-d]pyrimidine-5-carbonyl)-pyridin-3-yl]-amide | LCMS (system 8): $R_t$ = 1.79 min; m/z 447 [M + H]$^+$.<br>Prep HPLC (method 5)<br>(Acid: WO2009098448) |
| 460 | 3-Fluoro-N-[5-(7-isopropyl-7H-pyrrolo[2,3-d]pyrimidine-5-carbonyl)-pyridin-3-yl]-isonicotinamide | LCMS (system 8): $R_t$ = 1.53 min; m/z 405 [M + H]$^+$.<br>Prep HPLC (method 5) |
| 461 | 2-Methyl-imidazo[1,2-a]pyrimidine-3-carboxylic acid [5-(7-isopropyl-7H-pyrrolo[2,3-d]pyrimidine-5-carbonyl)-pyridin-3-yl]-amide | LCMS (system 8): $R_t$ = 1.52 min; m/z 441 [M + H]$^+$.<br>Prep HPLC (method 5) |
| 462 | 5-Methyl-isoxazole-3-carboxylic acid [5-(7-isopropyl-7H-pyrrolo[2,3-d]pyrimidine-5-carbonyl)-pyridin-3-yl]-amide | LCMS (system 8): $R_t$ = 1.57 min; m/z 391 [M + H]$^+$.<br>Prep HPLC (method 5) |
| 463 | 4,6-Dimethoxy-pyrimidine-2-carboxylic acid [5-(7-isopropyl-7H-pyrrolo[2,3-d]pyrimidine-5-carbonyl)-pyridin-3-yl]-amide | LCMS (system 8): $R_t$ = 1.62 min; m/z 448 [M + H]$^+$.<br>Prep HPLC (method 5) |
| 464 | 6-Methyl-pyrazine-2-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 402 [M + H]$^+$.<br>Prep HPLC (method 5) |

-continued

| Example | Name | Data |
|---|---|---|
| 465 | 1-Methyl-1H-imidazole-4-carboxylic acid [5-(7-isopropyl-7H-pyrrolo[2,3-d]pyrimidine-5-carbonyl)-pyridin-3-yl]-amide | LCMS (system 8): $R_t$ = 1.49 min; m/z 390 [M + H]$^+$. Prep HPLC (method 5) |
| 466 | 5-Chloro-pyridine-2-carboxylic acid[5-(7-isopropyl-7H-pyrrolo[2,3-d]pyrimidine-5-carbonyl)-pyridin-3-yl]-amide | LCMS (system 8): $R_t$ = 1.71 min; m/z 421 [M + H]$^+$. Prep HPLC (method 5) |
| 467 | 1,8-Naphthyridine-2-carboxylic acid[5-(7-isopropyl-7H-pyrrolo[2,3-d]pyrimidine-5-carbonyl)-pyridin-3-yl]-amide | LCMS (system 8): $R_t$ = 1.68 min; m/z 438 [M + H]$^+$. Prep HPLC (method 5) |
| 468 | 1-Methyl-1H-imidazole-2-carboxylic acid [5-(7-isopropyl-7H-pyrrolo[2,3-d]pyrimidine-5-carbonyl)-pyridin-3-yl]-amide | LCMS (system 8): $R_t$ = 1.59 min; m/z 390 [M + H]$^+$. Prep HPLC (method 5) |
| 469 | 5-Methoxymethyl-isoxazole-3-carboxylic acid [5-(7-isopropyl-7H-pyrrolo[2,3-d]pyrimidine-5-carbonyl)-pyridin-3-yl]-amide | LCMS (system 8): $R_t$ = 1.56 min; m/z 421 [M + H]$^+$. Prep HPLC (method 5) |
| 470 | Phthalazine-1-carboxylic acid [5-(7-isopropyl-7H-pyrrolo[2,3-d]pyrimidine-5-carbonyl)-pyridin-3-yl]-amide | LCMS (system 8): $R_t$ = 1.67 min; m/z 438 [M + H]$^+$. Prep HPLC (method 5) |
| 471 | 5,6-Dihydro-4H-pyrrolo[1,2-b]pyrazole-3-carboxylic acid [5-(7-isopropyl-7H-pyrrolo[2,3-d]pyrimidine-5-carbonyl)-pyridin-3-yl]-amide | LCMS (system 8): $R_t$ = 1.55 min; m/z 416 [M + H]$^+$. Prep HPLC (method 5) |
| 472 | 5-Bromo-pyrimidine-4-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 467 [M + H]$^+$. Prep HPLC (method 5) |
| 473 | 6-Cyano-N-[5-(7-isopropyl-7H-pyrrolo[2,3-d]pyrimidine-5-carbonyl)-pyridin-3-yl]-nicotinamide | LCMS (system 8): $R_t$ = 1.55 min; m/z 412 [M + H]$^+$. Prep HPLC (method 5) |
| 474 | Pyrazolo[1,5-a]pyrimidine-3-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 427 [M + H]$^+$. Prep HPLC (method 5) |
| 475 | 3-Methyl-1H-pyrazolo[3,4-b]pyridine-5-carboxylic acid [5-(7-isopropyl-7H-pyrrolo[2,3-d]pyrimidine-5-carbonyl)-pyridin-3-yl]-amide | LCMS (system 8): $R_t$ = 1.53 min; m/z 441 [M + H]$^+$. Prep HPLC (method 5) |
| 476 | 7-Methyl-pyrazolo[1,5-a]pyridine-2-carboxylic acid [5-(7-isopropyl-7H-pyrrolo[2,3-d]pyrimidine-5-carbonyl)-pyridin-3-yl]-amide | LCMS (system 8): $R_t$ = 1.73 min; m/z 440 [M + H]$^+$. Prep HPLC (method 5) |
| 477 | 5-Methyl-oxazole-4-carboxylic acid [5-(7-isopropyl-7H-pyrrolo[2,3-d]pyrimidine-5-carbonyl)-pyridin-3-yl]-amide | LCMS (system 8): $R_t$ = 1.59 min; m/z 391 [M + H]$^+$. Prep HPLC (method 5) |
| 478 | Thieno[3,4-c]pyridine-6-carboxylic acid [5-(7-isopropyl-7H-pyrrolo[2,3-d]pyrimidine-5-carbonyl)-pyridin-3-yl]-amide | LCMS (system 8): $R_t$ = 1.74 min; m/z 443 [M + H]$^+$. Prep HPLC (method 5) (Acid: WO 2002100857) |
| 479 | 2,6-Dimethyl-pyrimidine-4-carboxylic acid [5-(7-isopropyl-7H-pyrrolo[2,3-d]pyrimidine-5-carbonyl)-pyridin-3-yl]-amide | LCMS (system 8): $R_t$ = 1.65 min; m/z 416 [M + H]$^+$. Prep HPLC (method 5) |
| 480 | 4-Cyano-pyridine-2-carboxylic acid [5-(7-isopropyl-7H-pyrrolo[2,3-d]pyrimidine-5-carbonyl)-pyridin-3-yl]-amide | LCMS (system 8): $R_t$ = 1.62 min; m/z 412 [M + H]$^+$. Prep HPLC (method 5). |
| 481 | 5-Methoxymethyl-1-methyl-1H-pyrazole-3-carboxylic acid [5-(7-isopropyl-7H-pyrrolo[2,3-d]pyrimidine-5-carbonyl)-pyridin-3-yl]-amide | LCMS (system 8): $R_t$ = 1.56 min; m/z 434 [M + H]$^+$. Prep HPLC (method 5). (Acid: Prep 299) |
| 482 | 4,5-Dichloro-1H-imidazole-2-carboxylic acid [5-(7-isopropyl-7H-pyrrolo[2,3-d]pyrimidine-5-carbonyl)-pyridin-3-yl]-amide | LCMS (system 8): $R_t$ = 1.68 min; m/z 444 [M + H]$^+$. Prep HPLC (method 5). (Acid: Angewandte Chemie, 1988, 1417-1418) |
| 483 | 4-Methoxy-8-methyl-1,7-naphthyridine-2-carboxylic acid [5-(7-isopropyl-7H-pyrrolo[2,3-d]pyrimidine-5-carbonyl)-pyridin-3-yl]-amide | LCMS (system 8): $R_t$ = 1.78 min; m/z 482 [M + H]$^+$. Prep HPLC (method 5) |

-continued

| Example | Name | Data |
|---|---|---|
| | d]pyrimidine-5-carbonyl)-pyridin-3-yl]-amide | (Acid: can be prepared using chemistry outlined in WO07011811) |
| 484 | 2-Ethyl-4-methyl-oxazole-5-carboxylic acid [5-(7-isopropyl-7H-pyrrolo[2,3-d]pyrimidine-5-carbonyl)-pyridin-3-yl]-amide | LCMS (system 8): $R_t$ = 1.63 min; m/z 419 [M + H]$^+$. Prep HPLC (method 5) |
| 485 | N-[5-(7-Isopropyl-7H-pyrrolo[2,3-d]pyrimidine-5-carbonyl)-pyridin-3-yl]-5-methoxy-nicotinamide | LCMS (system 8): $R_t$ = 1.57 min; m/z 417 [M + H]$^+$. Prep HPLC (method 5) |
| 486 | 1H-Pyrazolo[3,4-b]pyridine-5-carboxylic acid [5-(7-isopropyl-7H-pyrrolo[2,3-d]pyrimidine-5-carbonyl)-pyridin-3-yl]-amide | LCMS (system 8): $R_t$ = 1.49 min; m/z 427 [M + H]$^+$. Prep HPLC (method 5) |
| 487 | 3H-Imidazo[4,5-b]pyridine-6-carboxylic acid [5-(7-isopropyl-7H-pyrrolo[2,3-d]pyrimidine-5-carbonyl)-pyridin-3-yl]-amide | LCMS (system 8): $R_t$ = 1.44 min; m/z 427 [M + H]$^+$. Prep HPLC (method 5) |
| 488 | 8-Methoxy-imidazo[1,2-a]pyrazine-2-carboxylic acid [5-(7-isopropyl-7H-pyrrolo[2,3-d]pyrimidine-5-carbonyl)-pyridin-3-yl]-amide | LCMS (system 8): $R_t$ = 1.61 min; m/z 457 [M + H]$^+$. Prep HPLC (method 5) (Acid: can be made from the appropriate halo derivative e.g. WO07028051) |
| 489 | N-[5-(7-Isopropyl-7H-pyrrolo[2,3-d]pyrimidine-5-carbonyl)-pyridin-3-yl]-isonicotinamide | LCMS (system 8): $R_t$ = 1.51 min; m/z 387 [M + H]$^+$. Prep HPLC (method 5) |
| 490 | 3-Methyl-pyridine-2-carboxylic acid[5-(7-isopropyl-7H-pyrrolo[2,3-d]pyrimidine-5-carbonyl)-pyridin-3-yl]-amide | LCMS (system 8): $R_t$ = 1.70 min; m/z 401 [M + H]$^+$. Prep HPLC (method 5) |
| 491 | Furo[2,3-b]pyridine-5-carboxylic acid [5-(7-isopropyl-7H-pyrrolo[2,3-d]pyrimidine-5-carbonyl)-pyridin-3-yl]-amide | LCMS (system 8): $R_t$ = 1.59 min; m/z 427 [M + H]$^+$. Prep HPLC (method 5) (Acid: WO 9516688) |
| 492 | 3-Isopropyl-1,2,4-triazolo[4,3-a]pyridine-6-carboxylic acid [5-(7-isopropyl-7H-pyrrolo[2,3-d]pyrimidine-5-carbonyl)-pyridin-3-yl]-amide | LCMS (system 8): $R_t$ = 1.57 min; m/z 469 [M + H]$^+$. Prep HPLC (method 5) |
| 493 | Oxazole-4-carboxylic acid [5-(7-isopropyl-7H-pyrrolo[2,3-d]pyrimidine-5-carbonyl)-pyridin-3-yl]-amide | LCMS (system 8): $R_t$ = 1.50 min; m/z 377 [M + H]$^+$. Prep HPLC (method 5) |
| 494 | 3-Chloro-pyridine-2-carboxylic acid[5-(7-isopropyl-7H-pyrrolo[2,3-d]pyrimidine-5-carbonyl)-pyridin-3-yl]-amide | LCMS (system 8): $R_t$ = 1.62 min; m/z 421 [M + H]$^+$. Prep HPLC (method 5) |
| 495 | Imidazo[1,2-a]pyrimidine-6-carboxylic acid [5-(7-isopropyl-7H-pyrrolo[2,3-d]pyrimidine-5-carbonyl)-pyridin-3-yl]-amide | LCMS (system 8): $R_t$ = 1.44 min; m/z 427 [M + H]$^+$. Prep HPLC (method 5) (Acid-Prep 300) |
| 496 | 5-Cyclopropyl-isoxazole-3-carboxylic acid [5-(7-isopropyl-7H-pyrrolo[2,3-d]pyrimidine-5-carbonyl)-pyridin-3-yl]-amide | LCMS (system 8): $R_t$ = 1.67 min; m/z 417 [M + H]$^+$. Prep HPLC (method 5) |
| 497 | 5-Cyclopropyl-2H-pyrazole-3-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 416 [M + H]$^+$. Prep HPLC (method 5) |
| 498 | 4,7-Dimethyl-pyrazolo[5,1-c][1,2,4]triazine-3-carboxylic acid [5-(7-isopropyl-7H-pyrrolo[2,3-d]pyrimidine-5-carbonyl)-pyridin-3-yl]-amide | LCMS (system 8): $R_t$ = 1.69 min; m/z 456 [M + H]$^+$. Prep HPLC (method 5) |
| 499 | N-[5-(7-Isopropyl-7H-pyrrolo[2,3-d]pyrimidine-5-carbonyl)-pyridin-3-yl]-4-methyl-nicotinamide | LCMS (system 8): $R_t$ = 1.51 min; m/z 401 [M + H]$^+$. Prep HPLC (method 5) |
| 500 | 1-Cyclobutyl-1H-imidazole-4-carboxylic acid [5-(7-isopropyl-7H-pyrrolo[2,3-d]pyrimidine-5-carbonyl)-pyridin-3-yl]-amide | LCMS (system 8): $R_t$ = 1.64 min; m/z 430 [M + H]$^+$. Prep HPLC (method 5) (Acid-Prep 288) |
| 501 | Pyrazolo[1,5-a]pyridine-2-carboxylic acid [5-(7-isopropyl-7H-pyrrolo[2,3-d]pyrimidine-5-carbonyl)-pyridin-3-yl]-amide | LCMS (system 8): $R_t$ = 1.65 min; m/z 426 [M + H]$^+$. Prep HPLC (method 5) |

-continued

| Example | Name | Data |
|---|---|---|
| 502 | Tetrazolo[1,5-a]pyridine-6-carboxylic acid [5-(7-isopropyl-7H-pyrrolo[2,3-d]pyrimidine-5-carbonyl)-pyridin-3-yl]-amide | LCMS (system 8): $R_t$ = 1.51 min; m/z 428 [M + H]$^+$. Prep HPLC (method 5) Commercial |
| 503 | 5,6,7,8-Tetrahydro-1,2,4-triazolo[4,3-a]pyridine-3-carboxylic acid [5-(7-isopropyl-7H-pyrrolo[2,3-d]pyrimidine-5-carbonyl)-pyridin-3-yl]-amide | LCMS (system 8): $R_t$ = 1.60 min; m/z 431 [M + H]$^+$. Prep HPLC (method 5) Commercial |
| 504 | 2-Methyl-5-trifluoromethyl-oxazole-4-carboxylic acid [5-(7-isopropyl-7H-pyrrolo[2,3-d]pyrimidine-5-carbonyl)-pyridin-3-yl]-amide | LCMS (system 8): $R_t$ = 1.69 min; m/z 459 [M + H]$^+$. Prep HPLC (method 5) |
| 505 | 1H-Pyrrolo[3,2-b]pyridine-6-carboxylic acid [5-(7-isopropyl-7H-pyrrolo[2,3-d]pyrimidine-5-carbonyl)-pyridin-3-yl]-amide | LCMS (system 8): $R_t$ = 1.36 min; m/z 426 [M + H]$^+$. Prep HPLC (method 5) |
| 506 | Pyrazolo[3,4-b]pyridine-6-carboxylic acid [5-(7-isopropyl-7H-pyrrolo[2,3-d]pyrimidine-5-carbonyl)-pyridin-3-yl]-amide | LCMS (system 8): $R_t$ = 1.57 min; m/z 427 [M + H]$^+$. Prep HPLC (method 5) |
| 507 | 2H-Indazole-3-carboxylic acid [5-(7-isopropyl-7H-pyrrolo[2,3-d]pyrimidine-5-carbonyl)-pyridin-3-yl]-amide | LCMS (system 8): $R_t$ = 1.65 min; m/z 426 [M + H]$^+$. Prep HPLC (method 5) |
| 508 | 3-Methyl-isoxazolo[5,4-b]pyridine-5-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 442 [M + H]$^+$. Prep HPLC (method 5) (Acid-Synthesis, 2009, 1858-1864) |
| 509 | Pyridazine-4-carboxylic acid [5-(7-isopropyl-7H-pyrrolo[2,3-d]pyrimidine-5-carbonyl)-pyridin-3-yl]-amide | LCMS (system 8): $R_t$ = 1.45 min; m/z 388 [M + H]$^+$. Prep HPLC (method 5) |
| 510 | 2,3-Dihydro-1,4-dioxino[2,3-c]pyridine-7-carboxylic acid [5-(7-isopropyl-7H-pyrrolo[2,3-d]pyrimidine-5-carbonyl)-pyridin-3-yl]-amide | LCMS (system 8): $R_t$ = 1.66 min; m/z 445 [M + H]$^+$. Prep HPLC (method 5) (Acid: WO 2010/067332) |
| 511 | 1H-Pyrazolo[3,4-b]pyridine-3-carboxylic acid [5-(7-isopropyl-7H-pyrrolo[2,3-d]pyrimidine-5-carbonyl)-pyridin-3-yl]-amide | LCMS (system 8): $R_t$ = 1.58 min; m/z 427 [M + H]$^+$. Prep HPLC (method 5) (Acid: WO 2011/084486) |
| 512 | 5-Fluoro-1H-indazole-3-carboxylic acid [5-(7-isopropyl-7H-pyrrolo[2,3-d]pyrimidine-5-carbonyl)-pyridin-3-yl]-amide | LCMS (system 8): $R_t$ = 1.68 min; m/z 444 [M + H]$^+$. Prep HPLC (method 5) |
| 513 | 2,5-Dimethyl-2H-pyrazole-3-carboxylic acid [5-(7-isopropyl-7H-pyrrolo[2,3-d]pyrimidine-5-carbonyl)-pyridin-3-yl]-amide | LCMS (system 8): $R_t$ = 1.59 min; m/z 404 [M + H]$^+$. Prep HPLC (method 5) |
| 514 | Thiazolo[4,5-b]pyridine-7-carboxylic acid [5-(7-isopropyl-7H-pyrrolo[2,3-d]pyrimidine-5-carbonyl)-pyridin-3-yl]-amide | LCMS (system 8): $R_t$ = 1.56 min; m/z 444 [M + H]$^+$. Prep HPLC (method 5) |
| 515 | 6-Chloro-imidazo[1,2-b]pyridazine-2-carboxylic acid [5-(7-isopropyl-7H-pyrrolo[2,3-d]pyrimidine-5-carbonyl)-pyridin-3-yl]-amide | LCMS (system 8): $R_t$ = 1.68 min; m/z 461 [M + H]$^+$. Prep HPLC (method 5) |

Example 517

2-(5,8-Dihydro-6H-[1,7]naphthyridin-7-yl)-N-[5-(7-isopropyl-7H-pyrrolo[2,3-d]pyrimidine-5-carbonyl)-pyridin-3-yl]-acetamide

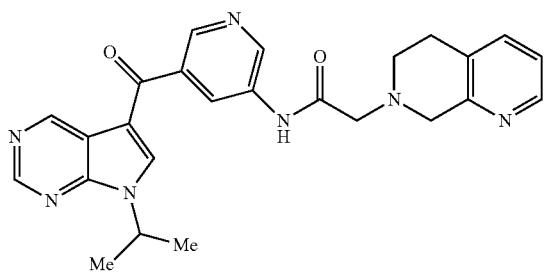 [SMILES: CC(C)n1cc(C(=O)c2cncc(NC(=O)CN3CCc4cccnc4C3)c2)c2cncnc21]

To a DMF solution of (5,8-Dihydro-6H-[1,7]naphthyridin-7-yl)-acetic acid hydrochloride (Preparation 235) (34.2 mg, 0.18 mmol) were added (5-Amino-pyridin-3-yl)-(7-isopropyl-7H-pyrrolo[2,3-d]pyrimidin-5-yl)-methanone (Preparation 95) (50 mg, 0.18 mmol), HATU (136.4 mg, 0.36 mmol) and Hunig's base (0.092 ml, 0.54 mmol). The mixture was heated at 50° C. for 20 hours and then diluted with ethyl acetate, washed with water, brine, dried over sodium sulphate and evaporated to dryness in vacuo. The crude solid was purified over preparative TLC eluting with 5% MeOH/EtOAc to afford the title compound as off white solid in 26% yield, 21 mg. $^1$H NMR (400 MHz, DMSO-D6) δ: 1.55 (d, 6H), 2.85-2.92 (m, 4H), 3.45 (s, 2H), 3.80 (s, 2H), 5.10 (m, 1H), 7.19 (dd, 1H), 7.56 (d, 1H), 8.32 (d, 1H), 8.53 (s, 1H), 8.56 (t, 1H), 8.73 (d, 1H), 8.99 (s, 1H), 9.07 (d, 1H), 9.45 (s, 1H), 10.31 (s, 1H); LCMS (system 9): $R_t$=1.77 min; m/z 456 [M+H]$^+$.

Example 518

2-Hydroxy-N-[5-(7-isopropyl-7H-pyrrolo[2,3-d]pyrimidine-5-carbonyl)-pyridin-3-yl]-2-phenyl-acetamide

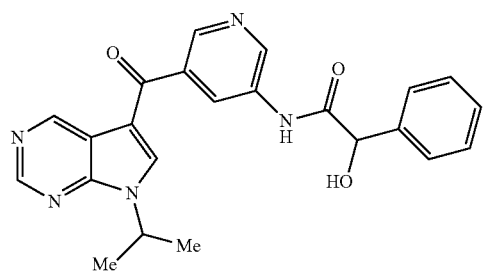 [SMILES: CC(C)n1cc(C(=O)c2cncc(NC(=O)C(O)c3ccccc3)c2)c2cncnc21]

To stirred solution of N-[5-(7-Isopropyl-7H-pyrrolo[2,3-d]pyrimidine-5-carbonyl)-pyridin-3-yl]-2-phenyl-2-(tetrahydro-pyran-2-yloxy)-acetamide (60 mg, 0.12 mmol) (Preparation 237) in dioxane (1 mL) was added dioxane-HCl (1 mL of a 4N solution) at 00° C. The mixture was stirred at room temperature for 2 hours. All the volatiles were removed in vacuo and the solid obtained was triturated with diethyl ether to afford the title compound as a yellowish solid in 78% yield, 42 mg.

$^1$H NMR (400 MHz, DMSO-D6) δ: 1.55 (d, 6H), 5.08-5.12 (m, 1H), 5.19 (s, 1H), 7.30 (t, 1H), 7.37 (t, 2H), 7.53 (d, 2H), 8.56 (s, 1H), 8.63 (s, 1H), 8.76 (br s, 1H), 9.05 (s, 1H), 9.17 (br s, 1H), 9.48 (br s, 1H), 10.56 (s, 1H); LCMS (system 10): $R_t$=2.81 min; m/z 416 [M+H]$^+$.

Example 519

N-[2-Ethoxy-5-(7-isopropyl-7H-pyrrolo[2,3-d]pyrimidine-5-carbonyl)-pyridin-3-yl]-2-(5-methyl-3-trifluoromethyl-pyrazol-1-yl)-acetamide

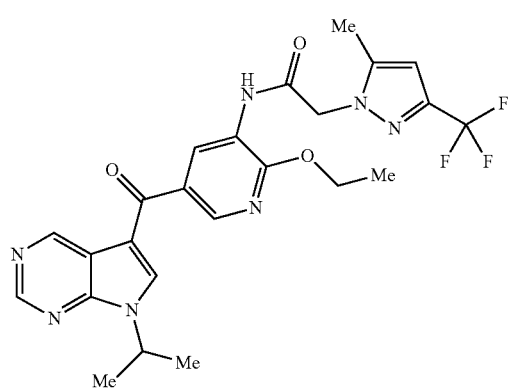 [SMILES: CCOc1ncc(C(=O)c2cn(C(C)C)c3ncncc23)cc1NC(=O)Cn1nc(C(F)(F)F)cc1C]

The title compound was prepared according to the method described for Example 1 using (5-Amino-6-ethoxy-pyridin-3-yl)-(7-isopropyl-7H-pyrrolo[2,3-d]pyrimidin-5-yl)-methanone (Preparation 242) and (5-Methyl-3-trifluoromethyl-pyrazol-1-yl)-acetic acid to afford the title compound as off white solid in 50% yield, 40 mg.

$^1$H NMR (400 MHz, CDCl3) δ: 1.38 (t, 3H), 1.60 (d, 6H), 2.38 (s, 3H), 4.50 (q, 2H), 4.95 (s, 2H), 5.14-5.22 (m, 1H), 6.44 (s, 1H), 7.93 (s, 1H), 8.41 (s, 1H), 8.44 (s, 1H), 8.99 (s, 1H), 9.04 (s, 1H), 9.57 (s, 1H); LCMS (system 10): $R_t$=3.48 min; m/z 516 [M+H]$^+$.

Example 520

N-[5-(2-Amino-7-tert-butyl-7H-pyrrolo[2,3-d]pyrimidine-5-carbonyl)-pyridin-3-yl]-2-(4-cyano-phenyl)-acetamide

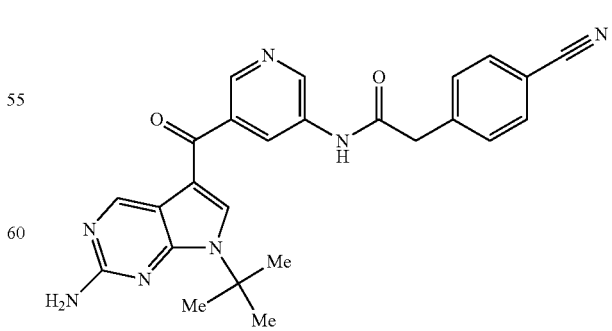

The title compound was prepared according to the method described for Example 1 using (2-amino-7-tert-butyl-7H- pyrrolo[2,3-d]pyrimidin-5-yl)-(5-amino-pyridin-3-yl)-methanone (see Preparation 65) and 4-cyano phenyl acetic acid to afford the title compound as off white solid in 58%, 23 mg.

LCMS (system 10): R$_t$=2.78 min; m/z 454 [M+H]$^+$.

Example 521

2-(4-Chloro-phenyl)-3-hydroxy-N-[5-(7-isopropyl-7H-pyrrolo[2,3-d]pyrimidine-5-carbonyl)-pyridin-3-yl]-propionamide

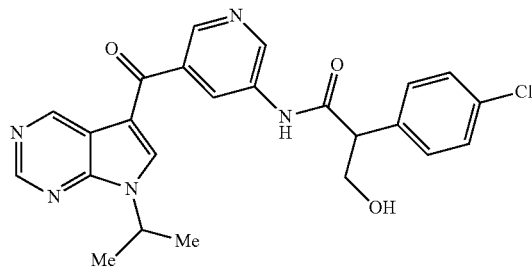 [SMILES: CC(C)n1cc(C(=O)c2cncc(NC(=O)C(CO)c3ccc(Cl)cc3)c2)c2cncnc21]

2-(4-Chloro-phenyl)-3-hydroxy-propionic acid (570 mg, 2.84 mmol) (Preparation 244) was added to a solution of (5-Amino-pyridin-3-yl)-(7-isopropyl-7H-pyrrolo[2,3-d]pyrimidin-5-yl)-methanone (200 mg, 0.71 mmol) (Preparation 95) in THF (5 mL). Di-isopropyl ethylamine (0.64 mL, 3.56 mmol), EDCI.HCl (273 mg, 1.42 mmol) and HOBT (193 mg, 1.42 mmol) were added and the mixture was stirred at 25° C. for 48 hours. The reaction mixture was quenched with saturated aqueous sodium bicarbonate solution (2 mL) and extracted with ethyl acetate (3×15 mL). The combined organic layer was washed with water (5 mL), brine (5 mL), dried over sodium sulphate and evaporated in vacuo. The crude material was purified by preparative TLC (dichloromethane:methanol 93:7) to afford the title compound as a yellow solid in 3% yield, 10 mg.

$^1$H NMR (400 MHz, DMSO-D6) δ: 1.55 (d, 6H), 3.58-3.61 (m, 1H), 3.88-3.91 (m, 1H), 4.04 (t, 1H), 5.07-5.13 (m, 2H), 7.41 (s, 4H), 8.47 (s, 1H), 8.50 (s, 1H), 8.72 (s, 1H), 8.99 (s, 2H), 9.43 (s, 1H), 10.65 (s, 1H); LCMS (system 10): R$_t$=2.99 min; m/z 464 [M+H]$^+$.

Example 522

2-(4-Cyano-phenyl)-N-{5-[7-(1-hydroxymethyl-cyclopropyl)-7H-pyrrolo[2,3-d]pyrimidine-5-carbonyl]-pyridin-3-yl}-acetamide

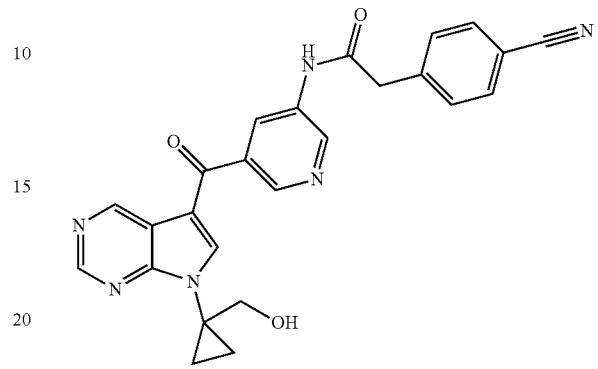

(4-Cyano-phenyl)-acetic acid (6.1 mg, 0.04 mmol) was added to a solution of (5-Amino-pyridin-3-yl)-{7-[1-(tetrahydro-pyran-2-yloxymethyl)-cyclopropyl]-7H-pyrrolo[2,3-d]pyrimidin-5-yl}-methanone (15 mg, 0.04 mmol) (Preparation 251) in THF (1 mL). Then 1-propylphosphonic acid cyclic anhydride (0.07 mL, 0.11 mmol) and triethylamine (0.02 mL, 0.13 mmol) were added and the mixture was stirred at 25° C. for 4 hours. The reaction mixture was quenched with saturated aqueous sodium bicarbonate solution (2 mL) and extracted with ethyl acetate (3×5 mL). The combined organic layer was washed with water (5 mL), brine (5 mL), dried over sodium sulphate and evaporated in vacuo. The crude was dissolved in methanol (1 mL), PTSA (5 mg) was added and stirred at room temperature for 16 hours. The reaction mixture was quenched with saturated aqueous sodium bicarbonate solution (2 mL) and extracted with dichloromethane (5×5 mL). The combined organic layer was washed with brine (5 mL), dried over sodium sulphate and evaporated in vacuo. The crude material was purified by preparative TLC (dichloromethane:methanol 95:5) to afford the title compound as a white solid in 58% yield, 10 mg.

$^1$H NMR (400 MHz, DMSO-D6) δ: 1.13-1.15 (m, 2H), 1.27-1.29 (m, 2H), 3.66 (d, 2H), 3.87 (s, 2H), 5.00 (t, 1H), 7.56 (d, 2H), 7.82 (d, 2H), 8.22 (s, 1H), 8.45 (s, 1H), 8.74 (s, 1H), 8.96 (s, 1H), 9.00 (s, 1H), 9.44 (s, 1H), 10.73 (s, 1H); LCMS (system 10): R$_t$=2.57 min; m/z 453 [M+H]$^+$.

The following Examples were prepared according to the method described above for Example 522 starting from (5-Amino-pyridin-3-yl)-[7-(3-methyl-oxetan-3-yl)-7H-pyrrolo[2,3-d]pyrimidin-5-yl]-methanone (Preparation 251) and the appropriate acids.

| Example | Name | Data |
| --- | --- | --- |
| 523 | 2-(5-Chloro-pyridin-2-yl)-N-{5-[7-(1-hydroxymethyl-cyclopropyl)-7H-pyrrolo[2,3-d]pyrimidine-5-carbonyl]-pyridin-3-yl}-acetamide | LCMS (system 10): Rt = 2.53 min; m/z 463 [M + H]+ |
| 524 | N-{5-[7-(1-Hydroxymethyl-cyclopropyl)-7H-pyrrolo[2,3-d]pyrimidine-5-carbonyl]-pyridin-3-yl}-2-(4-trifluoromethyl-phenyl)-acetamide | LCMS (system 10): R$_t$ = 2.89 min; m/z 496 [M + H]$^+$. |
| 525 | N-{5-[7-(1-Hydroxymethyl-cyclopropyl)-7H-pyrrolo[2,3-d]pyrimidine-5-carbonyl]-pyridin-3-yl}-2-(3-trifluoromethyl-pyrazol-1-yl)-acetamide | LCMS (system 9): R$_t$ = 2.71 min; m/z 486 [M + H]$^+$. |

Example 526

1-(3-Cyclopropyl-1'-methyl-1'H-[1,4']bipyrazolyl-5-yl)-3-[5-(7-isopropyl-7H-pyrrolo[2,3-d]pyrimidine-5-carbonyl)-pyridin-3-yl]-urea

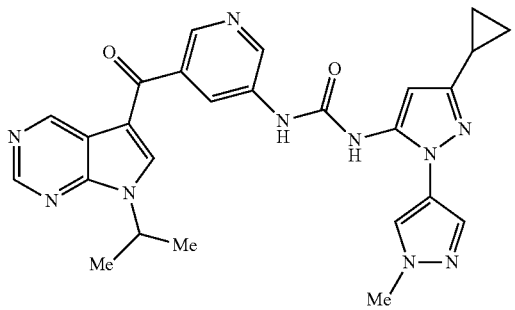 [SMILES: CC(C)n1cc(C(=O)c2cncc(NC(=O)Nc3cc(C4CC4)nn3-c3cnn(C)c3)c2)c2cncnc21]

Phenyl chloroformate (0.03 mL, 0.24 mmol) was added slowly to a solution of 3-Cyclopropyl-1'-methyl-1'H-[1,4']bipyrazolyl-5-ylamine (Preparation 297, 40 mg, 0.19 mmol) and pyridine (0.03 mL) in THF (2 mL) at 00° C. and the mixture was stirred at room temperature for 4 hours. A solution of (5-Amino-pyridin-3-yl)-(7-isopropyl-7H-pyrrolo[2,3-d]pyrimidin-5-yl)-methanone (Preparation 95) (55.4 mg, 0.19 mmol) in DMF (1 mL) and was then added and the reaction mixture heated at 100° C. for 16 hours. The mixture was cooled and diluted with ethyl acetate (15 mL), and washed with aqueous saturated $NaHCO_3$ solution (2×10 mL), water (10 mL), brine (10 mL), dried over sodium sulphate and evaporated to dryness in vacuo. The crude material was purified over preparative TLC plate (eluting with 5% methanol in DCM) to afford the title compound as off white solid in 15% yield, 15 mg. $^1$H NMR (400 MHz, DMSO-d6) δ: 0.64-0.65 (m, 2H), 0.85-0.88 (m, 2H), 1.56 (d, 6H), 1.82-1.85 (m, 1H), 3.89 (s, 3H), 5.09-5.12 (m, 1H), 6.10 (s, 1H), 7.66 (s, 1H), 8.05 (s, 1H), 8.36 (s, 1H), 8.52 (s, 1H), 8.61 (br s, 1H), 8.65 (s, 1H), 8.78 (s, 1H), 8.99 (s, 1H), 9.45 (s, 2H); LCMS (system 10): $R_t$=2.75 min; m/z 511 [M+H]$^+$.

Example 527

1-(3-tert-Butyl-1'-methyl-1'H-[1,4']bipyrazolyl-5-yl)-3-[5-(7-isopropyl-7H-pyrrolo[2,3-d]pyrimidine-5-carbonyl)-pyridin-3-yl]-urea The title compound was prepared according to the method described for Example 526 using (5-Amino-pyridin-3-yl)-(7-isopropyl-7H-pyrrolo[2,3-d]pyrimidin-5-yl)-methanone (Preparation 95) and 3-tert-Butyl-1'-methyl-1'H-[1,4']bipyrazolyl-5-ylamine (Preparation 296) to afford the title compound as yellow solid in 35% yield, 17 mg. LCMS (system 10): $R_t$=3.01 min; m/z 527 [M+H]$^+$.

The following Examples were prepared according to the method described above for Example 1, starting from (2-amino-7-tert-butyl-7H-pyrrolo[2,3-d]pyrimidin-5-yl)(5-aminopyridin-3-yl)methanone (Preparation 65) and the appropriate acids.

| Example | Name | Data |
|---|---|---|
| 528 | N-[5-(2-Amino-7-tert-butyl-7H-pyrrolo[2,3-d]pyrimidine-5-carbonyl)-pyridin-3-yl]-2-(1H-benzoimidazol-2-yl)-acetamide | LCMS (system 10): Rt = 2.79 min; m/z 469 [M + H]+. |
| 529 | N-[5-(2-Amino-7-tert-butyl-7H-pyrrolo[2,3-d]pyrimidine-5-carbonyl)-pyridin-3-yl]-2-(5-bromo-pyridin-2-yl)-acetamide | LCMS (system 10): $R_t$ = 2.94 min; m/z 508 [M + H]$^+$ |
| 530 | N-[5-(2-Amino-7-tert-butyl-7H-pyrrolo[2,3-d]pyrimidine-5-carbonyl)-pyridin-3-yl]-2-(5-cyano-pyridin-2-yl)-acetamide | LCMS (system 10): $R_t$ = 2.78 min; m/z 455 [M + H]$^+$ (acid can be prepared by cyanation of an appropriate bromo derivative |

The following Examples were prepared according to the method described for Example 522 using (5-Amino-pyridin-3-yl)-{7-[(S)-1-methyl-2-(tetrahydro-pyran-2-yloxy)-ethyl]-7H-pyrrolo[2,3-d]pyrimidin-5-yl}-methanone (Preparation 33) and the appropriate acid.

| Example | Name | Data |
|---|---|---|
| 531 | 2-(4-Difluoromethoxy-phenyl)-N-{5-[7-((S)-2-hydroxy-1-methyl-ethyl)-7H-pyrrolo[2,3-d]pyrimidine-5-carbonyl]-pyridin-3-yl}-acetamide | LCMS (system 9): $R_t$ = 2.80 min; m/z 482 [M + H]$^+$ |
| 532 | N-{5-[7-((S)-2-Hydroxy-1-methyl-ethyl)-7H-pyrrolo[2,3-d]pyrimidine-5-carbonyl]-pyridin-3-yl}-2-indazol-2-yl-acetamide | LCMS (system 9): Rt = 2.58 min; m/z 456 [M + H]$^+$ |
| 533 | 2-(1H-Benzoimidazol-2-yl)-N-{5-[7-((S)-2-hydroxy-1-methyl-ethyl)-7H-pyrrolo[2,3-d]pyrimidine-5-carbonyl]-pyridin-3-yl}-acetamide | LCMS (system 10): Rt = 2.42 min; m/z 456 [M + H]+. |

-continued

| Example | Name | Data |
|---|---|---|
| 534 | N-{5-[7-((S)-2-Hydroxy-1-methyl-ethyl)-7H-pyrrolo[2,3-d]pyrimidine-5-carbonyl]-pyridin-3-yl}-2-(4-trifluoromethoxy-phenyl)-acetamide | LCMS (system 9): Rt = 2.99 min; m/z 500 [M + H]$^+$ |
| 535 | 2-(3,4-Difluoro-phenyl)-N-{5-[7-((S)-2-hydroxy-1-methyl-ethyl)-7H-pyrrolo[2,3-d]pyrimidine-5-carbonyl]-pyridin-3-yl}-acetamide | LCMS (system 9): Rt = 2.75 min; m/z 452 [M + H]$^+$ |

The following Examples were prepared according to the Method described for d]pyrimidin-5-yl]methanone (Preparation 186) and the appropriate acid.

| Example | Name | Data |
|---|---|---|
| 536 | 2-(5-Chloro-pyridin-2-yl)-N-{5-[7-(2-methoxy-1,1-dimethyl-ethyl)-7H-pyrrolo[2,3-d]pyrimidine-5-carbonyl]-pyridin-3-yl}-acetamide | LCMS (system 10): $R_t$ = 2.92 min; m/z 479 [M + H]$^+$ |
| 537 | 2-(5-Fluoro-pyridin-2-yl)-N-{5-[7-(2-methoxy-1,1-dimethyl-ethyl)-7H-pyrrolo[2,3-d]pyrimidine-5-carbonyl]-pyridin-3-yl}-acetamide | LCMS (system 10): $R_t$ = 2.79 min; m/z 463 [M + H]$^+$. |
| 538 | 2-(3-Cyclopropyl-pyrazol-1-yl)-N-{5-[7-(2-methoxy-1,1-dimethyl-ethyl)-7H-pyrrolo[2,3-d]pyrimidine-5-carbonyl]-pyridin-3-yl}-acetamide | LCMS (system 10): $R_t$ = 2.89 min; m/z 474 [M + H]$^+$. |
| 539 | 2-(4-Fluoro-phenyl)-N-{5-[7-(2-methoxy-1,1-dimethyl-ethyl)-7H-pyrrolo[2,3-d]pyrimidine-5-carbonyl]-pyridin-3-yl}-acetamide | LCMS (system 10): $R_t$ = 3.03 min; m/z 462 [M + H]$^+$. |

Example 540

N-[5-(7-tert-Butyl-7H-pyrrolo[2,3-d]pyrimidine-5-carbonyl)-pyridin-3-yl]-2-(4-fluoro-phenyl)-N-methyl-acetamide

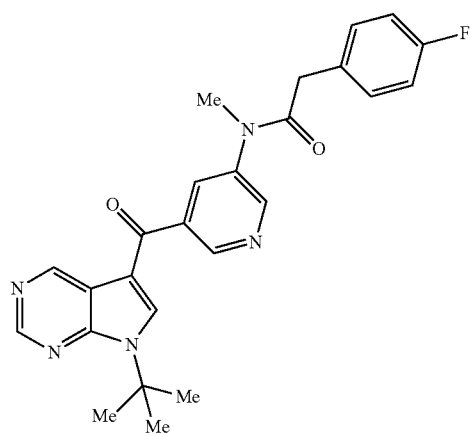 [SMILES: CN(C(=O)Cc1ccc(F)cc1)c1cncc(C(=O)c2cn(C(C)(C)C)c3ncncc23)c1]

To a stirred solution of N-[5-(7-tert-Butyl-7H-pyrrolo[2,3-d]pyrimidine-5-carbonyl)-pyridin-3-yl]-2-(4-fluoro-phenyl)-acetamide (Example 546, 115 mg, 0.27 mmol) in anhydrous THF (4.5 mL), was added NaH (60% in paraffin oil, 10.7 mg, 0.27 mmol) at 0° C. under nitrogen and the resulting mixture stirred for 10 min. MeI (0.017 mL, 0.27 mmol) was then added and the reaction mixture was stirred at room temperature for 1 hour. Aqueous saturated ammonium chloride (5 mL) was added and the mixture extracted with ethyl acetate (2×10 mL). The organic phase was washed with water (10 mL), brine (10 mL), dried over sodium sulphate and evaporated to dryness in vacuo. The crude material was purified via preparative TLC (eluting with 5% methanol in DCM) to afford the title compound as off white solid in 46% yield, 55 mg. $^1$H NMR (400 MHz, DMSO-D6) δ: 1.79 (s, 9H), 3.28 (s, 3H), 3.58 (br, 2H), 7.08-7.20 (m, 4H), 8.20 (s, 1H), 8.32 (s, 1H), 8.83 (s, 1H), 8.97 (br, 1H), 9.01 (s, 1H), 9.50 (s, 1H); LCMS (system 10): R$_t$=3.08 min; m/z 446 [M+H]$^+$.

Example 541

[5-(7-tert-Butyl-7H-pyrrolo[2,3-d]pyrimidine-5-carbonyl)-pyridin-3-yl]-carbamic acid tert-butyl ester

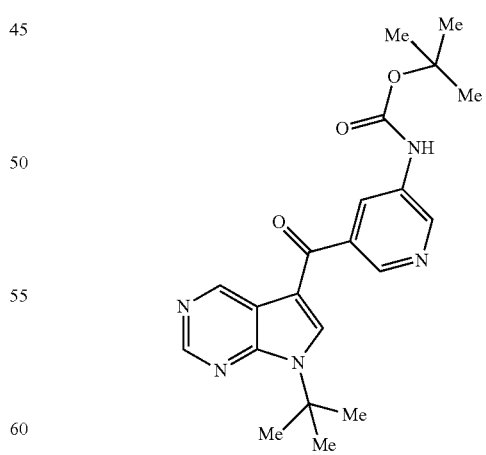

To a stirred solution of (5-Amino-pyridin-3-yl)-(7-tert-butyl-7H-pyrrolo[2,3-d]pyrimidin-5-yl)-methanone (Preparation 31) (200 mg, 0.68 mmol) in DCM (4 mL) was added boc-anhydride (0.155 mL, 0.68 mmol) and Hunig's base (0.24 mL, 1.36 mmol) and the reaction mixture was stirred at room temperature for 16 hours. It was diluted with DCM (15 mL) and washed with water (2×10 mL), brine (10 mL), dried over sodium sulphate and evaporated to dryness in vacuo. The crude material was purified by column chromatography on silica gel (Methanol:DCM 2:98) to afford the title compound as light brown gum in 41% yield, 110 mg. LCMS (system 10): $R_t$=3.16 min; m/z 396 [M+H]$^+$.

Example 542

[5-(7-tert-Butyl-7H-pyrrolo[2,3-d]pyrimidine-5-carbonyl)-pyridin-3-yl]-methyl-carbamic acid tert-butyl ester The title compound was prepared according to the method described for Example 540 using [5-(7-tert-Butyl-7H-pyrrolo[2,3-d]pyrimidine-5-carbonyl)-pyridin-3-yl]-carbamic acid tert-butyl ester (Example 541) to afford the title compound as yellow solid in 79% yield, 90 mg. LCMS (system 10): $R_t$=3.83 min; m/z 410 [M+H]$^+$.

Example 543

N-[5-(7-tert-Butyl-7H-pyrrolo[2,3-d]pyrimidine-5-carbonyl)-pyridin-3-yl]-2-(5-chloro-pyridin-2-yl)-N-methyl-acetamide

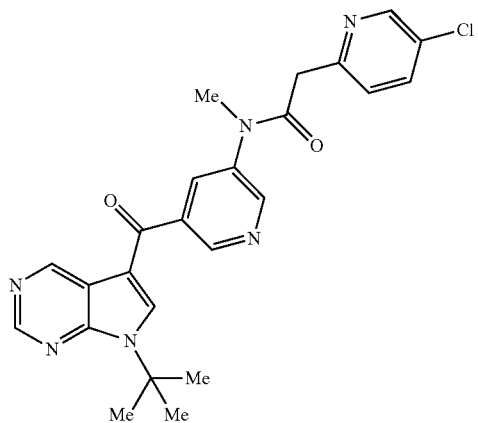 [SMILES: CN(C(=O)Cc1ccc(Cl)cn1)c1cncc(C(=O)c2cn(C(C)(C)C)c3ncncc23)c1]

The title compound was prepared according to the method described for Example 1 using (7-tert-butyl-7H-pyrrolo[2,3-d]pyrimidin-5-yl)-(5-methylamino-pyridin-3-yl)-methanone (Preparation 187) and (5-chloro-pyridin-2-yl)-acetic acid (see Preparation 90) to afford the title compound as off white solid in 21% yield, 25 mg. $^1$H NMR (400 MHz, DMSO-D6) δ: 1.78 (s, 9H), 3.32 (s, 3H), 3.77 (brs, 2H), 7.26 (br, 1H), 7.83 (br, 1H), 8.21 (s, 1H), 8.32 (s, 1H), 8.48 (s, 1H), 8.85 (s, 1H), 8.97 (s, 1H), 9.02 (s, 1H), 9.51 (s, 1H); LCMS (system 10): $R_t$=3.29 min; m/z 463.2 [M+H]$^+$.

Example 544

N-[5-(7-tert-Butyl-7H-pyrrolo[2,3-d]pyrimidine-5-carbonyl)-pyridin-3-yl]-2-(4-chloro-phenyl)-N-methyl-acetamide The title compound was prepared according to the method described for Example 1 using (7-tert-Butyl-7H-pyrrolo[2,3-d]pyrimidin-5-yl)-(5-methylamino-pyridin-3-yl)-methanone (Preparation 187) and (4-chloro-phenyl)-acetic acid to afford the title compound as off white solid in 45% yield, 21 mg.

LCMS (system 10): $R_t$=3.28 min; m/z 462 [M+H]$^+$.

The following Examples were prepared according to the method described above for Example 1, starting from (5-aminopyridin-3-yl)(7-tert-butyl-7H-pyrrolo[2,3-d]pyrimidin-5-yl)methanone (Preparation 31) and the appropriate acids.

| Example | Name | Data |
|---|---|---|
| 545 | N-[5-(7-tert-Butyl-7H-pyrrolo[2,3-d]pyrimidine-5-carbonyl)-pyridin-3-yl]-2-(4-chloro-phenyl)-acetamide | LCMS (system 10): $R_t$ = 3.18 min; m/z 448 [M + H]$^+$. |
| 546 | N-[5-(7-tert-Butyl-7H-pyrrolo[2,3-d]pyrimidine-5-carbonyl)-pyridin-3-yl]-2-(4-fluoro-phenyl)-acetamide | LCMS (system 10): $R_t$ = 3.08 min; m/z 432 [M + H]$^+$. |

The following Examples were prepared according to the method described for Example 1 starting from [2-Amino-7-(2-methoxy-1,1-dimethyl-ethyl)-7H-pyrrolo[2,3-d]pyrimidin-5-yl]-(5-amino-pyridin-3-yl)-methanone (Preparation 261) and the appropriate acid.

| Example | Name | Data |
|---|---|---|
| 547 | N-{5-[2-Amino-7-(2-methoxy-1,1-dimethyl-ethyl)-7H-pyrrolo[2,3-d]pyrimidine-5-carbonyl]-pyridin-3-yl}-2-(5-chloro-pyridin-2-yl)-acetamide | LCMS (system 10): $R_t$ = 2.85 min; m/z 494 [M + H]$^+$. (Acid: Prep 90) |
| 548 | N-{5-[2-Amino-7-(2-methoxy-1,1-dimethyl-ethyl)-7H-pyrrolo[2,3-d]pyrimidine-5-carbonyl]-pyridin-3-yl}-2-(5-fluoro-pyridin-2-yl)-acetamide | LCMS (system 10): $R_t$ = 2.77 min; m/z 478 [M + H]$^+$. (Acid Prep 92) |
| 549 | N-{5-[2-Amino-7-(2-methoxy-1,1-dimethyl-ethyl)-7H-pyrrolo[2,3-d]pyrimidine-5-carbonyl]-pyridin-3-yl}-2-(3-trifluoromethyl-pyrazol-1-yl)-acetamide | LCMS (system 10): $R_t$ = 3.02 min; m/z 517 [M + H]$^+$. (Acid Prep 85) |
| 550 | N-{5-[2-Amino-7-(2-methoxy-1,1-dimethyl-ethyl)-7H-pyrrolo[2,3-d]pyrimidine-5-carbonyl]-pyridin-3-yl}-2-(4-trifluoromethyl-[1,2,3]triazol-1-yl)-acetamide | LCMS (system 10): $R_t$ = 2.93 min; m/z 518 [M + H]$^+$. (Acid Prep 81) |
| 551 | N-{5-[2-Amino-7-(2-methoxy-1,1-dimethyl-ethyl)-7H-pyrrolo[2,3-d]pyrimidine-5-carbonyl]-pyridin-3-yl}-2-(4-trifluoromethyl-pyrazol-1-yl)-acetamide | LCMS (system 10): $R_t$ = 3.01 min; m/z 517 [M + H]$^+$. (Acid Prep 85) |

| Example | Name | Data |
|---|---|---|
| 552 | N-{5-[2-Amino-7-(2-methoxy-1,1-dimethyl-ethyl)-7H-pyrrolo[2,3-d]pyrimidine-5-carbonyl]-pyridin-3-yl}-2-(4-cyclopropyl-[1,2,3]triazol-1-yl)-acetamide | LCMS (system 10): $R_t$ = 2.69 min; m/z 490 [M + H]$^+$. (Acid Prep 83) |

The following Examples were prepared according to the method described for Example 522 using (5-Amino-pyridin-3-yl)-{7-[(S)-1-methyl-2-(tetrahydro-pyran-2-yloxy)-ethyl]-7H-pyrrolo[2,3-d]pyrimidin-5-yl}-methanone (Preparation 49) and the appropriate acid.

| Example | Name | Data |
|---|---|---|
| 553 | N-{5-[2-Amino-7-(2-hydroxy-1,1-dimethyl-ethyl)-7H-pyrrolo[2,3-d]pyrimidine-5-carbonyl]-pyridin-3-yl}-2-indazol-2-yl-acetamide | LCMS (system 10): $R_t$ = 2.67 min; m/z 485 [M + H]$^+$. |
| 554 | N-{5-[2-Amino-7-(2-hydroxy-1,1-dimethyl-ethyl)-7H-pyrrolo[2,3-d]pyrimidine-5-carbonyl]-pyridin-3-yl}-2-(4-oxo-4H-quinazolin-3-yl)-acetamide | LCMS (system 10): $R_t$ = 2.52 min; m/z 513 [M + H]$^+$. |
| 555 | N-{5-[2-Amino-7-(2-hydroxy-1,1-dimethyl-ethyl)-7H-pyrrolo[2,3-d]pyrimidine-5-carbonyl]-pyridin-3-yl}-2-(3,5-difluoro-pyridin-2-yl)-acetamide | LCMS (system 9): $R_t$ = 2.07 min; m/z 482 [M + H]$^+$. Acid Prep 265) |
| 556 | N-{5-[2-Amino-7-(2-hydroxy-1,1-dimethyl-ethyl)-7H-pyrrolo[2,3-d]pyrimidine-5-carbonyl]-pyridin-3-yl}-2-(5-methyl-pyridin-2-yl)-acetamide | LCMS (system 9): $R_t$ = 1.36 min; m/z 460 [M + H]$^+$. Acid Prep 274 |
| 557 | N-(5-{[2-amino-7-(2-hydroxy-1,1-dimethylethyl)-7H-pyrrolo[2,3-d]pyrimidin-5-yl]carbonyl}pyridin-3-yl)-2-{4-[methyl(methylsulfonyl)amino]phenyl}-acetamide | LCMS (system 9): $R_t$ = 2.19 min; m/z 552 [M + H]$^+$. Acid Prep 271 |
| 558 | N-{5-[2-Amino-7-(2-hydroxy-1,1-dimethyl-ethyl)-7H-pyrrolo[2,3-d]pyrimidine-5-carbonyl]-pyridin-3-yl}-2-(1H-benzoimidazol-2-yl)-acetamide | LCMS (system 9): $R_t$ = 1.42 min; m/z 485 [M + H]$^+$. |
| 559 | N-{5-[2-Amino-7-(2-hydroxy-1,1-dimethyl-ethyl)-7H-pyrrolo[2,3-d]pyrimidine-5-carbonyl]-pyridin-3-yl}-2-(2-oxo-5-trifluoromethyl-2H-pyridin-1-yl)-acetamide | LCMS (system 9): $R_t$ = 2.18 min; m/z 530 [M + H]$^+$. |
| 560 | N-{5-[2-Amino-7-(2-hydroxy-1,1-dimethyl-ethyl)-7H-pyrrolo[2,3-d]pyrimidine-5-carbonyl]-pyridin-3-yl}-2-(5-chloro-3-fluoro-pyridin-2-yl)-acetamide | LCMS (system 9): $R_t$ = 2.23 min; m/z 498 [M + H]$^+$. |
| 561 | N-{5-[2-Amino-7-(2-hydroxy-1,1-dimethyl-ethyl)-7H-pyrrolo[2,3-d]pyrimidine-5-carbonyl]-pyridin-3-yl}-2-(5-ethoxy-pyridin-2-yl)-acetamide | LCMS (system 10): $R_t$ = 2.64 min; m/z 490 [M + H]$^+$ (acid can be prepared from the appropriate bromide using the method in WO2011/114271) |
| 562 | N-{5-[2-Amino-7-(2-hydroxy-1,1-dimethyl-ethyl)-7H-pyrrolo[2,3-d]pyrimidine-5-carbonyl]-pyridin-3-yl}-2-(5-trifluoromethyl-pyridin-2-yl)-acetamide | LCMS (system 9): $R_t$ = 2.40 min; m/z 514 [M + H]$^+$. |
| 563 | N-{5-[2-Amino-7-(2-hydroxy-1,1-dimethyl-ethyl)-7H-pyrrolo[2,3-d]pyrimidine-5-carbonyl]-pyridin-3-yl}-2-(4-trifluoromethyl-pyrazol-1-yl)-acetamide | LCMS (system 9): $R_t$ = 2.39 min; m/z 503 [M + H]$^+$. Acid prep 85 |
| 564 | N-{5-[2-Amino-7-(2-hydroxy-1,1-dimethyl-ethyl)-7H-pyrrolo[2,3-d]pyrimidine-5-carbonyl]-pyridin-3-yl}-2-(4-methanesulfonylamino-phenyl)-acetamide | LCMS (system 9) $R_t$ = 4.47 min (12 min run); m/z 538 [M + H]$^+$. |

The following Examples were prepared according to the method described for Examples 73-87 using (5-Amino-pyridin-3-yl)-{7-[(S)-1-methyl-2-(tetrahydro-pyran-2-yloxy)-ethyl]-7H-pyrrolo[2,3-d]pyrimidin-5-yl}-methanone (Preparation 49) and the appropriate acid.

| Example | Name | Data |
|---|---|---|
| 565 | N-{5-[2-Amino-7-(2-hydroxy-1,1-dimethyl-ethyl)-7H-pyrrolo[2,3-d]pyrimidine-5-carbonyl]-pyridin-3-yl}-2-(4-difluoromethoxy-phenyl)-acetamide | LCMS (system 9): $R_t$ = 2.56 min; m/z 511 $[M + H]^+$. |
| 567 | N-{5-[2-Amino-7-(2-hydroxy-1,1-dimethyl-ethyl)-7H-pyrrolo[2,3-d]pyrimidine-5-carbonyl]-pyridin-3-yl}-2-(4-trifluoromethoxy-phenyl)-acetamide | LCMS (system 9): $R_t$ = 2.74 min; m/z 529 $[M + H]^+$. |
| 568 | N-{5-[2-Amino-7-(2-hydroxy-1,1-dimethyl-ethyl)-7H-pyrrolo[2,3-d]pyrimidine-5-carbonyl]-pyridin-3-yl}-2-(3,4-difluoro-phenyl)-acetamide | LCMS (system 9): $R_t$ = 2.50 min; m/z 481 $[M + H]^+$. |
| 569 | N-{5-[2-Amino-7-(2-hydroxy-1,1-dimethyl-ethyl)-7H-pyrrolo[2,3-d]pyrimidine-5-carbonyl]-pyridin-3-yl}-2-(5-chloro-pyrimidin-2-yl)-acetamide | LCMS (system 10): $R_t$ = 2.35 min; m/z 481 $[M + H]^+$ (acid can be prepared by oxidation of the appropriate aldehyde WO04110453) |

Example 570

2-(4-Cyano-phenyl)-N-[5-(7H-pyrrolo[2,3-d]pyrimidine-5-carbonyl)-pyridin-3-yl]-acetamide

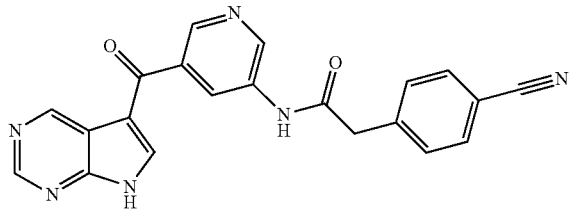 [SMILES: N#Cc1ccc(CC(=O)Nc2cncc(C(=O)c3c[nH]c4ncncc34)c2)cc1]

The title compound was prepared according to the method described for Example 343 using 2-(4-Cyano-phenyl)-N-{5-[7-(2-trimethylsilanyl-ethoxymethyl)-7H-pyrrolo[2,3-d]pyrimidine-5-carbonyl]-pyridin-3-yl}-acetamide (Preparation 277) to afford the title compound as a white solid in 99% yield, $^1$H NMR (400 MHz, DMSO-$d_6$) δ: 3.87 (s, 2H), 7.55 (d, 2H), 7.81 (d, 2H), 8.36 (s, 1H), 8.47 (s, 1H), 8.72 (s, 1H), 8.97 (m, 2H), 9.47 (s, 1H), 10.66 (s, 1H), 13.14 (s, 1H); LCMS (System 10): $R_t$=2.48 min; m/z 383 $[M+H]^+$.

The following Examples were prepared according to the method described above for Example 1, starting from (5-Amino-pyridin-3-yl)-[7-(3-methyl-oxetan-3-yl)-7H-pyrrolo[2,3-d]pyrimidin-5-yl]-methanone (Preparation 222) and the appropriate acid.

| Example | Name | Data |
|---|---|---|
| 571 | N-{5-[7-(3-Methyl-oxetan-3-yl)-7H-pyrrolo[2,3-d]pyrimidine-5-carbonyl]-pyridin-3-yl}-2-(4-trifluoromethyl-phenyl)-acetamide | LCMS (System 10): $R_t$ = 3.02 min; m/z 496 $[M + H]^+$ |
| 572 | N-{5-[7-(3-Methyl-oxetan-3-yl)-7H-pyrrolo[2,3-d]pyrimidine-5-carbonyl]-pyridin-3-yl}-2-(3-trifluoromethyl-phenyl)-acetamide | LCMS (System 10): Rt = 2.98 min; m/z 496 $[M + H]^+$. |
| 573 | 2-(3-Fluoro-4-trifluoromethyl-phenyl)-N-{5-[7-(3-methyl-oxetan-3-yl)-7H-pyrrolo[2,3-d]pyrimidine-5-carbonyl]-pyridin-3-yl}-acetamide | LCMS (System 10): Rt = 3.01 min; m/z 514 $[M + H]^+$. |
| 574 | N-{5-[7-(3-Methyl-oxetan-3-yl)-7H-pyrrolo[2,3-d]pyrimidine-5-carbonyl]-pyridin-3-yl}-3-trifluoromethyl-benzamide | LCMS (System 10): Rt = 3.00 min; m/z 482 $[M + H]^+$. |
| 575 | N-{5-[7-(3-Methyl-oxetan-3-yl)-7H-pyrrolo[2,3-d]pyrimidine-5-carbonyl]-pyridin-3-yl}-3-trifluoromethoxy-benzamide | LCMS (System 10): Rt = 3.05 min; m/z 498 $[M + H]^+$ |

Example 576

N-{5-[2-Amino-7-(2-hydroxy-1,1-dimethyl-ethyl)-7H-pyrrolo[2,3-d]pyrimidine-5-carbonyl]-pyridin-3-yl}-2-(4-cyclopropyl-pyrazol-1-yl)-acetamide

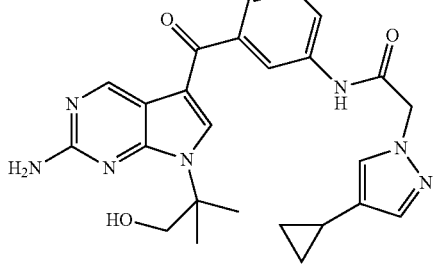

The title compound was prepared according to the method described for Example 1 using {2-amino-7-[1,1-dimethyl-2-(tetrahydro-pyran-2-yloxy)-ethyl]-7H-pyrrolo[2,3-d]pyrimidin-5-yl}-(5-amino-pyridin-3-yl)-methanone (Preparation 49) and (4-Cyclopropyl-pyrazol-1-yl)-acetic acid to afford the title compound as a white solid in 72% yield, 16.5 mg.

LCMS (System 10): $R_t$=2.62 min; m/z 475 [M+H]$^+$.

Example 577

N-[5-(2-Amino-7-tert-butyl-7H-pyrrolo[2,3-d]pyrimidine-5-carbonyl)-pyridin-3-yl]-2-(4-cyclopropyl-pyrazol-1-yl)-acetamide The title compound was prepared according to the method described for Example 1 using (2-Amino-7-tert-butyl-7H-pyrrolo[2,3-d]pyrimidin-5-yl)-(5-amino-pyridin-3-yl)-methanone (see Preparation 65) and (4-cyclopropyl-pyrazol-1-yl)-acetic acid to afford the title compound as a pale yellow solid in 16% yield, 12 mg. LCMS (System 10): $R_t$=2.80 min; m/z 459 [M+H]$^+$.

Example 578

N-[5-(2-Amino-7-bicyclo[1.1.1]pent-1-yl-7H-pyrrolo[2,3-d]pyrimidine-5-carbonyl)-pyridin-3-yl]-2-(5-fluoro-pyridin-2-yl)-acetamide

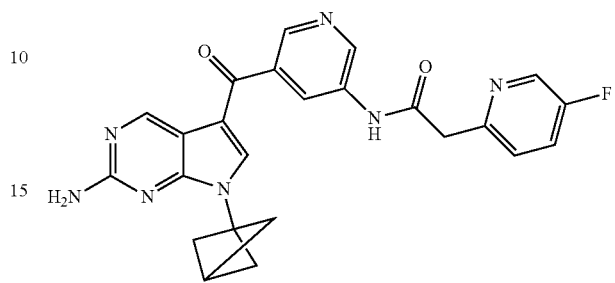

To a solution of (5-amino-pyridin-3-yl)-[7-bicyclo[1.1.1]pent-1-yl-2-(4-methoxy-benzylamino)-7H-pyrrolo[2,3-d]pyrimidin-5-yl]-methanone (Preparation 287) (50 mg, 0.11 mmol) in THF (5 mL) at room temperature was added 5-fluoro pyridine-2-yl acetic acid (27 mg, 0.17 mmol), TEA (0.08 mL, 0.56 mmol) and 1-propylphosphonic acid cyclic anhydride (50% solution in EtOAc, 0.20 mL, 0.34 mmol). The resulting mixture was before stirred for 18 hours. The mixture was concentrated under reduced pressure and the residue was partitioned between saturated sodium bicarbonate solution (10 mL) and ethyl acetate (25 mL). The organic phase was dried over sodium sulphate and concentrated under reduced pressure. TFA (1.5 mL) was added and the resulting mixture stirred at room temperature for 18 hours. The mixture was concentrated under reduced pressure and the residue partitioned between saturated sodium bicarbonate (10 mL) and ethyl acetate (30 mL). The organic phase was dried over sodium sulphate, concentrated under reduced pressure purified by Preparative TLC (MeOH:DCM 5:95) to afford the title compound as off white solid in 31% yield, 16 mg. $^1$H NMR (400 MHz, DMSO-$d_6$) δ: 2.32 (s, 6H), 2.66 (s, 1H), 3.94 (s, 2H), 6.57 (s, 2H), 7.49 (m, 1H), 7.69-7.73 (m, 2H), 8.38 (s, 1H), 8.50 (d, 1H), 8.65 (d, 1H), 8.92 (s, 1H), 8.96 (d, 1H), 10.67 (s, 1H); LCMS (System 10): $R_t$=2.85 min; m/z 458 [M+H]$^+$.

The following Examples were prepared according to the method described above for Example 578 starting from ((5-Amino-pyridin-3-yl)-[7-bicyclo[1.1.1]pent-1-yl-2-(4-methoxy-benzylamino)-7H-pyrrolo[2,3-d]pyrimidin-5-yl]-methanone (Preparation 287) and the appropriate acid.

| Example | Name | Data |
| --- | --- | --- |
| 579 | N-[5-(2-Amino-7-bicyclo[1.1.1]pent-1-yl-7H-pyrrolo[2,3-d]pyrimidine-5-carbonyl)-pyridin-3-yl]-2-(3-methanesulfonyl-phenyl)-acetamide | LCMS (System 10): Rt = 2.87 min; m/z 517 [M + H]$^+$. |
| 580 | N-[5-(2-Amino-7-bicyclo[1.1.1]pent-1-yl-7H-pyrrolo[2,3-d]pyrimidine-5-carbonyl)-pyridin-3-yl]-2-(3-trifluoromethyl-pyrazol-1-yl)-acetamide | LCMS (System 10): Rt = 2.92 min; m/z 497 [M + H]$^+$. |
| 581 | N-[5-(2-Amino-7-bicyclo[1.1.1]pent-1-yl-7H-pyrrolo[2,3-d]pyrimidine-5-carbonyl)-pyridin-3-yl]-2-(4-trifluoromethyl-[1,2,3]triazol-1-yl)-acetamide | LCMS (System 10): Rt = 2.89 min; m/z 498 [M + H]$^+$. (Acid : Prep 81 ) |
| 582 | N-[5-(2-Amino-7-bicyclo[1.1.1]pent-1-yl-7H-pyrrolo[2,3-d]pyrimidine-5-carbonyl)-pyridin-3-yl]-2-(4-cyano-phenyl)-acetamide | LCMS (System 10): Rt = 2.94 min; m/z 464 [M + H]$^+$. |
| 583 | N-[5-(2-Amino-7-bicyclo[1.1.1]pent-1-yl-7H-pyrrolo[2,3-d]pyrimidine-5-carbonyl)-pyridin-3-yl]-2-(5-chloro-pyridin-2-yl)-acetamide | LCMS (system 9): Rt = 6.28 min; m/z 474 [M + H]$^+$. (Acid Prep 90) |

Examples 584-5923 illustrate compounds of general formula:

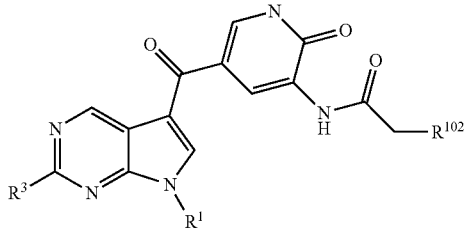

that fall into general formula (I) by virtue of pyridone tautomerism.

(S)-2-tert-Butyldimethylsilyloxy-1-methylethylamine (120 g, 636 mmol) was added to (4,6-dichloropyrimidin-5-yl)acetaldehyde (52.8 g, 276 mmol) in ethanol (500 mL). The mixture was heated to reflux for 45 minutes. The reaction mixture was evaporated in vacuo then the residue was diluted with water (400 mL) and extracted with ethyl acetate (600 mL). The organic extract was evaporated in vacuo and the crude material was purified by column chromatography on silica gel (gradient of pentane:EtOAc 90:10 to 80:20) to afford the title compound as a yellow liquid in 67% yield, 60.4 g.

$^1$H NMR (400 MHz, CDCl$_3$) δ: −0.92 (s, 6H), 0.80 (s, 9H), 1.58 (d, 3H), 3.86 (m, 2H), 5.04 (m, 1H), 6.59 (d, 1H), 7.40 (d, 1H), 8.60 (s, 1H).

| Example | Name | Data |
|---|---|---|
| 584 | 2-(4-cyanophenyl)-N-(2-oxo-5-{[7-(propan-2-yl)-7H-pyrrolo[2,3-d]pyrimidin-5-yl]carbonyl}-1,2-dihydropyridin-3-yl)acetamide | LCMS Rt = 5.25 min; m/z 441 [M + H]+ |
| 585 | N-(2-oxo-5-{[7-(propan-2-yl)-7H-pyrrolo[2,3-d]pyrimidin-5-yl]carbonyl}-1,2-dihydropyridin-3-yl)-2-[2-(trifluoromethoxy)phenoxy]acetamide | LCMS Rt = 4.04 min; m/z 516 [M + H]+ |
| 586 | 2-(2-cyclopropyl-1,3-oxazol-4-yl)-N-(2-oxo-5-{[7-(propan-2-yl)-7H-pyrrolo[2,3-d]pyrimidin-5-yl]carbonyl}-1,2-dihydropyridin-3-yl)acetamide | LCMS Rt = 3.39 min; m/z 447 [M + H]+ |
| 587 | 2-[5-methyl-3-(trifluoromethyl)-1H-pyrazol-1-yl]-N-(2-oxo-5-{[7-(propan-2-yl)-7H-pyrrolo[2,3-d]pyrimidin-5-yl]carbonyl}-1,2-dihydropyridin-3-yl)acetamide | LCMS Rt = 3.51 min; m/z 488 [M + H]+ |
| 588 | N-(2-oxo-5-{[7-(propan-2-yl)-7H-pyrrolo[2,3-d]pyrimidin-5-yl]carbonyl}-1,2-dihydropyridin-3-yl)-2-(quinolin-7-yl)acetamide | LCMS Rt = 3.51 min; m/z 485 [M + H]+ |
| 589 | 2-(4-chlorophenyl)-N-(2-oxo-5-{[7-(propan-2-yl)-7H-pyrrolo[2,3-d]pyrimidin-5-yl]carbonyl}-1,2-dihydropyridin-3-yl)acetamide | LCMS Rt = 3.82 min; m/z 450 [M + H]+ |
| 590 | 2-(5-chloropyridin-2-yl)-N-(2-oxo-5-{[7-(propan-2-yl)-7H-pyrrolo[2,3-d]pyrimidin-5-yl]carbonyl}-1,2-dihydropyridin-3-yl)acetamide | LCMS Rt = 3.22 min; m/z 451 [M + H]+ |
| 591 | N-(2-oxo-5-{[7-(propan-2-yl)-7H-pyrrolo[2,3-d]pyrimidin-5-yl]carbonyl}-1,2-dihydropyridin-3-yl)-2-[4-(trifluoromethyl)-1H-1,2,3-triazol-1-yl]acetamide | LCMS Rt = 3.31 min; m/z 475 [M + H]+ |
| 592 | N-(5-{[2-Amino-7-(2-hydroxy-1,1-dimethylethyl)-7H-pyrrolo[2,3-d]pyrimidin-5-yl]carbonyl}-2-oxo-pyridin-3-yl)-2-(5-chloropyridin-2-yl))acetamide | |
| 593 | N-[5-({7-[(1 S)-2-Hydroxy-1-methylethyl]-7H-pyrrolo[2,3-d]pyrimidin-5-yl}carbonyl)-2-oxo-pyridin-3-yl]-2-[4-(trifluoromethyl)phenyl]acetamide | m/z 500, RT 4.94 |

Preparation 1: 7-[(1S)-2-{[tert-Butyl(dimethyl)silyl]oxy}-1-methylethyl]-4-chloro-7H-pyrrolo[2,3-d]pyrimidine

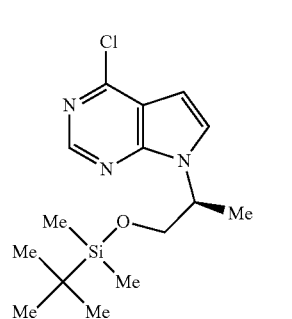 [SMILES: C[C@@H](CO[Si](C)(C)C(C)(C)C)n1ccc2c(Cl)ncnc21]

Preparation 2: 7-(2-{[tert-Butyl(dimethyl)silyl]oxy}-1,1-dimethylethyl)-4-chloro-7H-pyrrolo[2,3-d]pyrimidine

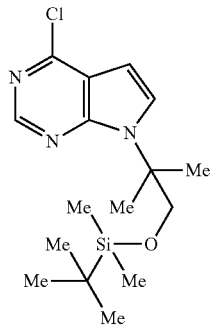 [SMILES: CC(C)(CO[Si](C)(C)C(C)(C)C)n1ccc2c(Cl)ncnc21]

The title compound was prepared according to the method described for Preparation 1 using (4,6-dichloropyrimidin-5-yl)acetaldehyde and 1-{[tert-butyl(dimethyl)silyl]oxy}-2-methylpropan-2-amine to afford the title compound as a yellow oil in 38% yield, 377 mg.

¹H NMR (400 MHz, CDCl₃) δ: 0.00 (s, 6H), 0.94 (s, 9H), 1.97 (s, 6H), 4.28 (s, 2H), 6.78 (d, 1H), 7.66 (d, 1H), 8.83 (s, 1H).

Preparation 3: (2R)-2-(4-Chloro-7H-pyrrolo[2,3-d]pyrimidin-7-yl)propan-1-ol

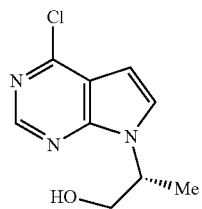 [SMILES: C[C@H](CO)n1ccc2c(Cl)ncnc21]

The title compound was prepared according to the method described for Preparation 1 using (4,6-dichloropyrimidin-5-yl)acetaldehyde and (R)-2-amino-1-propanol to afford the title compound as a yellow solid in 100% yield, 11.12 g.

LCMS (system 2): R$_t$=0.89 min; m/z 212 [M+H]⁺.

Preparation DL3: (R,S) 7-[2-{[tert-Butyl(dimethyl)silyl]oxy}-1-methylethyl]-4-chloro-7H-pyrrolo[2,3-d]pyrimidine

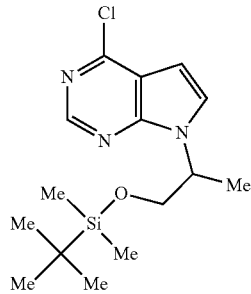 [SMILES: CC(CO[Si](C)(C)C(C)(C)C)n1ccc2c(Cl)ncnc21]

The title compound was prepared according to the method described for Preparation 1 using (4,6-dichloropyrimidin-5-yl)acetaldehyde and 2-tert-butyldimethylsilyloxy-1-methylethylamine to afford the title compound as an orange oil in 77% yield, 4.08 g.

¹H NMR (400 MHz, CDCl3) δ: −0.90 (s, 6H), 0.82 (s, 9H), 1.58 (d, 3H), 3.84 (m, 2H), 5.05 (m, 1H), 6.59 (d, 1H), 7.42 (d, 1H), 8.60 (s, 1H).

Preparation 4: (2S)-2-(4-Chloro-7H-pyrrolo[2,3-d]pyrimidin-7-yl)propan-1-ol

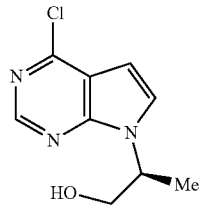

The title compound was prepared according to the method described for Preparation 1 using (4,6-dichloropyrimidin-5-yl)acetaldehyde and (S)-2-amino-1-propanol to afford the title compound as a cream solid in 98% yield, 10.9 g.

¹H NMR (400 MHz, DMSO-D6) δ: 1.42 (d, 3H), 3.72 (m, 2H), 4.89 (m, 1H), 6.63 (d, 1H), 7.83 (d, 1H), 8.59 (s, 1H).

Preparation 5: 7-tert-Butyl-4-chloro-7H-pyrrolo[2,3-d]pyrimidine

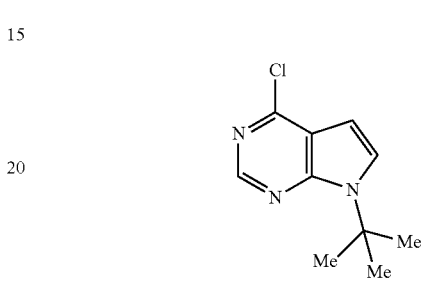

The title compound was prepared according to the method described for Preparation 1 using (4,6-dichloropyrimidin-5-yl)acetaldehyde and tert-butylamine to afford the title compound as a yellow liquid in 77% yield, 1.61 g.

¹H NMR (400 MHz, DMSO-D6) δ: 1.75 (s, 9H), 6.60 (d, 1H), 7.79 (d, 1H), 8.63 (s, 1H).

Preparation 6: 4-Chloro-7-[(1R)-1-methyl-2-(tetrahydro-2H-pyran-2-yloxy)ethyl]-7H-pyrrolo[2,3-d]pyrimidine

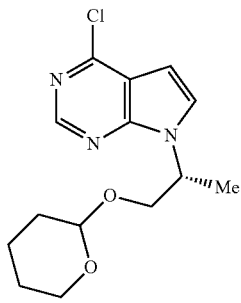 [SMILES: C[C@H](COC1CCCCO1)n1ccc2c(Cl)ncnc21]

2,3-Dihydropyran (25.0 mL, 270 mmol) was added to (2R)-2-(4-chloro-7H-pyrrolo[2,3-d]pyrimidin-7-yl)propan-1-ol (11.00 g, 51.97 mmol) (see Preparation 3) and pyridinium toluene-4-sulphonate (3.92 g, 15.6 mmol) in DCM (150 mL). The reaction mixture was washed with water (200 mL) and the aqueous phase was extracted with DCM (2×150 mL). The combined organic phases were dried over magnesium sulfate and evaporated in vacuo. The crude material was purified by column chromatography on silica gel (gradient of heptane:EtOAc 100:0 to 70:30) to afford the title compound as a yellow oil in 100% yield, 15.65 g.

LCMS (system 2): R$_t$=1.30 min; m/z 296 [M+H]⁺.

Preparation 7: 4-Chloro-7-[(1S)-1-methyl-2-(tetrahydro-2H-pyran-2-yloxy)ethyl]-7H-pyrrolo[2,3-d]pyrimidine

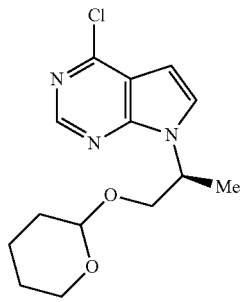 [SMILES: C[C@@H](COC1CCCCO1)n1ccc2c(Cl)ncnc21]

The title compound was prepared according to the method described for Preparation 6 using (2S)-2-(4-chloro-7H-pyrrolo[2,3-d]pyrimidin-7-yl)propan-1-ol (see Preparation 4) to afford the title compound as a yellow oil in 87% yield, 11.5 g.

$^1$H NMR (400 MHz, CDCl$_3$) δ: 1.43-1.71 (m, 9H), 3.42 (m, 1H), 3.57 (m, 1H), 3.69 (m, 1H), 4.00 (m, 1H), 4.52 (m, 1H), 5.19 (m, 1H), 6.60 (d, 1H), 7.44 (d, 1H), 8.61 (s, 1H).

Preparation 8: 7-[(1S)-2-{[tert-Butyl(dimethyl)silyl]oxy}-1-methylethyl]-7H-pyrrolo[2,3-d]pyrimidine

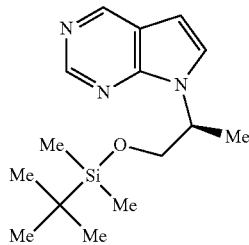 [SMILES: C[C@@H](CO[Si](C)(C)C(C)(C)C)n1ccc2cncnc21]

Palladium (10% on carbon, 18 g) was added to 7-[(1S)-2-{[tert-butyl(dimethyl)silyl]oxy}-1-methylethyl]-4-chloro-7H-pyrrolo[2,3-d]pyrimidine (182 g, 558 mmol) (see Preparation 1) in ethanol (900 mL) and concentrated ammonia solution (100 mL) and hydrogenated (60 psi, 20° C.) for 18 hours. The reaction mixture was filtered through Arbocel™ and the filtrate was evaporated in vacuo. Diethyl ether (300 mL) was added to the residue and the mixture was filtered. The filtrate was evaporated in vacuo to afford the title compound as an orange oil in 94% yield, 162.7 g.

$^1$H NMR (400 MHz, CDCl$_3$) δ: −0.90 (s, 3H), 0.80 (s, 9H), 1.58 (d, 3H), 3.86 (m, 2H), 5.06 (m, 1H), 6.53 (d, 1H), 7.40 (d, 1H), 8.83 (s, 1H), 8.96 (s, 1H).

Preparation 9: 7-(2-{[tert-Butyl(dimethyl)silyl]oxy}-1,1-dimethylethyl)-7H-pyrrolo[2,3-d]pyrimidine

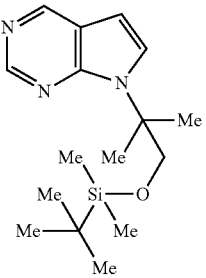

The title compound was prepared according to the method described for Preparation 8 using 7-(2-{[tert-butyl(dimethyl)silyl]oxy}-1,1-dimethylethyl)-4-chloro-7H-pyrrolo[2,3-d]pyrimidine (see Preparation 2) to afford the title compound as a white solid in 97% yield, 327 mg.

$^1$H NMR (400 MHz, CDCl$_3$) δ: 0.01 (s, 6H), 0.94 (s, 9H), 2.02 (s, 6H), 4.30 (s, 2H), 6.92 (d, 1H), 7.84 (d, 1H), 9.13 (s, 1H), 9.21 (s, 1H).

Preparation 10: (R,S) 7-(2-{[tert-Butyl(dimethyl)silyl]oxy}-1-methylethyl)-7H-pyrrolo[2,3-d]pyrimidine

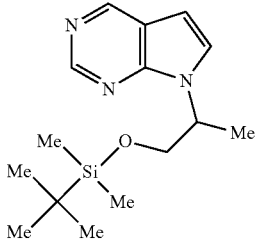 [SMILES: CC(CO[Si](C)(C)C(C)(C)C)n1ccc2cncnc21]

The title compound was prepared according to the method described for Preparation 8 using (R,S) 7-(2-{[tert-butyl(dimethyl)silyl]oxy}-1-methylethyl)-4-chloro-7H-pyrrolo[2,3-d]pyrimidine (see Preparation DL3) to afford the title compound as a brown liquid in 78% yield, 1.12 g.

$^1$H NMR (400 MHz, DMSO-D6) δ: 0.01 (s, 6H), 0.88 (s, 9H), 1.69 (d, 3H), 4.09 (m, 2H), 5.20 (m, 1H), 6.84 (d, 1H), 7.92 (d, 1H), 8.96 (s, 1H), 9.18 (s, 1H).

Preparation 11: 7-[(1R)-1-Methyl-2-(tetrahydro-2H-pyran-2-yloxy)ethyl]-7H-pyrrolo[2,3-d]pyrimidine

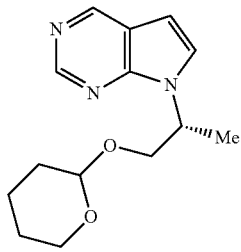 [SMILES: C[C@H](COC1CCCCO1)n1ccc2cncnc21]

The title compound was prepared according to the method described for Preparation 8 using 4-chloro-7-[(1R)-1-methyl-2-(tetrahydro-2H-pyran-2-yloxy)ethyl]-7H-pyrrolo[2,3-d]pyrimidine (see Preparation 6) to afford the title compound as a yellow oil in 100% yield, 13.78 g.

LCMS (system 2): R$_t$=0.73 min; m/z 262 [M+H]$^+$.

Preparation 12: 7-[(1S)-1-Methyl-2-(tetrahydro-2H-pyran-2-yloxy)ethyl]-7H-pyrrolo[2,3-d]pyrimidine

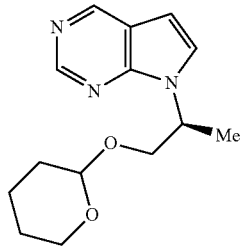 [SMILES: C[C@@H](COC1CCCCO1)n1ccc2cncnc21]

The title compound was prepared according to the method described for Preparation 8 using 4-chloro-7-[(1S)-1-methyl-2-(tetrahydro-2H-pyran-2-yloxy)ethyl]-7H-pyrrolo[2,3-d]pyrimidine (see Preparation 7) to afford the title compound as a colourless oil in 90% yield, 9.18 g.

$^1$H NMR (400 MHz, CDCl$_3$) δ: 1.44-1.69 (m, 9H), 3.42 (m, 1H), 3.57 (m, 1H), 3.69 (m, 1H), 4.02 (m, 1H), 4.54 (m, 1H), 5.27 (m, 1H), 6.69 (d, 1H), 7.57 (d, 1H), 8.91 (s, 1H), 8.99 (s, 1H).

Preparation 13: 7-tert-Butyl-7H-pyrrolo[2,3-d]pyrimidine

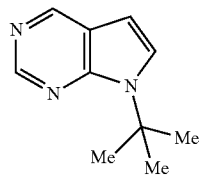 [SMILES: CC(C)(C)n1ccc2cncnc21]

The title compound was prepared according to the method described for Preparation 8 using 7-tert-butyl-4-chloro-7H-pyrrolo[2,3-d]pyrimidine (see Preparation 5) to afford the title compound as a yellow liquid in 94% yield, 1.27 g.

$^1$H NMR (400 MHz, DMSO-D6) δ: 1.75 (s, 9H), 6.57 (d, 1H), 7.66 (d, 1H), 8.78 (s, 1H), 8.98 (s, 1H).

Preparation 14: 7-[(1S)-2-{[tert-Butyl(dimethyl)silyl]oxy}-1-methylethyl]-5-iodo-7H-pyrrolo[2,3-d]pyrimidine

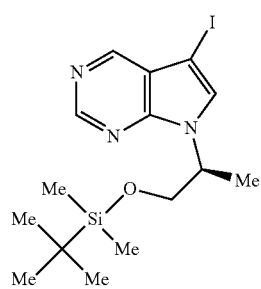 [SMILES: C[C@@H](CO[Si](C)(C)C(C)(C)C)n1cc(I)c2cncnc21]

N-Iodosuccinimide (124 g, 553 mmol) was added to 7-[(1S)-2-{[tert-butyl(dimethyl)silyl]oxy}-1-methylethyl]-7H-pyrrolo[2,3-d]pyrimidine (153.4 g, 526 mmol) (see Preparation 8) in acetonitrile (700 mL). The mixture was stirred at room temperature for 16 hours then saturated aqueous sodium thiosulfate (700 mL) was added. The mixture was extracted with EtOAc (800 mL) then the organic extract was dried over magnesium sulfate and evaporated in vacuo. The crude material was purified by column chromatography on silica gel (gradient of pentane:EtOAc 90:10 to 80:20) to afford the title compound as a yellow solid in 66% yield, 145 g. $^1$H NMR (400 MHz, CDCl$_3$) δ: −0.90 (d, 6H) 0.80 (s, 9H) 1.58 (d, 3H) 3.84 (m, 2H) 5.07 (m, 1H) 7.48 (s, 1H) 8.73 (s, 1H) 8.86 (s, 1H).

Preparation 15: 7-(2-{[tert-Butyl(dimethyl)silyl]oxy}-1,1-dimethylethyl)-5-iodo-7H-pyrrolo[2,3-d]pyrimidine

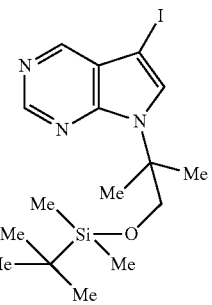

The title compound was prepared according to the method described for Preparation 14 using 7-(2-{[tert-butyl(dimethyl)silyl]oxy}-1,1-dimethylethyl)-7H-pyrrolo[2,3-d]pyrimidine (see Preparation 9) to afford the title compound as a brown oil in 59% yield, 270 mg.

$^1$H NMR (400 MHz, CDCl$_3$) δ: 0.01 (s, 6H), 0.92 (s, 9H), 2.00 (s, 6H), 4.20 (s, 2H), 7.95 (s, 1H), 9.02 (s, 1H), 9.16 (s, 1H).

Preparation 16: (R,S) 7-(2-{[tert-Butyl(dimethyl)silyl]oxy}-1-methylethyl)-5-iodo-7H-pyrrolo[2,3-d]pyrimidine

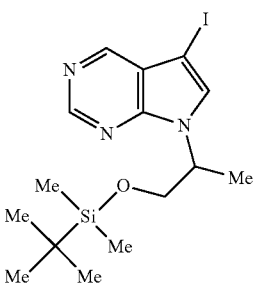 [SMILES: CC(CO[Si](C)(C)C(C)(C)C)n1cc(I)c2cncnc21]

The title compound was prepared according to the method described for Preparation 14 using (R,S) 7-(2-{[tert-butyl(dimethyl)silyl]oxy}-1-methylethyl)-7H-pyrrolo[2,3-d]pyrimidine (see Preparation 10) to afford the title compound as a yellow liquid in 74% yield, 1.18 g.

LCMS (system 1): R$_t$=4.03 min; m/z 418 [M+H]$^+$.

Preparation 17: 5-Iodo-7-[(1R)-1-methyl-2-(tetrahydro-2H-pyran-2-yloxy)ethyl]-7H-pyrrolo[2,3-d]pyrimidine

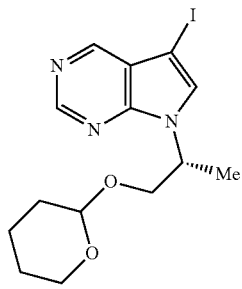 [SMILES: C[C@H](COC1CCCCO1)n1cc(I)c2cncnc21]

The title compound was prepared according to the method described for Preparation 14 using 7-[(1R)-1-methyl-2-(tetrahydro-2H-pyran-2-yloxy)ethyl]-7H-pyrrolo[2,3-d]pyrimidine (see Preparation 11) to afford the title compound as a brown oil in 34% yield, 7.50 g.

$^1$H NMR (400 MHz, CDCl$_3$) δ: 1.43-1.74 (m, 9H), 3.42 (m, 1H), 3.54 (m, 1H), 3.67 (m, 1H), 3.99 (m, 1H), 4.54 (m, 1H), 5.23 (m, 1H), 7.51 (s, 1H), 8.74 (s, 1H), 8.88 (s, 1H).

Preparation 18: 5-iodo-7-[(1S)-1-methyl-2-(tetrahydro-2H-pyran-2-yloxy)ethyl]-7H-pyrrolo[2,3-d]pyrimidine

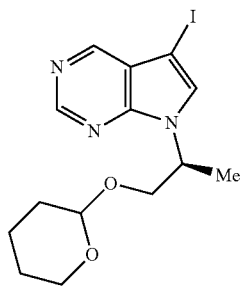 [SMILES: C[C@@H](COC1CCCCO1)n1cc(I)c2cncnc21]

The title compound was prepared according to the method described for Preparation 14 using 7-[(1S)-1-methyl-2-(tetrahydro-2H-pyran-2-yloxy)ethyl]-7H-pyrrolo[2,3-d]pyrimidine (see Preparation 12) to afford the title compound as a brown oil in 71% yield, 9.68 g.

$^1$H NMR (400 MHz, CDCl$_3$) δ: 1.44-1.65 (m, 9H), 3.45 (m, 1H), 3.56 (m, 1H), 3.67 (m, 1H), 3.99 (m, 1H), 4.54 (m, 1H), 5.24 (m, 1H), 7.51 (s, 1H), 8.76 (s, 1H), 8.89 (s, 1H).

Preparation 19: 7-tert-Butyl-5-iodo-7H-pyrrolo[2,3-d]pyrimidine

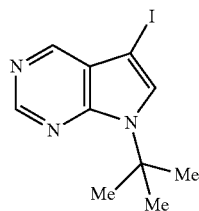

The title compound was prepared according to the method described for Preparation 14 using 7-tert-butyl-7H-pyrrolo[2,3-d]pyrimidine (see Preparation 13) to afford the title compound as a yellow solid in 71% yield, 1.55 g.

LCMS (system 1): R$_t$=3.12 min; m/z 302 [M+H]$^+$.

Preparation 20: (R,S) Methyl 2-(5-iodo-7H-pyrrolo[2,3-d]pyrimidin-7-yl)propanoate

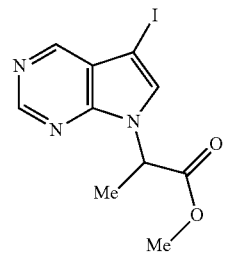 [SMILES: COC(=O)C(C)n1cc(I)c2cncnc21]

Methyl-2-bromopropionate (6.83 mL, 61.2 mmol) was added to a mixture of 5-iodo-7H-pyrrolo[2,3-d]pyrimidine (15.0 g, 61.0 mmol) and cesium carbonate (35.9 g, 110.0 mmol) in DMF (75 mL). The mixture was stirred at room temperature for 4 hours. The reaction mixture was diluted with water (250 mL) and extracted with diethyl ether (100 mL). The organic layer was washed with brine (70 mL), dried over magnesium sulfate and evaporated in vacuo to afford the title compound as an off-white solid in 83% yield, 16.87 g.

$^1$H NMR (400 MHz, CDCl$_3$) δ: 1.82 (d, 3H), 3.76 (s, 3H), 5.72 (q, 1H), 7.48 (s, 1H), 8.76 (s, 1H), 8.89 (s, 1H).

Preparation 21: Methyl 2-(5-iodo-7H-pyrrolo[2,3-d]pyrimidin-7-yl)-2-methylpropanoate

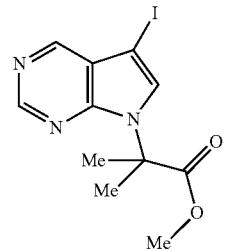 [SMILES: COC(=O)C(C)(C)n1cc(I)c2cncnc21]

Potassium t-butoxide (71.3 mL, 71.3 mmol, 1.0 M in THF) was added to (R,S) methyl 2-(5-iodo-7H-pyrrolo[2,3-d]pyrimidin-7-yl)propanoate (16.9 g, 50.9 mmol) (see Preparation 20) and iodomethane (4.44 mL, 71.3 mmol) in THF (100 mL). The mixture was stirred at room temperature for 15 minutes then water (20 mL) and aqueous HCl (0.3 mL, 2M) was added. THF was removed by evaporation in vacuo then the aqueous residue was extracted with EtOAc (250 mL). The organic phase was dried over magnesium sulfate and evaporated in vacuo. The crude solid was purified by column chromatography on silica gel (80:20 pentane:EtOAc) to afford the title compound as a white solid in 51% yield, 8.92 g.

¹H NMR (400 MHz, CDCl₃) δ: 1.93 (s, 6H), 3.68 (s, 3H), 7.43 (s, 1H), 8.75 (s, 1H), 8.85 (s, 1H).

Preparation 22: 2-(5-Iodo-7H-pyrrolo[2,3-d]pyrimidin-7-yl)-2-methylpropan-1-ol

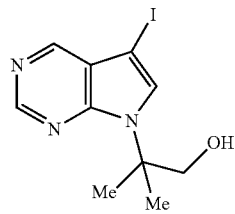 [SMILES: CC(C)(CO)n1cc(I)c2cncnc21]

Lithium borohydride (32.3 mL, 64.6 mmol, 2.0 M in THF) was added to methyl 2-(5-iodo-7H-pyrrolo[2,3-d]pyrimidin-7-yl)-2-methylpropanoate (8.92 g, 25.9 mmol) (see Preparation 21) in ethanol (70 mL). The mixture was stirred at room temperature for 17 hours then water (70 mL) was added. The mixture was evaporated in vacuo then the residue was partitioned between DCM (250 mL) and water (50 mL). The aqueous phase was extracted with DCM:MeOH (90:10, 2×250 mL) and the combined organic phases were dried over magnesium sulfate and evaporated in vacuo to afford the title compound as an off-white solid in 100% yield, 8.20 g.

¹H NMR (400 MHz, DMSO-d6) δ: 1.65 (s, 6H), 3.16 (d, 2H), 7.77 (s, 1H), 8.67 (s, 1H), 8.80 (s, 1H).

Preparation 23: 5-[(Diphenylmethylene)amino]-N-methoxy-N-methylnicotinamide

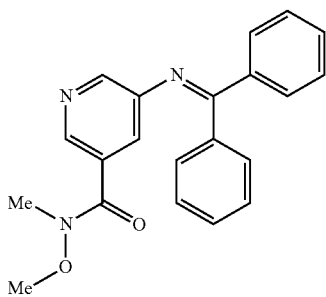 [SMILES: CON(C)C(=O)c1cncc(N=C(c2ccccc2)c2ccccc2)c1]

Benzophenone imine (205 mL, 1.22 mol) was added to 5-bromo-N-methoxy-N-methylisonicotinamide (250 g, 1.02 mol), tris(dibenzylideneacetone)dipalladium (28.0 g, 31.0 mmol), 2-di-tert-butylphosphino-2',4',6'-triisopropylbiphenyl (34.7 g, 82.0 mmol) and freshly ground potassium phosphate tribasic (541 g, 2.55 mol) in 1,2-dimethoxyethane (2500 mL). The mixture was stirred at 50° C. for 17 hours. The reaction mixture was filtered through Arbocel™ and the pad was washed with EtOAc (500 mL). The filtrate was evaporated in vacuo and the crude material was purified by column chromatography on silica gel (gradient of heptane: EtOAc 70:30 to 0:100) to afford the title compound as an orange gum in 51% yield, 180.0 g.

¹H NMR (400 MHz, DMSO-D6) δ: 3.19 (s, 3H), 3.37 (s, 3H), 7.18-7.23 (m, 2H), 7.29 (m, 1H), 7.32-7.39 (m, 3H), 7.46-7.53 (m, 2H), 7.57 (m, 1H), 7.67-7.73 (m, 2H), 8.09 (d, 1H), 8.27 (d, 1H).

Preparation 24: {7-[(1S)-2-{[tert-Butyl(dimethyl)silyl]oxy}-1-methylethyl]-7H-pyrrolo[2,3-d]pyrimidin-5-yl}{5-[(diphenylmethylene)amino]pyridin-3-yl}methanone

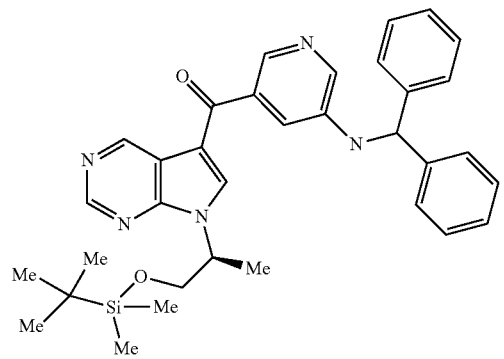 [SMILES: C[C@@H](CO[Si](C)(C)C(C)(C)C)n1cc(C(=O)c2cncc(NC(c3ccccc3)c3ccccc3)c2)c2cncnc21]

Isopropyl magnesium chloride (68.8 mL, 138 mmol, 2.0 M in THF) was added to 7-[(1S)-2-{[tert-butyl(dimethyl)silyl]oxy}-1-methylethyl]-5-iodo-7H-pyrrolo[2,3-d]pyrimidine (52.2 g, 125 mmol) (see Preparation 14) in THF (400 mL) at 0° C., under nitrogen. The mixture was stirred at 0° C. for 1 hour then a solution of 5-[(diphenylmethylene)amino]-N-methoxy-N-methylnicotinamide (47.5 g, 138 mmol) (see Preparation 23) in THF (100 mL) was added dropwise at 0° C. The mixture was warmed to room temperature and stirred at this temperature for 16 hours. The reaction mixture was quenched with 10% aqueous ammonium chloride (250 mL) and extracted with ethyl acetate (2×250 mL).

The combined organic extracts were washed with brine (250 mL), dried over sodium sulfate, evaporated in vacuo and the crude material was purified by column chromatography on silica gel (gradient of EtOAc:pentane 10:90 to 60:40) to afford the title compound as a colourless gum in 88% yield, 63.2 g.

R_t=7.94 min; m/z 576 [M+H]⁺.

Preparation 25: [7-(2-{[tert-Butyl(dimethyl)silyl]oxy}-1,1-dimethylethyl)-7H-pyrrolo[2,3-d]pyrimidin-5-yl]{5-[(diphenylmethylene)amino]pyridin-3-yl}methanone

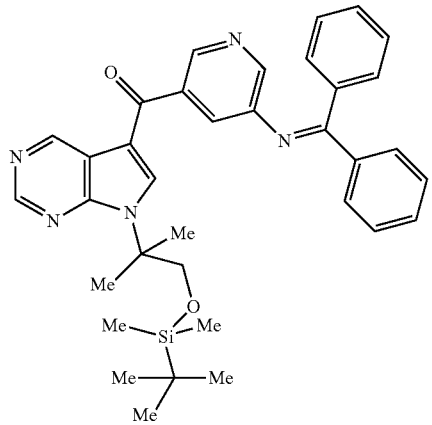 [SMILES: CC(C)(CO[Si](C)(C)C(C)(C)C)n1cc(C(=O)c2cncc(N=C(c3ccccc3)c3ccccc3)c2)c2cncnc21]

153

The title compound was prepared according to the method described for Preparation 24 using 7-(2-{[tert-butyl(dimethyl)silyl]oxy}-1,1-dimethylethyl)-5-iodo-7H-pyrrolo[2,3-d]pyrimidine (see Preparation 15) and 5-[(diphenylmethylene)amino]-N-methoxy-N-methylnicotinamide (see Preparation 23) to afford the title compound as a colourless gum in 56% yield, 1.49 g.

$^{1}$H NMR (400 MHz, CDCl$_{3}$) δ: 0.21 (s, 6H), 0.67 (s, 9H), 1.80 (s, 6H), 4.10 (s, 2H), 7.14 (d, 2H), 7.33 (m, 3H), 7.45 (m, 2H), 7.54 (m, 1H), 7.58 (t, 1H), 7.79 (d, 2H), 7.89 (s, 1H), 8.18 (d, 1H), 8.58 (d, 1H), 9.01 (s, 1H), 9.60 (s, 1H).

Preparation 26: (5-Bromopyridin-3-yl){7-[(1R)-1-methyl-2-(tetrahydro-2H-pyran-2-yloxy)ethyl]-7H-pyrrolo[2,3-d]pyrimidin-5-yl}methanone

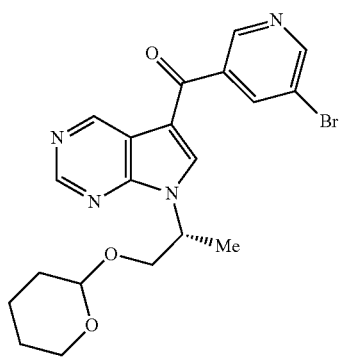 [SMILES: C[C@H](COC1CCCCO1)n1cc(C(=O)c2cncc(Br)c2)c2cncnc21]

The title compound was prepared according to the method described for Preparation 24 using 5-iodo-7-[(1R)-1-methyl-2-(tetrahydro-2H-pyran-2-yloxy)ethyl]-7H-pyrrolo[2,3-d]pyrimidine (see Preparation 17) and 5-bromo-N-methoxy-N-methylnicotinamide to afford the title compound as a brown oil in 66% yield, 215 mg.

LCMS (system 2): R$_t$=1.27 min; m/z 447 [M+H]$^{+}$.

Preparation 27: (5-Bromopyridin-3-yl){7-[(1S)-1-methyl-2-(tetrahydro-2H-pyran-2-yloxy)ethyl]-7H-pyrrolo[2,3-d]pyrimidin-5-yl}methanone

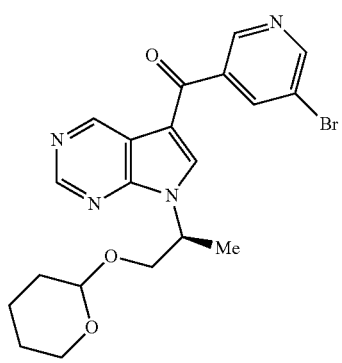 [SMILES: C[C@@H](COC1CCCCO1)n1cc(C(=O)c2cncc(Br)c2)c2cncnc21]

The title compound was prepared according to the method described for Preparation 24 using 5-iodo-7-[(1S)-1-methyl-2-(tetrahydro-2H-pyran-2-yloxy)ethyl]-7H-pyrrolo[2,3-d]pyrimidine (see Preparation 18) and 5-bromo-N-methoxy-N-methylnicotinamide to afford the title compound as a colourless oil in 32% yield, 181 mg.

LCMS (system 2): R$_t$=1.27 min; m/z 447 [M+H]$^{+}$.

154

Preparation 28: (R,S) {7-[2-{[tert-Butyl(dimethyl)silyl]oxy}-1-methylethyl]-7H-pyrrolo[2,3-d]pyrimidin-5-yl}{5-[(diphenylmethylene)amino]pyridin-3-yl}methanone

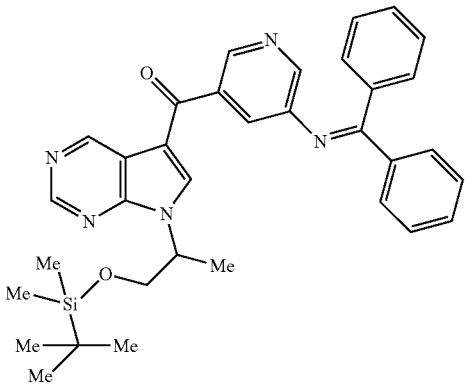 [SMILES: CC(CO[Si](C)(C)C(C)(C)C)n1cc(C(=O)c2cncc(N=C(c3ccccc3)c3ccccc3)c2)c2cncnc21]

$^n$Butyllithium (0.57 mL, 1.31 mmol, 2.3 M in hexanes) was added to (R,S) 7-(2-{[tert-butyl(dimethyl)silyl]oxy}-1-methylethyl)-5-iodo-7H-pyrrolo[2,3-d]pyrimidine (500 mg, 1.19 mmol) (see Preparation 16) in dry ether (20 mL) at −78° ° C. and the reaction mixture was stirred for 30 minutes. Then 5-[(diphenylmethylene)amino]-N-methoxy-N-methylnicotinamide (372 mg, 1.07 mmol) (see Preparation 23) in dry ether (25 mL) was added drop wise at the same temperature. After 15 minutes the mixture was quenched with saturated aqueous ammonium chloride (50 mL) and extracted with ethyl acetate (70 mL). The organic extract was dried over sodium sulfate, evaporated in vacuo and purified by column chromatography on silica gel (hexane:EtOAc 70:30) to afford the title compound as an off-white solid in 19% yield, 134 mg.

LCMS (System 4): R$_t$=4.53 min; m/z 576 [M+H]$^{+}$.

Preparation 29: (R,S) (5-Bromopyridin-3-yl)(7-tert-butyl-7H-pyrrolo[2,3-d]pyrimidin-5-yl)methanol

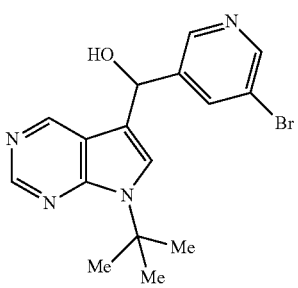 [SMILES: CC(C)(C)n1cc(C(O)c2cncc(Br)c2)c2cncnc21]

The title compound was prepared according to the method described for Preparation 28 using 7-tert-butyl-5-iodo-7H-pyrrolo[2,3-d]pyrimidine (see Preparation 19) and 5-bromo-pyridine-3-carbaldehyde to afford the title compound as a colourless oil in 37% yield, 486 mg.

LCMS (System 4): R$_t$=2.94 min; m/z 362 [M+H]$^{+}$.

Preparation 30: (5-Bromopyridin-3-yl)(7-tert-butyl-7H-pyrrolo[2,3-d]pyrimidin-5-yl)methanone

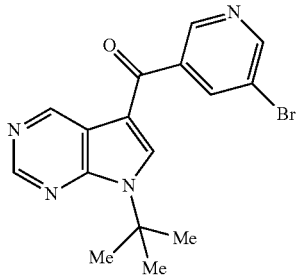 [SMILES: CC(C)(C)n1cc(C(=O)c2cncc(Br)c2)c2cncnc21]

2-Iodoxybenzoic acid (909 mg, 3.25 mmol) was added to (R,S) (5-bromopyridin-3-yl)(7-tert-butyl-7H-pyrrolo[2,3-d]pyrimidin-5-yl)methanol (405 mg, 1.34 mmol) (see Preparation 29) in ethyl acetate (30 mL) and the mixture was refluxed for 4 hours. The mixture was filtered and the filtrate was evaporated in vacuo to afford the title compound as a white solid in 95% yield, 554 mg.

LCMS (system 4): $R_t$=3.28 min; m/z 360 [M+H]$^+$.

Preparation 31: (5-Aminopyridin-3-yl)(7-tert-butyl-7H-pyrrolo[2,3-d]pyrimidin-5-yl)methanone

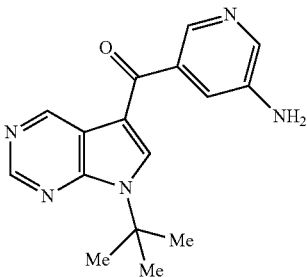 [SMILES: CC(C)(C)n1cc(C(=O)c2cncc(N)c2)c2cncnc21]

Copper sulfate pentahydrate (55 mg, 0.24 mmol) was added to (5-bromopyridin-3-yl)(7-tert-butyl-7H-pyrrolo[2,3-d]pyrimidin-5-yl)methanone (292 mg, 0.81 mmol) (see Preparation 30) and concentrated ammonia solution (20 mL). The mixture was heated in a sealed vessel at 140° C. for 17 hours. The reaction mixture was evaporated in vacuo and the residue was stirred in aqueous hydrochloric acid (10 mL, 2M) at room temperature for 17 hours. The reaction mixture was basified to pH 9 using saturated aqueous sodium carbonate then extracted with DCM (3×20 mL). The combined organic extracts were dried over magnesium sulfate and evaporated in vacuo to afford the title compound as a white solid in 49% yield, 240 mg.

LCMS (System 4): $R_t$=2.68 min; m/z 296 [M+H]$^+$.

Preparation 32: (5-Aminopyridin-3-yl){7-[(1S)-2-hydroxy-1-methylethyl]-7H-pyrrolo[2,3-d]pyrimidin-5-yl}methanone

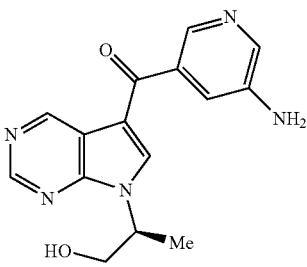 [SMILES: C[C@@H](CO)n1cc(C(=O)c2cncc(N)c2)c2cncnc21]

The title compound was prepared according to the method described for Preparation 31 using (5-bromopyridin-3-yl){7-[(1S)-1-methyl-2-(tetrahydro-2H-pyran-2-yloxy)ethyl]-7H-pyrrolo[2,3-d]pyrimidin-5-yl}methanone (see Preparation 27) to afford the title compound as a white solid in 10% yield, 134 mg.

LCMS (system 2): $R_t$=0.59 min; m/z 298 [M+H]$^+$.

Preparation 33: (5-Aminopyridin-3-yl){7-[(1S)-1-methyl-2-(tetrahydro-2H-pyran-2-yloxy)ethyl]-7H-pyrrolo[2,3-d]pyrimidin-5-yl}methanone

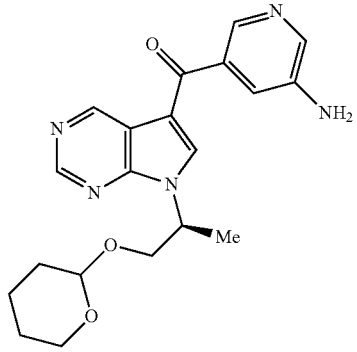 [SMILES: C[C@@H](COC1CCCCO1)n1cc(C(=O)c2cncc(N)c2)c2cncnc21]

Benzophenone imine (0.40 mL, 2.4 mmol) was added to (5-bromopyridin-3-yl){7-[(1S)-1-methyl-2-(tetrahydro-2H-pyran-2-yloxy)ethyl]-7H-pyrrolo[2,3-d]pyrimidin-5-yl}methanone (891 mg, 2.0 mmol) (see Preparation 27), tris(dibenzylideneacetone)dipalladium (55 mg, 0.06 mmol), 2-di-tert-butylphosphino-2',4',6'-triisopropylbiphenyl (68 mg, 0.16 mmol) and freshly ground potassium phosphate tribasic (1.06 g, 5.0 mmol) in 1,2-dimethoxyethane (4 mL). The mixture was stirred at 50° C. for 17 hours. The reaction mixture diluted with DCM (10 mL), filtered through Arbocel™ and the pad was washed with DCM (5 mL). The filtrate was evaporated in vacuo and the crude material was dissolved in THF (10 mL). Aqueous citric acid (5 mL, 2M) was added and the mixture was stirred at room temperature for 16 hours. Water (40 mL) was added then sodium hydroxide was added to basify the mixture. The mixture was extracted with EtOAc (3×40 mL) and the combined organic extracts were dried over magnesium sulfate and evaporated in vacuo. The residue was purified by column chromatography on silica gel (gradient of EtOAc:MeOH 100:0 to 80:20) to afford the title compound as a white solid in 70% yield, 506 mg.

LCMS (system 1): $R_t$=3.27 min; m/z 382 [M+H]$^+$.

Preparation 34: 2-(2H-Benzotriazol-2-yl)-N-[5-({7-[(1S)-1-methyl-2-(tetrahydro-2H-pyran-2-yloxy)ethyl]-7H-pyrrolo[2,3-d]pyrimidin-5-yl}carbonyl)pyridin-3-yl]acetamide

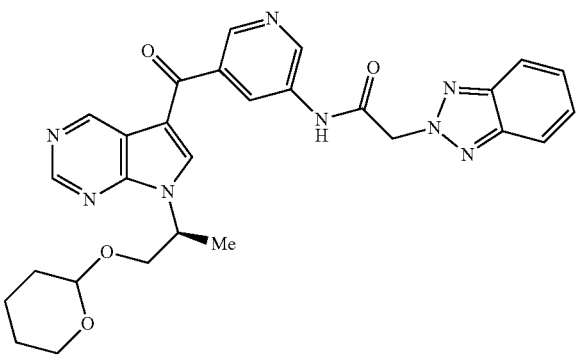 [SMILES: C[C@@H](COC1CCCCO1)n1cc(C(=O)c2cncc(NC(=O)Cn3nc4ccccc4n3)c2)c2cncnc21]

The title compound was prepared according to the method described for Example 1 using (5-aminopyridin-3-yl){7-[(1S)-1-methyl-2-(tetrahydro-2H-pyran-2-yloxy)ethyl]-7H-pyrrolo[2,3-d]pyrimidin-5-yl}methanone (see Preparation 33) and benzotriazol-2-yl-acetic acid to afford the title compound as a yellow solid in 72% yield, 70 mg.

LCMS (system 5): R$_t$=2.98 min; m/z 541 [M+H]$^+$.

Preparation 35: 2-(2,4-Difluorophenyl)-N-[5-({7-[(1S)-1-methyl-2-(tetrahydro-2H-pyran-2-yloxy)ethyl]-7H-pyrrolo[2,3-d]pyrimidin-5-yl}carbonyl)pyridin-3-yl]acetamide

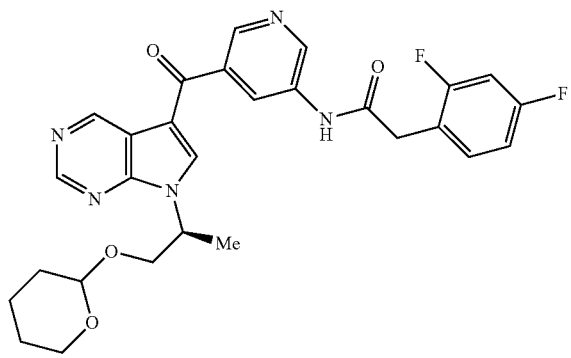 [SMILES: C[C@@H](COC1CCCCO1)n1cc(C(=O)c2cncc(NC(=O)Cc3ccc(F)cc3F)c2)c2cncnc21]

The title compound was prepared according to the method described for Example 1 using (5-aminopyridin-3-yl){7-[(1S)-1-methyl-2-(tetrahydro-2H-pyran-2-yloxy)ethyl]-7H-pyrrolo[2,3-d]pyrimidin-5-yl}methanone (see Preparation 33) and 2,5-difluorophenylacetic acid to afford the title compound as a yellow solid in 75% yield, 75 mg.

LCMS (system 5): R$_t$=3.08 min; m/z 536 [M+H]$^+$.

Preparation 36: (5-Aminopyridin-3-yl){7-[(1R)-1-methyl-2-(tetrahydro-2H-pyran-2-yloxy)ethyl]-7H-pyrrolo[2,3-d]pyrimidin-5-yl}methanone

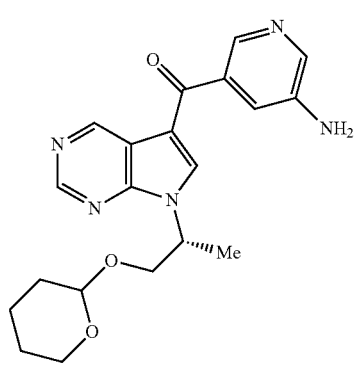 [SMILES: C[C@H](COC1CCCCO1)n1cc(C(=O)c2cncc(N)c2)c2cncnc21]

Copper (I) oxide (9.2 mg, 0.06 mmol) was added to (5-bromopyridin-3-yl){7-[(1R)-1-methyl-2-(tetrahydro-2H-pyran-2-yloxy)ethyl]-7H-pyrrolo[2,3-d]pyrimidin-5-yl}methanone (285 mg, 0.64 mmol) (see Preparation 26) and concentrated ammonia solution (2 mL) in 1-methyl-2-pyrrolidinone (0.5 mL). The mixture was heated in a sealed vessel at 80° C. for 17 hours. Ethyl acetate (5 mL) and water (5 mL) were added to the reaction mixture and then filtered through a glass fibre filter. The organic phase was dried over magnesium sulfate and evaporated in vacuo. The crude solid was purified by column chromatography on silica gel (gradient of EtOAc:MeOH:cNH3 100:0:0 to 95:5:0.5) to afford the title compound as a colourless oil in 70% yield, 171 mg.

LCMS (system 2): R$_t$=0.78 min; m/z 382 [M+H]$^+$.

Preparation 37: (5-Aminopyridin-3-yl){7-[(1S)-2-{[tert-butyl(dimethyl)silyl]oxy}-1-methylethyl]-7H-pyrrolo[2,3-d]pyrimidin-5-yl}methanone

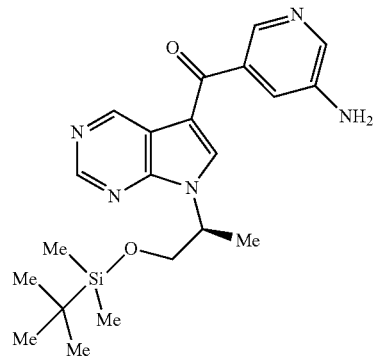 [SMILES: C[C@@H](CO[Si](C)(C)C(C)(C)C)n1cc(C(=O)c2cncc(N)c2)c2cncnc21]

Aqueous citric acid (120 mL, 2.0 M) was added to {7-[(1S)-2-{[tert-butyl(dimethyl)silyl]oxy}-1-methylethyl]-7H-pyrrolo[2,3-d]pyrimidin-5-yl}{5-[(diphenylmethylene)amino]pyridin-3-yl}methanone (63.2 g, 110 mmol) (see Preparation 24) in THF (274 mL) and the mixture was stirred at room temperature for 17 hours. The mixture was cooled to 0°, water (200 mL) added and the mixture was basified using sodium hydroxide (28 g). The mixture was extracted with ethyl acetate (150 mL) then the aqueous phase was extracted with ethyl acetate (2×200 mL). The combined organic phases were washed with brine (600 mL), dried over sodium sulfate and evaporated in vacuo to afford the title compound as a semi-solid in quantitative yield, 45.2 g.

LCMS (system 2): R$_t$=1.16 min; m/z 412 [M+H]$^+$.

Preparation 38: (5-Aminopyridin-3-yl)[7-(2-{[tert-butyl(dimethyl)silyl]oxy}-1,1-dimethylethyl)-7H-pyrrolo[2,3-d]pyrimidin-5-yl]methanone

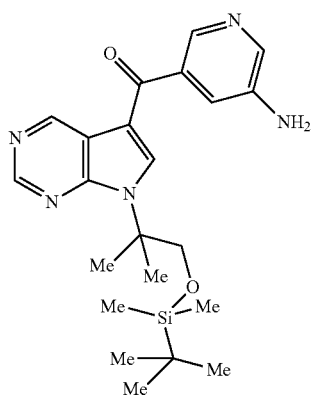 [SMILES: CC(C)(CO[Si](C)(C)C(C)(C)C)n1cc(C(=O)c2cncc(N)c2)c2cncnc21]

The title compound was prepared according to the method described for Preparation 37 using [7-(2-{[tert-butyl(dimethyl)silyl]oxy}-1,1-dimethylethyl)-7H-pyrrolo[2,3-d]pyrimidin-5-yl]{5-[(diphenylmethylene)amino]pyridin-3-yl}methanone (see Preparation 25) to afford the title compound as a white solid in 81% yield, 872 mg.

¹H NMR (400 MHz, DMSO-d6) δ: 0.22 (s, 6H), 0.63 (s, 9H), 1.66 (s, 6H), 4.12 (s, 2H), 5.65 (s, 2H), 7.27 (dd, 1H), 8.08 (s, 1H), 8.14-8.17 (m, 2H), 8.97 (s, 1H), 9.45 (s, 1H).

Preparation 39: (R,S) (5-Aminopyridin-3-yl){7-[2-{[tert-butyl(dimethyl)silyl]oxy}-1-methylethyl]-7H-pyrrolo[2,3-d]pyrimidin-5-yl}methanone

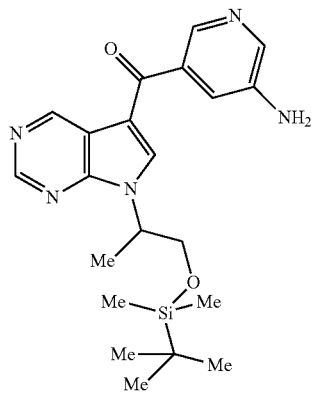 [SMILES: CC(CO[Si](C)(C)C(C)(C)C)n1cc(C(=O)c2cncc(N)c2)c2cncnc21]

The title compound was prepared according to the method described for Preparation 37 using (R,S) {7-[2-{[tert-butyl(dimethyl)silyl]oxy}-1-methylethyl]-7H-pyrrolo[2,3-d]pyrimidin-5-yl}{5-[(diphenylmethylene)amino]pyridin-3-yl}methanone (see Preparation 28) to afford the title compound as a white solid in 89% yield, 86 mg.

LCMS (System 4): R$_t$=1.37 min; m/z 412 [M+H]⁺.

Preparation 40:
2-Chloro-5-iodo-7H-pyrrolo[2,3-d]pyrimidine

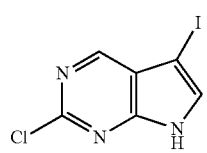 [SMILES: Clc1ncc2c(I)c[nH]c2n1]

N-Iodosuccinimide (742 g, 3.30 mol) was added to 2-chloro-7H-pyrrolo[2,3-d]pyrimidine (482.5 g, 3.14 mol) in acetonitrile (2500 mL) at 12° C. The mixture was stirred at room temperature for 1 hour then sodium metabisulphite (650 g in 4500 mL of water) was added. The mixture was stirred for 1 hour then filtered to afford the title compound as a orange solid in 82% yield, 716.2 g.

¹H NMR (400 MHz, DMSO-D6) δ: 7.83 (s, 1H), 8.63 (s, 1H), 12.73 (s, 1H).

Preparation 41: Methyl 2-(2-chloro-5-iodo-7H-pyrrolo[2,3-d]pyrimidin-7-yl)-2-methylpropanoate

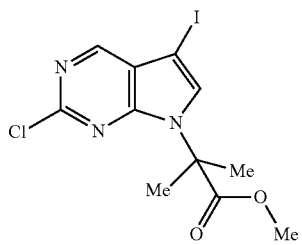 [SMILES: COC(=O)C(C)(C)n1cc(I)c2cnc(Cl)nc21]

Methyl 2-bromo-2-methylpropanoate (663 mL, 5.13 mmol) was added to 2-chloro-5-iodo-7H-pyrrolo[2,3-d]pyrimidine (358.1 g, 1.28 mol) (see Preparation 40), potassium iodide (21.3 g, 128 mmol) and cesium carbonate (1670 g, 5.13 mol) in DMF (7162 mL). The mixture was heated at 60° C. for 19 hours. The reaction mixture was diluted with water (7000 mL) and stirred at room temperature for 42 hours. The mixture was filtered and the solid was washed with water (500 mL) to afford the title compound as a beige solid in 92% yield, 445.8 g.

¹H NMR (400 MHz, CDCl₃) δ: 1.89 (s, 6H), 3.65 (s, 3H), 7.39 (s, 1H), 8.56 (s, 1H).

Preparation 42: 2-(2-Chloro-5-iodo-7H-pyrrolo[2,3-d]pyrimidin-7-yl)-2-methylpropanoic acid

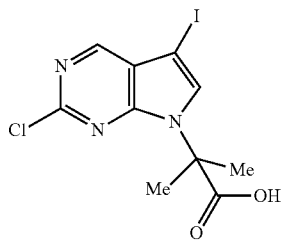 [SMILES: CC(C)(C(=O)O)n1cc(I)c2cnc(Cl)nc21]

Lithium hydroxide monohydrate (4.08 g, 97.5 mmol) was added to methyl 2-(2-chloro-5-iodo-7H-pyrrolo[2,3-d]pyrimidin-7-yl)-2-methylpropanoate (18.5 g, 48.7 mmol) (see Preparation 41) in THF (185 mL) and water (45 mL). The mixture was stirred at 60° C. for 3 hours then the reaction mixture volume was reduced to one third by evaporation in vacuo. The aqueous residue was acidified using aqueous HCl (2.0 M) then extracted with EtOAc (4×200 mL). The organic phase was evaporated in vacuo and the crude material was triturated with hexane (100 mL) to afford the title compound as a white solid in 90% yield, 16.0 g.

LCMS (system 5) R$_t$=2.24 min; m/z 366 [M+H]⁺.

Preparation 43: 2-(2-Chloro-5-iodo-7H-pyrrolo[2,3-d]pyrimidin-7-yl)-2-methylpropan-1-ol

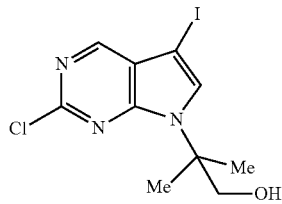 [SMILES: CC(C)(CO)n1cc(I)c2cnc(Cl)nc21]

Route a

Isobutyl chloroformate (6.6 mL, 50.02 mmol) was added to 2-(2-chloro-5-iodo-7H-pyrrolo[2,3-d]pyrimidin-7-yl)-2-methylpropanoic acid (16.6 g, 45.48 mmol) (see Preparation 42) and triethylamine (12.64 mL, 90.9 mmol) in THF (300 mL) at 0° C. under nitrogen. The mixture was stirred at room temperature for 3 hours then filtered through a short plug of Celite™. The filtrate was cooled to 0° C. and sodium borohydride (8.6 g, 227.6 mmol) in water (300 mL) was added. The mixture was stirred for 10 minutes at 0° C., extracted with ethyl acetate (3×150 mL) then the organic extract was washed with brine (150 mL) and dried over sodium sulfate. The solution was evaporated in vacuo and the residue was triturated with hexane to afford the title compound as a white solid in 63% yield, 10.0 g.

$^1$H NMR (400 MHz, DMSO-$D_6$) δ: 1.64 (s, 6H), 3.85 (d, 2H), 4.99 (t, 1H), 7.82 (s, 1H), 8.63 (s, 1H).

Route b

Diisobutylaluminium hydride (300 mL, 300 mmol, 1M in THF) was added dropwise to methyl 2-(2-chloro-5-iodo-7H-pyrrolo[2,3-d]pyrimidin-7-yl)-2-methylpropanoate (51.8 g, 136 mmol) (see Preparation 41) in THF (150 mL) at 0° C. The mixture was stirred for 90 minutes then methanol (27.9 mL) and aqueous HCl (20 mL, 2M) was added. Water (100 mL), aqueous HCl (280 mL, 2M) and EtOAc (150 mL) were added and the mixture was stirred at room temperature for 30 minutes. The mixture was filtered and the solid was washed with water (150 mL) and tertbutylmethyl ether (150 mL) to afford the title compound as a white solid in 56% yield, 26.8 g.

LCMS (System 1) $R_t$=4.88 min; m/z 352 [M+H]$^+$.

Preparation 44: 7-(2-{[tert-Butyl(dimethyl)silyl]oxy}-1,1-dimethylethyl)-2-chloro-5-iodo-7H-pyrrolo[2,3-d]pyrimidine

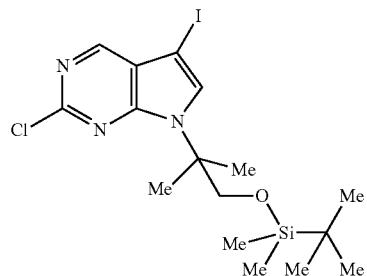 [SMILES: CC(C)(CO[Si](C)(C)C(C)(C)C)n1cc(I)c2cnc(Cl)nc21]

t-Butyldimethylsilyl chloride (78.8 g, 518 mmol) was added to 2-(2-chloro-5-iodo-7H-pyrrolo[2,3-d]pyrimidin-7-yl)-2-methylpropan-1-ol (140 g, 398 mmol) (see Preparation 43) and imidazole (67.8 g, 996 mmol) in DMF (996 mL) at 0° C. The mixture was stirred at room temperature for 16 hours. The mixture was poured into saturated aqueous sodium bicarbonate (1500 mL) and extracted with heptane:EtOAc (1:1, 1500 mL). The organic extract was washed with brine (2×900 mL) then dried over magnesium sulfate and evaporated in vacuo to afford the title compound as a brown gum in 96% yield, 178.2 g.

LCMS (System 1) $R_t$=8.32 min; m/z 466 [M+H]$^+$.

Preparation 45: 2-Chloro-7-[1,1-dimethyl-2-(tetrahydro-2H-pyran-2-yloxy)ethyl]-5-iodo-7H-pyrrolo[2,3-d]pyrimidine

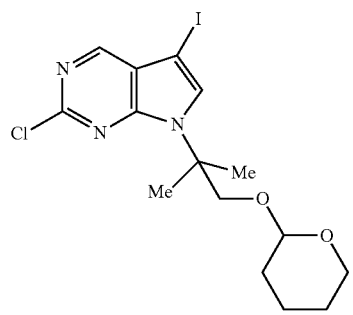 [SMILES: CC(C)(COC1CCCCO1)n1cc(I)c2cnc(Cl)nc21]

The title compound was prepared according to the method described for Preparation 6 using 2-(2-chloro-5-iodo-7H-pyrrolo[2,3-d]pyrimidin-7-yl)-2-methylpropan-1-ol (see Preparation 43) to afford the title compound as a yellow oil in 74% yield, 7.3 g. LCMS (system 5) $R_t$=4.01 min; m/z 436 [M+H]$^+$.

Preparation 46: (5-Bromopyridin-3-yl)[7-(2-{[tert-butyl(dimethyl)silyl]oxy}-1,1-dimethylethyl)-2-chloro-7H-pyrrolo[2,3-d]pyrimidin-5-yl]methanone

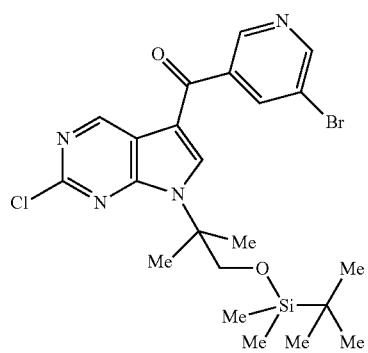 [SMILES: CC(C)(CO[Si](C)(C)C(C)(C)C)n1cc(C(=O)c2cncc(Br)c2)c2cnc(Cl)nc21]

The title compound was prepared according to the method described for Preparation 28 using 7-(2-{[tert-butyl(dimethyl)silyl]oxy}-1,1-dimethylethyl)-2-chloro-5-iodo-7H-pyrrolo[2,3-d]pyrimidine (see Preparation 44) and 5-bromo-N-methoxy-N-methylnicotinamide to afford the title compound as a yellow solid in 42% yield, 1.40 g.

¹H NMR (400 MHz, CDCl₃) δ: −0.18 (s, 6H), 0.63 (s, 9H), 1.72 (s, 6H), 4.09 (s, 2H), 8.24 (s, 1H), 8.39 (s, 1H), 8.95 (s, 1H), 8.99 (d, 1H), 9.36 (s, 1H).

Preparation 47: (5-Bromopyridin-3-yl){2-chloro-7-[1,1-dimethyl-2-(tetrahydro-2H-pyran-2-yloxy)ethyl]-7H-pyrrolo[2,3-d]pyrimidin-5-yl}methanone

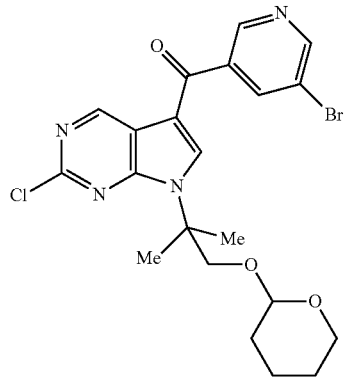 [SMILES: CC(C)(COC1CCCCO1)n1cc(C(=O)c2cncc(Br)c2)c2cnc(Cl)nc21]

The title compound was prepared according to the method described for Preparation 28 using 2-chloro-7-[1,1-dimethyl-2-(tetrahydro-2H-pyran-2-yloxy)ethyl]-5-iodo-7H-pyrrolo[2,3-d]pyrimidine (see Preparation 45) and 5-bromo-N-methoxy-N-methylnicotinamide to afford the title compound as a yellow solid in 41% yield, 3.0 g.
¹H NMR (400 MHz, CDCl₃) δ: 1.42-1.62 (m, 6H), 1.83 (s, 6H), 3.35-3.39 (m, 1H), 3.53-3.56 (m, 1H), 3.85 (d, 1H), 4.22 (d, 1H), 4.47 (m, 1H), 7.98 (s, 1H), 8.25 (s, 1H), 8.87 (s, 1H), 8.94 (s, 1H), 9.45 (s, 1H).

Preparation 48: [2-Amino-7-(2-hydroxy-1,1-dimethylethyl)-7H-pyrrolo[2,3-d]pyrimidin-5-yl](5-aminopyridin-3-yl)methanone

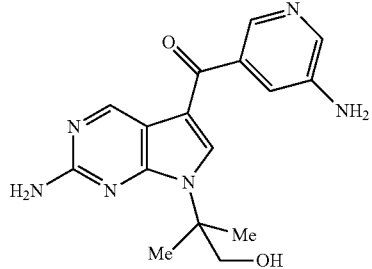 [SMILES: CC(C)(CO)n1cc(C(=O)c2cncc(N)c2)c2cnc(N)nc21]

The title compound was prepared according to the method described for Preparation 36 using (5-bromopyridin-3-yl)[7-(2-{[tert-butyl(dimethyl)silyl]oxy}-1,1-dimethylethyl)-2-chloro-7H-pyrrolo[2,3-d]pyrimidin-5-yl]methanone (see Preparation 46) to afford the title compound as a yellow solid in 48% yield, 300 mg.
¹H NMR (400 MHz, DMSO-D₆) δ: 1.64 (s, 6H), 3.90 (d, 2H), 5.07 (t, 1H), 5.60 (s, 2H), 6.50 (s, 2H), 7.23 (s, 1H), 7.61 (s, 1H), 8.11 (m, 2H), 8.93 (s, 1H).
[7-(2-{[tert-Butyl(dimethyl)silyl]oxy}-1,1-dimethylethyl)-2-amino-7H-pyrrolo[2,3-d]pyrimidin-5-yl]{5-aminopyridin-3-yl}methanone (Preparation 48a) was also isolated from the reaction mixture.

¹H NMR (400 MHz, DMSO) δ: −0.18 (s, 6H), 0.66 (s, 9H), 1.67 (s, 6H), 4.05 (s, 2H), 5.59 (s, 2H), 6.51 (s, 2H), 7.19 (s, 1H), 7.57 (s, 1H), 8.07 (s, 1H), 8.10 (s, 1H), 8.93 (s, 1H).

Preparation 49: {2-Amino-7-[1,1-dimethyl-2-(tetrahydro-2H-pyran-2-yloxy)ethyl]-7H-pyrrolo[2,3-d]pyrimidin-5-yl}(5-aminopyridin-3-yl)methanone

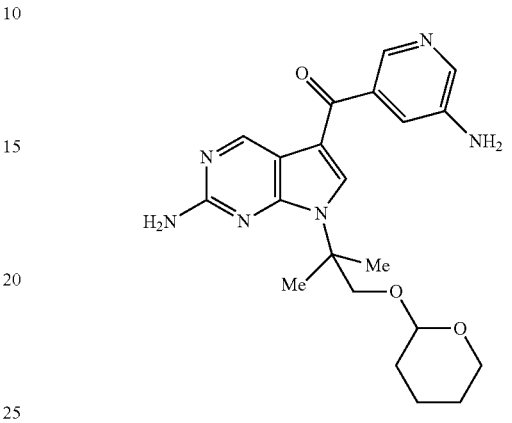

The title compound was prepared according to the method described for Preparation 36 using (5-bromopyridin-3-yl){2-chloro-7-[1,1-dimethyl-2-(tetrahydro-2H-pyran-2-yloxy)ethyl]-7H-pyrrolo[2,3-d]pyrimidin-5-yl}methanone (see Preparation 47) to afford the title compound as a yellow solid in 52% yield, 1.3 g.
LCMS (system 5) R$_t$=2.72 min; m/z 411 [M+H]⁺.

Preparation 50: [7-(2-{[tert-Butyl(dimethyl)silyl]oxy}-1,1-dimethylethyl)-2-chloro-7H-pyrrolo[2,3-d]pyrimidin-5-yl]{5-[(diphenylmethylene)amino]pyridin-3-yl}methanone

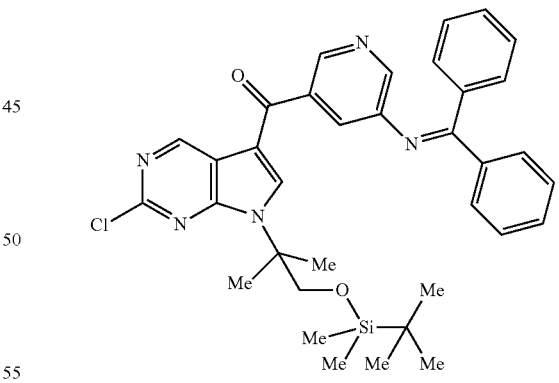

Isopropyl magnesium chloride (105 mL, 210 mmol, 2.0 M in THF) was added to 7-(2-{[tert-butyl(dimethyl)silyl]oxy}-1,1-dimethylethyl)-2-chloro-5-iodo-7H-pyrrolo[2,3-d]pyrimidine (89.0 g, 190 mmol) (see Preparation 44) in THF (450 mL) at 0° C., under nitrogen. The mixture was stirred at 0° C. for 1 hour then a solution of 5-[(diphenylmethylene)amino]-N-methoxy-N-methylnicotinamide (72.6 g, 210 mmol) (see Preparation 23) in THF (200 mL) was added dropwise at 0° C. The mixture was warmed to room temperature and stirred at this temperature for 16 hours. The reaction mixture was quenched with 10% aqueous ammonium chloride (500 mL)

and the organic phase was separated. The aqueous phase was extracted with ethyl acetate (2×300 mL). The combined organic extracts were washed with brine (400 mL), dried over sodium sulfate, evaporated in vacuo and the crude material was purified by column chromatography on silica gel (gradient of heptane:EtOAc 100:0 to 60:40) to afford the title compound as a colourless gum in 66% yield, 78.9 g.

LCMS (System 1) $R_t$=8.60 min; m/z 624 [M+H]$^+$.

Preparation 51: (5-Aminopyridin-3-yl){7-(2-{[tert-butyl(dimethyl)silyl]oxy}-1,1-dimethylethyl)-2-[(2,4-dimethoxybenzyl)amino]-7H-pyrrolo[2,3-d]pyrimidin-5-yl}methanone

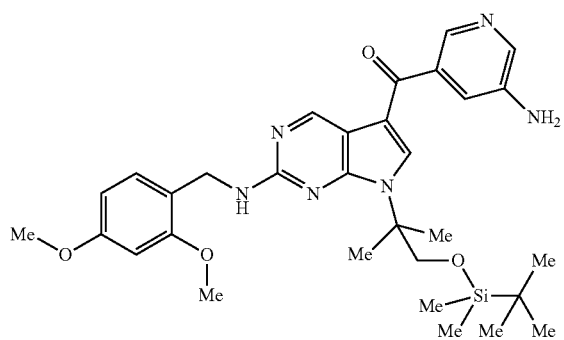 [SMILES: COc1ccc(CNc2ncc3c(C(=O)c4cncc(N)c4)cn(C(C)(C)CO[Si](C)(C)C(C)(C)C)c3n2)c(OC)c1]

2,4-Dimethoxybenzylamine (99.4 g, 594 mmol) was added to [7-(2-{[tert-butyl(dimethyl)silyl]oxy}-1,1-dimethylethyl)-2-chloro-7H-pyrrolo[2,3-d]pyrimidin-5-yl]{5-[(diphenylmethylene)amino]pyridin-3-yl}methanone (53.0 g, 85 mmol) (see Preparation 50) and 4-dimethylaminopyridine (2.07 g, 17.0 mmol) in 1,4-dioxane (170 mL). The mixture was heated to reflux for 2 days then cooled to room temperature and filtered. The filtrate was evaporated in vacuo, the residue was dissolved in EtOAc (300 mL) and washed with saturated aqueous ammonium chloride (500 mL). The organic phase was dried over magnesium sulfate and evaporated in vacuo.

The crude residue was dissolved in THF (200 mL) and aqueous citric acid (200 mL, 2M) was added. The mixture was stirred at room temperature for 5 hours then diluted with water (200 mL). The mixture was extracted with EtOAc (300 mL) and the organic extract was washed with aqueous potassium carbonate (300 mL, 2M). The organic phase was dried over magnesium sulfate, evaporated in vacuo and the residue was purified by column chromatography on silica (gradient of pentane:EtOAc 100:0 to 0:100, followed by EtOAc:MeOH 95:5) to afford the title compound as a colourless oil in 78% yield, 39.0 g.

LCMS (System 1) $R_t$=5.97 min; m/z 591 [M+H]$^+$.

Preparation 52: N-[5-({2-Amino-7-[1,1-dimethyl-2-(tetrahydro-2H-pyran-2-yloxy)ethyl]-7H-pyrrolo[2,3-d]pyrimidin-5-yl}carbonyl)pyridin-3-yl]-2-(4-cyclopropyl-1H-1,2,3-triazol-1-yl)acetamide

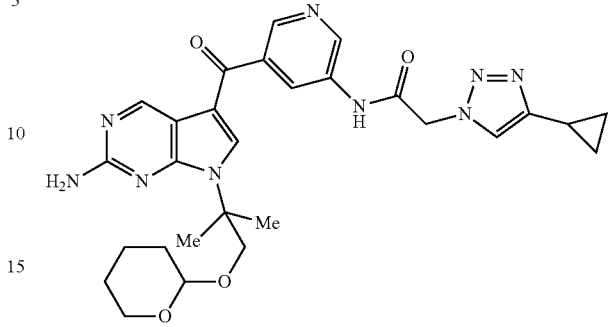

The title compound was prepared according to the method described for Example 1 using {2-amino-7-[1,1-dimethyl-2-(tetrahydro-2H-pyran-2-yloxy)ethyl]-7H-pyrrolo[2,3-d]pyrimidin-5-yl}(5-aminopyridin-3-yl)methanone (see Preparation 49) and (4-cyclopropyl-1H-1,2,3-triazol-1-yl)acetic acid (see Preparation 83) to afford the title compound as a yellow solid in 86% yield, 70 mg.

LCMS (system 5): $R_t$=2.87 min; m/z 560 [M+H]$^+$.

Preparation 53: (R,S) Methyl 2-(2-chloro-5-iodo-7H-pyrrolo[2,3-d]pyrimidin-7-yl)propanoate

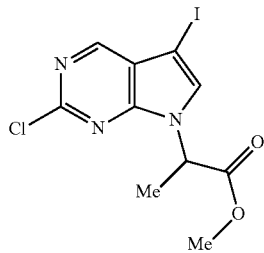 [SMILES: COC(=O)C(C)n1cc(I)c2cnc(Cl)nc21]

The title compound was prepared according to the method described for Preparation using 2-chloro-5-iodo-7H-pyrrolo[2,3-d]pyrimidine (see Preparation 40) to afford the title compound as a brown solid in 62% yield, 18.0 g.

$^1$H NMR (400 MHz, CDCl$_3$) δ: 1.77 (d, 3H), 3.75 (s, 3H), 5.67 (q, 1H), 7.46 (s, 1H), 8.58 (s, 1H).

Preparation 54: (R,S) 2-(2-Chloro-5-iodo-7H-pyrrolo[2,3-d]pyrimidin-7-yl)propan-1-ol

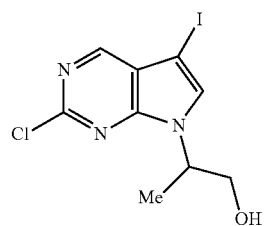 [SMILES: CC(CO)n1cc(I)c2cnc(Cl)nc21]

The title compound was prepared according to the method described for Preparation 22 using (R,S) methyl 2-(2-chloro-5-iodo-7H-pyrrolo[2,3-d]pyrimidin-7-yl)propanoate (see Preparation 53) to afford the title compound as a yellow solid in 75% yield, 11.0 g. $^1$H NMR (400 MHz, DMSO-D$_6$) δ: 1.40 (d, 3H), 3.62-3.74 (m, 2H), 4.83 (m, 1H), 4.98 (t, 1H), 8.03 (s, 1H), 8.64 (s, 1H).

Preparation 55: 7-(2-{[tert-Butyl(dimethyl)silyl]oxy}-1-methylethyl)-2-chloro-5-iodo-7H-pyrrolo[2,3-d]pyrimidine

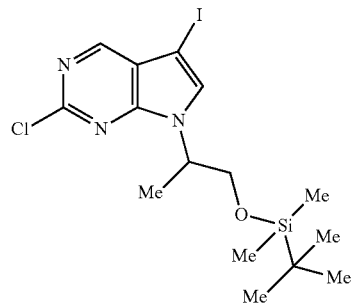 [SMILES: CC(CO[Si](C)(C)C(C)(C)C)n1cc(I)c2cnc(Cl)nc21]

The title compound was prepared according to the method described for Preparation 44 using 2-(2-chloro-5-iodo-7H-pyrrolo[2,3-d]pyrimidin-7-yl)propan-1-ol (see Preparation 54) to afford the title compound as a yellow solid in 89% yield, 12.50 g.

$^1$H NMR (400 MHz, CDCl$_3$) δ: −0.09 (s, 6H), 0.80 (s, 9H), 1.53 (d, 3H), 3.80 (d, 2H), 5.04 (m, 1H), 7.46 (s, 1H), 8.55 (s, 1H).

The enantiomers were separated using a Chiralpak IC 20×250 mm, 98:2:0.1 heptane:IPA:diethylamine (flow rate—18.0 mL/minute).

Enantiomer 1 Yield 5.2 g, 99% e.e. (first eluting peak at 7.10 mins)

Enantiomer 2 Yield 5.0 g, 99% e.e. (second eluting peak at 7.64 mins)

Preparation 56: (5-Bromopyridin-3-yl)[7-(2-{[tert-butyl(dimethyl)silyl]oxy}-1-methylethyl)-2-chloro-7H-pyrrolo[2,3-d]pyrimidin-5-yl]methanone (enantiomer 1)

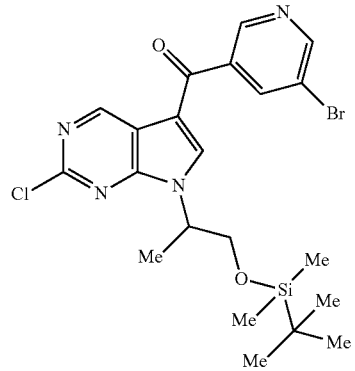 [SMILES: CC(CO[Si](C)(C)C(C)(C)C)n1cc(C(=O)c2cncc(Br)c2)c2cnc(Cl)nc21]

The title compound was prepared according to the method described for Preparation 28 using 7-(2-{[tert-butyl(dimethyl)silyl]oxy}-1-methylethyl)-2-chloro-5-iodo-7H-pyrrolo[2,3-d]pyrimidine (see Preparation 55, enantiomer 1) and 5-bromo-N-methoxy-N-methylnicotinamide to afford the title compound as a yellow solid in 30% yield, 1.0 g. $^1$H NMR (400 MHz, DMSO-D$_6$) δ: −0.14 (s, 6H), 0.61 (s, 9H), 1.52 (d, 3H), 3.91-3.96 (m, 2H), 5.00 (m, 1H), 8.37 (s, 1H), 8.58 (s, 1H), 8.95 (s, 1H), 9.00 (s, 1H), 9.33 (s, 1H).

Preparation 57: [2-Amino-7-(2-hydroxy-1-methylethyl)-7H-pyrrolo[2,3-d]pyrimidin-5-yl](5-aminopyridin-3-yl)methanone (enantiomer 1)

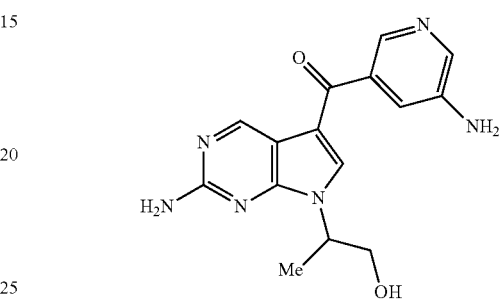

The title compound was prepared according to the method described for Preparation 36 using (5-bromopyridin-3-yl)[7-(2-{[tert-butyl(dimethyl)silyl]oxy}-1-methylethyl)-2-chloro-7H-pyrrolo[2,3-d]pyrimidin-5-yl]methanone (see Preparation 56) to afford the title compound as a yellow solid in 51% yield, 450 mg.

$^1$H NMR (400 MHz, DMSO-D$_6$) δ: 1.41 (d, 3H), 3.66 (m, 2H), 4.74 (m, 1H), 5.01 (t, 1H), 5.59 (s, 2H), 6.55 (s, 2H), 7.22 (s, 1H), 7.83 (s, 1H), 8.11-8.13 (m, 2H), 8.91 (s, 1H); LCMS (system 5) R$_t$=1.72 min; m/z 313 [M+H]$^+$.

Preparation 58: (5-Bromopyridin-3-yl)[7-(2-{[tert-butyl(dimethyl)silyl]oxy}-1-methylethyl)-2-chloro-7H-pyrrolo[2,3-d]pyrimidin-5-yl]methanone (enantiomer 2)

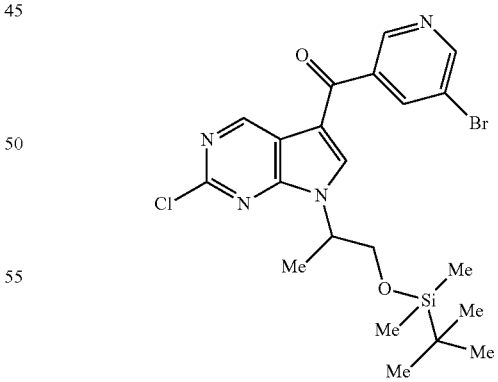

The title compound was prepared according to the method described for Preparation 28 using 7-(2-{[tert-butyl(dimethyl)silyl]oxy}-1-methylethyl)-2-chloro-5-iodo-7H-pyrrolo[2,3-d]pyrimidine (see Preparation 55, enantiomer 2) and 5-bromo-N-methoxy-N-methylnicotinamide to afford the title compound as a yellow solid in 30% yield, 1.4 g. $^1$H NMR (400 MHz, DMSO-D$_6$) δ: −0.14 (s, 6H), 0.61 (s, 9H), 1.52 (d, 3H), 3.91-3.96 (m, 2H), 5.00 (m, 1H), 8.37 (s, 1H), 8.58 (s, 1H), 8.95 (s, 1H), 9.00 (s, 1H), 9.33 (s, 1H).

Preparation 59: [2-Amino-7-(2-hydroxy-1-methylethyl)-7H-pyrrolo[2,3-d]pyrimidin-5-yl](5-aminopyridin-3-yl)methanone (enantiomer 2)

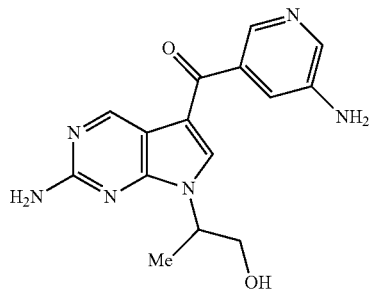 [SMILES: CC(CO)n1cc(C(=O)c2cncc(N)c2)c2cnc(N)nc21]

The title compound was prepared according to the method described for Preparation 36 using (5-bromopyridin-3-yl)[7-(2-{[tert-butyl(dimethyl)silyl]oxy}-1-methylethyl)-2-chloro-7H-pyrrolo[2,3-d]pyrimidin-5-yl]methanone (see Preparation 58) to afford the title compound as a yellow solid in 51% yield, 450 mg.

LCMS (system 5) $R_t$=1.70 min; m/z 313 [M+H]$^+$.

Preparation 60: 5-Bromo-N-tert-butyl-2-chloropyrimidin-4-amine

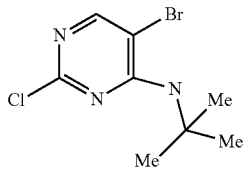 [SMILES: CC(C)(C)Nc1nc(Cl)ncc1Br]

tert-Butylamine (5.28 g, 72 mmol) was added to 5-bromo-2,4-dichloropyrimidine (15 g, 66 mmol) and triethylamine (19.9 g, 197 mmol) in acetonitrile (450 mL) at room temperature and the mixture was stirred at room temperature for 16 hours. Then the mixture was evaporated in vacuo and the crude residue was partitioned between EtOAc (450 mL) and water (400 mL). The organic layer was separated, washed with brine (400 mL) then dried over sodium sulfate and evaporated in vacuo. The residue was purified by column chromatography on silica gel (hexane:EtOAc 88:12) to afford the title compound as a yellow oil in 52% yield, 8.8 g.

LCMS (system 5): $R_t$=3.46 min; m/z 265 [M+H]$^+$.

Preparation 61: N-tert-Butyl-2-chloro-5-[(E)-2-ethoxyvinyl]pyrimidin-4-amine

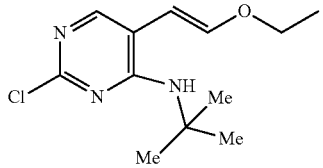 [SMILES: CCO/C=C/c1cnc(Cl)nc1NC(C)(C)C]

Catecholborane (7.8 g, 65.4 mmol) in THF (50 mL) was added dropwise to a solution of 40% ethoxyacetylene in hexane (12.8 mL, 72.5 mmol) under nitrogen at 0-5° C. The mixture was stirred for 2 hours at room temperature then heated at 70° C. for 2 hours. The mixture was then cooled to room temperature and a solution of 5-bromo-N-tert-butyl-2-chloropyrimidin-4-amine (10 g, 37.8 mmol) (see Preparation 60) in THF (50 mL) was added. The solution was degassed with argon for about 25 minutes followed by the addition of Pd(PPh$_3$)$_4$ (1.3 g, 1.13 mmol) and powdered sodium hydroxide (4.53 g, 113 mmol). The mixture was heated at 70° C. for 16 hours and then cooled to room temperature. EtOAc (200 mL) was added and the mixture was filtered through a Celite™ pad. The filtrate was evaporated in vacuo and the residue was purified by column chromatography on silica gel (gradient of hexane:EtOAc 93:7 to 90:10) to afford the title compound as a yellow oil in 55% yield, 5.3 g.

LCMS (system 5): $R_t$=3.65 min; m/z 256 [M+H]$^+$.

Preparation 62: 7-tert-Butyl-2-chloro-7H-pyrrolo[2,3-d]pyrimidine

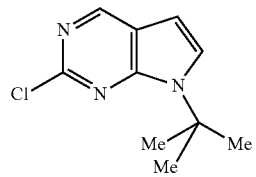 [SMILES: CC(C)(C)n1ccc2cnc(Cl)nc21]

Concentrated HCl (25 mL) was added to N-tert-butyl-2-chloro-5-[(E)-2-ethoxyvinyl]pyrimidin-4-amine (5.3 g, 20.72 mmol) (see Preparation 61) in isopropanol (210 mL) and the mixture was heated at reflux for 4 hours. The reaction mixture was then evaporated in vacuo and the residue was basified with saturated aqueous NaHCO$_3$ and extracted with EtOAc (200 mL). The organic extract was dried over sodium sulfate and evaporated in vacuo. The residue was purified by column chromatography on silica gel (gradient of hexane:EtOAc 93:7 to 90:10) to afford the title compound as a yellow oil in 85% yield, 3.7 g.

LCMS (system 5): $R_t$=3.42 min; m/z 210 [M+H]$^+$.

Preparation 63: 7-tert-Butyl-2-chloro-5-iodo-7H-pyrrolo[2,3-d]pyrimidine

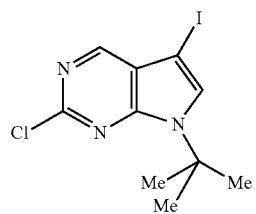 [SMILES: CC(C)(C)n1cc(I)c2cnc(Cl)nc21]

The title compound was prepared according to the method described for Preparation 14 using 7-tert-butyl-2-chloro-7H-pyrrolo[2,3-d]pyrimidine (see Preparation 62) to afford the title compound as a brown solid in 87% yield, 4.7 g.

$^1$H NMR (400 MHz, CDCl$_3$) δ: 1.55 (s, 9H), 7.39 (s, 1H), 8.54 (s, 1H).

Preparation 64: (5-Bromopyridin-3-yl)(7-tert-butyl-2-chloro-7H-pyrrolo[2,3-d]pyrimidin-5-yl)methanone

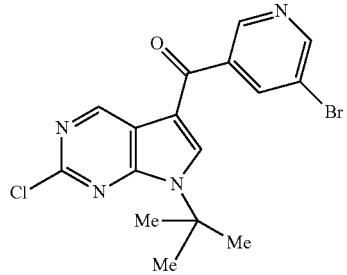 [SMILES: CC(C)(C)n1cc(C(=O)c2cncc(Br)c2)c2cnc(Cl)nc21]

The title compound was prepared according to the method described for Preparation 28 using 7-tert-butyl-2-chloro-5-iodo-7H-pyrrolo[2,3-d]pyrimidine (see Preparation 63) and 5-bromo-N-methoxy-N-methylnicotinamide to afford the title compound as a brown oil in 36% yield, 2.1 g.

$^1$H NMR (400 MHz, CDCl3) δ: 1.82 (s, 9H), 7.78 (s, 1H), 8.25 (s, 1H), 8.88 (s, 1H), 8.92 (s, 1H), 9.44 (s, 1H).

Preparation 65: (2-Amino-7-tert-butyl-7H-pyrrolo[2,3-d]pyrimidin-5-yl)(5-aminopyridin-3-yl)methanone

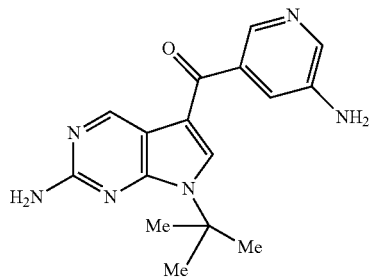 [SMILES: CC(C)(C)n1cc(C(=O)c2cncc(N)c2)c2cnc(N)nc21]

The title compound was prepared according to the method described for Preparation 36 using (5-bromopyridin-3-yl)(7-tert-butyl-2-chloro-7H-pyrrolo[2,3-d]pyrimidin-5-yl)methanone (see Preparation 64) to afford the title compound as a white solid in 55% yield, 870 mg.

LCMS (system 5): R$_t$=2.42 min; m/z 311 [M+H]$^+$.

Preparations 66 to 70 were prepared according to Example 1, starting from (5-aminopyridin-3-yl){7-[(1S)-2-{[tert-butyl(dimethyl)silyl]oxy}-1-methylethyl]-7H-pyrrolo[2,3-d]pyrimidin-5-yl}methanone (see Preparation 37) and the appropriate acids of formula:

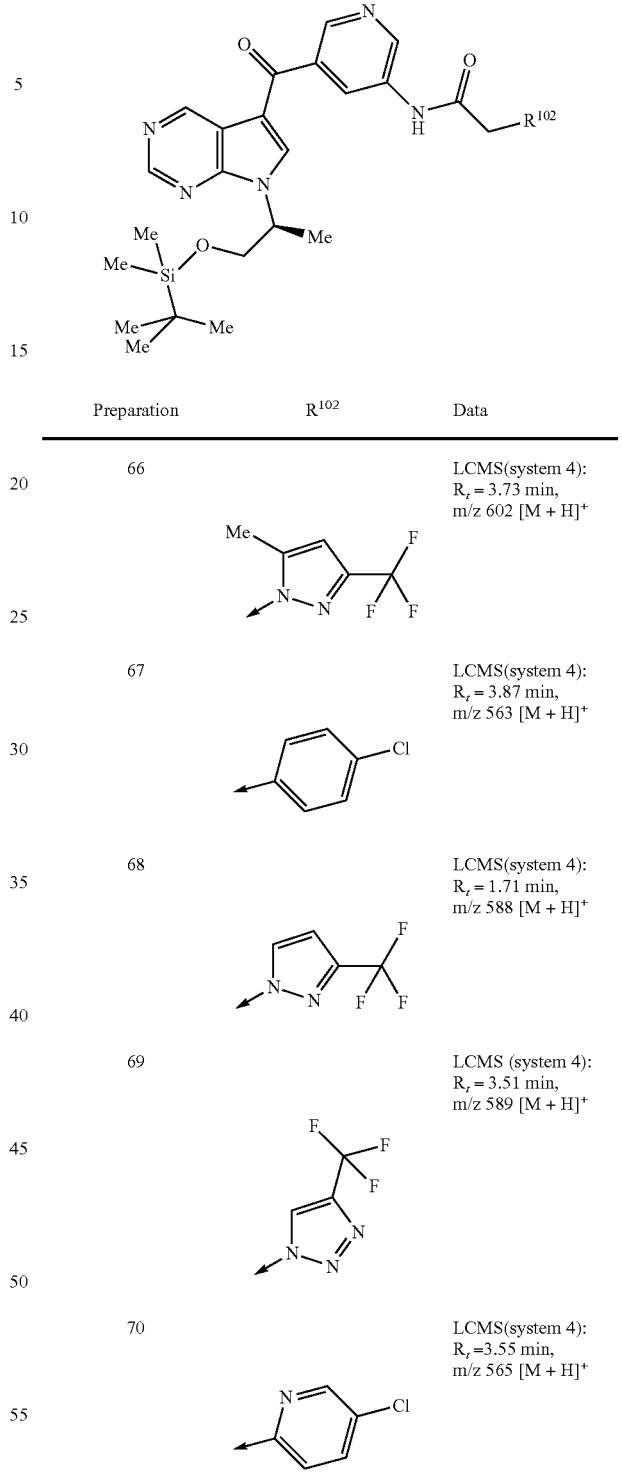

| Preparation | R$^{102}$ | Data |
|---|---|---|
| 66 | Me-pyrazole-CF$_3$ | LCMS(system 4): R$_t$ = 3.73 min, m/z 602 [M + H]$^+$ |
| 67 | 4-Cl-phenyl | LCMS(system 4): R$_t$ = 3.87 min, m/z 563 [M + H]$^+$ |
| 68 | pyrazole-CF$_3$ | LCMS(system 4): R$_t$ = 1.71 min, m/z 588 [M + H]$^+$ |
| 69 | triazole-CF$_3$ | LCMS (system 4): R$_t$ = 3.51 min, m/z 589 [M + H]$^+$ |
| 70 | 6-Cl-pyridin-3-yl | LCMS(system 4): R$_t$ =3.55 min, m/z 565 [M + H]$^+$ |

Preparations 71 to 78 were prepared according to the method described above for Example 1, starting from (5-aminopyridin-3-yl)[7-(2-{[tert-butyl(dimethyl)silyl]oxy}-1,1-dimethylethyl)-7H-pyrrolo[2,3-d]pyrimidin-5-yl]methanone (see Preparation 38) and the appropriate acids of formula:

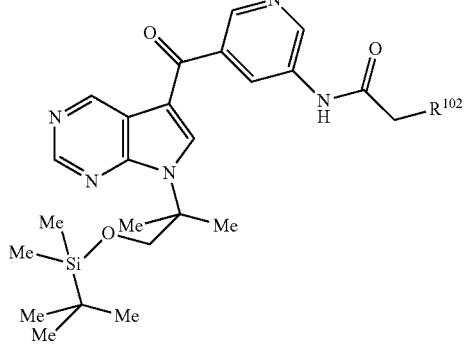

| Preparation | R102 | Data |
|---|---|---|
| 71 | 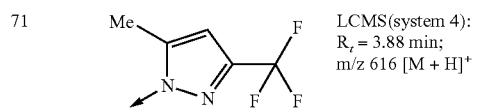 | LCMS(system 4):<br>$R_t$ = 3.88 min;<br>m/z 616 [M + H]+ |
| 72 | 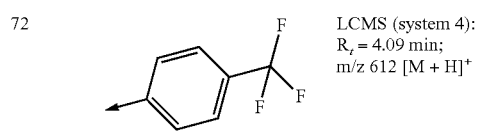 | LCMS (system 4):<br>$R_t$ = 4.09 min;<br>m/z 612 [M + H]+ |
| 73 | 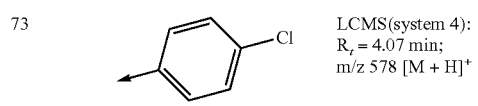 | LCMS(system 4):<br>$R_t$ = 4.07 min;<br>m/z 578 [M + H]+ |
| 74 | 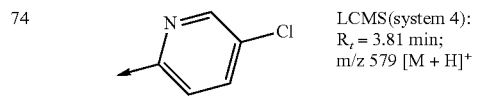 | LCMS(system 4):<br>$R_t$ = 3.81 min;<br>m/z 579 [M + H]+ |
| 75 | 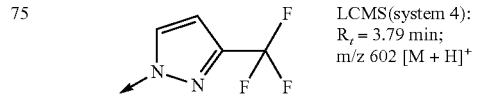 | LCMS(system 4):<br>$R_t$ = 3.79 min;<br>m/z 602 [M + H]+ |
| 76 | 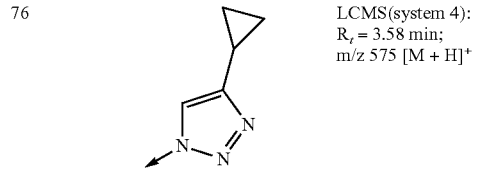 | LCMS(system 4):<br>$R_t$ = 3.58 min;<br>m/z 575 [M + H]+ |
| 77 | 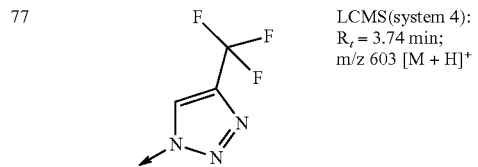 | LCMS(system 4):<br>$R_t$ = 3.74 min;<br>m/z 603 [M + H]+ |
| 78 | 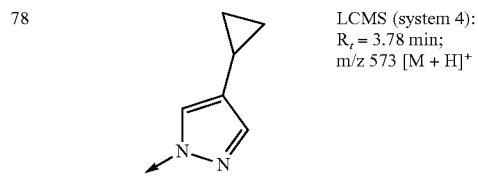 | LCMS (system 4):<br>$R_t$ = 3.78 min;<br>m/z 573 [M + H]+ |

Preparation 79: Ethyl (3-cyclopropyl-1H-pyrazol-1-yl)acetate

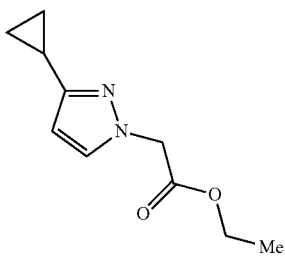 [SMILES: CCOC(=O)Cn1ccc(C2CC2)n1]

Potassium carbonate (7.67 g, 55.56 mmol) was added to 3-cyclopropyl-1H-pyrazole (2.0 g, 18.52 mmol) in dry DMF (20 mL) at 25° C. and the mixture was stirred for 20 minutes. Ethyl bromoacetate (2.06 mL, 18.52 mmol) was added then the mixture was stirred for 2 days at room temperature. The reaction mixture was neutralized with aqueous HCl (1.0 M), extracted with ether (40 mL) and the organic extract was washed with brine (30 mL), dried over sodium sulfate then evaporated in vacuo. The residue was purified by column chromatography on silica gel (hexane:EtOAc 88:12) to afford the title compound as a yellow oil in 42% yield, 1.50 g.

$^1$H NMR (400 MHz, DMSO) δ: 0.59 (d, 2H), 0.83 (d, 2H), 1.19 (t, 3H), 1.83 (m, 1H), 4.13 (q, 2H), 4.91 (s, 2H), 5.94 (d, 1H), 7.54 (d, 1H).

Preparation 80: (3-Cyclopropyl-1H-pyrazol-1-yl)acetic acid

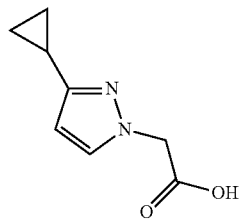 [SMILES: O=C(O)Cn1ccc(C2CC2)n1]

The title compound was prepared according to the method described for Preparation 42 using ethyl (3-cyclopropyl-1H-pyrazol-1-yl)acetate (see Preparation 79) to afford the title compound as a white solid in 83% yield, 4.06 g.

LCMS (system 4): $R_t$=1.16 min; m/z 167 [M+H]+.

Preparation 81: [4-(Trifluoromethyl)-1H-1,2,3-triazol-1-yl]acetic acid

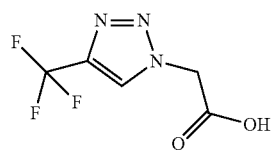 [SMILES: O=C(O)Cn1cc(C(F)(F)F)nn1]

Trifluoromethyl acetylene (22.0 g, 0.234 mol) in THF (210 mL) was added to sodium ascorbate (2.77 g, 14.0 mmol), ethyl azidoacetate (27.1 g, 0.210 mol) and copper sulfate (4.76 mL, 0.3 M in water) in water (105 mL). The mixture was stirred at room temperature for 240 hours then evaporated in vacuo. The residue was extracted with EtOAc (500 mL) and the organic phase was dried over magnesium sulfate then evaporated in vacuo.

Sodium hydroxide (7.32 g, 0.183 mol) in water (30 mL) was added to the residue (32.7 g, 0.146 mol) in methanol (50 mL) and the mixture was stirred at room temperature for 17 hours. The methanol was evaporated in vacuo and the residue was diluted with water (10 mL). Potassium hydrogen sulfate (26.6 g, 0.195 mol) in water (70 mL) was added. The solution was evaporated in vacuo and the crude solid was purified by crystallisation using water to afford the title compound as a white solid in 75% yield, 25.8 g.

$^1$H NMR (400 MHz, DMSO-d6) δ: 5.40 (s, 2H), 8.85 (s, 1H), 13.50 (br s, 1H).

Preparation 82: Ethyl (4-cyclopropyl-1H-1,2,3-triazol-1-yl)acetate

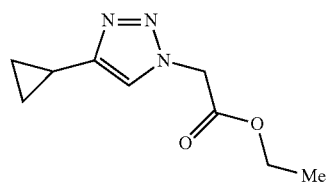 [SMILES: CCOC(=O)Cn1cc(C2CC2)nn1]

Cyclopropylacetyene (15 g, 0.116 mol), ethyl azidoacetate (11.5 g, 0.174 mol), triethylamine (0.32 mL, 2.33 mmol) and copper iodide (442 mg, 2.33 mmol) in acetonitrile (100 mL) were stirred at 25° C. for 18 hours. The mixture was evaporated in vacuo and the residue was partitioned between water (100 mL) and ethyl acetate (100 mL). The organic phase was dried over sodium sulfate, evaporated in vacuo and purified by column chromatography on silica gel (EtOAc:Hexane 40:60) to afford the title compound as a colorless liquid in 95% yield, 21.6 g.

$^1$H NMR (400 MHz, DMSO) δ: 0.68 (m, 2H), 0.90 (m, 2H), 1.21 (t, 3H), 1.95 (m, 1H), 4.17 (q, 2H), 5.29 (s, 2H), 7.81 (s, 1H).

Preparation 83: (4-Cyclopropyl-1H-1,2,3-triazol-1-yl)acetic acid

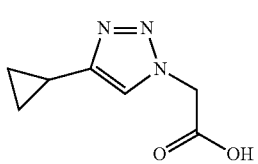 [SMILES: O=C(O)Cn1cc(C2CC2)nn1]

The title compound was prepared according to the method described for Preparation 42 using ethyl (4-cyclopropyl-1H-1,2,3-triazol-1-yl)acetate (see Preparation 82) to afford the title compound as a yellow solid in 63% yield, 13.0 g.

LCMS (system 4): R$_t$=1.86 min; m/z 186[M+H]$^+$.

Preparation 84: tert-Butyl[4-(trifluoromethyl)-1H-pyrazol-1-yl]acetate

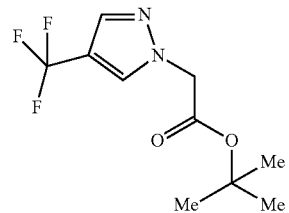 [SMILES: CC(C)(C)OC(=O)Cn1cc(C(F)(F)F)cn1]

The title compound was prepared according to the method described for Preparation 79 using 4-(trifluoromethyl)-1H-pyrazole and tert butyl bromoacetate to afford the title compound as a yellow solid in 24% yield, 1.32 g.

LCMS (system 4): R$_t$=3.64 min; m/z 251 [M+H]$^+$.

Preparation 85: [4-(Trifluoromethyl)-1H-pyrazol-1-yl]acetic acid

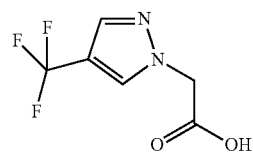

Trifluoroacetic acid (10 mL) was added to tert-butyl[4-(trifluoromethyl)-1H-pyrazol-1-yl]acetate (1.3 g, 5.2 mmol) (see Preparation 84) in dry DCM (10 mL) and the mixture was stirred for 18 hours at 25° C. Then the mixture was evaporated in vacuo and the residue was purified by trituration with diethyl ether:pentane (1:9, 2 mL) to afford the title compound as a white solid in 79% yield, 800 mg.

LCMS (system 4): R$_t$=1.39 min; m/z 193 [M+H]$^+$.

Preparation 86: tert-Butyl[4-bromo-1H-pyrazol-1-yl]acetate

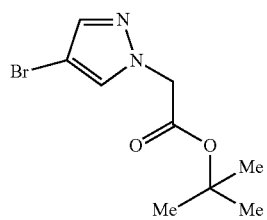 [SMILES: CC(C)(C)OC(=O)Cn1cc(Br)cn1]

The title compound was prepared according to the method described for Preparation 79 using 4-bromo-1H-pyrazole and tert butyl bromoacetate to afford the title compound as a yellow solid in 34% yield, 48.0 g.

¹H NMR (400 MHz, CDCl3) δ: 1.42 (s, 9H), 4.70 (s, 2H), 7.40 (s, 2H).

Preparation 87: tert-Butyl (4-cyclopropyl-1H-pyrazol-1-yl)acetate

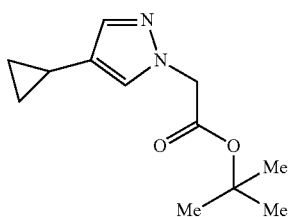 [SMILES: CC(C)(C)OC(=O)Cn1cc(C2CC2)cn1]

Palladium acetate (215 mg, 0.957 mmol) was added to tert-butyl[4-bromo-1H-pyrazol-1-yl]acetate (5 g, 19.14 mmol) (see Preparation 86), cyclopropyl boronic acid (8.22 g, 95.74 mmol), potassium phosphate (8.12 g, 38.29 mmol) and tricyclohexylphosphine (537 mg, 1.91 mmol) in toluene:water (60 mL:15 mL). The mixture was degassed for 20 minutes then refluxed for 18 hours. The reaction mixture was filtered through Celite™, the filtrate was evaporated in vacuo and the residue was purified by column chromatography on silica gel (gradient of EtOAc:hexane 15:85) to afford the title compound as an off white solid in 21% yield, 1.3 g.

LCMS (System 4): $R_t$=3.17 min; m/z 223[M+H]⁺.

Preparation 88: (4-Cyclopropyl-1H-pyrazol-1-yl)acetic acid

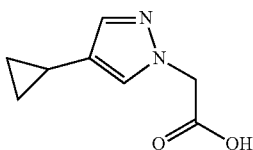 [SMILES: O=C(O)Cn1cc(C2CC2)cn1]

The title compound was prepared according to the method described for Preparation 85 using tert-butyl (4-cyclopropyl-1H-pyrazol-1-yl)acetate (see Preparation 87) to afford the title compound as a yellow solid in 75% yield, 1.0 g.

LCMS (system 4): $R_t$=1.13 min; m/z 165[M+H]⁺.

Preparation 89: Ethyl (5-chloropyridin-2-yl)acetate

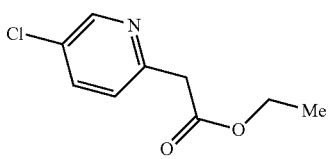 [SMILES: CCOC(=O)Cc1ccc(Cl)cn1]

Cesium carbonate (71 g, 218 mmol) was added to 2-bromo-5-chloropyridine (14 g, 73 mmol) and diethyl malonate (22 mL, 145 mmol) in dry 1,4-dioxane (280 mL) and the solution was degassed with argon for 30 minutes. Then copper (I) oxide (2.8 g, 14.55 mmol) and picolinic acid (3.6 g, 29 mmol) were added and the mixture was stirred in a sealed vessel at 130° C. for 24 hours. The mixture was cooled to room temperature, quenched with water (100 mL) and extracted with EtOAc (3×100 ml). The organic extracts were washed with water (200 mL), brine (200 mL), dried over sodium sulfate and evaporated in vacuo. The residue was purified by column chromatography on silica gel (EtOAc:Hexane 92:8) to afford the title compound as a yellow oil in 54% yield, 8.0 g.

¹H NMR (400 MHz, DMSO-$d_6$) δ: 1.17 (t, 3H), 3.85 (s, 2H), 4.08 (q, 2H), 7.42 (d, 1H), 7.90 (dd, 1H), 8.54 (d, 1H).

Preparation 90: (5-Chloropyridin-2-yl)acetic acid

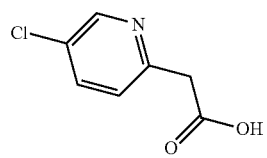 [SMILES: O=C(O)Cc1ccc(Cl)cn1]

The title compound was prepared according to the method described for Preparation 42 using ethyl (5-chloropyridin-2-yl)acetate (see Preparation 89) to afford the title compound as a brown solid in 51% yield, 3.5 g.

LCMS (system 4): $R_t$=1.00 min; m/z 172 [M+H]⁺.

Preparation 91: Ethyl (5-fluoropyridin-2-yl)acetate

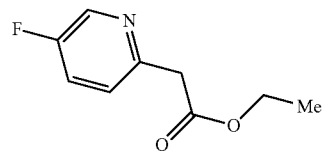 [SMILES: CCOC(=O)Cc1ccc(F)cn1]

The title compound was prepared according to the method described for Preparation 89 using 2-bromo-5-fluoropyridine to afford the title compound as a yellow oil in 20% yield, 5 g.

¹H NMR (400 MHz, DMSO-$d_6$) δ: 1.17 (t, 3H), 3.84 (s, 2H), 4.08 (q, 2H), 7.42-7.45 (m, 1H), 7.67-7.72 (m, 1H), 8.48 (d, 1H).

Preparation 92: (5-Fluoropyridin-2-yl)acetic acid

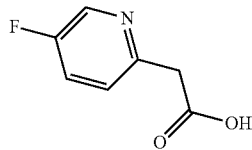 [SMILES: O=C(O)Cc1ccc(F)cn1]

The title compound was prepared according to the method described for Preparation 42 using ethyl (5-fluoropyridin-2-yl)acetate (see Preparation 91) to afford the title compound as a brown solid in 57% yield, 2.4 g.

¹H NMR (400 MHz, DMSO-$d_6$) δ: 3.75 (s, 2H), 7.41-7.44 (m, 1H), 7.65-7.70 (m, 1H), 8.47 (d, 1H), 12.50 (br s, 1H).

Preparation 93: 5-Iodo-7-isopropyl-7H-pyrrolo[2,3-d]pyrimidine

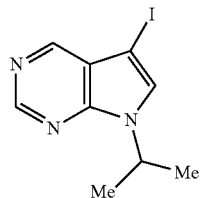 [SMILES: CC(C)n1cc(I)c2cncnc21]

To a mixture of 5-iodo-7H-pyrrolo[2,3-d]pyrimidine (Preparation 201, 2.90 g, 12.0 mmol) and cesium carbonate (5.78 g, 17.8 mmol) in DMF (45 mL) was added 2-iodopropane (1.78 mL, 17.8 mmol). The mixture was stirred at room temperature for 3 hours. The reaction mixture was then poured onto saturated aqueous ammonium chloride (500 mL) and a solid precipitated. The solid was collected by filtration, rinsed with water (200 mL) and dried under reduced pressure for 17 hours to afford the title compound as a brown solid in 77% yield, 2.61 g.

$^1$H NMR (400 MHz, CDCl$_3$) δ: 1.53 (d, 6H), 5.15 (m, 1H), 7.40 (s, 1H), 8.73 (s, 1H), 8.88 (s, 1H); LCMS (system 2): R$_t$=1.02 min; m/z 288 [M+H]$^+$.

Preparation 94: (5-Bromopyridin-3-yl)(7-isopropyl-7H-pyrrolo[2,3-d]pyrimidin-5-yl)methanone

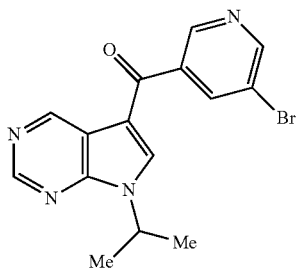 [SMILES: CC(C)n1cc(C(=O)c2cncc(Br)c2)c2cncnc21]

To a stirred solution of 5-iodo-7-isopropyl-7H-pyrrolo[2,3-d]pyrimidine (Preparation 93, 4.85 g, 16.9 mmol) in THF (90 mL) at 0° C., under nitrogen was added isopropyl magnesium chloride (9.28 mL, 18.6 mmol, 2.0 M in diethyl ether). The mixture was stirred at 0° C. for 1 hour then a solution of 5-bromo-N-methoxy-N-methylnicotinamide (Preparation 227, 4.55 g, 18.6 mmol) in THF (10 mL) was added dropwise at 0° C. The mixture was warmed to room temperature and stirred for 16 hours. The reaction mixture was quenched with saturated aqueous ammonium chloride (200 mL) and extracted with ethyl acetate (3×200 mL). The combined organics were concentrated under reduced pressure and purified by silica gel column chromatography eluting with gradient of EtOAc:DCM 95:5 to 50:50 to afford a light brown oil. The crude material was recrystallised using EtOAc:heptane (15:200 mL) to afford the title compound as a white solid in 33% yield, 2.16 g.

$^1$H NMR (400 MHz, CDCl$_3$) δ: 1.60 (d, 6H), 5.20 (m, 1H), 7.79 (s, 1H), 8.28 (dd, 1H), 8.90 (d, 1H), 8.95 (d, 1H), 9.03 (s, 1H), 9.59 (s, 1H); LCMS (system 2): R$_t$=1.36 min; m/z 346 [M+H]$^+$.

Preparation 95: (5-Aminopyridin-3-yl)(7-isopropyl-7H-pyrrolo[2,3-d]pyrimidin-5-yl)methanone

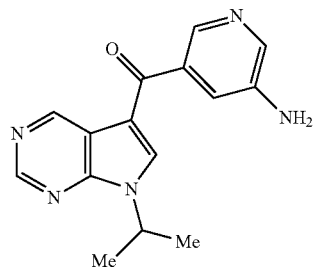 [SMILES: CC(C)n1cc(C(=O)c2cncc(N)c2)c2cncnc21]

The title compound was prepared according to the method described for Preparation 31 using (5-bromopyridin-3-yl)(7-isopropyl-7H-pyrrolo[2,3-d]pyrimidin-5-yl)methanone (Preparation 94) to afford the title compound as a white solid in 69% yield, 1.20 g.

$^1$H NMR (400 MHz, CDCl$_3$) δ: 1.58 (d, 6H), 3.98 (br s, 2H), 5.18 (m, 1H), 7.39 (dd, 1H), 7.89 (s, 1H), 8.29 (br s, 1H), 8.43 (br s, 1H), 9.01 (s, 1H), 9.59 (s, 1H); LCMS (system 2): R$_t$=0.50 min; m/z 282 [M+H]$^+$.

Preparation 96: 4-Chloro-7-oxetan-3-yl-7H-pyrrolo[2,3-d]pyrimidine

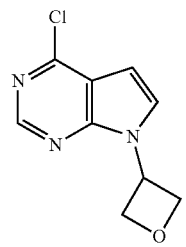 [SMILES: Clc1ncnc2c1ccn2C1COC1]

The title compound was prepared according to the method described for Preparation 1 using (4,6-dichloropyrimidin-5-yl)acetaldehyde (Preparation 208) and oxetan-3-amine to afford the title compound as a yellow solid in 67% yield, 2.81 g.

LCMS (system 1): R$_t$=1.92 min; m/z 210, 212 [M+H]$^+$.

Preparation 97: 7-Oxetan-3-yl-7H-pyrrolo[2,3-d]pyrimidine

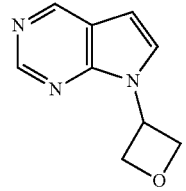 [SMILES: c1ncc2ccn(C3COC3)c2n1]

The title compound was prepared according to the method described for Preparation 8 using 4-chloro-7-oxetan-3-yl- 7H-pyrrolo[2,3-d]pyrimidine (Preparation 96) to afford the title compound as a white solid in 90% yield, 1.20 g.

$^1$H NMR (400 MHz, DMSO-d$_6$) δ: 4.97-5.06 (m, 4H), 5.96 (m, 1H), 6.74 (d, 1H), 8.04 (d, 1H), 8.80 (s, 1H), 9.03 (s, 1H).

Preparation 98:
5-Iodo-7-oxetan-3-yl-7H-pyrrolo[2,3-d]pyrimidine

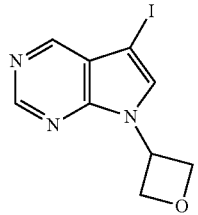 [SMILES: Ic1cn(C2COC2)c2ncncc12]

The title compound was prepared according to the method described for Preparation 14 using 7-oxetan-3-yl-7H-pyrrolo[2,3-d]pyrimidine (Preparation 97) to afford the title compound as a white solid in 49% yield, 999 mg.

$^1$H NMR (400 MHz, DMSO-d$_6$) δ: 4.92-5.08 (m, 4H), 5.94 (m, 1H), 8.28 (s, 1H), 8.75 (s, 1H), 8.85 (s, 1H).

Preparation 99: {5-[(Diphenylmethylene)amino]pyridin-3-yl}(7-oxetan-3-yl-7H-pyrrolo[2,3-d]pyrimidin-5-yl)methanone

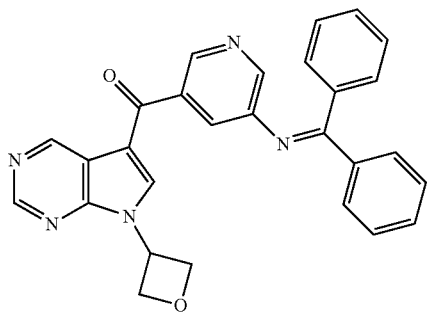 [SMILES: O=C(c1cncc(N=C(c2ccccc2)c2ccccc2)c1)c1cn(C2COC2)c2ncncc12]

The title compound was prepared according to the method described for Preparation 94 using 5-iodo-7-oxetan-3-yl-7H-pyrrolo[2,3-d]pyrimidine (Preparation 98) and 5-[(diphenylmethylene)amino]-N-methoxy-N-methylnicotinamide (Preparation 23) to afford the title compound as a yellow solid in 55% yield, 253 mg.

$^1$H NMR (400 MHz, DMSO-d$_6$) δ: 4.95-5.06 (m, 2H), 5.15-5.24 (m, 2H), 5.96 (m, 1H), 7.21-7.80 (m, 11H), 8.22 (d, 1H), 8.52 (s, 1H), 8.62 (m, 1H), 9.01 (s, 1H), 9.44 (s, 1H).

Preparation 100: (5-Aminopyridin-3-yl)(7-oxetan-3-yl-7H-pyrrolo[2,3-d]pyrimidin-5-yl)methanone

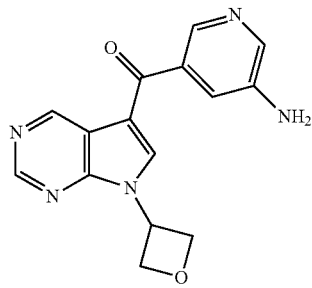 [SMILES: Nc1cncc(C(=O)c2cn(C3COC3)c3ncncc23)c1]

The title compound was prepared according to the method described for Preparation 37 using {5-[(diphenylmethylene)amino]pyridin-3-yl}(7-oxetan-3-yl-7H-pyrrolo[2,3-d]pyrimidin-5-yl)methanone (Preparation 99) to afford the title compound as a yellow solid in 96% yield, 128 mg.

$^1$H NMR (400 MHz, DMSO-d$_6$) δ: 4.95-5.04 (m, 2H), 5.14-5.22 (m, 2H), 5.66 (br s, 2H), 5.97 (m, 1H), 7.33 (m, 1H), 8.19 (d, 1H), 8.25 (d, 1H), 8.62 (s, 1H), 9.00 (s, 1H), 9.46 (s, 1H).

Preparation 101: 5-Iodo-7-{[2-(trimethylsilyl)ethoxy]methyl}-7H-pyrrolo[2,3-d]pyrimidine

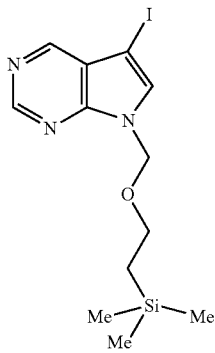 [SMILES: C[Si](C)(C)CCOCn1cc(I)c2cncnc21]

To a stirred solution of 5-iodo-7H-pyrrolo[2,3-d]pyrimidine (Preparation 201, 735 mg, 3.00 mmol) in DMF (5 mL) at 0° C. was added to sodium hydride (132 mg, 3.30 mmol, 60% in oil). The mixture was stirred at room temperature for 30 minutes, cooled to −20° C. and 2-(trimethylsilyl)ethoxymethyl chloride (0.58 mL, 3.30 mmol) added. The reaction mixture was stirred at −20° C. for 3 hours then water (30 mL) was added. The mixture was extracted with EtOAc (2×50 mL) and the combined organic phases were dried over magnesium sulphate and evaporated under reduced pressure. The crude solid was purified by column chromatography on silica gel, eluting with a gradient of heptane:EtOAc 100:0 to 50:50), to afford the title compound as a white solid in 61% yield, 691 mg.

$^1$H NMR (400 MHz, DMSO-d$_6$) δ: −0.11 (s, 9H), 0.81 (t, 2H), 3.51 (t, 2H), 5.61 (s, 2H), 8.01 (s, 1H), 8.77 (s, 1H), 8.89 (s, 1H).

Preparation 102: {5-[(Diphenylmethylene)amino]pyridin-3-yl}(7-{[2-(trimethylsilyl)ethoxy]methyl}-7H-pyrrolo[2,3-d]pyrimidin-5-yl)methanone

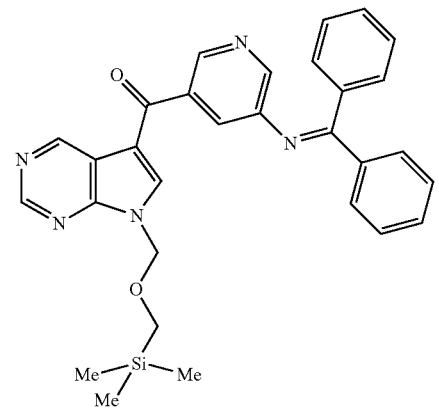 [SMILES: C[Si](C)(C)COCn1cc(C(=O)c2cncc(N=C(c3ccccc3)c3ccccc3)c2)c2cncnc21]

The title compound was prepared according to the method described for Preparation 28 using 5-iodo-7-{[2-(trimethylsilyl)ethoxy]methyl}-7H-pyrrolo[2,3-d]pyrimidine (Preparation 101) and 5-[(diphenylmethylene)amino]-N-methoxy-N-methylnicotinamide (Preparation 23) to afford the title compound as a yellow oil in 32% yield, 460 mg.

$^1$H NMR (400 MHz, DMSO-d$_6$) δ: −0.11 (s, 9H), 0.84 (m, 2H), 3.59 (m, 2H), 5.71 (s, 2H), 7.27 (m, 2H), 7.37 (m, 3H), 7.51 (m, 2H), 7.59 (m, 2H), 7.73 (d, 2H), 8.22 (d, 1H), 8.38 (s, 1H), 8.56 (d, 1H), 9.00 (s, 1H), 9.45 (s, 1H); LCMS (system 9): R$_t$=2.36 min; m/z 534 [M+H]$^+$.

Preparation 103: (5-Aminopyridin-3-yl)(7-{[2-(trimethylsilyl)ethoxy]methyl}-7H-pyrrolo[2,3-d]pyrimidin-5-yl)methanone

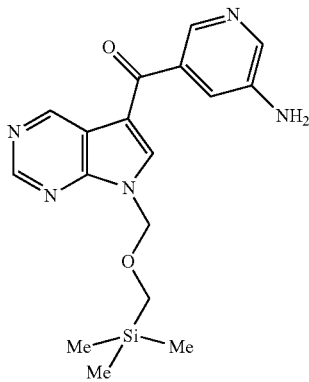 [SMILES: C[Si](C)(C)COCn1cc(C(=O)c2cncc(N)c2)c2cncnc21]

The title compound was prepared according to the method described for Preparation 37 using {5-[(diphenylmethylene)amino]pyridin-3-yl}(7-{[2-(trimethylsilyl)ethoxy]methyl}-7H-pyrrolo[2,3-d]pyrimidin-5-yl)methanone (Preparation 102) to afford the title compound as a colourless oil in 73% yield, 2.10 g.

$^1$H NMR (400 MHz, DMSO-d$_6$) δ: 0.09 (s, 9H), 0.84 (t, 2H), 3.60 (t, 2H), 5.66 (m, 4H), 7.30 (s, 1H), 8.18 (s, 2H), 8.55 (s, 1H), 9.02 (s, 1H), 9.47 (s, 1H); LCMS (system 9): R$_t$=3.25 min; m/z 370 [M+H]$^+$.

Preparation 104: 2-(4-chlorophenyl)-N-(5-(7-((2-(trimethylsilyl)ethoxy)methyl)-7H-pyrrolo[2,3-d]pyrimidine-5-carbonyl)pyridin-3-yl)acetamide

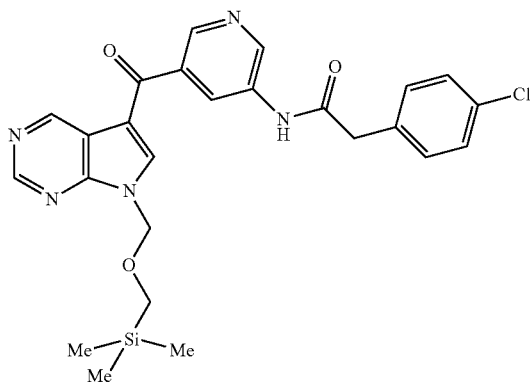 [SMILES: C[Si](C)(C)COCn1cc(C(=O)c2cncc(NC(=O)Cc3ccc(Cl)cc3)c2)c2cncnc21]

The title compound was prepared according to the method described for Examples 73-87 using (5-aminopyridin-3-yl)(7-{[2-(trimethylsilyl)ethoxy]methyl}-7H-pyrrolo[2,3-d]pyrimidin-5-yl)methanone (Preparation 103) and 4-chlorophenylacetic acid to afford the title compound as a white solid in 66% yield, 223 mg.

$^1$H NMR (400 MHz, DMSO-d$_6$) δ: −0.11 (s, 9H), 0.82 (t, 3H), 3.60 (t, 2H), 3.74 (s, 2H), 5.70 (s, 2H), 7.37 (t, 4H), 8.47 (s, 1H), 8.60 (s, 2H), 8.72 (s, 1H), 8.98 (s, 1H), 9.03 (s, 1H), 9.48 (s, 1H);

LCMS (system 9): R$_t$=3.50 min; m/z 522 [M+H]$^+$.

Preparation 105: N-[5-({7-[(1S)-2-{[tert-butyl(dimethyl)silyl]oxy}-1-methylethyl]-7H-pyrrolo[2,3-d]pyrimidin-5-yl}carbonyl)pyridin-3-yl]-2-[3-(trifluoromethyl)phenyl]acetamide

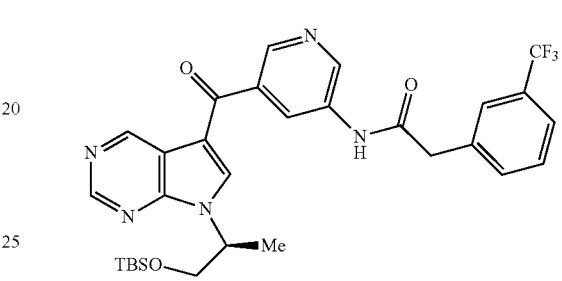

Prepared according to Example 1, using (S) (5-aminopyridin-3-yl){2-{[tert-butyl(dimethyl)silyl]oxy}-1-methylethyl]-7H-pyrrolo[2,3-d]pyrimidin-5-yl}methanone (Preparation 37) and 3-trifluoromethylphenylacetic acid with DIPEA as base.

$^1$H NMR (400 MHz, DMSO) δ: −0.24 (s, 3H), −0.18 (s, 3H), 0.56 (s, 9H), 1.52 (d, 3H), 3.86 (m, 3H), 3.94 (m, 1H), 5.06 (m, 1H), 7.58 (t, 1H), 7.63 (t, 2H), 7.72 (s, 1H), 8.45 (s, 1H), 8.50 (s, 1H), 8.67 (d, 1H), 8.93 (d, 1H), 8.98 (s, 1H), 9.45 (s, 1H), 10.73 (s, 1H).

LCMS (System 9): R$_t$=3.89 min; m/z 598 [M+H]$^+$.

Preparation 106:
5-[(Diphenylmethylene)amino]nicotinaldehyde

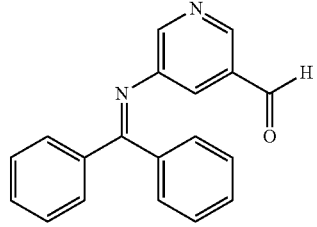 [SMILES: O=Cc1cncc(N=C(c2ccccc2)c2ccccc2)c1]

To a stirred solution of 5-[(diphenylmethylene)amino]-N-methoxy-N-methylnicotinamide (Preparation 23, 7.50 g, 0.021 mol) in THF (150 mL) at −70° C. was added diisopropylaluminium hydride (42 mL, 0.042 mol, 1.0 M in THF) and the resulting mixture stirred at −70° C. for 2 hours. Water (20 mL) and ethyl acetate (100 mL) were added. The organic phase was separated, concentrated under reduced pressure and purified by silica gel column chromatography eluting with EtOAc: petroleum ether 1:10 to afford the title compound as a brown solid in 65% yield, 4 g.

The title compound can also be prepared according to the following process:

A mixture of 5-bromonicotinaldehyde (2790 mg, 15.0 mmol), diphenylmethanimine (3.01 mL, 18 mmol), Pd$_2$(dba)$_3$ (412 mg, 0.45 mmol), di-tert-butyl(2',4',6'-triisopropyl-[1,1'-biphenyl]-2-yl)phosphine (510 mg, 1.2 mmol) and K$_3$PO$_4$ (7960 mg, 37.5 mmol) in DME (30.0 mL) was stirred at 50° C. for 16 hours. After cooling to room temperature, the reaction was diluted with DCM (50 mL) and the mixture filtered through a pad of arbocel. The filter cake was washed with DCM (50 mL) and the filtrate concentrated under reduced pressure. The crude material was recrystallized from ethyl acetate/heptane to give the desired compound as a solid in 78% yield, 3341 mg.

1H NMR (400 MHz, DMSO-d$_6$) δ: 7.18-7.26 (m, 2H), 7.30-7.39 (m, 3H), 7.47-7.54 (m, 2H), 7.55-7.62 (m, 2H), 7.68-7.75 (m, 2H), 8.25 (d, 1H), 8.63 (d, 1H), 10.00 (s, 1H).

Preparation 107: 2,2,3,3,9,9,10,10-octamethyl-4,8-dioxa-3,9-disilaundecan-6-ol

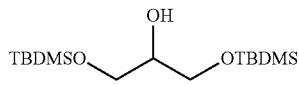 [SMILES: CC(C)(C)[Si](C)(C)OCC(O)CO[Si](C)(C)C(C)(C)C]

To a stirred solution of glycerol (4.01 mL, 55 mmol) and imidazole (18.7 g, 275 mmol) in DMF (150 mL) at 0° C. was added tert-butyldimethylsilyl chloride (17.2 g, 113 mmol) in DMF (33 mL). The reaction mixture was allowed to warm to room temperature and stirred for 16 hours. Water (500 mL) was added to the reaction mixture and the resulting mixture extracted with heptane (500 mL×3). The combined organic layers were washed with water (300 mL), dried over MgSO$_4$ and concentrated under reduced pressure. The crude material was purified by silica gel column chromatography with a gradient elutant of heptane:EtOAc 100:0 to 80:20 to afford the title compound as a colorless oil in 68% yield, 11.9 g.

1H NMR (400 MHz, DMSO-d$_6$) δ: 0.03 (s, 12H), 0.86 (s, 18H), 3.40-3.59 (m, 5H), 4.58 (d, 1H).

Preparation 108: 2,2,3,3,9,9,10,10-octamethyl-4,8-dioxa-3,9-disilaundecan-6-yl trifluoromethanesulfonate

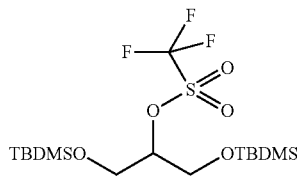 [SMILES: CC(C)(C)[Si](C)(C)OCC(CO[Si](C)(C)C(C)(C)C)OS(=O)(=O)C(F)(F)F]

To a stirred solution of 2,2,3,3,9,9,10,10-octamethyl-4,8-dioxa-3,9-disilaundecan-6-ol (Preparation 107, 6410 mg, 20 mmol) and pyridine (2.42 mL, 30 mmol) in DCM (40 mL) at −50° C. was added trifluoromethanesulfonic anhydride (5.05 mL, 30 mmol) and the reaction stirred at −30° C. for 2 hours. Aqueous 1 N HCl (40 mL) was added to the reaction and the mixture was extracted with DCM (40 mL×3). The combined organic layers were concentrated under reduced pressure to obtain a colourless oil which was used in the next step (Preparation 196) without further purification.

Preparation 109: 4-Chloro-[7-methyl-7H-pyrrolo[2,3-d]pyrimidin-5-yl]{5-[(diphenylmethylene)amino]pyridin-3-yl}methanone

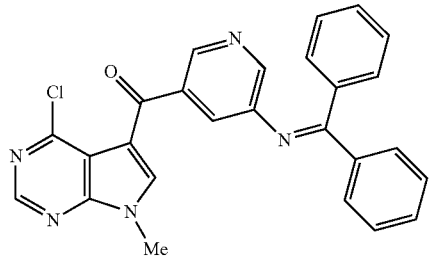 [SMILES: Cn1cc(C(=O)c2cncc(N=C(c3ccccc3)c3ccccc3)c2)c2c(Cl)ncnc21]

The title compound was prepared according to the method described for Preparation 28 followed by Preparation 30 using 4-chloro-5-iodo-7-methyl-7H-pyrrolo[2,3-d]pyrimidine (Preparation 226) and 5-[(diphenylmethylene)amino]nicotinaldehyde (Preparation 106) to afford the title compound as a yellow solid (11.0 g, 48%).

$^1$H NMR (400 MHz, CDCl$_3$) δ: 3.87 (s, 3H), 7.06 (m, 2H), 7.28 (m, 2H), 7.37 (m, 2H), 7.45 (m, 3H), 7.70 (m, 3H), 8.15 (d, 1H), 8.49 (d, 1H), 8.69 (s, 1H).

Preparation 110: (5-Aminopyridin-3-yl)(7-methyl-7H-pyrrolo[2,3-d]pyrimidin-5-yl)methanone

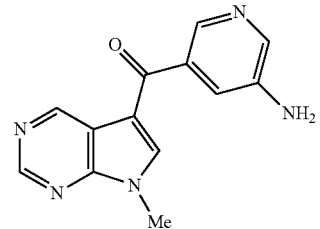 [SMILES: Cn1cc(C(=O)c2cncc(N)c2)c2cncnc21]

Citric acid (2 M, 200 mL) was added to 4-chloro-[7-methyl-7H-pyrrolo[2,3-d]pyrimidin-5-yl]{5-[(diphenylmethylene)amino]pyridin-3-yl}methanone (Preparation 109, 30 g, 0.066 mol) in THF (200 mL) and the mixture was stirred at room temperature for 30 minutes. Ether (200 mL) was added and the phases were separated. The aqueous layer was neutralised with aqueous sodium carbonate then the solid was collected by filtration and dried under vacuum to give (5-aminopyridin-3-yl)(4-chloro-7-methyl-7H-pyrrolo[2,3-d]pyrimidin-5-yl)methanone as a brown solid, 18 g, 95%

Methanethiol sodium salt (15.5 g, 0.22 mol) was added to 5-aminopyridin-3-yl)(4-chloro-7-methyl-7H-pyrrolo[2,3-d]pyrimidin-5-yl)methanone (21 g, 0.073 mol) in methanol (300 mL) and the mixture was stirred at room temperature for 7 hours. The reaction mixture was poured into ice-water (200 mL) and the precipitate was filtered. The filter cake was washed with water (100 mL) then acetone (20 mL) to afford the (5-aminopyridin-3-yl)[7-methyl-4-(methylthio)-7H-pyrrolo[2,3-d]pyrimidin-5-yl]methanone as a brown solid, 15 g, 69%

Raney nickel (10 g) was added to (5-aminopyridin-3-yl)[7-methyl-4-(methylthio)-7H-pyrrolo[2,3-d]pyrimidin-5-yl]

methanone (1.5 g, 5.0 mmol) and conc ammonia (150 mL) in 1,4 dioxane (150 mL). The mixture was refluxed for 6 hours then filtered. The filtrate was evaporated in vacuo and purified by prep HPLC (method 4) to afford the title compound as a brown solid in 100% yield, 1.9 g.

$^1$H NMR (400 MHz, DMSO-D6) δ: 3.88 (s, 3H), 5.63 (s, 2H), 7.27 (m, 1H), 8.14-8.18 (m, 2H), 8.40 (s, 1H), 8.97 (s, 1H), 9.42 (s, 1H).

Preparation 111: 2,2,3,3,6,9,9,10,10-Nonamethyl-4, 8-dioxa-3,9-disilaundecan-6-amine

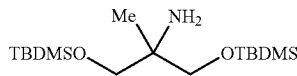

The title compound was prepared according to the method described for Preparation 44 using 2-amino-2-methyl-1,3-propanediol to afford the title compound as a colourless oil in 100% yield, 23.0 g.

$^1$H NMR (400 MHz, CDCl$_3$) δ: 0.05 (s, 12H), 0.87-0.99 (m, 21H), 3.36-3.42 (m, 4H).

Preparation 112: 7-[2-{[tert-Butyl(dimethyl)silyl] oxy}-1-({[tert-butyl(dimethyl)silyl]oxy}methyl)-1-methylethyl]-4-chloro-7H-pyrrolo[2,3-d]pyrimidine

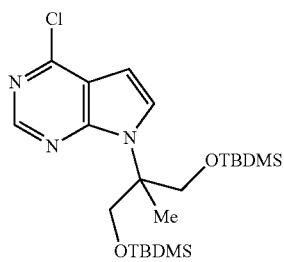 [SMILES: CC(CO[Si](C)(C)C(C)(C)C)(CO[Si](C)(C)C(C)(C)C)n1ccc2c(Cl)ncnc21]

The title compound was prepared according to the method described for Preparation 1 using 2,2,3,3,6,9,9,10,10-nonamethyl-4,8-dioxa-3,9-disilaundecan-6-amine (Preparation 111) to afford the title compound as a colourless gum in 75% yield, 8.91 g.

$^1$H NMR (400 MHz, CDCl$_3$) δ: 0.09-0.11 (m, 12H), 0.78-0.79 (m, 18H), 1.74 (s, 3H), 4.06-4.09 (m, 2H), 4.29-4.31 (m, 2H), 6.52 (m, 1H), 7.44-7.45 (m, 1H), 8.56 (m, 1H).

Preparation 113: 7-[2-{[tert-Butyl(dimethyl)silyl] oxy}-1-({[tert-butyl(dimethyl)silyl]oxy}methyl)-1-methylethyl]-7H-pyrrolo[2,3-d]pyrimidine

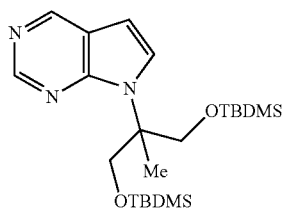 [SMILES: CC(CO[Si](C)(C)C(C)(C)C)(CO[Si](C)(C)C(C)(C)C)n1ccc2cncnc21]

The title compound was prepared according to the method described for Preparation 8 using 7-[2-{[tert-butyl(dimethyl) silyl]oxy}-1-({[tert-butyl(dimethyl)silyl]oxy}methyl)-1-methylethyl]-4-chloro-7H-pyrrolo[2,3-d]pyrimidine (Preparation 112) to afford the title compound as a yellow oil in 99% yield, 8.14 g.

$^1$H NMR (400 MHz, CDCl$_3$) δ: −0.13 (s, 6H), −0.10 (s, 6H), 0.78 (s, 18H), 1.75 (s, 3H), 4.11 (d, 2H), 4.33 (d, 2H), 6.45 (d, 1H), 7.41 (d, 1H), 8.78 (s, 1H), 8.90 (s, 1H).

Preparation 114: 7-[2-{[tert-Butyl(dimethyl)silyl] oxy}-1-({[tert-butyl(dimethyl)silyl]oxy}methyl)-1-methylethyl]-5-iodo-7H-pyrrolo[2,3-d]pyrimidine

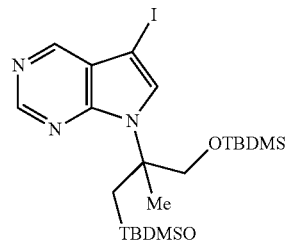

The title compound was prepared according to the method described for Preparation 14 using 7-[2-{[tert-butyl(dimethyl)silyl]oxy}-1-({[tert-butyl(dimethyl)silyl] oxy}methyl)-1-methylethyl]-7H-pyrrolo[2,3-d]pyrimidine (Preparation 113) to afford the title compound as a yellow oil in 88% yield, 7.98 g.

$^1$H NMR (400 MHz, CDCl$_3$) δ: −0.10 (s, 12H), 0.79 (s, 18H), 1.75 (s, 3H), 4.07 (d, 2H), 4.27 (d, 2H), 7.49 (s, 1H), 8.70 (s, 1H), 8.82 (s, 1H).

Preparation 115: {7-[2-{[tert-Butyl(dimethyl)silyl] oxy}-1-({[tert-butyl(dimethyl)silyl]oxy}methyl)-1-methylethyl]-7H-pyrrolo[2,3-d]pyrimidin-5-yl}{5-[(diphenylmethylene)amino]pyridin-3-yl}methanone

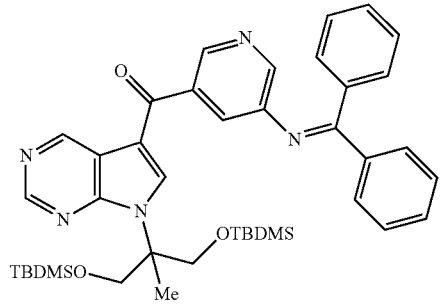 [SMILES: CC(CO[Si](C)(C)C(C)(C)C)(CO[Si](C)(C)C(C)(C)C)n1cc(C(=O)c2cncc(N=C(c3ccccc3)c3ccccc3)c2)c2cncnc21]

The title compound was prepared according to the method described for Preparation 28 using 7-[2-{[tert-butyl(dimethyl)silyl]oxy}-1-({[tert-butyl(dimethyl)silyl] oxy}methyl)-1-methylethyl]-5-iodo-7H-pyrrolo[2,3-d]pyrimidine (Preparation 114) and 5-[(diphenylmethylene) amino]-N-methoxy-N-methylnicotinamide (Preparation 23) to afford the title compound as a yellow foam in 69% yield, 1.76 g.

$^1$H NMR (400 MHz, CDCl$_3$) δ: 0.10-0.12 (m, 12H), 0.73-0.76 (m, 18H), 1.77 (s, 3H), 4.06-4.09 (m, 2H), 4.34-4.36 (m, 2H), 7.11-7.16 (m, 2H), 7.28-7.33 (m, 3H), 7.42-7.47 (m,

2H), 7.50-7.54 (m, 2H), 7.78-7.80 (m, 2H), 7.93 (s, 1H), 8.15-8.16 (m, 1H), 8.56 (m, 1H), 8.94 (s, 1H), 9.58 (s, 1H).

Preparation 116: (5-Aminopyridin-3-yl){7-[2-{[tert-butyl(dimethyl)silyl]oxy}-1-({[tert-butyl(dimethyl)silyl]oxy}methyl)-1-methylethyl]-7H-pyrrolo[2,3-d]pyrimidin-5-yl}methanone

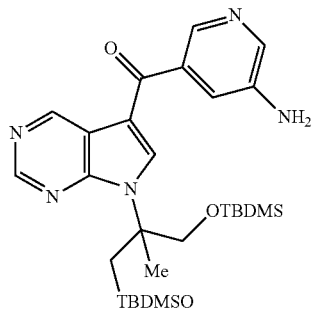 [SMILES: CC(CO[Si](C)(C)C(C)(C)C)(CO[Si](C)(C)C(C)(C)C)n1cc(C(=O)c2cncc(N)c2)c2cncnc21]

The title compound was prepared according to the method described for Preparation 37 using {7-[2-{[tert-butyl(dimethyl)silyl]oxy}-1-({[tert-butyl(dimethyl)silyl]oxy}methyl)-1-methylethyl]-7H-pyrrolo[2,3-d]pyrimidin-5-yl}{5-[(diphenylmethylene)amino]pyridin-3-yl}methanone (Preparation 115) to afford the title compound as a yellow foam in 85% yield, 1.15 g.

LCMS (System 1): R$_t$=4.01 min; m/z 556 [M+H]$^+$.

Preparation 117: 1-Isopropyl-3-trifluoromethyl-1H-pyrazole-4-carboxylic acid ethyl ester

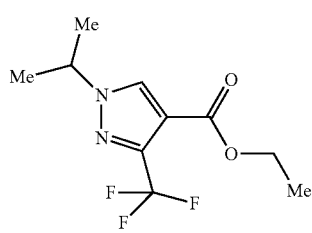 [SMILES: CCOC(=O)c1cn(C(C)C)nc1C(F)(F)F]

To a suspension of 5-trifluoromethyl-1H-pyrazole-4-carboxylic acid ethyl ester (13 g, 62.5 mmol) and cesium carbonate (61.1 g, 187.5 mmol) in DMF (70 mL) was added 2-iodo-propane (6.86 mL, 68.75 mmol) and the resulting mixture allowed to stir at room temperature for 16 hours. The crude reaction mixture was poured onto water (100 mL) and extracted with EtOAc (100 mL×3). The combined organics were washed with water (50 mL×2), brine (50 mL), dried over sodium sulphate, filtered and concentrated under reduced pressure to afford the title compound as an off-white solid in 65% yield, 10.2 g.

$^1$H NMR (400 MHz, CDCl$_3$) δ: 1.33 (t, 3H), 1.53 (d, 6H), 4.30 (q, 2H), 4.50-4.57 (m, 1H), 8.00 (s, 1H); LCMS (system 9): R$_t$=3.55 min; m/z 251 [M+H]$^+$.

Preparation 118: (1-Isopropyl-3-trifluoromethyl-1H-pyrazol-4-yl)-methanol

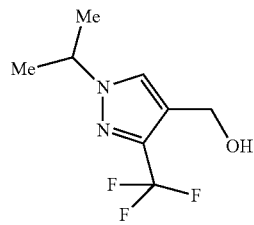 [SMILES: CC(C)n1cc(CO)c(C(F)(F)F)n1]

The title compound was prepared according to the method described for Preparation 183 using 1-isopropyl-3-trifluoromethyl-1H-pyrazole-4-carboxylic acid ethyl ester (Preparation 117) to afford the title compound an off-white solid in 97% yield, 8.3 g.

$^1$H NMR (400 MHz, CDCl$_3$) δ: 1.50 (d, 6H), 1.72 (t, 1H), 4.47-4.54 (m, 1H), 4.65 (d, 2H), 7.50 (s, 1H); LCMS (system 9): R$_t$=2.77 min; m/z 209 [M+H]$^+$.

Preparation 119: (1-Isopropyl-3-trifluoromethyl-1H-pyrazol-4-yl)-acetonitrile

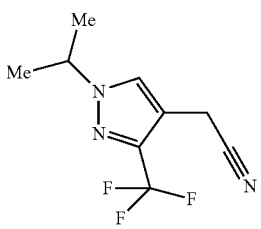 [SMILES: CC(C)n1cc(CC#N)c(C(F)(F)F)n1]

The title compound was prepared according to the method described for Preparation 184 using (1-isopropyl-3-trifluoromethyl-1H-pyrazol-4-yl)-methanol (Preparation 118) to afford the title compound as an off-white solid in 58% yield, 5 g.

$^1$H NMR (400 MHz, DMSO-d$_6$) δ: 1.42 (d, 6H), 3.92 (s, 2H), 4.56-4.63 (m, 1H), 8.06 (s, 1H).

Preparation 120: 2-Chloro-5-iodo-7-isopropyl-7H-pyrrolo[2,3-d]pyrimidine

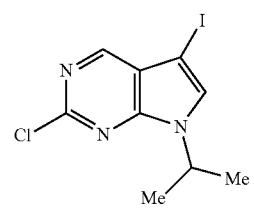 [SMILES: CC(C)n1cc(I)c2cnc(Cl)nc21]

The title compound was prepared according to the method described for Preparation 93 using 2-chloro-5-iodo-7-isopropyl-7H-pyrrolo[2,3-d]pyrimidine (Preparation 40) to afford the title compound as a white solid in 87% yield, 5.5 g.

$^1$H NMR (400 MHz, CDCl$_3$) δ: 1.50 (d, 6H), 5.10 (m, 1H), 7.36 (s, 1H), 8.55 (s, 1H); LCMS (System 10) R$_t$=3.6 min; m/z 322 [M+H]$^+$.

Preparation 121: (5-Bromopyridin-3-yl)(2-chloro-7-isopropyl-7H-pyrrolo[2,3-d]pyrimidin-5-yl)methanone

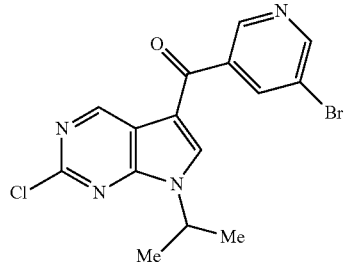 [SMILES: CC(C)n1cc(C(=O)c2cncc(Br)c2)c2cnc(Cl)nc21]

The title compound was prepared according to the method described for Preparation 28 using 2-chloro-5-iodo-7-isopropyl-7H-pyrrolo[2,3-d]pyrimidine (Preparation 120) and 5-bromo-N-methoxy-N-methylnicotinamide to afford the title compound as a yellow solid in 41% yield, 1.2 g.

$^1$H NMR (400 MHz, DMSO-D$_6$) δ: 1.54 (d, 6H), 5.02 (m, 1H), 8.41 (d, 1H), 8.63 (s, 1H), 9.0 (m, 2H), 9.33 (s, 1H).

Preparation 122: (2-Amino-7-isopropyl-7H-pyrrolo[2,3-d]pyrimidin-5-yl)(5-aminopyridin-3-yl)methanone

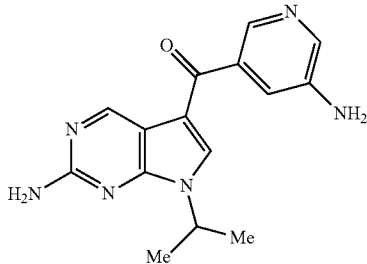 [SMILES: CC(C)n1cc(C(=O)c2cncc(N)c2)c2cnc(N)nc21]

The title compound was prepared according to the method described for Preparation 31 using (5-bromopyridin-3-yl)(2-chloro-7-isopropyl-7H-pyrrolo[2,3-d]pyrimidin-5-yl)methanone (Preparation 121) to afford the title compound as a yellow solid in 58% yield, 500 mg.

$^1$H NMR (400 MHz, DMSO-D$_6$) δ: 1.47 (d, 6H), 4.82-4.86 (m, 1H), 5.60 (s, 2H), 6.58 (s, 2H), 7.23 (s, 1H), 7.88 (s, 1H), 8.12 (m, 2H), 8.91 (s, 1H); LCMS (System 9) R$_t$=0.99 min; m/z 297 [M+H]$^+$.

Preparation 123: (1-Isopropyl-3-trifluoromethyl-1H-pyrazol-4-yl)-acetic acid

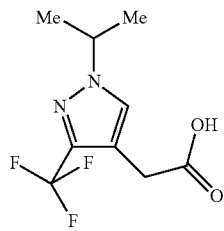 [SMILES: CC(C)n1cc(CC(=O)O)c(C(F)(F)F)n1]

The title compound was prepared according to the method described for Preparation 185 using (1-isopropyl-3-trifluoromethyl-1H-pyrazol-4-yl)-acetonitrile (Preparation 119) to afford the title compound as off-white solid in 82% yield, 4.5 g.

$^1$H NMR (400 MHz, DMSO-d$_6$) δ: 1.41 (d, 6H), 3.50 (s, 2H), 4.52-4.58 (m, 1H), 7.89 (s, 1H), 12.35 (br, 1H); LCMS (system 10): R$_t$=1.56 min; m/z 235 [M−H]$^-$.

Preparation 124: (3-Cyclopropyl-1-methyl-1H-pyrazol-4-yl)-acetonitrile

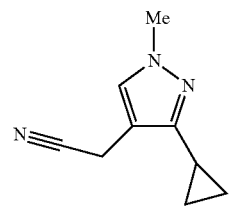 [SMILES: Cn1cc(CC#N)c(C2CC2)n1]

To a suspension of potassium tert-butoxide (8.95 g, 79.9 mmol) in DME (250 mL)-78° C. under nitrogen was added a solution of 1-(isocyanomethyl sulfonyl)-4-methyl benzene (9.36 g, 47.94 mmol) in DME (50 ml). After stirring for 10 minutes, a solution of 3-cyclopropyl-1-methyl-1H-pyrazole-4-carbaldehyde (6 g, 39.95 mmol) in DME (100 mL) was added. The resulting mixture was allowed to stir at −78° C. for 1 hour and then at room temperature for 1 hour. Methanol (50 mL) was added and the resulting mixture refluxed for 1 hour. The reaction mixture was quenched with saturated ammonium chloride solution (200 mL) and extracted with EtOAc (2×200 mL). The combined organic layers were washed with brine (2×50 mL), dried over sodium sulphate, filtered and concentrated under reduced pressure. The crude material was purified by silica gel column chromatography eluting with hexane:EtOAc 90:10 to afford the title compound an off-white solid in 67% yield, 4.3 g.

$^1$H NMR (400 MHz, DMSO-d$_6$) δ: 0.67-0.7 (m, 2H), 0.79-0.83 (m, 2H), 1.75-1.80 (m, 1H), 3.68 (s, 3H), 3.79 (s, 2H), 7.54 (s, 1H); LCMS (system 9): R$_t$=2.53 min; m/z 162 [M+H]$^+$.

Preparation 125: (3-Cyclopropyl-1-methyl-1H-pyrazol-4-yl)-acetic acid

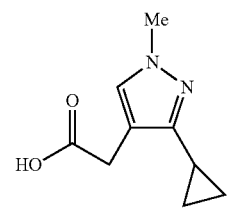 [SMILES: Cn1cc(CC(=O)O)c(C2CC2)n1]

The title compound was prepared according to the method described for Preparation 141 using (3-Cyclopropyl-1-methyl-1H-pyrazol-4-yl)-acetonitrile (Preparation 124) to afford the title compound as solid in 83% yield, 4 g.

$^1$H NMR (400 MHz, DMSO-d$_6$) δ: 0.62-0.66 (m, 2H), 0.73-0.77 (m, 2H), 1.67-1.74 (m, 1H), 3.38 (s, 2H), 3.66 (s, 3H), 7.40 (s, 1H), 12.22 (br, 1H); LCMS (system 9): R$_t$=1.97 min; m/z 181 [M+H]$^+$.

Preparation 126: (3-Cyano-4-fluoro-phenyl)-acetic acid

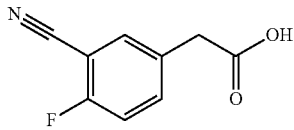 [SMILES: N#Cc1cc(CC(=O)O)ccc1F]

To a solution of (3-bromo-4-fluoro-phenyl)-acetic acid (10 g, 42.9 mmol) in DMF (65 mL) was added copper (I) cyanide (7.7 g, 85.8 mmol) and heated at 130° C. for 24 hrs. The reaction mixture was cooled to room temperature and diluted with ethyl acetate (250 mL). The organic layer was washed with water (5×50 mL), brine (50 mL), dried over sodium filtered and concentrated under reduced pressure. The crude material was re-crystallized from diethyl ether and hexane to afford the title compound as a yellow solid in 65% yield, 5 g.

$^1$H NMR (400 MHz, DMSO-d$_6$) δ: 3.68 (s, 2H), 7.48 (t, 1H), 7.66-7.71 (m, 1H), 7.82 (dd, 1H), 12.53 (br s, 1H); LCMS (system 10): R$_t$=1.39 min; m/z 178 [M−H]$^−$.

Preparation 127: (3-Cyano-4-fluoro-phenyl)-acetic acid ethyl ester

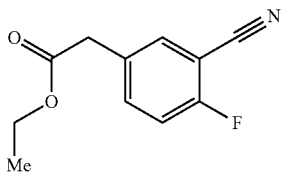 [SMILES: CCOC(=O)Cc1ccc(F)c(C#N)c1]

To a suspension of (3-cyano-4-fluoro-phenyl)-acetic acid (500 mg, 2.79 mmol) (Preparation 126) and potassium carbonate (770 mg, 5.58 mmol) in DMF (5 mL) was added ethyl iodide (0.89 mL, 11.16 mmol) and the reaction mixture stirred at room temperature for 4 hours. The crude reaction mixture was poured onto water (10 mL) and extracted with ethyl acetate (3×15 mL). The combined organic layers were washed with water (5×10 mL), brine (10 mL), dried over sodium sulphate, filtered and concentrated under reduced pressure to afford the title compound as an off-white solid in 87% yield, 500 mg.

$^1$H NMR (400 MHz, CDCl$_3$) δ: 1.26 (t, 3H), 3.61 (s, 2H), 4.16 (q, 2H), 7.17 (t, 1H), 7.49-7.55 (m, 2H).

Preparation 128: (3-Amino-benzo[d]isoxazol-5-yl)-acetic acid ethyl ester

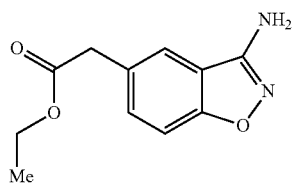 [SMILES: CCOC(=O)Cc1ccc2onc(N)c2c1]

To a solution of (3-cyano-4-fluoro-phenyl)-acetic acid ethyl ester (Preparation 127, 400 mg, 1.93 mmol) and acetohydroxamic acid (362 mg, 4.83 mmol) in DMF (40 mL) and water (15 mL) was added potassium carbonate (1.6 g, 11.58 mmol) and the reaction mixture stirred at room temperature for 12 hours. The reaction mixture was diluted with water (100 mL) and the resulting white precipitate and collected by filtration. The crude material was purified by silica gel column chromatography eluting with a gradient of dichloromethane:methanol 100:0 to 97:3 to afford the title compound as an off-white solid in 59% yield, 250 mg.

LCMS (system 9): R$_t$=2.87 min; m/z 221 [M+H]$^+$.

Preparation 129: (3-Amino-benzo[d]isoxazol-5-yl)-acetic acid

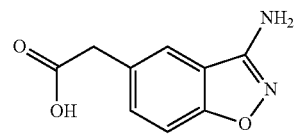 [SMILES: Nc1noc2ccc(CC(=O)O)cc12]

The title compound was prepared according to the method described for Preparation 141 using (3-amino-benzo[d]isoxazol-5-yl)-acetic acid ethyl ester (Preparation 128) to afford the title compound as an off-white solid in 69% yield, 30 mg.

$^1$H NMR (400 MHz, DMSO-d$_6$) δ: 3.65 (s, 2H), 6.36 (br s, 2H), 7.36-7.42 (m, 2H), 7.69 (s, 1H), 12.37 (br s, 1H); LCMS (system 10): R$_t$=1.65 min; m/z 193 [M+H]$^+$.

Preparation 130: Imidazo[1,2-a]pyridin-7-yl-acetic acid ethyl ester

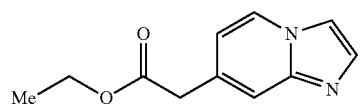 [SMILES: CCOC(=O)Cc1ccn2ccnc2c1]

To a stirred solution of 7-bromo-imidazo[1,2-a]pyridine (600 mg, 3.0 mmol) and diethyl malonate (0.93 mL, 6.1 mmol) in dry dioxane (15 mL) was added cesium carbonate (3 gm, 9.1 mmol). Argon was bubbled through the mixture for 10 minutes and then copper (I) iodide (116 mg, 0.61 mmol) and picolinic acid (150 mg, 1.22 mmol) were added. The resultant mixture was heated in a sealed tube at 130° C. for 24 hours. The reaction mixture was cooled to room temperature, quenched with water (10 mL) and extracted with EtOAc (3×20 mL). The combined organic layers were washed with water (2×10 mL), brine (10 mL), dried over sodium sulphate, filtered and concentrated under reduced pressure. The crude material was purified by silica gel column chromatography eluting with a gradient of dichloromethane:methanol 100:0 to 98:2 to afford the title compound as an off-white gum in 29% yield, 180 mg.

LCMS (system 10): R$_t$=2.61 min; m/z 205 [M+H]$^+$.

Preparation 131: N-(5-{[7-(2-{[tert-butyl(dimethyl)silyl]oxy}-1,1-dimethylethyl)-7H-pyrrolo[2,3-d]pyrimidin-5-yl]carbonyl}pyridin-3-yl)-2-(4-cyanophenyl)acetamide

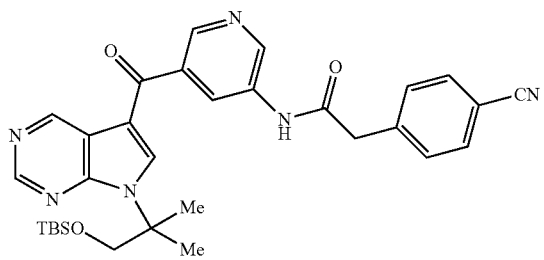 [SMILES: CC(C)(CO[Si](C)(C)C(C)(C)C)n1cc(C(=O)c2cncc(NC(=O)Cc3ccc(C#N)cc3)c2)c2cncnc21]

Prepared according to the method described for Example 1 using (5-aminopyridin-3-yl)[7-(2-{[tert-butyl(dimethyl)silyl]oxy}-1,1-dimethylethyl)-7H-pyrrolo[2,3-d]pyrimidin-5-yl]methanone (Preparation 38), and 4-cyanophenylacetic acid with DIPEA.

$^1$H NMR (400 MHz, DMSO) δ: −0.26 (s, 6H), 0.58 (s, 9H), 1.75 (s, 6H), 3.86 (s, 2H), 4.10 (s, 2H), 7.54 (d, 2H), 7.82 (d, 2H), 8.16 (s, 1H), 8.51 (s, 1H), 8.68 (s, 1H), 8.88 (s, 1H), 8.98 (s, 1H), 9.47 (s, 1H), 10.73 (s, 1H);

LCMS (System 9): $R_t$=3.80 min; m/z 569 [M+H]$^+$.

Preparation 132: Imidazo[1,2-a]pyridin-7-yl-acetic acid

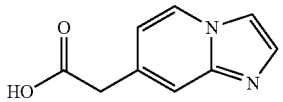 [SMILES: O=C(O)Cc1ccn2ccnc2c1]

To a solution of imidazo[1,2-a]pyridin-7-yl-acetic acid ethyl ester (180 mg, 0.65 mmol) (Preparation 130) in dioxane (4 mL) at 0° C. was added 2 N aqueous sodium hydroxide solution (4 mL). Then reaction mixture was heated at 90° C. for 6 hours. After cooling to 0° C., the mixture was acidified to pH 4 with 2 N aqueous hydrochoric acid and extracted with 20% isopropanol in dichoromethane (8×10 mL). The combined organics were dried over sodium sulfate and concentrated under reduced pressure to afford the title compound as an off-white solid in 70% yield, 80 mg.

LCMS (system 10): $R_t$=1.40 min; m/z 177 [M+H]$^+$.

Preparation 133: Pyrazolo[3,4-b]pyridin-1-yl-acetic acid ethyl ester

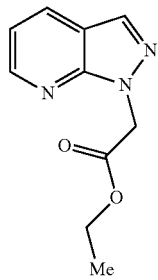 [SMILES: CCOC(=O)Cn1ncc2cccnc21]

To a solution of 7-aza indazole (250 mg, 2.1 mmol) and ethyl bromoacetate (0.47 mL, 4.2 mmol) in DMF (8 mL) was added K$_2$CO$_3$ (1.16 gm, 8.4 mmol) and the resulting mixture stirred at 70° C. for 16 hours. The reaction mixture was cooled to room temperature and diluted with ethyl acetate (20 mL). The organic layer was washed with water (2×5 mL), brine (5 mL), dried over sodium sulphate, filtered and concentrated under reduced pressure. The crude material was purified using silica gel column chromatography eluting with EtOAc:hexane 10:90 to afford the title compound as an off-white solid in 49% yield, 210 mg.

$^1$H NMR (400 MHz, DMSO-d$_6$) δ: 1.19 (t, 3H), 4.14 (q, 2H), 5.35 (s, 2H), 7.25-7.28 (m, 1H), 8.22 (s, 1H), 8.29 (d, 1H), 8.55 (d, 1H).

Preparation 134: Pyrazolo[3,4-b]pyridin-1-yl-acetic acid

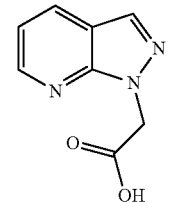

To a stirred solution of pyrazolo[3,4-b]pyridin-1-yl-acetic acid ethyl ester (210 mg, 1.02 mmol) (Preparation 133) in THF (4 mL) and water (1 mL) at 0° C. was added LiOH.H$_2$O (129 mg, 3.06 mmol). The reaction mixture was stirred at room temperature for 2 hours. The pH was of the mixture was adjusted to pH 4 with 2 N aqueous hydrochoric acid and extracted with 20% isopropanol in dichloromethane (8×5 mL). The combined organics were dried over sodium sulfate, filtered and concentrated under reduced pressure to afford the title compound as an off-white solid in 40% yield, 70 mg.

$^1$H NMR (400 MHz, DMSO-d$_6$) δ: 5.22 (s, 2H), 7.25 (dd, 1H), 8.19 (s, 1H), 8.27 (dd, 1H), 8.55 (dd, 1H), 13.15 (brs, 1H); LCMS (system 9): $R_t$=1.93 min; m/z 178 [M+H]$^+$.

Preparation 135: 1-Cyclopropyl-5-trifluoromethyl-1H-pyrazole-4-carboxylic acid ethyl ester

4,4,4-Trifluoro-3-oxo-butyric acid ethyl ester (16 g, 86.4 mmol) was dissolved in acetic anhydride (33.6 g, 329.6 mmol) and triethyl orthoformate (38.4 g, 260 mmol) was added to the mixture. The resultant mixture was refluxed for 18 hours. The mixture was concentrated under reduced pressure to obtain 20 g of 2-[1-Ethoxy-meth-(E)-ylidene]-4,4,4-trifluoro-3-oxo-butyric acid ethyl ester as crude. This was taken in EtOH (50 mL) and added to a suspension of cyclopropyl hydrazine hydrochloride (9.95 g, 91.7 mmol) and DIPEA (28.3 ml, 166.7 mmol) in EtOH (150 mL) at −20° C. The resultant mixture was slowly warmed to room temperature and stirred for 16 hours. The mixture was concentrated under reduced pressure and residue formed was partitioned between EtOAc (50 mL) and water (50 mL). The organic layer was washed with 2N HCl (25 mL), water (25 mL), brine (25 mL), dried (Na$_2$SO$_4$) and evaporated in vacuo. The crude material was purified by column chromatography on silica gel (EtOAc:Hexane 5:95) to afford the title compound as off white sticky solid in 7% yield, 1.4 g.

$^1$H NMR (400 MHz, DMSO-D6) δ: 1.10-1.21 (m, 4H), 1.26 (t, 3H), 3.90 (m, 1H), 4.26 (q, 2H), 7.98 (s, 1H).

Preparation 136: N-(5-{[7-(2-{[tert-butyl(dimethyl) silyl]oxy}-1,1-dimethylethyl)-7H-pyrrolo[2,3-d] pyrimidin-5-yl]carbonyl}pyridin-3-yl)-2-[3-(trifluoromethyl)phenyl]acetamide

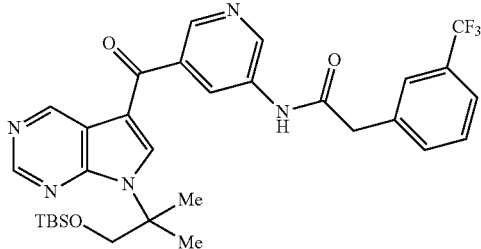 [SMILES: CC(C)(CO[Si](C)(C)C(C)(C)C)n1cc(C(=O)c2cncc(NC(=O)Cc3cccc(C(F)(F)F)c3)c2)c2cncnc21]

Prepared according to the method described for Example 1 using (5-aminopyridin-3-yl)[7-(2-{[tert-butyl(dimethyl)silyl]oxy}-1,1-dimethylethyl)-7H-pyrrolo[2,3-d]pyrimidin-5-yl]methanone (Preparation 38), and 3-trifluoromethylphenylacetic acid with DIPEA.

$^1$H NMR (400 MHz, DMSO) δ: –0.27 (s, 6H), 0.56 (s, 9H), 1.75 (s, 6H), 3.87 (s, 2H), 4.09 (s, 2H), 7.57-7.64

Preparation 137: (1-Cyclopropyl-5-trifluoromethyl-1H-pyrazol-4-yl)-methanol

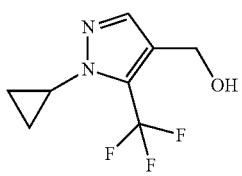 [SMILES: OCc1cnn(C2CC2)c1C(F)(F)F]

A solution of 1-Cyclopropyl-5-trifluoromethyl-1H-pyrazole-4-carboxylic acid ethyl ester (Preparation 135, 1.4 g, 5.64 mmol) in dry toluene (25 mL) was cooled to –78° C. and DIBAL-H (11.8 mL of 1.2 M solution in toluene, 14.1 mmol) was added dropwise to it. The reaction mixture was stirred at –78° C. for 2 hours and poured into 2N HCl (10 mL). This was stirred for a further 4 hours at room temperature followed by extraction with EtOAc (2×25 mL) and the combined organic layers were washed with water (2×10 mL), brine (10 mL) dried (Na$_2$SO$_4$) and evaporated in vacuo to afford the title compound as off white solid in 100% yield, 1.2 g.

$^1$H NMR (400 MHz, DMSO-D6) δ: 1.03-1.17 (m, 4H), 3.68-3.73 (m, 1H), 4.42 (d, 2H), 5.15 (t, 1H), 7.51 (s, 1H); LCMS (system 10): R$_t$=2.68 min; m/z 207 [M+H]$^+$ Preparation 138: N-(5-{[7-(2-{[tert-butyl(dimethyl) silyl]oxy}-1,1-dimethylethyl)-7H-pyrrolo[2,3-d] pyrimidin-5-yl]carbonyl}pyridin-3-yl)-2-(4-isopropyl-1H-1,2,3-triazol-1-yl)acetamide

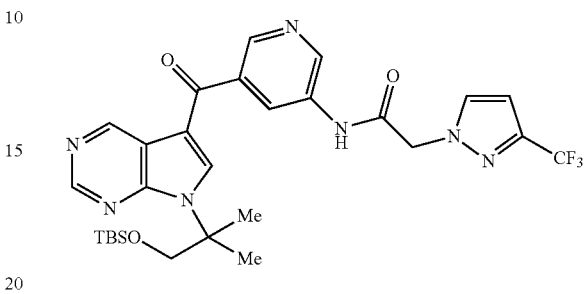

Prepared according to the method described for Example 1 using (5-aminopyridin-3-yl)[7-(2-{[tert-butyl(dimethyl)silyl]oxy}-1,1-dimethylethyl)-7H-pyrrolo[2,3-d]pyrimidin-5-yl]methanone (Preparation 38), and [4-(trifluoromethyl)-1H-pyrazol-1-yl]acetic acid (Preparation 85) with DIPEA as base.

LCMS (System 9): R$_t$=3.67 min; m/z 577 [M+H]$^+$.

Preparation 139: (1-Cyclopropyl-5-trifluoromethyl-1H-pyrazol-4-yl)-acetonitrile

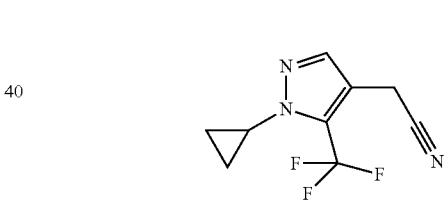

A solution of (1-Cyclopropyl-5-trifluoromethyl-1H-pyrazol-4-yl)-methanol (Preparation 137, 1.2 g, 5.82 mmol) in DCM (15 mL) was cooled to 0° C. and thionyl chloride (0.85 mL, 11.7 mmol) was added. The reaction mixture was stirred at 0° C. for 2 hours and diluted with DCM. The organic layer was washed with water, brine and dried (Na$_2$SO$_4$) and evaporated in vacuo. The crude residue obtained was dissolved in dioxane (25 mL) and water (25 mL) and tetrabutyl ammonium bromide (1.38 g, 4.28 mmol) was added. The reaction mixture was stirred for 10 mins followed by the addition of KCN (1.28 g, 19.82 mmol) and resultant mixture was stirred for a further 16 hours at room temperature. The mixture was diluted with EtOAc (50 mL) and washed with water (1×10 mL), brine (1×10 mL), dried (Na$_2$SO$_4$) and evaporated in vacuo. The crude material was purified by column chromatography on silica gel (Hexane:EtOAc 10:90) to afford the title compound as light yellow solid in 56% yield, 700 mg.

$^1$H NMR (400 MHz, CDCl$_3$) δ: 1.06-1.13 (m, 2H), 1.24-1.29 (m, 2H), 3.61-3.62 (m, 1H), 3.66 (s, 2H), 7.49 (s, 1H).

Preparation 140: N-(5-{[7-(2-{[tert-butyl(dimethyl)silyl]oxy}-1,1-dimethylethyl)-7H-pyrrolo[2,3-d]pyrimidin-5-yl]carbonyl}pyridin-3-yl)-2-quinolin-7-ylacetamide

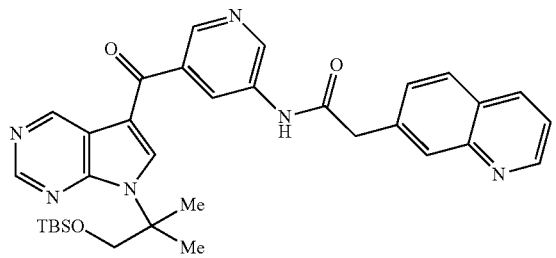 [SMILES: CC(C)(CO[Si](C)(C)C(C)(C)C)n1cc(C(=O)c2cncc(NC(=O)Cc3ccc4cccnc4c3)c2)c2cncnc21]

Prepared according to the method described for Example 1 using (5-aminopyridin-3-yl)[7-(2-{[tert-butyl(dimethyl)silyl]oxy}-1,1-dimethylethyl)-7H-pyrrolo[2,3-d]pyrimidin-5-yl]methanone (Preparation 38), and 2-quinolin-7-ylacetic acid with DIPEA as base.

¹H NMR (400 MHz, DMSO) δ: −0.28 (s, 6H), 0.55 (s, 9H), 1.74 (s, 6H), 3.98 (s, 2H), 4.09 (s, 2H), 7.51 (m, 1H), 7.60 (m, 1H), 7.94 (m, 1H), 8.00 (s, 1H), 8.16 (s, 1H), 8.33 (m, 1H), 8.54 (m, 1H), 8.67 (s, 1H), 8.84 (m, 1H), 8.91 (s, 1H), 8.98 (s, 1H), 9.47 (s, 1H), 10.77 (s, 1H);

LCMS (System 9): $R_t$=3.72 min; m/z 595 [M+H]⁺.

Preparation 141: (1-Cyclopropyl-5-trifluoromethyl-1H-pyrazol-4-yl)-acetic acid

To a solution of (1-Cyclopropyl-5-trifluoromethyl-1H-pyrazol-4-yl)-acetonitrile (Preparation 139, 700 mg, 3.25 mmol) in EtOH (15 mL) was added aqueous 1N NaOH (15 mL). The resulting solution was heated at 60° C. for 16 hours. The mixture was concentrated and the residue was dissolved in water (10 mL) and washed with EtOAc. The pH of aqueous layer was adjusted to 5 using 1N HCl and extracted with 10% IPA in DCM (4×30 mL). The organic layer was dried (Na₂SO₄) and evaporated in vacuo to afford the title compound as a solid in 85% yield, 650 mg.

¹H NMR (400 MHz, DMSO-D6) δ: 1.04-1.07 (m, 2H), 1.11-1.16 (m, 2H), 3.55 (s, 2H), 3.69-3.73 (m, 1H), 7.47 (s, 1H), 12.45 (br, 1H); LCMS (system 10): $R_t$=1.50 min; m/z 233 [M−H]⁺.

Preparation 142 N-[5-({7-[(1R)-1-methyl-2-(tetrahydro-2H-pyran-2-yloxy)ethyl]-7H-pyrrolo[2,3-d]pyrimidin-5-yl}carbonyl)pyridin-3-yl]-2-[3-(trifluoromethyl)phenyl]acetamide

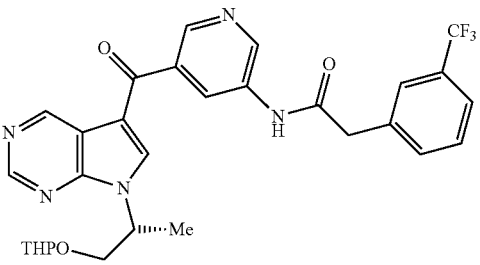

Prepared according to the method described above for Example 1, using (5-aminopyridin-3-yl){7-[(1R)-1-methyl-2-(tetrahydro-2H-pyran-2-yloxy)ethyl]-7H-pyrrolo[2,3-d]pyrimidin-5-yl}methanone (Preparation 36) and 3-trifluoromethylphenylacetic acid with DIPEA as base.

¹H NMR (400 MHz, DMSO-d₆) δ: 1.29-1.42 (m, 5H), 1.54 (d, 3H), 3.50 (m, 1H), 3.71 (m, 1H), 3.86 (s, 2H), 3.93 (m, 1H), 4.05 (m, 1H), 4.44 (s, 1H), 4.58 (s, 1H), 5.17 (m, 1H), 7.56 (m, 1H), 7.63 (m, 2H), 7.72 (s, 1H), 8.47 (m, 2H), 8.70 (s, 1H), 8.96 (m, 2H), 9.45 (s, 1H), 10.72 (s, 1H);

LCMS (System 9): $R_t$=3.56 min; m/z 568 [M+H]⁺.

Preparation 143: 5-Trifluoromethyl-1H-pyrazole-4-carboxylic acid ethyl ester

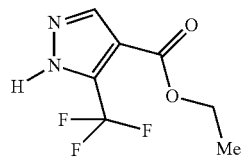 [SMILES: CCOC(=O)c1cn[nH]c1C(F)(F)F]

To a suspension of hydrazine hydrochloride (10 g, 147 mmol) in EtOH (500 mL), DIPEA (45.3 mL, 267 mmol) was added slowly at −20° C. and stirred for 10 mins. Then 2-[1-Ethoxy-meth-(E)-ylidene]-4,4,4-trifluoro-3-oxo-butyric acid ethyl ester (Preparation 135, 32 g, 133.33 mmol) was added to above solution and the resulting mixture was stirred at room temperature for 16 hours. The reaction mixture was concentrated under reduced pressure and residue was partitioned between EtOAc (200 mL) and water (50 mL). The organic layer was washed with water (25 mL), dried (Na₂SO₄) and evaporated in vacuo. The crude material was purified by column chromatography on silica gel (Hexane: EtOAc 90:10) to afford the title compound as off white solid in 43% yield, 13 g.

¹H NMR (400 MHz, DMSO-D6) δ: 1.26 (t, 3H), 4.25 (q, 2H), 8.57 (s, 1H), 14.10 (br s, 1H).

Preparation 144: N-[5-({7-[(1R)-1-methyl-2-(tetrahydro-2H-pyran-2-yloxy)ethyl]-7H-pyrrolo[2,3-d]pyrimidin-5-yl}carbonyl)pyridin-3-yl]-2-(4-isopropyl-1H-1,2,3-triazol-1-yl)acetamide

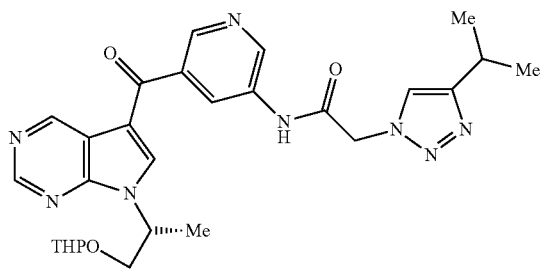

Prepared according to the method described above for Example 1, using (5-aminopyridin-3-yl){7-[(1R)-1-methyl-2-(tetrahydro-2H-pyran-2-yloxy)ethyl]-7H-pyrrolo[2,3-d]pyrimidin-5-yl}methanone (Preparation 36) and (4-isopropyl-1H-1,2,3-triazol-1-yl)acetic acid with DIPEA as base.

¹H NMR (400 MHz, DMSO-$d_6$) δ: 1.22 (6H, d), 1.23-1.30 (m, 5H), 1.54 (d, 3H), 3.4 (1H, m), 3.72 (m, 1H), 3.88 (m, 1H), 3.95 (m, 1H), 4.10 (m, 1H), 4.45 (s, 1H), 4.59 (s, 1H), 5.20 (1H, m), 5.36 (s, 2H), 7.88 (s, 1H), 8.43 (m, 1H), 8.53 (d, 1H), 8.75 (s, 1H), 8.97 (m, 2H), 9.45 (s, 1H), 10.96 (s, 1H); LCMS (System 9): $R_t$=2.86 min; m/z 533 [M+H]⁺.

Preparation 145: 1-Cyclopropyl-3-trifluoromethyl-1H-pyrazole-4-carboxylic acid ethyl ester

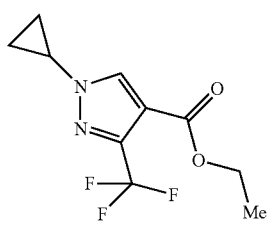 [SMILES: CCOC(=O)c1cn(C2CC2)nc1C(F)(F)F]

Cyclopropyl boronic acid (11 g, 127 mmol), Copper acetate (17.4 g, 95.7 mmol), Pyridine (17.7 g, 223 mmol) and triethylamine (22.4 mL, 160 mmol) were added successively to a solution of 5-Trifluoromethyl-1H-pyrazole-4-carboxylic acid ethyl ester (Preparation 143, 6.63 g, 31.9 mmol) in THF (70 mL) and the resulting mixture was allowed to stir at 60° C. for 36 hours. The reaction mixture was filtered over a celite bed and filtrate was concentrated in vacuo and diluted with EtOAc (200 mL). The organic layer was washed with 1N HCl (1×25 mL), brine (1×25 mL) and dried (Na₂SO₄) and evaporated in vacuo. The crude material was purified by column chromatography on silica gel (Hexane:EtOAc 85:15) to afford the title compound as brown solid in 29% yield, 2.3 g.

¹H NMR (400 MHz, CDCl3) δ: 1.08-1.14 (m, 2H), 1.17-1.21 (m, 2H), 1.33 (t, 3H), 3.62-3.67 (m, 1H), 4.30 (q, 2H), 8.01 (s, 1H); LCMS (system 10): $R_t$=3.39 min; m/z 249 [M+H]⁺.

Preparation 146: (1-Cyclopropyl-3-trifluoromethyl-1H-pyrazol-4-yl)-methanol

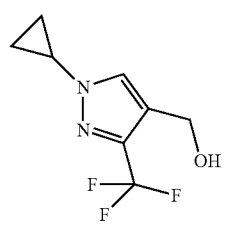 [SMILES: OCc1cn(C2CC2)nc1C(F)(F)F]

A solution of 1-Cyclopropyl-3-trifluoromethyl-1H-pyrazole-4-carboxylic acid ethyl ester (Preparation 145, 3.5 g, 14.11 mmol) in dry toluene (70 mL) was cooled to −78° C. and DIBAL-H (29.4 mL of a 1.2 M solution in toluene, 35.3 mmol) was added dropwise to it. The reaction mixture was stirred at −78° C. for 2 hours and then poured into 2N HCl (25 mL) followed by further stirring for 2 hours at room temperature. The mixture was extracted with EtOAc (2×50 mL) and the combined organic layers were washed with water (2×15 mL), brine (15 mL) and dried (Na₂SO₄) and evaporated in vacuo to afford the title compound as off white solid in 100% yield, 3 g.

¹H NMR (400 MHz, CDCl3) δ: 1.02-1.07 (m, 2H), 1.11-1.16 (m, 2H), 1.68 (t, 1H), 3.57-3.63 (m, 1H), 4.64 (d, 2H), 7.53 (s, 1H); LCMS (system 10): $R_t$=2.57 min; m/z 207 [M+H]⁺.

Preparation 147: (1-Cyclopropyl-3-trifluoromethyl-1H-pyrazol-4-yl)-acetonitrile

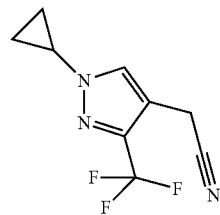 [SMILES: N#CCc1cn(C2CC2)nc1C(F)(F)F]

The title compound was prepared according to the method described for Preparation 139 using (1-Cyclopropyl-3-trifluoromethyl-1H-pyrazol-4-yl)-methanol (Preparation 146) to afford the title compound as yellow solid in 70% yield, 2.2

¹H NMR (400 MHz, DMSO-D6) δ: 0.98-1.03 (m, 2H), 1.06-1.11 (m, 2H), 3.83-3.88 (m, 1H), 3.91 (s, 2H), 8.08 (s, 1H); LCMS (system 10): R$_t$=3.10 min; m/z 216 [M+H]⁺. g.

Preparation 148: (1-Cyclopropyl-3-trifluoromethyl-1H-pyrazol-4-yl)-acetic acid

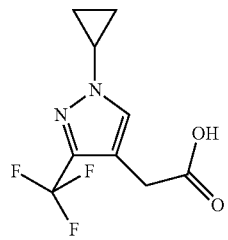

The title compound was prepared according to the method described for Preparation 141 using (1-Cyclopropyl-3-trifluoromethyl-1H-pyrazol-4-yl)-acetonitrile (Preparation 147) to afford the title compound as a solid in 79% yield, 1.9 g.

¹H NMR (400 MHz, DMSO-D6) δ: 0.96-1.07 (m, 4H), 3.49 (s, 2H), 3.76-3.84 (m, 1H), 7.91 (s, 1H), 12.27 (br, 1H); LCMS (system 10): R$_t$=1.41 min; m/z 233 [M−H]⁺.

Preparation 149: (7-isopropyl-7H-pyrrolo[2,3-d]pyrimidin-5-yl)[5-(methylamino)pyridin-3-yl]methanone

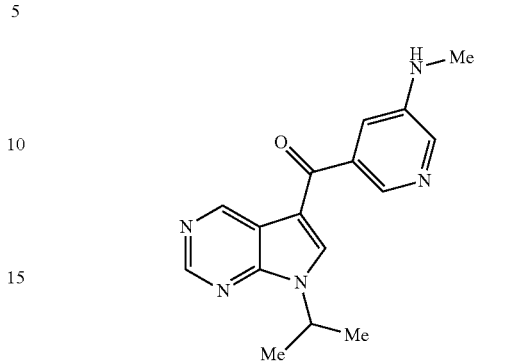

The title compound was prepared according to the method described for Preparation 31 using (5-bromopyridin-3-yl)(7-isopropyl-7H-pyrrolo[2,3-d]pyrimidin-5-yl)methanone (Preparation 94) and methylamine (20 mL) in 13% yield, 78 mg.

LCMS (system 2): R$_t$=0.91 min; m/z 296 [M+H]⁺

The following Preparations were prepared according to the method described above for Example 1, using (5-aminopyridin-3-yl){7-[(1R)-1-methyl-2-(tetrahydro-2H-pyran-2-yloxy)ethyl]-7H-pyrrolo[2,3-d]pyrimidin-5-yl}methanone (Preparation 36) and the corresponding carboxylic acid with DIPEA. All carboxylic acids are commercially available unless otherwise mentioned.

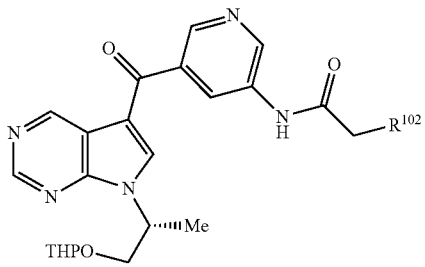

| Preparation | Name | R¹⁰² | Data |
|---|---|---|---|
| 150 | N-[5-({7-[(1R)-1-methyl-2-(tetrahydro-2H-pyran-2-yloxy)ethyl]-7H-pyrrolo[2,3-d]pyrimidin-5-yl}carbonyl)pyridin-3-yl]-2-[1-isopropyl-5-(trifluoromethyl)-1H-pyrazol-4-yl]acetamide | | LCMS (System 9): R$_t$ = 3.24 min; m/z 600 [M + H]⁺ Using (Prep 185). |
| 151 | 2-(4-cyanophenyl)-N-[5-({7-[(1R)-1-methyl-2-(tetrahydro-2H-pyran-2-yloxy)ethyl]-7H-pyrrolo[2,3-d]pyrimidin-5-yl}carbonyl)pyridin-3-yl]acetamide | | LCMS (System 9): R$_t$ = 2.94 min; m/z 525 [M + H]⁺. |
| 152 | N-[5-({7-[(1R)-1-methyl-2-(tetrahydro-2H-pyran-2-yloxy)ethyl]-7H-pyrrolo[2,3-d]pyrimidin-5-yl}carbonyl)pyridin-3-yl]-2-[3-(methylsulfonyl)phenyl]acetamide | | LCMS (System 9): R$_t$ = 2.82 min; m/z 578 [M + H]⁺ |

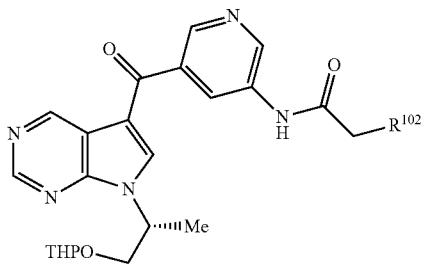

| Preparation | Name | R[102] | Data |
|---|---|---|---|
| 153 | N-[5-({7-[(1R)-1-methyl-2-(tetrahydro-2H-pyran-2-yloxy)ethyl]-7H-pyrrolo[2,3-d]pyrimidin-5-yl}carbonyl)pyridin-3-yl]-2-quinolin-7-ylacetamide | 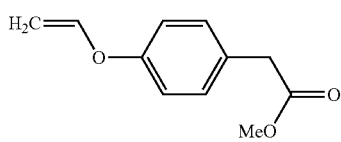 | LCMS (System 9): $R_t$ = 2.97 min; m/z 551 [M + H]+. |

Preparation 154: Ethyl (2-cyclopropyl-1,3-oxazol-4-yl)acetate

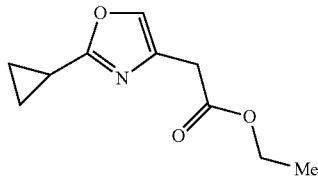 [SMILES: CCOC(=O)Cc1coc(C2CC2)n1]

Ethyl 4-chloroacetoacetate (20.0 g, 122.0 mmol) was added to cyclopropanecarboxamide (3.52 g, 41.5 mmol) in toluene (100 mL) and 1,4-dioxane (100 mL). The mixture was refluxed at 120° C. for 17 hours then evaporated in vacuo. The crude solid was purified by column chromatography on silica gel (80:20 petroleum ether: EtOAc) to afford the title compound as a white solid in 50% yield, 4.00 g.

$^1$H NMR (300 MHz, DMSO-d$_6$) δ: 0.80-1.00 (m, 4H), 1.20 (t, 3H), 2.10 (m, 1H), 3.50 (s, 2H), 4.10 (q, 2H), 7.80 (s, 1H).

Preparation 155: (2-Cyclopropyl-1,3-oxazol-4-yl)acetic acid

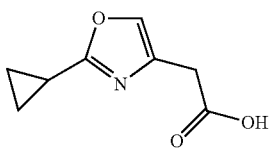 [SMILES: O=C(O)Cc1coc(C2CC2)n1]

Lithium hydroxide monohydrate (7.83 g, 186.7 mmol) was added to ethyl (2-cyclopropyl-1,3-oxazol-4-yl)acetate (Preparation 154, 7.00 g, 35.9 mmol) in THF (200 mL) and water (100 mL). The mixture was stirred at room temperature for 2 hours then the reaction mixture volume was reduced to one third by evaporation in vacuo. The aqueous residue was acidified using aqueous HCl (1.0 M) then extracted with EtOAc (200 mL). The organic phase was evaporated in vacuo and the crude material was triturated with diethyl ether (100 mL) to afford the title compound as a white solid in 66% yield, 4.00 g.

$^1$H NMR (300 MHz, CDCl$_3$) δ: 1.05 (m, 4H), 2.10 (m, 1H), 3.60 (s, 2H), 7.40 (s, 1H), 10.00 (br s, 1H).

Preparation 156: Methyl[2-(vinyloxy)phenyl]acetate

Copper acetate (1.42 g, 7.82 mmol) was added to DCM (6 mL) and stirred for 20 minutes, with a drying tube attached. Trivinylcycloboroxane (1.24 g, 5.16 mmol), cesium carbonate (2.55 g, 7.82 mmol) and methyl 2-hydroxyphenyl acetate (1.30 g, 7.82 mmol) were added and the mixture stirred at room temperature for 17 hours. Saturated aqueous sodium bicarbonate (25 mL) was added and the mixture was extracted with DCM (20 mL). The organic phase was filtered, dried over magnesium sulphate and evaporated in vacuo to afford the title compound as a black oil in 52% yield, 784 mg. This material was used crude in subsequent steps.

$^1$H NMR (400 MHz, CDCl$_3$) δ: 3.67 (s, 2H), 3.39 (s, 3H), 4.40 (dd, 1H), 4.69 (dd, 1H), 6.59 (dd, 1H), 6.97-7.08 (m, 2H), 7.23-7.28 (m, 2H).

Preparation 157: Methyl[4-(vinyloxy)phenyl]acetate

The title compound was prepared according to the method described for Preparation 156 using methyl 4-hydroxyphenyl acetate to afford the title compound as a colourless oil in 70% yield, 914 mg.

¹H NMR (400 MHz, CDCl₃) δ: 3.58 (s, 2H), 3.39 (s, 3H), 4.42 (m, 1H), 4.75 (m, 1H), 6.62 (m, 1H), 6.94-6.97 (m, 2H), 7.21-7.24 (m, 2H).

Preparation 158: Methyl[3-(vinyloxy)phenyl]acetate

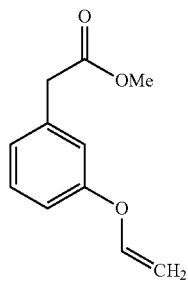

The title compound was prepared according to the method described for Preparation 156 using methyl 3-hydroxyphenyl acetate to afford the title compound as a colourless oil in 56% yield, 835 mg.

¹H NMR (400 MHz, CDCl₃) δ: 3.61 (s, 2H), 3.70 (s, 3H), 4.44 (m, 1H), 4.78 (m, 1H), 6.63 (m, 1H), 6.89-6.94 (m, 2H), 7.00 (m, 1H), 7.27 (m, 1H).

Preparation 159: Methyl[5-(vinyloxy)pyridin-3-yl]acetate

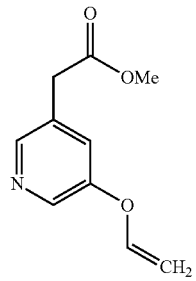

The title compound was prepared according to the method described for Preparation 156 using methyl (5-hydroxypyridin-3-yl)acetate to afford the title compound as a yellow oil in 25% yield, 76 mg.

LCMS (system 2): R$_f$=0.85 min; m/z 194 [M+H]⁺.

Preparation 160: [2-(Cyclopropyloxy)phenyl]acetic acid

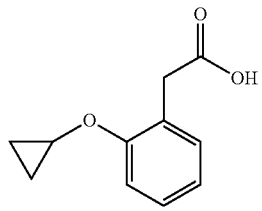 [SMILES: O=C(O)Cc1ccccc1OC1CC1]

Diethyl zinc (2.34 mL, 2.34 mmol, 1M in heptane) was cooled to 0° C. under nitrogen then chloroiodomethane (0.35 mL, 4.68 mmol) in DCE (1 mL) was added drop-wise. The mixture was stirred under nitrogen at 0° C. for 20 minutes then methyl[2-(vinyloxy)phenyl]acetate (Preparation 156, 150 mg, 0.78 mmol) in DCE (1 mL) was added. The reaction mixture was stirred at 00° C. for 30 minutes then stirred at room temperature for 17 hours. Saturated aqueous ammonium chloride (10 mL) was added and the mixture was extracted with DCM (4×8 mL). The combined organic phases were dried over magnesium sulphate and evaporated in vacuo. Sodium hydroxide (3.28 mL, 3.28 mmol, 1 M) was added to the residue in THF (3 mL). The mixture was heated at 80° C. for 17 hours then evaporated in vacuo. Hydrochloric acid (10 mL, 1 M) was added to the residue then extracted with EtOAc (10 mL). The organic phase was evaporated in vacuo to afford the title compound as a yellow oil in 53% yield, 83 mg.

¹H NMR (400 MHz, CDCl₃) δ: 0.65-0.71 (m, 4H), 3.54 (s, 2H), 3.71 (m, 1H), 6.82-6.87 (m, 2H), 7.05-7.23 (m, 2H).

Preparation 161: [4-(Cyclopropyloxy)phenyl]acetic acid

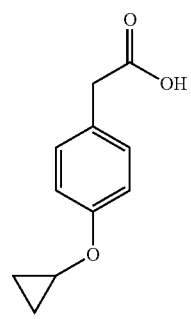 [SMILES: O=C(O)Cc1ccc(OC2CC2)cc1]

Prepared according to the method described for Preparation 160 using methyl[4-(vinyloxy)phenyl]acetate (Preparation 157) to afford the title compound as a colourless oil in 44% yield, 360 mg.

¹H NMR (400 MHz, CDCl₃) δ: 0.65-0.71 (m, 4H), 3.59 (s, 2H), 3.71 (m, 1H), 6.99-7.02 (m, 2H), 7.16-7.20 (m, 2H).

Preparation 162: [3-(Cyclopropyloxy)phenyl]acetic acid

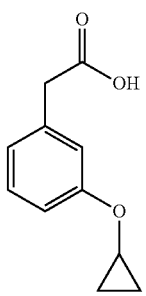 [SMILES: O=C(O)Cc1cccc(OC2CC2)c1]

The title compound was prepared according to the method described for Preparation 160 using methyl[3-(vinyloxy)phenyl]acetate (Preparation 158) to afford the title compound as a colourless oil in 33% yield, 50 mg.

¹H NMR (400 MHz, CDCl₃) δ: 0.74-0.81 (m, 4H), 3.57-3.67 (m, 2H), 3.72 (m, 1H), 6.74-7.03 (m, 3H), 7.22 (m, 1H).

Preparation 163:
[5-(Cyclopropyloxy)pyridin-3-yl]acetic acid

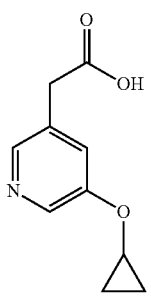 [SMILES: O=C(O)Cc1cncc(OC2CC2)c1]

The title compound was prepared according to the method described for Preparation 160 using methyl[5-(vinyloxy)pyridin-3-yl]acetate (Preparation 159) to afford the title compound as a yellow oil in 38% yield, 28 mg.
LCMS (system 2): R$_f$=0.55 min; m/z 194 [M+H]⁺.

Preparation 164:
[4-Cyano-3-(trifluoromethyl)phenyl]acetic acid

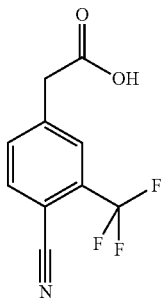 [SMILES: N#Cc1ccc(CC(=O)O)cc1C(F)(F)F]

Lithium diisopropylamide (13.8 mL, 24.8 mmol, 1.8M in THF) was added to 4-methyl-2-(trifluoromethyl)benzonitrile (2.30 g, 12.4 mmol) in THF (20 mL) at −78° C. and stirred for minutes at −78° C. Excess solid carbon dioxide was added then the mixture was stirred at room temperature for 17 hours. Saturated aqueous ammonium chloride (10.5 mL) and EtOAc (20 mL) were added then the aqueous layer was acidified with HCl acid solution (1 M). This was extracted with EtOAc (3×15 mL) and the combined organic phases were dried over sodium sulphate and evaporated in vacuo to afford the title compound as a brown oil in 88% yield, 2.52 g.
¹H NMR (400 MHz, CDCl₃) δ: 3.81 (s, 2H), 7.62 (d, 1H), 7.73 (s, 1H), 7.83 (d, 1H).

Preparation 165: (2-Methylquinolin-7-yl)acetic acid

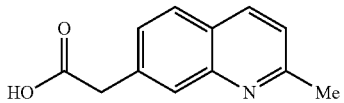 [SMILES: Cc1ccc2ccc(CC(=O)O)cc2n1]

Crotonic aldehyde (33.0 mL, 0.40 mol) was added to 3-aminophenylacetic acid (30.0 g, 0.20 mmol) in concentrated hydrochloric acid (400 mL) and toluene (100 mL) at 110° C. The mixture was heated at 1100 for 90 minutes. The aqueous layer was separated, washed with diethyl ether (350 mL) then neutralised with aqueous ammonia. The aqueous solution was washed with chloroform (3×500 mL) and the organic phase was evaporated in vacuo. The solid residue was refluxed with chloroform (900 mL) and methanol (100 mL) then the solution was decanted and purified by column chromatography on silica gel (gradient of chloroform:MeOH 9:1 to 4:1) to afford a mixture of isomeric acids. This was purified by fractional crystallisation using isopropanol to afford the title compound as a white solid in 12% yield, 4.90 g.
¹H NMR (400 MHz, DMSO-d6) δ: 2.64 (s, 3H), 3.78 (s, 2H), 7.37 (d, 1H), 7.44 (dd, 1H), 7.80 (s, 1H), 7.84 (d, 1H), 8.19 (d, 1H), 12.40 (br s, 1H).

Preparation 166: Ethyl
(3-isopropyl-5-methyl-1H-pyrazol-1-yl)acetate

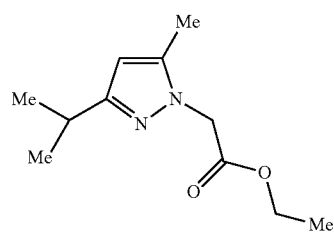 [SMILES: CCOC(=O)Cn1nc(C(C)C)cc1C]

Ethyl bromoacetate (1.00 mL, 9.03 mmol) was added to 5-isopropyl-3-methyl-1H-pyrazole (1.07 g, 8.60 mmol) and potassium carbonate (3.57 g, 25.9 mol) in DMF (10 mL). The mixture was stirred at room temperature for 17 hours then EtOAc (20 mL) and aqueous HCl (20 mL, 1 M) were added. The organic phase was dried over magnesium sulphate then evaporated in vacuo. The residue was purified by column chromatography on silica gel (hexane:EtOAc 4:1) to afford the title compound as a yellow oil in 34% yield, 607 mg.
¹H NMR (400 MHz, CDCl₃) δ: 1.26 (m, 9H), 2.03 (s, 3H), 2.96 (m, 1H), 4.21 (q, 2H), 4.78 (s, 2H), 7.13 (s, 1H).

Preparation 167:
(3-Isopropyl-5-methyl-1H-pyrazol-1-yl)acetic acid

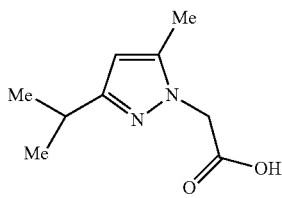 [SMILES: Cc1cc(C(C)C)nn1CC(=O)O]

Lithium hydroxide (342 mg, 8.15 mmol) in water (4 mL) was added to ethyl (3-isopropyl-5-methyl-1H-pyrazol-1-yl)acetate (Preparation 166, 571 mg, 2.72 mmol) in methanol (4 mL) and the mixture was stirred at room temperature for 30 minutes. Aqueous hydrochloric acid (2 M) was added to acidify the mixture then the solution was extracted with EtOAc (10 mL). The organic phase was dried over magnesium sulphate and evaporated in vacuo to afford the title compound as a cream solid in 66% yield, 328 mg. m/z 183 [M+H]+.

Preparation 168: Ethyl (6-chloro-1H-indazol-3-yl)acetate

Concentrated sulphuric acid (0.25 mL) was added to a solution of 2-(6-chloro-1H-indazol-3-yl)acetic acid (2.024 g, 9.60 mmol) in EtOH (10 mL). The mixture was heated at 80° C. for 4 hours then evaporated in vacuo. The residue was partitioned between EtOAc (30 mL) and 5% aqueous sodium bicarbonate (30 mL). The organic phase was dried over sodium sulphate, evaporated in vacuo and purified by column chromatography on silica gel (DCM:MeOH 99:1) to afford the compound 3 as a white solid in 83% yield, 1.90 g.

$^1$H NMR (400 MHz, DMSO-$d_6$) δ: 1.17 (t, 3H), 4.00 (s, 2H), 4.10 (q, 2H), 7.11 (d, 1H), 7.56 (s, 1H), 7.74 (d, 1H), 13.00 (s, 1H).

Preparation 169: Ethyl (6-chloro-1-methyl-1H-indazol-3-yl)acetate

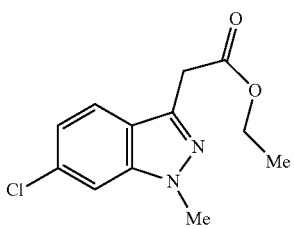 [SMILES: CCOC(=O)Cc1nn(C)c2cc(Cl)ccc12]

Sodium hydride (24 mg, 0.602 mmol, 60% in oil) was added to ethyl (6-chloro-1H-indazol-3-yl)acetate (Preparation 168, 120 mg, 0.502 mmol) in THF (4 mL) at 0° C. and the mixture was stirred for 30 minutes. Then iodomethane (0.09 mL, 1.508 mmol) was added. The mixture was stirred at room temperature for 30 mins then water (4 mL) was added. The mixture was evaporated in vacuo and the aqueous residue was acidified with aqueous HCl (6 M). This was extracted with ethyl acetate (10 mL) and the organic phase was dried over sodium sulphate and evaporated in vacuo to afford the title compound as a white solid in 100% yield, 150 mg.

$^1$H NMR (400 MHz, DMSO-$d_6$) δ: 1.18 (t, 3H), 3.89 (s, 3H), 4.07 (s, 2H), 4.13 (q, 2H), 7.15 (d, 1H), 7.56 (s, 1H), 7.74 (d, 1H);

LCMS (System 9): $R_t$=3.48 min; m/z 253 [M+H]+.

Preparation 170: (6-Chloro-1-methyl-1H-indazol-3-yl)acetic acid

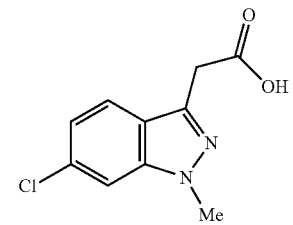 [SMILES: Cn1nc(CC(=O)O)c2ccc(Cl)cc21]

Aqueous potassium hydroxide (5.93 mL, 10%) was added to ethyl (6-chloro-1-methyl-1H-indazol-3-yl)acetate (Preparation 169, 1.78 g, 0.704 mol) in MeOH (30 mL). The mixture was stirred for 1 hour at 25° C. then the methanol was evaporated in vacuo. The aqueous residue was washed with diethyl ether (30 mL) then acidified with aqueous HCl (6 M). The mixture was extracted with ethyl acetate (30 mL) and the organic phase was dried over sodium sulphate, evaporated in vacuo and purified by column chromatography on silica gel (DCM:MeOH 95:5) to afford the title compound as a white solid in 56% yield, 865 mg.

$^1$H NMR (400 MHz, DMSO-d6) δ: 3.79 (s, 2H), 4.14 (s, 3H), 7.12 (d, 1H), 7.73 (d, 1H), 7.83 (s, 1H). 12.51 (s, 1H).

Preparation 171: Ethyl (5-fluoro-1H-indazol-1-yl)acetate

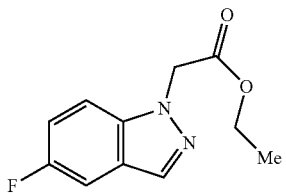 [SMILES: CCOC(=O)Cn1ncc2cc(F)ccc21]

The title compound was prepared according to the method described for Preparation 93 using 5-fluoro-1H-indazole and ethyl bromoacetate to afford the title compound as an off-white solid in 53% yield, 260 mg.

$^1$H NMR (400 MHz, CDCl$_3$) δ: 1.24 (t, 3H), 4.22 (q, 2H), 5.13 (s, 2H), 7.17 (m, 1H), 7.28 (m, 1H), 7.37 (d, 1H), 7.99 (s, 1H); LCMS (System 9): $R_t$=3.14 min; m/z 223 [M+H]+.

Preparation 172: (5-Fluoro-1H-indazol-1-yl)acetic acid

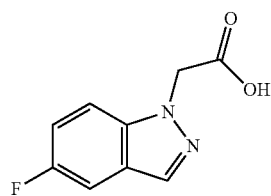 [SMILES: O=C(O)Cn1ncc2cc(F)ccc21]

The title compound was prepared according to the method described for Preparation 155 using ethyl (5-fluoro-1H-indazol-1-yl)acetate (Preparation 171) to afford the title compound as a yellow solid in 62% yield, 140 mg.

$^1$H NMR (400 MHz, DMSO-d$_6$) δ: 5.26 (s, 2H), 7.28 (m, 1H), 7.54 (dd, 1H), 7.68 (dd, 1H), 8.06 (s, 1H), 13.11 (br s, 1H).

LCMS (System 9): R$_t$=1.49 min; m/z 193 [M−H]

Preparation 173: Ethyl (5-fluoro-2H-indazol-2-yl)acetate

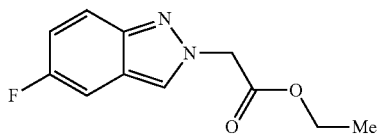 [SMILES: CCOC(=O)Cn1cc2cc(F)ccc2n1]

The title compound was prepared according to the method described for Preparation 93 using 5-fluoro-1H-indazole and ethyl bromoacetate to afford the title compound as an off-white solid in 27% yield, 130 mg.

$^1$H NMR (400 MHz, CDCl$_3$) δ: 1.26 (t, 3H), 4.25 (q, 2H), 5.17 (s, 2H), 7.06-7.11 (m, 1H), 7.21-7.24 (m, 1H), 7.64-7.68 (m, 1H), 7.96 (s, 1H); LCMS (System 9): R$_t$=3.04 min; m/z 223 [M+H]$^+$ Preparation 174: (5-Fluoro-2H-indazol-2-yl)acetic acid

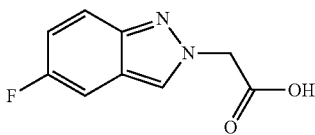 [SMILES: O=C(O)Cn1cc2cc(F)ccc2n1]

The title compound was prepared according to the method described for Preparation 155 using ethyl (5-fluoro-2H-indazol-2-yl)acetate (Preparation 173) to afford the title compound as a yellow solid in 100% yield, 160 mg.

LCMS (System 9): R$_t$=1.49 min; m/z 193 [M−H]$^-$

Preparation 175: Ethyl (7-fluoro-1H-indazol-1-yl)acetate

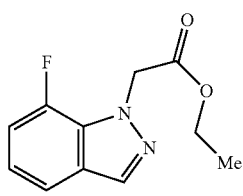 [SMILES: CCOC(=O)Cn1ncc2cccc(F)c21]

The title compound was prepared according to the method described for Preparation 93 using 7-fluoro-1H-indazole and ethyl bromoacetate to afford the title compound as an off-white solid in 41% yield, 200 mg.

$^1$H NMR (400 MHz, CDCl$_3$) δ: 1.29 (t, 3H), 4.22 (q, 2H), 5.28 (s, 2H), 6.98-7.07 (m, 2H), 7.49 (m, 1H), 8.02 (d, 1H).

Preparation 176: (7-Fluoro-1H-indazol-1-yl)acetic acid

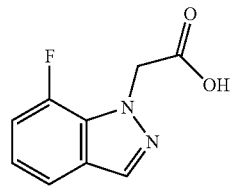 [SMILES: O=C(O)Cn1ncc2cccc(F)c21]

The title compound was prepared according to the method described for Preparation 155 using ethyl (7-fluoro-1H-indazol-1-yl)acetate (Preparation 175) to afford the title compound as a yellow solid in 68% yield, 120 mg.

$^1$H NMR (400 MHz, DMSO-d$_6$) δ: 5.27 (s, 2H), 7.12 (m, 1H), 7.23 (m, 1H), 7.60 (d, 1H), 8.17 (d, 1H), 13.18 (br s, 1H); LCMS (System 9):

R$_t$=1.38 min; m/z 195 [M+H]$^+$

Preparation 177: Ethyl (7-fluoro-2H-indazol-2-yl)acetate

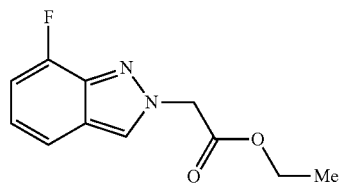 [SMILES: CCOC(=O)Cn1cc2cccc(F)c2n1]

The title compound was prepared according to the method described for Preparation 93 using 7-fluoro-1H-indazole and ethyl bromoacetate to afford the title compound as an off-white solid in 35% yield, 175 mg.

$^1$H NMR (400 MHz, CDCl3) δ: 1.28 (t, 3H), 4.25 (q, 2H), 5.28 (s, 2H), 6.93 (m, 1H), 6.99 (m, 1H), 7.43 (d, 1H), 8.06 (d, 1H).

Preparation 178: (7-Fluoro-2H-indazol-2-yl)acetic acid

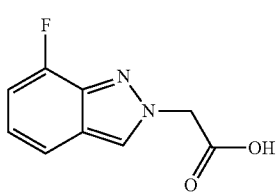 [SMILES: O=C(O)Cn1cc2cccc(F)c2n1]

The title compound was prepared according to the method described for Preparation 155 using ethyl (7-fluoro-2H-indazol-2-yl)acetate (Preparation 177) to afford the title compound as a yellow solid in 75% yield, 110 mg.

¹H NMR (400 MHz, DMSO-d₆) δ: 5.34 (s, 2H), 6.97-7.05 (m, 2H), 7.56 (d, 1H), 8.50 (d, 1H), 13.30 (br s, 1H); LCMS (System 9): $R_t$=1.40 min; m/z 195 [M+H]⁺

Preparation 179: Ethyl 1H-pyrazolo[3,4-b]pyridin-1-ylacetate

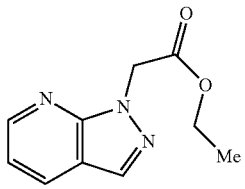 [SMILES: CCOC(=O)Cn1ncc2cccnc21]

The title compound was prepared according to the method described for Preparation 93 using 1H-pyrazolo[3,4-b]pyridine and ethyl bromoacetate to afford the title compound as an off-white solid in 49% yield, 210 mg.

¹H NMR (400 MHz, DMSO-d₆) δ: 1.19 (t, 3H), 4.14 (q, 2H), 5.35 (s, 2H), 7.27 (m, 1H), 8.27 (s, 1H), 8.29 (d, 1H), 8.55 (d, 1H).

Preparation 180: 1H-Pyrazolo[3,4-b]pyridin-1-ylacetic acid

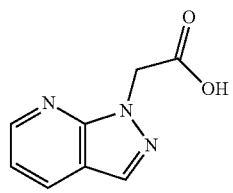 [SMILES: O=C(O)Cn1ncc2cccnc21]

The title compound was prepared according to the method described for Preparation 155 using ethyl 1H-pyrazolo[3,4-b]pyridin-1-ylacetate (see Preparation 179) to afford the title compound as a yellow solid in 40% yield, 70 mg.

¹H NMR (400 MHz, DMSO-d₆) δ: 5.22 (s, 2H), 7.25 (dd, 1H), 8.19 (s, 1H), 8.27 (dd, 1H), 8.55 (dd, 1H), 13.15 (br s, 1H).

Preparation 181: tert-Butyl 1H-indazol-6-ylacetate

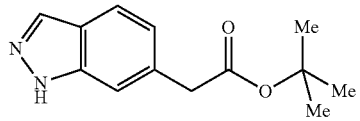 [SMILES: CC(C)(C)OC(=O)Cc1ccc2cn[nH]c2c1]

6-Bromo-1H-indazole (1.3 g, 6.6 mmol) and t-butylacetate (1.33 mL, 9.9 mmol) in toluene (20 mL) were degassed with argon for 15 mins. Then the mixture was cooled to 0° C. and LiHMDS (16.5 mL, 16.5 mmol, 1M in hexane) was added dropwise. Bis(dibenzylideneacetone)palladium (380 mg, 0.66 mmol) and tri-t-butyl phosphine tetrafluoroborate (383 mg, 1.32 mmol) were added and the mixture was stirred at 10° C. for 2 hours. The mixture was quenched with water (10 mL) then extracted with EtOAc (3×25 mL). The combined organic phases were washed with water (2×10 mL), brine (10 mL) and dried over sodium sulphate (Na₂SO₄). The filtrate was evaporated in vacuo and purified by column chromatography on silica gel (hexane:EtOAc 80:20) to afford the title compound as a white solid (65%, 1.00 g).

¹H NMR (400 MHz, CDCl₃) δ: 1.43 (s, 9H), 3.64 (s, 2H), 7.08 (dd, 1H), 7.39 (s, 1H), 7.69 (d, 1H), 8.03 (s, 1H), 10.05 (br s, 1H).

Preparation 182: 1H-Indazol-6-ylacetic acid

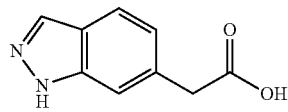 [SMILES: O=C(O)Cc1ccc2cn[nH]c2c1]

Hydrochloric acid (10 mL, 4 M in 1.4 dioxane) was added to tert-butyl 1H-indazol-6-ylacetate (Preparation 181, 1.00 g, 4.3 mmol) in 1,4 dioxane (5 mL) at 0° C. and the mixture was stirred at room temperature for 16 hours. The mixture was evaporated in vacuo and the residue was triturated with dry ether to afford the title compound as a white solid in 100% yield, 800 mg.

¹H NMR (400 MHz, CDCl₃) δ: 3.69 (s, 2H), 7.00 (d, 1H), 7.41 (s, 1H), 7.67 (d, 1H), 8.02 (s, 1H), 12.81 (br s, 1H).

Preparation 183: [1-Isopropyl-5-(trifluoromethyl)-1H-pyrazol-4-yl]methanol

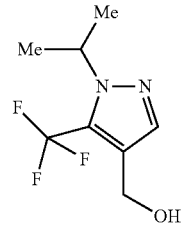 [SMILES: CC(C)n1ncc(CO)c1C(F)(F)F]

Diisobutylaluminium hydride (99 mL, 120 mmol, 1.2 M solution in toluene) was added to ethyl 1-isopropyl-5-(trifluoromethyl)-1H-pyrazole-4-carboxylate (WO 2007071900, 12 g, 48 mmol) in toluene (220 mL) at −78° C. The reaction mixture was stirred at −78° C. for 2 hours then poured into aqueous HCl (100 mL, 2 M). The mixture was stirred for 4 hours at room temperature then extracted with EtOAc (400 mL). The organic phase was washed with water (200 mL), brine (200 mL) and dried over sodium sulphate. The filtrate was evaporated in vacuo to afford the title compound as a colourless oil in 100% yield, 10.5 g.

¹H NMR (400 MHz, CDCl₃) δ: 1.51 (d, 6H), 4.57-4.66 (m, 3H), 7.58 (s, 1H).

¹H NMR (400 MHz, CDCl3) δ: 1.26 (s, 4H), 3.83 (s, 2H), 6.47 (d, 1H), 7.26 (d, 1H), 8.83 (s, 1H), 8.88 (s, 1H); LCMS (system 10): $R_t$=1.67 min; m/z 189.9 [M+H]⁺.

Preparation 184: [1-Isopropyl-5-(trifluoromethyl)-1H-pyrazol-4-yl]acetonitrile

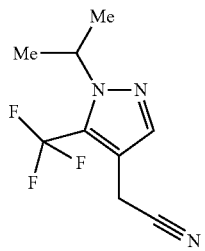 [SMILES: CC(C)n1ncc(CC#N)c1C(F)(F)F]

Thionyl chloride (5.26 mL, 72 mmol) was added to [1-isopropyl-5-(trifluoromethyl)-1H-pyrazol-4-yl]methanol (Preparation 183, 7.5 g, 36 mmol) in DCM (75 mL) at 0° C. and the mixture was stirred for 2 hours. The mixture was diluted with DCM (30 mL) and the organic phase was washed with water (75 mL), brine (75 mL) and dried over sodium sulphate. The filtrate was evaporated in vacuo to afford 4-(chloromethyl)-1-isopropyl-5-(trifluoromethyl)-1H-pyrazole in 86% yield, 7 g.

Tetrabutyl ammonium bromide (7.95 gm, 24.7 mmol) was added to 4-(chloromethyl)-1-isopropyl-5-(trifluoromethyl)-1H-pyrazole (7 g, 31 mmol) in dioxane (75 mL) and water (75 mL) and the mixture was stirred for 10 min. Potassium cyanide (7.42 g, 114 mmol) was added and the mixture was stirred for 16 hours at room temperature. The mixture was diluted with EtOAc (100 mL) then the organic phase was washed with water (100 mL), brine (100 mL) and dried over sodium sulphate. The filtrate was evaporated in vacuo and purified by column chromatography on silica gel (hexane: EtOAc 90:10) to afford the title compound as a white solid in 100% yield, 7.00 g.

$^1$H NMR (400 MHz, DMSO-d$_6$) δ: 1.43 (d, 6H), 3.99 (s, 2H), 4.61 (m, 1H), 7.71 (s, 1H).

Preparation 185: [1-Isopropyl-5-(trifluoromethyl)-1H-pyrazol-4-yl]acetic acid

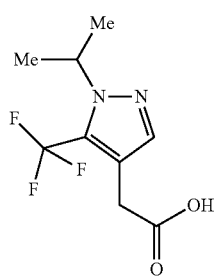

Aqueous sodium hydroxide (150 mL of a 1 M solution) was added to [1-isopropyl-5-(trifluoromethyl)-1H-pyrazol-4-yl]acetonitrile (Preparation 184, 6.2 g, 28.6 mmol) in EtOH (150 mL) and the mixture was heated at 60° C. for 16 hours. The mixture was evaporated in vacuo and the residue was dissolved in water (50 mL) then washed with EtOAc (100 mL). The aqueous phase was acidified to pH 5 using 1N HCl and extracted with 10% IPA in DCM (4×100 mL). The combined organic phases were dried over sodium sulphate and evaporated in vacuo to afford the title compound as a white solid in 75% yield, 5.0 g.

$^1$H NMR (400 MHz, DMSO-d$_6$) δ: 1.42 (d, 6H), 3.56 (s, 2H), 4.58 (m, 1H), 7.57 (s, 1H), 12.28 (br s, 1H).

Preparation 186: (5-Amino-pyridin-3-yl)-[7-(2-methoxy-1,1-dimethyl-ethyl)-7H-pyrrolo[2,3-d]pyrimidin-5-yl]-methanone

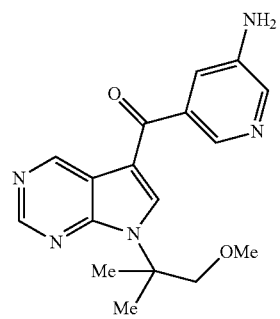 [SMILES: COCC(C)(C)n1cc(C(=O)c2cncc(N)c2)c2cncnc21]

The title compound was prepared according to the method described for Preparation 65 using (5-Bromo-pyridin-3-yl)-[7-(2-methoxy-1,1-dimethyl-ethyl)-7H-pyrrolo[2,3-d]pyrimidin-5-yl]-methanone (Preparation 263) to afford the title compound as off white solid in 41% yield, 650 mg.

$^1$H NMR (400 MHz, DMSO-D6) δ 1.76 (s, 6H), 3.19 (s, 3H), 3.96 (s, 2H), 5.65 (s, 2H), 7.30 (s, 1H), 8.05 (s, 1H), 8.16 (s, 2H), 8.97 (s, 1H), 9.44 (s, 1H); LCMS (system 10): R$_t$=2.56 min; m/z 327 [M+H]$^+$.

Preparation 187: (7-tert-Butyl-7H-pyrrolo[2,3-d]pyrimidin-5-yl)-(5-methylamino-pyridin-3-yl)-methanone

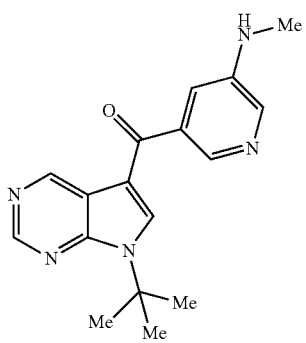 [SMILES: CNc1cncc(C(=O)c2cn(C(C)(C)C)c3ncncc23)c1]

[5-(7-tert-Butyl-7H-pyrrolo[2,3-d]pyrimidine-5-carbonyl)-pyridin-3-yl]-methyl-carbamic acid tert-butyl ester (Example 542) was treated with 4N HCl in Dioxane at room temperature for 2 hours. The solvent was removed in vacuo and the solid obtained was triturated with diethyl ether to afford the title compound as white solid in 100% yield, 76 mg.

¹H NMR (400 MHz, DMSO-D6) δ: 1.80 (s, 9H), 2.84 (s, 3H), 7.27 (br s, 1H), 8.21 (d, 1H), 8.29 (s, 1H), 8.41 (s, 1H), 9.03 (s, 1H), 9.49 (s, 1H); LCMS (system 10): R_t=2.74 min; m/z 310 [M+H]⁺.

Preparation 188: 1,5-naphthyridin-3-ylacetic acid

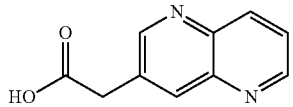 [SMILES: O=C(O)Cc1cnc2cccnc2c1]

A mixture of 3-bromo-1,5-naphthyridine (540 mg, 2.58 mmol), diethylmalonate (0.8 mL, 5.17 mmol) and cesium carbonate (2.53 g, 7.75 mmol) in 1,4-dioxane (6 mL) was degassed with argon for 15 min then picolinic acid (64 mg, 0.517 mmol) and CuI (50 mg, 0.258 mmol) was added. The mixture was heated in a sealed tube at 110° C. for 24 hours then cooled to room temperature, diluted with ethyl acetate (10 mL), washed with water (10 mL) and brine (10 mL). The organic phase was dried over sodium sulphate then evaporated in vacuo and purified by column chromatography on silica gel (hexane:EtOAc 70:30) to afford 450 mg of ethyl 1,5-naphthyridin-3-ylacetate.

Sodium hydroxide (10 mL, 2.0 M) was added to ethyl 1,5-naphthyridin-3-ylacetate in 1,4-dioxane (10 mL) and the mixture was heated at 100° C. for 6 hours. The reaction mixture was cooled to room temperature and acidified to pH 4 using aqueous 2M HCl and then evaporated in vacuo. The residue was azeotroped with toluene (2×15 mL) then dissolved in THF (50 mL) and stirred at 40° C. for 30 min. The mixture was filtered, the filtrate was evaporated in vacuo and the residue was triturated with diethyl ether to afford the title compound as an off white solid, 200 mg.

¹H NMR (400 MHz, DMSO-d₆) δ: 3.94 (s, 2H), 7.76 (m, 1H), 8.31 (s, 1H), 8.42 (d, 1H), 8.91 (d, 1H), 8.99 (dd, 1H), 12.65 (br s, 1H); LCMS (System 10): R_t=1.49 min; m/z 187 [M–H]⁺

Preparation 189: Tert-butyl 1H-pyrazolo[4,3-b]pyridin-1-ylacetate

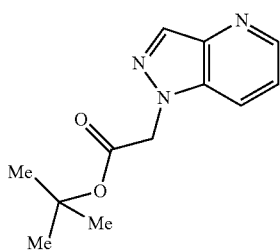 [SMILES: CC(C)(C)OC(=O)Cn1ncc2ncccc21]

Tert-butyl bromoacetate (0.55 mL, 3.69 mmol) was added to 1H-pyrazolo[4,3-b]pyridine (220 mg, 1.85 mmol) and Cs₂CO₃ (723 mg, 2.22 mmol) in anhydrous DMF (7 mL). The mixture was stirred at room temperature for 1 hour. The reaction mixture was diluted with ethyl acetate (50 mL), washed with water (3×30 mL), brine (30 mL), dried over sodium sulphate, evaporated in vacuo and purified by column chromatography on silica gel (hexane:EtOAc 80:20) to afford a colourless gum in 51% yield, 220 mg.

¹H NMR (400 MHz, DMSO-D₆) δ: 1.39 (s, 9H), 5.32 (s, 2H), 7.42 (dd, 1H), 8.14 (d, 1H), 8.32 (s, 1H), 8.55 (d, 1H).

Preparation 190: 1H-Pyrazolo[4,3-b]pyridin-1-ylacetic acid

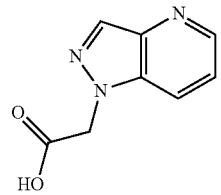 [SMILES: O=C(O)Cn1ncc2ncccc21]

Tert-butyl 1H-pyrazolo[4,3,b]pyridin-1-ylacetate (Preparation 189, 220 mg, 0.944 mmol) was dissolved in HCl (4 mL, 4.0 M in 1,4 dioxane) and stirred under nitrogen at room temperature for 4 hours. The mixture was evaporated in vacuo and the residue was triturated with anhydrous diethyl ether to afford the title compound as an off white solid in 60% yield, 120 mg.

¹H NMR (400 MHz, DMSO-D₆) δ: 5.36 (s, 2H), 7.51 (dd, 1H), 8.30 (d, 1H), 8.36 (s, 1H), 8.62 (d, 1H); LCMS (System 10): R_t=1.39 min; m/z 176 [M–H]⁺.

Preparation 192: 2-(3-formylphenyl)-N-{5-[(7-isopropyl-7H-pyrrolo[2,3-d]pyrimidin-5-yl)carbonyl]pyridin-3-yl}acetamide

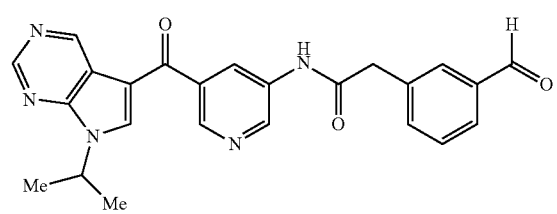 [SMILES: CC(C)n1cc(C(=O)c2cncc(NC(=O)Cc3cccc(C=O)c3)c2)c2cncnc21]

Dess Martin Periodinane (392 mg, 0.93 mmol) was added to a solution of (2-[3-(hydroxymethyl)phenyl]-N-{5-[(7-isopropyl-7H-pyrrolo[2,3-d]pyrimidin-5-yl)carbonyl]pyridin-3-yl}acetamide (Preparation 193, 265 mg, 0.62 mmol) in dichloromethane (15 mL) and the mixture was stirred at room temperature for 18 hours. Water (10 mL) was added and the aqueous layer extracted with a 95:5 mixture of dichloromethane/methanol (3×10 mL). The combined organic layers were dried over magnesium sulfate and concentrated in vacuo. The residue was purified by column chromatography using silica gel (gradient of dichloromethane to dichloromethane/methanol (10:1 to 9:1) to afford the title compound as a brown solid in 80% yield, 211 mg.

LCMS (System 4): R_t=2.11 min; m/z 428 [M+H]⁺.

Preparation 193: 2-[3-(hydroxymethyl)phenyl]-N-{5-[(7-isopropyl-7H-pyrrolo[2,3-d]pyrimidin-5-yl)carbonyl]pyridin-3-yl}acetamide

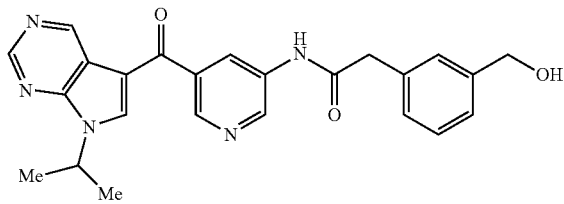 [SMILES: CC(C)n1cc(C(=O)c2cncc(NC(=O)Cc3cccc(CO)c3)c2)c2cncnc21]

A mixture of (5-aminopyridin-3-yl)(7-isopropyl-7H-pyrrolo[2,3-d]pyrimidin-5-yl)methanone (Preparation 95, 250 mg, 0.89 mmol), [4-(hydroxymethyl)phenyl]acetic acid (177 mg, 1.06 mmol) and HATU (505 mg, 1.33 mmol) in pyridine (7 mL) was stirred at 50° C. for 3 hours, then at room temperature for 18 hours. The mixture was concentrated in vacuo and azeotroped with toluene. The residue was purified by column chromatography using silica gel (gradient of dichloromethane to dichloromethane/methanol (10:1 to 9:1) to afford the title compound as a gum. This material was dissolved in a 9:1 mixture of dichloromethane/methanol (1.5 mL) and added dropwise to diethyl ether (100 mL), the resulting precipitate was filtered off and dried in vacuo to afford the title compound as a white solid, 412 mg, which was used crude in subsequent reactions.

LCMS (System 2): $R_t$=1.33 min; m/z 430 [M+H]$^+$.

Preparation 194: (5-((Diphenylmethylene)amino)pyridin-3-yl)(7H-pyrrolo[2,3-d]pyrimidin-5-yl)methanol

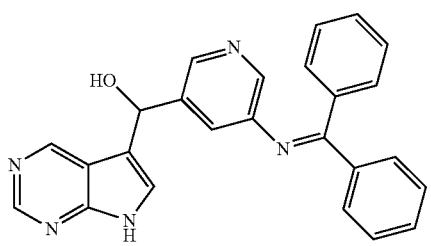 [SMILES: OC(c1cncc(N=C(c2ccccc2)c2ccccc2)c1)c1c[nH]c2ncncc12]

A mixture of 7H-pyrrolo[2,3-d]pyrimidine (Preparation 202, 953 mg, 8.0 mmol), 5-[(diphenylmethylene)amino]nicotinaldehyde (Preparation 106, 3340 mg, 11.7 mmol) and KOH (1350 mg, 24 mmol) in MeOH (16 mL) was stirred for 16 hours at room temperature. The reaction was neutralized with saturated aqueous ammonium chloride solution and the mixture was extracted with EtOAc (3×200 mL). The combined organic layers were dried over sodium sulfate and concentrated in vacuo to obtain a crude residue. The crude material was purified by column chromatography on silica gel (EtOAc:MeOH=100:0 to 80:20,) to give the desired compound as a solid in 62% yield, 2003 mg.

$^1$H NMR (400 MHz, DMSO-d6) δ: 5.88-5.99 (m, 2H), 6.96-6.99 (m, 1H), 7.04-7.14 (m, 3H), 7.16-7.27 (m, 3H), 7.43-7.51 (m, 2H), 7.51-7.58 (m, 1H), 7.64-7.69 (m, 2H), 7.89 (d, 1H), 8.21 (d, 1H), 8.72 (s, 1H), 8.73 (s, 1H), 11.92 (br s, 1H)

Preparation 195: (5-((Diphenylmethylene)amino)pyridin-3-yl)(7H-pyrrolo[2,3-d]pyrimidin-5-yl)methanone

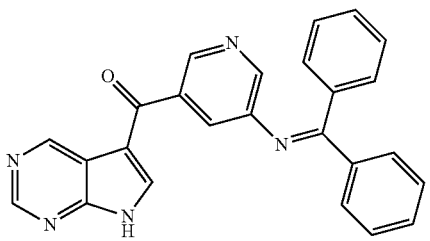 [SMILES: O=C(c1cncc(N=C(c2ccccc2)c2ccccc2)c1)c1c[nH]c2ncncc12]

To a stirred solution of (5-((Diphenylmethylene)amino)pyridin-3-yl)(7H-pyrrolo[2,3-d]pyrimidin-5-yl)methanol (Preparation 194, 1820 mg, 4.5 mmol) in MeCN (45 mL) was added MnO$_2$ (1960 mg, 22.5 mmol) portionwise and the resulting mixture stirred at 50° C. overnight. Another portion of MnO$_2$ (1960 mg, 22.5 mmol) was added to the reaction and the mixture heated to reflux for 5 hr. After cooling to room temperature, the reaction mixture was filtered through a pad of arbocel, the filter cake rinsed with DCM (100 mL) and the resulting filtrate concentrated in vacuo. The resulting material was purified by column chromatography on silica gel (gradient of EtOAc:MeOH 100:0 to 90:10) to give the desired compound as a solid in 61% yield, 1120 mg.

1H NMR (400 MHz, DMSO-d6) δ: 7.24-7.33 (m, 2H), 7.37-7.64 (m, 7H), 7.64-7.78 (m, 3H), 8.28 (d, 1H), 8.53 (d, 1H), 8.94 (s, 1H), 9.41 (s, 1H), 13.09 (br s, 1H)

Preparation 196: (5-aminopyridin-3-yl){7-[2-{[tert-butyl(dimethyl)silyl]oxy}-1-({[tert-butyl(dimethyl)silyl]oxy}methyl)ethyl]-7H-pyrrolo[2,3-d]pyrimidin-5-yl}methanone

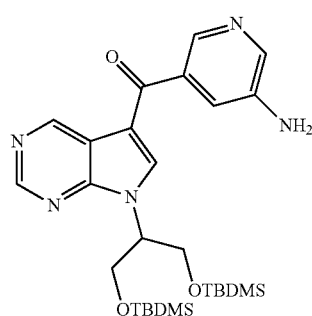 [SMILES: CC(C)(C)[Si](C)(C)OCC(CO[Si](C)(C)C(C)(C)C)n1cc(C(=O)c2cncc(N)c2)c2cncnc21]

A mixture of (5-((Diphenylmethylene)amino)pyridin-3-yl)(7H-pyrrolo[2,3-d]pyrimidin-5-yl)methanone (Preparation 195, 1120 mg, 2.77 mmol) and Cs$_2$CO$_3$ (2710 mg, 8.31 mmol) in DMF (10 mL) was stirred at room temperature for 30 min. A solution of crude 2,2,3,3,9,9,10,10-octamethyl-4,8-dioxa-3,9-disilaundecan-6-yl trifluoromethanesulfonate (Preparation 108) in DMF (3.8 mL) was then added to the reaction and the resulting mixture stirred at room temperature for 16 hours. The reaction was quenched with saturated aqueous ammonium chloride solution (100 mL) and the mixture extracted with EtOAc (100 mL×3). The combined organic layers were washed with water (200 mL), dried over sodium sulfate and concentrated in vacuo. The resulting material was purified by column chromatography on silica gel (gradient of heptane:EtOAc 100:0 to 50:50) to provide (5-((diphenylmethylene)amino)pyridin-3-yl)(7-(2,2,3,3,9,9,10,10-octamethyl-4,8-dioxa-3,9-disilaundecan-6-yl)-7H-pyrrolo[2,3-d]pyrimidin-5-yl)methanone.

The above material was dissolved in THF (20 mL) and aqueous 1N citric acid (20 mL) was added to the solution. The reaction mixture was stirred for 4 hours at room temperature, diluted with water (100 mL) and basified with NaOH to pH 7. The resulting mixture was extracted with EtOAc (3×150 mL), the combined organic fractions were dried over Na₂SO₄ and concentrated in vacuo. The resulting material was purified by column chromatography on silica gel (heptane:EtOAc=40:60 to 0:100) to give the desired compound as a white solid in 49% yield, 739 mg.

1H NMR (400 MHz, DMSO-d6) δ: −0.11 (s, 6H), −0.07 (s, 6H), 0.68 (s, 18H), 3.99-4.16 (m, 4H), 5.01-5.11 (m, 1H), 5.65 (br s, 2H), 7.21-7.26 (m, 1H), 8.13 (d, 1H), 8.17 (d, 1H), 8.38 (s, 1H), 8.98 (s, 1H), 9.44 (s, 1H).

Preparation 197:
3-(3-(trifluoromethyl)-3H-diazirin-3-yl)benzoic acid

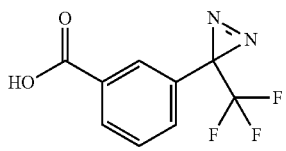 [SMILES: O=C(O)c1cccc(C2(C(F)(F)F)N=N2)c1]

Ethyl 3-(3-(trifluoromethyl)-3H-diazirin-3-yl)benzoate (Preparation 198, 60 mg, 0.23 mmol) was stirred in a 2:1 mixture of THF:water (2 mL). Lithium hydroxide (5 mg. 0.23 mmol) was added and the mixture stirred at 25° C. for 18 hours. The reaction mixture was acidified to pH 1 using 6M aqueous hydrochloric acid and then extracted with ethyl acetate (3×20 mL). The combined organic extracts were dried over magnesium sulfate and evaporated in vacuo to afford the title compound as a solid in 75% yield, 40 mg. This material was used in the next step without further purification.

Preparation 198 Methyl
3-(3-(trifluoromethyl)-3H-diazirin-3-yl)benzoate

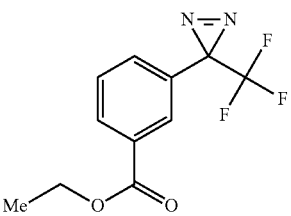 [SMILES: CCOC(=O)c1cccc(C2(C(F)(F)F)N=N2)c1]

Ethyl 3-(3-(trifluoromethyl)diaziridin-3-yl)benzoate (Preparation 199, 226 mg, 0.87 mmol) was stirred in methanol (10 mL) with triethylamine (0.36 mL, 2.61 mmol). Iodine (662 mg, 2.61 mmol) was dissolved in 2 mL methanol and added portion-wise until an orange-brown colour persisted. The reaction mixture was evaporated in vacuo and the residue was diluted with 1M aq. NaOH (30 mL) and then extracted with EtOAc (3×30 mL). The combined organic extracts were dried (MgSO₄) and evaporated in vacuo to afford the title compound as a gum in 27% yield, 60 mg. This material was used in the next step without further purification.

¹H NMR (400 MHz, CDCl₃) δ: 1.40 (t, 3H), 4.38 (q, 2H), 7.46-7.51 (m, 2H), 7.83 (s, 1H), 8.08 (d, 1H).

Preparation 199: Ethyl
3-(3-(trifluoromethyl)diaziridin-3-yl)benzoate

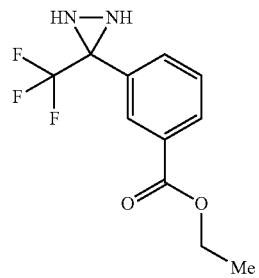 [SMILES: CCOC(=O)c1cccc(C2(C(F)(F)F)NN2)c1]

To a solution of ethyl 3-(2,2,2-trifluoroacetyl)benzoate (500 mg, 2.15 mmol) in ethanol was added pyridine (5 mL) and hydroxylamine hydrochloride (500 mg, 7.2 mmol) and the resulting mixture stirred at 57° C. for 3 hours. The reaction mixture was cooled and passed through an ion exchange column eluting with methanol (30 mL). The methanol solution was evaporated in vacuo to give (E)-ethyl 3-(2,2,2-trifluoro-1-(hydroxyimino)ethyl)benzoate as an oil in 71% yield, 401 mg which was used in the next step without further purification. To a stirred solution of (E)-ethyl 3-(2,2,2-trifluoro-1-(hydroxyimino)ethyl)benzoate (401 mg, 1.54 mmol) in dichloromethane (10 mL) was added DMAP (17 mg, 0.14 mmol) and the mixture cooled to 0° C. 4-methylbenzene-1-sulfonyl chloride (331 mg, 1.74 mmol) was added portion-wise as a solution in dichloromethane (5 mL). The reaction mixture was then left to stand at room temperature for 18 hours. The mixture was diluted with water (10 mL) and the organic layer separated, dried over magnesium sulfate and evaporated in vacuo to afford (E)-ethyl 3-(2,2,2-trifluoro-1-((tosyloxy)imino)ethyl)benzoate as an oil in 78% yield, 500 mg. This material was used in the next step without further purification. A mixture of (E)-ethyl 3-(2,2,2-trifluoro-1-((tosyloxy)imino)ethyl)benzoate (500 mg, 1.2 mmol) in diethyl-ether (5 mL) in a 3-necked flask equipped with an internal thermometer and condenser was cooled to −78° C. Ammonia gas was introduced for 5 min and then stirring continued for 45 min. The reaction mixture was warmed to −33° C. and stirred for 2 hours after which it was allowed to warm to room temperature overnight with stirring.

The mixture was evaporated in vacuo and the crude material purified by column chromatography on silica gel (gradient of dichloromethane:ethyl acetate 100:0 to 90:10) to afford the title compound as a gum in 76% yield, 240 mg.

¹H NMR (400 MHz, CDCl₃) δ: 1.31 (t, 3H), 4.31 (q, 2H), 7.40-7.44 (m, 1H), 7.74 (d, 1H), 8.02 (d, 1H), 8.20 (s, 1H).

Preparation 200: 3-(2,2,2-trifluoroacetyl)benzoic acid

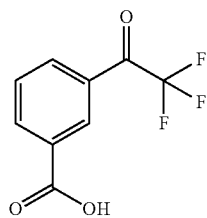 [SMILES: O=C(O)c1cccc(C(=O)C(F)(F)F)c1]

The title compound was prepared according to the method described for Preparation 42 starting from ethyl 3-(2,2,2-trifluoroacetyl)benzoate to afford the title compound as a white solid in 26% yield, 23 mg.

¹H NMR (400 MHz, CDCl₃) δ: 7.71 (t, 1H), 8.32 (d, 1H), 8.45 (d, 1H), 8.80 (s, 1H).

Preparation 201: 5-iodo-7H-pyrrolo[2,3-d]pyrimidine

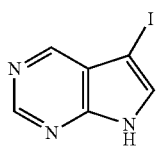

A mixture of 7H-pyrrolo[2,3-d]pyrimidine (Preparation 202, 28.0 g, 235 mmol) and N-iodosuccinimide (55.4 g, 246 mmol) in acetonitrile (470 mL) was stirred at room temperature for 16 hours. The solids were filtered, rinsed with acetonitrile (150 mL) and dried in vacuo. The solid was dissolved in 1.5 L of 1N aqueous sodium hydroxide solution and to it was added 2N aqueous hydrogen chloride solution until ~pH 9. The resulting precipitate was filtered, rinsed with water (300 mL), and dried in vacuo for 16 hours at 70° C., ~10 mbar, to afford the title compound in 81% yield, 46.84 g.

¹H NMR (400 MHz, DMSO-d₆) δ: 7.82 (s, 1H), 8.73 (s, 1H), 8.80 (s, 1H), 12.56 (br s, 1H); LCMS (system 1): R$_t$=0.87 min; m/z 246 [M+H]⁺.

Preparation 202: 7H-pyrrolo[2,3-d]pyrimidine

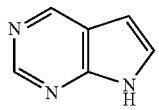

In each of four separate reaction vessels, 4-chloro-7H-pyrrolo[2,3-d]pyrimidine (50.0 g, 260 mmol) was suspended in ethanol (1.4 L) and concentrated ammonium hydroxide solution (140 mL). 10% palladium on carbon (2.5 g) was added to each vessel and the mixture was pressurized to 20 psi hydrogen and stirred at room temperature overnight. Those reactions still containing starting material were charged with another 1 g of 10% palladium on carbon, pressurized to 20 psi hydrogen and stirred until the starting material had been consumed. The reaction mixture was filtered over Arbocel, washed with ethanol, and the filtrate was evaporated to obtain a white solid. The four crude reaction products were combined, suspended in 500 mL water and extracted with ethyl acetate (3×500 mL). The organic layers were combined, dried over magnesium sulfate, filtered and the filtrate was concentrated in vacuo to obtain 122 g of a white solid. The aqueous layer was further extracted with 5% methanol in ethyl acetate (3×500 mL), the organic layers combined, dried over magnesium sulfate, filtered and the filtrate concentrated in vacuo to obtain another 30 g of white solid. The solids were combined to obtain the title compound in 98% yield, 152 g.

¹H NMR (400 MHz, CDCl₃) δ: 6.63 (dd, 1H), 7.43 (dd, 1H), 8.96 (s, 1H), 9.07 (s, 1H), 11.65 (br. s., 1H).

Preparation 203: N-(5-{7-[3-(tert-Butyl-dimethyl-silanyloxymethyl)-oxetan-3-yl]-7H-pyrrolo[2,3-d]pyrimidine-5-carbonyl}-pyridin-3-yl)-2-(4-chloro-phenyl)acetamide

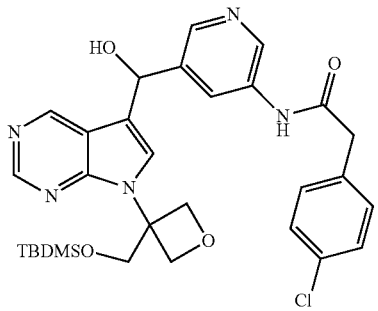 [SMILES: CC(C)(C)[Si](C)(C)OCC1(n2cc(C(O)c3cncc(NC(=O)Cc4ccc(Cl)cc4)c3)c3cncnc32)COC1]

(5-Amino-pyridin-3-yl)-{7-[3-(tert-butyl-dimethyl-silanyloxymethyl)-oxetan-3-yl]-7H-pyrrolo[2,3-d]pyrimidin-5-yl}-methanone (Preparation 216, 30 mg, 0.068 mmol) was dissolved in dry pyridine (2 mL) under nitrogen and to this was added (4-chloro-phenyl)-acetic acid (17 mg, 0.102 mmol), followed by HATU (39 mg, 0.102 mmol). The reaction was heated to 50° C. and stirred overnight. The reaction was cooled to room temperature, diluted with dichloromethane and saturated aqueous sodium bicarbonate was added. The phases were separated and the aqueous layer was extracted with dichloromethane (3×5 mL). The combined organics were concentrated to dryness to afford N-(5-{7-[3-(tert-butyl-dimethyl-silanyloxymethyl)-oxetan-3-yl]-7H-pyrrolo[2,3-d]pyrimidine-5-carbonyl}-pyridin-3-yl)-2-(4-chloro-phenyl)-acetamide as a pale yellow solid 35 mg, 87% yield.

¹H NMR (400 MHz, CDCl₃) δ –0.23 (s, 6H) 0.65 (s, 9H) 3.77 (s, 2H) 4.26 (s, 2H) 4.89 (d, J=7.6 Hz, 2H) 5.27 (d, J=7.8

Hz, 2H) 7.30 (d, J=8.6 Hz, 2H) 7.37-7.44 (m, 2H) 7.72 (s, 1H) 8.49 (s, 1H) 8.70 (d, J=2.3 Hz, 1H) 8.78 (s, 1H) 8.94 (s, 1H) 9.64 (s, 1H).

Preparation 204: N-(5-{7-[3-(tert-Butyl-dimethyl-silanyloxymethyl)-oxetan-3-yl]-7H-pyrrolo[2,3-d]pyrimidine-5-carbonyl}-pyridin-3-yl)-2-(4-trifluoromethyl-phenyl)-acetamide

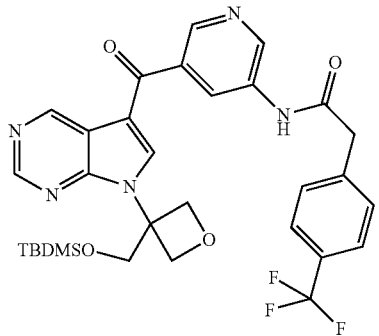 [SMILES: CC(C)(C)[Si](C)(C)OCC1(n2cc(C(=O)c3cncc(NC(=O)Cc4ccc(C(F)(F)F)cc4)c3)c3cncnc32)COC1]

(5-Amino-pyridin-3-yl)-{7-[3-(tert-butyl-dimethyl-silanyloxymethyl)-oxetan-3-yl]-7H-pyrrolo[2,3-d]pyrimidin-5-yl}-methanone (Preparation 216, 30 mg, 0.068 mmol) was dissolved in dry pyridine (2 mL) under nitrogen and to this was added (4-trifluoromethyl-phenyl)-acetic acid (21 mg, 0.102 mmol), followed by HATU (39 mg, 0.102 mmol). The reaction mixture was heated to 50° C. and stirred overnight. The reaction was then cooled to room temperature, diluted with dichloromethane (5 mL) and saturated aqueous sodium bicarbonate was added (5 mL). The phases were separated and the aqueous layer was extracted with dichloromethane (3×5 mL). The combined organics were concentrated to dryness to afford N-(5-{7-[3-(tert-butyl-dimethyl-silanyloxymethyl)-oxetan-3-yl]-7H-pyrrolo[2,3-d]pyrimidine-5-carbonyl}-pyridin-3-yl)-2-(4-trifluoromethyl-phenyl)-acetamide as a pale yellow solid 39 mg, 92% yield.

$^1$H NMR (400 MHz, DMSO-d$_6$) δ−0.29 (s, 6H) 0.58 (s, 9H) 3.84 (s, 2H) 4.16 (s, 2H) 4.77 (d, J=7.4 Hz, 2H) 5.21 (d, J=7.4 Hz, 2H) 7.56 (d, J=7.8 Hz, 2H) 7.68 (d, J=7.8 Hz, 2H) 8.28 (s, 1H) 8.46 (t, J=2.1 Hz, 1H) 8.69 (d, J=2.0 Hz, 1H) 8.91-8.95 (m, 2H) 9.46 (s, 1H) 10.71 (s, 1H).

Preparation 205: 2-Allyl-malonic acid diethyl ester

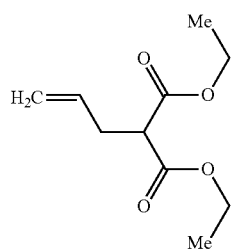

Malonic acid diethyl ester (100 g, 0.625 mol) was added dropwise at 0° C. to a mixture of sodium ethoxide (46.8 g, 0.688 mol) in ethanol (1 L). The reaction mixture was stirred for 4 hours. 3-Bromo-propene (83.2 g, 0.688 moles) was added dropwise to the mixture at 0° C. After addition, the mixture was warmed to reflux and stirred overnight. The mixture was cooled to room temperature, filtered and the solvent was removed in vacuo to afford the title compound in 86% yield, 100 g which was used for the next step without further purification.

Preparation 206: 5-Allyl-6-hydroxy-3H-pyrimidin-4-one

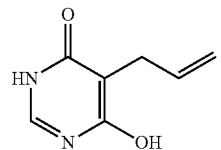

2-Allyl-malonic acid diethyl ester (Preparation 205, 100 g, 0.5 mol) was added dropwise to a mixture of sodium methoxide (27 g, 0.5 mol) in ethanol (1 L) at 0-5° C. and the mixture was stirred at this temperature for 10 min. Formamidine acetate (51.9 g, 0.5 mol) was added and the mixture was stirred at room temperature overnight. The solvent was removed in vacuo, and aqueous hydrochloric acid (36.5%) and water were added to adjust the pH to approximately 3 at 0-20° C. The resulting mixture was filtered to afford the title compound as a colorless solid in 57% yield, 87.12 g.

$^1$H NMR (400 MHz, DMSO-d$_6$) δ: 2.96 (d, 1H), 4.89 (m, 2H), 5.76 (m, 1H), 7.89 (s, 1H).

Preparation 207: 5-Allyl-4,6-dichloro-pyrimidine

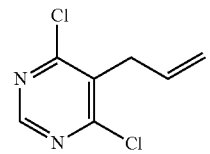

5-Allyl-6-hydroxy-3H-pyrimidin-4-one (Preparation 206, 40 g, 0.263 mol) was added to POCl$_3$ (100 mL) at room temperature. The solution was stirred and warmed to reflux for 8 hours. The mixture was evaporated in vacuo to remove most of the POCl$_3$. The residue was poured slowly onto ice-water, which was extracted with ethyl acetate (500 mL×4), washed with brine (300 mL), dried over sodium sulfate and evaporated in vacuo to afford the title compound as a yellow oil in 59% yield, 31 g.

$^1$H NMR (400 MHz, CDCl$_3$) δ: 3.59 (m, 2H), 5.09 (m, 2H), 5.79 (m, 1H), 8.59 (s, 1H).

Preparation 208: (4,6-Dichloro-pyrimidin-5-yl)-acetaldehyde

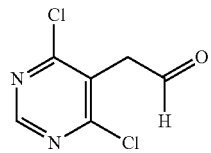 [SMILES: O=CCc1c(Cl)ncnc1Cl]

To a stirred solution of 5-Allyl-4,6-dichloro-pyrimidine (Preparation 207, 30 g, 0.159 mole) in dry dichloromethane (400 mL) was bubbled ozone at −70° C. for 30 min. After excess ozone was purged by nitrogen gas, dimethyl sulfide (10 mL) was added at −5° C., and the reaction was stirred for 2 hours. The mixture was washed with water, brine, dried over sodium sulfate, and evaporated in vacuo. The crude material was purified by trituration from pentane-diethyl ether to afford the title compound as a colorless solid in 84% yield, 10 g.

$^1$H NMR (400 MHz, CDCl$_3$) δ: 4.15 (s, 2H), 8.74 (s, 1H), 9.80 (s, 1H).

Preparation 209: 2-(4-Chloro-pyrrolo[2,3-d]pyrimidin-7-yl)-2-hydroxymethyl-propane-1,3-diol

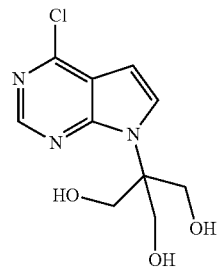 [SMILES: OCC(CO)(CO)n1ccc2c(Cl)ncnc21]

Trisamine (1.27 g, 10.5 mmol) was added to 4,6-Dichloro-pyrimidin-5-yl)-acetaldehyde (Preparation 208, 1.0 g, 5.2 mmol) in ethanol (40 mL) and stirred at reflux temperature for 16 hours. The reaction mixture was evaporated in vacuo and partitioned between dichloromethane and aqueous saturated sodium bicarbonate. The separated aqueous phase was extracted with dichloromethane twice more and the combined organics were washed with saturated brine and evaporated in vacuo to afford the title compound as a pale yellow foam in 74% yield, 1.0 g.

$^1$H NMR (400 MHz, CDCl$_3$) δ ppm 2.97 (br. s, 1H), 3.09-3.27 (m, 2H), 3.51 (d, J=9.18 Hz, 1H), 3.83-4.00 (m, 4H), 4.06 (d, J=11.13 Hz, 1H), 5.43 (dd, J=6.44, 1.76 Hz, 1H), 6.16 (dd, J=10.74, 4.69 Hz, 1H), 8.40 (s, 1H); LCMS (System 2): R$_t$=1.04 min; m/z 258 [M+H]$^+$.

Preparation 210: Toluene-4-sulfonic acid 2-(4-chloro-pyrrolo[2,3-d]pyrimidin-7-yl)-3-hydroxy-2-hydroxymethyl-propyl ester

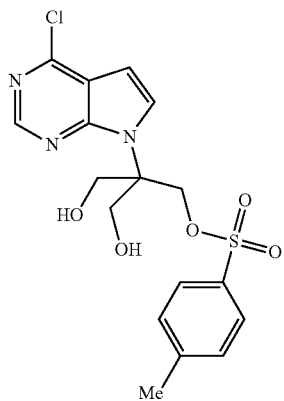 [SMILES: Cc1ccc(S(=O)(=O)OCC(CO)(CO)n2ccc3c(Cl)ncnc32)cc1]

Triethylamine (0.879 mL, 6.31 mmol) and trimethylamine hydrochloride (253 mg, 2.65 mmol) were added to a solution of 2-(4-chloro-pyrrolo[2,3-d]pyrimidin-7-yl)-2-hydroxymethyl-propane-1,3-diol (Preparation 209, 650 mg, 2.52 mmol) in dichloromethane (20 mL) at 00° C. The mixture was treated portion-wise with tosyl chloride (505 mg, 2.65 mmol) and stirred at 00° C. for 16 hours. The reaction mixture was treated with water and stirred for 10 min. The resulting mixture was washed with citric acid, saturated aqueous sodium bicarbonate, and saturated brine, then evaporated in vacuo. The crude product was purified by column chromatography on silica gel (gradient of EtOAc:DCM 0:100 to 30:70) to afford the title compound as a colorless solid in 55% yield, 570 mg.

LCMS (system 2): R$_t$=1.28 min; m/z 412 [M+H]$^+$.

Preparation 211: [3-(4-Chloro-pyrrolo[2,3-d]pyrimidin-7-yl)-oxetan-3-yl]-methanol

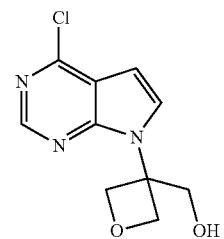 [SMILES: OCC1(n2ccc3c(Cl)ncnc32)COC1]

$^n$Butyllithium (12.2 mL, 30.6 mmol, 2.5 M in hexanes) was added to toluene-4-sulfonic acid 2-(4-chloro-pyrrolo[2,3-d]pyrimidin-7-yl)-3-hydroxy-2-hydroxymethyl-propyl ester (Preparation 210, 5.73 g, 13.9 mmol) in THF (100 mL) at 0° C. and stirred for 5 min. The reaction mixture was then warmed to room temperature and stirred for 16 hours, at which point it was quenched with saturated aqueous ammonium chloride. The resulting mixture was extracted with ethyl acetate (100 mL×3) and the combined organic phases were dried (MgSO$_4$) and concentrated in vacuo. The crude product was triturated with dichloromethane and filtered to afford the title compound in 36% yield, 1.2 g.

$^1$H NMR (400 MHz, MeOH-d$_4$) δ: 4.15 (s, 2H), 4.92 (d, J=7.22 Hz, 2H), 5.22 (d, J=7.03 Hz, 2H), 6.69 (d, J=3.51 Hz, 1H), 7.51 (d, J=3.71 Hz, 1H), 8.51 (s, 1H).

Preparation 212: 7-[3-(tert-Butyl-dimethyl-silanyloxymethyl)-oxetan-3-yl]-4-chloro-7H-pyrrolo[2,3-d]pyrimidine

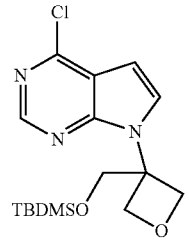 [SMILES: CC(C)(C)[Si](C)(C)OCC1(n2ccc3c(Cl)ncnc32)COC1]

Imidazole (277 mg, 4.07 mmol) was added to [3-(4-Chloro-pyrrolo[2,3-d]pyrimidin-7-yl)-oxetan-3-yl]-methanol (Preparation 211, 650 mg, 2.71 mmol) in dichloromethane (10 mL), and this mixture was treated with a solution of t-butyldimethylsilyl chloride (495 mg, 3.25 mmol) in dichloromethane (5 mL). The resulting mixture was stirred at room temperature for 16 hours, then quenched with Preparation 213: 7-[3-(tert-Butyl-dimethyl-silanyloxymethyl)-oxetan-3-yl]-7H-pyrrolo[2,3-d]pyrimidine

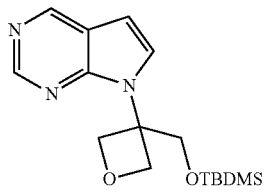 [SMILES: CC(C)(C)[Si](C)(C)OCC1(n2ccc3cncnc32)COC1]

The title compound was prepared according to the method described for Preparation 8 using 7-[3-(tert-Butyl-dimethyl-silanyloxymethyl)-oxetan-3-yl]-4-chloro-7H-pyrrolo[2,3-d]pyrimidine (Preparation 212) to afford the title compound as a brown oil in 82% yield, 650 mg.

$^1$H NMR (400 MHz, CDCl$_3$) δ: −0.24 (s, 6H), 0.76 (s, 9H), 4.24 (s, 2H), 4.91 (d, J=7.03 Hz, 2H), 5.22 (d, J=7.03 Hz, 2H), 6.55 (d, J=3.51 Hz, 1H), 7.08 (d, J=3.71 Hz, 1H), 8.78 (s, 1H), 8.97 (s, 1H); LCMS (system 2): R$_t$=0.90 min; m/z 320 [M+H]$^+$.

Preparation 214: 7-[3-(tert-Butyl-dimethyl-silanyloxymethyl)-oxetan-3-yl]-5-iodo-7H-pyrrolo[2,3-d]pyrimidine

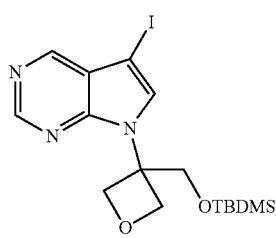 [SMILES: CC(C)(C)[Si](C)(C)OCC1(n2cc(I)c3cncnc32)COC1]

The title compound was prepared according to the method described for Preparation 14 using 7-[3-(tert-Butyl-dimethyl-silanyloxymethyl)-oxetan-3-yl]-7H-pyrrolo[2,3-d]pyrimidine (Preparation 213) and DMF to afford the title compound as a brown solid in 75% yield, 675 mg.

$^1$H NMR (400 MHz, CDCl$_3$) δ: −0.24 (s, 6H), 0.77 (s, 9H), 4.20 (s, 2H), 4.88 (d, J=7.22 Hz, 2H), 5.21 (d, J=7.03 Hz, 2H), 7.17 (s, 1H), 8.77 (s, 1H), 8.81 (s, 1H); LCMS (system 2): R$_t$=1.55 min; m/z 446 [M+H]$^+$.

Preparation 215: (7-(3-(((tert-Butyldimethylsilyl)oxy)methyl)oxetan-3-yl)-7H-pyrrolo[2,3-d]pyrimidin-5-yl)(5-((diphenylmethylene)amino)pyridin-3-yl)methanone

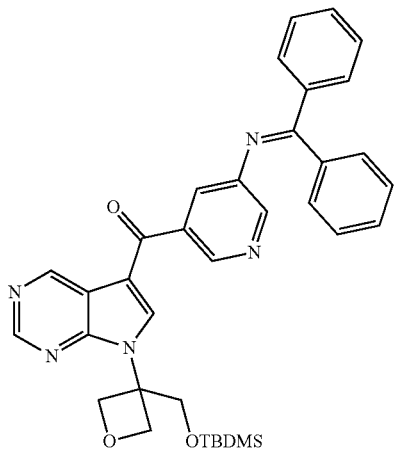 [SMILES: CC(C)(C)[Si](C)(C)OCC1(n2cc(C(=O)c3cncc(N=C(c4ccccc4)c4ccccc4)c3)c3cncnc32)COC1]

The title compound was prepared according to the method described for Preparation 24 using 7-[3-(tert-butyl-dimethyl-silanyloxymethyl)-oxetan-3-yl]-5-iodo-7H-pyrrolo[2,3-d]pyrimidine (Preparation 214) and 5-[(Diphenylmethylene)amino]-N-methoxy-N-methylnicotinamide (Preparation 23) to afford the title compound as a purple solid in 51% yield, 240 mg.

$^1$H NMR (400 MHz, CDCl$_3$) δ: 0.20 (s, 6H), 0.70 (s, 9H), 4.28 (s, 2H), 4.89 (d, J=7.22 Hz, 2H), 5.20 (d, J=7.22 Hz, 2H), 7.11-7.18 (m, 2H), 7.33 (m, 3H), 7.40-7.48 (m, 2H), 7.49-7.57 (m, 3H), 7.79 (d, J=7.42 Hz, 2H), 8.18 (d, J=2.54 Hz, 1H), 8.60 (d, J=1.95 Hz, 1H), 8.93 (s, 1H), 9.60 (s, 1H).

Preparation 216: (5-Amino-pyridin-3-yl)-{7-[3-(tert-butyl-dimethyl-silanyloxymethyl)-oxetan-3-yl]-7H-pyrrolo[2,3-d]pyrimidin-5-yl}-methanone

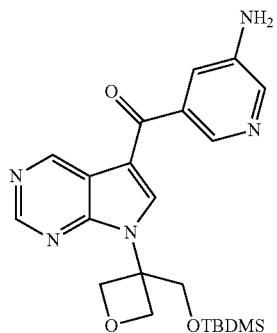 [SMILES: CC(C)(C)[Si](C)(C)OCC1(n2cc(C(=O)c3cncc(N)c3)c3cncnc32)COC1]

The title compound was prepared according to the method described for Preparation 37 using (7-(3-(((tert-butyldimethylsilyl)oxy)methyl)oxetan-3-yl)-7H-pyrrolo[2,3-d]pyrimidin-5-yl)(5-((diphenylmethylene)amino)pyridin-3-yl)methanone (Preparation 215) to afford the title compound as a colourless solid in 76% yield, 132 mg.

¹H NMR (400 MHz, CDCl₃) δ: 0.01 (s, 6H), 0.88 (s, 9H), 4.11 (br. s, 2H), 4.45 (s, 2H), 5.17 (m, 2H), 5.40 (m, 2H), 7.58 (s, 1H), 7.80 (s, 1H), 8.45 (s, 1H), 8.61 (s, 1H), 9.15 (s, 1H), 9.83 (s, 1H).

Preparation 217: 2-(4-chloro-7H-pyrrolo[2,3-d]pyrimidin-7-yl)-2-methylpropane-1,3-diol

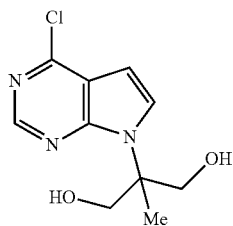 [SMILES: CC(CO)(CO)n1ccc2c(Cl)ncnc21]

The title compound was prepared according to the method described for Preparation 1 using (4,6-dichloropyrimidin-5-yl)acetaldehyde (Preparation 208) and 2-amino-2-methylpropane-1,3-diol to afford the title compound as a yellow liquid in 79% yield, 3.88 g.

¹H NMR (400 MHz, DMSO-d₆) δ: 1.66 (s, 3H), 3.86 (dd, 2H), 4.13 (dd, 2H), 4.92 (t, 2H), 6.58 (d, 1H), 7.73 (d, 1H), 8.59 (s, 1H).

Preparation 218: 4-chloro-7-(3-methyloxetan-3-yl)-7H-pyrrolo[2,3-d]pyrimidine

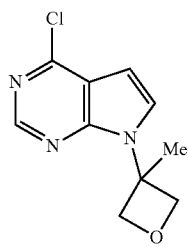 [SMILES: CC1(n2ccc3c(Cl)ncnc32)COC1]

n-BuLi (6.6 mL of a 2.5 M solution in hexane, 16.5 mmol) was added to a solution of 2-(4-chloro-7H-pyrrolo[2,3-d]pyrimidin-7-yl)-2-methylpropane-1,3-diol (Preparation 217, 3.63 g, 15.0 mmol), in THF (80 mL) at −78° C. The reaction mixture was allowed to warm to −50° C. in 2 hours and TsCl (3.15 mg, 16.5 mmol) in THF (20 mL) was added to the reaction. The reaction was allowed to warm to 0° C. in 3 hours and additional n-BuLi (6.6 mL of a 2.5 M solution in hexane solution, 16.5 mmol) was slowly added to the reaction mixture. The mixture was stirred for 1 hour at 0° C. and stirred at 60° C. for 16 hours. After cooling to room temperature, the reaction was quenched by 50 mL of saturated aqueous NH₄Cl solution and 100 mL of water, and the mixture was extracted with EtOAc (3×100 mL). The combined organic layers were dried over MgSO₄ and concentrated in vacuo. The crude residue was purified by column chromatogranhy on silica gel (gradient of EtOAc:heptane 20:80 to 70:30) to give a solid in 55% yield, 1.87 mg.

¹H NMR (400 MHz, DMSO-d₆) δ: 1.79 (s, 3H) 4.72 (d, 2H) 5.15 (d, 2H) 6.69 (d, 1H) 7.78 (d, 1H) 8.59 (s, 1H).

Preparation 219: 7-(3-methyloxetan-3-yl)-7H-pyrrolo[2,3-d]pyrimidine

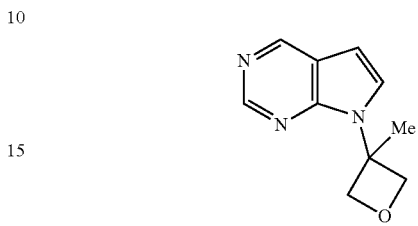

The title compound was prepared according to the method described for Preparation 8 using 4-chloro-7-(3-methyloxetan-3-yl)-7H-pyrrolo[2,3-d]pyrimidine (Preparation 218) to afford the title compound as a yellow liquid in 22% yield, 0.341 g.

¹H NMR (400 MHz, DMSO-d₆) δ: 1.81 (s, 3H), 4.72-4.77 (m, 2H), 5.16-5.21 (m, 2H), 6.69 (d, 1H), 7.66 (d, 1H), 8.76 (s, 1H), 9.02 (s, 1H).

The title compound may also be prepared according to the following method:

LiHMDS (14.5 mL of a 1M solution in THF, 14.5 mmol) was added slowly to a solution of 2-Methyl-2-pyrrolo[2,3-d]pyrimidin-7-yl-propane-1,3-diol (Preparation 278, 3 g, 14.5 mmol) in anhydrous THF (200 mL) over a period of 2 hours (using a syringe pump) under nitrogen at 00° C. After completion of the addition, the reaction mixture was stirred for an additional 40 min before TsCl (2.76 g, 14.5 mmol) as a solution in THF (50 mL) was slowly added. The mixture was stirred for another 1 hour at 00° C. TLC showed consumption of starting material and another equivalent of LiHMDS (14.5 mL, 14.5 mmol) was added to the mixture and it was heated at 600 for 16 hours. Sat. aq. NH₄Cl solution (200 mL) was then added and the mixture then extracted with EtOAc (3×100 mL). The combined organic layers were dried (Na₂SO₄) and evaporated in vacuo. The crude material was purified by column chromatography on silica gel (gradient of EtOAc:Hexane 3:7 to 2:3) to afford the title compound as a colourless gum in 37% yield, 1 g.

Preparation 220: 5-iodo-7-(3-methyloxetan-3-yl)-7H-pyrrolo[2,3-d]pyrimidine

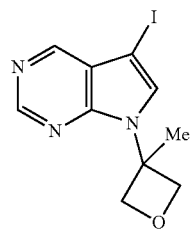 [SMILES: CC1(n2cc(I)c3cncnc32)COC1]

The title compound was prepared according to the method described for Preparation 14 using 7-(3-methyloxetan-3-yl)-7H-pyrrolo[2,3-d]pyrimidine (Preparation 219) to afford the title compound as a yellow solid in 78% yield, 0.44 g.

¹H NMR (400 MHz, DMSO-D6) δ: 1.80 (s, 3H), 4.71 (d, 2H), 5.18 (d, 2H), 7.94 (s, 1H), 8.76 (s, 1H), 8.82 (s, 1H).

Preparation 221: (5-((diphenylmethylene)amino)pyridin-3-yl)(7-(3-methyloxetan-3-yl)-7H-pyrrolo[2,3-d]pyrimidin-5-yl)methanone

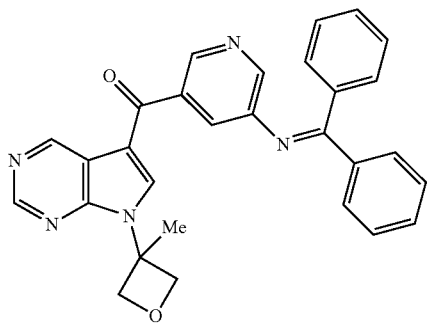 [SMILES: CC1(n2cc(C(=O)c3cncc(N=C(c4ccccc4)c4ccccc4)c3)c3cncnc32)COC1]

The title compound was prepared according to the method described for Preparation 24 using 5-iodo-7-(3-methyloxetan-3-yl)-7H-pyrrolo[2,3-d]pyrimidine (Preparation 220) to afford the title compound.

LCMS (system 2): R$_f$=1.24 min; m/z 474 [M+H]⁺.

Preparation 222: (5-aminopyridin-3-yl)[7-(3-methyloxetan-3-yl)-7H-pyrrolo[2,3-d]pyrimidin-5-yl]methanone The title compound was prepared according to the method described for Preparation 37 using (5-((diphenylmethylene)amino)pyridin-3-yl)(7-(3-methyloxetan-3-yl)-7H-pyrrolo[2,3-d]pyrimidin-5-yl)methanone (Preparation 221) to afford the title compound as a white solid in 14% yield over two steps, 64 mg.

¹H NMR (400 MHz, DMSO-d₆) δ: 1.89 (s, 3H), 4.75 (d, 2H), 5.23 (d, 2H), 5.64 (br s, 2H), 7.29-7.36 (m, 1H), 8.17 (d, 1H), 8.24 (d, 1H), 8.41 (s, 1H), 8.95 (s, 1H), 9.46 (s, 1H); LCMS (System 4): R$_f$=2.30 min; m/z 310 [M+H]⁺.

Preparation 223: N-[5-({7-[3-({[tert-butyl(dimethyl)silyl]oxy}methyl)oxetan-3-yl]-7H-pyrrolo[2,3-d]pyrimidin-5-yl}carbonyl)pyridin-3-yl]-2-(5-chloropyridin-2-yl)acetamide

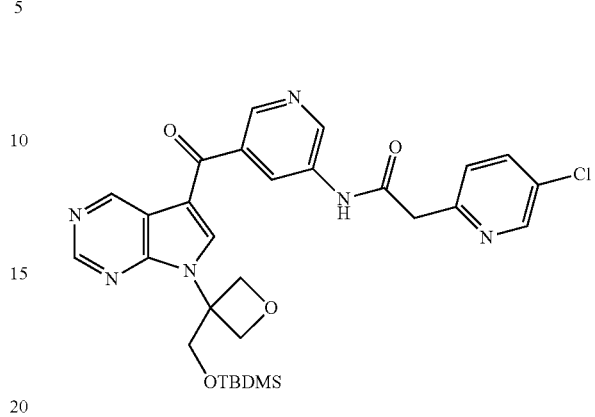

(5-Amino-pyridin-3-yl)-{7-[3-(tert-butyl-dimethyl-silanyloxymethyl)-oxetan-3-yl]-7H-pyrrolo[2,3-d]pyrimidin-5-yl}-methanone (Preparation 216, 30 mg, 0.068 mmol) was added to a stirred mixture of (5-chloropyridin-2-yl)acetic acid (17.5 mg, 0.102 mmol) and HATU (38.8 mg, 0.102 mmol) in pyridine (2 ml). The reaction mixture was warmed to 50° C. and stirred at this temperature for 14 hours. The reaction was then cooled and a further portion of HATU (38.8 mg, 0.102 mmol) was added. The reaction was warmed to 50° C. and stirred at this temperature for 8 hours and then allowed to cool to room temperature and stirred for a further 60 hours. The reaction mixture was then diluted with DCM (20 ml) and the resultant solution quenched with saturated NaHCO₃ (20 ml). The layers were separated and the aqueous layer extracted with DCM (3×20 ml). The combined organic layers were washed with brine (20 ml) and then concentrated in vacuo to give the crude product as a pale yellow oil (35 mg) which was taken forward for use in the preparation of Example 238.

Preparation 224: N-[5-({7-[3-({[tert-butyl(dimethyl)silyl]oxy}methyl)oxetan-3-yl]-7H-pyrrolo[2,3-d]pyrimidin-5-yl}carbonyl)pyridin-3-yl]-2-[3-(trifluoromethyl)-1H-pyrazol-1-yl]acetamide

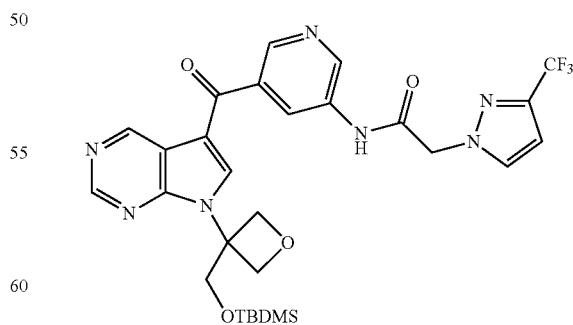

(5-Amino-pyridin-3-yl)-{7-[3-(tert-butyl-dimethyl-silanyloxymethyl)-oxetan-3-yl]-7H-pyrrolo[2,3-d]pyrimidin-5-yl}-methanone (Preparation 216, 30 mg, 0.068 mmol) was added to a stirred mixture of [3-(trifluoromethyl)-1H-pyrazol-1-yl]acetic acid (19.8 mg, 0.102 mmol) and HATU (38.8 mg, 0.102 mmol) in pyridine (2 ml). The reaction mixture was warmed to 50° C. and stirred at this temperature for 14 hours. The reaction mixture was then cooled to room temperature and diluted with DCM (20 ml) and the resultant solution quenched with saturated NaHCO₃ (20 ml). The layers were separated and the aqueous layer extracted with DCM (3×20 ml). The combined organic layers were washed with saturated brine (20 ml) and then concentrated in vacuo to give the crude product as a pale yellow solid (44 mg) which was taken forward crude for use in the preparation of Example 239.

Preparation 225:
4-Chloro-5-iodo-7H-pyrrolo[2,3-d]pyrimidine

To a suspension of 4-chloro-7H-pyrrolo[2,3-d]pyrimidine (70.5 g, 0.45 mol) in DCM (1.8 L) was added N-iodosuccinimide (120 g, 0.54 mol) in portions. After addition, the mixture was stirred at room temperature overnight. The solid was filtered and washed with water (250 mL), MeOH (280 mL) and CH₂Cl₂ (280 mL) sequentially. The solid was dried under vacuum to afford 4-chloro-5-iodo-7H-pyrrolo[2,3-d]pyrimidine as a brown solid in 79% yield, 107 g.

Preparation 226: 4-Chloro-5-iodo-7-methyl-7H-pyrrolo[2,3-d]pyrimidine

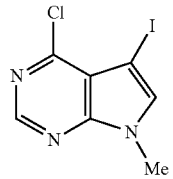 [SMILES: Cn1cc(I)c2c(Cl)ncnc21]

To a mixture of 4-chloro-5-iodo-7H-pyrrolo[2,3-d]pyrimidine (Preparation 225, 30 g, 0.1 mol), Cs₂CO₃ (50 g, 0.15 mol) in DMF (150 mL), MeI (28.4 g, 0.2 mol) was added dropwise at 0° C. After addition, the mixture was stirred at room temperature for 10 hours. The reaction mixture was cooled to 0° C. and quenched by the addition of water (500 mL). Then the solid was collected by filtration and washed with Et₂O (100 mL) to afford 4-chloro-5-iodo-7-methyl-7H-pyrrolo[2,3-d]pyrimidine as a brown solid in 61% yield, 20 g.

Preparation 227:
5-Bromo-N-methoxy-N-methyl-nicotinamide

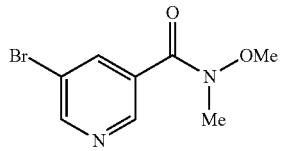 [SMILES: CON(C)C(=O)c1cncc(Br)c1]

To a solution of 5-bromo-nicotinic acid (100 g, 0.5 mol) in THF (2 L) at 0° C., (COCl)₂ (95 g, 0.74 mol) was added. After stirring for 0.5 h, Et₃N (152 g, 1.5 mol) and O, N-dimethyl hydroxylamine. HCl (140 g, 1.5 mol) were added. The reaction mixture was stirred at room temperature for 2.5 hours and then water (200 mL) and EtOAc (500 mL) were added. The organic layer was separated, dried (MgSO₄) and concentrated in vacuo to afford 5—the title compound as a brown oil in 82% yield, 100%.

Preparation 228: (4-Chloro-7-methyl-7H-pyrrolo[2,3-d]pyrimidin-5-yl)(5-((diphenylmethylene)amino)pyridin-3-yl)methanol

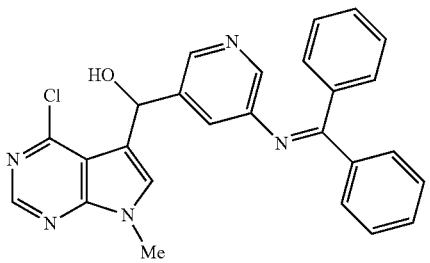 [SMILES: Cn1cc(C(O)c2cncc(N=C(c3ccccc3)c3ccccc3)c2)c2c(Cl)ncnc21]

To stirred solution of 4-chloro-5-iodo-7-methyl-7H-pyrrolo[2,3-d]pyrimidine (Preparation 226, 6.6 g, 22.7 mmol) in THF (130 mL) was added n-BuLi (18.2 mL of a 2.5M solution in hexane, 45 mmol) at −75° C. under N₂, and the mixture was stirred for 50 min. A solution of 5-((diphenylmethylene)amino)nicotinaldehyde (Preparation 106, 6.5 g, 22.7 mmol) in dry THF (50 mL) was added and the mixture was stirred at −70° C. for 80 min. The mixture was quenched with sat. aq. NH₄Cl solution and extracted with EtOAc (300 mL). The organic layer was dried (Na₂SO₄) and concentrated in vacuo to give the title compound as a brown solid in 48% yield, 5.2 g.

Preparation 229: (4-chloro-7-methyl-7H-pyrrolo[2,3-d]pyrimidin-5-yl)(5-((diphenylmethylene)amino)pyridin-3-yl)methanone

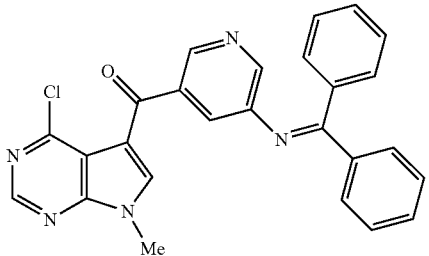 [SMILES: Cn1cc(C(=O)c2cncc(N=C(c3ccccc3)c3ccccc3)c2)c2c(Cl)ncnc21]

To a solution of (4-chloro-7-methyl-7H-pyrrolo[2,3-d]pyrimidin-5-yl)(5-((diphenylmethylene)amino)pyridin-3-yl)methanol (Preparation 228, 11.4 g, 25 mmol) in CH₂Cl₂ (150 mL), Dess-Martin periodinane (15.9 g, 37 mmol) was added in portions. The reaction mixture was stirred at room temperature for 10 hours and then aqueous NaOH (30 mL) was added. The mixture was stirred for a further 0.5 hours. The mixture was then separated and the aqueous layer was exacted by CH₂Cl₂ (100 mL×2). The combined organic layers were concentrated and washed with ether to provide the title compound as a brown solid in 99% yield, 11 g.

¹H NMR (400 MHz, CDCl₃) δ 3.87 (s, 3H), 7.06 (m, 2H), 7.27 (m, 3H), 7.37 (m, 2H), 7.45 (m, 3H), 7.71 (m, 2H), 8.15 (d, J=2.4, 1H), 8.49 (d, J=1.2, 1H), 8.68 (s, 1H).

Preparation 230: (5-Amino-pyridin-3-yl)-(4-chloro-7-methyl-7H-pyrrolo[2,3-d]pyrimidin-5-yl)-methanone

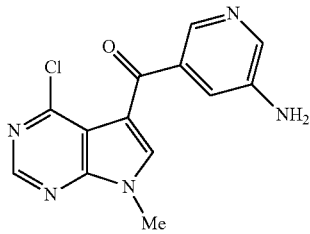 [SMILES: Cn1cc(C(=O)c2cncc(N)c2)c2c(Cl)ncnc21]

A solution of [5-(benzhydrylidene-amino)pyridin-3-yl]-(4-chloro-7-methyl-7H-pyrrolo[2,3-d]pyrimidin-5-yl)-methanone (Preparation 229, 30 g, 0.066 mol) in THF (200 mL) was added aq. citric acid (200 mL), the mixture was stirred for 30 min at room temperature. Ether was added and the layers were separated. The aqueous layer was adjusted to pH7 by aqueous Na₂CO₃. Then the mixture was filtered. The filter cake was evaporated with toluene and the residue was washed with EtOAc (200 mL) to give the title compound as a brown solid in 95% yield, 18 g.

Preparation 231: (5-Amino-pyridin-3-yl)-(7-methyl-4-methylsulfanyl-7H-pyrrolo[2,3-d]pyrimidin-5-yl)-methanone

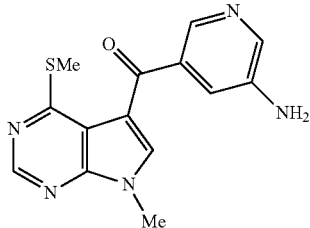 [SMILES: CSc1ncnc2c1c(C(=O)c1cncc(N)c1)cn2C]

To a solution of (5-amino-pyridin-3-yl)-(4-chloro-7-methyl-7H-pyrrolo[2,3-d]pyrimidin-5-yl)-methanone (Preparation 230, 21 g, 0.073 mol) in MeOH (300 mL) was added CH₃SNa (15.5 g, 0.22 mol). The resulting mixture was stirred for 7 hours at room temperature. The mixture was poured into ice-water (200 mL), the precipitate was filtered, the filter cake was washed with water (100 mL) then acetone (20 mL) to give (5-amino-pyridin-3-yl)-(7-methyl-4-methylsulfanyl-7H-pyrrolo[2,3-d]pyrimidin-5-yl)-methanone as a brown solid in 69% yield, 15 g.

Preparation 232: (5-Amino-pyridin-3-yl)-(7-methyl-7H-pyrrolo[2,3-d]pyrimidin-5-yl)-methanone

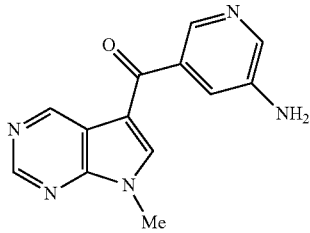 [SMILES: Cn1cc(C(=O)c2cncc(N)c2)c2cncnc21]

A mixture of (5-amino-pyridin-3-yl)-(7-methyl-4-methylsulfanyl-7H-pyrrolo[2,3-d]pyrimidin-5-yl)-methanone (Preparation 231, 1.5 g, 5 mmol), Raney Ni (10 g) and NH₃H₂O (150 mL) in dioxane (150 mL) was refluxed for 6 hours. The mixture was filtered and the filtrate was concentrated. The residue was purified via preparative HPLC to give (5-amino-pyridin-3-yl)-(7-methyl-7H-pyrrolo[2,3-d]pyrimidin-5-yl)-methanone as a brown solid in 15% yield, 0.19 g. ¹H NMR (400 MHz DMSO-d₆) 3.88 (s, 3H), 5.63 (s, 2H), 7.27-7.28 (m, 1H), 8.15-8.18 (m, 2H), 8.40 (s, 1H), 8.97 (s, 1H), 9.42 (s, 1H).

Preparation 233:
5,6,7,8-Tetrahydro-[1,7]naphthyridine hydrochloride

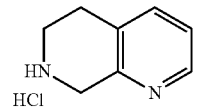

A methanolic solution (25 mL) of 7-Benzyl-5,6,7,8-tetrahydro-[1,7]naphthyridine (J. Het. Chem. 2001, 38, 535) (1.5 g, 6.69 mmol) was degassed with argon for 20 min followed by the addition of 4N HCl in dioxane (2 mL) and Pd/C (300 mg, 20 wt %) and stirred under 50 psi hydrogen pressure at room temperature for 24 h. After completion of the reaction the mixture was filtered on a short pad of celite and washed with methanol (4×25 mL). The filtrate was evaporated to dryness in vacuo and crystallized from methanol to afford the title compound as yellowish solid in 65% yield (calculated as 2HCl salt), 900 mg.

¹H NMR (400 MHz, DMSO-D6) δ: 3.10 (t, 2H), 3.40 (q, 2H), 4.36 (s, 2H), 7.50 (dd, 1H), 7.91 (d, 1H), 8.55 (d, 1H), 9.96 (brs, 2H); LCMS (system 10): R_f=1.56 min; m/z 135.2 [M+H]⁺.

Preparation 234:
(5,8-Dihydro-6H-[1,7]naphthyridin-7-yl)-acetic acid tert-butyl ester

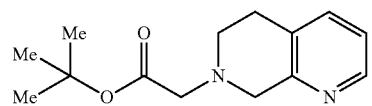 [SMILES: CC(C)(C)OC(=O)CN1CCc2cccnc2C1]

A DMF solution (8 mL) of 5,6,7,8-Tetrahydro-[1,7]naphthyridinehydrochloride (Preparation 233, 400 mg, 1.93 mmol), bromo-acetic acid tert-butyl ester (414.1 mg, 2.12 mmol) and triethylamine (1.64 mL, 11.92 mmol) was heated at 80° C. for 16 hours. The reaction mixture was diluted with EtOAc (40 mL), washed with water (3×25 mL), brine (20 mL), dried over Na₂SO₄ and evaporated to dryness in vacuo to afford the title compound as colorless sticky solid in 100% yield, 480 mg.

¹H NMR (400 MHz, DMSO-D6) δ: 1.43 (s, 9H), 2.81 (s, 4H), 3.34 (s, 2H), 3.72 (s, 2H), 7.16 (dd, 1H), 7.51 (d, 1H), 8.29 (d, 1H); LCMS (system 10): R_f=3.02 min; m/z 249.4 [M+H]⁺.

Preparation 235:
(5,8-Dihydro-6H-[1,7]naphthyridin-7-yl)-acetic acid hydrochloride

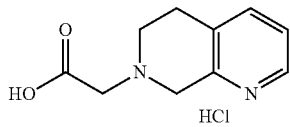 [SMILES: O=C(O)CN1CCc2cccnc2C1 ; Cl]

(5,8-Dihydro-6H-[1,7]naphthyridin-7-yl)-acetic acid tert-butyl ester (Preparation 234, 1.25 g, 5.03 mmol) was treated with 4N HCl in dioxane (25 ml) at room temperature for 2 hours. The mixture was evaporated to dryness in vacuo and the solid residue was triturated with diethyl ether to afford the title compound as white solid in 78% yield (calculated as HCl salt), 900 mg.
$^1$H NMR (400 MHz, MeOD) δ: 3.38 (t, 2H), 3.79 (t, 2H), 4.38 (s, 2H), 4.84 (s, 2H), 7.79 (dd, 1H), 8.25 (d, 1H), 8.70 (d, 1H).

Preparation 236:
Phenyl-[(tetrahydro-pyran-2-yloxy)]-acetic acid

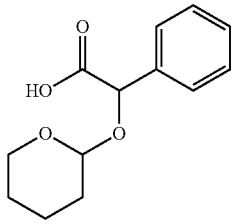 [SMILES: O=C(O)C(OC1CCCCO1)c1ccccc1]

To a stirred solution of hydroxy-phenyl-acetic acid (2 g, 13.4 mmol) in DCM (30 mL) was added PTSA (51.2 mg, 0.27 mmol) at 0° C. followed by the addition of 3,4-dihydro-2H-pyran (1.55 g, 18.4 mmol). The mixture was stirred at 0° C. for another 15 min and then gradually warmed up to room temperature and stirred for a further 1.5 hours. The reaction mixture was diluted with DCM (100 mL). The organic phase was washed with saturated aq. Na$_2$CO$_3$ (2×20 mL), water (20 mL), brine (20 mL), dried (Na$_2$SO$_4$) and evaporated in vacuo. The crude material was purified by column chromatography on silica gel (EtOAc:petroleum ether 2:5) to afford the title compound as a yellow sticky solid in 48% yield, 1.5 g. LCMS (system 10): R$_t$=1.82 min; m/z 237 [M+H]$^+$.

Preparation 237: N-[5-(7-Isopropyl-7H-pyrrolo[2,3-d]pyrimidine-5-carbonyl)-pyridin-3-yl]-2-phenyl-2-(tetrahydro-pyran-2-yloxy)-acetamide

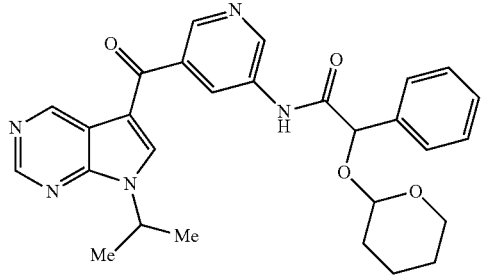 [SMILES: CC(C)n1cc(C(=O)c2cncc(NC(=O)C(OC3CCCCO3)c3ccccc3)c2)c2cncnc21]

The title compound was prepared according to the method described for Example 1 using phenyl-[(tetrahydro-pyran-2-yloxy)]-acetic acid (Preparation 236) and (5-Amino-pyridin-3-yl)-(7-isopropyl-7H-pyrrolo[2,3-d]pyrimidin-5-yl)-methanone (Preparation 95) to afford the title compound as a yellow solid in 68% yield, 60 mg.
LCMS (system 10): R$_t$=3.56 min; m/z 500.2 [M+H]$^+$.

Preparation 238: 5-Bromo-6-hydroxy-nicotinic acid

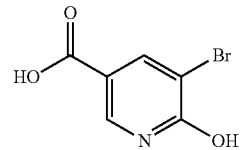 [SMILES: O=C(O)c1cnc(O)c(Br)c1]

Bromine (3.6 mL, 70.5 mmol) was added dropwise to a suspension of 6-Hydroxy-nicotinic acid (7 g, 50.32 mmol) in water (70 mL) at 00° C. and the mixture was stirred at room temperature for 4 hours. The precipitated solid was filtered, washed with cold water and dried to get the title compound as off white solid in 82% yield, 9 g.
$^1$H NMR (400 MHz, DMSO-D6) δ: 8.03 (d, 1H), 8.14 (d, 1H), 12.57 (br s, 1H).

Preparation 239:
5-Bromo-6-hydroxy-N-methoxy-N-methyl-nicotinamide

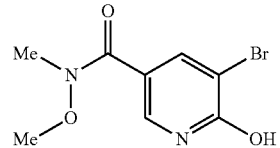 [SMILES: CON(C)C(=O)c1cnc(O)c(Br)c1]

5-Bromo-6-hydroxy-nicotinic acid (Preparation 238, 4 g, 18.4 mmol), HATU (13.95 g, 36.71 mmol), O,N-Dimethyl-hydroxylamine hydrochloride (2.15 g, 22.02 mmol) and DIPEA (15.82 mL, 91.75 mmol) were taken in anhydrous DMF (30 mL). The mixture was stirred at room temperature for 16 hours. The reaction mixture was diluted with EtOAc (150 mL), washed with saturated aq. Na$_2$CO$_3$ (2×50 mL), water (4×30 mL), brine (30 mL), dried (Na$_2$SO$_4$) and evaporated in vacuo. The crude mixture was purified by column chromatography on silica gel (gradient of EtOAc:Hex 4:6 to 6:4) to afford the title compound as light yellow sticky solid in 38%, 1.8 g.
$^1$H NMR (400 MHz, DMSO-D6) δ: 3.22 (s, 3H), 3.61 (s, 3H), 7.95 (d, 1H), 8.14 (d, 1H), 12.45 (br s, 1H); LCMS (system 10): R$_t$=1.67 min; m/z 261, 263 [M+H]$^+$.

Preparation 240:
5-Bromo-6-ethoxy-N-methoxy-N-methyl-nicotinamide

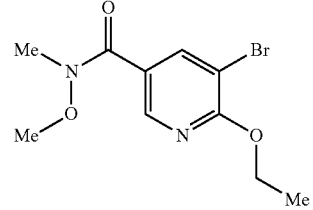 [SMILES: CCOc1ncc(C(=O)N(C)OC)cc1Br]

A mixture of 5-bromo-6-hydroxy-N-methoxy-N-methyl-nicotinamide (Preparation 239, 1.80 g, 6.90 mmol), ethyl iodide (2.8 mL, 34.5 mmol) and silver carbonate (3.8 g, 13.8 mmol) in DCM (10 mL) was stirred at room temperature for 40 hours. The reaction mixture was diluted with DCM (50 mL), washed with water (2×30 mL), brine (20 mL), dried (Na₂SO₄) and evaporated in vacuo. The crude material was purified by column chromatography on silica gel (EtOAc: petroleum ether 2:5) to afford the title compound as a yellow sticky solid in 30% yield, 600 mg.

¹H NMR (400 MHz, CDCl3) δ: 1.44 (t, 3H), 3.35 (s, 3H), 3.57 (s, 3H), 4.47 (q, 2H), 8.23 (d, 1H), 8.54 (d, 1H).

Preparation 241: (5-Bromo-6-ethoxy-pyridin-3-yl)-(7-isopropyl-7H-pyrrolo[2,3-d]pyrimidin-5-yl)-methanone

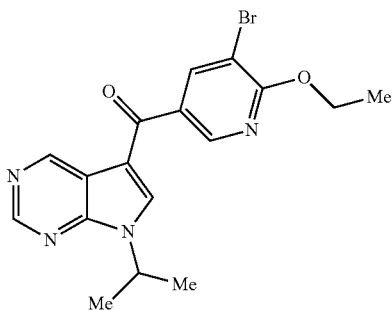 [SMILES: CCOc1ncc(C(=O)c2cn(C(C)C)c3ncncc23)cc1Br]

A solution of 5-Iodo-7-isopropyl-7H-pyrrolo[2,3-d]pyrimidine (Preparation 93, 530 mg, 1.85 mmol) in anhydrous diethyl ether (8 mL) was cooled to −78° C. under nitrogen and n-BuLi (1 mL of a 2.03M solution in Hexane, 2.03 mmol) was added drop wise over a period of 10 min. Just after the completion of addition of n-BuLi, a solution of 5-Bromo-6-ethoxy-N-methoxy-N-methyl-nicotinamide (Preparation 240) in anhydrous diethyl ether (7 mL) was added slowly to the mixture and it was stirred at the same temperature for another 1 hour. The reaction mixture was warmed to room temperature and allowed to stir for another hour before being quenched with sat. aq. NH₄Cl (15 mL). The mixture was extracted with EtOAc (3×15 mL), washed with water (20 mL), brine (15 mL), dried (Na₂SO₄) and evaporated in vacuo. The crude material was purified by column chromatography on silica gel (EtOAc:petroleum ether 2:10) to afford the title compound as a yellow gum in 49% yield, 350 mg.

¹H NMR (400 MHz, CDCl3) δ: 1.50 (t, 3H), 1.60 (d, 6H), 4.55 (q, 2H), 5.15-5.20 (m, 1H), 7.82 (s, 1H), 8.32 (d, 1H), 8.57 (d, 1H), 9.00 (s, 1H), 9.53 (s, 1H).

Preparation 242: (5-Amino-6-ethoxy-pyridin-3-yl)-(7-isopropyl-7H-pyrrolo[2,3-d]pyrimidin-5-yl)-methanone

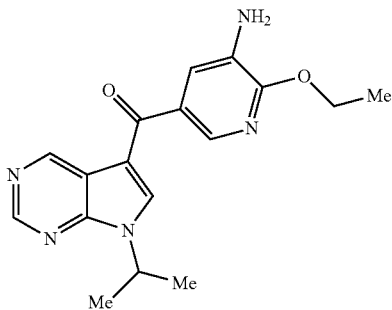 [SMILES: CCOc1ncc(C(=O)c2cn(C(C)C)c3ncncc23)cc1N]

Copper(I) oxide (38.6 mg, 0.27 mmol) was added to (5-Bromo-6-ethoxy-pyridin3-yl)-(7-isopropyl-7H-pyrrolo[2,3-d]pyrimidin-5-yl)-methanone (Preparation 241, 350 mg, 0.89 mmol) in concentrated ammonia solution (6 mL) and NMP (1 mL). The mixture was heated in a sealed vessel at 130° C. for 17 hours. The reaction mixture was cooled to room temperature and diluted with water (10 ml). It was extracted with 20% i-PrOH in DCM (6×50 mL), dried (Na₂SO₄) and evaporated in vacuo. The crude material was purified by column chromatography on silica gel (MeOH: DCM 5:95) to afford the title compound as a yellow solid in 24% yield, 70 mg. LCMS (system 10): R$_t$=2.99 min; m/z 326 [M+H]⁺.

Preparation 243: 2-(4-Chloro-phenyl)-3-hydroxy-propionic acid methyl ester

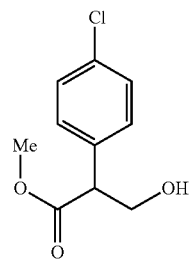 [SMILES: COC(=O)C(CO)c1ccc(Cl)cc1]

To a stirred solution of (4-Chloro-phenyl)-acetic acid methyl ester (2 g, 10.8 mmol) in DMSO (22 mL) was added sodium methoxide (29.2 mg, 0.54 mmol) at 0° C. Paraformaldehyde (342 mg, 11.4 mmol) was then added and the reaction mixture was stirred at room temperature for 4 hours. The reaction mixture was diluted with EtOAc (100 mL), washed with water (3×20 mL), brine (20 mL), dried (Na₂SO₄) and evaporated in vacuo. The crude material was purified by column chromatography on silica gel (gradient of hexane: EtOAc 100:0 to 84:16) to afford the title compound as a colourless gum in 52% yield, 1.2 g.

¹H NMR (400 MHz, CDCl3) δ: 2.23 (t, 1H), 3.70 (s, 3H), 3.79-3.83 (m, 2H), 4.05-4.12 (m, 1H), 7.20 (d, 2H), 7.30 (d, 2H); LCMS (system 10): R$_t$=3.03 min; m/z 215 [M+H]⁺.

Preparation 244: 2-(4-Chloro-phenyl)-3-hydroxy-propionic acid

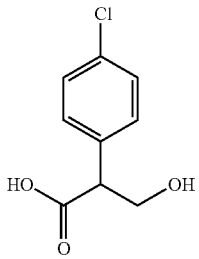 [SMILES: O=C(O)C(CO)c1ccc(Cl)cc1]

To a stirred solution of 2-(4-Chloro-phenyl)-3-hydroxy-propionic acid methyl ester (Preparation 243, 500 mg, 2.33 mmol) in THF (7 mL) was added a solution of lithium hydroxide monohydrate (244 mg, 5.82 mmol) in water (2 mL) dropwise at 0° C. and the resulting mixture stirred at room temperature for 1 hour. The reaction mixture was acidified (pH~3) with 2N hydrochloric acid and extracted with DCM (3×20 mL). The combined organic layers were washed with brine (10 mL), dried (Na$_2$SO$_4$) and evaporated in vacuo to afford the title compound as a white solid in 90% yield, 420 mg.

$^1$H NMR (400 MHz, DMSO-D6) δ: 3.58 (dd, 1H), 3.66 (t, 1H), 3.87 (t, 1H), 7.32 (d, 2H), 7.38 (d, 2H), 12.36 (br, 1H).

Preparation 245: 1-(4-Chloro-pyrrolo[2,3-d]pyrimidin-7-yl)-cyclopropanecarboxylic acid methyl ester

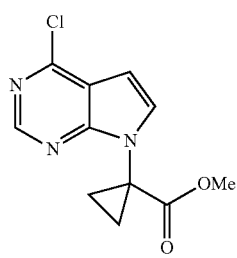 [SMILES: COC(=O)C1(n2ccc3c(Cl)ncnc32)CC1]

To a stirred solution of (4,6-dichloro-pyrimidin-5-yl)acetaldehyde (Preparation 208, 2 g, 10.5 mmol) and 1-Aminocyclopropane-carboxylicacidmethylester hydrochloride (1.33 g, 11.6 mmol) in ethanol (30 mL) was added triethylamine (4.4 mL, 31.6 mmol) and the mixture heated in a sealed tube at 100° C. for 10 hours. Acetic acid (1.21 mL, 21.1 mmol) was then added and the mixture heated at 100° C. for additional 16 hours. The reaction mixture was cooled to room temperature and diluted with DCM (200 mL). The organic layer was washed with water (2×50 mL), brine (50 mL), dried (Na$_2$SO$_4$) and evaporated in vacuo. The crude material was purified by column chromatography on silica gel (gradient of hexane:EtOAc 100:0 to 90:10) to afford the title compound as a solid in 35% yield, 900 mg.

$^1$H NMR (400 MHz, CDCl3) δ: 1.63-1.66 (m, 2H), 1.96-1.99 (m, 2H), 3.63 (s, 3H), 6.60 (d, 1H), 7.23 (d, 1H), 8.65 (s, 1H); LCMS (system 10): R$_t$=2.89 min; m/z 252.1 [M+H]$^+$.

Preparation 246: 1-Pyrrolo[2,3-d]pyrimidin-7-yl-cyclopropanecarboxylic acid methyl ester

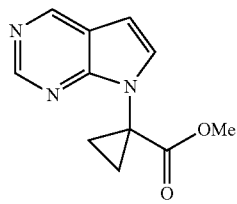 [SMILES: COC(=O)C1(n2ccc3cncnc32)CC1]

A solution of 1-(4-chloro-pyrrolo[2,3-d]pyrimidin-7-yl)-cyclopropanecarboxylic acid methyl ester (Preparation 245, 920 mg, 3.65 mmol) in ethanol (20 mL) was degassed with argon for 15 min. Ammonium hydroxide (4 mL) and 10% palladium on charcoal were added and the reaction mixture was stirred at room temperature under hydrogen (balloon pressure) for 5 hours. The reaction mixture was filtered on a celite bed, washed with ethanol (2×10 mL) and the filtrate was evaporated in vacuo. The crude material was purified by column chromatography on silica gel (gradient of DCM:methanol 100:0 to 98:2) to afford the title compound as a gum in 59% yield, 470 mg.

$^1$H NMR (400 MHz, CDCl3) δ: 1.63-1.66 (m, 2H), 1.95-1.99 (m, 2H), 3.63 (s, 3H), 6.55 (d, 1H), 7.20 (d, 1H), 8.90 (s, 1H), 8.94 (s, 1H); LCMS (system 10): R$_t$=2.22 min; m/z 218.2 [M+H]$^+$.

Preparation 247: (1-Pyrrolo[2,3-d]pyrimidin-7-yl-cyclopropyl)-methanol

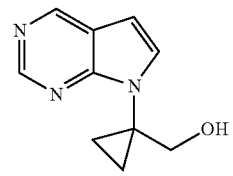 [SMILES: OCC1(n2ccc3cncnc32)CC1]

To a stirred solution of 1-Pyrrolo[2,3-d]pyrimidin-7-yl-cyclopropanecarboxylic acid methyl ester (Preparation 246, 610 mg, 2.80 mmol) in ethanol (15 mL) was added sodium borohydride (318.7 mg, 8.42 mmol) and the mixture heated to reflux for 16 hours. The reaction mixture was quenched with water (5 mL) and extracted with EtOAc (3×10 mL). The combined organic layers were washed with water (5 mL), brine (5 mL), dried (Na$_2$SO$_4$) and evaporated in vacuo. The crude material was purified by column chromatography on silica gel (gradient of DCM:methanol 100:0 to 98:2) to afford the title compound as a light yellow solid in 47% yield, 250 mg.

$^1$H NMR (400 MHz, CDCl3) δ: 1.26 (s, 4H), 3.83 (s, 2H), 6.47 (d, 1H), 7.26 (d, 1H), 8.83 (s, 1H), 8.88 (s, 1H); LCMS (system 10): R$_t$=1.67 min; m/z 189.9 [M+H]$^+$.

Preparation 248: 7-[1-(Tetrahydro-pyran-2-yloxymethyl)-cyclopropyl]-7H-pyrrolo[2,3-d]pyrimidine

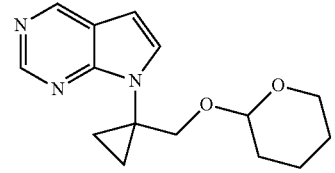 [SMILES: c1ncc2ccn(C3(COC4CCCCO4)CC3)c2n1]

To a stirred solution of (1-Pyrrolo[2,3-d]pyrimidin-7-yl-cyclopropyl)-methanol (Preparation 247, 240 mg, 1.27 mmol) in THF (12 mL) was added 3,4-dihydro-2H-pyran (0.46 mL, 5.07 mmol) followed by addition of PTSA (24 mg, 0.13 mmol). The reaction mixture was stirred at 60° C. for 4 hours. The reaction mixture was cooled to room temperature, quenched with saturated aqueous sodium bicarbonate solution (15 mL) and extracted with dichloromethane (3×25 mL). The combined organic layer was washed with brine (10 mL), dried over sodium sulphate and evaporated in vacuo. The crude material was purified by column chromatography on silica gel (gradient of dichloromethane:methanol 100:0 to 98:2) to afford the title compound as a light brown gum in 90% yield, 320 mg.

$^1$H NMR (400 MHz, CDCl3) δ: 1.18-1.26 (m, 4H), 1.31-1.55 (m, 5H), 1.67-1.69 (m, 1H), 3.28-3.31 (m, 1H), 3.44 (t,

1H), 3.68 (d, 1H), 3.88 (d, 1H), 4.46 (s, 1H), 6.45 (d, 1H), 7.33 (d, 1H), 8.88-8.90 (m, 2H); LCMS (system 10): R$_t$=2.82 min; m/z 274.6 [M+H]$^+$.

Preparation 249: 5-Iodo-7-[1-(tetrahydro-pyran-2-yloxymethyl)-cyclopropyl]-7H-pyrrolo[2,3-d]pyrimidine

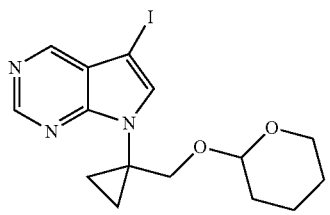 [SMILES: Ic1cn(C2(COC3CCCCO3)CC2)c2ncncc12]

To a stirred solution of 7-[1-(Tetrahydro-pyran-2-yloxymethyl)-cyclopropyl]-7H-pyrrolo[2,3-d]pyrimidine (Preparation 248, 390 mg, 1.43 mmol) in DMF (8 mL) was added N-iodosuccinimide (481.5 mg, 2.14 mmol) and stirred at room temperature for 4 hours. The reaction mixture was quenched with water (8 mL) and extracted with ethyl acetate (3×20 mL). The combined organic layer was washed with water (5×15 mL), brine (10 mL), dried over sodium sulphate and evaporated in vacuo. The crude material was purified by column chromatography on silica gel (gradient of dichloromethane:methanol 100:0 to 99:1) to afford the title compound as a solid in 79% yield, 450 mg.

$^1$H NMR (400 MHz, CDCl3) δ: 1.18-1.70 (m, 10H), 3.28-3.32 (m, 1H), 3.42 (t, 1H), 3.65 (d, 1H), 3.87 (d, 1H), 4.47 (s, 1H), 7.44 (s, 1H), 8.70 (s, 1H), 8.90 (s, 1H); LCMS (system 10): R$_t$=3.28 min; m/z 400.2 [M+H]$^+$.

Preparation 250: (5-Bromo-pyridin-3-yl)-{7-[1-(tetrahydro-pyran-2-yloxymethyl)-cyclopropyl]-7H-pyrrolo[2,3-d]pyrimidin-5-yl}-methanone

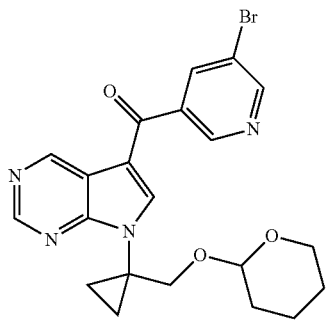 [SMILES: O=C(c1cncc(Br)c1)c1cn(C2(COC3CCCCO3)CC2)c2ncncc12]

To a stirred solution of 5-Iodo-7-[1-(tetrahydro-pyran-2-yloxymethyl)-cyclopropyl]-7H-pyrrolo[2,3-d]pyrimidine (Preparation 249, 450 mg, 1.13 mmol) in diethyl ether (6 mL) was added n-butyl lithium (2M in hexane, 0.62 mL, 1.24 mmol) drop wise at −70° C. Then a solution of 5-Bromo-N-methoxy-N-methyl-nicotinamide (304 mg, 1.24 mmol) in diethyl ether (2.5 mL) was added drop wise at −70° C. and stirred at same temperature for another 30 minutes. The reaction was allowed to warm to room temperature slowly. The reaction was quenched with saturated aqueous ammonium chloride solution (10 mL) and extracted with ethyl acetate (3×20 mL). The combined organic layer was washed with water (20 mL), brine (20 mL), dried over sodium sulphate and evaporated in vacuo. The crude material was purified by column chromatography on silica gel (gradient of dichloromethane:methanol 100:0 to 98:2) to afford the title compound as a light brown sticky solid in 35% yield, 250 mg.

$^1$H NMR (400 MHz, DMSO-D6) δ: 1.25-1.57 (m, 10H), 3.17-3.28 (m, 2H), 3.64 (d, 1H), 3.95 (d, 1H), 4.57 (s, 1H), 8.36 (s, 1H), 8.40 (s, 1H), 8.96 (s, 1H), 8.99 (s, 1H), 9.02 (s, 1H), 9.45 (s, 1H); LCMS (system 10): R$_t$=3.17 min; m/z 456.8, 459 [M+H]$^+$.

Preparation 251: (5-Amino-pyridin-3-yl)-{7-[1-(tetrahydro-pyran-2-yloxymethyl)-cyclopropyl]-7H-pyrrolo[2,3-d]pyrimidin-5-yl}-methanone

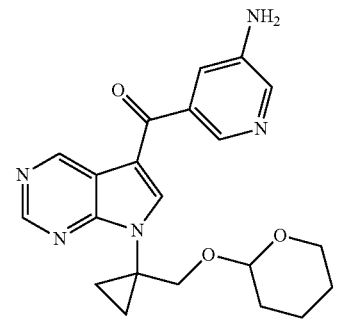 [SMILES: Nc1cncc(C(=O)c2cn(C3(COC4CCCCO4)CC3)c3ncncc23)c1]

To a stirred solution of (5-Bromo-pyridin-3-yl)-{7-[1-(tetrahydro-pyran-2-yloxymethyl)-cyclopropyl]-7H-pyrrolo[2,3-d]pyrimidin-5-yl}-methanone (Preparation 250, 200 mg, 0.45 mmol) in 1-Methyl-pyrrolidin-2-one (1.5 mL) was added ammonium hydroxide (15 mL). Then copper (I) oxide (3 mg, 0.02 mmol) was added and the reaction mixture was heated in a sealed tube at 130° C. for 16 hours. The reaction mixture was cooled to room temperature, extracted with 10% methanol in dichloromethane (5×25 mL). The combined organic layer was dried over sodium sulphate and evaporated in vacuo. The crude material was purified by column chromatography on silica gel (gradient of dichloromethane:methanol 100:0 to 96:4) to afford the title compound as a white sticky solid in 45% yield, 80 mg.

$^1$H NMR (400 MHz, DMSO-D6) δ: 1.17-1.53 (m, 10H), 3.17-3.28 (m, 2H), 3.63 (d, 1H), 3.94 (d, 1H), 4.55 (s, 1H), 5.64 (s, 2H), 7.27 (s, 1H), 8.18-8.20 (m, 3H), 8.99 (s, 1H), 9.42 (s, 1H); LCMS (system 10): R$_t$=2.59 min; m/z 394.1 [M+H]$^+$.

Preparation 252: (S)-2-Pyrrolo[2,3-d]pyrimidin-7-yl-propan-1-ol

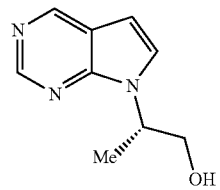 [SMILES: C[C@@H](CO)n1ccc2cncnc21]

The title compound was prepared according to the method described for Preparation 8 using (2S)-2-(4-Chloro-7H-pyrrolo[2,3-d]pyrimidin-7-yl)propan-1-ol (Preparation 4) to afford the title compound as a white solid in 100% yield, 2.8 g.

¹H NMR (400 MHz, DMSO-d6) δ: 1.43 (d, 3H), 3.68-3.79 (m, 2H), 4.89-4.94 (m, 1H), 4.97 (t, 1H), 6.61 (d, 1H), 7.71 (d, 1H), 8.75 (s, 1H), 8.97 (s, 1H).

Preparation 253:
(2-Hydroxy-1,1-dimethyl-ethyl)-carbamic acid tert-butyl ester

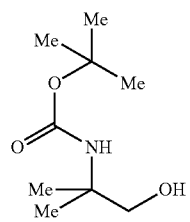 [SMILES: CC(C)(CO)NC(=O)OC(C)(C)C]

To a mixture of 2-Amino-2-methyl-propan-1-ol (2 g, 22.43 mmol) and triethyl amine (3.12 mL, 22.43 mmol) in THF was added boc-anhydride (4.89 g, 22.43 mmol) slowly at 0° C. and was stirred at room temperature for 16 hours. The reaction mixture was diluted with ethyl acetate, washed with water, brine, dried over sodium sulphate and evaporated in vacuo to afford the title compound as colourless oil in 92% yield, 3.9 g.

¹H NMR (400 MHz, CDCl₃) δ: 1.23 (s, 6H), 1.42 (s, 9H), 3.56-3.58 (d, 2H), 4.00 (brs, 1H), 4.62 (brs, 1H).

Preparation 254:
(2-Methoxy-1,1-dimethyl-ethyl)-carbamic acid tert-butyl ester

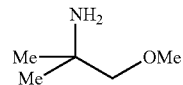

KOH (3.47 g, 61.82 mmol) was added to a solution of (2-Hydroxy-1,1-dimethyl-ethyl)-carbamic acid tert-butyl ester (Preparation 253, 3.9 g, 20.6 mmol) in 1,4-dioxane (30 mL) followed by the slow addition of dimethyl sulphate at room temperature. The mixture was further allowed to stir at room temperature for 48 hours. Reaction mass was filtered through a short pad of celite, washed with DCM (3×50 mL). The combined filtrate was washed with water (2×50 mL), brine (30 mL), dried over sodium sulphate and evaporated in vacuo to afford the title compound as yellow oil in 88% yield, 3.7 g.

¹H NMR (400 MHz, CDCl₃) δ: 1.27 (s, 6H), 1.41 (s, 9H), 3.29 (s, 2H), 3.35 (s, 3H), 4.73 (brs, 1H).

Preparation 255:
2-Methoxy-1,1-dimethyl-ethylamine

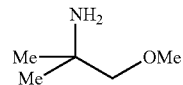

TFA (5.8 mL, 78.7 mmol) was added slowly to a DCM (25 mL) solution of (2-Methoxy-1,1-dimethyl-ethyl)-carbamic acid tert-butyl ester (Preparation 254, 3.2 g, 15.74 mmol) at 00° C. The mixture was allowed to stir at room temperature for another 3 hours and then all the volatiles were removed in vacuo. The residue was treated with aqueous saturated NaHCO₃ solution (50 mL) and extracted with a mixture of IPA/DCM (1:4) (4×50 mL). The combined organics was dried over sodium sulphate and evaporated to dryness in vacuo to afford the title compound as light brown oil in 100% yield, 1.6 g.

1H NMR (400 MHz, CDCl₃) δ: 1.32 (s, 6H), 3.30 (s, 2H), 3.35 (s, 3H), 7.80 (brs, 2H).

Preparation 256: (5-Bromo-2-chloro-pyrimidin-4-yl)-(2-methoxy-1,1-dimethyl-ethyl)-amine

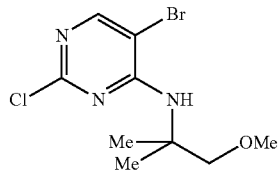 [SMILES: COCC(C)(C)Nc1nc(Cl)ncc1Br]

Triethyl amine (73.1 mL, 526.6 mmol) was added slowly to a solution of 5-Bromo-2,4-dichloro-pyrimidine (40 g, 175.5 mmol) in acetonitrile (400 mL) at 00° C. and then 2-Methoxy-1,1-dimethyl-ethylamine (Preparation 255, 23.4 g, 263.3 mmol) was added to the mixture portion wise. The reaction mixture was stirred for another 16 hours at room temperature. TLC showed the presence of unreacted starting pyrimidine, but the reaction was not continued further. All the volatiles were removed in vacuo and the residue was taken in ethyl acetate, washed with water, brine, dried over sodium sulphate and evaporated to dryness in vacuo. The crude material was purified by column chromatography on silica gel (100-200 mesh, gradient of ethyl acetate:hexane 1:9 to 2:4) to afford the title compound as white solid in 23% yield (10 g of starting pyrimidine was recovered), 12 g.

¹H NMR (400 MHz, DMSO-D6) δ: 1.40 (s, 6H), 3.32 (s, 3H), 3.48 (s, 2H), 6.19 (s, 1H), 8.29 (s, 1H); LCMS (system 10): R_t=3.56 min; m/z 294, 296 [M+H]⁺.

Preparation 257: [2-Chloro-5-((E)-2-ethoxy-vinyl)-pyrimidin-4-yl]-(2-methoxy-1,1-dimethyl-ethyl)-amine

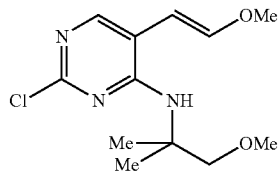 [SMILES: CO/C=C/c1cnc(Cl)nc1NC(C)(C)COC]

251

The title compound was prepared according to the method described for Preparation 61 using (5-Bromo-2-chloro-pyrimidin-4-yl)-(2-methoxy-1,1-dimethyl-ethyl)-amine (Preparation 256), catechol borane and ethoxyacetylene (40% in hexane) to afford the title compound as light brown gum in 44% yield, 2.6 g.

1H NMR (400 MHz, DMSO-D6) δ: 1.25 (t, 3H), 1.37 (s, 6H), 3.26 (s, 3H), 3.56 (s, 2H), 3.92 (q, 2H), 5.74 (d, 1H), 6.12 (s, 1H), 6.94 (d, 1H), 7.88 (s, 1H); LCMS (system 10): R$_t$=3.65 min; m/z 286.3 [M+H]$^+$.

Preparation 258: 2-Chloro-7-(2-methoxy-1,1-dimethyl-ethyl)-7H-pyrrolo[2,3-d]pyrimidine

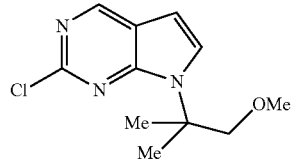 [SMILES: COCC(C)(C)n1ccc2cnc(Cl)nc21]

The title compound was prepared according to the method described for Preparation 62 using [2-Chloro-5-((E)-2-ethoxy-vinyl)-pyrimidin-4-yl]-(2-methoxy-1,1-dimethyl-ethyl)-amine (Preparation 257) to afford the title compound as off white solid in 91% yield, 2 g.

$^1$H NMR (400 MHz, DMSO-D6) δ 1.68 (s, 6H), 3.17 (s, 3H), 3.85 (s, 2H), 6.62 (d, 1H), 7.63 (d, 1H), 8.90 (s, 1H); LCMS (system 10): R$_t$=3.29 min; m/z 240 [M+H]$^+$.

Preparation 259: 2-Chloro-5-iodo-7-(2-methoxy-1,1-dimethyl-ethyl)-7H-pyrrolo[2,3-d]pyrimidine

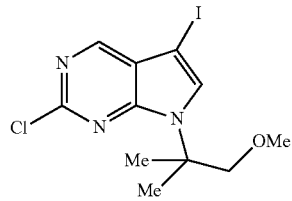 [SMILES: COCC(C)(C)n1cc(I)c2cnc(Cl)nc21]

The title compound was prepared according to the method described for Preparation 63 using 2-Chloro-7-(2-methoxy-1,1-dimethyl-ethyl)-7H-pyrrolo[2,3-d]pyrimidine (Preparation 258) to afford the title compound as yellowish solid in 75% yield, 2.3 g.

$^1$H NMR (400 MHz, DMSO-D6) δ: 1.67 (s, 6H), 3.17 (s, 3H), 3.83 (s, 2H), 7.81 (s, 1H), 8.64 (s, 1H); LCMS (system 10): R$_t$=3.65 min; m/z 365.8 [M+H]$^+$.

Preparation 260: (5-Bromo-pyridin-3-yl)-[2-chloro-7-(2-methoxy-1,1-dimethyl-ethyl)-7H-pyrrolo[2,3-d]pyrimidin-5-yl]-methanone

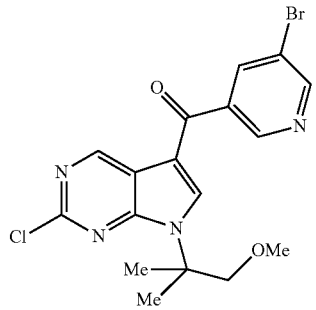 [SMILES: COCC(C)(C)n1cc(C(=O)c2cncc(Br)c2)c2cnc(Cl)nc21]

The title compound was prepared according to the method described for Preparation 64 using 2-Chloro-5-iodo-7-(2-methoxy-1,1-dimethyl-ethyl)-7H-pyrrolo[2,3-d]pyrimidine (Preparation 259) and 5-Bromo-N-methoxy-N-methyl-nicotinamide to afford the title compound as yellow gum in 34% yield, 900 mg.

$^1$H NMR (400 MHz, DMSO-D6) δ: 1.73 (s, 6H), 3.21 (s, 3H), 3.90 (s, 2H), 8.22 (s, 1H), 8.42 (t, 1H), 8.98 (t, 2H), 9.35 (s, 1H).

Preparation 261: [2-Amino-7-(2-methoxy-1,1-dimethyl-ethyl)-7H-pyrrolo[2,3-d]pyrimidin-5-yl]-(5-amino-pyridin-3-yl)-methanone

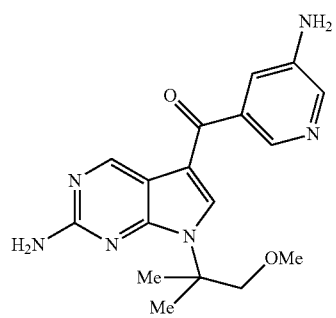 [SMILES: COCC(C)(C)n1cc(C(=O)c2cncc(N)c2)c2cnc(N)nc21]

The title compound was prepared according to the method described for Preparation 65 using (5-Bromo-pyridin-3-yl)-[2-chloro-7-(2-methoxy-1,1-dimethyl-ethyl)-7H-pyrrolo[2,3-d]pyrimidin-5-yl]-methanone (Preparation 260) to afford the title compound as yellow solid in 41% yield, 300 mg.

$^1$H NMR (400 MHz, DMSO-D6) δ: 1.68 (s, 6H), 3.19 (s, 3H), 3.89 (s, 2H), 5.61 (s, 2H), 6.54 (s, 2H), 7.23 (s, 1H), 7.55 (s, 1H), 8.11 (dd, 2H), 8.93 (s, 1H); LCMS (system 10): R$_t$=2.40 min; m/z 341.2 [M+H]$^+$.

Preparation 262: 5-Iodo-7-(2-methoxy-1,1-dimethyl-ethyl)-7H-pyrrolo[2,3-d]pyrimidine

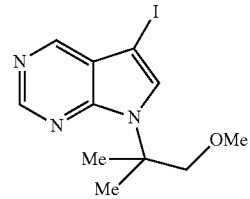 [SMILES: COCC(C)(C)n1cc(I)c2cncnc21]

An anhydrous THF (100 mL) solution of 2-(5-Iodo-pyrrolo[2,3-d]pyrimidin-7-yl)-2-methyl-propan-1-ol (Preparation 22) (32 g, 100.91 mmol) was added slowly to a suspension of NaH (60% in paraffin oil, 2.98 g, 121.13 mmol) in anhydrous THF (200 mL) at 00° C. under nitrogen. The mixture was warmed to room temperature and stirred for another 30 minutes and again cooled to 00° C. and methyl iodide (19 mL, 302.82 mmol) was added drop wise. The reaction mixture was stirred at room temperature for 2 hours, quenched with aqueous saturated ammonium chloride, and extracted with ethyl acetate. The organic layer was washed with brine, dried over sodium sulphate and evaporated to dryness in vacuo. The crude material was purified by column chromatography on silica (100-200 mesh, gradient of hexane: EtOAc 100:0 to 70:30) to afford the title compound as a yellow sticky solid in 22% yield, 7.5 g.

<sup>1</sup>H NMR (400 MHz, DMSO-D6) δ: 1.70 (s, 6H), 3.15 (s, 3H), 3.89 (s, 2H), 7.77 (s, 1H), 8.70 (s, 1H), 8.82 (s, 1H); LCMS (system 10): $R_t$=3.42 min; m/z 331.6 [M+H]$^+$.

Preparation 263: (5-Bromo-pyridin-3-yl)-[7-(2-methoxy-1,1-dimethyl-ethyl)-7H-pyrrolo[2,3-d]pyrimidin-5-yl]-methanone

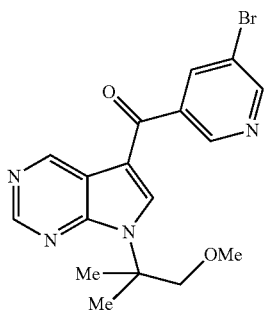 [SMILES: COCC(C)(C)n1cc(C(=O)c2cncc(Br)c2)c2cncnc21]

The title compound was prepared according to the method described for Preparation 64 using 5-Iodo-7-(2-methoxy-1,1-dimethyl-ethyl)-7H-pyrrolo[2,3-d]pyrimidine (Preparation 262) and 5-Bromo-N-methoxy-N-methyl-nicotinamide to afford the title compound as light brown gum in 51% yield, 3 g.

<sup>1</sup>H NMR (400 MHz, DMSO-d$_6$) δ: 1.76 (s, 6H), 3.19 (s, 3H), 3.96 (s, 2H), 8.17 (s, 1H), 8.42 (t, 1H), 8.98 (brs, 2H), 9.00 (s, 1H), 9.47 (s, 1H); LCMS (system 10): $R_t$=3.13 min; m/z 388.6, 390.6 [M+H]$^+$.

Preparation 264: 2-(3,5-Difluoro-pyridin-2-yl)-malonic acid diethyl ester

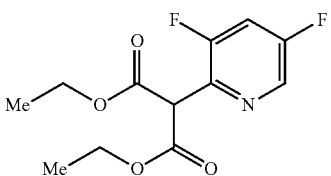 [SMILES: CCOC(=O)C(C(=O)OCC)c1ncc(F)cc1F]

To a stirred solution of 2,3,5-trifluoro-pyridine (2 g, 15.02 mmol) in dimethyl sulfoxide (20 mL) was added diethyl malonate (4.60 g, 28.72 mmol). Then cesium carbonate (9.35 g, 28.72 mmol) was added and the reaction mixture was heated to 110° C. for 16 hours. The reaction mixture was cooled to room temperature and diluted with ethyl acetate (100 mL). The organic layer was washed with water (2×25 mL), brine (25 mL), dried over sodium sulphate and evaporated in vacuo to afford the title compound as oil in 85% yield, 3.5 g.

<sup>1</sup>H NMR (400 MHz, CDCl$_3$): δ: 1.25-1.30 (m, 6H), 4.20-4.29 (m, 4H), 4.88 (s, 1H), 7.77-7.81 (m, 1H), 8.01 (s, 1H).

Preparation 265: (3,5-Difluoro-pyridin-2-yl)-acetic acid

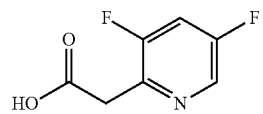 [SMILES: O=C(O)Cc1ncc(F)cc1F]

To a stirred solution of 2-(3,5-difluoro-pyridin-2-yl)-malonic acid diethyl ester (1 g, 3.56 mmol) (Preparation 264) in THF (15 mL) was added a solution of lithium hydroxide monohydrate (462 mg, 10.4 mmol) in water (4 mL) dropwise at 0° C. and the mixture heated to reflux for 2 hours. The reaction mixture was cooled to room temperature, acidified (pH ~3) with 2N hydrochloric acid and extracted with 20% isopropanol-dichloromethane (5×20 mL). The combined organic layers were dried (Na$_2$SO$_4$) and evaporated in vacuo. The crude material was purified by column chromatography on silica gel (gradient of DCM: MeOH 100:0 to 95:5) to afford the title compound as a solid in 53% yield, 336 mg.

<sup>1</sup>H NMR (400 MHz, DMSO-D6) δ 3.32 (s, 2H), 7.74-7.79 (m, 1H), 7.99 (t, 1H); LCMS (system 10): $R_t$=0.65 min; m/z 174 [M+H]$^+$.

Preparation 266: (4-Nitro-phenyl)-acetic acid ethyl ester

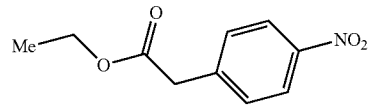 [SMILES: CCOC(=O)Cc1ccc([N+](=O)[O-])cc1]

To a stirred solution of (4-nitro-phenyl)-acetic acid (3 g, 16.4 mmol) in ethanol (30 mL) was added sulphuric acid (1 mL) and the reaction mixture was heated to reflux for 16 hours. The reaction mixture was neutralized with 2N aq. NaOH solution and extracted with EtOAc (3×50 mL). The combined organic layers were dried (Na$_2$SO$_4$) and evaporated in vacuo to afford the title compound as a light yellow oil in 98% yield, 3.4 g.

<sup>1</sup>H NMR (400 MHz, CDCl$_3$) δ: 1.25 (t, 3H), 3.71 (s, 2H), 4.16 (q, 2H), 7.45 (d, 2H), 8.18 (d, 2H).

Preparation 267: (4-Amino-phenyl)-acetic acid ethyl ester

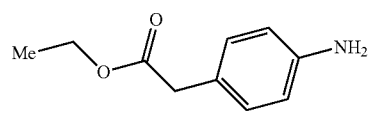 [SMILES: CCOC(=O)Cc1ccc(N)cc1]

A solution of (4-nitro-phenyl)-acetic acid ethyl ester (Preparation 266, 3.4 g, 16.1 mmol) in methanol (100 mL) was degassed with argon for 15 min, treated with 10% palladium on charcoal (700 mg), and then stirred at room temperature under hydrogen (balloon pressure) for 16 hours. The reaction mixture was filtered through celite, washed with methanol (2×20 mL) and the filtrate was evaporated in vacuo to afford the title compound as an oil in 96% yield, 2.8 g.

$^1$H NMR (400 MHz, CDCl$_3$) δ: 1.23 (t, 3H), 3.47 (s, 2H), 3.60 (br s, 2H), 4.11 (q, 2H), 6.63 (d, 2H), 7.05 (d, 2H).

Preparation 268: (4-Formylamino-phenyl)-acetic acid ethyl ester

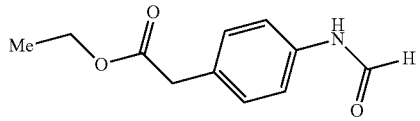 [SMILES: CCOC(=O)Cc1ccc(NC=O)cc1]

A mixture of acetic anhydride (0.33 mL, 3.57 mmol) and formic acid (0.17 mL, 4.46 mmol) was heated at 60° C. for 2 hours. The reaction mixture was cooled to 0° C., a solution of (4-amino-phenyl)-acetic acid ethyl ester (Preparation 267, 500 mg, 2.79 mmol) in THF (10 mL) was added slowly to the reaction mixture and the reaction was allowed to stir at room temperature for 16 hours. The reaction mixture was neutralized with sat. aq. Na$_2$CO$_3$ solution and extracted with diethyl ether (2×25 mL). The combined organic layers were dried (Na$_2$SO$_4$) and evaporated in vacuo. The crude material was purified by column chromatography on silica gel (gradient of DCM:MeOH 100:0 to 98:2) to afford the title compound as an oil in 93% yield, 500 mg.

$^1$H NMR (400 MHz, DMSO-d$_6$) δ: 1.17 (t, 3H), 3.59 (s, 2H), 4.05 (q, 2H), 7.20 (d, 2H), 7.52 (d, 2H), 8.25 (d, 1H), 10.15 (s, 1H).

Preparation 269: (4-Methylamino-phenyl)-acetic acid ethyl ester

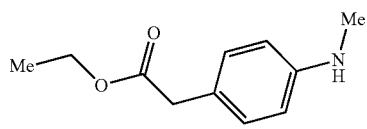 [SMILES: CCOC(=O)Cc1ccc(NC)cc1]

To a stirred solution of (4-formylamino-phenyl)-acetic acid ethyl ester (Preparation 268, 500 mg, 2.41 mmol) in THF (10 mL) was added borane-dimethyl sulphide complex (0.3 mL, 3.13 mmol) at 0° C. and the mixture stirred at room temperature for 1 hour. The reaction mixture was quenched with MeOH (5 mL) and evaporated in vacuo. The crude material was purified by column chromatography on silica gel (gradient of hexane:EtOAc 100:0 to 75:25) to afford the title compound as an oil in 91% yield, 460 mg.

$^1$H NMR (400 MHz, CDCl$_3$) δ: 1.23 (t, 3H), 2.81 (s, 3H), 3.48 (s, 2H), 3.66 (br s, 1H), 4.11 (q, 2H), 6.56 (d, 2H), 7.09 (d, 2H).

Preparation 270: [4-(Methanesulfonyl-methyl-amino)-phenyl]-acetic acid ethyl ester

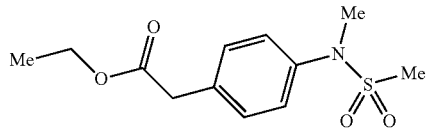 [SMILES: CCOC(=O)Cc1ccc(N(C)S(C)(=O)=O)cc1]

To a stirred solution of (4-methylamino-phenyl)-acetic acid ethyl ester (Preparation 269, 418 mg, 2.16 mmol) in pyridine (4 mL) was added methanesulfonyl chloride (0.25 mL, 3.24 mmol) and the mixture stirred at room temperature for 3 hours. The reaction mixture was quenched with water (10 mL) and extracted with EtOAc (3×15 mL). The combined organic layers were washed with water (10 mL), brine (10 mL), dried (Na$_2$SO$_4$) and evaporated in vacuo to afford the title compound as a gum in 78% yield, 460 mg.

$^1$H NMR (400 MHz, CDCl$_3$) δ: 1.25 (t, 3H), 2.82 (s, 3H), 3.30 (s, 3H), 3.59 (s, 2H), 4.14 (q, 2H), 7.28-7.33 (m, 4H).

Preparation 271: [4-(Methanesulfonyl-methyl-amino)-phenyl]-acetic acid

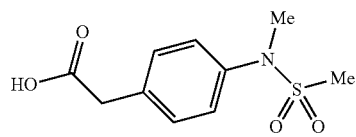 [SMILES: CN(c1ccc(CC(=O)O)cc1)S(C)(=O)=O]

The title compound was prepared according to the method described for Preparation 265 using [4-(methanesulfonyl-methyl-amino)-phenyl]-acetic acid ethyl ester (Preparation 270) to afford the title compound as a solid in 85% yield, 350 mg.

$^1$H NMR (400 MHz, DMSO-D6) δ: 2.92 (s, 3H), 3.21 (s, 3H), 3.55 (s, 2H), 7.28 (d, 2H), 7.33 (d, 2H); LCMS (system 10): R$_t$=1.05 min; m/z 244 [M+H]$^+$.

Preparation 272: 2-Iodo-5-methyl-pyridine

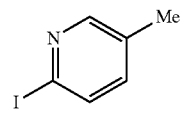

To a stirred solution of 2-bromo-5-methyl-pyridine (2 g, 11.6 mmol) in acetonitrile (25 mL) was added sodium iodide (6.97 g, 46.5 mmol) and the mixture heated to reflux. Acetyl chloride (1.24 mL, 17.44 mmol) was added dropwise under reflux conditions and the reaction mixture was heated to reflux for 16 hours. The reaction mixture was cooled to room temperature, quenched with sat. aq. Na$_2$CO$_3$ solution (15 mL) and extracted with EtOAc (3×25 mL). The combined organic layers were washed with brine (10 mL), dried (Na$_2$SO$_4$) and evaporated in vacuo to afford the title compound as an oil in 55% yield, 1.4 g.

LCMS (system 10): R$_t$=3.10 min; m/z 220 [M+H]$^+$.

Preparation 273: 2-(5-Methyl-pyridin-2-yl)-malonic acid diethyl ester

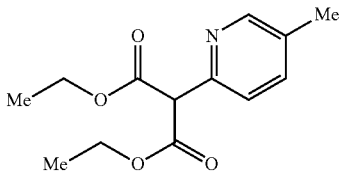 [SMILES: CCOC(=O)C(C(=O)OCC)c1ccc(C)cn1]

To a stirred solution of 2-Iodo-5-methyl-pyridine (Preparation 272, 1 g, 4.57 mmol) and diethyl malonate (2.08 mL, 13.70 mmol) in anhydrous dioxane (12 mL) was added cesium carbonate (4.46 gm, 13.7 mmol) and the solution was degassed with argon for min. CuI (174 mg, 0.91 mmol) and picolinic acid (225 mg, 1.83 mmol) were added and the resultant mixture was heated in a sealed tube at 100° C. for 16 hours. The reaction mixture was cooled to room temperature, quenched with water (25 mL) and extracted with EtOAc (3×25 ml). The combined organic layers were washed with water (2×10 mL) and brine (10 mL), dried ($Na_2SO_4$) and evaporated in vacuo. The crude material was purified by column chromatography on silica gel (gradient of hexane: EtOAc 100:0 to 90:10) to afford the title compound as an oil in 23% yield, 300 mg.

$^1$H NMR (400 MHz, DMSO-D6) δ: 1.15-1.18 (m, 6H), 2.29 (s, 3H), 4.12-4.17 (m, 4H), 5.01 (s, 1H), 7.30 (d, 1H), 7.62 (dd, 1H), 8.34 (s, 1H).

Preparation 274: (5-Methyl-pyridin-2-yl)-acetic acid

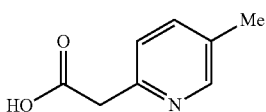 [SMILES: Cc1ccc(CC(=O)O)nc1]

The title compound was prepared according to the method described for Preparation 265 using 2-(5-methyl-pyridin-2-yl)-malonic acid diethyl ester (Preparation 273) to afford the title compound as a solid in 83% yield, 100 mg.

$^1$H NMR (400 MHz, DMSO-D6) δ: 2.26 (s, 3H), 3.64 (s, 2H), 7.21 (d, 1H), 7.53 (d, 1H), 8.29 (s, 1H); LCMS (system 10): $R_t$=0.73 min; m/z 152 [M+H]$^+$.

Preparation 275: [1,2,4]triazolo[1,5-a]pyridine-7-carboxylic acid

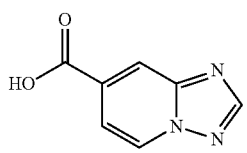 [SMILES: O=C(O)c1ccn2ncnc2c1]

To a solution of methyl 2-aminoisonicotinate (28.8 g, 191 mmol) in DMF (97.5 mL) was added DMF-DMA (70.6 mL, 496 mmol) and the mixture heated to 130° C. for 12 hours. The mixture was then concentrated to give a residue. To the residue was added MeOH (381 mL), followed by $NH_2OHSO_4$ (31.9 g, 248 mmol) and the resulting mixture was stirred at room temperature overnight. The reaction mixture was concentrated to give methyl[1,2,4]triazolo[1,5-a]pyridine-7-carboxylate in 18% yield, 6 g. To a solution of methyl[1,2,4]triazolo[1,5-a]pyridine-7-carboxylate (3 g, 16 mmol) in methanol was added 1M aq. LiOH (70 mL) and the resulting mixture stirred for 10 hours at room temperature. The pH was adjusted to 5-6 using aq. HCl and the whole mixture extracted with EtOAc (30 mL×3). The combined organic layers were dried ($Na_2SO_4$) and concentrated in vacuo to give the title compound as a white solid in 38% yield, 1.05 g. 1H NMR (400 MHz, DMSO-d6) δ: 7.56-7.58 (m, 1H), 8.32 (m, 1H), 8.66 (m, 1H), 9.04-9.06 (m, 1H), 13.5-14.0 (s, 1H).

Preparation 276: 1-methyl-1H-pyrrolo[2,3-c]pyridine-3-carboxylic acid

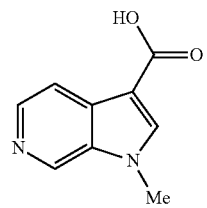 [SMILES: Cn1cc(C(=O)O)c2ccncc21]

1-methyl-1H-pyrrolo[2,3-c]pyridine-3-carbaldehyde (WO 05066132) (6.5 g, 40.6 mmol) was dissolved in a mixture of THF (120 mL) and tert-butyl alcohol (40 mL) under nitrogen. 2-Methyl-2-butene (120 mL of a 2M solution in THF, 46 mmol) was added followed by a solution of $NaClO_2$ (11.0 g, 122 mmol) and $NaH_2PO_4$ (21.9 g, 183 mmol) in water (30 mL). The reaction mixture was stirred at room temperature overnight under nitrogen. The reaction mixture was concentrated in vacuo to remove organic solvents, and the residue was filtered. The precipitate contained the title compound as a white solid in 57% yield, 4.1 g.

1H NMR (400 MHz, DMSO-d6) δ: 3.96 (S, 3H), 7.87-7.89 (d, 1H), 8.23 (s, 1H), 8.28 (d, 1H), 8.91 (s, 1H), 12.3 (s, 1H).

Preparation 277: 2-(4-Cyano-phenyl)-N-{5-[7-(2-trimethylsilanyl-ethoxymethyl)-7H-pyrrolo[2,3-d]pyrimidine-5-carbonyl]-pyridin-3-yl}-acetamide

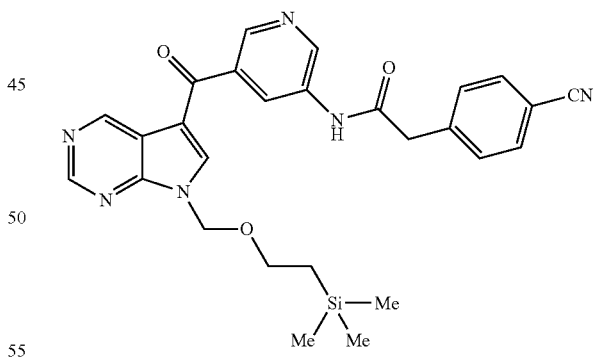

The title compound was prepared according to the method described for Example 1 using (5-Amino-pyridin-3-yl)-[7-(2-trimethylsilanyl-ethoxymethyl)-7H-pyrrolo[2,3-d]pyrimidin-5-yl]-methanone (Preparation 103) and 4-cyanophenylacetic acid to afford the title compound as an off-white solid in 71% yield, 235 mg.

$^1$H NMR (400 MHz, DMSO-D6) δ: −0.11 (s, 9H), 0.82 (t, 2H), 3.59 (t, 2H), 3.87 (s, 2H), 5.70 (s, 2H), 7.55 (d, 2H), 7.82 (d, 2H), 8.47 (s, 1H), 8.61 (s, 1H), 8.73 (s, 1H), 8.98 (s, 1H), 9.04 (s, 1H), 9.48 (s, 1H), 10.75 (s, 1H); LCMS (System 10): $R_t$=3.25 min; m/z 513 [M+H]$^+$.

Preparation 278: 2-Methyl-2-pyrrolo[2,3-d]pyrimidin-7-yl-propane-1,3-diol

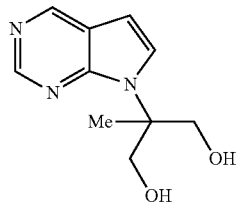 [SMILES: CC(CO)(CO)n1ccc2cncnc21]

The title compound was prepared according to the method described for Preparation 246 using 2-(4-Chloro-pyrrolo[2,3-d]pyrimidin-7-yl)-2-methyl-propane-1,3-diol (Preparation 217) to afford the title compound as an off-white solid in 93% yield, 800 mg.

$^1$H NMR (400 MHz, DMSO-D6) δ: 1.65 (s, 3H), 3.87-3.91 (m, 2H), 4.10-4.14 (m, 2H), 4.94 (t, 2H), 6.55 (d, 1H), 7.63 (d, 1H), 8.72 (s, 1H), 8.95 (s, 1H).

Preparation 279: N-(5-{7-[2-(tert-Butyl-dimethyl-silanyloxy)-1,1-dimethyl-ethyl]-7H-pyrrolo[2,3-d]pyrimidine-5-carbonyl}-pyridin-3-yl)-2-(4-cyclopropyl-pyrazol-1-yl)-acetamide

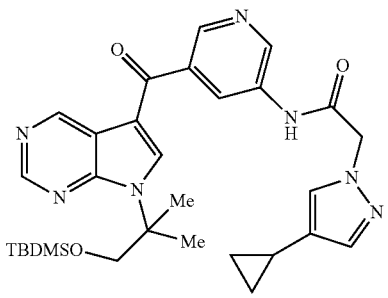 [SMILES: CC(C)(CO[Si](C)(C)C(C)(C)C)n1cc(C(=O)c2cncc(NC(=O)Cn3cc(C4CC4)cn3)c2)c2cncnc21]

The title compound was prepared according to the method described for Example 1 using (5-Amino-pyridin-3-yl)-{7-[2-(tert-butyl-dimethyl-silanyloxy)-1,1-dimethyl-ethyl]-7H-pyrrolo[2,3-d]pyrimidin-5-yl}-methanone (Preparation 38) and (4-Cyclopropyl-1H-pyrazol-1-yl)acetic acid (Preparation 88) to afford the title compound as an an off-white solid in 41% yield, 55 mg.

$^1$H NMR (400 MHz, DMSO-D6) δ: −0.24 (s, 6H), 0.46 (m, 2H), 0.60 (s, 9H), 0.79 (m, 2H), 1.67 (m, 1H), 1.75 (s, 6H), 4.11 (s, 2H), 4.98 (s, 2H), 7.26 (s, 1H), 7.52 (s, 1H), 8.16 (s, 1H), 8.46 (s, 1H), 8.71 (d, 1H), 8.91 (d, 1H), 8.99 (s, 1H), 9.47 (s, 1H), 10.75 (s, 1H); LCMS (System 10): R$_t$=3.78 min; m/z 574 [M+H]$^+$.

Preparation 280: Bicyclo[1.1.1]pent-1-yl-(5-bromo-2-chloro-pyrimidin-4-yl)-amine

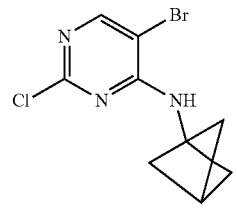 [SMILES: Clc1ncc(Br)c(NC23CC4CC42C3)n1]

To a solution of 5-Bromo-2,4-dichloro-pyrimidine (6 g, 26.3 mmol) and bicyclo[1.1.1]pent-1-ylamine (4.7 g, 39.5 mmol) in acetonitrile (60 mL), was added TEA (16.5 mL, 118 mmol), and the mixture was stirred at 25° C. for 18 hours. The volatiles were removed in vacuo and the residue partitioned between water and EtOAc. The organic phase was dried (Na$_2$SO$_4$) and evaporated in vacuo. Purification by column chromatography on silica gel (EtOAc:Hexane 1:99) afforded the title compound as a white solid in 82% yield, 4.8 g.

$^1$H NMR (400 MHz, DMSO-D6) δ: 2.10 (d, 6H), 2.48-2.50 (m, 1H), 8.26 (d, 2H); LCMS (System 10): R$_t$=3.64 min; m/z 276 [M+H]$^+$.

Preparation 281: Bicyclo[1.1.1]pent-1-yl-[2-chloro-5-((Z)-2-ethoxy-vinyl)-pyrimidin-4-yl]-amine

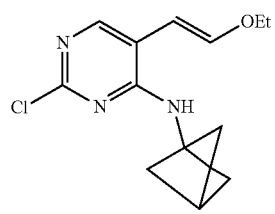 [SMILES: CCO/C=C/c1cnc(Cl)nc1NC12CC3CC31C2]

To a stirred solution of Bicyclo[1.1.1]pent-1-yl-(5-bromo-2-chloro-pyrimidin-4-yl)-amine (Preparation 280, 2 g, 7.29 mmol) in dry toluene (70 mL) was added (Z)-1-ethoxy-2-(tributylstannyl)ethene (2.7 mL, 8.03 mmol). The reaction mixture was purged with N$_2$ for min and then Pd(PPh$_3$)$_4$ (421 mg, 0.36 mmol) was added, followed by degassing for another 20 min and heating to 110° C. under N$_2$ overnight. The reaction was cooled to room temperature, quenched with a 2M solution of KF and filtered through a pad of Celite. The filtrate was partitioned between water (50 mL) and EtOAc (200 mL). The organic phase was washed with brine (2×25 mL), dried (Na$_2$SO$_4$) and evaporated in vacuo. The crude residue was purified by column chromatography on silica gel (EtOAc: Hexane 18: 82) to afford the title compound as a pale green solid in 77% yield, 1.5 g.

$^1$H NMR (400 MHz, DMSO-D6) δ: 1.24 (t, 3H), 2.08 (d, 6H), 2.47 (m, 1H), 3.99 (q, 2H), 5.17 (d, 1H), 6.55 (d, 1H), 7.90 (s, 1H), 8.39 (s, 1H); LCMS (System 10): R$_t$=3.54 min; m/z 266 [M+H]$^+$.

Preparation 282: 7-Bicyclo[1.1.1]pent-1-yl-2-chloro-7H-pyrrolo[2,3-d]pyrimidine

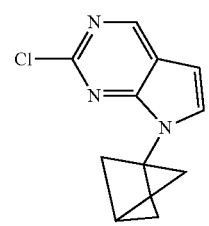 [SMILES: Clc1ncc2ccn(C34CC5CC53C4)c2n1]

The title compound was prepared according to the method described for Preparation 62 using bicyclo[1.1.1]pent-1-yl-[2-chloro-5-((Z)-2-ethoxy-vinyl)-pyrimidin-4-yl]-amine (Preparation 281) to afford the title compound as an off-white solid in 89% yield, 1.4 g. $^1$H NMR (400 MHz, DMSO-D6) δ:

2.41 (d, 6H), 2.69 (m, 1H), 6.67 (d, 1H), 7.61 (d, 1H), 8.92 (s, 1H); LCMS (System 10): R$_t$=3.45 min; m/z 220 [M+H]$^+$.

Preparation 283: 7-Bicyclo[1.1.1]pent-1-yl-2-chloro-5-iodo-7H-pyrrolo[2,3-d]pyrimidine

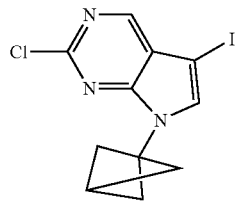 [SMILES: Clc1ncc2c(I)cn(C34CC(C3)C4)c2n1]

The title compound was prepared according to the method described for Preparation 63 using 7-bicyclo[1.1.1]pent-1-yl-2-chloro-7H-pyrrolo[2,3-d]pyrimidine (Preparation 282) to afford the title compound as a brown solid in 72% yield, 1.3 g.
$^1$H NMR (400 MHz, DMSO-D6) δ: 2.40 (d, 6H), 2.68 (m, 1H), 7.90 (s, 1H), 8.67 (s, 1H); LCMS (System 10): R$_t$=3.89 min; m/z 346 [M+H]$^+$.

Preparation 284: (7-Bicyclo[1.1.1]pent-1-yl-2-chloro-7H-pyrrolo[2,3-d]pyrimidin-5-yl)-(5-bromo-pyridin-3-yl)-methanone

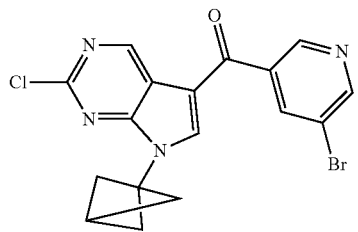 [SMILES: O=C(c1cncc(Br)c1)c1cn(C23CC(C2)C3)c2nc(Cl)ncc12]

The title compound was prepared according to the method described for Preparation 64 using 7-bicyclo[1.1.1]pent-1-yl-2-chloro-5-iodo-7H-pyrrolo[2,3-d]pyrimidine (Preparation 283) to afford the title compound as an off-white solid in 58% yield, 1.1 g. $^1$H NMR (400 MHz, DMSO-D6) δ: 2.47 (d, 6H), 2.72 (m, 1H), 8.40-8.42 (m, 2H), 8.99-9.00 (m, 2H), 9.33 (s, 1H); LCMS (System 10): R$_t$=3.73 min; m/z 405 [M+H]$^+$.

Preparation 285: [7-Bicyclo[1.1.1]pent-1-yl-2-(4-methoxy-benzylamino)-7H-pyrrolo[2,3-d]pyrimidin-5-yl]-(5-bromo-pyridin-3-yl)-methanone

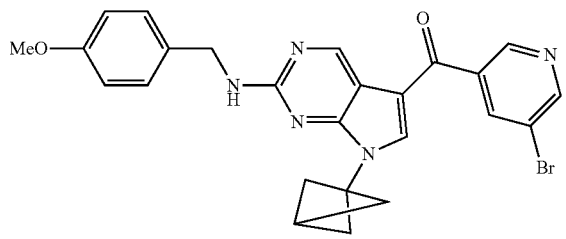 [SMILES: COc1ccc(CNc2ncc3c(C(=O)c4cncc(Br)c4)cn(C45CC(C4)C5)c3n2)cc1]

To a solution of (7-Bicyclo[1.1.1]pent-1-yl-2-chloro-7H-pyrrolo[2,3-d]pyrimidin-5-yl)-(5-bromo-pyridin-3-yl)-methanone (Preparation 284, 1.1 g, 2.72 mmol) and 4-methoxy benzyl amine (1.06 mL, 8.16 mmol) in dioxane (40 mL), DIPEA (1.7 mL, 10.8 mmol) was added and mixture was heated at 110° C. under microwave irradiation for 6 hours. The volatiles were removed in vacuo and the residue was partitioned between water (50 mL) ethyl acetate (150 mL). Organic phase was dried over sodium sulphate, evaporated in vacuo and purified by column chromatography on silica gel (gradient of EA:Hexane 25:75) to afford the title compound as off white solid in 84% yield, 1.15 g.
$^1$H NMR (400 MHz, DMSO-D6) δ: 2.35 (d, 6H), 2.64 (m, 1H), 3.70 (s, 3H), 4.45 (d, 2H), 6.85 (d, 2H), 7.27 (d, 2H), 7.75 (s, 2H), 8.32 (m, 1H), 8.91-8.94 (m, 2H); LCMS (System 10): R$_t$=3.81 min; m/z 504.2 [M+H]$^+$.

Preparation 286: [5-(Benzhydrylidene-amino)-pyridin-3-yl]-[7-bicyclo[1.1.1]pent-1-yl-2-(4-methoxy-benzylamino)-7H-pyrrolo[2,3-d]pyrimidin-5-yl]-methanone

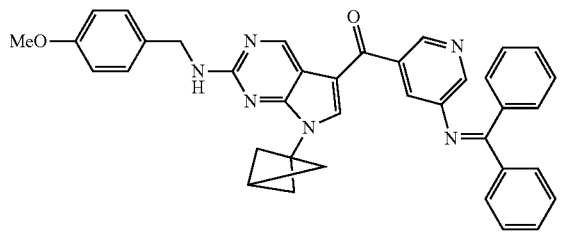 [SMILES: COc1ccc(CNc2ncc3c(C(=O)c4cncc(N=C(c5ccccc5)c5ccccc5)c4)cn(C45CC(C4)C5)c3n2)cc1]

To a stirred solution of [7-Bicyclo[1.1.1]pent-1-yl-2-(4-methoxy-benzylamino)-7H-pyrrolo[2,3-d]pyrimidin-5-yl]-(5-bromo-pyridin-3-yl)-methanone (Preparation 285, 1.18 g, 2 mmol) and benzophenoneimine (0.50 mL, 3 mmol) in dry toluene (50 mL), cesium carbonate (3.2 g, 10 mmol) was added and the reaction mixture was purged under N$_2$ for 20 min and then Pd(OAc)$_2$ (45 mg, 0.2 mmol) and BINAP (125 mg, 0.2 mmol) were added followed by degassing for another 10 min and refluxing overnight. The reaction mass was cooled to room temperature and filtered through a pad of Celite. The filtrate was partitioned between water (25 mL) and EtOAc (100 mL). The organic phase was washed with brine (10 mL), dried (Na$_2$SO$_4$) and evaporated in vacuo. Purification by column chromatography on silica gel (EtOAc:Hexane 25:75) afforded the title compound as a yellow solid in 85% yield, 1.1 g.
$^1$H NMR (400 MHz, DMSO-D6) δ: 2.36 (d, 6H), 2.65 (m, 1H), 3.70 (s, 3H), 4.44 (d, 2H), 6.84 (d, 2H), 7.24-7.29 (m, 4H), 7.36-7.37 (m, 3H), 7.50-7.52 (m, 4H), 7.58 (m, 1H), 7.70-7.72 (m, 3H), 8.15 (d, 1H), 8.48 (d, 1H), 8.89 (s, 1H); LCMS (System 9): R$_t$=4.02 min; m/z 605 [M+H]$^+$.

Preparation 287: (5-Amino-pyridin-3-yl)-[7-bicyclo[1.1.1]pent-1-yl-2-(4-methoxy-benzylamino)-7H-pyrrolo[2,3-d]pyrimidin-5-yl]-methanone

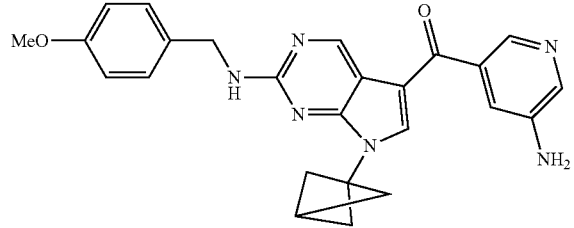 [SMILES: COc1ccc(CNc2ncc3c(C(=O)c4cncc(N)c4)cn(C45CC(C4)C5)c3n2)cc1]

To a solution of [5-(Benzhydrylidene-amino)-pyridin-3-yl]-[7-bicyclo[1.1.1]pent-1-yl-2-(4-methoxy-benzylamino)-

7H-pyrrolo[2,3-d]pyrimidin-5-yl]-methanone (Preparation 286, 475 mg, 0.78 mmol) in THF (15 mL), citric acid (15 mL of a 1N aq. solution) was added at room temperature and the reaction mixture stirred for 2 hours. The reaction was then quenched with sat. aq. $Na_2CO_3$ solution and extracted with EtOAc (2×25 mL). The combined organic phases were dried ($Na_2SO_4$) and evaporated in vacuo. Purification by column chromatography on neutral alumina (Methanol:DCM 3:97) to afford the title compound as a pale yellow solid in 92% yield, 320 mg.

$^1$H NMR (400 MHz, DMSO-D6) δ: 2.36 (d, 6H), 2.64 (m, 1H), 3.70 (s, 3H), 4.45 (d, 2H), 5.59 (s, 2H), 6.84 (d, 2H), 7.22 (m, 1H), 7.28 (d, 2H), 7.57 (s, 1H), 7.72 (br s, 1H), 8.10-8.12 (m, 2H), 8.92 (s, 1H); LCMS (System 10): $R_t$=3.10 min; m/z 441 [M+H]$^+$.

Preparation 288:
1-Cyclobutyl-1H-imidazole-4-carboxylic acid hydrochloride

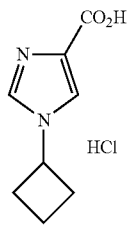 [SMILES: O=C(O)c1cn(C2CCC2)cn1 ; Cl]

Ethyl 3-(dimethylamino)-2-isocyanoacrylate (WO 2007042545) (45 g, 0.27 mol) was added to cyclobutylamine (50 g, 0.70 mol) and heated to reflux for 2 hours. The solution was then cooled and concentrated. The residue was purified by column chromatography over silica gel (3:1 EtOAc:Heptane). The oily residue was triturated with TBME:heptane (1:1) and the resulting solid was collected and dried, giving 1-cyclobutyl-1H-imidazole-4-carboxylic acid ethyl ester (35 g, 67%, second crop not harvested). 1-Cyclobutyl-1H-imidazole-4-carboxylic acid ethyl ester (35 g, 0.21 mol) was dissolved in 6 N HCl (300 mL) and refluxed for 1 day. The solution was concentrated to dryness in vacuo. The solid was azeotroped with toluene, triturated with toluene and then dried under vacuum, giving the title compound 88% yield, 37.2 g, m/z 167 [M+H]$^+$.

Preparation 289:
(2-Methylimidazo[2,1-b][1,3]thiazol-6-yl)acetic Acid Hydrochloride

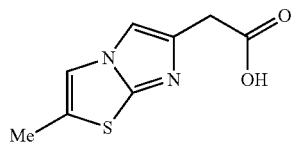 [SMILES: Cc1cn2cc(CC(=O)O)nc2s1]

Ethyl 4-bromo-3-oxobutanoate (92 g, 0.35 mol) was added to a solution of 5-methylthiazol-2-amine (40 g, 0.35 mol) in acetone (400 mL). The mixture was left to stand overnight and then evaporated to give 2-amino-3-(4-ethoxy-2,4-dioxobutyl)-5-methylthiazol-3-ium bromide in 82% yield, 101 g. 2-amino-3-(4-ethoxy-2,4-dioxobutyl)-5-methylthiazol-3-ium bromide (101 g, 0.28 mol) was then refluxed in ethanol (250 mL) for 2 hours. The solvent was then evaporated to give ethyl 2-(2-methylimidazo[2,1-b]thiazol-6-yl)acetate hydrobromide as yellow crystals in 97% yield, 85 g. Solid $K_2CO_3$ was added to a solution of ethyl 2-(2-methylimidazo[2,1-b]thiazol-6-yl)acetate hydrobromide (85 g, 0.28 mol) in water (300 mL) to pH ~8. The product was extracted with chloroform (3×100 mL), and the combined extracts were dried over $Na_2SO_4$ and evaporated to give ethyl 2-(2-methylimidazo[2,1-b]thiazol-6-yl)acetate in 84% yield 52 g. Ethyl 2-(2-methylimidazo[2,1-b]thiazol-6-yl)acetate (52 g, 0.23 mol) was refluxed in 10% aqueous HCl (150 mL) for 2 hours. The solution was evaporated to dryness to give the title compound as brown crystals in 59% yield 32.3 g; m/z 197 [M+H]$^+$.

Preparation 290: 3-Methyl-5-(trifluoromethyl)-1H-pyrazole-4-carboxylic acid

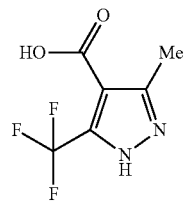 [SMILES: Cc1n[nH]c(C(F)(F)F)c1C(=O)O]

To a solution of benzyl acetoacetate (57.6 g, 300 mmol) in MeOH (50 mL) in a 350 mL pressure vessel was added $H_2NMe$ (150 mL of a 2M solution in MeOH, 300 mmol) and acetic acid (2 mL). The capped vessel was placed in an oil bath at 70° C. and the reaction mixture was stirred for 16 hours. After the mixture had cooled to room temperature, the solvent was evaporated in vacuo leaving a yellow emulsion, which was dissolved in EtOAc (500 mL) and $MgSO_4$ was added to remove water. The drying agent was filtered off, and the solvent evaporated in vacuo to give benzyl 3-(Methylamino)but-2-enoate as a viscous yellow oil in quantitative yield 60 g which was used without further purification.

To a solution of benzyl 3-(methylamino)but-2-enoate (60 g, 300 mmol) and pyridine (27 mL, 330 mmol) in THF (500 mL), cooled to −20° C., was added triflic anhydride (45 mL, 315 mmol) over a 30 min period. During the addition, the temperature was kept below −10° C. The reaction mixture was allowed to warm to room temperature overnight resulting in a yellow clear reaction mixture. The solvent was evaporated in vacuo and the orange residue was taken up in water (1 L) and $Et_2O$ (1 L). Upon shaking the mixture well in a 3-L separatory funnel, all solid material dissolved. The organic layer was separated and washed with water (3×500 mL), brine (500 mL) and dried over $MgSO_4$. Filtration and evaporation of the solvent in vacuo provided benzyl 3-(Methylamino)-2-(trifluoroacetyl)but-2-enoate as an off-white solid in 97% yield, 90 g that was used without additional purification.

To a solution of benzyl 3-(methylamino)-2-(trifluoroacetyl)but-2-enoate (90 g, 300 mmol) in a mixture of THF (900 mL) and acetic acid (100 mL) was added hydrazine monohydrate (14.6 mL, 300 mmol) over a 5 min period. The reaction mixture was heated to reflux for 3 hours, allowed to cool to room temperature and the solvents were evaporated in vacuo to afford a bright yellow mass. The mass was dissolved in EtOAc (1 L) and water (1 L) with gentle heating, allowed to cool to room temperature and the aqueous layer was neutralized to pH 7-8 with $NaHCO_3$. This mixture was transferred to a 3-L separating funnel, the layers were mixed vigorously, separated and the organic layer was washed with water (3×500 mL) dried (MgSO₄), filtered and evaporated in vacuo to give benzyl 3-methyl-5-(trifluoromethyl)-1H-pyrazole-4-carboxylate as an off-white solid in 89% yield 74 g that was used without further purification.

A mixture of benzyl 3-methyl-5-(trifluoromethyl)-1H-pyrazole-4-carboxylate (74 g, 285 mmol), Pd/C (45 g, 10% on C) and EtOAc (1 L) was treated in a Parr apparatus at room temperature with H₂ (15 psi) for 5 hours. The catalyst was filtered off over Celite and the solvent was removed in vacuo. Et₂O (1 L) and water (200 mL) were added and the aqueous layer was made slightly basic (pH 8-9) with Na₂CO₃. The layers were separated and the aqueous layer was extracted with Et₂O (5×200 mL). To the aqueous layer was added dropwise conc. HCl until pH 4-5 and followed by extraction with Et₂O (3×500 mL). The combined organic layers were dried (MgSO₄), filtered, evaporated in vacuo to give the title compound in 74% yield 7.4 g; m.p. 308-310° C. (dec.) m/z 195 [M+H]⁺

Preparation 291: Ethyl[4-(3-Hydroxyphenyl)-1H-1,2,3-triazol-1-yl]acetate

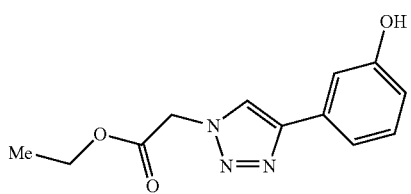 [SMILES: CCOC(=O)Cn1cc(-c2cccc(O)c2)nn1]

Ethyl azidoacetate (14.9 g, 115 mmol) was dissolved in tert-butanol (200 mL), and 95% 3-hydroxybenzonitrile (13.7 g, 110 mmol) was added. A solution of sodium ascorbate (2.18 g, 11 mmol) in water (100 mL) was added, followed by a 0.3 M solution of copper sulfate under argon. The mixture was stirred at room temperature for 12 hours. The solution was evaporated to dryness in vacuo, the residue was dissolved in EtOAc (100 mL), dried (MgSO₄), filtered, evaporated in vacuo to give the title compound as brown crystals in ~100% (27.7 g) yield.
MS m/z 246 [M−H]⁻

Preparation 292: [4-(3-Hydroxyphenyl)-1H-1,2,3-triazol-1-yl]acetic Acid Hydrate

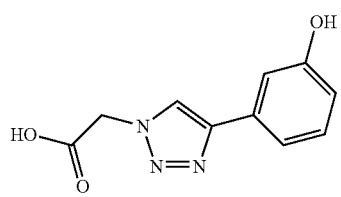 [SMILES: O=C(O)Cn1cc(-c2cccc(O)c2)nn1]

Ethyl[4-(3-Hydroxyphenyl)-1H-1,2,3-triazol-1-yl]acetate (Preparation 291, 27.2 g, 0.110 mol) was dissolved in methanol (200 mL), and a solution of NaOH (4.84 g, 121 mmol) in water (40 mL) was added. The solution was kept at room temperature for 24 hours. Methanol was evaporated in vacuo, water (120 mL) was added, and the solution was refluxed with activated charcoal. The mixture was filtered, and 11 M HCl was added to the filtrate. The mixture was dissolved by addition of water (120 mL) and cooled to carry out the crystallization. The crystals were filtered, washed with water (2×25 mL), and evaporated to dryness to afford the title compound as brown crystals (mp 186.3-188.7° C.) in 99.0% yield 23.9 g. MS m/z 218 [M−H]⁻

Preparation 293: Ethyl[4-(1-hydroxycyclopentyl)-1H-1,2,3-triazol-1-yl]acetate

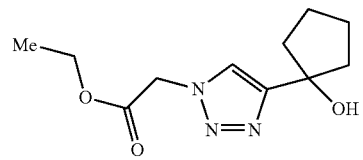 [SMILES: CCOC(=O)Cn1cc(C2(O)CCCC2)nn1]

Ethyl azidoacetate (2.58 g, 20 mmol) was dissolved in tert-butanol (15 mL), and 1-hydroxycyclopentanecarbonitrile (2.20 g, 20 mmol) was added. A solution of sodium ascorbate (0.792 g, 4 mmol) in water (10 mL) followed by a 0.3 M solution of copper sulfate (0.67 mL) was added to the mixture, and stirring continued at room temperature for a further 48 hours. The solution was evaporated to dryness in vacuo and the residue was dissolved in EtOAc (50 mL), dried (MgSO₄), filtered and evaporated in vacuo to afford the title compound as green-yellow crystals in 98% yield, 4.69 g. MS m/z 238 [M−H]⁻

Preparation 294: [4-(1-hydroxycyclopentyl)-1H-1,2,3-triazol-1-yl]acetic acid

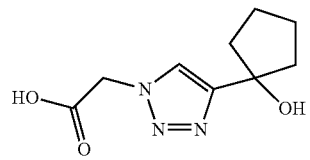 [SMILES: O=C(O)Cn1cc(C2(O)CCCC2)nn1]

To a solution of ethyl[4-(1-hydroxycyclopentyl)-1H-1,2,3-triazol-1-yl]acetate (Preparation 293, 36.4 g, 151 mmol) in water (50 mL), was added a solution of NaOH (7.60 g, 190 mmol) in water (25 mL). The solution was refluxed with activated charcoal, filtered through Celite, and NaHSO₄ (25.8 g, 190 mmol) added. EtOAc (50 mL) was added to the filtrate. The formed precipitate was separated by filtration, dissolved in EtOAc (100 mL), and the solution was filtered. The water layer was extracted with EtOAc (10×50 mL), and the combined extracts were evaporated to a volume of 100 mL. The precipitate was filtered, washed with ethyl acetate (2×50 mL), and concentrated under reduced pressure to afford the title compound as a colorless crystalline substance in 87% yield, 27.8 g. mp 124.0-126.0° C.; MS m/z 212 [M+H]⁺

Preparation 295: Di-tert-butyl 1-(1-methyl-1H-pyrazol-4-yl)hydrazine-1,2-dicarboxylate

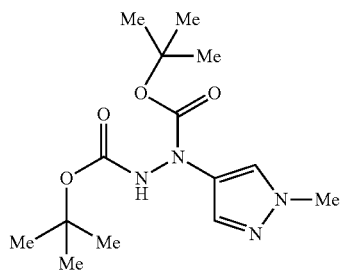 [SMILES: Cn1cc(N(NC(=O)OC(C)(C)C)C(=O)OC(C)(C)C)cn1]

To a solution of 4-iodo-1-methyl-1H-pyrazole (21 g, 0.12 mol) in dry ether (200 mL) at −78° C. was added n-BuLi (84.5 mL of a 2.5 M solution in hexane, 0.18 mol) over a period of 30 min and the mixture stirred for a further 30 min. A solution of di-tert-butyl(Z)-diazene-1,2-dicarboxylate (30.4 g, 0.12 mol) in ether (100 ml) was added to the reaction mixture over a period of 10 min and the resultant mixture stirred at −78° C. for 1 hour. The reaction was warmed to 0° C. and quenched with ice-water and extracted with ether (3×100 mL). The organic layer was separated, dried (Na$_2$SO$_4$) and evaporated in vacuo. The crude material was washed with hexane and then dried under vacuum to give the title compound in 30% yield, 11.2 g.

$^1$H NMR (400 MHz, DMSO-d6): δ 9.60 (s, 1H), 7.62 (s, 1H), 7.25 (s, 1H), 3.76 (s, 3H), 1.44 (m, 18H). LCMS: 313 (M+H)+

Preparation 296: 3-tert-butyl-1'-methyl-1'H-1,4'-bipyrazol-5-amine

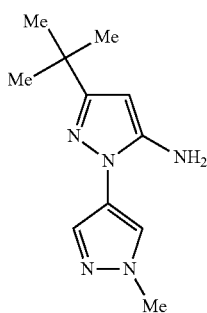 [SMILES: Cn1cc(-n2nc(C(C)(C)C)cc2N)cn1]

A mixture of di-tert-butyl 1-(1-methyl-1H-pyrazol-4-yl) hydrazine-1,2-dicarboxylate (Preparation 295, 12.3 g, 0.039 mol) and 4,4-dimethyl-3-oxopentanenitrile (5.4 g, 0.043 mol) was dissolved in MeOH (36 mL) and HCl (12 mL) was added slowly. The reaction mixture was stirred at 65° C. for 16 hours. The reaction was distilled to remove MeOH and basified with sat. aq. NaHCO$_3$ solution to pH~8 followed by extraction with DCM. The organic layer was separated, dried (Na$_2$SO$_4$) followed by concentration in vacuo. The crude mixture was purified by column chromatography on silica gel (hexane:EtOAc 50:50) to give the title compound in 41% yield, 7.2 g.

$^1$H NMR (400 MHz, DMSO-d6) d 7.91 (s, 1H), 7.58 (s, 1H), 5.28 (s, 1H), 5.04 (s, 2H), 3.81 (s, 3H), 1.21 (s, 9H); LCMS: m/z 220 [M+H]+.

Preparation 297: 3-cyclopropyl-1'-methyl-1'H-1,4'-bipyrazol-5-amine

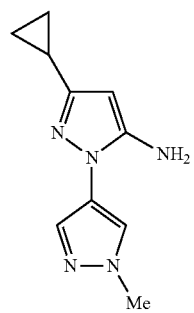 [SMILES: Cn1cc(-n2nc(C3CC3)cc2N)cn1]

The title compound was prepared according to the method described for Preparation 296: using di-tert-butyl 1-(1-methyl-1H-pyrazol-4-yl)hydrazine-1,2-dicarboxylate (Preparation 295) and 3-cyclopropyl-3-oxopropanenitrile to afford the title compound in 48% yield, 1.7 g.

$^1$HNMR (400 MHZ, DMSO-d6): 0.55-0.57 (m, 2H), 0.75-0.80 (m, 2H), 1.68-1.72 (m, 1H), 3.83 (s, 3H), 5.08-5.09 (m, 3H), 7.57 (s, 1H), 7.90 (s, 1H).
LCMS: [M+H]+ 204

Preparation 298: N-[5-({7-[3-({[tert-butyl(dimethyl)silyl]oxy}methyl)oxetan-3-yl]-7H-pyrrolo[2,3-d]pyrimidin-5-yl}carbonyl)pyridin-3-yl]-2-(4-chlorophenyl)acetamide

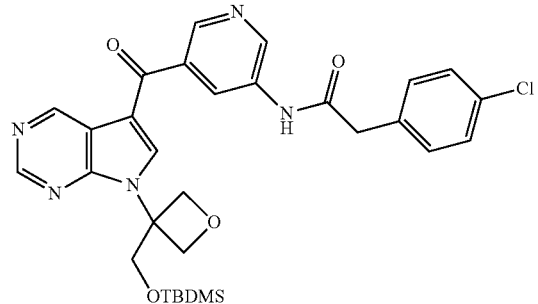 [SMILES: CC(C)(C)[Si](C)(C)OCC1(n2cc(C(=O)c3cncc(NC(=O)Cc4ccc(Cl)cc4)c3)c3cncnc32)COC1]

The title compound was prepared according to the method described for Preparation 223 using (5-aminopyridin-3-yl)(7-(3-methyloxetan-3-yl)-7H-pyrrolo[2,3-d]pyrimidin-5-yl)methanone (Preparation 222) to afford the title compound as a white solid in 87% yield, 35 mg.

LCMS (System 2): R$_t$=1.49 min; m/z 592 [M+H]+.

Preparation 299: 5-(methoxymethyl)-1-methyl-1H-pyrazole-3-carboxylic acid

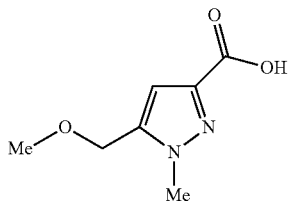 [SMILES: COCc1cc(C(=O)O)nn1C]

To a solution of ethyl 5-(methoxymethyl)-1-methyl-1H-pyrazole-3-carboxylate (WO9743277) (177 mg, 0.893 mmol) in MeOH, a 0.5 M solution of LiOH was added (5.3 mL, 2.68 mmol). The reaction was stirred at room temperature overnight. The solution was evaporated to dryness and the residue was adjusted to pH5 with a 2 N HCl solution. The aqueous solution was extracted with EtOAc and the organic layer was dried over $Na_2SO_4$ and evaporated in vacuo to give the title compound as a white solid 95%, 145 mg.

$^1$H NMR (400 MHz, methanol-d4) 6.68 (s, 1H), 4.44 (s, 2H), 3.84 (s, 3H), 3.29 (s, 3H). MS m/z 171 [M+H]$^+$

Preparation 300: Imidazo[1,2-a]pyrimidine-6-carboxylic acid

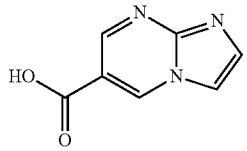 [SMILES: O=C(O)c1cnc2nccn2c1]

A mixture of 6-bromoimidazo[1,2-a]pyrimidine (1.17 g, 6 mmol), BINAP (18 mg, 0.06 mmol), PdCl2 (6 mg) in MeOH (30 mL) and triethylamine (1.8 mL) was heated to 80° C. under CO (50 psi) for 12 hours in DMF (97.5 mL). DMF-DMA (70.6 mL, 495.8 mmol) was added and the mixture heated to 130° C. for 12 hours. The mixture was filtered and concentrated to give methyl imidazo[1,2-a]pyrimidine-6-carboxylate (365 mg, 35%) as a yellow solid which was used in the next step without further purification. To a solution of methyl imidazo[1,2-a]pyrimidine-6-carboxylate (365 mg, 2.1 mmol) in methanol was added 1M aq. LiOH (9.0 mL) and the resulting mixture was stirred for 10 hours at room temperature. The pH was adjusted to 5-6 using aq. HCl and the whole mixture extracted with EtOAc (3×30 mL). The combined organic layers were dried over $Na_2SO_4$ and evaporated in vacuo to give the title compound as white solid in 39% yield, 133 mg $^1$H NMR (400 MHz, DMSO-d6): δ9.15 (m, 1H), 8.8 (m, 1H), 7.9 (m, 1H), 7.65 (m, 1H),

Preparation 301: [1,2,4]triazolo[1,5-a]pyridine-7-carboxylic acid

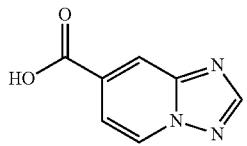 [SMILES: O=C(O)c1ccn2ncnc2c1]

To a solution of methyl 2-aminoisonicotinate (28.8 g, 191 mmol) in DMF (97.5 mL) was added DMF-DMA (70.6 mL, 496 mmol) and the mixture heated to 130° C. for 12 hours. The mixture was then concentrated to give a residue. To the residue was added methanol (381 mL), followed by NH2OHSO4 (31.9 g, 248 mmol) and the resulting mixture was stirred at room temperature overnight. The reaction mixture was concentrated to give methyl[1,2,4]triazolo[1,5-a]pyridine-7-carboxylate in 18% yield, 6 g. To a solution of methyl[1,2,4]triazolo[1,5-a]pyridine-7-carboxylate (3 g, 16 mmol) in methanol was added 1M aq. LiOH (70 mL) and the resulting mixture stirred for 10 hours at room temperature. The pH was adjusted to 5-6 using aq. HCl and the whole mixture extracted with EtOAc (30 mL×3). The combined organic layers were dried over $Na_2SO_4$ and concentrated in vacuo to give the title compound as white solid in 38% yield, 1.05 g 1H NMR (400 MHz, DMSO-d6): δ13.5-14.0 (s, 1H), 9.04-9.06 (m, 1H), 8.66 (m, 1H), 8.32 (m, 1H), 67.56-7.58 (m, 1H).

Preparation 302: 1-methyl-1H-pyrrolo[2,3-c]pyridine-3-carboxylic acid

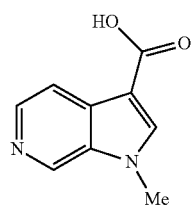

1-methyl-1H-pyrrolo[2,3-c]pyridine-3-carbaldehyde (WO 05066132) (6.5 g, 40.6 mmol) was dissolved in a mixture solvent of THF (120 mL) and t-butyl alcohol (40 mL) under nitrogen. A 2M 2-methyl-2-butene solution in THF (120 mL, 46 mmol) was added followed by a solution of $NaClO_2$ (11.02 g, 122 mmol) and $NaH_2PO_4$ (21.9 g, 183 mmol) in water (30 mL). The reaction mixture was stirred at room temperature overnight under nitrogen. The reaction mixture was concentrated in vacuo to remove organic solvents, and the residue was filtered. The precipitate contained the title compound as white solid in 57% yield, 4.1 g.

1H NMR: DMSO-d6 400 MHz: δ 3.96 (S, 3H), 7.87-7.89 (d, 1H), 8.23 (s, 1H), 8.28 (d, 1H), 8.91 (s, 1H), 12.3 (s, 1H).

Preparation 303: 2-((tert-butoxycarbonyl)amino)-2-(4-chlorophenyl)acetic acid

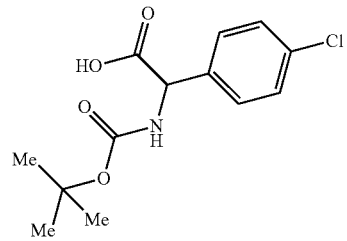 [SMILES: CC(C)(C)OC(=O)NC(C(=O)O)c1ccc(Cl)cc1]

To 4-chlorophenylglycine (1.50 g, 8.08 mmol) and sodium hydroxide (0.65 g, 16.2 mmol) in water (20 mL) was added di-tert-butyl dicarbonate (1.76 g, 8.08 mmol) in acetonitrile (15 mL) and the mixture was stirred at room temperature for 18 hours. The mixture was then washed with DCM (20 mL)

and acidified using 2N HCl. The resulting aqueous layer was extracted with DCM (2×25 mL) and the combined organic layers were washed with brine before being dried over MgSO$_4$, filtered and evaporated in vacuo to give the title compound as a colourless oil in 87% yield, 2.00 g.

Preparation 304: tert-Butyl (1-(4-chlorophenyl)-2-((5-(7-isopropyl-7H-pyrrolo[2,3-d]pyrimidine-5-carbonyl)pyridin-3-yl)amino)-2-oxoethyl)carbamate

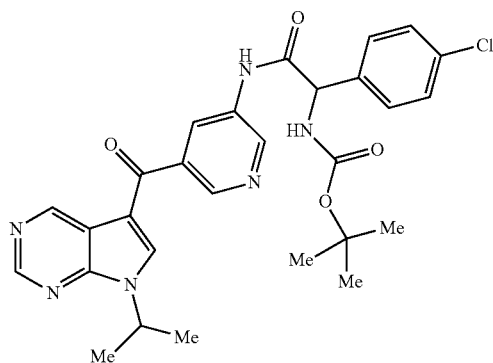 [SMILES: CC(C)n1cc(C(=O)c2cncc(NC(=O)C(NC(=O)OC(C)(C)C)c3ccc(Cl)cc3)c2)c2cncnc21]

To pyridine (4 mL) in a sealed vessel was added 2-((tert-butoxycarbonyl)amino)-2-(4-chlorophenyl)acetic acid (67 mg, 0.24 mmol) (see Preparation 303), (5-aminopyridin-3-yl)(7-isopropyl-7H-pyrrolo[2,3-d]pyrimidin-5-yl)methanone (52 mg, 0.18 mmol) (see Preparation 95) and N,N,N',N'-tetramethyl-O-(7-azabenzotriazol-1-yl)uronium hexafluorophosphate (105 mg, 0.28 mmol). The reaction was heated at 50° C. for 18 hours and then evaporated in vacuo and purified by column chromatography (gradient of 100:0 to 88:12 DCM:MeOH) to give the title compound in 49% yield, 64 mg. LCMS (basic): R$_t$=0.81 min; m/z 549 [M+H]$^+$.

Biological Activity

Isolated TRK Enzyme assays use the HTRF KinEASE-TK kit (Cisbio Cat#62TKOPEJ) with recombinant His-tagged cytoplasmic domains of each TRK receptor sourced from Invitrogen (see table below). This activity-assay measures the phosphorylation of tyrosine residues within a substrate from the HTRF kit which has been validated by Cisbio for a variety of tyrosine kinases including the TRK receptors.

Assay Details:

| Target | Invitrogen Cat# | Amino acids | FAC enzyme | FAC ATP | Assay Reaction Time |
|---|---|---|---|---|---|
| TRKA | PV3144 (NTRK1) | aa 441-796 | 4 nM | 40 uM | 35 min |
| TRKB | PV3616 (NTRK2) | aa 526-838 | 1 nM | 1.4 uM | 40 min |
| TRKC | PV3617 (NTRK3) | aa 510-825 | 10 nM | 15 uM | 30 min |

0.5 mM stock solutions of test compounds are prepared and serially diluted in 100% DMSO. A standard curve using the compound of Example 135 disclosed in WO2005/116035 of 150 uM is also prepared on each test plate. High percentage effect (HPE) is defined by 150 uM PF-00593157-00 and 0% effect (ZPE) is defined by 100% DMSO. Greiner low volume black plates containing 0.2 ul of serially diluted compound, standard and HPE/ZPE are created using the Bravo nanoliter dispenser. 1× enzyme buffer is prepared from 5× Enzymatic Buffer from the Cisbio KinEASE TK kit using MilliQ water. The buffer is then supplemented with 10 mM MgCl and 2 mM DTT (both from Sigma). In the case of TRKB, the buffer is also supplemented with 125 nM Supplement Enzymatic Buffer (SEB) from the Cisbio kit.

2×FAC of enzyme and 2×FAC ATP diluted in 1× complete enzyme buffer is incubated at room temperature for 20 minutes to preactivate the enzyme. Following this preactivation step, 5 ul/well of enzyme+ATP mix is added using a Multidrop Micro to the assay plate, spotted with 0.2 ul 100% DMSO compound. This is left for 20 mins at room temperature before adding 5 ul of 2 uM TK-substrate-Biotin (from the Cisbio kit) diluted in 1× enzyme buffer (1 uM FAC) using the Multidrop Micro. The reaction is incubated at room temperature for the optimized assay reaction time (see table). The reaction is stopped by adding 10 ul/well HTRF Detection Buffer containing 0.25 uM Streptavidin-XL665 (0.125 uM FAC) and 1:200 TK Antibody-Cryptate using a Multidrop.

After the Detection Reagent addition, plates are covered and incubated at room temperature for 60 minutes. HTRF signal is read using an Envision reader, measured as a ratio of emissions at two different wavelengths, 620 nm and 665 nm. Any compound that inhibits the action of the TRK kinase will have a lower fluorescence ratio value 665/620 nM than compounds which do not inhibit the TRK kinase. Test compound data are expressed as percentage inhibition defined by HPE and ZPE values for each plate. Percentage inhibition in the presence of test compound is plotted against compound concentration on a log scale to determine an IC$_{50}$ from the resultant sigmoid curve. Cell Based Assays were carried out using Cell lines from DiscoveRx utilising their PathHunter technology and reagents in an antagonist assay:

| Target | DiscoveRx cell line Cat# | Cognate Neurotrophin |
|---|---|---|
| TRKA | 93-0462C3 | NGF |
| TRKA co expressed with p75 | 93-0529C3 | NGF |
| TRKB | 93-0463C3 | BDNF |
| TRKB co expressed with p75 | 93-0530C3 | BDNF |
| TRKC | 93-0464C3 | NT3 |
| TRKC co expressed with p75 | 93-0531C3 | NT3 |

The assays are based upon DiscoveRx's proprietary Enzyme Fragment Complementation (EFC) technology. In the case of the TRK cell lines, the enzyme acceptor (EA) protein is fused to a SH2 protein and the TRK receptor of interest has been tagged with a Prolink tag.

Upon neurotrophin binding, the TRK receptor becomes phosphorylated, and the tagged SH2 protein binds. This results in functional complementation and restored 3-Galactosidase activity which is can be measured using the luminescent Galacton Star substrate within the PathHunter reagent kits.

Generally, small molecule inhibitors bind to the kinase domain so are not competing with the neurotrophin (agonist) which binds to an extracellular site. This means that the IC$_{50}$ is a good measure of affinity and should be unaffected by concentration neurotrophin stimulant.

Cryopreserved PathHunter cells are used from either in-house produced batches or bulk batches bought directly from DiscoveRx. Cryopreserved cells are resuscitated, spun 1000 rpm for 4 min to remove freezing media, and resuspended in MEM+0.5% horse serum (both Invitrogen) to 5e⁵ cells/ml. The cells are then plated using a Multidrop into Greiner white tissue culture treated plates at 20 ul/well and incubated for 24 h at 37° C., 5% $CO_2$, high humidity. On the day of the assay, the cell plates are allowed to cool to room temperature for 30 min prior to the assay.

4 mM stock solutions of test compounds are prepared and serially diluted in 100% DMSO. A standard curve using the compound of Example 135, WO2005/116035 at a top concentration of 150 uM is also prepared on each test plate. High percentage effect (HPE) is defined by 150 uM of the compound of Example 135, WO2005/116035 and 0% effect (ZPE) is defined by 100% DMSO. Plates containing 1 ul of serially diluted compound, standard and HPE/ZPE are diluted 1/66 in assay buffer (PBS minus $Ca^{2+}$, minus $Mg^{2+}$ with 0.05% pluronic F127) using a Wellmate. Using a Platemate Plus, 5 ul of 1/66 diluted test compounds is then transferred to the cell plate and allowed to reach equilibrium by incubating for 30 min at room temperature before addition of agonist stimulus: 10 ul/well of 2 nM (0.571 nM FAC) of the cognate neurotrophin (Peprotech) diluted in agonist buffer (HBSS with 0.25% BSA). Final assay concentration of the test compounds is 8.66 µM, (the compound of Example 135, WO2005/116035 FAC is 0.325 uM). The plates are left at room temperature for a further 2 hours before addition of 10 ul of the DiscoveRx PathHunter detection reagent (made up by adding 1 part Galacton Star, 5 parts Emerald II and 19 parts Cell Assay Buffer as per the manufacturer's instructions).

After reagent addition, plates are covered and incubated at room temperature for 60 minutes. Luminescence signal is read using an Envision. Test compound data are expressed as percentage inhibition defined by HPE and ZPE values for each plate. Percentage inhibition in the presence of test compound is plotted against compound concentration on a log scale to determine an $IC_5$ so from the resultant sigmoid curve.

Brain Penetration Assays
In Vitro
MDCK-BCRP: MDCK-BCRP data were collected according to the method described in "A 96-Well Efflux Assay To Identify ABCG2 Substrates Using a Stably Transfected MDCK II Cell Line" http://pubs.acs.org/doi/full/10.1021/mp050088t Yongling Xiao, Ralph Davidson, Arthur Smith, Dennis Pereira, Sabrina Zhao, John Soglia, David Gebhard, Sonia de Morais, and David B. Duignan, *Mol. Pharm.,* 2006, 3 (1), pp 45-54.

MDCK-MDR1: MDCK-MDR1 data were collected according to the method described in "Are MDCK Cells Transfected with the Human MDR1 Gene a Good Model of the Human Intestinal Mucosa?"

http://www.springerlink.com/content/qfhqlqbr4fnp3 khf/fulltext.pdf

Fuxing Tang, Kazutoshi Horie, and Ronald T. Borchardt, *Pharmaceutical Research,* Vol. 19, No. 6, June 2002.

In Vivo
Brain penetration was measured according to the method described in "Assessing brain free fraction in early drug discovery". Read, K; Braggio, S., Expert Opinion Drug Metab Toxicol. (2010) 6 (3) 337-344.

| Ex. No. | TrkA enzyme potency (nM) | TrkB enzyme potency (nM) | TrkA cell potency (nM) | TrkB cell potency (nM) | TrkC cell potency (nM) | MDCK MDR1 Papp AB (×10−6 cm/sec) | MDCK MDR1 Papp BA (×10−6 cm/sec) | RRCK BCRP Papp AB (×10−6 cm/sec) | RRCK BCRP Papp BA (×10−6 cm/sec) |
|---|---|---|---|---|---|---|---|---|---|
| 1 | 3.7 | | 9.5 | 1.5 | | 5.5 | 14 | | |
| 2 | 8.4 | 113 | 5.3 | 3.9 | 1.1 | <1 | 15 | | |
| 3 | 4.1 | | 5.1 | 1.8 | | 8.7 | 20 | | |
| 4 | 3.9 | 162 | 5.7 | 6.5 | 4.4 | <1 | 13 | 12 | 39 |
| 5 | 2.6 | 73 | 3.5 | 3.6 | 2.0 | 1.5 | 14 | | |
| 6 | 2.5 | | 2.0 | 1.3 | | 6.9 | 16 | | |
| 7 | 11 | 41 | 2.1 | 0.8 | | 5.6 | 20 | | |
| 8 | 2.4 | 15 | 1.9 | 2.0 | 2.3 | 1.8 | 15 | | |
| 9 | 3.7 | 94 | 13 | 6.6 | 5.9 | <1 | 20 | 9 | 43 |
| 10 | 5.7 | 78 | 30 | 18 | 18 | <1 | 14 | | |
| 11 | 3.3 | 197 | 17 | 11 | 6.6 | <1 | 23 | | |
| 12 | 9.2 | 547 | 68 | 22 | | <1 | 3.1 | | |
| 13 | 20 | 449 | 1130 | 184 | | <1 | 1.0 | | |
| 14 | 13 | 773 | 41 | 15 | 4.8 | <1 | 21 | | |
| 15 | 17 | 514 | 143 | 40 | | <1 | 15 | | |
| 16 | 16 | 445 | 99 | 15 | | | | | |
| 17 | 23 | | 103 | 45 | | <1 | 13 | | |
| 18 | 128 | | >8660 | 5300 | | <1 | <1 | | |
| 19 | 249 | 5480 | 1840 | 206 | | <1 | 8.5 | | |
| 20 | 14 | 635 | 22 | 19 | | <1 | 17 | | |
| 21 | 71 | | 5740 | 1770 | | <1 | 1.3 | | |
| 22 | 25 | | 596 | 190 | | <1 | 6.9 | | |
| 23 | 26 | | 93 | 52 | | <1 | 31 | | |
| 24 | 125 | 427 | 37 | 27 | 8.9 | <1 | 10 | | |
| 25 | 24 | 433 | 65 | 19 | | <1 | 13 | | |
| 26 | 3.5 | 30 | 14 | 5.9 | 8.6 | <1 | 16 | 7.5 | 32 |
| 27 | 2.8 | 55 | 3.9 | 5.4 | 3.2 | <1 | 17 | | |
| 28 | 4.9 | 75 | 2.7 | 1.9 | | <1 | 20 | | |
| 29 | 2.8 | 68 | 5.8 | 4.0 | | 1.3 | 23 | | |
| 30 | 4.0 | 98 | 11 | 7.5 | | <1 | 15 | | |
| 31 | 18 | | 401 | 198 | | <1 | 2.6 | | |
| 32 | 9.0 | 423 | 87 | 59 | 18 | <1 | 3.4 | | |
| 33 | 5.7 | 96 | 2.0 | 1.6 | | 1.0 | 24 | | |
| 34 | 3.6 | 200 | 23 | 25 | 13 | <1 | 11 | | |
| 35 | 8.9 | 223 | 103 | 37 | | <1 | 5.3 | | |
| 36 | 4.5 | 303 | 11 | 13 | 13 | <1 | 12 | | |
| 37 | 67 | | 2250 | 571 | | | | | |
| 38 | 7.2 | | 1060 | 589 | | <1 | 2.1 | | |

-continued

| Ex. No. | TrkA enzyme potency (nM) | TrkB enzyme potency (nM) | TrkA cell potency (nM) | TrkB cell potency (nM) | TrkC cell potency (nM) | MDCK MDR1 Papp AB (×10−6 cm/sec) | MDCK MDR1 Papp BA (×10−6 cm/sec) | RRCK BCRP Papp AB (×10−6 cm/sec) | RRCK BCRP Papp BA (×10−6 cm/sec) |
|---|---|---|---|---|---|---|---|---|---|
| 39 | 24 | >8660 | 4710 | | | <1 | <1 | | |
| 40 | 67 | | 2580 | 506 | | <1 | 2.4 | | |
| 41 | 7.6 | | 203 | 70 | | <1 | 6.3 | | |
| 42 | 3.8 | 191 | 44 | 27 | 13 | <1 | 9.5 | | |
| 43 | 5.1 | 136 | 17 | 19 | 11 | <1 | 13 | | |
| 44 | 12 | | 996 | 554 | | <1 | 1.6 | | |
| 45 | 25 | | >8660 | 3790 | | <1 | <1 | | |
| 46 | 3.2 | 94 | 6.0 | 4.2 | 0.9 | <1 | 18 | 7 | 31 |
| 47 | 25 | 27 | 35 | 13 | | <1 | 21 | | |
| 48 | 1.7 | 40 | 2.9 | 3.6 | 2.5 | <1 | 12 | | |
| 49 | 2.1 | 37 | 3.1 | 2.1 | 2.1 | <1 | 17 | | |
| 50 | 6.6 | 143 | 10.0 | 2.1 | | <1 | 24 | | |
| 51 | 7.8 | 198 | 35 | 7.5 | 9.9 | <1 | 11 | | |
| 52 | 3.1 | 103 | 22 | 16 | 8.1 | <1 | 9.1 | | |
| 53 | 4.0 | 163 | 16 | 5.0 | 8.6 | <1 | 13 | | |
| 54 | 6.7 | | 368 | 174 | | <1 | 1.3 | | |
| 55 | 7.0 | 179 | 12 | 4.5 | | <1 | 20 | | |
| 56 | 9.5 | 962 | 451 | 517 | | 1.1 | 1.0 | | |

| Example | Trka enzyme (IC50) | Example | Trka enzyme (IC50) | Example | Trka enzyme (IC50) |
|---|---|---|---|---|---|
| 65 | 55.6 | 109 | 65.1 | 153 | 71.5 |
| 66 | 3.55 | 110 | 36.5 | 154 | 94.1 |
| 67 | 4.15 | 111 | 46.2 | 155 | 49.1 |
| 68 | 12.1 | 112 | 57.8 | 156 | 133 |
| 69 | 10.9 | 113 | 300 | 157 | 174 |
| 70 | 22.8 | 114 | 976 | 158 | 230 |
| 71 | 135 | 115 | 102 | 159 | 234 |
| 72 | 63.3 | 116 | 103 | 160 | 1080 |
| 73 | 283 | 117 | 68.4 | 161 | 6270 |
| 74 | 1210 | 118 | 2550 | 162 | 324 |
| 75 | 567 | 119 | 233 | 163 | 1840 |
| 76 | 173 | 120 | 53 | 164 | 133 |
| 77 | 64.3 | 121 | 5200 | 165 | 3400 |
| 78 | 203 | 122 | 5840 | 166 | 110 |
| 79 | 1580 | 123 | 143 | 167 | 3470 |
| 80 | 392 | 124 | 244 | 168 | 702 |
| 81 | 197 | 125 | 148 | 169 | 3100 |
| 82 | 908 | 126 | 95.7 | 170 | 3100 |
| 83 | 355 | 127 | 1330 | 171 | 1280 |
| 84 | 2860 | 128 | 206 | 172 | 3840 |
| 85 | 70.8 | 129 | 3860 | 173 | 9810 |
| 86 | 95.5 | 130 | 284 | 174 | 210 |
| 87 | 63.2 | 131 | 831 | 175 | 2590 |
| 88 | 56.6 | 132 | 131 | 176 | 165 |
| 89 | 21.7 | 133 | 681 | 177 | 3100 |
| 90 | 8.81 | 134 | 330 | 178 | 3100 |
| 91 | 1030 | 135 | 312 | 179 | 3080 |
| 92 | 41.5 | 136 | 334 | 180 | 3100 |
| 93 | 12.4 | 137 | 496 | 181 | 3100 |
| 94 | 54.8 | 138 | 8310 | 182 | 543 |
| 95 | 3.95 | 139 | 65.7 | 183 | 1850 |
| 96 | 5.45 | 140 | 219 | 184 | 579 |
| 97 | 4.86 | 141 | 59.5 | 185 | 67.4 |
| 98 | 5.16 | 142 | 1380 | 186 | 719 |
| 99 | 19.5 | 143 | 4730 | 187 | 2630 |
| 100 | 25.6 | 144 | 71.5 | 188 | 277 |
| 101 | 204 | 145 | 37.4 | 189 | 836 |
| 102 | 42.9 | 146 | 573 | 190 | 820 |
| 103 | 41.7 | 147 | 76.4 | 191 | 873 |
| 104 | 20 | 148 | 93.4 | 192 | 173 |
| 105 | 25.6 | 149 | 3570 | 193 | 3570 |
| 106 | 14.8 | 150 | 51 | 194 | 101 |
| 107 | 12.3 | 151 | 232 | 195 | 835 |
| 108 | 7.63 | 152 | 82.5 | 196 | 791 |
| 197 | 430 | 242 | 8.71 | 287 | 4350 |
| 198 | 2350 | 243 | 38.4 | 288 | 43.1 |
| 199 | 22.1 | 244 | 4.69 | 289 | 1370 |
| 200 | 10.1 | 245 | 4.7 | 290 | 167 |

-continued

| Example | Trka enzyme (IC50) | Example | Trka enzyme (IC50) | Example | Trka enzyme (IC50) |
|---|---|---|---|---|---|
| 201 | 482 | 246 | 35.6 | 291 | 3230 |
| 202 | 412 | 247 | 71 | 292 | 37.7 |
| 203 | 316 | 248 | 23.7 | 293 | 20.2 |
| 204 | 4.24 | 249 | 35.8 | 294 | 61.4 |
| 205 | 12.2 | 250 | 3.48 | 295 | 31.9 |
| 206 | 123 | 251 | 33.1 | 296 | 47.7 |
| 207 | 110 | 252 | 5.18 | 297 | 299 |
| 208 | 129 | 253 | 3.92 | 298 | 1460 |
| 209 | 272 | 254 | 52.6 | 299 | 539 |
| 210 | 185 | 255 | 42.7 | 300 | 52.2 |
| 211 | 34.9 | 256 | 1.09 | 301 | 428 |
| 212 | 59 | 257 | 12.2 | 302 | 156 |
| 213 | 3.03 | 258 | 11.8 | 303 | 1220 |
| 214 | 65.9 | 259 | 8.62 | 304 | 3900 |
| 215 | 4.4 | 260 | 16.8 | 305 | 2640 |
| 216 | 31.6 | 261 | 128 | 306 | N/D |
| 217 | 83.3 | 262 | 32.3 | 307 | N/D |
| 218 | 1210 | 263 | 73.6 | 308 | 592 |
| 219 | 286 | 264 | 84.8 | 309 | 53.9 |
| 220 | 462 | 265 | 69 | 310 | 98.4 |
| 221 | 3100 | 266 | 2950 | 311 | 238 |
| 222 | 692 | 267 | 2120 | 312 | 166 |
| 223 | 1660 | 268 | 579 | 313 | N/D |
| 224 | 3100 | 269 | 557 | 314 | 835 |
| 225 | 27.7 | 270 | 343 | 315 | 39.1 |
| 226 | 3.61 | 271 | 39 | 316 | N/D |
| 227 | 12.5 | 272 | 697 | 317 | N/D |
| 228 | 14.9 | 273 | 342 | 318 | N/D |
| 229 | 138 | 274 | 38.6 | 319 | 188 |
| 230 | 63.7 | 275 | 5100 | 320 | 3100 |
| 231 | N/D | 276 | 295 | 321 | 3100 |
| 232 | 274 | 277 | 434 | 322 | 9800 |
| 233 | 96.5 | 278 | 54.3 | 323 | 3100 |
| 234 | 84.9 | 279 | 439 | 324 | 3100 |
| 235 | 70.5 | 280 | 498 | 325 | 111 |
| 236 | 25.2 | 281 | 161 | 326 | 2980 |
| 237 | 73.9 | 282 | 1010 | 327 | 3100 |
| 238 | 9.36 | 283 | 297 | 328 | 3100 |
| 239 | 22.6 | 284 | 2020 | 329 | 9810 |
| 240 | 19.2 | 285 | 7820 | 330 | 3100 |
| 241 | 45.3 | 286 | 19.5 | 331 | 9810 |
| 332 | 2180 | 381 | 2780 | 426 | 228 |
| 333 | 9800 | 382 | 45.7 | 427 | 93.4 |
| 334 | 1550 | 383 | 130 | 428 | 960 |
| 336 | 9800 | 384 | 4770 | 429 | 2740 |
| 337 | 4280 | 385 | 81.6 | 430 | 297 |
| 338 | 2730 | 386 | 9800 | 431 | 235 |

-continued

| Example | Trka enzyme (IC50) | Example | Trka enzyme (IC50) | Example | Trka enzyme (IC50) |
|---|---|---|---|---|---|
| 339 | 251 | 387 | 6880 | 432 | 2790 |
| 340 | 451 | 388 | 165 | 433 | 246 |
| 343 | 53.9 | 389 | 84.3 | 434 | 99.9 |
| 344 | 326 | 390 | 9800 | 435 | 5490 |
| 345 | 362 | 391 | 246 | 436 | 205 |
| 346 | 253 | 392 | 135 | 437 | 107 |
| 347 | 155 | 393 | 1360 | 438 | 31.2 |
| 348 | 36.6 | 394 | 7120 | 439 | 22.5 |
| 350 | 153 | 395 | 1350 | 440 | 676 |
| 351 | 21.1 | 396 | 177 | 441 | 8390 |
| 352 | 62.6 | 397 | 9800 | 442 | 36.6 |
| 353 | N/D | 398 | 138 | 443 | 47.7 |
| 354 | N/D | 399 | 153 | 444 | 496 |
| 355 | 302 | 400 | 593 | 445 | 5.51 |
| 356 | 56.3 | 401 | 132 | 446 | 812 |
| 357 | 302 | 402 | 9800 | 447 | 919 |
| 358 | 9800 | 403 | 1220 | 448 | 272 |
| 359 | 9800 | 404 | 118 | 449 | 155 |
| 360 | 956 | 405 | 1630 | 450 | 3150 |
| 361 | 7640 | 406 | 2640 | 451 | 7170 |
| 362 | 1910 | 407 | 2600 | 452 | 542 |
| 363 | 1030 | 408 | 654 | 453 | 634 |
| 364 | 5040 | 409 | 70.4 | 454 | 633 |
| 365 | 2040 | 410 | 9800 | 455 | 1070 |
| 366 | 354 | 411 | 9800 | 456 | 6960 |
| 367 | 5640 | 412 | 5.18 | 457 | 674 |
| 368 | 753 | 413 | 9800 | 458 | 213 |
| 369 | 3000 | 414 | 158 | 459 | 4.06 |
| 370 | 3540 | 415 | 2590 | 460 | 9800 |
| 371 | 97 | 416 | 52 | 461 | 9800 |
| 372 | 9800 | 417 | 71.2 | 462 | 1320 |
| 373 | 813 | 418 | 40.2 | 463 | 186 |
| 374 | 224 | 419 | 15.1 | 464 | 3010 |
| 375 | 9800 | 420 | 9800 | 465 | 2130 |
| 376 | 5100 | 421 | 1730 | 466 | 400 |
| 377 | 2630 | 422 | 451 | 467 | 538 |
| 378 | 716 | 423 | 1330 | 468 | 5100 |
| 379 | 56.3 | 424 | 4310 | 469 | 523 |
| 380 | 422 | 425 | 796 | 470 | 166 |
| 471 | 751 | 517 | 4390 | 562 | 3.75 |
| 472 | 1720 | 518 | 7.3 | 563 | 3.11 |
| 473 | 7280 | 519 | 47.9 | 564 | 1.57 |
| 474 | 4420 | 520 | 4.57 | 565 | 17.9 |
| 475 | 643 | 521 | 92.7 | 567 | 20.8 |
| 476 | 65 | 522 | 43.7 | 568 | 12.1 |
| 477 | 3030 | 523 | 11.4 | 569 | 34.4 |
| 478 | 587 | 524 | 4.53 | 570 | 6970 |
| 479 | 2160 | 525 | 9.48 | 571 | 2.92 |
| 480 | 531 | 526 | 1.51 | 572 | 9.5 |
| 481 | 313 | 527 | 4.64 | 573 | 17.9 |
| 482 | 6860 | 528 | 2.25 | 574 | 14.2 |
| 483 | 118 | 529 | 3.93 | 575 | 3.09 |
| 484 | 192 | 530 | 5.9 | 576 | 296 |
| 485 | 20 | 531 | 52.4 | 577 | 1.9 |
| 486 | 805 | 532 | 11.1 | 578 | 6.07 |
| 487 | 9800 | 533 | 31.3 | 579 | 8.11 |
| 488 | 64.6 | 534 | 20.3 | 580 | 0.825 |
| 489 | 9800 | 535 | 51.2 | 581 | 3.21 |
| 490 | 9800 | 536 | 1.57 | 582 | 9.79 |
| 491 | 1410 | 537 | 10.6 | 583 | 0.681 |
| 492 | 1690 | 538 | 1.51 | 584 | 581 |
| 493 | 848 | 539 | 4.08 | 585 | 36.7 |
| 494 | 2570 | 540 | 153 | 586 | 1000 |
| 495 | 9.80E+03 | 541 | N/D | 587 | 20.5 |
| 496 | 199 | 542 | N/D | 588 | 334 |
| 497 | 43.5 | 543 | 50 | 589 | 31.3 |
| 498 | 2340 | 544 | 31.6 | 590 | 71.2 |
| 499 | 9.80E+09 | 545 | 2.95 | 591 | 142 |
| 500 | 25.8 | 546 | 5.34 | | |
| 501 | 201 | 547 | 3.88 | | |
| 502 | 6280 | 548 | 21.2 | | |
| 503 | 963 | 549 | 3.22 | | |
| 504 | 1020 | 550 | 16.1 | | |
| 505 | 1630 | 551 | 2.78 | | |
| 506 | 67 | 552 | 7.62 | | |

-continued

| Example | Trka enzyme (IC50) | Example | Trka enzyme (IC50) | Example | Trka enzyme (IC50) |
|---|---|---|---|---|---|
| 507 | 5.45 | 553 | 4.4 | | |
| 508 | 1630 | 554 | 270 | | |
| 509 | 9800 | 555 | 150 | | |
| 510 | 249 | 556 | 3.16 | | |
| 511 | 144 | 557 | 9.47 | | |
| 512 | 12.6 | 558 | 5.56 | | |
| 513 | 1890 | 559 | 374 | | |
| 514 | 9800 | 560 | 1610 | | |
| 515 | 1140 | 561 | 112 | | |

All publications cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

We claim:
1. A compound of Formula (I):

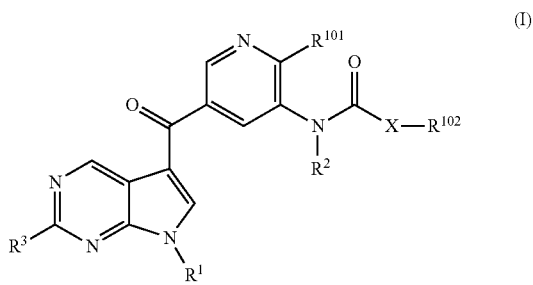

or a pharmaceutically acceptable salt thereof, wherein
$R^1$ is H, or $C_{1-5}$ alkyl optionally substituted by up to 3 substituents independently selected from OH, CON$(R^5R^6)$, $SO_2R^7$, $SR^7$, $OR^7$, $CH_2OH$, $CO_2R^5$, $SONR^7R^7$, $NR^7SO_2R^5$, CN, $NO_2$ and $R^8$, or a ring system selected from $C_{3-5}$ cycloalkyl, propellanyl, or a 4-6 membered saturated heterocyclyl ring, which ring system has up to 3 ring hetero-atoms selected from N, O and S, and which ring system is optionally substituted by up to 3 substituents independently selected from methyl, OH, CON$(R^5R^6)$, $SO_2R^7$, $OR^7$, $CH_2OH$, $CO_2R^5$, $SONR^7R^7$, $NR^7SO_2R^5$, CN, $NO_2$ and $R^8$;
$R^2$ is H or methyl;
$R^3$ is H, $NH_2$ or NH($C_{1-3}$ alkyl optionally substituted with up to 3 substituents independently selected from OH and O($C_{1-3}$ alkyl));
$R^{101}$ is H, OH, methyl, cyclopropyl, methoxy, ethyl, ethoxy or CN,
X is a bond, O, $(CH-R^4)_n$, $NR^{104}$, $OCH_2$ or $CH_2O$;
$R^4$ is independently H, $CH_3$, $CH_2OH$, $CH_2OCH_3$, OH, $NH_2$, $NHCH_3$, $N(CH_3)_2$, $CH_2NH_2$, $CH_2NHCH_3$, or $CH_2N(CH_3)_2$;
$R^{104}$ is H, $C_{1-3}$ alkyl or a $C_{4-6}$ saturated carbocycle, each of which is optionally substituted by up to 3 substituents independently selected from $C_{1-3}$ alkyl, $CH_2OH$ and $NH_2$;
n is 1 or 2;

$R^{102}$ is a ring system which is a 3-7 membered monocyclic carbocyclic or heterocyclic system, or an 8-14-membered bicyclic system, which ring system may be saturated or partially or fully unsaturated, wherein the heterocyclic ring system may have up to 5 ring heteroatoms selected from N, S, and O, wherein the bicyclic ring system can be 2 rings (carbocyclic-carbocyclic, carbocyclic-heterocyclic, heterocyclic-carbocyclic or heterocyclic-heterocyclic) fused or linked by a single bond, which ring system is optionally substituted by up to 3 substituents independently selected from, where possible -halo, CN, $NR^5R^6$, $SO_2R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by up to 3 halogen, OH, $O(C_{1-3}$ alkyl), $O(C_{3-6}$ cycloalkyl optionally substituted by up to 3 OH and/or $C_{1-3}$ alkoxy groups, $O(C_{1-3}$ alkyl substituted by up to 3 halogen), $O(C_{1-3}$ alkyl substituted by up to 3 OH and/or $C_{1-3}$ alkoxy groups), $NR^5SO_2R^7$, =O, $R^8$, $C(O)R^8$, $NO_2$, $NR^5CO_2R^7$, $NR^5COR^7$, $OR^8$, $S(O)R^7$, and $CH_2R^8$;

$R^5$ and $R^6$ are each independently H, or $C_{1-5}$ alkyl optionally substituted by up to 3 substituents independently selected from OH, $CONR^7R^7$, $SO_2R^7$, $OR^7$, $CH_2OH$, $CO_2R^7$, $SONR^7R^7$, $NR^7SO_2R^7$, CN, $NO_2$ and $R^9$, or a ring system selected from $C_{3-5}$ cycloalkyl, propellanyl, or a 4-6 membered saturated heterocyclyl ring, which ring system is optionally substituted by up to 3 substituents independently selected from OH, $CON(R^7R^7)$, $SO_2R^7$, $CO_2R^7$, $SONR^7R^7$, $NR^7SO_2R^7$, CN, $NO_2$, halo, $NR^7R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by 1 to 3 halogen, $O(C_{3-6}$ cycloalkyl optionally substituted by up to 3 OH and/or $C_{1-3}$ alkoxy groups, $O(C_{1-3}$ alkyl substituted by up to 3 halogen, $O(C_{1-3}$ alkyl substituted by up to 3 OH and/or $C_{1-3}$ alkoxy, $NR^7SO_2R^7$, =O, $NO_2$, $NR^7CO_2R^7$, and $S(O)R^7$, or $R^5$ and $R^6$ together with the N to which they are attached can be a 4-7 membered ring optionally including up to 2 further ring hetero-atoms independently selected from N, O, S, which ring is optionally substituted by $C_{1-3}$ alkoxy and/or $C_{1-3}$ alkyl;

$R^7$ is H, $C_{1-5}$ alkyl or $C_{1-5}$ alkoxy, which $C_{1-5}$ alkyl or $C_{1-5}$ alkoxy is optionally substituted by up to 3 substituents independently selected from halogen;

$R^8$ is a is a ring system which is a 3-7 membered monocyclic carbocyclic or heterocyclic system, or an 8-14-membered bicyclic system, which ring system may be saturated or partially or fully unsaturated, wherein the heterocyclic ring system may have up to 5 ring heteroatoms selected from N, S, and O, wherein the bicyclic ring system can be 2 rings (carbocyclic-carbocyclic, carbocyclic-heterocyclic, heterocyclic-carbocyclic or heterocyclic-heterocyclic) fused or linked by a single bond, which ring system is optionally substituted by up to 3 substituents independently selected from, where possible -halo, CN, $NR^5R^6$, $SO_2R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by 1 to 3 halogen, OH, $O(C_{1-3}$ alkyl), $O(C_{3-6}$ cycloalkyl optionally substituted by up to 3 OH and/or $C_{1-3}$ alkoxy groups, $O(C_{1-3}$ alkyl substituted by up to 3 halogen, $O(C_{1-3}$ alkyl substituted by up to 3 OH and/or $C_{1-3}$ alkoxy, $NR^5SO_2R^7$, =O, $NO_2$, $NR^7COR^7$, $NR^5CO_2R^7$, and $S(O)R^7$;

$R^9$ is a is a ring system which is a 3-7 membered monocyclic carbocyclic or heterocyclic system, or an 8-14-membered bicyclic system, which ring system may be saturated or partially or fully unsaturated, wherein the heterocyclic ring system may have up to 5 ring heteroatoms selected from N, S, and O, wherein the bicyclic ring system can be 2 rings (carbocyclic-carbocyclic, carbocyclic-heterocyclic, heterocyclic-carbocyclic or heterocyclic-heterocyclic) fused or linked by a single bond, which ring system is optionally substituted by up to 3 substituents independently selected from, where possible -halo, CN, $NR^7R^7$, $SO_2R^7$, $SR^7$, $C_{1-4}$ alkyl optionally substituted by up to 3 OH and/or $C_{1-3}$ alkoxy groups, $C_{3-6}$ cycloalkyl optionally substituted by up to 3 OH and/or $C_{1-3}$ alkoxy groups, $C_{1-3}$ alkyl substituted by 1 to 3 halogen, OH, $O(C_{1-3}$ alkyl), $O(C_{3-6}$ cycloalkyl optionally substituted by up to 3 OH and/or $C_{1-3}$ alkoxy groups, $O(C_{1-3}$ alkyl substituted by up to 3 halogen, $O(C_{1-3}$ alkyl substituted by up to 3 OH and/or $C_{1-3}$ alkoxy, $NR^7SO_2R^7$, =O, $NO_2$, $NR^7CO_2R^7$, $NR^7COR^7$, and $S(O)R^7$;

wherein each CH moiety can be replaced by a CF moiety.

2. The compound or salt according to claim 1 wherein $R^1$ is H or $C_{1-5}$ alkyl wherein the $C_{1-5}$ alkyl is optionally substituted with 1 or 2 OH groups; or $R^1$ is $C_{1-5}$ alkyl substituted with $CONH_2$, $CONHCH_3$, $CON(CH_3)_2$, $CO_2H$, $CO_2CH_3$, $OCH_3$, $SCH_3$, or $SO_2CH_3$; or $R^1$ is $C_{3-5}$cycloalkyl, propellanyl, or oxetanyl, wherein the $C_{3-5}$cycloalkyl, propellanyl, or oxetanyl is optionally substituted with methyl, OH or $CH_2OH$.

3. The compound or salt according to claim 1 wherein $R^1$ is t-butyl, hydroxy-t-butyl, dihdyroxy-t-butyl, 1-hydroxyprop-2-yl or 1,3-dihydroxyprop-2-yl.

4. The compound or salt according to claim 3 wherein $R^2$ is H.

5. The compound or salt according to claim 4 wherein $R^3$ is H or $NH_2$.

6. The compound or salt according to claim 4 wherein $R^3$ is $NH_2$.

7. The compound or salt according to claim 4 wherein $R^3$ is H.

8. The compound or salt according to claim 7 wherein $R^{101}$ is H.

9. The compound or salt according to claim 7 wherein $R^{101}$ is OH.

10. The compound or salt according to claim 9 wherein X is a bond, O, $CH_2$, $C_2H_4$, $CH(CH_3)$, $CH(CH_2OH)$, $CH_2O$, $CH(NH_2)$, CH(OH) or NH.

11. The compound or salt according to claim 9 wherein X is $CH_2$.

12. The compound or salt according to claim 11 wherein $R^{102}$ is an optionally substituted nitrogen-containing ring system which is linked to the X moiety via a nitrogen ring atom.

13. The compound or salt according to claim 11 wherein $R^{102}$ is an optionally substituted ring system where the ring system is selected from -benzimidazolyl, benzisoxazolyl, benzofuranyl, benzoxazolyl, benzotriazolyl, biphenyl, bipyrazolyl, cinnolinyl, cyclobutylimidazolyl, cyclobutylpyrazolyl, cyclobutylthiazolyl, cyclopentyltriazolyl, cyclopropylisoxazolyl, cyclopropyloxazolyl, cyclopropylpyrazolyl, cyclopropyltriazolyl, diazirenylphenyl, dihydronaphthyridinyl, dihydropyrrolopyrazolyl, dioxinopyridinyl, furazanyl, furopyridinyl, furopyrrolyl, imidazolyl, imidazopyrazinyl, imidazopyridazinyl, imidazopyridinyl, imidazopyrimidinyl, imidazothiadiazolyl, imidazothiazolyl, indanyl, indazolyl, indolyl, isoindolyl, isoxazolopyridinyl, isoxazolyl, isoquinolinyl, naphthyridinyl, oxazolyl, phenyl, phenylcyclopropyl, phenylimidazolyl, phenylpyrazolyl, phenylpyrrolyl, phenyltetrazolyl, phthalazinyl, purinyl, pyrazinyl, pyrazolyl, pyrazolopyridinyl, pyrazolopyrimidinyl, pyrazolotriazinyl, pyridinyl, pyridazinyl, pyridinyltriazolyl, pyrimidinyl, pyrroloimidazolyl, pyrrolopyrazinyl, pyrrolopyrimidinyl, pyrrolopyridinyl, pyrrolyl, quinolinyl, quinazolyl, quinoxalinyl, tetrahydrobenzisoxazolyl, tetrahydrocyclopentapyrazolyl, tetrahydrotriazolopyridinyl, tetrazolopyridazinyl, tetrazolopyridinyl, thiazolyl, thiazolopyridinyl, thiazolopyrimidinyl, thienylpyrazolyl, thienopyridinyl, triazolopyridinyl and triazolyl.

14. The compound or salt according to claim 13 where the optional substituents are independently selected from, where possible -halo, methyl, ethyl, propyl, isopropyl, cyclopropyl, $CF_3$, $CHF_2$, $CH_2F$, $CH_2OCH_3$, CN, $CH_2OH$, $OCH_3$, =O, $NH_2$, $SCH_3$, $SO_2CH_3$, phenoxy, fluorophenoxy, benzyl, $SCF_3$, $OCF_3$, $SO_2CF_3$, $NHSO_2CH_3$, $NHSO_2CF_3$, benzoyl, azetidinylmethyl, fluoroazetidinylmethyl and morpholinomethyl.

15. The compound or salt according to claim 11 wherein $R^{102}$ is selected from the group consisting of phenyl, pyrazol-1-yl, 1,2,3-triazol-1-yl, benzotriazol-2-yl, pyridin-2-yl, pyridin-3-yl and pyridin-4-yl, each of which is optionally substituted by halo, methyl, ethyl, propyl, isopropyl, cyclopropyl, $CF_3$, $CHF_2$, $CH_2F$, $CH_2OCH_3$, CN, $CH_2OH$, $OCH_3$, =O, $NH_2$, $SCH_3$, $SO_2CH_3$, phenoxy, fluorophenoxy, benzyl, $SCF_3$, $OCF_3$, $SO_2CF_3$, $NHSO_2CH_3$, $NHSO_2CF_3$, benzoyl, azetidinylmethyl, fluoroazetidinylmethyl and/or morpholinomethyl.

16. The compound or salt according to claim 15 with $R^5$ and $R^6$ groups present, wherein $R^5$ and $R^6$ are each independently H, $C_{1-3}$ alkyl optionally substituted by $C_{1-3}$ alkoxy, $C_{3-5}$ cycloalkyl, propellanyl, oxetanyl, tetrahydrofuranyl or pyranyl, or $R^5$ and $R^6$ together with the N to which they are attached can be an azetidine, pyrrolidine, piperidine, piperazine or morpholine ring, which ring is optionally substituted by $C_{1-3}$ alkoxy and/or $C_{1-3}$ alkyl.

17. A compound of Formula (IA):

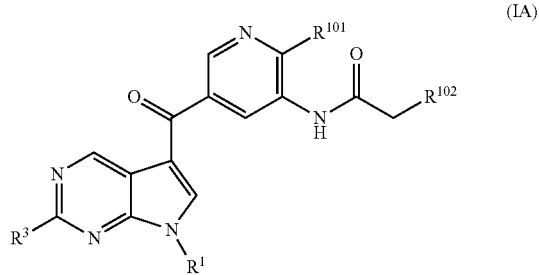

(IA)

or a pharmaceutically acceptable salt thereof, wherein
$R^3$ is H or $NH_2$;
$R^1$ is $C_{2-4}$ alkyl optionally substituted by 1 or 2 OH groups;
$R^{101}$ is H or OH; and
$R^{102}$ is phenyl or an aromatic or partially unsaturated 5- or 6-membered heterocycle, which heterocycle is optionally fused to a further phenyl or 5-7 membered aromatic or partially unsaturated heterocyclic ring, wherein each heterocycle has from 1 to 3 ring heteroatoms selected from N, O and S, and which ring system is optionally substituted by up to 3 substituents independently selected from halo, $CF_3$, $C_{1-4}$ alkyl and $C_{3-5}$ cycloalkyl.

18. The compound or salt according to claim 17 wherein $R^{101}$ is H.

19. The compound or salt according to claim 18 wherein $R^1$ is t-butyl, hydroxy-t-butyl or 1-hydroxyprop-2-yl; and $R^{102}$ is 4-trifluoromethylphenyl, 4-chlorophenyl, 2,4-difluorophenyl, 5-chloropyridin-2-yl, 5-fluoropyridin-2-yl, 3-trifluoromethylpyrazolyl-1-yl, 4-trifluoromethylpyrazol-1-yl, 3-trifluoromethyl-5-methylpyrazol-1-yl, 3-cyclopropylpyrazol-1-yl, 4-cyclopropylpyrazol-1-yl, 4-trifluoromethyl (1,2,3-triazol-1-yl), 4-cyclopropyl-(1,2,3-triazol-1-yl), or benzotriazol-2-yl.

20. The compound according to claim 1, selected from the group consisting of
N-(5-{[2-amino-7-(2-hydroxy-1,1-dimethylethyl)-7H-pyrrolo[2,3-d]pyrimidin-5-yl]carbonyl}pyridin-3-yl)-2-[4-(trifluoromethyl)phenyl]acetamide;
N-(5-{[2-amino-7-(2-hydroxy-1,1-dimethylethyl)-7H-pyrrolo[2,3-d]pyrimidin-5-yl]carbonyl}pyridin-3-yl)-2-(4-chlorophenyl)acetamide;
N-(5-{[2-amino-7-(2-hydroxy-1,1-dimethylethyl)-7H-pyrrolo[2,3-d]pyrimidin-5-yl]carbonyl}pyridin-3-yl)-2-(5-fluoropyridin-2-yl)acetamide;
N-(5-{[2-amino-7-(2-hydroxy-1,1-dimethylethyl)-7H-pyrrolo[2,3-d]pyrimidin-5-yl]carbonyl}pyridin-3-yl)-2-[3-(trifluoromethyl)-1H-pyrazol-1-yl]acetamide;
N-(5-{[2-amino-7-(2-hydroxy-1,1-dimethylethyl)-7H-pyrrolo[2,3-d]pyrimidin-5-yl]carbonyl}pyridin-3-yl)-2-(3-cyclopropyl-1H-pyrazol-1-yl)acetamide;
N-{5-[(2-amino-7-tert-butyl-7H-pyrrolo[2,3-d]pyrimidin-5-yl)carbonyl]pyridin-3-yl}-2-(4-cyclopropyl-1H-1,2,3-triazol-1-yl)acetamide;
N-{5-[(2-amino-7-tert-butyl-7H-pyrrolo[2,3-d]pyrimidin-5-yl)carbonyl]pyridin-3-yl}-2-[4-(trifluoromethyl)-1H-pyrazol-1-yl]acetamide;
N-{5-[(2-amino-7-tert-butyl-7H-pyrrolo[2,3-d]pyrimidin-5-yl)carbonyl]pyridin-3-yl}-2-[4-(trifluoromethyl)-1H-1,2,3-triazol-1-yl]acetamide;
N-{5-[(2-amino-7-tert-butyl-7H-pyrrolo[2,3-d]pyrimidin-5-yl)carbonyl]pyridin-3-yl}-2-(5-chloropyridin-2-yl)acetamide;
N-(5-{[2-Amino-7-(2-hydroxy-1,1-dimethylethyl)-7H-pyrrolo[2,3-d]pyrimidin-5-yl]carbonyl}pyridin-3-yl)-2-(5-chloropyridin-2-yl)acetamide;
N-{5-[(7-tert-butyl-7H-pyrrolo[2,3-d]pyrimidin-5-yl)carbonyl]pyridin-3-yl}-2-[4-(trifluoromethyl)-1H-1,2,3-triazol-1-yl]acetamide;
2-(4-chlorophenyl)-N-[5-({7-[(1S)-2-hydroxy-1-methylethyl]-7H-pyrrolo[2,3-d]pyrimidin-5-yl}carbonyl)pyridin-3-yl]acetamide
N-{5-[(7-tert-butyl-7H-pyrrolo[2,3-d]pyrimidin-5-yl)carbonyl]pyridin-3-yl}-2-[4-(trifluoromethyl)-1H-pyrazol-1-yl]acetamide;
N-[5-({7-[(1S)-2-Hydroxy-1-methylethyl]-7H-pyrrolo[2,3-d]pyrimidin-5-yl}carbonyl)pyridin-3-yl]-2-[4-(trifluoromethyl)phenyl]acetamide;
N-[5-({7-[(1R)-2-hydroxy-1-methylethyl]-7H-pyrrolo[2,3-d]pyrimidin-5-yl}carbonyl)pyridin-3-yl]-2-[4-(trifluoromethyl)phenyl]acetamide;
2-(4-chlorophenyl)-N-[5-({7-[(1R)-2-hydroxy-1-methylethyl]-7H-pyrrolo[2,3-d]pyrimidin-5-yl}carbonyl)pyridin-3-yl]acetamide;
N-(5-{[7-(2-hydroxy-1,1-dimethylethyl)-7H-pyrrolo[2,3-d]pyrimidin-5-yl]carbonyl}pyridin-3-yl)-2-[5-methyl-3-(trifluoromethyl)-1H-pyrazol-1-yl]acetamide;
2-(5-chloropyridin-2-yl)-N-(5-{[7-(2-hydroxy-1,1-dimethylethyl)-7H-pyrrolo[2,3-d]pyrimidin-5-yl]carbonyl}pyridin-3-yl)acetamide;

N-(5-{[2-Amino-7-(2-hydroxy-1-methylethyl)-7H-pyrrolo[2,3-d]pyrimidin-5-yl]carbonyl}pyridin-3-yl)-2-(4-chlorophenyl)acetamide;

N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)phenyl]acetamide;

N-(5-{[2-amino-7-(2-hydroxy-1-methylethyl)-7H-pyrrolo[2,3-d]pyrimidin-5-yl]carbonyl}pyridin-3-yl)-2-(4-chlorophenyl)acetamide;

N-(5-{[2-amino-7-(2-hydroxy-1-methylethyl)-7H-pyrrolo[2,3-d]pyrimidin-5-yl]carbonyl}pyridin-3-yl)-2-[4-(trifluoromethyl)phenyl]acetamide;

N-(5-{[2-Amino-7-(2-hydroxy-1,1-dimethylethyl)-7H-pyrrolo[2,3-d]pyrimidin-5-yl]carbonyl}pyridin-3-yl)-2-[5-methyl-3-(trifluoromethyl)-1H-pyrazol-1-yl]acetamide; and N-{5-[(7-tert-butyl-7H-pyrrolo[2,3-d]pyrimidin-5-yl)carbonyl]pyridin-3-yl}-2-(4-cyclopropyl-1H-1,2,3-triazol-1-yl)acetamide;

or a pharmaceutically acceptable salt thereof.

21. N-[5-({7-[(1S)-2-Hydroxy-1-methylethyl]-7H-pyrrolo[2,3-d]pyrimidin-5-yl}carbonyl)pyridin-3-yl]-2-[4-(trifluoromethyl)phenyl]acetamide or a pharmaceutically acceptable salt thereof.

22. A compound that is

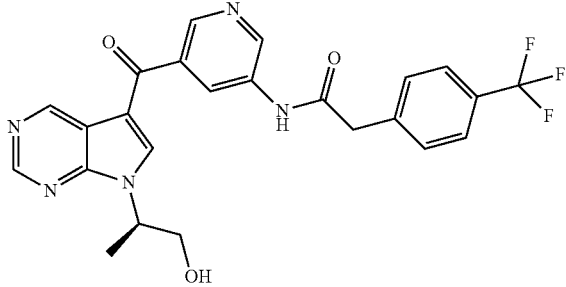 [SMILES: C[C@H](CO)n1cc(C(=O)c2cncc(NC(=O)Cc3ccc(C(F)(F)F)cc3)c2)c2cncnc21]

23. N-[5-({7-[(1R)-2-Hydroxy-1-methylethyl]-7H-pyrrolo[2,3-d]pyrimidin-5-yl}carbonyl)pyridin-3-yl]-2-[5-methyl-3-(trifluoromethyl)-1H-pyrazol-1-yl]acetamide or a pharmaceutically acceptable salt thereof.

24. A compound that is

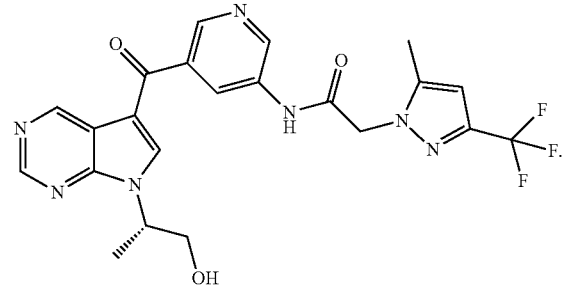 [SMILES: Cc1cc(C(F)(F)F)nn1CC(=O)Nc1cncc(C(=O)c2cn([C@@H](C)CO)c3ncncc23)c1]

25. N-(5-{[2-Amino-7-(2-hydroxy-1,1-dimethylethyl)-7H-pyrrolo[2,3-d]pyrimidin-5-yl]carbonyl}pyridin-3-yl)-2-(5-chloropyridin-2-yl)acetamide or a pharmaceutically acceptable salt thereof.

26. A compound that is

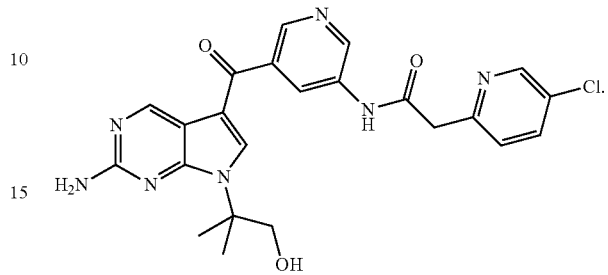

27. N-(5-{[2-Amino-7-(2-hydroxy-1,1-dimethylethyl)-7H-pyrrolo[2,3-d]pyrimidin-5-yl]carbonyl}pyridin-3-yl)-2-[5-methyl-3-(trifluoromethyl)-1H-pyrazol-1-yl]acetamide or a pharmaceutically acceptable salt thereof.

28. A compound that is

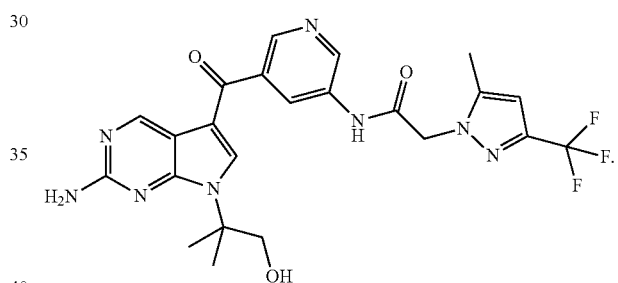

29. N-(5-{[2-Amino-7-(2-hydroxy-1,1-dimethylethyl)-7H-pyrrolo[2,3-d]pyrimidin-5-yl]carbonyl}pyridin-3-yl)-2-(4-cyclopropyl-1H-1,2,3-triazol-1-yl)acetamide or a pharmaceutically acceptable salt thereof.

30. A compound that is

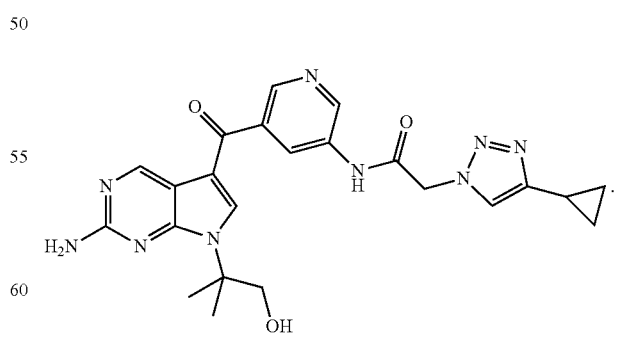

31. N-{5-[(2-amino-7-tert-butyl-7H-pyrrolo[2,3-d]pyrimidin-5-yl)carbonyl]pyridin-3-yl}-2-[3-(trifluoromethyl)-1H-pyrazol-1-yl]acetamide or a pharmaceutically acceptable salt thereof.

32. A compound that is

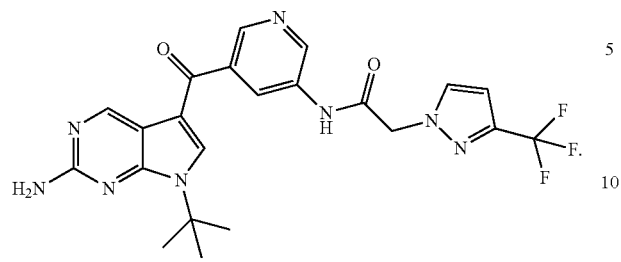

33. A pharmaceutical composition comprising a compound of claim 1, or a pharmaceutically acceptable salt thereof, and a pharmaceutically acceptable carrier.

34. A method of antagonizing a Trk receptor in a mammal, in need thereof, comprising administering to the mammal in need of such treatment, a therapeutically effective amount of a compound of claim 1.

35. A method of treatment of pain in a mammal, comprising administering to the mammal in need of such treatment a therapeutically effective amount of a compound of claim 1, or a pharmaceutically acceptable salt thereof.

* * * * *